US010583415B2

(12) United States Patent
Banyai et al.

(10) Patent No.: US 10,583,415 B2
(45) Date of Patent: Mar. 10, 2020

(54) DE NOVO SYNTHESIZED GENE LIBRARIES

(71) Applicant: Twist Bioscience Corporation, San Francisco, CA (US)

(72) Inventors: William Banyai, San Francisco, CA (US); Bill James Peck, Santa Clara, CA (US); Andres Fernandez, San Francisco, CA (US); Siyuan Chen, San Mateo, CA (US); Pierre Indermuhle, Berkeley, CA (US)

(73) Assignee: Twist Bioscience Corporation, San Francisco, CA (US)

( * ) Notice: Subject to any disclaimer, the term of this patent is extended or adjusted under 35 U.S.C. 154(b) by 0 days.

(21) Appl. No.: 16/409,608

(22) Filed: May 10, 2019

(65) Prior Publication Data
US 2019/0314783 A1  Oct. 17, 2019

Related U.S. Application Data

(63) Continuation of application No. 15/377,547, filed on Dec. 13, 2016, now Pat. No. 10,384,188, which is a continuation of application No. 15/187,721, filed on Jun. 20, 2016, now Pat. No. 9,555,388, which is a continuation of application No. 14/885,963, filed on Oct. 16, 2015, now Pat. No. 9,403,141, which is a continuation of application No. PCT/US2014/049834, filed on Aug. 5, 2014.

(60) Provisional application No. 61/862,445, filed on Aug. 5, 2013, provisional application No. 61/862,457, filed on Aug. 5, 2013.

(51) Int. Cl.
| | |
|---|---|
| *B01J 19/00* | (2006.01) |
| *C12N 15/10* | (2006.01) |
| *C40B 50/18* | (2006.01) |
| *C12N 15/66* | (2006.01) |
| *C12N 15/74* | (2006.01) |
| *C40B 50/00* | (2006.01) |
| *C40B 40/06* | (2006.01) |
| *C40B 50/14* | (2006.01) |
| *C12N 15/09* | (2006.01) |

(52) U.S. Cl.
CPC ...... *B01J 19/0046* (2013.01); *C12N 15/1093* (2013.01); *C12N 15/1096* (2013.01); *C12N 15/66* (2013.01); *C12N 15/74* (2013.01); *C40B 50/18* (2013.01); *B01J 2219/0059* (2013.01); *B01J 2219/00313* (2013.01); *B01J 2219/00317* (2013.01); *B01J 2219/00378* (2013.01); *B01J 2219/00497* (2013.01); *B01J 2219/00585* (2013.01); *B01J 2219/00587* (2013.01); *B01J 2219/00596* (2013.01); *B01J 2219/00605* (2013.01); *B01J 2219/00612* (2013.01); *B01J 2219/00619* (2013.01); *B01J 2219/00623* (2013.01); *B01J 2219/00637* (2013.01); *B01J 2219/00709* (2013.01); *B01J 2219/00722* (2013.01); *C12N 15/09* (2013.01); *C40B 40/06* (2013.01); *C40B 50/00* (2013.01); *C40B 50/14* (2013.01)

(58) Field of Classification Search
CPC . C12N 15/09; C12N 15/1093; C12N 15/1096
USPC .......................................................... 435/6.1
See application file for complete search history.

(56) References Cited

U.S. PATENT DOCUMENTS

| | | | |
|---|---|---|---|
| 3,549,368 A | 12/1970 | Collins et al. | |
| 3,920,714 A | 11/1975 | Streck | |
| 4,123,661 A | 10/1978 | Wolf et al. | |
| 4,415,732 A | 11/1983 | Caruthers et al. | |
| 4,613,398 A | 9/1986 | Chiong et al. | |
| 4,726,877 A | 2/1988 | Fryd et al. | |
| 4,808,511 A | 2/1989 | Holmes | |
| 4,837,401 A | 6/1989 | Hirose et al. | |
| 4,863,557 A | 9/1989 | Kokaku et al. | |
| 4,981,797 A | 1/1991 | Jessee et al. | |
| 4,988,617 A | 1/1991 | Landegren et al. | |
| 5,102,797 A | 4/1992 | Tucker et al. | |
| 5,118,605 A | 6/1992 | Urdea | |
| 5,137,814 A | 8/1992 | Rashtchian et al. | |
| 5,143,854 A | 9/1992 | Pirrung et al. | |
| 5,242,794 A | 9/1993 | Whiteley et al. | |
| 5,242,974 A | 9/1993 | Holmes | |
| 5,288,514 A | 2/1994 | Ellman et al. | |
| 5,299,491 A | 4/1994 | Kawada | |
| 5,384,261 A | 1/1995 | Winkler et al. | |
| 5,387,541 A | 2/1995 | Hodge et al. | |
| 5,395,753 A | 3/1995 | Prakash | |
| 5,431,720 A | 7/1995 | Nagai et al. | |
| 5,445,934 A | 8/1995 | Fodor et al. | |
| 5,449,754 A | 9/1995 | Nishioka | |
| 5,459,039 A | 10/1995 | Modrich et al. | |
| 5,474,796 A | 12/1995 | Brennan | |
| 5,476,930 A | 12/1995 | Letsinger et al. | |

(Continued)

FOREIGN PATENT DOCUMENTS

| | | |
|---|---|---|
| AU | 3157000 A | 9/2000 |
| CA | 2362939 A1 | 8/2000 |

(Continued)

OTHER PUBLICATIONS

Cheng et al (Nucleic Acids Research, vol. 30 No. 18 e93 7 pages (Year: 2002).*

(Continued)

*Primary Examiner* — Jane J Zara
(74) *Attorney, Agent, or Firm* — Wilson Sonsini Goodrich & Rosati

(57) ABSTRACT

De novo synthesized large libraries of nucleic acids are provided herein with low error rates. Further, devices for the manufacturing of high-quality building blocks, such as oligonucleotides, are described herein. Longer nucleic acids can be synthesized in parallel using microfluidic assemblies. Further, methods herein allow for the fast construction of large libraries of long, high-quality genes. Devices for the manufacturing of large libraries of long and high-quality nucleic acids are further described herein.

21 Claims, 82 Drawing Sheets

Specification includes a Sequence Listing.

(56) References Cited

U.S. PATENT DOCUMENTS

| | | |
|---|---|---|
| 5,487,993 A | 1/1996 | Herrnstadt et al. |
| 5,494,810 A | 2/1996 | Barany et al. |
| 5,501,893 A | 3/1996 | Laermer et al. |
| 5,508,169 A | 4/1996 | Deugau et al. |
| 5,510,270 A | 4/1996 | Fodor et al. |
| 5,514,789 A | 5/1996 | Kempe |
| 5,527,681 A | 6/1996 | Holmes et al. |
| 5,530,516 A | 6/1996 | Sheets |
| 5,556,750 A | 9/1996 | Modrich et al. |
| 5,586,211 A | 12/1996 | Dumitrou et al. |
| 5,641,658 A | 6/1997 | Adams et al. |
| 5,677,195 A | 10/1997 | Winkler et al. |
| 5,679,522 A | 10/1997 | Modrich et al. |
| 5,688,642 A | 11/1997 | Chrisey et al. |
| 5,700,637 A | 12/1997 | Southern et al. |
| 5,700,642 A | 12/1997 | Monforte et al. |
| 5,702,894 A | 12/1997 | Modrich et al. |
| 5,707,806 A | 1/1998 | Shuber |
| 5,712,124 A | 1/1998 | Walker |
| 5,739,386 A | 4/1998 | Holmes |
| 5,750,672 A | 5/1998 | Kempe |
| 5,780,613 A | 7/1998 | Letsinger et al. |
| 5,830,655 A | 11/1998 | Monforte et al. |
| 5,830,662 A | 11/1998 | Soares et al. |
| 5,834,252 A | 11/1998 | Stemmer et al. |
| 5,843,669 A | 12/1998 | Kaiser et al. |
| 5,843,767 A | 12/1998 | Beattie |
| 5,846,717 A | 12/1998 | Brow et al. |
| 5,854,033 A | 12/1998 | Lizardi |
| 5,858,754 A | 1/1999 | Modrich et al. |
| 5,861,482 A | 1/1999 | Modrich et al. |
| 5,863,801 A | 1/1999 | Southgate et al. |
| 5,869,245 A | 2/1999 | Yeung |
| 5,877,280 A | 3/1999 | Wetmur |
| 5,882,496 A | 3/1999 | Northrup et al. |
| 5,922,539 A | 7/1999 | Modrich et al. |
| 5,922,593 A | 7/1999 | Livingston |
| 5,928,907 A | 7/1999 | Woudenberg et al. |
| 5,962,272 A | 10/1999 | Chenchik et al. |
| 5,976,842 A | 11/1999 | Wurst |
| 5,976,846 A | 11/1999 | Passmore et al. |
| 5,989,872 A | 11/1999 | Luo et al. |
| 5,994,069 A | 11/1999 | Hall et al. |
| 6,001,567 A | 12/1999 | Brow et al. |
| 6,008,031 A | 12/1999 | Modrich et al. |
| 6,013,440 A | 1/2000 | Lipshutz et al. |
| 6,015,674 A | 1/2000 | Woudenberg et al. |
| 6,027,898 A | 2/2000 | Gjerde et al. |
| 6,028,189 A | 2/2000 | Blanchard |
| 6,028,198 A | 2/2000 | Liu et al. |
| 6,040,138 A | 3/2000 | Lockhart et al. |
| 6,077,674 A | 6/2000 | Schleifer et al. |
| 6,090,543 A | 7/2000 | Prudent et al. |
| 6,090,606 A | 7/2000 | Kaiser et al. |
| 6,103,474 A | 8/2000 | Dellinger et al. |
| 6,107,038 A | 8/2000 | Choudhary et al. |
| 6,110,682 A | 8/2000 | Dellinger et al. |
| 6,114,115 A | 9/2000 | Wagner, Jr. |
| 6,130,045 A | 10/2000 | Wurst et al. |
| 6,132,997 A | 10/2000 | Shannon |
| 6,136,568 A | 10/2000 | Hiatt et al. |
| 6,171,797 B1 | 1/2001 | Perbost |
| 6,180,351 B1 | 1/2001 | Cattell |
| 6,201,112 B1 | 3/2001 | Ach |
| 6,218,118 B1 | 4/2001 | Sampson et al. |
| 6,221,653 B1 | 4/2001 | Caren et al. |
| 6,222,030 B1 | 4/2001 | Dellinger et al. |
| 6,232,072 B1 | 5/2001 | Fisher |
| 6,235,483 B1 | 5/2001 | Wolber et al. |
| 6,242,266 B1 | 6/2001 | Schleifer et al. |
| 6,251,588 B1 | 6/2001 | Shannon et al. |
| 6,251,595 B1 | 6/2001 | Gordon et al. |
| 6,251,685 B1 | 6/2001 | Dorsel et al. |
| 6,258,454 B1 | 7/2001 | Lefkowitz et al. |
| 6,262,490 B1 | 7/2001 | Hsu et al. |
| 6,274,725 B1 | 8/2001 | Sanghvi et al. |
| 6,284,465 B1 | 9/2001 | Wolber |
| 6,287,776 B1 | 9/2001 | Hefti |
| 6,287,824 B1 | 9/2001 | Lizardi |
| 6,297,017 B1 | 10/2001 | Schmidt et al. |
| 6,300,137 B1 | 10/2001 | Earhart et al. |
| 6,306,599 B1 | 10/2001 | Perbost |
| 6,309,822 B1 | 10/2001 | Fodor et al. |
| 6,309,828 B1 | 10/2001 | Schleifer et al. |
| 6,312,911 B1 | 11/2001 | Bancroft et al. |
| 6,319,674 B1 | 11/2001 | Fulcrand et al. |
| 6,323,043 B1 | 11/2001 | Caren et al. |
| 6,329,210 B1 | 12/2001 | Schleifer |
| 6,346,423 B1 | 2/2002 | Schembri |
| 6,365,355 B1 | 4/2002 | McCutchen-Maloney |
| 6,372,483 B2 | 4/2002 | Schleifer et al. |
| 6,375,903 B1 | 4/2002 | Cerrina et al. |
| 6,376,285 B1 | 4/2002 | Joyner et al. |
| 6,384,210 B1 | 5/2002 | Blanchard |
| 6,387,636 B1 | 5/2002 | Perbost et al. |
| 6,399,394 B1 | 6/2002 | Dahm et al. |
| 6,399,516 B1 | 6/2002 | Ayon |
| 6,403,314 B1 | 6/2002 | Lange et al. |
| 6,406,849 B1 | 6/2002 | Dorsel et al. |
| 6,406,851 B1 | 6/2002 | Bass |
| 6,408,308 B1 | 6/2002 | Maslyn et al. |
| 6,419,883 B1 | 7/2002 | Blanchard |
| 6,428,957 B1 | 8/2002 | Delenstarr |
| 6,440,669 B1 | 8/2002 | Bass et al. |
| 6,444,268 B2 | 9/2002 | Lefkowitz et al. |
| 6,446,642 B1 | 9/2002 | Caren et al. |
| 6,446,682 B1 | 9/2002 | Viken |
| 6,451,998 B1 | 9/2002 | Perbost |
| 6,458,526 B1 | 10/2002 | Schembri et al. |
| 6,458,535 B1 | 10/2002 | Hall et al. |
| 6,458,583 B1 | 10/2002 | Bruhn et al. |
| 6,461,812 B2 | 10/2002 | Barth et al. |
| 6,461,816 B1 | 10/2002 | Wolber et al. |
| 6,469,156 B1 | 10/2002 | Schafer et al. |
| 6,472,147 B1 | 10/2002 | Janda et al. |
| 6,492,107 B1 | 12/2002 | Kauffman et al. |
| 6,518,056 B2 | 2/2003 | Schembri et al. |
| 6,521,427 B1 | 2/2003 | Evans |
| 6,521,453 B1 | 2/2003 | Crameri et al. |
| 6,555,357 B1 | 4/2003 | Kaiser et al. |
| 6,558,908 B2 | 5/2003 | Wolber et al. |
| 6,562,611 B1 | 5/2003 | Kaiser et al. |
| 6,566,495 B1 | 5/2003 | Fodor et al. |
| 6,582,908 B2 | 6/2003 | Fodor et al. |
| 6,582,938 B1 | 6/2003 | Su et al. |
| 6,586,211 B1 | 7/2003 | Staehler et al. |
| 6,587,579 B1 | 7/2003 | Bass |
| 6,589,739 B2 | 7/2003 | Fisher |
| 6,599,693 B1 | 7/2003 | Webb |
| 6,602,472 B1 | 8/2003 | Zimmermann et al. |
| 6,610,978 B2 | 8/2003 | Yin et al. |
| 6,613,513 B1 | 9/2003 | Parce et al. |
| 6,613,523 B2 | 9/2003 | Fischer |
| 6,613,560 B1 | 9/2003 | Tso et al. |
| 6,613,893 B1 | 9/2003 | Webb |
| 6,621,076 B1 | 9/2003 | Van et al. |
| 6,630,581 B2 | 10/2003 | Dellinger et al. |
| 6,632,641 B1 | 10/2003 | Brennan et al. |
| 6,635,226 B1 | 10/2003 | Tso et al. |
| 6,642,373 B2 | 11/2003 | Manoharan et al. |
| 6,649,348 B2 | 11/2003 | Bass et al. |
| 6,660,338 B1 | 12/2003 | Hargreaves |
| 6,664,112 B2 | 12/2003 | Mulligan et al. |
| 6,670,127 B2 | 12/2003 | Evans |
| 6,670,461 B1 | 12/2003 | Wengel et al. |
| 6,673,552 B2 | 1/2004 | Frey |
| 6,682,702 B2 | 1/2004 | Barth et al. |
| 6,689,319 B1 | 2/2004 | Fisher et al. |
| 6,692,917 B2 | 2/2004 | Neri et al. |
| 6,702,256 B2 | 3/2004 | Killeen et al. |
| 6,706,471 B1 | 3/2004 | Brow et al. |
| 6,706,875 B1 | 3/2004 | Goldberg et al. |
| 6,709,852 B1 | 3/2004 | Bloom et al. |
| 6,709,854 B2 | 3/2004 | Donahue et al. |

(56) References Cited

U.S. PATENT DOCUMENTS

| | | |
|---|---|---|
| 6,713,262 B2 | 3/2004 | Gillibolian et al. |
| 6,716,629 B2 | 4/2004 | Hess et al. |
| 6,716,634 B1 | 4/2004 | Myerson |
| 6,723,509 B2 | 4/2004 | Ach |
| 6,728,129 B2 | 4/2004 | Lindsey et al. |
| 6,743,585 B2 | 6/2004 | Dellinger et al. |
| 6,753,145 B2 | 6/2004 | Holcomb et al. |
| 6,768,005 B2 | 7/2004 | Mellor et al. |
| 6,770,748 B2 | 8/2004 | Imanishi et al. |
| 6,770,892 B2 | 8/2004 | Corson et al. |
| 6,773,676 B2 | 8/2004 | Schembri |
| 6,773,888 B2 | 8/2004 | Li et al. |
| 6,780,982 B2 | 8/2004 | Lyamichev et al. |
| 6,787,308 B2 | 9/2004 | Balasubramanian et al. |
| 6,789,965 B2 | 9/2004 | Barth et al. |
| 6,790,620 B2 | 9/2004 | Bass et al. |
| 6,794,499 B2 | 9/2004 | Wengel et al. |
| 6,796,634 B2 | 9/2004 | Caren et al. |
| 6,800,439 B1 | 10/2004 | McGall et al. |
| 6,814,846 B1 | 11/2004 | Berndt |
| 6,815,218 B1 | 11/2004 | Jacobson et al. |
| 6,824,866 B1 | 11/2004 | Glazer et al. |
| 6,830,890 B2 | 12/2004 | Lockhart et al. |
| 6,833,246 B2 | 12/2004 | Balasubramanian |
| 6,833,450 B1 | 12/2004 | McGall et al. |
| 6,835,938 B2 | 12/2004 | Ghosh et al. |
| 6,838,888 B2 | 1/2005 | Peck |
| 6,841,131 B2 | 1/2005 | Zimmermann et al. |
| 6,845,968 B2 | 1/2005 | Killeen et al. |
| 6,846,454 B2 | 1/2005 | Peck |
| 6,846,922 B1 | 1/2005 | Manoharan et al. |
| 6,852,850 B2 | 2/2005 | Myerson et al. |
| 6,858,720 B2 | 2/2005 | Myerson et al. |
| 6,879,915 B2 | 4/2005 | Cattell |
| 6,880,576 B2 | 4/2005 | Karp et al. |
| 6,884,580 B2 | 4/2005 | Caren et al. |
| 6,887,715 B2 | 5/2005 | Schembri |
| 6,890,723 B2 | 5/2005 | Perbost et al. |
| 6,890,760 B1 | 5/2005 | Webb |
| 6,893,816 B1 | 5/2005 | Beattie |
| 6,897,023 B2 | 5/2005 | Fu et al. |
| 6,900,047 B2 | 5/2005 | Bass |
| 6,900,048 B2 | 5/2005 | Perbost |
| 6,911,611 B2 | 6/2005 | Wong et al. |
| 6,914,229 B2 | 7/2005 | Corson et al. |
| 6,916,113 B2 | 7/2005 | De Goor et al. |
| 6,916,633 B1 | 7/2005 | Shannon |
| 6,919,181 B2 | 7/2005 | Hargreaves |
| 6,927,029 B2 | 8/2005 | Lefkowitz et al. |
| 6,929,951 B2 | 8/2005 | Corson et al. |
| 6,936,472 B2 | 8/2005 | Earhart et al. |
| 6,938,476 B2 | 9/2005 | Chesk |
| 6,939,673 B2 | 9/2005 | Bass et al. |
| 6,943,036 B2 | 9/2005 | Bass |
| 6,946,285 B2 | 9/2005 | Bass |
| 6,950,756 B2 | 9/2005 | Kincaid |
| 6,951,719 B1 | 10/2005 | Dupret et al. |
| 6,958,119 B2 | 10/2005 | Yin et al. |
| 6,960,464 B2 | 11/2005 | Jessee et al. |
| 6,969,488 B2 | 11/2005 | Bridgham et al. |
| 6,976,384 B2 | 12/2005 | Hobbs et al. |
| 6,977,223 B2 | 12/2005 | George et al. |
| 6,987,263 B2 | 1/2006 | Hobbs et al. |
| 6,989,267 B2 | 1/2006 | Kim et al. |
| 6,991,922 B2 | 1/2006 | Dupret et al. |
| 7,008,037 B2 | 3/2006 | Caren et al. |
| 7,025,324 B1 | 4/2006 | Slocum et al. |
| 7,026,124 B2 | 4/2006 | Barth et al. |
| 7,027,930 B2 | 4/2006 | Cattell |
| 7,028,536 B2 | 4/2006 | Karp et al. |
| 7,029,854 B2 | 4/2006 | Collins et al. |
| 7,034,290 B2 | 4/2006 | Lu et al. |
| 7,041,445 B2 | 5/2006 | Chenchik et al. |
| 7,045,289 B2 | 5/2006 | Allawi et al. |
| 7,051,574 B2 | 5/2006 | Peck |
| 7,052,841 B2 | 5/2006 | Delenstarr |
| 7,062,385 B2 | 6/2006 | White et al. |
| 7,064,197 B1 | 6/2006 | Rabbani et al. |
| 7,070,932 B2 | 7/2006 | Leproust et al. |
| 7,075,161 B2 | 7/2006 | Barth |
| 7,078,167 B2 | 7/2006 | Delenstarr et al. |
| 7,078,505 B2 | 7/2006 | Bass et al. |
| 7,094,537 B2 | 8/2006 | Leproust et al. |
| 7,097,974 B1 | 8/2006 | Staehler et al. |
| 7,101,508 B2 | 9/2006 | Thompson et al. |
| 7,101,986 B2 | 9/2006 | Dellinger et al. |
| 7,105,295 B2 | 9/2006 | Bass et al. |
| 7,115,423 B1 | 10/2006 | Mitchell |
| 7,122,303 B2 | 10/2006 | Delenstarr et al. |
| 7,122,364 B1 | 10/2006 | Lyamichev et al. |
| 7,125,488 B2 | 10/2006 | Li |
| 7,125,523 B2 | 10/2006 | Sillman |
| 7,128,876 B2 | 10/2006 | Yin et al. |
| 7,129,075 B2 | 10/2006 | Gerard et al. |
| 7,135,565 B2 | 11/2006 | Dellinger et al. |
| 7,138,062 B2 | 11/2006 | Yin et al. |
| 7,141,368 B2 | 11/2006 | Fisher et al. |
| 7,141,807 B2 | 11/2006 | Joyce et al. |
| 7,147,362 B2 | 12/2006 | Caren et al. |
| 7,150,982 B2 | 12/2006 | Allawi et al. |
| 7,153,689 B2 | 12/2006 | Tolosko et al. |
| 7,163,660 B2 | 1/2007 | Lehmann |
| 7,166,258 B2 | 1/2007 | Bass et al. |
| 7,179,659 B2 | 2/2007 | Stolowitz et al. |
| 7,183,406 B2 | 2/2007 | Belshaw et al. |
| 7,192,710 B2 | 3/2007 | Gellibolian et al. |
| 7,193,077 B2 | 3/2007 | Dellinger et al. |
| 7,198,939 B2 | 4/2007 | Dorsel et al. |
| 7,202,264 B2 | 4/2007 | Ravikumar et al. |
| 7,202,358 B2 | 4/2007 | Hargreaves |
| 7,205,128 B2 | 4/2007 | Ilsley et al. |
| 7,205,400 B2 | 4/2007 | Webb |
| 7,206,439 B2 | 4/2007 | Zhou et al. |
| 7,208,322 B2 | 4/2007 | Stolowitz et al. |
| 7,217,522 B2 | 5/2007 | Brenner |
| 7,220,573 B2 | 5/2007 | Shea et al. |
| 7,221,785 B2 | 5/2007 | Curry et al. |
| 7,226,862 B2 | 6/2007 | Staehler et al. |
| 7,227,017 B2 | 6/2007 | Mellor et al. |
| 7,229,497 B2 | 6/2007 | Stott et al. |
| 7,247,337 B1 | 7/2007 | Leproust et al. |
| 7,247,497 B2 | 7/2007 | Dahm et al. |
| 7,252,938 B2 | 8/2007 | Leproust et al. |
| 7,269,518 B2 | 9/2007 | Corson |
| 7,271,258 B2 | 9/2007 | Dellinger et al. |
| 7,276,336 B1 | 10/2007 | Webb et al. |
| 7,276,378 B2 | 10/2007 | Myerson |
| 7,276,599 B2 | 10/2007 | Moore et al. |
| 7,282,183 B2 | 10/2007 | Peck |
| 7,282,332 B2 | 10/2007 | Caren et al. |
| 7,282,705 B2 | 10/2007 | Brennen |
| 7,291,471 B2 | 11/2007 | Sampson et al. |
| 7,302,348 B2 | 11/2007 | Ghosh et al. |
| 7,306,917 B2 | 12/2007 | Prudent et al. |
| 7,314,599 B2 | 1/2008 | Roitman et al. |
| 7,323,320 B2 | 1/2008 | Oleinikov |
| 7,344,831 B2 | 3/2008 | Wolber et al. |
| 7,348,144 B2 | 3/2008 | Minor |
| 7,351,379 B2 | 4/2008 | Schleifer |
| 7,353,116 B2 | 4/2008 | Webb et al. |
| 7,361,906 B2 | 4/2008 | Ghosh et al. |
| 7,364,896 B2 | 4/2008 | Schembri |
| 7,368,550 B2 | 5/2008 | Dellinger et al. |
| 7,371,348 B2 | 5/2008 | Schleifer et al. |
| 7,371,519 B2 | 5/2008 | Wolber et al. |
| 7,371,580 B2 | 5/2008 | Yakhini et al. |
| 7,372,982 B2 | 5/2008 | Le Cocq |
| 7,384,746 B2 | 6/2008 | Lyamichev et al. |
| 7,385,050 B2 | 6/2008 | Dellinger et al. |
| 7,390,457 B2 | 6/2008 | Schembri |
| 7,393,665 B2 | 7/2008 | Brenner |
| 7,396,676 B2 | 7/2008 | Robotti et al. |
| 7,399,844 B2 | 7/2008 | Sampson et al. |
| 7,402,279 B2 | 7/2008 | Schembri |

(56) References Cited

U.S. PATENT DOCUMENTS

| | | |
|---|---|---|
| 7,411,061 B2 | 8/2008 | Myerson et al. |
| 7,413,709 B2 | 8/2008 | Roitman et al. |
| 7,417,139 B2 | 8/2008 | Dellinger et al. |
| 7,422,911 B2 | 9/2008 | Schembri |
| 7,427,679 B2 | 9/2008 | Dellinger et al. |
| 7,432,048 B2 | 10/2008 | Neri et al. |
| 7,435,810 B2 | 10/2008 | Myerson et al. |
| 7,439,272 B2 | 10/2008 | Xu |
| 7,476,709 B2 | 1/2009 | Moody et al. |
| 7,482,118 B2 | 1/2009 | Allawi et al. |
| 7,488,607 B2 | 2/2009 | Tom-Moy et al. |
| 7,504,213 B2 | 3/2009 | Sana et al. |
| 7,514,369 B2 | 4/2009 | Li et al. |
| 7,517,979 B2 | 4/2009 | Wolber |
| 7,524,942 B2 | 4/2009 | Wang et al. |
| 7,524,950 B2 | 4/2009 | Dellinger et al. |
| 7,527,928 B2 | 5/2009 | Neri et al. |
| 7,531,303 B2 | 5/2009 | Dorsel et al. |
| 7,534,561 B2 | 5/2009 | Sana et al. |
| 7,534,563 B2 | 5/2009 | Hargreaves |
| 7,537,936 B2 | 5/2009 | Dahm et al. |
| 7,541,145 B2 | 6/2009 | Prudent et al. |
| 7,544,473 B2 | 6/2009 | Brenner |
| 7,556,919 B2 | 7/2009 | Chenchik et al. |
| 7,563,600 B2 | 7/2009 | Oleinikov |
| 7,572,585 B2 | 8/2009 | Wang |
| 7,572,907 B2 | 8/2009 | Dellinger et al. |
| 7,572,908 B2 | 8/2009 | Dellinger et al. |
| 7,585,970 B2 | 9/2009 | Dellinger et al. |
| 7,588,889 B2 | 9/2009 | Wolber et al. |
| 7,595,350 B2 | 9/2009 | Xu |
| 7,604,941 B2 | 10/2009 | Jacobson |
| 7,604,996 B1 | 10/2009 | Stuelpnagel et al. |
| 7,608,396 B2 | 10/2009 | Delenstarr |
| 7,618,777 B2 | 11/2009 | Myerson et al. |
| 7,629,120 B2 | 12/2009 | Bennett et al. |
| 7,635,772 B2 | 12/2009 | McCormac |
| 7,648,832 B2 | 1/2010 | Jessee et al. |
| 7,651,762 B2 | 1/2010 | Xu et al. |
| 7,659,069 B2 | 2/2010 | Belyaev et al. |
| 7,678,542 B2 | 3/2010 | Lyamichev et al. |
| 7,682,809 B2 | 3/2010 | Sampson |
| 7,709,197 B2 | 5/2010 | Drmanac |
| 7,718,365 B2 | 5/2010 | Wang |
| 7,718,786 B2 | 5/2010 | Dupret et al. |
| 7,723,077 B2 | 5/2010 | Young et al. |
| 7,737,088 B1 | 6/2010 | Staehler et al. |
| 7,737,089 B2 | 6/2010 | Guimil et al. |
| 7,741,463 B2 | 6/2010 | Gormley et al. |
| 7,749,701 B2 | 7/2010 | Leproust et al. |
| 7,759,471 B2 | 7/2010 | Dellinger et al. |
| 7,776,021 B2 | 8/2010 | Borenstein et al. |
| 7,776,532 B2 | 8/2010 | Gibson et al. |
| 7,790,369 B2 | 9/2010 | Stahler et al. |
| 7,790,387 B2 | 9/2010 | Dellinger et al. |
| 7,807,356 B2 | 10/2010 | Sampson et al. |
| 7,807,806 B2 | 10/2010 | Allawi et al. |
| 7,811,753 B2 | 10/2010 | Eshoo |
| 7,816,079 B2 | 10/2010 | Fischer |
| 7,820,387 B2 | 10/2010 | Neri et al. |
| 7,829,314 B2 | 11/2010 | Prudent et al. |
| 7,855,281 B2 | 12/2010 | Dellinger et al. |
| 7,862,999 B2 | 1/2011 | Zheng et al. |
| 7,867,782 B2 | 1/2011 | Barth |
| 7,875,463 B2 | 1/2011 | Adaskin et al. |
| 7,879,541 B2 | 2/2011 | Kincaid |
| 7,879,580 B2 | 2/2011 | Carr et al. |
| 7,894,998 B2 | 2/2011 | Kincaid |
| 7,919,239 B2 | 4/2011 | Wang |
| 7,919,308 B2 | 4/2011 | Schleifer |
| 7,927,797 B2 | 4/2011 | Nobile et al. |
| 7,927,838 B2 | 4/2011 | Shannon |
| 7,932,025 B2 | 4/2011 | Carr et al. |
| 7,932,070 B2 | 4/2011 | Hogrefe et al. |
| 7,935,800 B2 | 5/2011 | Allawi et al. |
| 7,939,645 B2 | 5/2011 | Borns |
| 7,943,046 B2 | 5/2011 | Martosella et al. |
| 7,943,358 B2 | 5/2011 | Hogrefe et al. |
| 7,960,157 B2 | 6/2011 | Borns |
| 7,977,119 B2 | 7/2011 | Kronick et al. |
| 7,979,215 B2 | 7/2011 | Sampas |
| 7,998,437 B2 | 8/2011 | Berndt et al. |
| 7,999,087 B2 | 8/2011 | Dellinger et al. |
| 8,021,842 B2 | 9/2011 | Brenner |
| 8,021,844 B2 | 9/2011 | Wang |
| 8,034,917 B2 | 10/2011 | Yamada |
| 8,036,835 B2 | 10/2011 | Sampas et al. |
| 8,048,664 B2 | 11/2011 | Guan et al. |
| 8,053,191 B2 | 11/2011 | Blake |
| 8,058,001 B2 | 11/2011 | Crameri et al. |
| 8,058,004 B2 | 11/2011 | Oleinikov |
| 8,058,055 B2 | 11/2011 | Barrett et al. |
| 8,063,184 B2 | 11/2011 | Allawi et al. |
| 8,067,556 B2 | 11/2011 | Hogrefe et al. |
| 8,073,626 B2 | 12/2011 | Troup et al. |
| 8,076,064 B2 | 12/2011 | Wang |
| 8,076,152 B2 | 12/2011 | Robotti |
| 8,097,711 B2 | 1/2012 | Timar et al. |
| 8,137,936 B2 | 3/2012 | Macevicz |
| 8,148,068 B2 | 4/2012 | Brenner |
| 8,154,729 B2 | 4/2012 | Baldo et al. |
| 8,168,385 B2 | 5/2012 | Brenner et al. |
| 8,168,388 B2 | 5/2012 | Gormley et al. |
| 8,173,368 B2 | 5/2012 | Staehler et al. |
| 8,182,991 B1 | 5/2012 | Kaiser et al. |
| 8,194,244 B2 | 6/2012 | Wang et al. |
| 8,198,071 B2 | 6/2012 | Goshoo et al. |
| 8,202,983 B2 | 6/2012 | Dellinger et al. |
| 8,202,985 B2 | 6/2012 | Dellinger et al. |
| 8,206,952 B2 | 6/2012 | Carr et al. |
| 8,213,015 B2 | 7/2012 | Kraiczek et al. |
| 8,242,258 B2 | 8/2012 | Dellinger et al. |
| 8,247,221 B2 | 8/2012 | Fawcett et al. |
| 8,263,335 B2 | 9/2012 | Carr et al. |
| 8,268,605 B2 | 9/2012 | Sorge et al. |
| 8,283,148 B2 | 10/2012 | Sorge et al. |
| 8,288,093 B2 | 10/2012 | Hall et al. |
| 8,298,767 B2 | 10/2012 | Brenner et al. |
| 8,304,273 B2 | 11/2012 | Stellacci et al. |
| 8,309,307 B2 | 11/2012 | Barrett et al. |
| 8,309,706 B2 | 11/2012 | Dellinger et al. |
| 8,309,710 B2 | 11/2012 | Sierzchala et al. |
| 8,314,220 B2 | 11/2012 | Mullinax et al. |
| 8,318,433 B2 | 11/2012 | Brenner |
| 8,318,479 B2 | 11/2012 | Domansky et al. |
| 8,357,489 B2 | 1/2013 | Chua et al. |
| 8,357,490 B2 | 1/2013 | Froehlich et al. |
| 8,367,016 B2 | 2/2013 | Quan et al. |
| 8,367,335 B2 | 2/2013 | Staehler et al. |
| 8,380,441 B2 | 2/2013 | Webb et al. |
| 8,383,338 B2 | 2/2013 | Kitzman et al. |
| 8,415,138 B2 | 4/2013 | Leproust |
| 8,435,736 B2 | 5/2013 | Gibson et al. |
| 8,445,205 B2 | 5/2013 | Brenner |
| 8,445,206 B2 | 5/2013 | Bergmann et al. |
| 8,470,996 B2 | 6/2013 | Brenner et al. |
| 8,476,018 B2 | 7/2013 | Brenner |
| 8,476,598 B1 | 7/2013 | Pralle et al. |
| 8,481,292 B2 | 7/2013 | Casbon et al. |
| 8,481,309 B2 | 7/2013 | Zhang et al. |
| 8,491,561 B2 | 7/2013 | Borenstein et al. |
| 8,497,069 B2 | 7/2013 | Hutchison, III et al. |
| 8,500,979 B2 | 8/2013 | Elibol et al. |
| 8,501,454 B2 | 8/2013 | Liu et al. |
| 8,507,226 B2 | 8/2013 | Carr et al. |
| 8,507,239 B2 | 8/2013 | Lubys et al. |
| 8,507,272 B2 | 8/2013 | Zhang et al. |
| 8,530,197 B2 | 9/2013 | Li et al. |
| 8,552,174 B2 | 10/2013 | Dellinger et al. |
| 8,563,478 B2 | 10/2013 | Gormley et al. |
| 8,569,046 B2 | 10/2013 | Love et al. |
| 8,577,621 B2 | 11/2013 | Troup et al. |
| 8,586,310 B2 | 11/2013 | Mitra et al. |
| 8,614,092 B2 | 12/2013 | Zhang et al. |

(56) References Cited

U.S. PATENT DOCUMENTS

| | | |
|---|---|---|
| 8,642,755 B2 | 2/2014 | Sierzchala et al. |
| 8,664,164 B2 | 3/2014 | Ericsson et al. |
| 8,669,053 B2 | 3/2014 | Stuelpnagel et al. |
| 8,679,756 B1 | 3/2014 | Brenner et al. |
| 8,685,642 B2 | 4/2014 | Sampas |
| 8,685,676 B2 | 4/2014 | Hogrefe et al. |
| 8,685,678 B2 | 4/2014 | Casbon et al. |
| 8,715,933 B2 | 5/2014 | Oliver |
| 8,715,967 B2 | 5/2014 | Casbon et al. |
| 8,716,467 B2 | 5/2014 | Jacobson |
| 8,722,368 B2 | 5/2014 | Casbon et al. |
| 8,722,585 B2 | 5/2014 | Wang |
| 8,728,766 B2 | 5/2014 | Casbon et al. |
| 8,741,606 B2 | 6/2014 | Casbon et al. |
| 8,808,896 B2 | 8/2014 | Choo et al. |
| 8,808,986 B2 | 8/2014 | Jacobson et al. |
| 8,815,600 B2 | 8/2014 | Liu et al. |
| 8,889,851 B2 | 11/2014 | Leproust et al. |
| 8,932,994 B2 | 1/2015 | Gormley et al. |
| 8,962,532 B2 | 2/2015 | Shapiro et al. |
| 8,968,999 B2 | 3/2015 | Gibson et al. |
| 8,980,563 B2 | 3/2015 | Zheng et al. |
| 9,018,365 B2 | 4/2015 | Brenner et al. |
| 9,023,601 B2 | 5/2015 | Oleinikov |
| 9,051,666 B2 | 6/2015 | Oleinikov |
| 9,073,962 B2 | 7/2015 | Fracchia et al. |
| 9,074,204 B2 | 7/2015 | Anderson et al. |
| 9,085,797 B2 | 7/2015 | Gebeyehu et al. |
| 9,133,510 B2 | 9/2015 | Andersen et al. |
| 9,139,874 B2 | 9/2015 | Myers et al. |
| 9,150,853 B2 | 10/2015 | Hudson et al. |
| 9,187,777 B2 | 11/2015 | Jacobson et al. |
| 9,194,001 B2 | 11/2015 | Brenner |
| 9,216,414 B2 | 12/2015 | Chu |
| 9,217,144 B2 | 12/2015 | Jacobson et al. |
| 9,279,149 B2 | 3/2016 | Efcavitch et al. |
| 9,286,439 B2 | 3/2016 | Shapiro et al. |
| 9,295,965 B2 | 3/2016 | Jacobson et al. |
| 9,315,861 B2 | 4/2016 | Hendricks et al. |
| 9,328,378 B2 | 5/2016 | Earnshaw et al. |
| 9,347,091 B2 | 5/2016 | Bergmann et al. |
| 9,375,748 B2 | 6/2016 | Harumoto et al. |
| 9,376,677 B2 | 6/2016 | Mir et al. |
| 9,376,678 B2 | 6/2016 | Gormley et al. |
| 9,384,320 B2 | 7/2016 | Church |
| 9,384,920 B1 | 7/2016 | Bakulich |
| 9,388,407 B2 | 7/2016 | Jacobson |
| 9,394,333 B2 | 7/2016 | Wada et al. |
| 9,403,141 B2 | 8/2016 | William |
| 9,409,139 B2 | 8/2016 | Banyai et al. |
| 9,410,149 B2 | 8/2016 | Brenner et al. |
| 9,410,173 B2 | 8/2016 | Betts et al. |
| 9,416,411 B2 | 8/2016 | Stuelpnagel et al. |
| 9,422,600 B2 | 8/2016 | Ramu et al. |
| 9,487,824 B2 | 11/2016 | Kutyavin et al. |
| 9,499,848 B2 | 11/2016 | Carr et al. |
| 9,523,122 B2 | 12/2016 | Zheng et al. |
| 9,528,148 B2 | 12/2016 | Zheng et al. |
| 9,534,251 B2 | 1/2017 | Young et al. |
| 9,555,388 B2 | 1/2017 | Banyai et al. |
| 9,568,839 B2 | 2/2017 | Stahler et al. |
| 9,580,746 B2 | 2/2017 | Leproust et al. |
| 9,670,529 B2 | 6/2017 | Osborne et al. |
| 9,670,536 B2 | 6/2017 | Casbon et al. |
| 9,677,067 B2 | 6/2017 | Toro et al. |
| 9,695,211 B2 | 7/2017 | Wada et al. |
| 9,718,060 B2 | 8/2017 | Venter et al. |
| 9,745,573 B2 | 8/2017 | Stuelpnagel et al. |
| 9,745,619 B2 | 8/2017 | Rabbani et al. |
| 9,765,387 B2 | 9/2017 | Rabbani et al. |
| 9,771,576 B2 | 9/2017 | Gibson et al. |
| 9,833,761 B2 | 12/2017 | Banyai et al. |
| 9,834,774 B2 | 12/2017 | Carstens |
| 9,839,894 B2 | 12/2017 | Banyai |
| 9,879,283 B2 | 1/2018 | Ravinder et al. |
| 9,889,423 B2 | 2/2018 | Banyai |
| 9,895,673 B2 | 2/2018 | Peck et al. |
| 9,925,510 B2 | 3/2018 | Jacobson et al. |
| 9,932,576 B2 | 4/2018 | Raymond et al. |
| 9,981,239 B2 | 5/2018 | Banyai et al. |
| 10,053,688 B2 | 8/2018 | Cox |
| 10,272,410 B2 | 4/2019 | Banyai |
| 2001/0018512 A1 | 8/2001 | Blanchard |
| 2001/0039014 A1 | 11/2001 | Bass et al. |
| 2001/0055761 A1 | 12/2001 | Kanemoto et al. |
| 2002/0012930 A1 | 1/2002 | Rothberg et al. |
| 2002/0025561 A1 | 2/2002 | Hodgson |
| 2002/0076716 A1 | 6/2002 | Sabanayagam et al. |
| 2002/0081582 A1 | 6/2002 | Gao et al. |
| 2002/0094533 A1 | 7/2002 | Hess et al. |
| 2002/0095073 A1 | 7/2002 | Jacobs et al. |
| 2002/0119459 A1 | 8/2002 | Griffiths et al. |
| 2002/0132308 A1 | 9/2002 | Liu et al. |
| 2002/0155439 A1 | 10/2002 | Rodriguez et al. |
| 2002/0160536 A1 | 10/2002 | Regnier et al. |
| 2002/0164824 A1 | 11/2002 | Xiao et al. |
| 2003/0008411 A1 | 1/2003 | Van et al. |
| 2003/0022207 A1 | 1/2003 | Balasubramanian et al. |
| 2003/0022317 A1 | 1/2003 | Jack et al. |
| 2003/0044781 A1 | 3/2003 | Korlach et al. |
| 2003/0058629 A1 | 3/2003 | Hirai et al. |
| 2003/0064398 A1 | 4/2003 | Barnes |
| 2003/0068633 A1 | 4/2003 | Belshaw et al. |
| 2003/0082719 A1 | 5/2003 | Schumacher et al. |
| 2003/0100102 A1 | 5/2003 | Rothberg et al. |
| 2003/0108903 A1 | 6/2003 | Wang et al. |
| 2003/0120035 A1 | 6/2003 | Gao et al. |
| 2003/0138782 A1 | 7/2003 | Evans |
| 2003/0143605 A1 | 7/2003 | Lok et al. |
| 2003/0148291 A1 | 8/2003 | Robotti |
| 2003/0148344 A1 | 8/2003 | Rothberg et al. |
| 2003/0171325 A1 | 9/2003 | Gascoyne et al. |
| 2003/0186226 A1 | 10/2003 | Brennan et al. |
| 2003/0228602 A1 | 12/2003 | Parker et al. |
| 2003/0228620 A1 | 12/2003 | Du |
| 2004/0043509 A1 | 3/2004 | Stahler et al. |
| 2004/0053362 A1 | 3/2004 | De Luca et al. |
| 2004/0086892 A1 | 5/2004 | Crothers et al. |
| 2004/0087008 A1 | 5/2004 | Schembri |
| 2004/0106130 A1 | 6/2004 | Besemer et al. |
| 2004/0106728 A1 | 6/2004 | McGall et al. |
| 2004/0110133 A1 | 6/2004 | Xu et al. |
| 2004/0175710 A1 | 9/2004 | Haushalter |
| 2004/0175734 A1 | 9/2004 | Stahler et al. |
| 2004/0191810 A1 | 9/2004 | Yamamoto |
| 2004/0219663 A1 | 11/2004 | Page et al. |
| 2004/0236027 A1 | 11/2004 | Maeji et al. |
| 2004/0248161 A1 | 12/2004 | Rothberg et al. |
| 2004/0259146 A1 | 12/2004 | Friend et al. |
| 2005/0022895 A1 | 2/2005 | Barth et al. |
| 2005/0049796 A1 | 3/2005 | Webb et al. |
| 2005/0053968 A1 | 3/2005 | Bharadwaj et al. |
| 2005/0079510 A1 | 4/2005 | Berka et al. |
| 2005/0100932 A1 | 5/2005 | Lapidus et al. |
| 2005/0112608 A1 | 5/2005 | Grossman et al. |
| 2005/0112636 A1 | 5/2005 | Hurt et al. |
| 2005/0112679 A1 | 5/2005 | Myerson et al. |
| 2005/0124022 A1 | 6/2005 | Srinivasan et al. |
| 2005/0137805 A1 | 6/2005 | Lewin et al. |
| 2005/0208513 A1 | 9/2005 | Agbo et al. |
| 2005/0227235 A1 | 10/2005 | Carr et al. |
| 2005/0255477 A1 | 11/2005 | Carr et al. |
| 2005/0266045 A1 | 12/2005 | Canham et al. |
| 2005/0277125 A1 | 12/2005 | Benn et al. |
| 2005/0282158 A1 | 12/2005 | Landegren |
| 2006/0003381 A1 | 1/2006 | Gilmore et al. |
| 2006/0012784 A1 | 1/2006 | Ulmer |
| 2006/0012793 A1 | 1/2006 | Harris |
| 2006/0019084 A1 | 1/2006 | Pearson |
| 2006/0024678 A1 | 2/2006 | Buzby |
| 2006/0024711 A1 | 2/2006 | Lapidus et al. |
| 2006/0024721 A1 | 2/2006 | Pedersen |
| 2006/0076482 A1 | 4/2006 | Hobbs et al. |
| 2006/0078909 A1 | 4/2006 | Srinivasan et al. |

(56) References Cited

U.S. PATENT DOCUMENTS

| | | |
|---|---|---|
| 2006/0078927 A1 | 4/2006 | Peck et al. |
| 2006/0078937 A1 | 4/2006 | Korlach et al. |
| 2006/0127920 A1 | 6/2006 | Church et al. |
| 2006/0134638 A1 | 6/2006 | Mulligan et al. |
| 2006/0160138 A1 | 7/2006 | Church |
| 2006/0171855 A1 | 8/2006 | Yin et al. |
| 2006/0202330 A1 | 9/2006 | Reinhardt et al. |
| 2006/0203236 A1 | 9/2006 | Ji et al. |
| 2006/0203237 A1 | 9/2006 | Ji et al. |
| 2006/0207923 A1 | 9/2006 | Li |
| 2006/0219637 A1 | 10/2006 | Killeen et al. |
| 2007/0031857 A1 | 2/2007 | Makarov et al. |
| 2007/0031877 A1 | 2/2007 | Stahler et al. |
| 2007/0043516 A1 | 2/2007 | Gustafsson et al. |
| 2007/0054127 A1 | 3/2007 | Hergenrother et al. |
| 2007/0059692 A1 | 3/2007 | Gao et al. |
| 2007/0087349 A1 | 4/2007 | Staehler et al. |
| 2007/0099208 A1 | 5/2007 | Drmanac et al. |
| 2007/0122817 A1 | 5/2007 | Church et al. |
| 2007/0141557 A1 | 6/2007 | Raab et al. |
| 2007/0196854 A1 | 8/2007 | Stahler et al. |
| 2007/0207482 A1 | 9/2007 | Church et al. |
| 2007/0207487 A1 | 9/2007 | Emig et al. |
| 2007/0231800 A1 | 10/2007 | Roberts et al. |
| 2007/0238104 A1 | 10/2007 | Barrett et al. |
| 2007/0238106 A1 | 10/2007 | Barrett et al. |
| 2007/0238108 A1 | 10/2007 | Barrett et al. |
| 2007/0259344 A1 | 11/2007 | Leproust et al. |
| 2007/0259345 A1 | 11/2007 | Sampas |
| 2007/0259346 A1 | 11/2007 | Gordon et al. |
| 2007/0259347 A1 | 11/2007 | Gordon et al. |
| 2007/0269870 A1 | 11/2007 | Church et al. |
| 2008/0085514 A1 | 4/2008 | Peck et al. |
| 2008/0087545 A1 | 4/2008 | Jensen et al. |
| 2008/0161200 A1 | 7/2008 | Yu et al. |
| 2008/0182296 A1 | 7/2008 | Chanda et al. |
| 2008/0214412 A1 | 9/2008 | Stahler et al. |
| 2008/0227160 A1 | 9/2008 | Kool |
| 2008/0233616 A1 | 9/2008 | Liss |
| 2008/0287320 A1 | 11/2008 | Baynes et al. |
| 2008/0308884 A1 | 12/2008 | Kalvesten |
| 2008/0311628 A1 | 12/2008 | Shoemaker |
| 2009/0036664 A1 | 2/2009 | Peter |
| 2009/0053704 A1 | 2/2009 | Novoradovskaya et al. |
| 2009/0062129 A1 | 3/2009 | McKernan et al. |
| 2009/0087840 A1 | 4/2009 | Baynes et al. |
| 2009/0088679 A1 | 4/2009 | Wood et al. |
| 2009/0105094 A1 | 4/2009 | Heiner et al. |
| 2009/0170802 A1 | 7/2009 | Stahler et al. |
| 2009/0176280 A1 | 7/2009 | Hutchison, III et al. |
| 2009/0181861 A1 | 7/2009 | Li et al. |
| 2009/0194483 A1 | 8/2009 | Robotti et al. |
| 2009/0230044 A1 | 9/2009 | Bek |
| 2009/0238722 A1 | 9/2009 | Mora-Fillat et al. |
| 2009/0239759 A1 | 9/2009 | Balch |
| 2009/0263802 A1 | 10/2009 | Drmanac |
| 2009/0285825 A1 | 11/2009 | Kini et al. |
| 2009/0324546 A1 | 12/2009 | Notka et al. |
| 2010/0004143 A1 | 1/2010 | Shibahara |
| 2010/0047805 A1 | 2/2010 | Wang |
| 2010/0051967 A1 | 3/2010 | Bradley et al. |
| 2010/0069250 A1 | 3/2010 | White, III et al. |
| 2010/0090341 A1 | 4/2010 | Wan et al. |
| 2010/0099103 A1 | 4/2010 | Hsieh et al. |
| 2010/0160463 A1 | 6/2010 | Wang et al. |
| 2010/0167950 A1 | 7/2010 | Juang et al. |
| 2010/0173364 A1 | 7/2010 | Evans, Jr. et al. |
| 2010/0216648 A1 | 8/2010 | Staehler et al. |
| 2010/0256017 A1 | 10/2010 | Larman et al. |
| 2010/0258487 A1 | 10/2010 | Zelechonok et al. |
| 2010/0286290 A1 | 11/2010 | Lohmann et al. |
| 2010/0292102 A1 | 11/2010 | Nouri |
| 2010/0300882 A1 | 12/2010 | Zhang et al. |
| 2011/0009607 A1 | 1/2011 | Komiyama et al. |
| 2011/0082055 A1 | 4/2011 | Fox et al. |
| 2011/0114244 A1 | 5/2011 | Yoo et al. |
| 2011/0114549 A1 | 5/2011 | Yin et al. |
| 2011/0124049 A1 | 5/2011 | Li et al. |
| 2011/0124055 A1 | 5/2011 | Carr et al. |
| 2011/0126929 A1 | 6/2011 | Velasquez-Garcia et al. |
| 2011/0171651 A1 | 7/2011 | Richmond |
| 2011/0172127 A1 | 7/2011 | Jacobson et al. |
| 2011/0201057 A1 | 8/2011 | Carr et al. |
| 2011/0217738 A1 | 9/2011 | Jacobson |
| 2011/0230653 A1 | 9/2011 | Novoradovskaya et al. |
| 2011/0254107 A1 | 10/2011 | Bulovic et al. |
| 2011/0287435 A1 | 11/2011 | Grunenwald et al. |
| 2012/0003713 A1 | 1/2012 | Hansen et al. |
| 2012/0021932 A1 | 1/2012 | Mershin et al. |
| 2012/0027786 A1 | 2/2012 | Gupta et al. |
| 2012/0028843 A1 | 2/2012 | Ramu et al. |
| 2012/0032366 A1 | 2/2012 | Ivniski et al. |
| 2012/0046175 A1 | 2/2012 | Rodesch et al. |
| 2012/0050411 A1 | 3/2012 | Mabritto et al. |
| 2012/0094847 A1 | 4/2012 | Warthmann et al. |
| 2012/0129704 A1 | 5/2012 | Gunderson et al. |
| 2012/0149602 A1 | 6/2012 | Friend et al. |
| 2012/0164127 A1 | 6/2012 | Short et al. |
| 2012/0164633 A1 | 6/2012 | Laffler |
| 2012/0164691 A1 | 6/2012 | Eshoo et al. |
| 2012/0184724 A1 | 7/2012 | Sierzchala et al. |
| 2012/0220497 A1 | 8/2012 | Jacobson et al. |
| 2012/0231968 A1 | 9/2012 | Bruhn et al. |
| 2012/0238737 A1 | 9/2012 | Dellinger et al. |
| 2012/0258487 A1 | 10/2012 | Chang et al. |
| 2012/0264653 A1 | 10/2012 | Carr et al. |
| 2012/0270750 A1 | 10/2012 | Oleinikov |
| 2012/0270754 A1 | 10/2012 | Blake |
| 2012/0283140 A1 | 11/2012 | Chu |
| 2012/0288476 A1 | 11/2012 | Hartmann et al. |
| 2012/0289691 A1 | 11/2012 | Dellinger et al. |
| 2012/0315670 A1 | 12/2012 | Jacobson et al. |
| 2012/0322681 A1 | 12/2012 | Kung et al. |
| 2013/0005585 A1 | 1/2013 | Anderson et al. |
| 2013/0005612 A1 | 1/2013 | Carr et al. |
| 2013/0017642 A1 | 1/2013 | Milgrew et al. |
| 2013/0017977 A1 | 1/2013 | Oleinikov |
| 2013/0017978 A1 | 1/2013 | Kavanagh et al. |
| 2013/0035261 A1 | 2/2013 | Sierzchala et al. |
| 2013/0040836 A1 | 2/2013 | Himmler et al. |
| 2013/0045483 A1 | 2/2013 | Treusch et al. |
| 2013/0053252 A1 | 2/2013 | Xie et al. |
| 2013/0059296 A1 | 3/2013 | Jacobson et al. |
| 2013/0059761 A1 | 3/2013 | Jacobson et al. |
| 2013/0065017 A1 | 3/2013 | Sieber |
| 2013/0109595 A1 | 5/2013 | Routenberg |
| 2013/0109596 A1 | 5/2013 | Peterson et al. |
| 2013/0123129 A1 | 5/2013 | Zeiner et al. |
| 2013/0130321 A1 | 5/2013 | Staehler et al. |
| 2013/0137161 A1 | 5/2013 | Zhang et al. |
| 2013/0137173 A1 | 5/2013 | Zhang et al. |
| 2013/0137174 A1 | 5/2013 | Zhang et al. |
| 2013/0137861 A1 | 5/2013 | Leproust et al. |
| 2013/0164308 A1 | 6/2013 | Foletti et al. |
| 2013/0225421 A1 | 8/2013 | Li et al. |
| 2013/0244884 A1 | 9/2013 | Jacobson et al. |
| 2013/0252849 A1 | 9/2013 | Hudson et al. |
| 2013/0261027 A1 | 10/2013 | Li et al. |
| 2013/0281308 A1 | 10/2013 | Kung et al. |
| 2013/0296192 A1 | 11/2013 | Jacobson et al. |
| 2013/0296194 A1 | 11/2013 | Jacobson et al. |
| 2013/0298265 A1 | 11/2013 | Cunnac et al. |
| 2013/0309725 A1 | 11/2013 | Jacobson et al. |
| 2013/0323725 A1 | 12/2013 | Peter et al. |
| 2013/0330778 A1 | 12/2013 | Zeiner et al. |
| 2014/0011226 A1 | 1/2014 | Bernick et al. |
| 2014/0018441 A1 | 1/2014 | Fracchia et al. |
| 2014/0031240 A1 | 1/2014 | Behlke et al. |
| 2014/0038240 A1 | 2/2014 | Temme et al. |
| 2014/0106394 A1 | 4/2014 | Ko et al. |
| 2014/0141982 A1 | 5/2014 | Jacobson et al. |
| 2014/0170665 A1 | 6/2014 | Hiddessen et al. |
| 2014/0178992 A1 | 6/2014 | Nakashima et al. |
| 2014/0274729 A1 | 9/2014 | Kurn et al. |

(56) References Cited

U.S. PATENT DOCUMENTS

| | | |
|---|---|---|
| 2014/0274741 A1 | 9/2014 | Hunter et al. |
| 2014/0303000 A1 | 10/2014 | Armour et al. |
| 2014/0309119 A1 | 10/2014 | Jacobson et al. |
| 2014/0309142 A1 | 10/2014 | Tian |
| 2015/0010953 A1 | 1/2015 | Lindstrom et al. |
| 2015/0012723 A1 | 1/2015 | Park et al. |
| 2015/0031089 A1 | 1/2015 | Lindstrom |
| 2015/0038373 A1 | 2/2015 | Banyai et al. |
| 2015/0056609 A1 | 2/2015 | Daum et al. |
| 2015/0057625 A1 | 2/2015 | Coulthard |
| 2015/0065357 A1 | 3/2015 | Fox |
| 2015/0065393 A1 | 3/2015 | Jacobson |
| 2015/0099870 A1 | 4/2015 | Bennett et al. |
| 2015/0120265 A1 | 4/2015 | Amirav-Drory |
| 2015/0159152 A1 | 6/2015 | Allen et al. |
| 2015/0183853 A1 | 7/2015 | Sharma et al. |
| 2015/0191719 A1 | 7/2015 | Hudson et al. |
| 2015/0196917 A1 | 7/2015 | Kay et al. |
| 2015/0203839 A1 | 7/2015 | Jacobson et al. |
| 2015/0211047 A1 | 7/2015 | Borns |
| 2015/0225782 A1 | 8/2015 | Walder et al. |
| 2015/0240232 A1 | 8/2015 | Zamore et al. |
| 2015/0240280 A1 | 8/2015 | Gibson et al. |
| 2015/0261664 A1 | 9/2015 | Goldman et al. |
| 2015/0269313 A1 | 9/2015 | Church |
| 2015/0293102 A1 | 10/2015 | Shim |
| 2015/0307875 A1 | 10/2015 | Happe et al. |
| 2015/0321191 A1 | 11/2015 | Kendall et al. |
| 2015/0322504 A1 | 11/2015 | Lao et al. |
| 2015/0344927 A1 | 12/2015 | Sampson et al. |
| 2015/0353921 A9 | 12/2015 | Tian |
| 2015/0353994 A1 | 12/2015 | Myers et al. |
| 2015/0361420 A1 | 12/2015 | Hudson et al. |
| 2015/0361422 A1 | 12/2015 | Sampson et al. |
| 2015/0361423 A1 | 12/2015 | Sampson et al. |
| 2015/0368687 A1 | 12/2015 | Saaem et al. |
| 2015/0376602 A1 | 12/2015 | Jacobson et al. |
| 2016/0001247 A1 | 1/2016 | Oleinikov |
| 2016/0002621 A1 | 1/2016 | Nelson et al. |
| 2016/0002622 A1 | 1/2016 | Nelson et al. |
| 2016/0010045 A1 | 1/2016 | Cohen et al. |
| 2016/0017394 A1 | 1/2016 | Liang et al. |
| 2016/0017425 A1 | 1/2016 | Ruvolo et al. |
| 2016/0019341 A1 | 1/2016 | Harris et al. |
| 2016/0024138 A1 | 1/2016 | Gebeyehu et al. |
| 2016/0024576 A1 | 1/2016 | Chee et al. |
| 2016/0026753 A1 | 1/2016 | Krishnaswami et al. |
| 2016/0026758 A1 | 1/2016 | Jabara et al. |
| 2016/0032396 A1 | 2/2016 | Diehn et al. |
| 2016/0046973 A1 | 2/2016 | Efcavitch et al. |
| 2016/0046974 A1 | 2/2016 | Efcavitch et al. |
| 2016/0082472 A1 | 3/2016 | Perego et al. |
| 2016/0089651 A1 | 3/2016 | Banyai |
| 2016/0090592 A1 | 3/2016 | Banyai et al. |
| 2016/0096160 A1 | 4/2016 | Banyai et al. |
| 2016/0097051 A1 | 4/2016 | Jacobson et al. |
| 2016/0102322 A1 | 4/2016 | Ravinder et al. |
| 2016/0108466 A1 | 4/2016 | Nazarenko et al. |
| 2016/0122755 A1 | 5/2016 | Hall et al. |
| 2016/0122800 A1 | 5/2016 | Bernick et al. |
| 2016/0152972 A1 | 6/2016 | Stapleton et al. |
| 2016/0168611 A1 | 6/2016 | Efcavitch et al. |
| 2016/0184788 A1 | 6/2016 | Hall et al. |
| 2016/0200759 A1 | 7/2016 | Srivastava et al. |
| 2016/0215283 A1 | 7/2016 | Braman et al. |
| 2016/0229884 A1 | 8/2016 | Indermuhle et al. |
| 2016/0230175 A1 | 8/2016 | Carstens |
| 2016/0230221 A1 | 8/2016 | Bergmann et al. |
| 2016/0251651 A1 | 9/2016 | Banyai |
| 2016/0256846 A1 | 9/2016 | Smith et al. |
| 2016/0264958 A1 | 9/2016 | Toro et al. |
| 2016/0289758 A1 | 10/2016 | Akeson et al. |
| 2016/0289839 A1 | 10/2016 | Harumoto et al. |
| 2016/0303535 A1 | 10/2016 | Banyai et al. |
| 2016/0304862 A1 | 10/2016 | Igawa et al. |
| 2016/0304946 A1 | 10/2016 | Betts et al. |
| 2016/0310426 A1 | 10/2016 | Wu |
| 2016/0310927 A1 | 10/2016 | Banyai et al. |
| 2016/0333340 A1 | 11/2016 | Wu |
| 2016/0339409 A1 | 11/2016 | Banyai |
| 2016/0340672 A1 | 11/2016 | Banyai et al. |
| 2016/0348098 A1 | 12/2016 | Stuelpnagel et al. |
| 2016/0354752 A1 | 12/2016 | Banyai et al. |
| 2016/0355880 A1 | 12/2016 | Gormley et al. |
| 2017/0017436 A1 | 1/2017 | Church |
| 2017/0066844 A1 | 3/2017 | Glanville |
| 2017/0067099 A1 | 3/2017 | Zheng et al. |
| 2017/0073731 A1 | 3/2017 | Zheng et al. |
| 2017/0081660 A1 | 3/2017 | Cox |
| 2017/0081716 A1 | 3/2017 | Peck |
| 2017/0088887 A1 | 3/2017 | Makarov et al. |
| 2017/0095785 A1 | 4/2017 | Banyai |
| 2017/0096706 A1 | 4/2017 | Behlke et al. |
| 2017/0114404 A1 | 4/2017 | Behlke et al. |
| 2017/0141793 A1 | 5/2017 | Strauss et al. |
| 2017/0147748 A1 | 5/2017 | Staehler et al. |
| 2017/0151546 A1 | 6/2017 | Peck et al. |
| 2017/0159044 A1 | 6/2017 | Toro et al. |
| 2017/0175110 A1 | 6/2017 | Jacobson et al. |
| 2017/0218537 A1 | 8/2017 | Olivares |
| 2017/0233764 A1 | 8/2017 | Young et al. |
| 2017/0249345 A1 | 8/2017 | Malik et al. |
| 2017/0253644 A1 | 9/2017 | Steyaert et al. |
| 2017/0320061 A1 | 11/2017 | Venter et al. |
| 2017/0327819 A1 | 11/2017 | Banyai |
| 2017/0355984 A1 | 12/2017 | Evans et al. |
| 2017/0357752 A1 | 12/2017 | Diggans |
| 2017/0362589 A1 | 12/2017 | Banyai |
| 2018/0029001 A1 | 2/2018 | Banyai |
| 2018/0051278 A1 | 2/2018 | Cox et al. |
| 2018/0051280 A1 | 2/2018 | Gibson et al. |
| 2018/0068060 A1 | 3/2018 | Ceze et al. |
| 2018/0101487 A1 | 4/2018 | Peck |
| 2018/0104664 A1 | 4/2018 | Fernandez |
| 2018/0126355 A1 | 5/2018 | Peck |
| 2018/0142289 A1 | 5/2018 | Zeitoun |
| 2018/0171509 A1 | 6/2018 | Cox |
| 2018/0236425 A1 | 8/2018 | Banyai et al. |
| 2018/0253563 A1 | 9/2018 | Peck et al. |
| 2018/0273936 A1 | 9/2018 | Cox et al. |
| 2018/0282721 A1 | 10/2018 | Cox et al. |
| 2018/0326388 A1 | 11/2018 | Banyai et al. |
| 2018/0355351 A1 | 12/2018 | Nugent et al. |
| 2019/0060345 A1 | 2/2019 | Harrison et al. |
| 2019/0118154 A1 | 4/2019 | Marsh et al. |
| 2019/0240636 A1 | 8/2019 | Peck et al. |

FOREIGN PATENT DOCUMENTS

| | | |
|---|---|---|
| CN | 1771336 A | 5/2006 |
| CN | 102159726 A | 8/2011 |
| CN | 103907117 A | 7/2014 |
| CN | 104734848 A | 6/2015 |
| DE | 10260805 A1 | 7/2004 |
| EP | 0090789 A1 | 10/1983 |
| EP | 0126621 B1 | 8/1990 |
| EP | 0753057 A1 | 1/1997 |
| EP | 1314783 A1 | 5/2003 |
| EP | 1363125 A2 | 11/2003 |
| EP | 1546387 A2 | 6/2005 |
| EP | 1153127 B1 | 7/2006 |
| EP | 1728860 A1 | 12/2006 |
| EP | 1072010 B1 | 4/2010 |
| EP | 2175021 A2 | 4/2010 |
| EP | 2330216 A1 | 6/2011 |
| EP | 1343802 B1 | 5/2012 |
| EP | 2504449 A1 | 10/2012 |
| EP | 2751729 A1 | 7/2014 |
| EP | 2872629 A1 | 5/2015 |
| EP | 2928500 A1 | 10/2015 |
| EP | 2971034 A1 | 1/2016 |
| EP | 3030682 A2 | 6/2016 |
| EP | 3044228 A4 | 4/2017 |
| EP | 2994509 B1 | 6/2017 |

(56) References Cited

FOREIGN PATENT DOCUMENTS

| | | |
|---|---|---|
| EP | 3204518 A1 | 8/2017 |
| JP | 2002536977 A | 11/2002 |
| JP | 2002538790 A | 11/2002 |
| JP | 2006503586 A | 2/2006 |
| JP | 2009294195 A | 12/2009 |
| WO | WO-9015070 A1 | 12/1990 |
| WO | WO-9210092 A1 | 6/1992 |
| WO | WO-9210588 A1 | 6/1992 |
| WO | WO-9309668 A1 | 5/1993 |
| WO | WO-9525116 A1 | 9/1995 |
| WO | WO-9526397 A1 | 10/1995 |
| WO | WO-9615861 A1 | 5/1996 |
| WO | WO-9710365 A1 | 3/1997 |
| WO | WO-9822541 A2 | 5/1998 |
| WO | WO-9841531 A2 | 9/1998 |
| WO | WO-9942813 A1 | 8/1999 |
| WO | WO-0013017 A2 | 3/2000 |
| WO | WO-0018957 A1 | 4/2000 |
| WO | WO-0042559 A1 | 7/2000 |
| WO | WO-0042560 A2 | 7/2000 |
| WO | WO-0042561 A2 | 7/2000 |
| WO | WO-0049142 A1 | 8/2000 |
| WO | WO-0156216 A2 | 8/2001 |
| WO | WO-0210443 A1 | 2/2002 |
| WO | WO-0156216 A3 | 3/2002 |
| WO | WO-0220537 A2 | 3/2002 |
| WO | WO-0224597 A2 | 3/2002 |
| WO | WO-0227638 A1 | 4/2002 |
| WO | WO-0233669 A1 | 4/2002 |
| WO | WO-02072791 A2 | 9/2002 |
| WO | WO-03040410 A1 | 5/2003 |
| WO | WO-03046223 A1 | 6/2003 |
| WO | WO-03054232 A2 | 7/2003 |
| WO | WO-03064026 A1 | 8/2003 |
| WO | WO-03064027 A2 | 8/2003 |
| WO | WO-03064699 A2 | 8/2003 |
| WO | WO-03065038 A2 | 8/2003 |
| WO | WO-03066212 A2 | 8/2003 |
| WO | WO-03089605 A2 | 10/2003 |
| WO | WO-03100012 A2 | 12/2003 |
| WO | WO-2004024886 A2 | 3/2004 |
| WO | WO-2004029220 A2 | 4/2004 |
| WO | WO-2004029586 A1 | 4/2004 |
| WO | WO-2004031351 A2 | 4/2004 |
| WO | WO-2004031399 A2 | 4/2004 |
| WO | WO-2004059556 A2 | 7/2004 |
| WO | WO-2005014850 A2 | 2/2005 |
| WO | WO-2005051970 A2 | 6/2005 |
| WO | WO-2005059096 A2 | 6/2005 |
| WO | WO-2005059097 A2 | 6/2005 |
| WO | WO-2006023144 | 3/2006 |
| WO | WO-2006076679 A1 | 7/2006 |
| WO | WO-2006116476 A1 | 11/2006 |
| WO | WO-2007120627 A2 | 10/2007 |
| WO | WO-2007137242 A2 | 11/2007 |
| WO | WO-2008006078 A2 | 1/2008 |
| WO | WO-2008027558 A2 | 3/2008 |
| WO | WO-2008045380 | 4/2008 |
| WO | WO-2008054543 A2 | 5/2008 |
| WO | WO-2008063134 A1 | 5/2008 |
| WO | WO-2008063135 A1 | 5/2008 |
| WO | WO-2008109176 A2 | 9/2008 |
| WO | WO-2010025310 A2 | 3/2010 |
| WO | WO-2010025566 A1 | 3/2010 |
| WO | WO-2010027512 A2 | 3/2010 |
| WO | WO-2010089412 A1 | 8/2010 |
| WO | WO-2010141433 A2 | 12/2010 |
| WO | WO-2010141433 A3 | 4/2011 |
| WO | WO-2011053957 A2 | 5/2011 |
| WO | WO-2011056872 A2 | 5/2011 |
| WO | WO-2011066185 A1 | 6/2011 |
| WO | WO-2011066186 A1 | 6/2011 |
| WO | WO-2011085075 A2 | 7/2011 |
| WO | WO-2011103468 A2 | 8/2011 |
| WO | WO-2011109031 A1 | 9/2011 |
| WO | WO-2011143556 A1 | 11/2011 |
| WO | WO-2011150168 A1 | 12/2011 |
| WO | WO-2011161413 A2 | 12/2011 |
| WO | WO-2012013913 A1 | 2/2012 |
| WO | WO-2012061832 A1 | 5/2012 |
| WO | WO-2012078312 A2 | 6/2012 |
| WO | WO-2012149171 A1 | 11/2012 |
| WO | WO-2012154201 A1 | 11/2012 |
| WO | WO-2013030827 A1 | 3/2013 |
| WO | WO-2013032850 A2 | 3/2013 |
| WO | WO-2013036668 A1 | 3/2013 |
| WO | WO-2013101896 A1 | 7/2013 |
| WO | WO-2013177220 A1 | 11/2013 |
| WO | WO-2014004393 A1 | 1/2014 |
| WO | WO-2014008447 A1 | 1/2014 |
| WO | WO-2014035693 A2 | 3/2014 |
| WO | WO-2014088693 A1 | 6/2014 |
| WO | WO-2014089160 A1 | 6/2014 |
| WO | WO-2014093330 A1 | 6/2014 |
| WO | WO-2014093694 A1 | 6/2014 |
| WO | WO-2014151696 A1 | 9/2014 |
| WO | WO-2014160004 A1 | 10/2014 |
| WO | WO-2014160059 A1 | 10/2014 |
| WO | WO-2015017527 A2 | 2/2015 |
| WO | WO-2015021080 A2 | 2/2015 |
| WO | WO-2015021280 A1 | 2/2015 |
| WO | WO-2015040075 A1 | 3/2015 |
| WO | WO-2015054292 A1 | 4/2015 |
| WO | WO-2015081114 A2 | 6/2015 |
| WO | WO-2015081142 A1 | 6/2015 |
| WO | WO-2015090879 A1 | 6/2015 |
| WO | WO-2015120403 A1 | 8/2015 |
| WO | WO-2015160004 A1 | 10/2015 |
| WO | WO-2015175832 A1 | 11/2015 |
| WO | WO-2016007604 A1 | 1/2016 |
| WO | WO-2016011080 A2 | 1/2016 |
| WO | WO-2016022557 A1 | 2/2016 |
| WO | WO-2016053883 A1 | 4/2016 |
| WO | WO-2016055956 A1 | 4/2016 |
| WO | WO-2016065056 A1 | 4/2016 |
| WO | WO-2016126882 A1 | 8/2016 |
| WO | WO-2016126987 A1 | 8/2016 |
| WO | WO-2016130868 A2 | 8/2016 |
| WO | WO-2016161244 A2 | 10/2016 |
| WO | WO-2016172377 A1 | 10/2016 |
| WO | WO-2016173719 A1 | 11/2016 |
| WO | WO-2016183100 A1 | 11/2016 |
| WO | WO-2017049231 A1 | 3/2017 |
| WO | WO-2017053450 A1 | 3/2017 |
| WO | WO-2017059399 A1 | 4/2017 |
| WO | WO-2017095958 A1 | 6/2017 |
| WO | WO-2017118761 A1 | 7/2017 |
| WO | WO-2017158103 A1 | 9/2017 |
| WO | WO-2017214574 A1 | 12/2017 |
| WO | WO-2018026920 A1 | 2/2018 |
| WO | WO-2018038772 A1 | 3/2018 |
| WO | WO-2018057526 A2 | 3/2018 |
| WO | WO-2018094263 A1 | 5/2018 |
| WO | WO-2018112426 A1 | 6/2018 |
| WO | WO-2018156792 A1 | 8/2018 |
| WO | WO-2018170164 A1 | 9/2018 |

OTHER PUBLICATIONS

Mitra et al (Nucleic Acids Research, vol. 27, No. 24, pages (Year: 1999).*
Cleary et al (Nature Methods, vol. 1, No. 3, (Year: 2004).*
Galka et al.: QuickLib, a method for building fully synthetic plasmid libraries by seamless cloning of degenerate oligonucleotides. PLOS ONE, 12, e0175146:1-9 (2017).
Galka et al.: QuickLib, a method for building fully synthetic plasmid libraries by seamless cloning of degenerate oligonucleotides. PLOS ONE, 12, e0175146:S1 figure (2017).
Galka et al.: QuickLib, a method for building fully synthetic plasmid libraries by seamless cloning of degenerate oligonucleotides. PLOS ONE, 12, e0175146:S1 Table (2017).

(56) References Cited

OTHER PUBLICATIONS

Galka et al.: QuickLib, a method for building fully synthetic plasmid libraries by seamless cloning of degenerate oligonucleotides. PLOS ONE, 12, e0175146:S2 figure (2017).
International Application No. PCT/US2018/019268 International Preliminary Report on Patentability dated Sep. 6, 2019.
International Application No. PCT/US2019/032992 International Search Report and Written Opinion dated Oct. 28, 2019.
International Application No. PCT/US2019/032992 Invitation to Pay Additional Fees dated Sep. 6, 2019.
Pierce and Wangh, Linear-after-the-exponential polymerase chain reaction and allied technologies Real-time detection strategies for rapid, reliable diagnosis from single cells Methods Mol. Med. 132:65-85 (2007) (Abstract only).
U.S. Appl. No. 15/015,059 Final Office Action dated Jul. 17, 2019.
U.S. Appl. No. 15/015,059 Office Action dated Aug. 19, 2019.
U.S. Appl. No. 15/151,316 Office Action dated Oct. 4, 2019.
U.S. Appl. No. 15/187,714 Final Office Action dated Sep. 17, 2019.
U.S. Appl. No. 15/268,422 Final Office Action dated Oct. 3, 2019.
U.S. Appl. No. 15/603,013 Final Office Action dated Nov. 6, 2019.
U.S. Appl. No. 15/619,322 Office Action dated Aug. 14, 2019.
U.S. Appl. No. 15/816,995 Office Action dated Sep. 20, 2019.
U.S. Appl. No. 15/835,243 Restriction Requirement dated Sep. 10, 2019.
U.S. Appl. No. 15/921,479 Office Action dated Nov. 12, 2019.
U.S. Appl. No. 15/960,319 Office Action dated Aug. 16, 2019.
U.S. Appl. No. 16/006,581 Office Action dated Sep. 25, 2019.
U.S. Appl. No. 16/239,453 Office Action dated Nov. 7, 2019.
U.S. Appl. No. 16/530,717 Office Action dated Sep. 6, 2019.
Abudayyeh et al., C2c2 is a single-component programmable RNA-guided RNA-targeting CRISPR effector. Science, available on line, Jun. 13, 2016, at: http://zlab.mit.edu/assets/reprints/Abudayyeh_OO_Science_2016.pdf , 17 pages.
Acevedo-Rocha et al. Directed evolution of stereoselective enzymes based on genetic selection as opposed to screening systems. J. Biotechnol. 191:3-10 (2014).
Adessi, et al. Solid phase DNA amplification: characterisation of primer attachment and amplification mechanisms. Nucleic Acids Res. 28(20):E87, 2000.
Alexeyev, Mikhail F. et al., "Gene synthesis, bacterial expression and purification of the Rickettsia prowazekii ATP/ADP translocase", Biochimica et Biophysics Acta, 1419:299-306, 1999.
Al-Housseiny et al., Control of interfacial instabilities using flow geometry Nature Physics, 8:747-750, 2012.
Amblard, Francois et al., "A magnetic manipulator for studying local rheology and micromechanical properties of biological systems", Rev. Sci. Instrum., 67(3):18-827, 1996.
Andoni and Indyk, Near-Optimal Hashing Algorithms for Approximate Nearest Neighbor in High Dimensions, Communications of the ACM, 51(1):117-122, 2008.
Arand et al. Structure of Rhodococcus erythropolis limonene-1,2-epoxide hydrolase reveals a novel active site. EMBO J. 22:2583-2592 (2003).
Arkles, et al. The Role of Polarity in the Structure of Silanes Employed in Surface Modification. Silanes and Other Coupling Agents. 5:51-64, 2009.
Arkles, Hydrophobicity, Hydrophilicity Reprinted with permission from the Oct. 2006 issue of Paint & Coatings Industry magazine, Retrieved on Mar. 19, 2016, 10 pages.
Assembly manual for the POSaM: The ISB Piezoelelctric Oligonucleotide Synthesizer and Microarrayer, The Institute for Systems Biology, May 28, 2004 (50 pages).
Assi et al. Massive-parallel adhesion and reactivity- measurements using simple and inexpensive magnetic tweezers. J. Appl. Phys. 92(9):5584-5586 (2002).
ATDBio, "Nucleic Acid Structure," Nucleic Acids Book, 9 pages, published on Jan. 22, 2005. from: http://www.atdbio.com/content/5/Nucleic-acid-structure.

ATDBio, "Solid-Phase Oligonucleotide Synthesis," Nucleic Acids Book, 20 pages, Published on Jul. 31, 2011. from: http://www.atdbio.com/content/17/Solid-phase-oligonucleotide-synthesis.
Au et al. Gene synthesis by a LCR-based approach: high level production of Leptin-L54 using synthetic gene in *Escherichia coli*. Biochemical and Biophysical Research Communications 248:200-203 (1998).
Baedeker, Mathias et al., Overexpression of a designed 2.2kb gene of eukaryotic phenylalanine ammonialyase in *Escherichia coli*. Febs Letters, 457:57-60, 1999.
Barbee, et al. Magnetic Assembly of High-Density DNA Arrays for Genomic Analyses. Anal Chem. 80(6):2149-2154, 2008.
Barton et al., A desk electrohydrodynamic jet printing system. Mechatronics, 20:611-616, 2010.
Beaucage, et al. Advances in the synthesis of oligonucleotides by the phosphoramidite approach. Tetrahedron. 48:2223-2311, 1992.
Beaucage, et al. Deoxynucleoside phosphoramidites—A new class of key intermediates for deoxypolynucleotide synthesis. Tetrahedron Lett. 22(20):1859-1862, 1981.
Beaucage, Serge L. et al., "The Chemical synthesis of DNA/RNA" Chapter 2 in: Encyclopedia of Cell Biology, 1:36-53, 2016.
Beaulieu, Martin et al., "PCR candidate region mismatch scanning adaptation to quantitative, high-throughput genotyping", Nucleic Acids Research, 29(5):1114-1124, 2001.
Beigelman, et al. Base-modified phosphoramidite analogs of pyrimidine ribonucleosides for RNA structure-activity studies. Methods Enzymol. 317:39-65, 2000.
Bethge et al., "Reverse synthesis and 3'-modification of RNA." Jan. 1, 2011, pp. 64-64, XP055353420. Retrieved from the Internet: URL:http://www.is3na.org/assets/events/Category%202-Medicinal%20Chemistry%20of%2001igonucleotides%20%2864-108%29.pdf .
Binkowski et al., Correcting errors in synthetic DNA through consensus shuffling. Nucleic Acids Research, 33(6):e55, 8 pages, 2005.
Biswas, Indranil et al., "Identification and characterization of a thermostable MutS homolog from Thennus aquaticus", The Journal of Biological Chemistry, 271(9):5040-5048, 1996.
Biswas, Indranil et al., "Interaction of MutS protein with the major and minor grooves of a heteroduplex DNA", The Journal of Biological Chemistry, 272(20):13355-13364, 1997.
Bjornson, Keith P. et al., "Differential and simultaneous adenosine Di- and Triphosphate binding by MutS", The Journal of Biological Chemistry, 278(20):18557-18562, 2003.
Blanchard, et al., "High-Density Oligonucleotide Arrays," Biosensors & Bioelectronics, 11(6/7):687-690, 1996.
Blanchard, in: Genetic Engineering, Principles and Methods, vol. 20, Ed. J. Sedlow, New York: Plenum Press, p. 111-124, 1979.
Blawat et al., Forward error correction for DNA data storage. Procedia Computer Science, 80:1011-1022, 2016.
Bonini and Mondino, Adoptive T-cell therapy for cancer: The era of engineered T cells. European Journal of Immunology, 45:2457-2469, 2015.
Bornholt et al., A DNA-Based Archival Storage System, in International Conference on Architectural Support for Programming Languages and Operating Systems (ASPLOS), Apr. 2-6, 2016, Atlanta, GA, 2016, 637-649.
Borovkov et al., High-quality gene assembly directly from unpurified mixtures of microassay-synthesized oligonucleotides. Nucleic Acid Research, 38(19):e180, 10 pages, 2010.
Brunet, Aims and methods of biosteganography. Journal of Biotechnology, 226:56-64, 2016.
Buermans et al., "Next Generation sequencing technology: Advances and applications," Biochimica et Biophysica Acta (BBA)—Molecular Basis of Disease, 1842:1931-1941, 2014.
Butler, et al. In situ synthesis of oligonucleotide arrays by using surface tension. J Am Chem Soc. 123(37):8887-94, 2001.
Calvert, Lithographically patterned self-assembled films. In: Organic Thin Films and Surfaces: Directions for The Nineties, vol. 20, p. 109, ed. By Abraham Ulman, San Diego: Academic Press, 1995.
Cardelli, Two-Domain DNA Strand Displacement, Electron. Proc. Theor. Comput. Sci., 26:47-61, 2010.

(56) References Cited

OTHER PUBLICATIONS

Carlson, "Time for New DNA Synthesis and Sequencing Cost Curves," 2014. [Online]. Available: http://www.synthesis.cc/synthesis/2014/02/time_for_new_cost_curves_2014. 10 pages.
Carr, et al. Protein-mediated error correction for de novo DNA synthesis. Nucleic Acids Res. 32(20):e162, 9 pages, 2004.
Carter and Friedman, DNA synthesis and Biosecurity: Lessons learned and options for the future. J. Craig Venter Institute, La Jolla, CA, 28 pages, Oct. 2015.
Caruthers, Chemical synthesis of deoxyoligonucleotides by the phosphoramidite method. In Methods in Enzymology, Chapter 15, 154:287-313, 1987.
Caruthers. Gene synthesis machines: DNA chemistry and its uses. Science 230(4723):281-285 (1985).
Caruthers, The Chemical Synthesis of DNA/RNA: Our Gift to Science. J. Biol. Chem., 288(2):1420-1427, 2013.
Casmiro, Danilo R. et al., "PCR-based gene synthesis and protein NMR spectroscopy", Structure, 5(11):1407-1412, 1997.
CeGaT. Tech Note available at https://www.cegat.de/web/wp-content/uploads/2018/06/Twist-Exome-Tech-Note.pdf (4 pgs.) (2018).
Cello, et al. Chemical synthesis of poliovirus cDNA: generation of infectious virus in the absence of natural template. Science. 297(5583):1016-8, 2000.
Chalmers, et al. Scaling up the ligase chain reaction-based approach to gene synthesis. Biotechniques. 30(2):249-52, 2001.
Chan, et al. Natural and engineered nicking endonucleases—from cleavage mechanism to engineering of strand-specificity. Nucleic Acids Res. 39(1):1-18, 2011.
Chen, et al. Chemical modification of gene silencing oligonucleotides for drug discovery and development. Drug Discov Today. 10(8):587-93 2005.
Chen et al., Programmable chemical controllers made from DNA, Nat. Nanotechnol., 8(10):755-762, 2013.
Cheng, et al. High throughput parallel synthesis of oligonucleotides with 1536 channel synthesizer. Nucleic Acids Res. 30(18):e93, 2002.
Chilamakuri et al. Performance comparison of four exome capture systems for deep sequencing. BMC Genomics 15(1):449 (2014).
Cho, et al. Capillary passive valve in microfluidic systems. NSTI—Nanotech. 2004; 1:263-266.
Chrisey et al., Fabrication of patterned DNA surfaces Nucleic Acids Research, 24(15):3040-3047 (1996).
Chung et al., One-step preparation of competent*Escherichia coli*:Transformation and storage of bacterial cells in the same solution. Proc Natl Acad Sci U S A. Apr. 1989;86(7):2172-2175.
Church et al., Next-generation digital information storage in DNA. Science, 337:6102, 1628-1629, 2012.
Cleary et al. Production of complex nucleic acid libraries using highly parallel in situ oligonucleotide synthesis. Nature Methods, 1(13):241-248, 2004.
Cohen et al., Human population: The next half century. Science, 302:1172-1175, 2003.
Crick. On protein synthesis. Symp Soc Exp Biol12:138-163,1958.
Cruse et al. Atlas of Immunology, Third Edition. Boca Raton:CRC Press (pp. 282-283) (2010).
Cutler, David J. et al., "High-throughput variation detection and genotyping using microarrays", Genome Research, vol. 11, 1913-19 (2001).
Dahl, et al. Circle-to-circle amplification for precise and sensitive DNA analysis. Proc Natl Acad Sci USA. Mar. 30, 2004;101(13):4548-53. Epub Mar. 15, 2004.
De Mesmaeker, et al. Backbone modifications in oligonucleotides and peptide nucleic acid systems. Curr Opin Struct Biol. Jun. 1995;5(3):343-55.
De Silva et al. New Trends of Digital Data Storage in DNA. BioMed Res Int. 2016:8072463 (2016).
Deamer, David W. et al., "Characterization of nucleic acids by nanopore analysis", Acc. Cham. Res., vol. 35, No. 10, 817-825 (2002).

Deaven, The Human Genome Project: Recombinant clones for mapping and sequencing DNA. Los Alamos Science, 20:218-249, 1992.
Deng et al., Targeted bisulfite sequencing reveals changes in DNA methylation associated with nuclear reprogramming Nature Biotechnology, 27:352-360 (2009).
Dietrich, Rudiger.et al., "Gene assembly based on blunt-ended double-stranded DNA-modules", Biotechnology Techniques, vol. 12, No. 1, 49-54 (Jan. 1998).
Dillon et al. Exome sequencing has higher diagnostic yield compared to simulated disease-specific panels in children with suspected monogenic disorders. Eur J Hum Genet 26(5):644- 651 (2018).
Dormitzer et al., Synthetic generation of influenza vaccine viruses for rapid response to pandemics. Sci Translational Medicine, 5(185):185ra68, 14 pages, 2013.
Doudna et al. Genome editing. The new frontier of genome engineering with CRISPR-Cas9. Science 346(6213):1258096-1-1258096-9, 2014.
Dower et al., High efficiency transformation of *E. coli* by high voltage electroporation. Nucleic Acids Res. 16(13):6127-45 (1988).
Dressman, et al. Transforming single DNA molecules into fluorescent magnetic particles for detection and enumeration of genetic variations. Proc Natl Acad Sci U S A. Jul. 22, 2003;100(15):8817-22. Epub Jul. 11, 2003.
Drmanac, et al. Human genome sequencing using unchained base reads on self-assembling DNA nanoarrays. Science. Jan. 1, 2010;327(5961):78-81. doi: 10.1126/science.1181498. Epub Nov. 5, 2009.
Droege and Hill, The Genome Sequencer FLXTM System-Longer reads, more applications, straight forward bioinformatics and more complete data sets Journal of Biotechnology, 136:3-10, 2008.
Duffy, et al. Rapid Prototyping of Microfluidic Systems in Poly(dimethylsiloxane). Anal Chem. Dec. 1, 1998;70(23):4974-84. doi: 10.1021/ac980656z.
Duggan, et al. Expression profiling using cDNA microarrays. Nat Genet. Jan. 1999;21(1 Suppl):10-4.
Dvorsky. Living Bacteria Can Now Store Data. GIZMODO internet publication. Retrieved from https://gizmodo.com/living-bacteria-can-now-store-data-1781773517 (4 pgs) (Jun. 10, 2016).
Eadie, et al. Guanine modification during chemical DNA synthesis. Nucleic Acids Res. Oct. 26, 1987;15(20):8333-49.
Eisen, Jonathan A., "A phylogenomic study of the MutS family of proteins", Nucleic Acids Research, vol. 26, No. 18, 4291-4300 (1998).
Ellis, et al. DNA assembly for synthetic biology: from parts to pathways and beyond. Integr Biol (Camb). Feb. 2011;3(2):109-18. doi: 10.1039/c0ib00070a. Epub Jan. 19, 2011.
El-Sagheer, et al. Biocompatible artificial DNA linker that is read through by DNA polymerases and is functional in *Escherichia coli*. Proc Natl Acad Sci U S A. Jul. 12, 2011;108(28):11338-43. doi: 10.1073/pnas.1101519108. Epub Jun. 27, 2011.
Elsik et al., The Genome sequence of taurine cattle: A window of ruminant biology and evolution. Science, 324:522-528, 2009.
Elsner et al., 172 nm excimer VUV-triggered photodegradation and micropatterning of aminosilane films, Thin Solid Films, 517:6772-6776 (2009).
Engler, et al. A one pot, one step, precision cloning method with high throughput capability. PLoS One. 2008;3(11):e3647. doi: 10.1371/journal.pone.0003647. Epub Nov. 5, 2008.
Engler, et al. Golden gate shuffling: a one-pot DNA shuffling method based on type IIs restriction enzymes. PLoS One. 2009;4(5):e5553. doi: 10.1371/journal.pone.0005553. Epub May 14, 2009.
Erlich and Zielinski, DNA fountain enables a robust and efficient storage architecture. Science, 355(6328):950-054, 2017.
European Patent Application No. 12827479.2 Extended European Search Report dated May 18, 2015.
European Patent Application No. 12827479.2 Partial European Search Report dated Jan. 29, 2015.
European Patent Application No. 14834665.3 Communication dated Jan. 16, 2018.

(56) References Cited

OTHER PUBLICATIONS

European Patent Application No. 14834665.3 extended European Search Report dated Apr. 28, 2017.
European Patent Application No. 14834665.3 Further Examination Report dated Nov. 28, 2018.
European Patent Application No. 14834665.3 Office Action dated May 2, 2018.
European Patent Application No. 16847497.1 Extended European Search Report dated Jan. 9, 2019.
European Patent Application No. 16871446.7 European Search Report dated Apr. 10, 2019.
Evans et al., DNA Repair Enzymes. Current Protocols in Molecular Biology 84:III:3.9:3.9.1-3.9.12 http://www.ncbi.nlm.nih.gov/pubmed/18972391 (Published online Oct. 1, 2008 Abstract only provided).
Fahy, et al. Self-sustained sequence replication (3SR): an isothermal transcription-based amplification system alternative to PCR. PCR Methods Appl. Aug. 1991;1(1):25-33.
Fedoryak, Olesya D. et al., "Brominated hydroxyquinoline as a photolabile protecting group with sensitivity to multiphoton excitation", Org. Lett., vol. 4, No. 2 , 3419-3422 (2002).
Ferretti et al., Total synthesis of a gene for bovine rhodopsin. PNAS, 83:599-603 (1986).
Finger et al., The wonders of Flap Endonucleases: Structure, function, mechanism and regulation. Subcell Biochem., 62:301-326, 2012.
Fodor et al., Light-directed, spatially addressable parallel chemical synthesis. Science. 251(4995):767-773 (1991).
Fogg et al., Structural basis for uracil recognition by archaeal family B DNA polymerases. Nature Structural Biology, 9(12):922-927, 2002.
Foldesi, et al. The synthesis of deuterionucleosides. Nucleosides Nucleotides Nucleic Acids. Oct.-Dec. 2000;19(10-12):1615-56.
Frandsen, et al. Efficient four fragment cloning for the construction of vectors for targeted gene replacement in filamentous fungi. BMC Molecular Biology 2008, 9:70.
Frandsen. Experimental setup. Dec. 7, 2010, 3 pages. http://www.rasmusfrandsen.dk/experimental_setup.htm.
Frandsen. The USER Friendly technology. USER cloning. Oct. 7, 2010, 2 pages. http://www.rasmusfrandsen.dk/user_cloning.htm.
Fullwood et al., Next-generation DNA sequencing of paired-end tags [PET] for transcriptome and genome analysis Genome Research, 19:521-532, 2009.
Galneder. et al., Microelectrophoresis of a bilayer-coated silica bead in an optical trap: application to enzymology. Biophysical Journal, vol. 80, No. 5, 2298-2309 (May 2001).
Gao, et al. A flexible light-directed DNA chip synthesis gated by deprotection using solution photogenerated acids. Nucleic Acids Res. Nov. 15, 2001;29(22):4744-50.
Gao et al. A method for the generation of combinatorial antibody libraries using pIX phage display. PNAS 99(20):12612-12616 (2002).
Gao, et al. Thermodynamically balanced inside-out (TBIO) PCR-based gene synthesis: a novel method of primer design for high-fidelity assembly of longer gene sequences. Nucleic Acids Res. Nov. 15, 2003;31(22):e143.
Garaj, et al. Graphene as a subnanometre trans-electrode membrane. Nature. Sep. 9, 2010;467(7312):190-3. doi: 10.1038/nature09379.
Garbow, Norbert et al., "Optical tweezing electrophoresis of isolated, highly charged colloidal spheres", Colloids and Surfaces A: Physiochem. Eng. Aspects, vol. 195, 227-241 (2001).
GeneArt Seamless Cloning and Assembly Kits. Life Technologies Synthetic Biology. 8 pages, available online Jun. 15, 2012.
Genomics 101. An Introduction to the Genomic Workflow. 2016 edition, 64 pages. Available at: http://www.frontlinegenomics.com/magazine/6757/genomics-101/.
Geu-Flores, et al. USER fusion: a rapid and efficient method for simultaneous fusion and cloning of multiple PCR products. Nucleic Acids Res. 2007;35(7):e55. Epub Mar. 27, 2007.
Gibson Assembly. Product Listing. Application Overview. 2 pages, available online Dec. 16, 2014.

Gibson, et al. Complete chemical synthesis, assembly, and cloning of a Mycoplasma genitalium genome. Science. Feb. 29, 2008;319(5867):1215-20. doi: 10.1126/science.1151721. Epub Jan. 24, 2008.
Gibson et al. Creation of a Bacterial Cell Controlled by a Chemically Synthesized Genome. Science 329(5989):52-56 (2010).
Goldfeder et al. Medical implications of technical accuracy in genome sequencing. Genome Med 8(1):24 (2016).
Goldman et al., Towards practical, high-capacity, low-maintenance information storage in synthesized DNA, Nature, 494(7435):77-80, 2013.
Gosse, Charlie et al. "Magnetic tweezers: micromanipulation and force measurement at the molecular level", Biophysical Journal, vol. 8, 3314-3329 (Jun. 2002).
Grass, et al., Robust chemical preservation of digital information on DNA in silica with error-correcting codes, Angew. Chemie—Int. Ed., 54(8):2552-2555, 2015.
Greagg et al., A read-ahead function in archaeal DNA polymerases detects promutagenic template-strand uracil. Proc. Nat. Acad. Sci. USA, 96:9045-9050, 1999.
Grovenor. Microelectronic materials. Graduate Student Series in Materials Science and Engineering. Bristol, England: Adam Hilger, 1989; p. 113-123.
Gu et al., Depletion of abundant sequences by hybridization (DASH): using Cas9 to remove unwanted high-abundance species in sequencing libraries and molecular counting applications. Genome Biology, 17:41, 13 pages, 2016.
Haber, Charbel et al., Magnetic tweezers for DNA micromanipulation, Rev. Sci. Instrum., vol. 71, No. 12, 4561-4570 (Dec. 2000).
Han et al. Linking T-cell receptor sequence to functional phenotype at the single-cell level. Nat Biotechnol 32(7):684-692 (2014).
Hanahan and Cold Spring Harbor Laboratory, Studies on transformation of *Escherichia coli* with plasmids J. Mol. Biol. 166:557-580 (1983).
Hanahan et al., Plasmid transformation of *Escherichia coli* and other bacteria. Methods Enzymol, vol. 204, p. 63-113 (1991).
Harada, et al. Unexpected substrate specificity of T4 DNA ligase revealed by in vitro selection. Nucleic Acids Res. May 25, 1993;21(10):2287-91.
Heckers Karl H. et al., "Error analysis of chemically synthesized polynucleotides", BioTechniques, vol. 24, No. 2, 256-260 (1998).
Herzer et al.: Fabrication of patterned silane based self-assembled monolayers by photolithography and surface reactions on silicon-oxide substrates Chem. Commun., 46:5634-5652 (2010).
Hoover et al., "DNAWorks: an automated method for designing oligonucleotides for PCR-based gene synthesis", Nucleic Acids Research, vol. 30, No. 10, e43, 7 pages (2002).
Hosu, Basarab G. et al., Magnetic tweezers for intracellular applications•, Rev. Sci. Instrum., vol. 74, No. 9, 4158-4163 (Sep. 2003).
Huang, Hayden et al., "Three-dimensional cellular deformation analysis with a two-photon magnetic manipulator workstation", Biophysical Journal, vol. 82, No. 4, 2211•2223 (Apr. 2002).
Hughes et al. Expression profiling using microarrays fabricated by an ink-jet oligonucleotide synthesizer Nat Biotech 4:342-347 (2001).
Hughes et al. Principles of early drug discovery. Br J Pharmacol 162(2):1239-1249, 2011.
Hutchison, et al. Cell-free cloning using phi29 DNA polymerase. Proc Natl Acad Sci U S A. Nov. 29, 2005;102(48):17332-6. Epub Nov. 14, 2005.
Imgur: The magic of the internet. Uploaded May 10, 2012, 2 pages, retrieved from: https://imgur.com/mEWuW.
In-Fusion Cloning: Accuracy, Not Background. Cloning & Competent Cells, ClonTech Laboratories, 3 pages, available online Jul. 6, 2014.
International Application No. PCT/US2017/026232 International Preliminary Report on Patentability dated Feb. 26, 2019.
International Application No. PCT/US2017/045105 International Preliminary Report on Patentability dated Feb. 5, 2019.
International Application No. PCT/US2017/052305 International Preliminary Report on Patentability dated Apr. 30, 2019.
International Application No. PCT/US2017/062391 International Preliminary Report on Patentability dated May 21, 2019.

(56) References Cited

OTHER PUBLICATIONS

International Application No. PCT/US2018/050511 International Search Report and Written Opinion dated Jan. 11, 2019.
International Application No. PCT/US2018/057857 International Search Report and Written Opinion dated Mar. 18, 2019.
International Application No. PCT/US2019/012218 International Search Report and Written Opinion dated Mar. 21, 2019.
Jackson, Brian A. et al., "Recognition of DNA base mismatches by a rhodium intercalator", J. Am. Chem. Soc., vol. 19, 12986•12987 (1997).
Jacobs et al. DNA glycosylases: In DNA repair and beyond. Chromosoma 121:1-20 (2012)—http://www.ncbi.nlm.nih.gov/pmc/articles/PMC3260424/.
Jacobus et al. Optimal cloning of PCR fragments by homologous recombination in *Escherichia soli*. PLoS One 10(3):e0119221 (2015).
Jager et al. Simultaneous Humoral and Cellular Immune Response against Cancer—Testis Antigen NY-ES0-1: Definition of Human Histocompatibility LeukocyteAntigen (HLA)-A2-binding Peptide Epitopes. J. Exp. Med. 187(2):265-270 (1998).
Jinek et al., A Programmable dual-RNA-guided DNA endonuclease in adaptive bacterial immunity. Science, 337:816-821, 2012.
Karagiannis and El-Osta, RNA interference and potential therapeutic applications of short interfering RNAs Cancer Gene Therapy, 12:787-795, 2005.
Ke, Song-Hua et al., "Influence of neighboring base pairs on the stability of single base bulges and base pairs in a DNA fragment", Biochemistry, Vo. 34, 4593-4600 (1995).
Kelley, Shana, et al. Single-base mismatch detection based on charge transduction through DNA, Nucleic Acids Research, vol. 27, No. 24, 4830-4837 (1999).
Kim et al., High-resolution patterns of quantum dots formed by electrohydrodynamic jet printing for light-emitting diodes. Nano Letters, 15:969-973, 2015.
Kim, Yang-Gyun et al., "Chimeric restriction endonuclease", Proc. Natl. Acad. Sci. USA, vol. 91, 883-887 (Feb. 1994).
Kim, Yang-Gyun, "The interaction between Z-ONA and the Zab domain of double-stranded RNA adenosine deaminase characterized using fusion nucleases", The Journal of Biological Chemistry, vol. 274, No. 27, 19081-19086 (1999).
Kim, Yan~Gyun et al., "Site-specific cleavage of DNA-RNA hybrids by zinc finger/Fok I cleavage domain fusions" Gene, vol. 203, 43-49 (1997).
Kinde, et al. Detection and quantification of rare mutations with massively parallel sequencing. Proc Natl Acad Sci U S A. Jun. 7, 2011;108(23):9530-5. Epub May 17, 2011.
Kodumal, et al. Total synthesis of long DNA sequences: synthesis of a contiguous 32-kb polyketide synthase gene cluster. Proc Natl Acad Sci USA. Nov. 2, 2004;101(44):15573-8. Epub Oct. 20, 2004.
Koike-Yusa et al., Genome-wide recessive genetic screening in mammalian cells with a lentiviral CRISPR-guide RNA library. Nature Biotechnology, 32:267-273, 2014 (with three pages of supplemental "Online Methods").
Kong et al., Parallel gene synthesis in a microfluidic device. Nucleic Acids Res., 35(8):e61 (2007).
Kong. Microfluidic Gene Synthesis. MIT Thesis. Submitted to the program in Media Arts and Sciences, School of Architecture and Planning, in partial fulfillment of the requirements for the degree of Doctor of Philosophy in Media Arts and Sciences at the Massachusetts Institute of Technology. 143 pages Jun. 2008.
Kopp, Martin U. et al., "Chemical amplification: continuous-flow PCR on a chip", Science, vol. 280, 1046-1048 (May 15, 1998).
Kosuri and Church, "Large-scale de novo DNA synthesis: technologies and applications," Nature Methods, 11:499-507, 2014. Available at: http://www.nature.com/nmeth/journal/v11/n5/full/nmeth.2918.html.
Kosuri, et al. A scalable gene synthesis by selective amplification of DNA pools from high-fidelity microchips. Nature Biotechnology. 2010; 28:1295-1299.

Krayden, Inc., A Guide to Silane Solutions. Silane coupling agents. 7 pages. Published on May 31, 2005 at: http://krayden.com/pdf/xia_silane_chemistry.pdf.
Lagally, et al. Single-Molecule DNA Amplification and Analysis in an Integrated Microfluidic Device. Analytical Chemistry. 2001;73(3): 565-570.
Lahue, R.S. et al., "DNA mismatch correction in a defined system", Science, vol. 425; No. 4914, 160-164 (Jul. 14, 1989).
Lambrinakos, A. et al., "Reactivity of potassium permanganate and tetraethylammonium chloride with mismatched bases and a simple mutation detection protocol",Nucleic Acids Research, vol. 27, No. 8, 1866- 1874 (1999).
Landegren, et al. A ligase-mediated gene detection technique. Science. Aug. 26, 1988;241(4869):1077-80.
Lang, Matthew J. et al., "An automated two-dimensional optical force clamp for single molecule studies", Biophysical Journal, vol. 83, 491•501 (Jul. 2002).
Lashkari, et al. An automated multiplex oligonucleotide synthesizer: development of high-throughput, low-cost DNA synthesis. Proc Natl Acad Sci U S A. Aug. 15, 1995;92(17):7912-5.
Lausted et al., "POSaM: a fast, flexible, open-source, inkjet oligonucleotide synthesizer and microarrayer," Genome Biology, 5:R58, 17 pages, 2004. available at https://www.ncbi.nlm.nih.gov/pmc/articles/PMC507883/.
Leamon, et al. A massively parallel PicoTiterPlate based platform for discrete picoliter-scale polymerase chain reactions. Electrophoresis. Nov. 2003;24(21):3769-77.
Lee: Covalent End-Immobilization of Oligonucleotides onto Solid Surfaces; Thesis, Massachusetts Institute of Technology, Aug. 2001 (315 pages).
Lee, Covalent end-immobilization of oligonucleotides onto solid surfaces. Thesis submitted to the Department of Chemical Engineering in Partial Fulfillment of the Requirements for the Degree of Doctor of Philosophy in Chemical Engineering at the Massachusetts Institute of Technology. Aug. 2001, 315 pages.
Lee, C.S. et al., "Microelectromagnets for the control of magnetic nanoparticles", Appl. Phys. Lett., vol. 79, No. 20, 3308-3310 (Nov. 12, 2001).
Lee, et al. A microfluidic oligonucleotide synthesizer. Nucleic Acids Research 2010 Vol: 38(8):2514-2521. Doi: 10.1093/nar/gkq092. 0.
Leproust, et al. Agilent's Microarray Platform: How High-Fidelity DNA Synthesis Maximizes the Dynamic Range of Gene Expression Measurements. 2008; 1-12. http://www.miltenyibiotec.com/~/media/Files/Navigation/Genomic%20Services/Agilent_DNA_Microarray_Platform.ashx.
Leproust et al., "Synthesis of high-quality libraries of long (150mer) oligonucleotides by a novel depurination controlled process," Nucleic Acids Research, 35(8):2522-2540, 2010.
Lesnikowski, et al. Nucleic acids and nucleosides containing carboranes. J. Organometallic Chem. 1999; 581:156-169.
Leumann. DNA analogues: from supramolecular principles to biological properties. Bioorg Med Chem. Apr. 2002;10(4):841-54.
Levene, et al. Zero-mode waveguides for single-molecule analysis at high concentrations. Science. Jan. 31, 2003;299(5607):682-6.
Lewontin and Harti, Population genetics in forensic DNA typing. Science, 254:1745-1750, 1991.
Li et al., Beating bias in the directed evolution of proteins: Combining high-fidelity on-chip solid-phase gene synthesis with efficient gene assembly for combinatorial library construction. First published Nov. 24, 2017, 2 pages. retrieved from: https://doi.org/10.1002/cbic.201700540.
Li et al. Beating Bias in the Directed Evolution of Proteins: Combining High-Fidelity on-Chip Solid-Phase Gene Synthesis with Efficient Gene Assembly for Combinatorial Library Construction. ChemBioChem 19:221-228 (2018).
Light source unit for printable patterning VUV-Aligner / USHIO Inc., Link here: https://www.ushio.co.jp/en/products/1005.html, published Apr. 25, 2016, printed from the internet on Aug. 2, 2016, 3 pages.
Limbachiya et al., Natural data storage: A review on sending information from now to then via Nature. ACM Journal on Emerging Technologies in Computing Systems, V(N):Article A, May 19, 2015, 17 pages.

(56) References Cited

OTHER PUBLICATIONS

Link Technologies. "Product Guide 2010." Nov. 27, 2009, 136 pages. XP055353191. Retrieved from the Internet: URL:http://www.linktech.co.uk/documents/517/517.pdf.
Lipshutz, Robert J. et al., "High density synthetic oligonucleotide arrays", Nature Genetics Supplement, vol. 21, 20-24 (Jan. 1999).
Lishanski, Alia et al., "Mutation detection by mismatch binding protein, MutS, in amplified DNA: application to the cystic fibrosis gene", Proc. Natl. Acad. Sci. USA, vol. 91, 2674-2678 (Mar. 1994).
Liu et al., Comparison of Next-Generation Sequencing Systems. Journal of Biomedicine and Biotechnology, 11 pages, 2012.
Liu, et al. Enhanced Signals and Fast Nucleic Acid Hybridization by Microfluidic Chaotic Mixing. Angew. Chem. Int. Ed. 2006; 45:3618-3623.
Liu et al., Rational design of CXCR4 specific antibodies with elongated CDRs. JACS, 136:10557-10560, 2014.
Lizardi, et al. Mutation detection and single-molecule counting using isothermal rolling-circle amplification. Nat Genet. Jul. 1998;19(3):225-32.
Li, Lin et al., "Functional domains in Fok I restriction endonuclease", Proc. Natl. Acad. Sci. USA, 89:4275-4279, 1992.
Lu, A.-Lien et al., "Methyl-directed repair of DNA base-pair mismatches in vitro", Proc. Natl. Acad. Sci. USA, 80:4639-4643, 1983.
Lund, et al. A validated system for ligation-free uracilexcision based assembly of expression vectors for mammalian cell engineering. DTU Systems of Biology. 2011. 1 page. http://www.lepublicsystemepco.com/files/modules/gestion_rubriques/REF-B036-Lund_Anne%20Mathilde.pdf.
Ma, et al. DNA synthesis, assembly and application in synthetic biology. Current Opinion in Chemical Biology. 16:260-267, 2012.
Ma et al., Versatile surface functionalization of cyclic olefin copolymer (COC) with sputtered SiO2 thin film for potential BioMEMS applications. Journal of Materials Chemistry, 11 pages, 2009.
Mahato et al., Modulation of gene expression by antisense and antigene oligodeoxynucleotides and small interfering RNA Expert Opin. Drug Delivery, 2(1):3-28, 2005.
Margulies, et al. Genome sequencing in open microfabricated high-density picolitre reactors. Nature. 437(7057):376-80, 2005.
Matteucci, et al. Synthesis of deoxyoligonucleotides on a polymer support. J. Am. Chem. Soc. 103(11):3185-3191, 1981.
Matzas et al., Next generation gene synthesis by targeted retrieval of bead-immobilized, sequence verified DNA clones from a high throughput pyrosequencing device. Nat. Biotechnol., 28(12):1291-1294, 2010.
Mazor et al.: Isolation of Full-Length IgG Antibodies from Combinatorial Libraries Expressed in Escherichia coli; Antony S. Dimitrov (ed.), Therapeutic Antibodies: Methods and Protocols, vol. 525, Chapter 11, pp. 217-239 (2009).
McBride & Caruthers, "An investigation of several deoxynucleoside phosphoramidites useful for synthesizing deoxyoligonucleotides." Tetrahedron Lett. 24: 245-248, 1983.
Mcgall, et al. Light-directed synthesis of high-density oligonucleotide arrays using semiconductor photoresists. Proc Natl Acad Sci U S A. 93(24):13555-60, 1996.
Mcgall, et al. The Efficiency of Light-Directed Synthesis of DNA Arrays on Glass Substrates. J. Am. Chem. Soc. 119(22):5081-5090, 1997.
Mei et al., Cell-free protein synthesis in microfluidic array devices Biotechnol. Prog., 23(6):1305-1311, 2007.
Mendel-Hartvig. Padlock probes and rolling circle amplification. New possibilities for sensitive gene detection. Comprehensive Summaries of Uppsala Dissertations from the Faculty of Medicine 1175. Uppsala University. 2002, 39 pages. http://www.diva-portal.org/smash/get/diva2:161926/FULLTEXT01.pdf.
Meyers and Friedland, Knowledge-based simulation of genetic regulation in bacteriophage lambda. Nucl. Acids Research, 12(1):1-16, 1984.
Meynert et al. Quantifying single nucleotide variant detection sensitivity in exome sequencing. BMC Bioinformatics 14:195 (2013).
Meynert et al. Variant detection sensitivity and biases in whole genome and exome sequencing. BMC Bioinformatics 15:247 (2014).
Milo and Phillips, Numbers here reflect the number of protein coding genes and excludes tRNA and non-coding RNA. Cell Biology by the Numbers, p. 286, 2015.
Mitra, et al. In situ localized amplification and contact replication of many individual DNA molecules. Nucleic Acids Res. 27(24):e34, 1999.
Morin et al., Profiling the HeLa S3 transcriptome using randomly primed cDNA and massively parallel short-read sequencing. Biotechniques, 45:81-94, 2008.
Morris and Stauss, Optimizing T-cell receptor gene therapy for hematologic malignancies. Blood, 127(26):3305-3311, 2016.
Muller, Caroline et al. "Protection and labelling of thymidine by a fluorescent photolabile group", Helvetica Chimica Acta, vol. 84, 3735-3741 (2001).
Mulligan. Commercial Gene Synthesis Technology PowerPoint presentation. BlueHeron® Biotechnology. Apr. 5, 2006 (48 pgs).
Nakatani, Kazuhiko et al., "Recognition of a single guanine bulge by 2-Acylamino-1 ,8-naphthyridine", J. Am. Chem. Soc., vol. 122, 2172-2177 (2000).
Eroshenko et al.: Gene Assembly from Chip-Synthesized Oligonucleotides; Current Protocols in Chemical biology 4: 1-17 (2012).
Jo et al.: Engineering therapeutic antibodies targeting G-protein-coupled receptors; Experimental & Molecular Medicine; 48; 9 pages (2016).
Lausted et al.: POSaM: a fast, flexible, open-source, inkjet oligonucleotide synthesizer and microarrayer; Genome Biology 2004, 5:R58.
Douthwaiteet al.: Affinity maturation of a novel antagonistic human monoclonal antibody with a long VH CDR3 targeting the Class A GPCR formyl-peptide receptor 1; mAbs, vol. 7, Iss. 1, pp. 152-166 (Jan. 1, 2015).
Neiman M.S,. Negentropy principle in information processing systems. Radiotekhnika, 1966, No. 211, p. 2-9.
Neiman M.S., On the bases of the theory of information retrieval. Radiotekhnika, 1967, No. 5, p. 2-10.
Neiman M.S., On the molecular memory systems and the directed mutations. Radiotekhnika, 1965, No. 6, pp. 1-8.
Neiman M.S., On the relationships between the reliability, performance and degree of microminiaturization at the molecular-atomic level. Radiotekhnika, 1965, No. 1, pp. 1-9.
Neiman M.S., Some fundamental issues of microminiaturization. Radiotekhnika, 1964, No. 1, pp. 3-12.
Nishikura, A short primer on RNAi: RNA-directed RNA polymerase acts as a key catalyst Cell, 107:415-418, 2001.
Nour-Eldin, et al. User Cloning and User Fusion: The Ideal Cloning Techniques for Small and Big Laboratories. Plant Secondary Metabolism Engineering. Methods in Molecular Biology vol. 643, 2010, pp. 185-200.
Ochman, et al. Genetic applications of an inverse polymerase chain reaction. Genetics. Nov. 1988;120(3):621-3.
Organick et al., Random access in large-scale DNA data storage. Nature Biotechnology, Advance Online Publication, 8 pages, 2018.
Organick et al., Scaling up DNA data storage and random access retrieval, bioRxiv, preprint first posted online Mar. 7, 2017, 14 pages.
Pan, et al. An approach for global scanning of single nucleotide variations. Proc Natl Acad Sci U S A. Jul. 9, 2002;99(14):9346-51.
Pankiewicz. Fluorinated nucleosides. Carbohydr Res. Jul. 10, 2000;327(1-2):87-105.
PCT/IL2012/000326 International Preliminary Report on Patentability dated Dec. 5, 2013.
PCT/IL2012/000326 International Search Report dated Jan. 29, 2013.
PCT/US14/049834 International Preliminary Report on Patentability dated Feb. 18, 2016.
PCT/US2014/049834 International Search Report and Written Opinion dated Mar. 19, 2015.
PCT/US2014/049834, "Invitation to Pay Additional Fees and, where applicable, protest fee," dated Jan. 5, 2015.
PCT/US2015/043605 International Preliminary Report on Patentability dated Feb. 16, 2017.

(56) References Cited

OTHER PUBLICATIONS

PCT/US2015/043605 International Search Report and Written Opinion dated Jan. 6, 2016.
PCT/US2015/043605 Invitation to Pay Additional Fees dated Oct. 28, 2015.
PCT/US2016/016459 International Preliminary Report on Patentability dated Aug. 17, 2017.
PCT/US2016/016459 International Search Report and Written Opinion dated Apr. 13, 2016.
PCT/US2016/016636 International Preliminary Report on Patentability dated Aug. 17, 2017.
PCT/US2016/016636 International Search Report and Written Opinion dated May 2, 2016.
PCT/US2016/028699 International Preliminary Report on Patentability dated Nov. 2, 2017.
PCT/US2016/028699 International Search Report and Written Opinion dated Jul. 29, 2016.
PCT/US2016/031674 International Preliminary Report on Patentability dated Nov. 23, 2017.
PCT/US2016/031674 International Search Report and Written Opinion dated Aug. 11, 2016.
PCT/US2016/052336 International Preliminary Report on Patentability dated Mar. 29, 2018.
PCT/US2016/052336 International Search Report and Written Opinion dated Dec. 7, 2016.
PCT/US2016/052916 International Preliminary Report on Patentability dated Apr. 5, 2018.
PCT/US2016/052916 International Search Report and Written Opinion dated Dec. 30, 2016.
PCT/US2016/064270 International Preliminary Report on Patentability dated Jun. 14, 2018.
PCT/US2016/064270 International Search Report and Written Opinion dated Apr. 28, 2017.
PCT/US2017/026232 International Search Report and Written Opinion dated Aug. 28, 2017.
PCT/US2017/036868 International Search Report and Written Opinion dated Aug. 11, 2017.
PCT/US2017/045105 International Search Report and Written Opinion dated Oct. 20, 2017.
PCT/US2017/052305 International Search Report and Written Opinion dated Feb. 2, 2018.
PCT/US2017/062391 International Search Report and Written Opinion dated Mar. 28, 2018.
PCT/US2017/066847 International Search Report and Written Opinion dated May 4, 2018.
PCT/US2018/022487 International Search Report and Written Opinion dated Aug. 1, 2018.
PCT/US2018/022493 International Search Report and Written Opinion dated Aug. 1, 2018.
PCT/US2018/037152 International Search Report and Written Opinion dated Aug. 28, 2018.
PCT/US2018/037161 International Search Report and Written Opinion dated Oct. 22, 2018.
PCT/US2018/037161 Invitation to Pay Additional Fees dated Aug. 27, 2018.
PCT/US2018/056783 International Search Report and Written Opinion of the International Searching Authority dated Dec. 20, 2018.
PCT/US2018/19268 International Search Report and Written Opinion dated Jun. 26, 2018.
PCT/US2018/19268 Invitation to Pay Additional Fees and, where applicable, protest fee dated May 2, 2018.
PCT/US2018/22487 Invitation to Pay Additional Fees and, where applicable, protest fee dated May 31, 2018.
PCT/US2018/22493 Invitation to Pay Additional Fees and, where applicable, protest fee dated May 31, 2018.
Pease, et al. Light-generated oligonucleotide arrays for rapid DNA sequence analysis. Proc Natl Acad Sci U S A. May 24, 1994;91(11):5022-6.
Peisajovich, et al. BBF RFC 28: A method for combinatorial multi-part assembly based on the type-lis restriction enzyme aarl. Sep. 16, 2009, 7 pages.
Pellois, et al. "Individually addressable parallel peptide synthesis on microchips", Nature Biotechnology, vol. 20 , 922-926 (Sep. 2002).
Petersen, et al. LNA: a versatile tool for therapeutics and genomics. Trends Biotechnol. Feb. 2003;21(2):74-81.
Pierce, et al. Linear-after-the-exponential polymerase chain reaction and allied technologies. Real-time detection strategies for rapid, reliable diagnosis from single cells. Methods Mol Med. 2007;132:65-85.
Pirrung. How to make a DNA chip. Angew. Chem. Int. Ed., 41:1276-1289, 2002.
Plesa et al., Multiplexed gene synthesis in emulsions for exploring protein functional landscapes. Science, 10.1126/science.aao5167, 10 pages, 2018.
Pon. Solid-phase supports for oligonucleotide synthesis. Methods Mol Biol. 1993;20:465-96.
Poster. Reimagine Genome Scale Research. 2016, 1 page. Available at http://www2.twistbioscience.com/Oligo_Pools_CRISPR_poster.
Powers et al. Optimal strategies for the chemical and enzymatic synthesis of bihelical deoxyribonucleic acids. J Am Chem Soc., 97(4):875-884, 1975.
Pray. "Discovery of DNA Structure and Function: Watson and Crick," Nature Education, 2008, 6 pages. available at: http://www.nature.com/scitable/topicpage/discovery-of-dna-structure-and-function-watson-397.
Prodromou, et al. Recursive PCR: a novel technique for total gene synthesis. Protein Eng. Dec. 1992;5(8):827-9.
Puigbo. Optimizer: a web server for optimizing the codon usage of DNA sequences. Nucleic Acid Research, 35(14):126-131, 2007.
Qian and Winfree, Scaling up digital circuit computation with DNA strand displacement cascades. Science, 332(6034):196-1201, 2011.
Qian, et al., Neural network computation with DNA strand displacement cascades, Nature, 475(7356):368-372, 2011.
Quan et al., "Parallel on-chip gene synthesis and application to optimization of protein expression," Nature Biotechnology, 29(5):449-452, 2011.
Rafalski and Morgante, Corn and humans: recombination and linkage disequilibrium in two genomes of similar size. Trends in Genetics, 20(2):103-111, 2004.
Raje and Murma, A Review of electrohydrodynamic-inkjet printing technology. International Journal of Emerging Technology and Advanced Engineering, 4(5):174-183, 2014.
Rastegari, et al., XNOR-Net: ImageNet Classification Using Binary Convolutional Neural Networks, in ECCV 2016, Part IV, LNCS 9908, p. 525-542, 2016.
Reimagine SequenceSpace, Reimagine Research, Twist Bioscience, Product Brochure, Published Apr. 6, 2016 online at: www2.twistbioscience.com/TB_Product_Brochure_04.2016, 8 pages.
RF Electric discharge type excimer lamp. Products Catalog. Excimer lamp light source "flat excimer," 16 pages dated Jan. 2016. From: http://www.hamamatsu.com/jp/en/product/category/1001/3026/index.html.
Richmond, et al. Amplification and assembly of chip-eluted DNA (AACED): a method for high-throughput gene synthesis. Nucleic Acids Res. Sep. 24, 2004;32(17):5011-8. Print 2004.
Roche. Restriction Enzymes from Roche Applied Science—A Tradition of Premium Quality and Scientific Support. FAQS and Ordering Guide. Roche Applied Science. Accessed Jan. 12, 2015, 37 pages.
Rogozin et al., Origin and evolution of spliceosomal introns. Biology Direct, 7:11, 2012.
Ruminy, et al., "Long-range identification of hepatocyte nuclear factor-3 (FoxA) high and low-affinity binding Sites with a chimeric nuclease", J. Mol. Bioi., vol. 310, 523-535 (2001).
Saaem et al., In situ synthesis of DNA microarray on functionalized cyclic olefin copolymer substrate ACS Applied Materials & Interfaces, 2(2):491-497, 2010.
Saboulard, et al. High-throughput site-directed mutagenesis using oligonucleotides synthesized on DNA chips. Biotechniques. Sep. 2005;39(3):363-8.

(56) References Cited

OTHER PUBLICATIONS

Sacconi, L. et al., Three-dimensional magneto-optic trap for microobject manipulation, Optics Letters, vol. 26, No. 17, 1359-1361 (Sep. 1, 2001).
Saiki et al. Analysis of enzymatically amplified beta-globin and HLA-DQ alpha DNA with allele-specific oligonucleotide probes. Nature 324:163-166 (1986).
Sandhu, et al. Dual asymmetric PCR: one-step construction of synthetic genes. Biotechniques. Jan. 1992;12(1):14-6.
Sargolzaei et al., Extent of linkage disequilibrium in Holstein cattle in North America. J.Dairy Science, 91:2106-2117, 2007.
Schaller, et al. Studies on Polynucleotides. XXV.1 The Stepwise Synthesis of Specific Deoxyribopolynucleotides (5). Further Studies on the Synthesis of Internucleotide Bond by the Carbodiimide Method. The Synthesis of Suitably Protected Dinucleotides as Intermediates in the Synthesis of Higher Oligonucleotides. J. Am. Chem. Soc. 1963; 85(23):3828-3835.
Schmalzing et al. Microchip electrophoresis: a method for highspeed SNP detection. Nucleic Acids Res 28(9):E43 (2000).
Schmitt et al., New strategies in engineering T-cell receptor genemodified T cells to more effectively target malignancies. Clinical Cancer Research, 21(23):5191-5197, 2015.
Seelig, et al., Enzyme-Free Nucleic Acid Logic Circuits, Science 314(5805):1585-1588, 2006.
Sharan et al. Recombineering: a homologous recombination-based method of genetic engineering. Nat Profile 4(2):1-37 (originally pp. 206-223) (2009).
Sharpe and Mount, Genetically modified T cells in cancer therapy: opportunities and challenges. Disease Models and Mechanisms, 8:337-350, 2015.
Simonyan and Zisserman, Very Deep Convolutional Networks for Large-Scale Image Recognition, Published as a conference paper at Int. Conf. Learn. Represent., pp. 1-14, 2015.
Singh-Gasson, Sangeet et al., Maskless fabrication of light-directed oligonucleotide microarrays using a digital micromirror array, Nature Biotechnology, vol. 17, 974-978 (Oct. 1999).
Skerra. Phosphorothioate primers improve the amplification of DNA sequences by DNA polymerases with proofreading activity. Nucleic Acids Res. Jul. 25, 1992; 20(14):3551-4.
Smith, et al. Generating a synthetic genome by whole genome assembly: phiX174 bacteriophage from synthetic oligonucleotides. Proc Natl Acad Sci U S A. Dec. 23, 2003;100(26):15440-5. Epub Dec. 2, 2003.
Smith, et al. Generation of cohesive ends on PCR products by UDG-mediated excision of dU, and application for cloning into restriction digest-linearized vectors. PCR Methods Appl. May 1993;2(4):328-32.
Smith, Jane et al., "Mutation detection with MutH, MutL, and MutS mismatch repair proteins", Proc. Natl. Acad. Sci. USA, vol. 93, 4374-4379 (Apr. 1996).
Smith Jane et al., "Removal of Polymerase-Produced mutant sequences from PCR products", Proc. Natl. Acad. Sci. USA, vol. 94, 6847-6850 (Jun. 1997).
Smith, Steven B. et al., "Direct mechanical measurements of the elasticity of single DNA molecules using magnetic beads", Science, vol. 258, 1122-1126 (Nov. 13, 1992).
Soni, et al. Progress toward ultrafast DNA sequencing using solid-state nanopores. Clin Chem. Nov. 2007;53(11):1996-2001. Epub Sep. 21, 2007.
Southern, et al. Analyzing and comparing nucleic acid sequences by hybridization to arrays of oligonucleotides: evaluation using experimental models. Genomics. Aug. 1992;13(4):1008-17.
Martinez-Torrecuadradaet al.: Targeting the Extracellular Domain of Fibroblast Growth Factor Receptor 3 with Human Single-Chain Fv Antibodies Inhibits Bladder Carcinoma Cell Line Proliferation; Clinical Cancer Research; vol. 11; pp. 6282-6290 (2005).
Sierzchala, Agnieszka B. et al., "Solid-phase oligodeoxynucleotide synthesis : a two-step cycle using peroxy anion deprotection", J. Am. Chem. Soc., vol. 125, No. 44, 13427-13441 (2003).
U.S. Appl. No. 15/187,714 Office Action dated Apr. 4, 2019.

U.S. Appl. No. 15/603,013 Office Action dated Jun. 26, 2019.
Sproat, et al. An efficient method for the isolation and purification of oligoribonucleotides. Nucleosides & Nucleotides. 1995; 14(1 &2):255-273.
Srivannavit et al., Design and fabrication of microwell array chips for a solution-based, photogenerated acid-catalyzed parallel oligonuclotide DNA synthesis. Sensors and Actuators A, 116:150-160, 2004.
Srivastava et al., "RNA synthesis: phosphoramidites for RNA synthesis in the reverse direction. Highly efficient synthesis and application to convenient introduction of ligands, chromophores and modifications of synthetic RNA at the 3'-end", Nucleic Acids Symposium Series, 52(1):103-104, 2008.
Steel, The Flow-Thru Chip A Three-dimensional biochip platform. In: Schena, Microarray Biochip Technology, Chapter 5, Natick, MA: Eaton Publishing, 2000, 33 pages.
Stemmer, et al. Single-step assembly of a gene and entire plasmid from large numbers of oligodeoxyribonucleotides. Gene. Oct. 16, 1995;164(1):49-53.
Stryer. "DNA Probes and genes can be synthesized by automated solid-phase methods." Biochemistry, 3rd edition, New York: W.H. Freeman and Company, 1988; 123-125.
Stutz, et al. Novel fluoride-labile nucleobase-protecting groups for the synthesis of 3'(2')-O-amino-acylated RNA sequences. Helv. Chim. Acta. 2000; 83(9):2477-2503.
Sullivan et al. Library construction and evaluation for site saturation mutagenesis. Enzyme Microb. Technol. 53:70-77 (2013).
Sun et al. Structure-Guided Triple-Code Saturation Mutagenesis: Efficient Tuning of the Stereoselectivity of an Epoxide Hydrolase. ACS Catal. 6:1590-1597 (2016).
Takahashi, Cell-free cloning using multiply-primed rolling circle amplification with modified RNA primers. Biotechniques. Jul. 2009;47(1):609-15. doi: 10.2144/000113155.
Tanase, M. et al., "Magnetic trapping of multicomponent nanowires", The Johns Hopkins University, Baltimore, Maryland, p. 1-3 (Jun. 25, 2001).
Taylor et al., Impact of surface chemistry and blocking strategies on DNA microarrays. Nucleic Acids Research, 31(16):e87, 19 pages, 2003.
The Hood Laboratory, "Beta Group. Assembly Manual for the POSaM: The ISB Piezoelelctric Oligonucleotide Synthesizer and Microarrayer," Inkjet Microarrayer Manual Version 1.2, 50 pages, May 28, 2004.
The SLIC, Gibson, CPEC and SLiCE assembly methods (and GeneArt Seamless, In-Fusion Cloning). 5 pages, available online Sep. 2, 2010.
Tian, et al. Accurate multiplex gene synthesis from programmable Dna microchips. Nature. 2004 Dec 23;432(7020)1 050-4. 0.
Tsai et al., Dimeric CRISPR RNA-guided Fokl nucleases for highly specific genome editing Nat. Biotechnol., 32(6):569-576, 2014.
Twist Bioscience | White Paper. DNA-Based Digital Storage. Retrieved from the internet, Twistbioscience.com, Mar. 27, 2018, 5 pages.
Unger, et al. Monolithic microfabricated valves and pumps by multilayer soft lithography. Science. Apr. 7, 2000;288(5463):113-6.
U.S. Appl. No. 14/241,874 Office Action dated Feb. 27, 2017.
U.S. Appl. No. 14/241,874 Office Action dated Jul. 14, 2016.
U.S. Appl. No. 14/241,874 Office Action dated May 4,2018.
U.S. Appl. No. 14/452,429 Notice of Allowance dated Jun. 7, 2016.
U.S. Appl. No. 14/452,429 Office Action dated Oct. 21, 2015.
U.S. Appl. No. 14/452,429 Restriction Requirement dated Dec. 12, 2014.
U.S. Appl. No. 14/885,962 Notice of Allowance dated Nov. 8, 2017 and Sep. 29, 2017.
U.S. Appl. No. 14/885,962 Office Action dated Dec. 16, 2016.
U.S. Appl. No. 14/885,962 Office Action dated Sep. 8, 2016.
U.S. Appl. No. 14/885,962 Restriction Requirement dated Mar. 1, 2016.
U.S. Appl. No. 14/885,963 Notice of Allowance dated May 24, 2016.
U.S. Appl. No. 14/885,963 Office Action dated Feb. 5, 2016.
U.S. Appl. No. 14/885,965 Office Action dated Aug. 28, 2018.
U.S. Appl. No. 14/885,965 Office Action dated Aug. 30, 2017.
U.S. Appl. No. 14/885,965 Office Action dated Feb. 10, 2017.

(56) References Cited

OTHER PUBLICATIONS

U.S. Appl. No. 14/885,965 Office Action dated Feb. 18, 2016.
U.S. Appl. No. 14/885,965 Office Action dated Jan. 4, 2018.
U.S. Appl. No. 14/885,965 Office Action dated Jul. 7, 2016.
U.S. Appl. No. 15/015,059 Office Action dated Feb. 7, 2019.
U.S. Appl. No. 15/135,434 Notice of Allowance dated Feb. 9, 2018.
U.S. Appl. No. 15/135,434 Office Action dated Nov. 30, 2017.
U.S. Appl. No. 15/135,434 Restriction Requirement dated Jul. 12, 2017.
U.S. Appl. No. 15/151,316 Office Action dated Jun. 7, 2018.
U.S. Appl. No. 15/154,879 Notice of Allowance dated Feb. 1, 2017.
U.S. Appl. No. 15/156,134 Office Action dated Apr. 4, 2019.
U.S. Appl. No. 15/187,714 Restriction Requirement dated Sep. 17, 2018.
U.S. Appl. No. 15/187,721 Notice of Allowance dated Dec. 7, 2016.
U.S. Appl. No. 15/187,721 Office Action dated Oct. 14, 2016.
U.S. Appl. No. 15/233,835 Notice of Allowance dated Oct. 4, 2017.
U.S. Appl. No. 15/233,835 Office Action dated Feb. 8, 2017.
U.S. Appl. No. 15/233,835 Office Action dated Jul. 26, 2017.
U.S. Appl. No. 15/233,835 Restriction Requirement dated Nov. 4, 2016.
U.S. Appl. No. 15/245,054 Office Action dated Mar. 21, 2017.
U.S. Appl. No. 15/245,054 Office Action dated Oct. 19, 2016.
U.S. Appl. No. 15/268,422 Office Action dated Mar. 1, 2019.
U.S. Appl. No. 15/268,422 Restriction Requirement dated Oct. 4, 2018.
U.S. Appl. No. 15/377,547 Final Office Action dated Feb. 8, 2019.
U.S. Appl. No. 15/377,547 Office Action dated Jul. 27, 2018.
U.S. Appl. No. 15/377,547 Office Action dated Mar. 24, 2017.
U.S. Appl. No. 15/377,547 Office Action dated Nov. 30, 2017.
U.S. Appl. No. 15/433,909 Non-Final Office Action dated Feb. 8, 2019.
U.S. Appl. No. 15/433,909 Restriction Requirement dated Sep. 17, 2018.
U.S. Appl. No. 15/602,991 Final Office Action dated Dec. 13, 2018.
U.S. Appl. No. 15/602,991 Notice of Allowance dated Oct. 25, 2017.
U.S. Appl. No. 15/602,991 Office Action dated May 31, 2018.
U.S. Appl. No. 15/602,991 Office Action dated May 31, 2019.
U.S. Appl. No. 15/602,991 Office Action dated Sep. 21, 2017.
U.S. Appl. No. 15/603,013 Office Action dated Jan. 30, 2018.
U.S. Appl. No. 15/603,013 Office Action dated Jul. 10, 2018.
U.S. Appl. No. 15/603,013 Office Action dated Oct. 20, 2017.
U.S. Appl. No. 15/682,100 Office Action dated Jan. 2, 2018.
U.S. Appl. No. 15/682,100 Restriction Requirement dated Nov. 8, 2017.
U.S. Appl. No. 15/709,274 Notice of Allowance dated Apr. 3, 2019.
U.S. Appl. No. 15/729,564 Final Office Action dated Dec. 13, 2018.
U.S. Appl. No. 15/729,564 Office Action dated Jan. 8, 2018.
U.S. Appl. No. 15/729,564 Office Action dated Jun. 6, 2018.
U.S. Appl. No. 15/729,564 Office Action dated May 30, 2019.
U.S. Appl. No. 15/816,995 Restriction Requirement dated Apr. 4, 2019.
U.S. Appl. No. 15/844,395 Restriction Requirement dated May 17, 2019.
U.S. Appl. No. 15/860,445 Final Office Action dated Dec. 13, 2018.
U.S. Appl. No. 15/860,445 Office Action dated May 30, 2018.
U.S. Appl. No. 15/921,479 Restriction Requirement dated May 24, 2019.
U.S. Appl. No. 14/452,429 Office Action dated Apr. 9, 2015.
U.S. Appl. No. 15/151,316Final Office Action dated Feb. 21, 2019.
Vaijayanthi, et al. Recent advances in oligonucleotide synthesis and their applications. Indian J Biochem Biophys. Dec. 2003;40(6):377-91.
Van Den Brulle, et al. A novel solid phase technology for high-throughput gene synthesis. Biotechniques. 2008; 45(3):340-343.
Van Der Werf et al. Limonene-1,2-epoxide hydrolase from Rhodococcus erythropolis DCL14 belongs to a novel class of epoxide hydrolases. J. Bacteriol. 180:5052-5057 (1998).

Van Tassell et al., SNP discovery and allele frequency estimation by deep sequencing of reduced representation libraries. Nature Methods, 5:247-252, 2008.
Vargeese, et al. Efficient activation of nucleoside phosphoramidites with 4,5-dicyanoimidazole during oligonucleotide synthesis. Nucleic Acids Res. Feb. 15, 1998;26(4):1046-50.
Verma et al. Modified oligonucleotides: synthesis and strategy for users. Annu Rev Biochem 67:99-134 (1998).
Vincent, et al. Helicase-dependent isothermal DNA amplification. EMBO Rep. Aug. 2004;5(8):795-800.
Visscher et al., "Construction of multiple-beam optical traps with nanometer-resolution position sensing", IEEE Journal of Selected Topics in Quantum Electronics, vol. 2, No. 4, 1066-1076 (Dec. 1996).
Voldmans Joel et al., "Holding forces of single-particle dielectrophoretic traps." Biophysical Journal, vol. 80, No. 1, 531-541 (Jan. 2001).
Vos, et al. AFLP:A new technique for DNA fingerprinting. Nucleic Acids Res. Nov. 11, 1995;23(21):4407-14.
Wagner et al., "Nucleotides, Part LXV, Synthesis of 2'-Deoxyribonucleoside 5'-Phosphoramidites: New Building Blocks for the Inverse (5'-3')-Oligonucleotide Approach." Helvetica Chimica Acta, 83(8):2023-2035, 2000.
Wah, David A. et al., "Structure of Fok I has implications for DNA cleavage", Proc. Natl. Acad. Sci. USA, vol. 95, 10564-10569 (Sep. 1998).
Wah, David A. et al., "Structure of the multimodular endonuclease Fok I bound to DNA", Nature, vol. 388, 97-100 ( Jul. 1997).
Walker, et al. Strand displacement amplification—an isothermal, in vitro DNA amplification technique. Nucleic Acids Res. Apr. 11, 1992;20(7):1691-6.
Wan et al., Deep Learning for Content-Based Image Retrieval: A comprehensive study. In Proceedings of the 22nd ACM International Conference on Multimedia—Nov. 3-7, 2014, Orlando, FL, p. 157-166, 2014.
Warr et al. Exome Sequencing: current and future perspectives. G3: (Bethesda) 5(8):1543-1550 (2015).
Weber, et al. A modular cloning system for standardized assembly of multigene constructs. PLoS One. Feb. 18, 2011;6(2):e16765. doi: 10.1371/journal.pone.0016765.
Welz, et al. 5-(Benzylmercapto)-1H-tetrazole as activator for 2'-O-TBDMS phosphoramidite building blocks in RNA synthesis. Tetrahedron Lett. 2002; 43(5):795-797.
Westin et al., Anchored multiplex amplification on a microelectronic chip array Nature Biotechnology, 18:199-202 (2000) (abstract only).
Whitehouse, Adrian et al. "Analysis of the mismatch and insertion/deletion binding properties of Thermus thermophilus, HB8, MutS", Biochemical and Biophysical Research Communications, vol. 233, 834-837 (1997).
Wiedenheft et al., RNA-guided genetic silencing systems in bacteria and archaea. Nature, 482:331-338, 2012.
Wijshoff, Herman. Structure and fluid-dynamics in Piezo inkjet printheads. Thesis. Venio, The Netherlands, published 2008, p. 1-185.
Wirtz, Denis, "Direct measurement of the transport properties of a single DNA molecule", Physical Review Letters, vol. 75, No. 12, 2436-2439 (Sep. 18, 1995).
Withers-Martinez, Chrislaine et al., "PCR-based gene synthesis as an efficient approach for expression of the A+ T-rich malaria genome", Protein Engineering, vol. 12, No. 12, 1113-1120 (1999).
Wood, Richard D. et al., "Human DNA repair genes", Science, vol. 291, 1284-1289 (Feb. 16, 2001).
Wosnick, et al. Rapid construction of large synthetic genes: total chemical synthesis of two different versions of the bovine prochymosin gene. Gene. 1987;60(1):115-27.
Wright and Church, An open-source oligomicroarray standard for human and mouse. Nature Biotechnology, 20:1082-1083, 2002.
Wu, et al. "Sequence-Specific Capture of Protein-DNA Complexes for Mass Spectrometric Protein Identification" PLoS ONE. Oct. 20, 2011, vol. 6, No. 10.
Wu, et al. RNA-mediated gene assembly from DNA arrays. Angew Chem Int Ed Engl. May 7, 2012;51(19):4628-32. doi: 10.1002/anie.201109058.

(56) References Cited

OTHER PUBLICATIONS

Wu, et al. Specificity of the nick-closing activity of bacteriophage T4 DNA ligase. Gene. 1989;76(2):245-54.

Wu, Xing-Zheng et al., "An improvement of the on-line electrophoretic concentration method for capillary electrophoresis of proteins an experimental factors affecting he concentration effect", Analytical Sciences, vol. 16, 329-331 (Mar. 2000).

Xiong, et al. A simple, rapid, high-fidelity and cost-effective PCR-based two-step DNA synthesis method for long gene sequences. Nucleic Acids Res. 2004, 32(12):e98.

Xiong et al., Chemical gene synthesis: Strategies, softwares, error corrections, and applications. FEMS Microbiol. Rev., 32:522-540, 2008.

Xiong, et al. Non-polymerase-cycling-assembly-based chemical gene synthesis: Strategies, methods, and progress. Biotechnology Advances. 26(2):121-134, 2008.

Xu et al., Design of 240,000 orthogonal 25mer DNA barcode probes. PNAS, 106(7):2289-2294, 2009.

Yang, et al "Purification, cloning, and characterization of the CEL I nuclease", Biochemistry, 39(13):3533-35, 2000.

Yazdi, et al., A Rewritable, Random-Access DNA-Based Storage System, Scientific Reports, 5, Article No. 14138, 27 pages, 2015.

Yehezkel et al., De novo DNA synthesis using single molecule PCR Nucleic Acids Research, 36(17):e107, 2008.

Yes HMDS vapor prime process application note Prepared by UC Berkeley and University of Texas at Dallas and re-printed by Yield Engineering Systems, Inc., 6 pages (http://www.yieldengineering.com/Portals/0/HMDS%20Application%20Note.pdf (Published online Aug. 23, 2013).

Youil, Rima et al., "Detection of 81 of 81 known mouse Beta-Giobin promoter mutations with T4 Endonuclease VII• The EMC Method", Genomics, 32:431-435, 1996.

Young, et al. Two-step total gene synthesis method. Nucleic Acids Res. 32(7):e59, 2004.

Zhang and Seelig, Dynamic DNA nanotechnology using strand-displacement reactions, Nat. Chem., 3(2):103-113, 2011.

Zheleznaya, et al. Nicking endonucleases. Biochemistry (Mosc). 74(13):1457-66, 2009.

Zheng et al. Manipulating the Stereoselectivity of Limonene Epoxide Hydrolase by Directed Evolution Based on Iterative Saturation Mutagenesis. J. Am. Chem. Soc. 132:15744-15751 (2010).

Zhirnov et al., Nucleic acid memory. Nature Materials, 15:366, 2016.

Zhou, et al. "Establishment and application of a loop-mediated isothermal amplification (LAMP) system for detection of cry1Ac transgenic sugarcane" Scientific Reports May 9, 2014, vol. 4, No. 4912.

Zhou et al., Microfluidic PicoArray synthesis of oligodeoxynucleotides and simultaneous assembling of multiple DNA sequences Nucleic Acids Research, 32(18):5409-5417, 2004.

\* cited by examiner a  Flowcell Open          Flowcell Closed b

Waste Collector

Wafer

Flowcell Body c

Waste Collector

P waste

P inlet

Wafer Seal

Inlet Manifold

Inkjet Assembly

- Inkjet assembly of 10 heads
- Inkjet heads have Silicon orifice plates with 256 nozzles on 254um centers
- 100 micron fly height
- Each head needs access to each well that traverses

Back-End Processing

1. Front-end processing result

2. Inkjet photoresist

3. Oxygen plasma etch back

4. Passive functionalization

5. Photoresist strip

6. Active functionalization

SECTION B-B

REACTION
WELL GROUP
1

**WELL LOCATIONS
WITHIN INDIVIDUAL CLUSTER**

(DEVICE VIEW)

ACTIVE FUNCTIONALIZATION

- Dilute concentration of hydroxyl groups in a sea of passive groups by applying mixed silanes

A 1.00mm

B

500μm

Various functional configurations

— Active    — Passive

A  B  C  D  E  F

1. Uniformly functionalized
2. Sharp top/bottom revolver edges, passive via
3. Topside revolver boarder, passive via
4. Topside cluster boarder, passive via
5. Sharp top revolver edge, active via
6. Sharp top revolver edge, active via + bottom

Resist wicking control structures

Post-litho resist patterns

A

B

C

Post-litho resist patterns

A

B

C

Error Correction Development

Three ECR methods evaluated:
- CorrectASE enzyme (Life Technologies)
- Surveyor enzyme (Transgenomic)
- MutSM2B2 beads (USBiological Life Sciences)

Best performance achieved with CorrectASE – error rate lower than 1 error in 5kb CorrectASE treatment of a 1kb Pioneer gene synthesized from low quality oligos ~ 50um gap, 10min Small section of wafer with an array of posts to increase surface area

SEQUENCE LISTING

<160> NUMBER OF SEQ ID NOS: 81

<210> SEQ ID NO 1
<211> LENGTH: 62
<212> TYPE: DNA
<213> ORGANISM: Artificial Sequence
<220> FEATURE:
<223> OTHER INFORMATION: Description of Artificial Sequence: Synthetic oligonucleotide

```
<220> FEATURE:
<221> NAME/KEY: modified_base
<222> LOCATION: (51)..(52)
<223> OTHER INFORMATION: Thymidine-succinyl hexamide CED phosphoramidite

<400> SEQUENCE: 1
agacaatcaa ccatttgggg tggacagcct tgacctctag acttcggcat ttttttttt      60 tt                                                                   62

<210> SEQ ID NO 2
<211> LENGTH: 112
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (101)..(102)
<223> OTHER INFORMATION: Thymidine-succinyl hexamide CED phosphoramidite

<400> SEQUENCE: 2
cgggatcctt atcgtcatcg tcgtacagat cccgacccat ttgctgtcca ccagtcatgc      60
tagccatacc atgatgatga tgatgatgag aacccgcat tttttttttt tt             112

<210> SEQ ID NO 3
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
atgcggggtt ctcatcatc                                                  19

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
cgggatcctt atcgtcatcg                                                 20

<210> SEQ ID NO 5
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
atgcggggtt ctcatcatc                                                  19

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
```

```
<400> SEQUENCE: 6
cgggatcctt atcgtcatcg                                              20

<210> SEQ ID NO 7
<211> LENGTH: 62
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
atgaccatga ttacggattc actggccgtc gttttacaac gtcgtgactg ggaaaaccct   60
gg                                                                 62

<210> SEQ ID NO 8
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
gccagctggc gaaaggggga tgtgctgcaa ggcgattaag ttgggtaacg ccagggtttt   60
cccagtcacg ac                                                      72

<210> SEQ ID NO 9
<211> LENGTH: 70
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9 cccccttcg ccagctggcg taatagcgaa gaggcccgca ccgatcgccc ttcccaacag    60
ttgcgcagcc                                                         70

<210> SEQ ID NO 10
<211> LENGTH: 69
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
cggcaccgct tctggtgccg gaaaccaggc aaagcgccat tcgccattca ggctgcgcaa   60
ctgttggga                                                          69

<210> SEQ ID NO 11
<211> LENGTH: 70
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
caccagaagc ggtgccggaa agctggctgg agtgcgatct tcctgaggcc gatactgtcg   60
tcgtcccctc                                                         70
```

```
<210> SEQ ID NO 12
<211> LENGTH: 75
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
gataggtcac gttggtgtag atgggcgcat cgtaaccgtg catctgccag tttgagggga      60
cgacgacagt atcgg                                                       75

<210> SEQ ID NO 13
<211> LENGTH: 74
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
cccatctaca ccaacgtgac ctatcccatt acggtcaatc cgccgtttgt tcccacggag      60
aatccgacgg gttg                                                        74

<210> SEQ ID NO 14
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14
gtctggcctt cctgtagcca gctttcatca acattaaatg tgagcgagta acaacccgtc      60
ggattctccg tg                                                          72

<210> SEQ ID NO 15
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
gctggctaca ggaaggccag acgcgaatta tttttgatgg cgttaactcg gcgtttcatc      60
tgtggtgcaa cgg                                                         73

<210> SEQ ID NO 16
<211> LENGTH: 74
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16
caggtcaaat tcagacggca aacgactgtc ctggccgtaa ccgacccagc gcccgttgca      60
ccacagatga aacg                                                        74

<210> SEQ ID NO 17
<211> LENGTH: 72
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 17
cgtttgccgt ctgaatttga cctgagcgca tttttacgcg ccggagaaaa ccgcctcgcg    60
gtgatggtgc tg                                                        72

<210> SEQ ID NO 18
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18
gccgctcatc cgccacatat cctgatcttc cagataactg ccgtcactcc agcgcagcac    60
catcaccgcg ag                                                        72

<210> SEQ ID NO 19
<211> LENGTH: 77
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19
aggatatgtg gcggatgagc ggcattttcc gtgacgtctc gttgctgcat aaaccgacta    60
cacaaatcag cgatttc                                                   77

<210> SEQ ID NO 20
<211> LENGTH: 78
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20
ctccagtaca gcgcggctga atcatcatt aaagcgagtg gcaacatgga aatcgctgat     60
ttgtgtagtc ggtttatg                                                  78

<210> SEQ ID NO 21
<211> LENGTH: 75
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 21
atttcagccg cgctgtactg gaggctgaag ttcagatgtg cggcgagttg cgtgactacc    60
tacgggtaac agttt                                                     75

<210> SEQ ID NO 22
<211> LENGTH: 71
<212> TYPE: DNA
<213> ORGANISM: Artificial Sequence
<220> FEATURE:
<223> OTHER INFORMATION: Description of Artificial Sequence: Synthetic
      oligonucleotide
```

```
<400> SEQUENCE: 22
aaaggcgcgg tgccgctggc gacctgcgtt tcaccctgcc ataaagaaac tgttacccgt      60
aggtagtcac g                                                          71

<210> SEQ ID NO 23
<211> LENGTH: 70
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 23
gcggcaccgc gcctttcggc ggtgaaatta tcgatgagcg tggtggttat gccgatcgcg      60
tcacactacg                                                            70

<210> SEQ ID NO 24
<211> LENGTH: 74
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 24
gatagagatt cgggatttcg gcgctccaca gtttcgggtt ttcgacgttc agacgtagtg      60
tgacgcgatc ggca                                                       74

<210> SEQ ID NO 25
<211> LENGTH: 74
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 25
gagcgccgaa atcccgaatc tctatcgtgc ggtggttgaa ctgcacaccg ccgacggcac      60
gctgattgaa gcag                                                       74

<210> SEQ ID NO 26
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 26
cagcagcaga ccattttcaa tccgcacctc gcggaaaccg acatcgcagg cttctgcttc      60
aatcagcgtg ccg                                                        73

<210> SEQ ID NO 27
<211> LENGTH: 74
<212> TYPE: DNA
<213> ORGANISM: Artificial Sequence
<220> FEATURE:
<223> OTHER INFORMATION: Description of Artificial Sequence: Synthetic
      oligonucleotide
```

```
<400> SEQUENCE: 27
cggattgaaa atggtctgct gctgctgaac ggcaagccgt tgctgattcg aggcgttaac      60
cgtcacgagc atca                                                       74

<210> SEQ ID NO 28
<211> LENGTH: 75
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 28
gcaggatatc ctgcaccatc gtctgctcat ccatgacctg accatgcaga ggatgatgct      60
cgtgacggtt aacgc                                                      75

<210> SEQ ID NO 29
<211> LENGTH: 75
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 29
cagacgatgg tgcaggatat cctgctgatg aagcagaaca actttaacgc cgtgcgctgt      60
tcgcattatc cgaac                                                      75

<210> SEQ ID NO 30
<211> LENGTH: 74
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 30
tccaccacat acaggccgta gcggtcgcac agcgtgtacc acagcggatg gttcggataa      60
tgcgaacagc gcac                                                       74

<210> SEQ ID NO 31
<211> LENGTH: 75
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 31
gctacggcct gtatgtggtg gatgaagcca atattgaaac ccacggcatg gtgccaatga      60
atcgtctgac cgatg                                                      75

<210> SEQ ID NO 32
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide
```

```
<400> SEQUENCE: 32
gcaccattcg cgttacgcgt tcgctcatcg ccggtagcca gcgcggatca tcggtcagac    60
gattcattgg cac                                                      73

<210> SEQ ID NO 33
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 33
cgcgtaacgc gaatggtgca gcgcgatcgt aatcacccga gtgtgatcat ctggtcgctg    60
gggaatgaat cag                                                      73

<210> SEQ ID NO 34
<211> LENGTH: 78
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 34
ggatcgacag atttgatcca gcgatacagc gcgtcgtgat tagcgccgtg gcctgattca    60
ttccccagcg accagatg                                                 78

<210> SEQ ID NO 35
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 35
gtatcgctgg atcaaatctg tcgatccttc ccgcccggtg cagtatgaag gcggcggagc    60
cgacaccacg gc                                                       72

<210> SEQ ID NO 36
<211> LENGTH: 71
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 36
cgggaagggc tggtcttcat ccacgcgcgc gtacatcggg caaataatat cggtggccgt    60
ggtgtcggct c                                                        71

<210> SEQ ID NO 37
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide
```

```
<400> SEQUENCE: 37
tggatgaaga ccagcccttc ccggctgtgc cgaaatggtc catcaaaaaa tggctttcgc    60
tacctggaga gac                                                       73

<210> SEQ ID NO 38
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 38
ccaagactgt tacccatcgc gtgggcgtat tcgcaaagga tcagcgggcg cgtctctcca    60
ggtagcgaaa gcc                                                       73

<210> SEQ ID NO 39
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 39
cgcgatgggt aacagtcttg gcggtttcgc taaatactgg caggcgtttc gtcagtatcc    60
ccgtttacag ggc                                                       73

<210> SEQ ID NO 40
<211> LENGTH: 78
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 40
gccgttttca tcatatttaa tcagcgactg atccacccag tcccagacga agccgccctg    60
taaacgggga tactgacg                                                  78

<210> SEQ ID NO 41
<211> LENGTH: 76
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 41
cagtcgctga ttaaatatga tgaaaacggc aacccgtggt cggcttacgg cggtgatttt    60
ggcgatacgc cgaacg                                                    76

<210> SEQ ID NO 42
<211> LENGTH: 67
<212> TYPE: DNA
<213> ORGANISM: Artificial Sequence
<220> FEATURE:
<223> OTHER INFORMATION: Description of Artificial Sequence: Synthetic
      oligonucleotide
```

```
<400> SEQUENCE: 42
gcggcgtgcg gtcggcaaag accagaccgt tcatacagaa ctggcgatcg ttcggcgtat    60
cgccaaa                                                              67

<210> SEQ ID NO 43
<211> LENGTH: 71
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 43
cgaccgcacg ccgcatccag cgctgacgga agcaaaacac cagcagcagt ttttccagtt    60
ccgtttatcc g                                                         71

<210> SEQ ID NO 44
<211> LENGTH: 79
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 44
ctcgttatcg ctatgacgga acaggtattc gctggtcact tcgatggttt gcccggataa    60
acggaactgg aaaaactgc                                                 79

<210> SEQ ID NO 45
<211> LENGTH: 75
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 45
aatacctgtt ccgtcatagc gataacgagc tcctgcactg gatggtggcg ctggatggta    60
agccgctggc aagcg                                                     75

<210> SEQ ID NO 46
<211> LENGTH: 76
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 46
gttcaggcag ttcaatcaac tgtttacctt gtggagcgac atccagaggc acttcaccgc    60
ttgccagcgg cttacc                                                    76

<210> SEQ ID NO 47
<211> LENGTH: 78
<212> TYPE: DNA
<213> ORGANISM: Artificial Sequence
<220> FEATURE:
<223> OTHER INFORMATION: Description of Artificial Sequence: Synthetic
      oligonucleotide
```

<400> SEQUENCE: 47
caaggtaaac agttgattga actgcctgaa ctaccgcagc cggagagcgc cgggcaactc    60
tggctcacag tacgcgta                                                  78

<210> SEQ ID NO 48
<211> LENGTH: 71
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 48
gcgctgatgt gcccggcttc tgaccatgcg gtcgcgttcg gttgcactac gcgtactgtg    60
agccagagtt g                                                         71

<210> SEQ ID NO 49
<211> LENGTH: 67
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 49
ccgggcacat cagcgcctgg cagcagtggc gtctggcgga aaacctcagt gtgacgctcc    60
ccgccgc                                                              67

<210> SEQ ID NO 50
<211> LENGTH: 71
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 50
ccagctcgat gcaaaaatcc atttcgctgg tggtcagatg cgggatggcg tgggacgcgg    60
cggggagcgt c                                                         71

<210> SEQ ID NO 51
<211> LENGTH: 78
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 51
cgaaatggat ttttgcatcg agctgggtaa taagcgttgg caatttaacc gccagtcagg    60
ctttctttca cagatgtg                                                  78

<210> SEQ ID NO 52
<211> LENGTH: 74
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 52
tgaactgatc gcgcagcggc gtcagcagtt gttttttatc gccaatccac atctgtgaaa    60
gaaagcctga ctgg    74

<210> SEQ ID NO 53
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 53
gccgctgcgc gatcagttca cccgtgcacc gctggataac gacattggcg taagtgaagc    60
gacccgcatt gac    73

<210> SEQ ID NO 54
<211> LENGTH: 71
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 54
ggcctggtaa tggcccgccg ccttccagcg ttcgacccag gcgttagggt caatgcgggt    60
cgcttcactt a    71

<210> SEQ ID NO 55
<211> LENGTH: 70
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 55
cgggccatta ccaggccgaa gcagcgttgt tgcagtgcac ggcagataca cttgctgatg    60
cggtgctgat    70

<210> SEQ ID NO 56
<211> LENGTH: 75
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 56
tccggctgat aaataaggtt ttcccctgat gctgccacgc gtgagcggtc gtaatcagca    60
ccgcatcagc aagtg    75

<210> SEQ ID NO 57
<211> LENGTH: 78
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 57
ggggaaaacc ttatttatca gccggaaaac ctaccggatt gatggtagtg gtcaaatggc     60
gattaccgtt gatgttga                                                   78

<210> SEQ ID NO 58
<211> LENGTH: 75
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 58
ggcagttcag gccaatccgc gccggatgcg gtgtatcgct cgccacttca acatcaacgg     60
taatcgccat ttgac                                                      75

<210> SEQ ID NO 59
<211> LENGTH: 71
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 59
gcggattggc ctgaactgcc agctggcgca ggtagcagag cgggtaaact ggctcggatt     60
agggccgcaa g                                                          71

<210> SEQ ID NO 60
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 60
ggcagatccc agcggtcaaa acaggcggca gtaaggcggt cgggatagtt ttcttgcggc     60
cctaatccga gc                                                         72

<210> SEQ ID NO 61
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 61
gttttgaccg ctgggatctg ccattgtcag acatgtatac cccgtacgtc ttcccgagcg     60
aaaacggtct gc                                                         72

<210> SEQ ID NO 62
<211> LENGTH: 69
<212> TYPE: DNA
<213> ORGANISM: Artificial Sequence
<220> FEATURE:
<223> OTHER INFORMATION: Description of Artificial Sequence: Synthetic
      oligonucleotide
```

```
<400> SEQUENCE: 62
gtcgccgcgc cactggtgtg ggccataatt caattcgcgc gtcccgcagc gcagaccgtt    60
ttcgctcgg                                                            69

<210> SEQ ID NO 63
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 63
accagtggcg cggcgacttc cagttcaaca tcagccgcta cagtcaacag caactgatgg    60
aaaccagcca tc                                                        72

<210> SEQ ID NO 64
<211> LENGTH: 75
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 64
gaaaccgtcg atattcagcc atgtgccttc ttccgcgtgc agcagatggc gatggctggt    60
ttccatcagt tgctg                                                     75

<210> SEQ ID NO 65
<211> LENGTH: 71
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 65
catggctgaa tatcgacggt ttccatatgg ggattggtgg cgacgactcc tggagcccgt    60
cagtatcggc g                                                         71

<210> SEQ ID NO 66
<211> LENGTH: 74
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 66
ttatttttga caccagacca actggtaatg gtagcgaccg gcgctcagct ggaattccgc    60
cgatactgac gggc                                                      74

<210> SEQ ID NO 67
<211> LENGTH: 3075
<212> TYPE: DNA
<213> ORGANISM: Artificial Sequence
<220> FEATURE:
<223> OTHER INFORMATION: Description of Artificial Sequence: Synthetic
      polynucleotide
```

```
<400> SEQUENCE: 67
atgaccatga ttacggattc actggccgtc gttttacaac gtcgtgactg ggaaaaccct       60
ggcgttaccc aacttaatcg ccttgcagca catccccctt tcgccagctg gcgtaatagc      120
gaagaggccc gcaccgatcg cccttcccaa cagttgcgca gcctgaatgg cgaatggcgc      180
tttgcctggt ttccggcacc agaagcggtg ccggaaagct ggctggagtg cgatcttcct      240
gaggccgata ctgtcgtcgt cccctcaaac tggcagatgc acggttacga tgcgcccatc      300
tacaccaacg tgacctatcc cattacggtc aatccgccgt ttgttcccac ggagaatccg      360
acgggttgtt actcgctcac atttaatgtt gatgaaagct ggctacagga aggccagacg      420
cgaattattt ttgatggcgt taactcggcg tttcatctgt ggtgcaacgg cgctgggtc      480 ggttacggcc aggacagtcg tttgccgtct gaatttgacc tgagcgcatt tttacgcgcc      540
ggagaaaacc gcctcgcggt gatggtgctg cgctggagtg acggcagtta tctggaagat      600
caggatatgt ggcggatgag cggcattttc cgtgacgtct cgttgctgca taaaccgact      660
acacaaatca gcgatttcca tgttgccact cgctttaatg atgatttcag ccgcgctgta      720
ctggaggctg aagttcagat gtgcggcgag ttgcgtgact acctacgggt aacagtttct      780
ttatggcagg tgaaacgca ggtcgccagc ggcaccgcgc ctttcggcgg tgaaattatc      840
gatgagcgtg gtggttatgc cgatcgcgtc acactacgtc tgaacgtcga aaacccgaaa      900
ctgtggagcg ccgaaatccc gaatctctat cgtgcggtgg ttgaactgca caccgccgac      960
ggcacgctga ttgaagcaga agcctgcgat gtcggtttcc gcgaggtgcg gattgaaaat     1020
ggtctgctgc tgctgaacgg caagccgttg ctgattcgag gcgttaaccg tcacgagcat     1080
catcctctgc atggtcaggt catggatgag cagacgatgg tgcaggatat cctgctgatg     1140
aagcagaaca actttaacgc cgtgcgctgt tcgcattatc cgaaccatcc gctgtggtac     1200
acgctgtgcg accgctacgg cctgtatgtg gtggatgaag ccaatattga aacccacggc     1260
atggtgccaa tgaatcgtct gaccgatgat ccgcgctggc taccggcgat gagcgaacgc     1320
gtaacgcgaa tggtgcagcg cgatcgtaat cacccgagtg tgatcatctg gtcgctgggg     1380
aatgaatcag gccacggcgc taatcacgac gcgctgtatc gctggataa atctgtcgat     1440 ccttcccgcc cggtgcagta tgaaggcggc ggagccgaca ccacggccac cgatattatt     1500
tgcccgatgt acgcgcgcgt ggatgaagac cagcccttcc cggctgtgcc gaaatggtcc     1560
atcaaaaaat ggcttctgct acctggagag acgcgcccgc tgatcctttg cgaatacgcc     1620
cacgcgatgg gtaacagtct tggcggtttc gctaaatact ggcaggcgtt tcgtcagtat     1680
ccccgtttac agggcggctt cgtctgggac tgggtggatc agtcgctgat taaatatgat     1740
gaaaacggca acccgtggtc ggcttacggc ggtgattttg gcgatacgcc gaacgatcgc     1800
cagttctgta tgaacggtct ggtctttgcc gaccgcacgc cgcatccagc gctgacggaa     1860
gcaaaacacc agcagcagtt tttccagttc cgtttatccg gcaaaccat cgaagtgacc     1920 agcgaatacc tgttccgtca tagcgataac gagctcctgc actggatggt ggcgctggat     1980
ggtaagccgc tggcaagcgg tgaagtgcct ctggatgtcg ctccacaagg taaacagttg     2040
attgaactgc ctgaactacc gcagccgag agcgccgggc aactctggct cacagtacgc     2100
gtagtgcaac cgaacgcgac cgcatggtca gaagccgggc acatcagcgc ctggcagcag     2160
tggcgtctgg cggaaaacct cagtgtgacg ctccccgccg cgtcccacgc catcccgcat     2220
ctgaccacca gcgaaatgga ttttgcatc gagctgggta ataagcgttg gcaatttaac     2280
cgccagtcag gctttctttc acagatgtgg attggcgata aaaaacaact gctgacgccg     2340
```

```
ctgcgcgatc agttcacccg tgcaccgctg gataacgaca ttggcgtaag tgaagcgacc    2400
cgcattgacc ctaacgcctg ggtcgaacgc tggaaggcgg cgggccatta ccaggccgaa    2460
gcagcgttgt tgcagtgcac ggcagataca cttgctgatg cggtgctgat tacgaccgct    2520
cacgcgtggc agcatcaggg gaaaaccttc tttatcagcc ggaaaaccta ccggattgat    2580
ggtagtggtc aaatggcgat taccgttgat gttgaagtgg cgagcgatac accgcatccg    2640
gcgcggattg gcctgaactg ccagctggcg caggtagcag agcgggtaaa ctggctcgga    2700
ttagggccgc aagaaaacta tcccgaccgc cttactgccg cctgttttga ccgctgggat    2760
ctgccattgt cagacatgta tacccgtac gtcttcccga cgcaaaacgg tctgcgctgc    2820
gggacgcgcg aattgaatta tggcccacac cagtggcgcg gcgacttcca gttcaacatc    2880
agccgctaca gtcaacagca actgatgaaa accagccatc gccatctgct gcacgcggaa    2940
gaaggcacat ggctgaatat cgacggtttc catatgggga ttggtggcga cgactcctgg    3000
agcccgtcag tatcggcgga attccagctg agcgccggtc gctaccatta ccagttggtc    3060
tggtgtcaaa aataa                                                     3075
```

<210> SEQ ID NO 68
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 68

```
atgaccatga ttacggattc actggcc                                          27
```

<210> SEQ ID NO 69
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 69

```
ttattttga caccagacca actggtaatg g                                      31
```

<210> SEQ ID NO 70
<211> LENGTH: 931
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 70

```
atgaccatga ttacggattc actggccgtc gttttacaac gtcgtgactg ggaaaaccct      60
ggcgttaccc aacttaatcg ccttgcagca catccccctt tcgccagctg gcgtaatagc     120
gaagaggccc gcaccgatcg cccttcccaa cagttgcgca gcctgaatgg cgaatggcgc     180
tttgcctggt ttccggcacc agaagcggtg ccggaaagct ggctggagtg cgatcttcct     240
gaggccgata ctgtcgtcgt cccctcaaac tggcagatgc acggttacga tgcgcccatc     300
tacaccaacg tgacctatcc cattacggtc aatccgccgt ttgttcccac ggagaatccg     360
acgggttgtt actcgctcac atttaatgtt gatgaaagct ggctacagga aggccagacg     420
cgaattattt ttgatggcgt taactcggcg tttcatctgt ggtgcaacgg gcgctgggtc     480
```

```
ggttacggcc aggacagtcg tttgccgtct gaatttgacc tgagcgcatt tttacgcgcc    540
ggagaaaacc gcctcgcggt gatggtgctg cgctggagtg acggcagtta tctggaagat    600
caggatatgt ggcggatgag cggcattttc cgtgacgtct cgttgctgca taaaccgact    660
acacaaatca gcgatttcca tgttgccact cgctttaatg atgatttcag ccgcgctgta    720
ctggaggctg aagttcagat gtgcggcgag ttgcgtgact acctacgggt aacagtttct    780
ttatggcagg gtgaaacgca ggtcgccagc ggcaccgcgc ctttcggcgg tgaaattatc    840
gatgagcgtg gtggttatgc cgatcgcgtc acactacgtc tgaacgtcga aaacccgaaa    900
ctgtggagcg ccgaaatccc gaatctctat c                                  931

<210> SEQ ID NO 71
<211> LENGTH: 163
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 71
atgaccatga ttacggattc actggccgtc gttttacaac gtcgtgactg ggaaaaccct    60
ggcgttaccc aacttaatcg ccttgcagca catccccctt tcgccagctg gcgtaatagc    120
gaagaggccc gcaccgatcg cccttcccaa cagttgcgca gcc                     163

<210> SEQ ID NO 72
<211> LENGTH: 175
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 72
gataggtcac gttggtgtag atgggcgcat cgtaaccgtg catctgccag tttgagggga    60
cgacgacagt atcggcctca ggaagatcgc actccagcca gctttccggc accgcttctg    120
gtgccggaaa ccaggcaaag cgccattcgc cattcaggct gcgcaactgt tggga         175

<210> SEQ ID NO 73
<211> LENGTH: 176
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 73
cccatctaca ccaacgtgac ctatcccatt acggtcaatc cgccgtttgt tcccacggag    60
aatccgacgg gttgttactc gctcacattt aatgttgatg aaagctggct acaggaaggc    120
cagacgcgaa ttatttttga tggcgttaac tcggcgtttc atctgtggtg caacgg        176

<210> SEQ ID NO 74
<211> LENGTH: 176
<212> TYPE: DNA
<213> ORGANISM: Artificial Sequence
<220> FEATURE:
<223> OTHER INFORMATION: Description of Artificial Sequence: Synthetic
      polynucleotide
```

<400> SEQUENCE: 74

```
gccgctcatc cgccacatat cctgatcttc cagataactg ccgtcactcc agcgcagcac    60
catcaccgcg aggcggtttt ctccggcgcg taaaaatgcg ctcaggtcaa attcagacgg   120
caaacgactg tcctggccgt aaccgaccca gcgcccgttg caccacagat gaaacg       176
```

<210> SEQ ID NO 75
<211> LENGTH: 177
<212> TYPE: DNA
<213> ORGANISM: Artificial Sequence
<220> FEATURE:
<223> OTHER INFORMATION: Description of Artificial Sequence: Synthetic
       polynucleotide

<400> SEQUENCE: 75

```
aggatatgtg gcggatgagc ggcattttcc gtgacgtctc gttgctgcat aaaccgacta    60
cacaaatcag cgatttccat gttgccactc gctttaatga tgatttcagc cgcgctgtac   120
tggaggctga agttcagatg tgcggcgagt tgcgtgacta cctacgggta acagttt      177
```

<210> SEQ ID NO 76
<211> LENGTH: 178
<212> TYPE: DNA
<213> ORGANISM: Artificial Sequence
<220> FEATURE:
<223> OTHER INFORMATION: Description of Artificial Sequence: Synthetic
       polynucleotide

<400> SEQUENCE: 76

```
gatagagatt cgggatttcg gcgctccaca gtttcgggtt ttcgacgttc agacgtagtg    60
tgacgcgatc ggcataacca ccacgctcat cgataatttc accgccgaaa ggcgcggtgc   120
cgctggcgac ctgcgtttca ccctgccata agaaactgt tacccgtagg tagtcacg     178
```

<210> SEQ ID NO 77
<211> LENGTH: 27
<212> TYPE: DNA
<213> ORGANISM: Artificial Sequence
<220> FEATURE:
<223> OTHER INFORMATION: Description of Artificial Sequence: Synthetic
       oligonucleotide

<400> SEQUENCE: 77

```
atgaccatga ttacggattc actggcc                                         27
```

<210> SEQ ID NO 78
<211> LENGTH: 27
<212> TYPE: DNA
<213> ORGANISM: Artificial Sequence
<220> FEATURE:
<223> OTHER INFORMATION: Description of Artificial Sequence: Synthetic
       oligonucleotide

<400> SEQUENCE: 78

```
gatagagatt cgggatttcg gcgctcc                                         27
```

<210> SEQ ID NO 79
<211> LENGTH: 134
<212> TYPE: DNA
<213> ORGANISM: Artificial Sequence
<220> FEATURE:
<223> OTHER INFORMATION: Description of Artificial Sequence: Synthetic
       polynucleotide

```
<400> SEQUENCE: 79
atctttgagt cttctgcttg gtcagacgag tgcatgtgcg tgacaaattg gcgcgaggag    60
ctcgtgtcat tcacaactgc tcttaggcta ctcaggcatg gtgagatgct acggtggttg   120
atggatacct agat                                                    134

<210> SEQ ID NO 80
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 80
cagaagactc aaagatatct aggtatccat caac                               34

<210> SEQ ID NO 81
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 81
gttgatggat acctagatat ctttgagtct tctg                               34
```

DE NOVO SYNTHESIZED GENE LIBRARIES

CROSS-REFERENCE

This application is a continuation of U.S. application Ser. No. 15/377,547, filed Dec. 13, 2016, issued as U.S. Pat. No. 10,384,188 on Aug. 20, 2019, which is a continuation of U.S. application Ser. No. 15/187,721, filed Jun. 20, 2016, issued as U.S. Pat. No. 9,555,388 on Jan. 31, 2017, which is a continuation of U.S. application Ser. No. 14/885,963, filed Oct. 16, 2015, issued as U.S. Pat. No. 9,403,141 on Aug. 2, 2016, which is a continuation of PCT Patent Application No. PCT/US2014/49834 filed on Aug. 5, 2014, which claims priority from U.S. Provisional Application No. 61/862,445, filed Aug. 5, 2013 and U.S. Provisional Application No. 61/862,457, filed Aug. 5, 2013, each of which is incorporated herein its entirety.

SEQUENCE LISTING

The instant application contains a Sequence Listing which has been submitted in ASCII format via EFS-Web. Said ASCII copy, made 44854-701_312 SL.txt and created on Oct. 16, 2015, is 30,873 bytes in size and is hereby incorporated by reference in its entirety.

BACKGROUND OF THE INVENTION

Highly efficient chemical gene synthesis with high fidelity and low cost has a central role in biotechnology and medicine, and in basic biomedical research.

De novo gene synthesis is a powerful tool for basic biological research and biotechnology applications. While various methods are known for the synthesis of relatively short fragments in a small scale, these techniques suffer from scalability, automation, speed, accuracy, and cost. There is a need for devices for simple, reproducible, scalable, less error-prone and cost-effective methods that guarantee successful synthesis of desired genes and are amenable to automation.

SUMMARY OF THE INVENTION

As noted above, there exists a pressing need for methods, devices and systems that can quickly synthesize large gene libraries or relatively longer oligonucleotide fragments efficiently with less error. Similarly, there is also a need for methods that can partition and mix liquid reagents in a microfluidic scale for large numbers of individually addressable reactions in parallel. The present invention addresses these needs and provides related advantages as well.

In one aspect, the present invention provides a gene library as described herein. The gene library comprises a collection of genes. In some embodiments, the collection comprises at least 100 different preselected synthetic genes that can be of at least 0.5 kb length with an error rate of less than 1 in 3000 bp compared to predetermined sequences comprising the genes. In another aspect, the present invention also provides a gene library that comprises a collection of genes. The collection may comprise at least 100 different preselected synthetic genes that can be each of at least 0.5 kb length. At least 90% of the preselected synthetic genes may comprise an error rate of less than 1 in 3000 bp compared to predetermined sequences comprising the genes. Desired predetermined sequences may be supplied by any method, typically by a user, e.g. a user entering data using a computerized system. In various embodiments, synthesized nucleic acids are compared against these predetermined sequences, in some cases by sequencing at least a portion of the synthesized nucleic acids, e.g. using next-generation sequencing methods. In some embodiments related to any of the gene libraries described herein, at least 90% of the preselected synthetic genes comprise an error rate of less than 1 in 5000 bp compared to predetermined sequences comprising the genes. In some embodiments, at least 0.05% of the preselected synthetic genes are error free. In some embodiments, at least 0.5% of the preselected synthetic genes are error free. In some embodiments, at least 90% of the preselected synthetic genes comprise an error rate of less than 1 in 3000 bp compared to predetermined sequences comprising the genes. In some embodiments, at least 90% of the preselected synthetic genes are error free or substantially error free. In some embodiments, the preselected synthetic genes comprise a deletion rate of less than 1 in 3000 bp compared to predetermined sequences comprising the genes. In some embodiments, the preselected synthetic genes comprise an insertion rate of less than 1 in 3000 bp compared to predetermined sequences comprising the genes. In some embodiments, the preselected synthetic genes comprise a substitution rate of less than 1 in 3000 bp compared to predetermined sequences comprising the genes. In some embodiments, the gene library as described herein further comprises at least 10 copies of each synthetic gene. In some embodiments, the gene library as described herein further comprises at least 100 copies of each synthetic gene. In some embodiments, the gene library as described herein further comprises at least 1000 copies of each synthetic gene. In some embodiments, the gene library as described herein further comprises at least 1000000 copies of each synthetic gene. In some embodiments, the collection of genes as described herein comprises at least 500 genes. In some embodiments, the collection comprises at least 5000 genes. In some embodiments, the collection comprises at least 10000 genes. In some embodiments, the preselected synthetic genes are at least 1 kb. In some embodiments, the preselected synthetic genes are at least 2 kb. In some embodiments, the preselected synthetic genes are at least 3 kb. In some embodiments, the predetermined sequences comprise less than 20 bp in addition compared to the preselected synthetic genes. In some embodiments, the predetermined sequences comprise less than 15 bp in addition compared to the preselected synthetic genes. In some embodiments, at least one of the synthetic genes differs from any other synthetic gene by at least 0.1%. In some embodiments, each of the synthetic genes differs from any other synthetic gene by at least 0.1%. In some embodiments, at least one of the synthetic genes differs from any other synthetic gene by at least 10%. In some embodiments, each of the synthetic genes differs from any other synthetic gene by at least 10%. In some embodiments, at least one of the synthetic genes differs from any other synthetic gene by at least 2 base pairs. In some embodiments, each of the synthetic genes differs from any other synthetic gene by at least 2 base pairs. In some embodiments, the gene library as described herein further comprises synthetic genes that are of less than 2 kb with an error rate of less than 1 in 20000 bp compared to preselected sequences of the genes. In some embodiments, a subset of the deliverable genes is covalently linked together. In some embodiments, a first subset of the collection of genes encodes for components of a first metabolic pathway with one or more metabolic end products. In some embodiments, the gene library as described herein further comprises selecting of the one or more metabolic end products, thereby constructing the collection of genes. In some embodiments, the one or more metabolic end products comprise a biofuel. In some embodiments, a second subset of the collection of genes encodes for components of a second metabolic pathway with one or more metabolic end products. In some embodiments, the gene library is in a space that is less than 100 m$^3$. In some embodiments, the gene library is in a space that is less than 1 m$^3$. In some embodiments, the gene library is in a space that is less than 1 m$^3$.

In another aspect, the present invention also provides a method of constructing a gene library. The method comprises the steps of: entering before a first timepoint, in a computer readable non-transient medium at least a first list of genes and a second list of genes, wherein the genes are at least 500 bp and when compiled into a joint list, the joint list comprises at least 100 genes; synthesizing more than 90% of the genes in the joint list before a second timepoint, thereby constructing a gene library with deliverable genes. In some embodiments, the second timepoint is less than a month apart from the first timepoint.

In practicing any of the methods of constructing a gene library as provided herein, the method as described herein further comprises delivering at least one gene at a second timepoint. In some embodiments, at least one of the genes differs from any other gene by at least 0.1% in the gene library. In some embodiments, each of the genes differs from any other gene by at least 0.1% in the gene library. In some embodiments, at least one of the genes differs from any other gene by at least 10% in the gene library. In some embodiments, each of the genes differs from any other gene by at least 10% in the gene library. In some embodiments, at least one of the genes differs from any other gene by at least 2 base pairs in the gene library. In some embodiments, each of the genes differs from any other gene by at least 2 base pairs in the gene library. In some embodiments, at least 90% of the deliverable genes are error free. In some embodiments, the deliverable genes comprises an error rate of less than 1/3000 resulting in the generation of a sequence that deviates from the sequence of a gene in the joint list of genes. In some embodiments, at least 90% of the deliverable genes comprise an error rate of less than 1 in 3000 bp resulting in the generation of a sequence that deviates from the sequence of a gene in the joint list of genes. In some embodiments, genes in a subset of the deliverable genes are covalently linked together. In some embodiments, a first subset of the joint list of genes encode for components of a first metabolic pathway with one or more metabolic end products. In some embodiments, any of the methods of constructing a gene library as described herein further comprises selecting of the one or more metabolic end products, thereby constructing the first, the second or the joint list of genes. In some embodiments, the one or more metabolic end products comprise a biofuel. In some embodiments, a second subset of the joint list of genes encode for components of a second metabolic pathway with one or more metabolic end products. In some embodiments, the joint list of genes comprises at least 500 genes. In some embodiments, the joint list of genes comprises at least 5000 genes. In some embodiments, the joint list of genes comprises at least 10000 genes. In some embodiments, the genes can be at least 1 kb. In some embodiments, the genes are at least 2 kb. In some embodiments, the genes are at least 3 kb. In some embodiments, the second timepoint is less than 25 days apart from the first timepoint. In some embodiments, the second timepoint is less than 5 days apart from the first timepoint. In some embodiments, the second timepoint is less than 2 days apart from the first timepoint. It is noted that any of the embodiments described herein can be combined with any of the methods, devices or systems provided in the current invention.

In another aspect, a method of constructing a gene library is provided herein. The method comprises the steps of: entering at a first timepoint, in a computer readable non-transient medium a list of genes; synthesizing more than 90% of the list of genes, thereby constructing a gene library with deliverable genes; and delivering the deliverable genes at a second timepoint. In some embodiments, the list comprises at least 100 genes and the genes can be at least 500 bp. In still yet some embodiments, the second timepoint is less than a month apart from the first timepoint.

In practicing any of the methods of constructing a gene library as provided herein, in some embodiments, the method as described herein further comprises delivering at least one gene at a second timepoint. In some embodiments, at least one of the genes differs from any other gene by at least 0.1% in the gene library. In some embodiments, each of the genes differs from any other gene by at least 0.1% in the gene library. In some embodiments, at least one of the genes differs from any other gene by at least 10% in the gene library. In some embodiments, each of the genes differs from any other gene by at least 10% in the gene library. In some embodiments, at least one of the genes differs from any other gene by at least 2 base pairs in the gene library. In some embodiments, each of the genes differs from any other gene by at least 2 base pairs in the gene library. In some embodiments, at least 90% of the deliverable genes are error free. In some embodiments, the deliverable genes comprises an error rate of less than 1/3000 resulting in the generation of a sequence that deviates from the sequence of a gene in the list of genes. In some embodiments, at least 90% of the deliverable genes comprise an error rate of less than 1 in 3000 bp resulting in the generation of a sequence that deviates from the sequence of a gene in the list of genes. In some embodiments, genes in a subset of the deliverable genes are covalently linked together. In some embodiments, a first subset of the list of genes encode for components of a first metabolic pathway with one or more metabolic end products. In some embodiments, the method of constructing a gene library further comprises selecting of the one or more metabolic end products, thereby constructing the list of genes. In some embodiments, the one or more metabolic end products comprise a biofuel. In some embodiments, a second subset of the list of genes encode for components of a second metabolic pathway with one or more metabolic end products. It is noted that any of the embodiments described herein can be combined with any of the methods, devices or systems provided in the current invention.

In practicing any of the methods of constructing a gene library as provided herein, in some embodiments, the list of genes comprises at least 500 genes. In some embodiments, the list comprises at least 5000 genes. In some embodiments, the list comprises at least 10000 genes. In some embodiments, the genes are at least 1 kb. In some embodiments, the genes are at least 2 kb. In some embodiments, the genes are at least 3 kb. In some embodiments, the second timepoint as described in the methods of constructing a gene library is less than 25 days apart from the first timepoint. In some embodiments, the second timepoint is less than 5 days apart from the first timepoint. In some embodiments, the second timepoint is less than 2 days apart from the first timepoint. It is noted that any of the embodiments described herein can be combined with any of the methods, devices or systems provided in the current invention.

In another aspect, the present invention also provides a method of synthesizing n-mer oligonucleotides on a substrate. The method comprises a) providing a substrate with resolved loci that are functionalized with a chemical moiety suitable for nucleotide coupling; and b) coupling at least two building blocks to a plurality of growing oligonucleotide chains each residing on one of the resolved loci at a rate of at least 12 nucleotides per hour according to a locus specific predetermined sequence, thereby synthesizing a plurality of oligonucleotides that are n basepairs long. Various embodiments related to the method of synthesizing n-mer oligonucleotides on a substrate are described herein.

In any of the methods of synthesizing n-mer oligonucleotides on a substrate as provided herein, in some embodiments, the methods further comprise coupling at least two building blocks to a plurality of growing oligonucleotide chains each residing on one of the resolved loci at a rate of at least 15 nucleotides per hour. In some embodiments, the method further comprises coupling at least two building blocks to a plurality of growing oligonucleotide chains each residing on one of the resolved loci at a rate of at least 20 nucleotides per hour. In some embodiments, the method further comprises coupling at least two building blocks to a plurality of growing oligonucleotide chains each residing on one of the resolved loci at a rate of at least 25 nucleotides per hour. In some embodiments, at least one resolved locus comprises n-mer oligonucleotides deviating from the locus specific predetermined sequence with an error rate of less than 1/500 bp. In some embodiments, at least one resolved locus comprises n-mer oligonucleotides deviating from the locus specific predetermined sequence with an error rate of less than 1/1000 bp. In some embodiments, at least one resolved locus comprises n-mer oligonucleotides deviating from the locus specific predetermined sequence with an error rate of less than 1/2000 bp. In some embodiments, the plurality of oligonucleotides on the substrate deviate from respective locus specific predetermined sequences at an error rate of less than 1/500 bp. In some embodiments, the plurality of oligonucleotides on the substrate deviate from respective locus specific predetermined sequences at an error rate of less than 1/1000 bp. In some embodiments, the plurality of oligonucleotides on the substrate deviate from respective locus specific predetermined sequences at an error rate of less than 1/2000 bp.

In practicing any of the methods of synthesizing n-mer oligonucleotides on a substrate as provided herein, in some embodiments, the building blocks comprise an adenine, guanine, thymine, cytosine, or uridine group, or a modified nucleotide. In some embodiments, the building blocks comprise a modified nucleotide. In some embodiments, the building blocks comprise dinucleotides or trinucleotides. In some embodiments, the building blocks comprise phosphoramidite. In some embodiments, n of the n-mer oligonucleotides is at least 100. In some embodiments, n is at least 200. In some embodiments, n is at least 300. In some embodiments, n is at least 400. In some embodiments, the surface comprises at least 100,000 resolved loci and at least two of the plurality of growing oligonucleotides can be different from each other.

In some embodiments, the method of synthesizing n-mer oligonucleotides on a substrate as described herein further comprises vacuum drying the substrate before coupling. In some embodiments, the building blocks comprise a blocking group. In some embodiments, the blocking group comprises an acid-labile DMT. In some embodiments, the acid-labile DMT comprises 4,4'-dimethoxytrityl. In some embodiments, the method of synthesizing n-mer oligonucleotides on a substrate as described herein further comprises oxidation or sulfurization. In some embodiments, the method of synthesizing n-mer oligonucleotides on a substrate as described herein further comprises chemically capping uncoupled oligonucleotide chains. In some embodiments, the method of synthesizing n-mer oligonucleotides on a substrate as described herein further comprises removing the blocking group, thereby deblocking the growing oligonucleotide chain. In some embodiments, the position of the substrate during the coupling step is within 10 cm of the position of the substrate during the vacuum drying step. In some embodiments, the position of the substrate during the coupling step is within 10 cm of the position of the substrate during the oxidation step. In some embodiments, the position of the substrate during the coupling step is within 10 cm of the position of the substrate during the capping step. In some embodiments, the position of the substrate during the coupling step is within 10 cm of the position of the substrate during the deblocking step. In some embodiments, the substrate comprises at least 10,000 vias providing fluid communication between a first surface of the substrate and a second surface of the substrate. In some embodiments, the substrate comprises at least 100,000 vias providing fluid communication between a first surface of the substrate and a second surface of the substrate. In some embodiments, the substrate comprises at least 1,000,000 vias providing fluid communication between a first surface of the substrate and a second surface of the substrate. It is noted that any of the embodiments described herein can be combined with any of the methods, devices or systems provided in the current invention.

In another aspect of the present invention, a system for conducting a set of parallel reactions is provided herein. The system comprises: a first surface with a plurality of resolved loci; a capping element with a plurality of resolved reactor caps. In some embodiments, the system aligns the plurality of resolved reactor caps with the plurality of resolved loci on the first surface forming a temporary seal between the first surface and the capping element, thereby physically dividing the loci on the first surface into groups of at least two loci into a reactor associated with each reactor cap. In some embodiments, each reactor holds a first set of reagents.

In some embodiments related to any of the systems for conducting a set of parallel reactions as described herein, upon release from the first surface, the reactor caps retain at least a portion of the first set of reagents. In some embodiments, the portion is about 30%. In some embodiments, the portion is about 90%. In some embodiments, the plurality of resolved loci resides on microstructures fabricated into a support surface. In some embodiments, the plurality of resolved loci is at a density of at least 1 per $mm^2$. In some embodiments, the plurality of resolved loci is at a density of at least 10 per $mm^2$. In some embodiments, the plurality of resolved loci are at a density of at least 100 per $mm^2$. In some embodiments, the microstructures comprise at least two channels in fluidic communication with each other. In some embodiments, the at least two channels comprise two channels with different width. In some embodiments, at least two channels comprise two channels with different length. In some embodiments, at least one of the channels is longer than 100 µm. In some embodiments, at least one of the channels is shorter than 1000 µm. In some embodiments, at least one of the channels is wider than 50 µm in diameter. In some embodiments, at least one of the channels is narrower than 100 µm in diameter. In some embodiments, the system further comprises a second surface with a plurality of resolved loci at a density of at least 0.1 per $mm^2$. In some embodiments, the system further comprises a second surface with a plurality of resolved loci at a density of at least 1 per mm². In some embodiments, the system further comprises a second surface with a plurality of resolved loci at a density of at least 10 per mm².

In some embodiments related to any of the systems for conducting a set of parallel reactions as described herein, the resolved loci of the first surface comprise a coating of reagents. In some embodiments, the resolved loci of the second surface comprise a coating of reagents. In some embodiments, the coating of reagents is covalently linked to the first or second surface. In some embodiments, the coating of reagents comprises oligonucleotides. In some embodiments, the coating of reagents has a surface area of at least 1.45 µm² per 1.0 µm² of planar surface area. In some embodiments, the coating of reagents has a surface area of at least 1.25 µm² per 1.0 µm² of planar surface area. In some embodiments, the coating of reagents has a surface area of at least 1 µm² per 1.0 µm² of planar surface area. In some embodiments, the resolved loci in the plurality of resolved loci comprise a nominal arclength of the perimeter at a density of at least 0.001 µm/µm². In some embodiments, the resolved loci in the plurality of resolved loci comprise a nominal arclength of the perimeter at a density of at least 0.01 µm/µm². In some embodiments, the resolved loci in the plurality of resolved loci of the first surface comprise a high energy surface. In some embodiments, the first and second surfaces comprise a different surface tension with a given liquid. In some embodiments, the high surface energy corresponds to a water contact angle of less than 20 degree. In some embodiments, the plurality of resolved loci are located on a solid substrate comprising a material selected from the group consisting of silicon, polystyrene, agarose, dextran, cellulosic polymers, polyacrylamides, PDMS, and glass. In some embodiments, the capping elements comprise a material selected from the group consisting of silicon, polystyrene, agarose, dextran, cellulosic polymers, polyacrylamides, PDMS, and glass. It is noted that any of the embodiments described herein can be combined with any of the methods, devices or systems provided in the current invention.

In yet another aspect, the present invention also provides an array of enclosures. The array of enclosures comprise: a plurality of resolved reactors comprising a first substrate and a second substrate comprising reactor caps; at least 2 resolved loci in each reactor. In some cases, the resolved reactors are separated with a releasable seal. In some cases, the reactor caps retain at least a part of the contents of the reactors upon release of the second substrate from the first substrate. In some embodiments, the reactor caps on the second substrate have a density of at least 0.1 per mm². In some embodiments, reactor caps on the second substrate have a density of at least 1 per mm². In some embodiments, reactor caps on the second substrate have a density of at least 10 per mm².

In some embodiments related to the array of enclosures as provided herein, the reactor caps retain at least 30% of the contents of the reactors. In some embodiments, the reactor caps retain at least 90% of the contents of the reactors. In some embodiments, the resolved loci are at a density of at least 2/mm². In some embodiments, the resolved loci are at a density of at least 100/mm². In some embodiments, the array of enclosures further comprises at least 5 resolved loci in each reactor. In some embodiments, the array of enclosures as described herein further comprises at least 20 resolved loci in each reactor. In some embodiments, the array of enclosures as described herein further comprises at least 50 resolved loci in each reactor. In some embodiments, the array of enclosures as described herein further comprises at least 100 resolved loci in each reactor.

In some embodiments related to the array of enclosures as described herein, the resolved loci reside on microstructures fabricated into a support surface. In some embodiments, the microstructures comprise at least two channels in fluidic communication with each other. In some embodiments, the at least two channels comprise two channels with different width. In some embodiments, the at least two channels comprise two channels with different length. In some embodiments, at least one of the channels is longer than 100 µm. In some embodiments, at least one of the channels is shorter than 1000 µm. In some embodiments, at least one of the channels is wider than 50 µm in diameter. In some embodiments, at least one of the channels is narrower than 100 µm in diameter. In some embodiments, the microstructures comprise a nominal arclength of the perimeter of the at least two channels that has a density of at least 0.01/square µm. In some embodiments, the microstructures comprise a nominal arclength of the perimeter of the at least two channels that has a density of at least 0.001 µm/square µm. In some embodiments, the resolved reactors are separated with a releasable seal. In some embodiments, the seal comprises a capillary burst valve.

In some embodiments related to the array of enclosures as described herein, the plurality of resolved loci of the first substrate comprise a coating of reagents. In some embodiments, the plurality of resolved loci of the second substrate comprises a coating of reagents. In some embodiments, the coating of reagents is covalently linked to the first or second surface. In some embodiments, the coating of reagents comprises oligonucleotides. In some embodiments, the coating of reagents has a surface area of at least 1 µm² per 1.0 µm² of planar surface area. In some embodiments, the coating of reagents has a surface area of at least 1.25 µm² per 1.0 µm² of planar surface area. In some embodiments, the coating of reagents has a surface area of at least 1.45 µm² per 1.0 µm² of planar surface area. In some embodiments, the plurality of resolved loci of the first substrate comprises a high energy surface. In some embodiments, the first and second substrates comprise a different surface tension with a given liquid. In some embodiments, the surface energy corresponds to a water contact angle of less than 20 degree. In some embodiments, the plurality of resolved loci or the reactor caps are located on a solid substrate comprising a material selected from the group consisting of silicon, polystyrene, agarose, dextran, cellulosic polymers, polyacrylamides, PDMS, and glass. It is noted that any of the embodiments described herein can be combined with any of the methods, devices, arrays or systems provided in the current invention.

In still yet another aspect, the present invention also provides a method of conducting a set of parallel reactions. The method comprises: (a) providing a first surface with a plurality of resolved loci; (b) providing a capping element with a plurality of resolved reactor caps; (c) aligning the plurality of resolved reactor caps with the plurality of resolved loci on the first surface and forming a temporary seal between the first surface and the capping element, thereby physically dividing the loci on the first surface into groups of at least two loci; (d) performing a first reaction, thereby forming a first set of reagents; and (e) releasing the capping element from the first surface, wherein each reactor cap retains at least a portion of the first set of reagents in a first reaction volume. In some embodiments, the portion is about 30%. In some embodiments, the portion is about 90%.

In some embodiments, the method of conducting a set of parallel reactions as described herein further comprises the steps of: (f) providing a second surface with a plurality of resolved loci; (g) aligning the plurality of resolved reactor caps with the plurality of resolved loci on the second surface and forming a temporary seal between the second surface and the capping element, thereby physically dividing the loci on the second surface; (h) performing a second reaction using the portion of the first set of reagents, thereby forming a second set of reagents; and (i) releasing the capping element from the second surface, wherein each reactor cap can retain at least a portion of the second set of reagents in a second reaction volume. In some embodiments, the portion is about 30%. In some embodiments, the portion is about 90%.

In practicing any of the methods of conducting a set of parallel reactions as described herein, the plurality of resolved loci can have a density of at least 1 per $mm^2$ on the first surface. In some embodiments, the plurality of resolved loci have a density of at least 10 per $mm^2$ on the first surface. In some embodiments, the plurality of resolved loci have a density of at least 100 per $mm^2$ on the first surface. In some embodiments, the plurality of resolved reactor caps have a density of at least 0.1 per $mm^2$ on the capping element. In some embodiments, the plurality of resolved reactor caps have a density of at least 1 per $mm^2$ on the capping element. In some embodiments, the plurality of resolved reactor caps have a density of at least 10 per $mm^2$ on the capping element. In some embodiments, the plurality of resolved loci have a density of more than 0.1 per $mm^2$ on the second surface. In some embodiments, the plurality of resolved loci have a density of more than 1 per $mm^2$ on the second surface. In some embodiments, the plurality of resolved loci have a density of more than 10 per $mm^2$ on the second surface.

In practicing any of the methods of conducting a set of parallel reactions as described herein, the releasing of the capping elements from the surface steps such as the releasing steps in (e) and (i) as described herein can be performed at a different velocity. In some embodiments, the resolved loci of the first surface comprise a coating of reagents for the first reaction. In some embodiments, the resolved loci of the second surface comprise a coating of reagents for the second reaction. In some embodiments, the coating of reagents is covalently linked to the first or second surface. In some embodiments, the coating of reagents comprises oligonucleotides. In some embodiments, the coating of reagents has a surface area of at least 1 $\mu m^2$ per 1.0 $\mu m^2$ of planar surface area. In some embodiments, the coating of reagents has a surface area of at least 1.25 $\mu m^2$ per 1.0 $\mu m^2$ of planar surface area. In some embodiments, the coating of reagents has a surface area of at least 1.45 $\mu m^2$ per 1.0 $\mu m^2$ of planar surface area. In some embodiments, the oligonucleotides are at least 25 bp. In some embodiments, the oligonucleotides are at least 200 bp. In some embodiments, the oligonucleotides are at least 300 bp. In some embodiments, the resolved loci of the first surface comprise a high energy surface. In some embodiments, the first and second surfaces comprise a different surface tension with a given liquid. In some embodiments, the surface energy corresponds to a water contact angle of less than 20 degree.

In some embodiments related to the method of conducting a set of parallel reactions as described herein, the plurality of resolved loci or the resolved reactor caps are located on a solid substrate comprising a material selected from the group consisting of silicon, polystyrene, agarose, dextran, cellulosic polymers, polyacrylamides, PDMS, and glass. In some embodiments, the first and second reaction volumes are different. In some embodiments, the first or second reaction comprises polymerase cycling assembly. In some embodiments, the first or second reaction comprises enzymatic gene synthesis, annealing and ligation reaction, simultaneous synthesis of two genes via a hybrid gene, shotgun ligation and co-ligation, insertion gene synthesis, gene synthesis via one strand of DNA, template-directed ligation, ligase chain reaction, microarray-mediated gene synthesis, solid-phase assembly, Sloning building block technology, or RNA ligation mediated gene synthesis. In some embodiments, the methods of conducting a set of parallel reactions as described herein further comprises cooling the capping element. In some embodiments, the method of conducting a set of parallel reactions as described herein further comprises cooling the first surface. In some embodiments, the method of conducting a set of parallel reactions as described herein further comprises cooling the second surface. It is noted that any of the embodiments described herein can be combined with any of the methods, devices, arrays or systems provided in the current invention.

In another aspect, the present invention provides a substrate having a functionalized surface. The substrate having a functionalized surface can comprise a solid support having a plurality of resolved loci. In some embodiments, the resolved loci are functionalized with a moiety that increases the surface energy of the solid support. In some embodiments, the resolved loci are localized on microchannels.

In some embodiments related to the substrate having a functionalized surface as described herein, the moiety is a chemically inert moiety. In some embodiments, the microchannels comprise a volume of less than 1 nl. In some embodiments, the microchannels comprise a density of the nominal arclength of the perimeter of 0.036 $\mu m$/square $\mu m$. In some embodiments, the functionalized surface comprises a nominal surface area of at least 1 $\mu m^2$ per 1.0 $\mu m^2$ of planar surface area of the substrate. In some embodiments, the functionalized surface comprises a nominal surface area of at least 1.25 $\mu m^2$ per 1.0 $\mu m^2$ of planar surface area of the substrate. In some embodiments, the functionalized surface comprises a nominal surface area of at least 1.45 $\mu m^2$ per 1.0 $\mu m^2$ of planar surface area of the substrate. In some embodiments, the resolved loci in the plurality of resolved loci comprise a coating of reagents. In some embodiments, the coating of reagents is covalently linked to the substrate. In some embodiments, the coating of reagents comprises oligonucleotides. In some embodiments, at least one of the microchannels is longer than 100 $\mu m$. In some embodiments, at least one of the microchannels is shorter than 1000 $\mu m$. In some embodiments, at least one of the microchannels is wider than 50 $\mu m$ in diameter. In some embodiments, at least one of the microchannels is narrower than 100 $\mu m$ in diameter. In some embodiments, the surface energy corresponds to a water contact angle of less than 20 degree. In some embodiments, the solid support comprises a material selected from the group consisting of silicon, polystyrene, agarose, dextran, cellulosic polymers, polyacrylamides, PDMS, and glass. In some embodiments, the plurality of resolved loci is at a density of at least 1/$mm^2$. In some embodiments, the plurality of resolved loci is at a density of at least 100/$mm^2$. It is noted that any of the embodiments described herein can be combined with any of the methods, devices, arrays, substrates or systems provided in the current invention.

In another aspect, the present invention also provides a method for synthesizing oligonucleotides on a substrate having a functionalized surface. The method comprises: (a) applying through at least one inkjet pump at least one drop of a first reagent to a first locus of a plurality of loci; (b) applying negative pressure to the substrate; and (c) applying through at least one inkjet pump at least one drop of a second reagent to the first locus.

In practicing any of the methods for synthesizing oligonucleotides on a substrate having a functionalized surface as described herein, the first and second reagents can be different. In some embodiments, the first locus is functionalized with a moiety that increases their surface energy. In some embodiments, the moiety is a chemically inert moiety. In some embodiments, the plurality of loci resides on microstructures fabricated into the substrate surface. In some embodiments, the microstructures comprise at least two channels in fluidic communication with each other. In some embodiments, the at least two channels comprise two channels with different width. In some embodiments, the at least two channels comprise two channels with different length. In some embodiments, at least one of the channels is longer than 100 µm. In some embodiments, at least one of the channels is shorter than 1000 µm. In some embodiments, at least one of the channels is wider than 50 µm in diameter. In some embodiments, at least one of the channels is narrower than 100 µm in diameter. In some embodiments, the substrate surface comprises a material selected from the group consisting of silicon, polystyrene, agarose, dextran, cellulosic polymers, polyacrylamides, PDMS, and glass.

In some embodiments related to the methods for synthesizing oligonucleotides on a substrate having a functionalized surface as described herein, the volume of the drop of the first and/or the second reagents is at least 2 pl. In some embodiments, the volume of the drop is about 40 pl. In some embodiments, the volume of the drop is at most 100 pl. In some embodiments, the microchannels comprise a density of the nominal arclength of the perimeter of at least 0.01 µm/µm$^2$. In some embodiments, the microchannels comprise a density of the nominal arclength of the perimeter of at least 0.001 µm/µm$^2$. In some embodiments, the functionalized surface comprises a nominal surface area of at least 1 µm$^2$ per 1.0 µm$^2$ of planar surface area of the substrate. In some embodiments, the functionalized surface comprises a nominal surface area of at least 1.25 µm$^2$ per 1.0 µm$^2$ of planar surface area of the substrate. In some embodiments, the functionalized surface comprises a nominal surface area of at least 1.45 µm$^2$ per 1.0 µm$^2$ of planar surface area of the substrate. In some embodiments, the pressure surrounding the substrate is reduced to less than 1 mTorr. It is noted that any of the embodiments described herein can be combined with any of the methods, devices, arrays, substrates or systems provided in the current invention.

In some embodiments, the method for synthesizing oligonucleotides on a substrate having a functionalized surface as described herein further comprises coupling at least a first building block originating from the first drop to a growing oligonucleotide chain on the first locus. In some embodiments, the building blocks comprise a blocking group. In some embodiments, the blocking group comprises an acid-labile DMT. In some embodiments, the acid-labile DMT comprises 4,4'-dimethoxytrityl. In some embodiments, the method for synthesizing oligonucleotides on a substrate having a functionalized surface as described herein further comprises oxidation or sulfurization. In some embodiments, the method for synthesizing oligonucleotides on a substrate having a functionalized surface as described herein further comprises chemically capping uncoupled oligonucleotide chains. In some embodiments, the method for synthesizing oligonucleotides on a substrate having a functionalized surface as described herein further comprises removing the blocking group, thereby deblocking the growing oligonucleotide chain. In some embodiments, the position of the substrate during the negative pressure application is within 10 cm of the position of the substrate during the coupling step. In some embodiments, the position of the substrate during the negative pressure application is within 10 cm of the position of the substrate during the oxidation step. In some embodiments, the position of the substrate during the negative pressure application is within 10 cm of the position of the substrate during the capping step. In some embodiments, the position of the substrate during the negative pressure application is within 10 cm of the position of the substrate during the deblocking step. In some embodiments, the first locus resides on a microstructure fabricated into the substrate surface. In some embodiments, at least one reagent for the oxidation step is provided by flooding the microstructure with a solution comprising the at least one reagent. In some embodiments, at least one reagent for the capping step is provided by flooding the microstructure with a solution comprising the at least one reagent. In some embodiments, the first locus resides on a microstructure fabricated into the substrate surface and at least one reagent for the deblocking step can be provided by flooding the microstructure with a solution comprising the at least one reagent. In some embodiments, the method for synthesizing oligonucleotides on a substrate having a functionalized surface as described herein further comprises enclosing the substrate within a sealed chamber. In some embodiments, the sealed chamber allows for purging of liquids from the first locus. In some embodiments, the method for synthesizing oligonucleotides on a substrate having a functionalized surface as described herein further comprises draining a liquid through a drain that is operably linked to the first locus. In some embodiments, after applying the negative pressure to the substrate, the moisture content on the substrate is less than 1 ppm. In some embodiments, the surface energy is increased corresponding to a water contact angle of less than 20 degree. It is noted that any of the embodiments described herein can be combined with any of the methods, devices, arrays, substrates or systems provided in the current invention.

In yet another aspect, the present invention provides a method of depositing reagents to a plurality of resolved loci. The method comprises applying through an inkjet pump at least one drop of a first reagent to a first locus of the plurality of loci; applying through an inkjet pump at least one drop of a second reagent to a second locus of the plurality of resolved loci. In some embodiments, the second locus is adjacent to the first locus. In still some embodiments, the first and second reagents are different. In still yet some embodiments, the first and second loci reside on microstructures fabricated into a support surface. In yet some embodiments, the microstructures comprise at least one channel that is more than 100 µm deep.

In practicing any of the methods of depositing reagents to a plurality of resolved loci as described herein, in some embodiments, the microstructures comprise at least two channels in fluidic communication with each other. In some embodiments, the at least two channels comprise two channels with different width. In some embodiments, the at least two channels comprise two channels with different length. In some embodiments, the first locus receives less than 0.1% of the second reagent and the second locus receives less than 0.1% of the first reagent. In some embodiments, the loci comprise a density of the nominal arclength of the perimeter of at least 0.01 µm/square µm. In some embodiments, the loci comprise a density of the nominal arclength of the perimeter of at least 0.001 µm/square µm. In some embodiments, the first and second loci comprise a coating of reagents. In some embodiments, the coating of reagents is covalently linked to the substrate. In some embodiments, the coating of reagents comprises oligonucleotides. In some embodiments, at least one of the channels is longer than 100 µm. In some embodiments, at least one of the channels is shorter than 1000 µm. In some embodiments, at least one of the channels is wider than 50 µm in diameter. In some embodiments, at least one of the channels is narrower than 100 µm in diameter. In some embodiments, the support surface comprises a material selected from the group consisting of silicon, polystyrene, agarose, dextran, cellulosic polymers, polyacrylamides, PDMS, and glass. In some embodiments, the plurality of resolved loci is at a density of at least 1/mm$^2$. In some embodiments, the plurality of resolved loci is at a density of at least 100/mm$^2$. In some embodiments, the volume of the drop is at least 2 pl. In some embodiments, the volume of the drop is about 40 pl. In some embodiments, the volume of the drop is at most 100 pl. It is noted that any of the embodiments described herein can be combined with any of the methods, devices, arrays, substrates or systems provided in the current invention.

In still yet another aspect, the present invention provides a microfluidic system. The microfluidic system comprises a first surface with a plurality of microwells at a density of at least 10 per mm$^2$; and a droplet inside one of the plurality of microwells. In some embodiments, the droplet inside one of the plurality of microwells has a Reynolds number at a range of about 1-1000. In some embodiments, the plurality of microwells is at a density of at least 1 per mm$^2$. In some embodiments, plurality of microwells is at a density of at least 10 per mm$^2$.

In some embodiments related to the microfluidic system as provided herein, the microfluidic system further comprises an inkjet pump. In some embodiments, the droplet is deposited by the inkjet pump. In some embodiments, the droplet is moving in the lower half of a first microwell dimension. In some embodiments, the droplet is moving in the middle third of a first microwell dimension. In some embodiments, the plurality of microwells is at a density of at least 100 per mm$^2$. In some embodiments, the first microwell dimension is larger than the droplet. In some embodiments, the microwell is longer than 100 µm. In some embodiments, the microwell is shorter than 1000 µm. In some embodiments, the microwell is wider than 50 µm in diameter. In some embodiments, the microwell is narrower than 100 µm in diameter. In some embodiments, the volume of the droplet is at least 2 pl. In some embodiments, the volume of the droplet is about 40 pl. In some embodiments, the volume of the droplet is at most 100 pl. In some embodiments, each of the plurality of microwells is fluidically connected to at least one microchannel. In some embodiments, the at least one microchannel is coated with a moiety that increases surface energy. In some embodiments, the moiety is a chemically inert moiety. In some embodiments, the surface energy corresponds to a water contact angle of less than 20 degree. In some embodiments, the microwells are formed on a solid support comprising a material selected from the group consisting of silicon, polystyrene, agarose, dextran, cellulosic polymers, polyacrylamides, PDMS, and glass. In some embodiments, the microchannels comprise a density of the nominal arclength of the perimeter of at least 0.01 µm/square µm. In some embodiments, the microchannels comprise a density of the nominal arclength of the perimeter of 0.001 µm/µm$^2$. In some embodiments, the surface coated with the moiety comprises a nominal surface area of at least 1 µm$^2$ per 1.0 µm$^2$ of planar surface area of the first surface. In some embodiments, the surface coated with the moiety comprises a nominal surface area of at least 1.25 µm$^2$ per 1.0 µm$^2$ of planar surface area of the first surface. In some embodiments, the surface coated with the moiety comprises a nominal surface area of at least 1.45 µm$^2$ per 1.0 µm$^2$ of planar surface area of the first surface. It is noted that any of the embodiments described herein can be combined with any of the methods, devices, arrays, substrates or systems provided in the current invention. In some embodiments, the droplet comprises a reagent that enables oligonucleotide synthesis. In some embodiments, the reagent is a nucleotide or nucleotide analog.

In another aspect, the present invention provides a method of depositing droplets to a plurality of microwells. The method comprises applying through an inkjet pump at least one droplet to a first microwell of the plurality of microwells. In some cases, the droplet inside one of the plurality of microwells has a Reynolds number at a range of about 1-1000. In some embodiments, the plurality of microwells has a density of at least 1/mm$^2$. In yet some cases, the plurality of microwells has a density of at least 10/mm$^2$.

In practicing any of the methods of depositing droplets to a plurality of microwells as provided herein, the plurality of microwells can have a density of at least 100/mm$^2$. In some embodiments, the microwell is longer than 100 µm. In some embodiments, the microwell is shorter than 1000 µm. In some embodiments, the microwell is wider than 50 µm in diameter. In some embodiments, the microwell is narrower than 100 µm in diameter. In some embodiments, the droplet is applied at a velocity of at least 2 m/sec. In some embodiments, the volume of the droplet is at least 2 pl. In some embodiments, the volume of the droplet is about 40 pl. In some embodiments, the volume of the droplet is at most 100 pl. In some embodiments, each of the plurality of microwells is fluidically connected to at least one microchannel. In some embodiments, the at least one microwell is coated with a moiety that increases surface energy. In some embodiments, the moiety is a chemically inert moiety. In some embodiments, the surface energy corresponds to a water contact angle of less than 20 degree. In some embodiments, the microwells are formed on a solid support comprising a material selected from the group consisting of silicon, polystyrene, agarose, dextran, cellulosic polymers, polyacrylamides, PDMS, and glass. In some embodiments, the microchannels comprise a density of the nominal arclength of the perimeter of at least 0.01 µm/square µm. In some embodiments, the microchannels comprise a density of the nominal arclength of the perimeter of at least 0.001 µm$^2$m/µm$^2$. In some embodiments, the surface coated with the moiety comprises a nominal surface area of at least 1 µm$^2$ per 1.0 µm$^2$ of planar surface area of the first surface. In some embodiments, the surface coated with the moiety comprises a nominal surface area of at least 1.25 µm$^2$ per 1.0 µm$^2$ of planar surface area of the first surface. In some embodiments, the surface coated with the moiety comprises a nominal surface area of at least 1.45 µm$^2$ per 1.0 µm$^2$ of planar surface area of the first surface. In some embodiments, a droplet inside a microwell is traveling in the middle third of the microwell. In some embodiments, a droplet inside a microwell is traveling in the bottom half of the microwell. In some embodiments, droplet comprises a reagent that enables oligonucleotide synthesis. In some embodiments, the reagent is a nucleotide or nucleotide analog. It is noted that any of the embodiments described herein can be combined with any of the methods, devices, arrays, substrates or systems provided in the current invention.

In another aspect, the present invention also provides a method of partitioning. The method of partitioning comprises contacting a first surface comprising a liquid at a first plurality of resolved loci with a second surface comprising a second plurality of resolved loci; determining a velocity of release such that a desired fraction of the liquid can be transferred from the first plurality of resolved loci to the second plurality of resolved loci; and detaching the second surface from the first surface at said velocity. In some embodiments, the first surface comprises a first surface tension with the liquid, and the second surface can comprise a second surface tension with the liquid.

In practicing any of the methods of partitioning as provided herein, a portion of the first surface can be coated with a moiety that increases surface tension. In some embodiments, the moiety is a chemically inert moiety. In some embodiments, the surface tension of the first surface corresponds to a water contact angle of less than 20 degree. In some embodiments, the surface tension of the second surface corresponds to a water contact angle of more than 90 degree. In some embodiments, the first surface comprises a material selected from the group consisting of silicon, polystyrene, agarose, dextran, cellulosic polymers, polyacrylamides, PDMS, and glass. In some embodiments, the plurality of resolved loci comprises a density of the nominal arclength of the perimeter of at least 0.01 $\mu m/\mu m^2$. In some embodiments, the plurality of resolved loci comprises a density of the nominal arclength of the perimeter of at least 0.001 $\mu m/\mu m^2$. In some embodiments, the surface coated with the moiety comprises a nominal surface area of at least 1 $\mu m^2$ per 1.0 $\mu m^2$ of planar surface area of the first surface. In some embodiments, the surface coated with the moiety comprises a nominal surface area of at least 1.25 $\mu m^2$ per 1.0 $\mu m^2$ of planar surface area of the first surface. In some embodiments, the surface coated with the moiety comprises a nominal surface area of at least 1.45 $\mu m^2$ per 1.0 $\mu m^2$ of planar surface area of the first surface. In some embodiments, the first plurality of resolved loci is at a density of at least 1/mm$^2$. In some embodiments, the first plurality of resolved loci is at a density of at least 100/mm$^2$. In some embodiments, the first or the second surface comprises microchannels holding at least a portion of the liquid. In some embodiments, the first or the second surface comprises nanoreactors holding at least a portion of the liquid. In some embodiments, the method of partitioning as described herein further comprises contacting a third surface with a third plurality of resolved loci. In some embodiments, the liquid comprises a nucleic acid. In some embodiments, the desired fraction is more than 30%. In some embodiments, the desired fraction is more than 90%. It is noted that any of the embodiments described herein can be combined with any of the methods, devices, arrays, substrates or systems provided in the current invention.

In yet another aspect, the present invention also provides a method of mixing as described herein. The method comprises: (a) providing a first substrate comprising a plurality of microstructures fabricated thereto; (b) providing a second substrate comprising a plurality of resolved reactor caps; (c) aligning the first and second substrates such that a first reactor cap of the plurality can be configured to receive liquid from n microstructures in the first substrate; and (d) delivering liquid from the n microstructures into the first reactor cap, thereby mixing liquid from the n microstructures forming a mixture.

In practicing any of the methods of mixing as described herein, the plurality of resolved reactor caps can be at a density of at least 0.1/mm$^2$. In some embodiments, the plurality of resolved reactor caps are at a density of at least 1/mm$^2$. In some embodiments, plurality of resolved reactor caps are at a density of at least 10/mm$^2$. In some embodiments, each of the plurality of microstructures can comprise at least two channels of different width. In some embodiments, the at least one of the channels is longer than 100 $\mu$m. In some embodiments, the at least one of the channels is shorter than 1000 $\mu$m. In some embodiments, the at least one of the channels is wider than 50 $\mu$m in diameter. In some embodiments, the at least one of the channels is narrower than 100 $\mu$m in diameter. In some embodiments, the at least one of the channels is coated with a moiety that increases surface energy. In some embodiments, the moiety is a chemically inert moiety. In some embodiments, the microstructures are formed on a solid support comprising a material selected from the group consisting of silicon, polystyrene, agarose, dextran, cellulosic polymers, polyacrylamides, PDMS, and glass. In some embodiments, the microchannels comprise a density of the nominal arclength of the perimeter of at least 0.01 $\mu m$/square $\mu m$. In some embodiments, the microchannels comprise a density of the nominal arclength of the perimeter of at least 0.001 $\mu m/\mu m^2$. In some embodiments, the surface coated with the moiety comprises a nominal surface area of at least 1 $\mu m^2$ per 1.0 $\mu m^2$ of planar surface area of the first surface. In some embodiments, the surface coated with the moiety comprises a nominal surface area of at least 1.25 $\mu m^2$ per 1.0 $\mu m^2$ of planar surface area of the first surface. In some embodiments, the surface coated with the moiety comprises a nominal surface area of at least 1.45 $\mu m^2$ per 1.0 $\mu m^2$ of planar surface area of the first surface. In some embodiments, the plurality of microstructures comprises a coating of reagents. In some embodiments, the coating of reagents is covalently linked to the first surface. In some embodiments, the coating of reagents comprises oligonucleotides. In some embodiments, the microstructures are at a density of at least 1/mm$^2$. In some embodiments, the microstructures are at a density of at least 100/mm$^2$.

In some embodiments related to the methods of mixing as described herein, after step (c), which is aligning the first and second substrates such that a first reactor cap of the plurality can be configured to receive liquid from n microstructures in the first substrate, there is a gap of less than 100 $\mu$m between the first and the second substrates. In some embodiments, after step (c), there is a gap of less than 50 $\mu$m between the first and the second substrates. In some embodiments, after step (c), there is a gap of less than 20 $\mu$m between the first and the second substrates. In some embodiments, after step (c), there is a gap of less than 10 $\mu$m between the first and the second substrates. In some embodiments, the mixture partially spreads into the gap. In some embodiments, the method of mixing further comprises sealing the gap by bringing the first and the second substrate closer together. In some embodiments, one of the two channels is coated with a moiety that increases surface energy corresponding to a water contact angle of less than 20 degree. In some embodiments, the moiety is a chemically inert moiety. In some embodiments, the delivering is performed by pressure. In some embodiments, the volume of the mixture is greater than the volume of the reactor cap. In some embodiments, the liquid comprises a nucleic acid. In some embodiments, n is at least 10. In some embodiments, n is at least 25. In some embodiments, n, the number of microstructures from which the liquid is mixed forming a mixture, can be at least 50. In some embodiments, n is at least 75. In some embodiments, n is at least 100. It is noted that any of the embodiments described herein can be combined with any of the methods, devices, arrays, substrates or systems provided in the current invention.

In yet another aspect, the present invention also provides a method of synthesizing n-mer oligonucleotides on a substrate as described herein. The method comprises: providing a substrate with resolved loci that are functionalized with a chemical moiety suitable for nucleotide coupling; and coupling at least two building blocks to a plurality of growing oligonucleotide chains each residing on one of the resolved loci according to a locus specific predetermined sequence without transporting the substrate between the couplings of the at least two building blocks, thereby synthesizing a plurality of oligonucleotides that are n basepairs long.

In practicing any of the methods of synthesizing n-mer oligonucleotides on a substrate as described herein, the method can further comprise coupling at least two building blocks to a plurality of growing oligonucleotide chains each residing on one of the resolved loci at a rate of at least 12 nucleotides per hour. In some embodiments, the method further comprises coupling at least two building blocks to a plurality of growing oligonucleotide chains each residing on one of the resolved loci at a rate of at least 15 nucleotides per hour. In some embodiments, the method further comprises coupling at least two building blocks to a plurality of growing oligonucleotide chains each residing on one of the resolved loci at a rate of at least 20 nucleotides per hour. In some embodiments, the method further comprises coupling at least two building blocks to a plurality of growing oligonucleotide chains each residing on one of the resolved loci at a rate of at least 25 nucleotides per hour. In some embodiments, at least one resolved locus comprises n-mer oligonucleotides deviating from the locus specific predetermined sequence with an error rate of less than 1/500 bp. In some embodiments, at least one resolved locus comprises n-mer oligonucleotides deviating from the locus specific predetermined sequence with an error rate of less than 1/1000 bp. In some embodiments, at least one resolved locus comprises n-mer oligonucleotides deviating from the locus specific predetermined sequence with an error rate of less than 1/2000 bp. In some embodiments, the plurality of oligonucleotides on the substrate deviate from respective locus specific predetermined sequences at an error rate of less than 1/500 bp. In some embodiments, the plurality of oligonucleotides on the substrate deviate from respective locus specific predetermined sequences at an error rate of less than 1/1000 bp. In some embodiments, the plurality of oligonucleotides on the substrate deviate from respective locus specific predetermined sequences at an error rate of less than 1/2000 bp.

In some embodiments related to the method of synthesizing n-mer oligonucleotides on a substrate as described herein, the building blocks comprise an adenine, guanine, thymine, cytosine, or uridine group, or a modified nucleotide. In some embodiments, the building blocks comprise a modified nucleotide. In some embodiments, the building blocks comprise dinucleotides. In some embodiments, the building blocks comprise phosphoramidite. In some embodiments, n is at least 100. In some embodiments, wherein n is at least 200. In some embodiments, n is at least 300. In some embodiments, n is at least 400. In some embodiments, the substrate comprises at least 100,000 resolved loci and at least two of the plurality of growing oligonucleotides are different from each other. In some embodiments, the method further comprise vacuum drying the substrate before coupling. In some embodiments, the building blocks comprise a blocking group. In some embodiments, the blocking group comprises an acid-labile DMT. In some embodiments, the acid-labile DMT comprises 4,4'-dimethoxytrityl. In some embodiments, the method further comprise oxidation or sulfurization. In some embodiments, the method further comprise chemically capping uncoupled oligonucleotide chains. In some embodiments, the method further comprise removing the blocking group, thereby deblocking the growing oligonucleotide chain. In some embodiments, the substrate comprises at least 10,000 vias providing fluid communication between a first surface of the substrate and a second surface of the substrate. In some embodiments, the substrate comprises at least 100,000 vias providing fluid communication between a first surface of the substrate and a second surface of the substrate. In some embodiments, the substrate comprises at least 1,000,000 vias providing fluid communication between a first surface of the substrate and a second surface of the substrate. It is noted that any of the embodiments described herein can be combined with any of the methods, devices, arrays, substrates or systems provided in the current invention.

In yet another aspect, the present invention also provides a method of constructing a gene library as described herein. The method comprises: entering at a first timepoint, in a computer readable non-transient medium a list of genes, wherein the list comprises at least 100 genes and wherein the genes are at least 500 bp; synthesizing more than 90% of the list of genes, thereby constructing a gene library with deliverable genes; preparing a sequencing library that represents the gene library; obtaining sequence information; selecting at least a subset of the deliverable genes based on the sequence information; and delivering the selected deliverable genes at a second timepoint, wherein the second timepoint is less than a month apart from the first timepoint.

In practicing any of the methods of constructing a gene library as described herein, the sequence information can be obtained via next-generation sequencing. The sequence information can be obtained by Sanger sequencing. In some embodiments, the method further comprises delivering at least one gene at a second timepoint. In some embodiments, at least one of the genes differ from any other gene by at least 0.1% in the gene library. In some embodiments, each of the genes differ from any other gene by at least 0.1% in the gene library. In some embodiments, at least one of the genes differ from any other gene by at least 10% in the gene library. In some embodiments, each of the genes differ from any other gene by at least 10% in the gene library. In some embodiments, at least one of the genes differ from any other gene by at least 2 base pairs in the gene library. In some embodiments, each of the genes differ from any other gene by at least 2 base pairs in the gene library. In some embodiments, at least 90% of the deliverable genes are error free. In some embodiments, the deliverable genes comprise an error rate of less than 1/3000 resulting in the generation of a sequence that deviates from the sequence of a gene in the list of genes. In some embodiments, at least 90% of the deliverable genes comprise an error rate of less than 1 in 3000 bp resulting in the generation of a sequence that deviates from the sequence of a gene in the list of genes. In some embodiments, a subset of the deliverable genes are covalently linked together. In some embodiments, a first subset of the list of genes encode for components of a first metabolic pathway with one or more metabolic end products. In some embodiments, the method further comprises selecting of the one or more metabolic end products, thereby constructing the list of genes. In some embodiments, the one or more metabolic end products comprise a biofuel. In some embodiments, a second subset of the list of genes encode for components of a second metabolic pathway with one or more metabolic end products. In some embodiments, the list comprises at least 500, genes. In some embodiments, the list comprises at least 5000 genes. In some embodiments, the list comprises at least 10000 genes. In some embodiments, the genes are at least 1 kb. In some embodiments, the genes are at least 2 kb. In some embodiments, the genes are at least 3 kb. In some embodiments, the second timepoint is less than 25 days apart from the first timepoint. In some embodiments, the second timepoint is less than 5 days apart from the first timepoint. In some embodiments, the second timepoint is less than 2 days apart from the first timepoint. It is noted that any of the embodiments described herein can be combined with any of the methods, devices, arrays, substrates or systems provided in the current invention.

Provided herein, in some embodiments, is a microfluidic device for nucleic acid synthesis, comprising a substantially planar substrate portion comprising n groupings of m microfluidic connections between opposite surfaces, wherein each one of the n*m microfluidic connections comprises a first channel and a second channel, and wherein the first channel within each of the n groupings is common to all m microfluidic connections, wherein the plurality of microfluidic connections span the substantially planar substrate portion along the smallest dimension of the substrate, and wherein n and m are at least 2. In some embodiments, the second channel is functionalized with a coating that is capable of facilitating the attachment of an oligonucleotide to the device. In some embodiments, the device further comprises a first oligonucleotide that is attached to the second channels in k of the n groupings. In some embodiments, k is 1. In some embodiments, the device further comprises a second oligonucleotide that is attached to 1 of the n groupings. In some embodiments, 1 is 1. In some embodiments, the none of the groupings in the 1 groupings are in the k groupings.

In some embodiments, the oligonucleotide is at least 10 nucleotides, 25 nucleotides, 50 nucleotides, 75 nucleotides, 100 nucleotides, 125 nucleotides, 150 nucleotides, or 200 nucleotides long.

In some embodiments, the first and the second oligonucleotides differ by at least 2 nucleotides, 3 nucleotides, 4 nucleotides, 5 nucleotides, or 10 nucleotides.

In some embodiments, the n*m microfluidic connections are at most 5 mm, 1.5 mm, 1.0 mm, or 0.5 mm long. In some embodiments, the first channel within each of the n groupings is at most 5 mm, 1.5 mm, 1.0 mm, or 0.5 mm long. In some embodiments, the first channel within each of the n groupings is at least 0.05 mm, 0.75 mm, 0.1 mm, 0.2 mm, 0.3 mm, or 0.4 mm long. In some embodiments, the second channel in each of the n*m microfluidic connections is at most 0.2 mm, 0.1 mm, 0.05 mm, 0.04 mm, or 0.03 mm long. In some embodiments, the second channel in each of the n*m microfluidic connections is at least 0.001 mm, 0.005 mm, 0.01 mm, 0.02 mm, or 0.03 mm long. In some embodiments, the cross section of the first channel within each of the n groupings is at least 0.01 mm, 0.025 mm, 0.05 mm, or 0.075 mm. In some embodiments, the cross section of the first channel within each of the n groupings is at most 1 mm, 0.5 mm, 0.25 mm, 0.1 mm, or 0.075 mm. In some embodiments, the cross section of the second channel in each of the n*m microfluidic connections is at least 0.001 mm, 0.05 mm, 0.01 mm, 0.015 mm, or 0.02 mm. In some embodiments, the cross section of the second channel in each of the n*m microfluidic connections is at most 0.25 mm, 0.125 mm, 0.050 mm, 0.025 mm, 0.02 mm. In some embodiments, the standard deviation in the cross section of the second channels in each of the n*m microfluidic connections is less than 25%, 20%, 15%, 10%, 5%, or 1% of the mean of the cross section. In some embodiments, the variation in the cross section within at least 90% of the second channels of the n*m microfluidic connections is at most 25%, 20%, 15%, 10%, 5%, or 1%.

In some embodiments, n is at least 10, 25, 50, 100, 1000, or 10000. In some embodiments, m is at least 3, 4, or 5.

In some embodiments, the substrate comprises at least 5%, 10%, 25%, 50%, 80%, 90%, 95%, or 99% silicon.

In some embodiments, at least 90% of the second channels of the n*m microfluidic connections is functionalized with a moiety that increases surface energy. In some embodiments, the surface energy is increased to a level corresponding to a water contact angle of less than 75, 50, 30, or 20 degrees.

In some embodiments, the aspect ratio for at least 90% of the second channels of the n*m microfluidic connections is less than 1, 0.5, or 0.3. In some embodiments, the aspect ratio for at least 90% of the first channels in the n groupings is less than 0.5, 0.3, or 0.2.

In some embodiments, the total length of at least 10%, 25%, 50%, 75%, 90%, or 95% of the n*m fluidic connections are within 10%, 20%, 30%, 40%, 50%, 100%, 200%, 500%, or 1000% of the smallest dimension of the substantially planar substrate.

In some embodiments, the substantially planar portion of the device is fabricated from a SOI wafer.

In another aspect, the invention relates to a method of nucleic acid amplification, comprising: (a) providing a sample comprising n circularized single stranded nucleic acids, each comprising a different target sequence; (b) providing a first adaptor that is hybridizable to at least one adaptor hybridization sequence on m of the n circularized single stranded nucleic acids; (c) providing conditions suitable for extending the first adaptor using the m circularized single stranded nucleic acids as a template, thereby generating m single stranded amplicon nucleic acids, wherein each of the m single stranded amplicon nucleic acids comprises a plurality of replicas of the target sequence from its template; (d) providing a first auxiliary oligonucleotide that is hybridizable to the first adaptor; and (e) providing a first agent under conditions suitable for the first agent to cut the m single stranded amplicon nucleic acids at a plurality of cutting sites, thereby generating a plurality of single stranded replicas of the target sequences in the m circularized single stranded nucleic acids. In some embodiments, n or m is at least 2. In some embodiments, n or m is at least 3, 4, 5, 6, 7, 8, 9, 10, 15, 20, 25, 50, 75, 100, 150, 200, 300, 400, or 500. In some embodiments, m is less than n. In some embodiments, the sample comprising the n circularized single stranded nucleic acid is formed by providing at least n linear single stranded nucleic acids, each comprising one of the different target sequences and circularizing the n linear single stranded nucleic acids, thereby generating the n circularized single stranded nucleic acids. In some embodiments, the first adaptor is hybridizable to both ends of the n linear single stranded nucleic acids concurrently. In some embodiments, the different target sequences in the n linear single stranded nucleic acids are flanked by a first and a second adaptor hybridization sequence. In some embodiments, the at least n linear single stranded nucleic acids are generated by de novo oligonucleotide synthesis. In some embodiments, the first adaptor hybridization sequence in each of the n linear single stranded nucleic acids differ by no more than two nucleotide bases. In some embodiments, the first or the second adaptor hybridization sequence is at least 5 nucleotides long. In some embodiments, the first or the second adaptor hybridization sequence is at most 75, 50, 45, 40, 35, 30, or 25 nucleotides long. In some embodiments, the ends of the n linear single stranded nucleic acids pair with adjacent bases on the first adaptor when the first adaptor is hybridized to the both ends of the linear single stranded nucleic acid concurrently. In some embodiments, the locations of the plurality of cutting sites are such that the adaptor hybridization sequence is severed from at least 5% of a remainder sequence portion of the m circularized single stranded nucleic acid replicas. In some embodiments, at least 5% of the sequence of the m circularized single stranded nucleic acid replicas other than the at least one adaptor hybridization sequence remains uncut. In some embodiments, the locations of the plurality of cutting sites are outside the at least one adaptor hybridization sequence. In some embodiments, the locations of the plurality of cutting sites are independent of the target sequences. In some embodiments, the locations of the plurality of cutting sites are determined by at least one sequence element within the sequence of the first adaptor or the first auxiliary oligonucleotide. In some embodiments, the sequence element comprises a recognition site for a restriction endonuclease. In some embodiments, the first auxiliary oligonucleotide or the first adaptor oligonucleotide comprises a recognition site for a Type IIS restriction endonuclease. In some embodiments, the recognition sites are at least 1, 2, 3, 4, 5, 6, 7, 8, 9, or 10 nucleotides away from the cutting sites. In some embodiments, the plurality of cutting sites are at junctures of single and double stranded nucleic acids. In some embodiments, the double stranded nucleic acids comprise the first adaptor and the first auxiliary oligonucleotide. In some embodiments, the single stranded nucleic acids consists essentially of the m different target sequences. In some embodiments, the m different target sequences have at most 95% pairwise similarity. In some embodiments, the m different target sequences have at most 90% pairwise similarity. In some embodiments, the m different target sequences have at most 80% pairwise similarity. In some embodiments, the m different target sequences have at most 50% pairwise similarity. In some embodiments, generating the m single stranded amplicon nucleic acid comprises strand displacement amplification. In some embodiments, the first auxiliary oligonucleotide comprises an affinity tag. In some embodiments, the affinity tag comprises biotin or biotin derivative. In some embodiments, the method further comprises isolating double stranded nucleic acids from the sample. In some embodiments, the isolating comprises affinity purification, chromatography, or gel purification. In some embodiments, the first agent comprises a restriction endonuclease. In some embodiments, the first agent comprises at least two restriction endonucleases. In some embodiments, the first agent comprises a Type IIS restriction endonuclease. In some embodiments, the first agent comprises a nicking endonuclease. In some embodiments, the first agent comprises at least two nicking endonucleases. In some embodiments, the first agent comprises at least one enzyme selected from the group consisting of MlyI, SchI, AlwI, BccI, BceAI, BsmAI, BsmFI, FokI, HgaI, PleI, SfaNI, BfuAI, BsaI, BspMI, BtgZI, EarI, BspQI, SapI, SgeI, BceFI, BslFI, BsoMAI, Bst71I, FaqI, AceIII, BbvII, BveI, LguI, BfuCI, DpnII, FatI, MboI, MluCI, Sau3AI, Tsp509I, BssKI, PspGI, StyD4I, Tsp45I, AoxI, BscFI, Bsp143I, BssMI, BseENII, BstMBI, Kzo9I, NedII, Sse9I, TasI, TspEI, AjnI, BstSCI, EcoRII, MaeIII, NmuCI, Psp6I, Mn1I, BspCNI, BsrI, BtsCI, HphI, HpyAV, MboII, AcuI, BciVI, BmrI, BpmI, BpuEI, BseRI, BsgI, BsmI, BsrDI, BtsI, EciI, MmeI, NmeAIII, Hin4II, TscAI, Bce83I, BmuI, BsbI, BscCI, NlaIII, Hpy99I, TspRI, FaeI, Hin1II, Hsp92II, SetI, TaiI, TscI, TscAI, TseFI, Nb.BsrDI, Nb.BtsI, AspCNI, BscGI, BspNCI, EcoHI, FinI, TsuI, UbaF11I, UnbI, Vpak11AI, BspGI, DrdII, Pfl1108I, UbaPI, Nt.AlwI, Nt.BsmAI, Nt.BstNBI, and Nt.BspQI, and variants thereof. In some embodiments, the first agent comprises essentially the same function, recognizes the same or essentially the same recognition sequence, or cuts at the same or essentially same cutting site, as any of the listed first agents and variants. In some embodiments, the at least two restriction enzymes comprise MlyI and BciVI or BfuCI and MlyI. In some embodiments, the method further comprises (a) partitioning the sample into a plurality of fractions; (b) providing at least one fraction with a second adaptor that is hybridizable to at least one adaptor hybridization sequence on k of the n different circularized single stranded nucleic acids; (c) providing conditions suitable for extending the second adaptor using the k circularized single stranded nucleic acids as a template, thereby generating k single stranded amplicon nucleic acids, wherein the second single stranded amplicon nucleic acid comprises a plurality of replicas of the target sequence from its template; (d) providing a second auxiliary oligonucleotide that is hybridizable to the second adaptor; and (e) providing a second agent under conditions suitable for the agent to cut the k single stranded amplicon nucleic acids at a second plurality of cutting sites, thereby generating a plurality of single stranded replicas of the target sequences in the k circularized single stranded nucleic acids. In some embodiments, the first and the second adaptors are the same. In some embodiments, the first and the second auxiliary oligonucleotides are the same. In some embodiments, the first and the second agents are the same. In some embodiments, k+m is less than n. In some embodiments, k is at least 2. In some embodiments, the sample comprising the n circularized single stranded nucleic acid is formed by single stranded nucleic acid amplification. In some embodiments, the single stranded nucleic acid amplification comprises: (a) providing a sample comprising at least m circularized single stranded precursor nucleic acids; (b) providing a first precursor adaptor that is hybridizable to the m circularized single stranded precursor nucleic acids; (c) providing conditions suitable for extending the first precursor adaptor using the m circularized single stranded precursor nucleic acids as a template, thereby generating m single stranded precursor amplicon nucleic acids, wherein the single stranded amplicon nucleic acid comprises a plurality of replicas of the m circularized single stranded precursor nucleic acid; (d) providing a first precursor auxiliary oligonucleotide that is hybridizable to the first precursor adaptor; and (e) providing a first precursor agent under conditions suitable for the first precursor agent to cut the first single stranded precursor amplicon nucleic acid at a plurality of cutting sites, thereby generating the m linear precursor nucleic acids. In some embodiments, the method further comprises circularizing the m linear precursor nucleic acids, thereby forming replicas of the m circularized single stranded precursor nucleic acids. In some embodiments, the m circularized single stranded precursor nucleic acid is amplified by at least 10, 100, 250, 500, 750, 1000, 1500, 2000, 3000, 4000, 5000, 10000-fold, or more in single stranded replicas. In some embodiments, at least one of the m circularized single stranded nucleic acids is at a concentration of about or at most about 100 nM, 10 nM, 1 nM, 50 pM, 1 pM, 100 fM, 10 fM, 1 fM, or less. In some embodiments, circularizing comprises ligation. In some embodiments, ligation comprises the use of a ligase selected from the group consisting of T4 DNA ligase, T3 DNA ligase, T7 DNA ligase, *E. coli* DNA ligase, Taq DNA ligase, and 9N DNA ligase.

In yet a further aspect, the invention, in various embodiments relates to a kit comprising: (a) a first adaptor; (b) a first auxiliary oligonucleotide that is hybridizable to the adaptor; (c) a ligase; and (d) a first cleaving agent, comprising at least one enzyme selected from the group consisting of MlyI, SchI, AlwI, BccI, BceAI, BsmAI, BsmFI, FokI, HgaI, PleI, SfaNI, BfuAI, BsaI, BspMI, BtgZI, EarI, BspQI, SapI, SgeI, BceFI, BslFI, BsoMAI, Bst71I, FaqI, AceIII, BbvII, BveI, LguI, BfuCI, DpnII, FatI, MboI, MluCI, Sau3AI, Tsp509I, BssMI, PspGI, StyD4I, Tsp45I, AoxI, BscFI, Bsp143I, BssMI, BseENII, BstMBI, Kzo9I, NedII, Sse9I, TasI, TspEI, AjnI, BstSCI, EcoRII, MaeIII, NmuCI, Psp6I, MnlI, BspCNI, BsrI, BtsCI, HphI, HpyAV, MboII, AcuI, BciVI, BmrI, BpmI, BpuEI, BseRI, BsgI, BsmI, BsrDI, BtsI, EciI, MmeI, NmeAIII, Hin4II, TscAI, Bce83I, BmuI, BsbI, BscCI, NlaIII, Hpy99I, TspRI, FaeI, Hin1II, Hsp92II, SetI, TaiI, TscI, TscAI, TseFI, Nb.BsrDI, Nb.BtsI, AspCNI, BscGI, BspNCI, EcoHI, FinI, TsuI, UbaF11I, UnbI, Vpak11AI, BspGI, DrdII, Pfl1108I, UbaPI, Nt.AlwI, Nt.BsmAI, Nt.BstNBI, and Nt.BspQI, and variants thereof. In some embodiments, the first agent comprises essentially the same function, recognizes the same or essentially the same recognition sequence, or cuts at the same or essentially same cutting site as any of the listed first agents and variants. In some embodiments, the kit further comprises a second cleaving agent. In some embodiments, the second cleaving agent comprises and enzyme selected from the group consisting of MlyI, SchI, AlwI, BccI, BceAI, BsmAI, BsmFI, FokI, HgaI, PleI, SfaNI, BfuAI, BsaI, BspMI, BtgZI, EarI, BspQI, SapI, SgeI, BceFI, BslFI, BsoMAI, Bst71I, FaqI, AceIII, BbvII, BveI, LguI, BfuCI, DpnII, FatI, MboI, MluCI, Sau3AI, Tsp509I, BssMI, PspGI, StyD4I, Tsp45I, AoxI, BscFI, Bsp143I, BssMI, BseENII, BstMBI, Kzo9I, NedII, Sse9I, TasI, TspEI, AjnI, BstSCI, EcoRII, MaeIII, NmuCI, Psp6I, MnlI, BspCNI, BsrI, BtsCI, HphI, HpyAV, MboII, AcuI, BciVI, BmrI, BpmI, BpuEI, BseRI, BsgI, BsmI, BsrDI, BtsI, EciI, MmeI, NmeAIII, Hin4II, TscAI, Bce83I, BmuI, BsbI, BscCI, NlaIII, Hpy99I, TspRI, FaeI, Hin1II, Hsp92II, SetI, TaiI, TscI, TscAI, TseFI, Nb.BsrDI, Nb.BtsI, AspCNI, BscGI, BspNCI, EcoHI, FinI, TsuI, UbaF11I, UnbI, Vpak11AI, BspGI, DrdII, Pfl1108I, UbaPI, Nt.AlwI, Nt.BsmAI, Nt.BstNBI, and Nt.BspQI, and variants thereof. In some embodiments, the second agent comprises essentially the same function, recognizes the same or essentially the same recognition sequence, or cuts at the same or essentially same cutting site as any of the listed second agents and variants. In some embodiments, the first cleaving agents comprises MlyI. In some embodiments, the second cleaving agent comprises BciVI or BfuCI.

In yet another aspect, the invention relates to a method of nucleic acid amplification, comprising: (a) providing a sample comprising n circularized single stranded nucleic acids, each comprising a different target sequence; (b) providing a first adaptor that is hybridizable to at least one adaptor hybridization sequence on m of the n circularized single stranded nucleic acids; (c) providing conditions suitable for extending the first adaptor using the m circularized single stranded nucleic acids as a template, thereby generating m single stranded amplicon nucleic acids, wherein each of the m single stranded amplicon nucleic acids comprises a plurality of replicas of the target sequence from its template; (d) generating double stranded recognition sites for a first agent on the m single stranded amplicon nucleic acids; and (e) providing the first agent under conditions suitable for the first agent to cut the m single stranded amplicon nucleic acids at a plurality of cutting sites, thereby generating a plurality of single stranded replicas of the target sequences in the m circularized single stranded nucleic acids. In some embodiments, the double stranded recognition sites comprise a first portion of the first adaptor on a first strand of the double stranded recognition sites and a second strand of the first adaptor on the second strand of the double stranded recognition sites. In some embodiments, the adaptor comprises a palindromic sequence. In some embodiments, the double stranded recognition sites are generated by hybridizing the first and second portions of the first adaptor to each other. In some embodiments, the m single stranded amplicon nucleic acids comprise a plurality of double stranded self-hybridized regions.

In a yet further aspect, the invention relates to a method for generating a long nucleic acid molecule, the method comprising the steps of: (a) providing a plurality of nucleic acids immobilized on a surface, wherein said plurality of nucleic acids comprises nucleic acids having overlapping complementary sequences; (b) releasing said plurality of nucleic acids into solution; and (c) providing conditions promoting: i) hybridization of said overlapping complementary sequences to form a plurality of hybridized nucleic acids; and ii) extension or ligation of said hybridized nucleic acids to synthesize the long nucleic acid molecule.

In another aspect, the invention relates to an automated system capable of processing one or more substrates, comprising: an inkjet print head for spraying a microdroplet comprising a chemical species on a substrate; a scanning transport for scanning the substrate adjacent to the print head to selectively deposit the microdroplet at specified sites; a flow cell for treating the substrate on which the microdroplet is deposited by exposing the substrate to one or more selected fluids; an alignment unit for aligning the substrate correctly relative to the print head each time when the substrate is positioned adjacent to the print head for deposition; and not comprising a treating transport for moving the substrate between the print head and the flow cell for treatment in the flow cell, wherein said treating transport and said scanning transport are different elements.

In yet another aspect, the invention relates to an automated system for synthesizing oligonucleotides on a substrate, said automated system capable of processing one or more substrates, comprising: an inkjet print head for spraying a solution comprising a nucleoside or activated nucleoside on a substrate; a scanning transport for scanning the substrate adjacent to the print head to selectively deposit the nucleoside at specified sites; a flow cell for treating the substrate on which the monomer is deposited by exposing the substrate to one or more selected fluids; an alignment unit for aligning the substrate correctly relative to the print head each time when the substrate is positioned adjacent to the print head for deposition; and not comprising a treating transport for moving the substrate between the print head and the flow cell for treatment in the flow cell, wherein said treating transport and said scanning transport are different elements.

In yet a further aspect, the invention relates to an automated system comprising: an inkjet print head for spraying a microdroplet comprising a chemical species on a substrate; a scanning transport for scanning the substrate adjacent to the print head to selectively deposit the microdroplet at specified sites; a flow cell for treating the substrate on which the microdroplet is deposited by exposing the substrate to one or more selected fluids; and an alignment unit for aligning the substrate correctly relative to the print head each time when the substrate is positioned adjacent to the print head for deposition; and wherein the system does NOT comprise a treating transport for moving the substrate between the print head and the flow cell for treatment in the flow cell.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 1A illustrates an example process for oligonucleotide synthesis on a substrate using an inkjet printer; FIG. 1B illustrates an example process for gene amplification in a resolved enclosure, or a nanoreactor. FIG. 1C illustrates an example of the use of a plurality of wafers linking microfluidic reactions for oligonucleotide synthesis and gene assembly in parallel.

In FIG. 2C, synthesized genes are cloned prior to shipment (FIG. 2C).

FIG. 9 part B illustrates a cross-sectional view of an exemplary flowcell and waste collector assembly. FIG. 9 part C illustrates a magnified cross-sectional view of an exemplary flowcell and waste collector assembly.

FIG. 10 part B illustrates a sintered metal insert in between a substrate (wafer) and the vacuum chuck and an optional thermal control element incorporated into the receiving element. FIG. 10 part C illustrates a cross-sectional view of the single groove vacuum chuck exemplified in FIG. 10 part A.

FIG. 35 part B illustrates a close-up view of the nanowells illustrated in FIG. 35 part A.

FIG. 36 part A illustrates a uniformly functionalized surface. FIG. 36 parts B-F illustrate differentially functionalized surfaces in various configurations.

FIG. 40 part A illustrates a bright field view of a post-lithographic resist pattern. FIG. 40 part B illustrates a dark field view of a post-lithographic resist pattern. FIG. 40 part C illustrates a cross-sectional schematic view of a post-lithographic resist pattern.

FIG. 41 part A illustrates a bright field view of a post-lithographic resist pattern. FIG. 41 part B illustrates a dark field view of a post-lithographic resist pattern. FIG. 41 part C illustrates a cross-sectional schematic view of a post-lithographic resist pattern.

FIG. 42 part A illustrates a bright field view. FIG. 42 part B illustrates a dark field view. FIG. 42 part C illustrates a cross-sectional schematic view.

FIG. 43 part A illustrates a bright field view of the Keratin chip fully loaded with DMSO. Hydrophilic and hydrophobic regions are indicated. FIG. 43 part B illustrates a dark field view of the Keratin chip fully loaded with DMSO. FIG. 43 part C illustrates a cross-sectional schematic view of the Keratin chip fully loaded with DMSO, indicating spontaneous wetting of the revolvers.

FIG. 53 part A illustrates a bright field view. FIG. 53 part B illustrates a dark field view. FIG. 53 part C illustrates a cross-sectional schematic view of the surface functionalization pattern and an aqueous fluid bulging out avoiding hydrophobic regions.

FIG. 56 part A depicts a line source/line drain design for a flowcell.

FIG. 56 part B depicts a point source/point drain design for a flowcell.

FIG. 58 part A shows oligos concentrated in a liquid in the revolver channels, and few or no oligonucleotides in a nanoreactor chamber. FIG. 58 part B schematizes oligonucleotides uniformly distributed through liquid in revolver chambers and in a nanoreactor chamber at a later time point relative to FIG. 58 part A.

FIG. 60 part A depicts a device in which oligos were synthesized. Wells 1-10 are marked. FIG. 60 part B depicts analysis of the genes assembled in the wells in FIG. 60 part A. Peaks corresponding to the gene in each well are labeled with the well number. FIG. 60 part C depicts electrophoresis of the oligos analyzed in FIG. 60 part B.

FIG. 61 part A presents a full, angled view of a block as disclosed herein. FIG. 61 part B presents an angled view of a cross-sectional slice through a block as disclosed herein.

DETAILED DESCRIPTION OF THE INVENTION

Figure 1A:
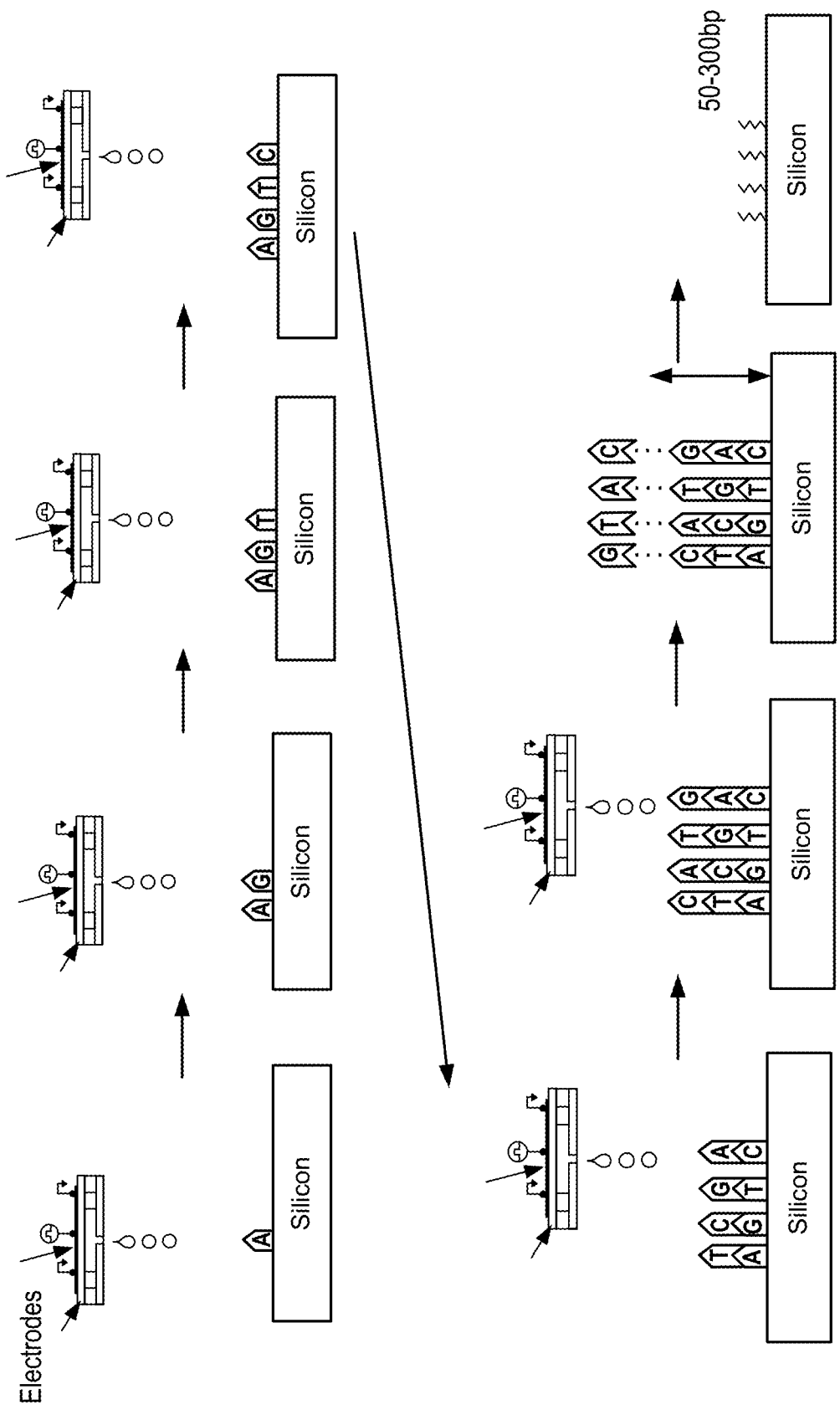
FIGS. 1A-1C demonstrate an example process outlining the gene synthesis and nanoreactor technologies.
Figure 1B:
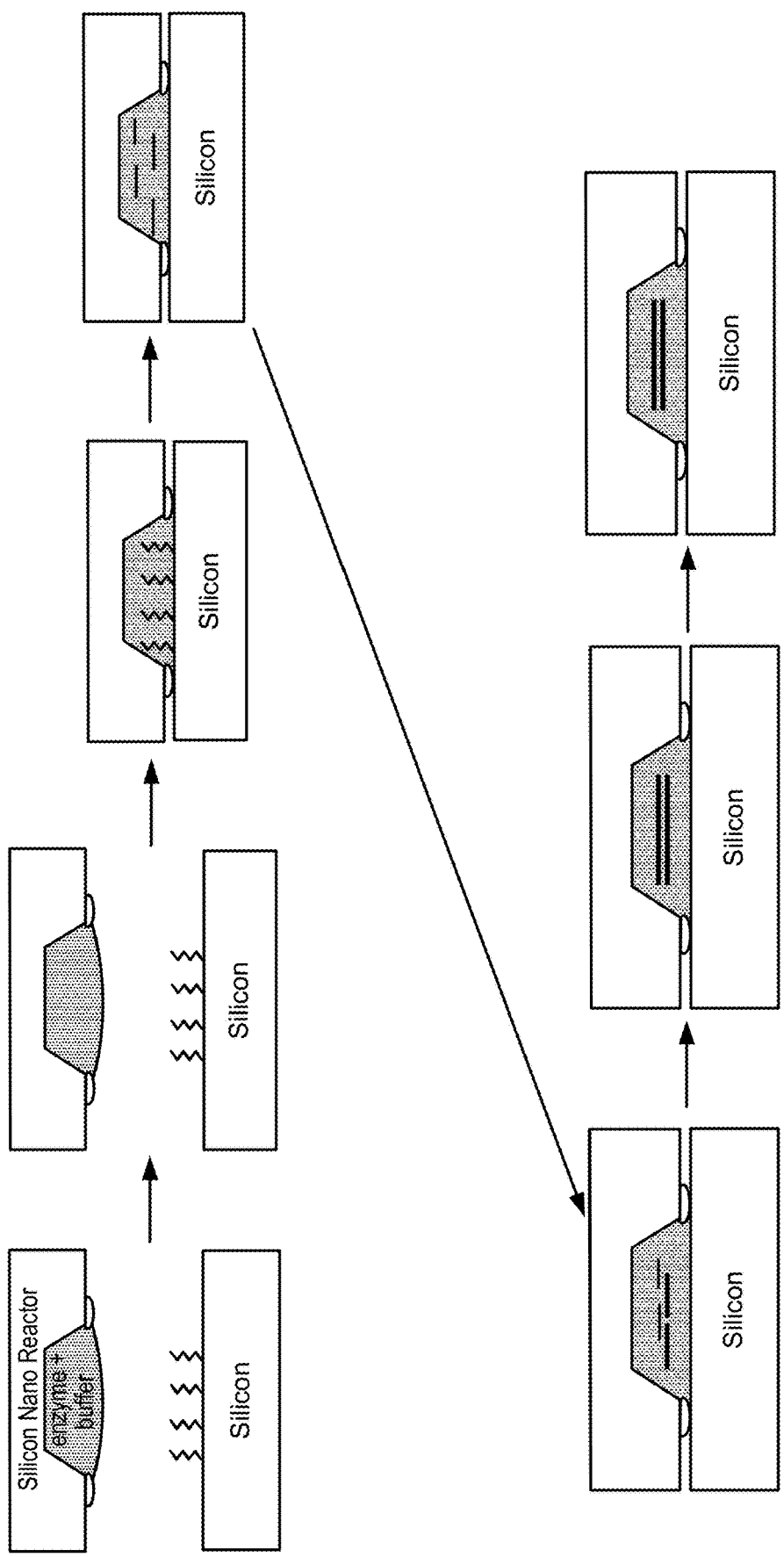

Throughout this disclosure, various aspects of this invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range to the tenth of the unit of the lower limit unless the context clearly dictates otherwise. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual values within that range, for example, 1.1, 2, 2.3, 5, and 5.9. This applies regardless of the breadth of the range. The upper and lower limits of these intervening ranges may independently be included in the smaller ranges, and are also encompassed within the invention, subject to any specifically excluded limit in the stated range. Where the stated range includes one or both of the limits, ranges excluding either or both of those included limits are also included in the invention, unless the context clearly dictates otherwise.

In one aspect, the present invention provides a gene library as described herein. The gene library comprises a collection of genes. In some embodiments, the collection comprises at least 100 different preselected synthetic genes that can be of at least 0.5 kb length with an error rate of less than 1 in 3000 bp compared to predetermined sequences comprising the genes. In another aspect, the present invention also provides a gene library that comprises a collection of genes. The collection may comprise at least 100 different preselected synthetic genes that can be each of at least 0.5 kb length. At least 90% of the preselected synthetic genes may comprise an error rate of less than 1 in 3000 bp compared to predetermined sequences comprising the genes. Desired predetermined sequences may be supplied by any method, typically by a user, e.g. a user entering data using a computerized system. In various embodiments, synthesized nucleic acids are compared against these predetermined sequences, in some cases by sequencing at least a portion of the synthesized nucleic acids, e.g. using next-generation sequencing methods. In some embodiments related to any of the gene libraries described herein, at least 90% of the preselected synthetic genes comprise an error rate of less than 1 in 5000 bp compared to predetermined sequences comprising the genes. In some embodiments, at least 0.05% of the preselected synthetic genes are error free. In some embodiments, at least 0.5% of the preselected synthetic genes are error free. In some embodiments, at least 90% of the preselected synthetic genes comprise an error rate of less than 1 in 3000 bp compared to predetermined sequences comprising the genes. In some embodiments, at least 90% of the preselected synthetic genes are error free or substantially error free. In some embodiments, the preselected synthetic genes comprise a deletion rate of less than 1 in 3000 bp compared to predetermined sequences comprising the genes. In some embodiments, the preselected synthetic genes comprise an insertion rate of less than 1 in 3000 bp compared to predetermined sequences comprising the genes. In some embodiments, the preselected synthetic genes comprise a substitution rate of less than 1 in 3000 bp compared to predetermined sequences comprising the genes. In some embodiments, the gene library as described herein further comprises at least 10 copies of each synthetic gene. In some embodiments, the gene library as described herein further comprises at least 100 copies of each synthetic gene. In some embodiments, the gene library as described herein further comprises at least 1000 copies of each synthetic gene. In some embodiments, the gene library as described herein further comprises at least 1000000 copies of each synthetic gene. In some embodiments, the collection of genes as described herein comprises at least 500 genes. In some embodiments, the collection comprises at least 5000 genes. In some embodiments, the collection comprises at least 10000 genes. In some embodiments, the preselected synthetic genes are at least 1 kb. In some embodiments, the preselected synthetic genes are at least 2 kb. In some embodiments, the preselected synthetic genes are at least 3 kb. In some embodiments, the predetermined sequences comprise less than 20 bp in addition compared to the preselected synthetic genes. In some embodiments, the predetermined sequences comprise less than 15 bp in addition compared to the preselected synthetic genes. In some embodiments, at least one of the synthetic genes differs from any other synthetic gene by at least 0.1%. In some embodiments, each of the synthetic genes differs from any other synthetic gene by at least 0.1%. In some embodiments, at least one of the synthetic genes differs from any other synthetic gene by at least 10%. In some embodiments, each of the synthetic genes differs from any other synthetic gene by at least 10%. In some embodiments, at least one of the synthetic genes differs from any other synthetic gene by at least 2 base pairs. In some embodiments, each of the synthetic genes differs from any other synthetic gene by at least 2 base pairs. In some embodiments, the gene library as described herein further comprises synthetic genes that are of less than 2 kb with an error rate of less than 1 in 20000 bp compared to preselected sequences of the genes. In some embodiments, a subset of the deliverable genes is covalently linked together. In some embodiments, a first subset of the collection of genes encodes for components of a first metabolic pathway with one or more metabolic end products. In some embodiments, the gene library as described herein further comprises selecting of the one or more metabolic end products, thereby constructing the collection of genes. In some embodiments, the one or more metabolic end products comprise a biofuel. In some embodiments, a second subset of the collection of genes encodes for components of a second metabolic pathway with one or more metabolic end products. In some embodiments, the gene library is in a space that is less than 100 m$^3$. In some embodiments, the gene library is in a space that is less than 1 m$^3$. In some embodiments, the gene library is in a space that is less than 1 m$^3$.

In another aspect, the present invention also provides a method of constructing a gene library. The method comprises the steps of: entering before a first timepoint, in a computer readable non-transient medium at least a first list of genes and a second list of genes, wherein the genes are at least 500 bp and when compiled into a joint list, the joint list comprises at least 100 genes; synthesizing more than 90% of the genes in the joint list before a second timepoint, thereby constructing a gene library with deliverable genes. In some embodiments, the second timepoint is less than a month apart from the first timepoint.

In practicing any of the methods of constructing a gene library as provided herein, the method as described herein further comprises delivering at least one gene at a second timepoint. In some embodiments, at least one of the genes differs from any other gene by at least 0.1% in the gene library. In some embodiments, each of the genes differs from any other gene by at least 0.1% in the gene library. In some embodiments, at least one of the genes differs from any other gene by at least 10% in the gene library. In some embodiments, each of the genes differs from any other gene by at least 10% in the gene library. In some embodiments, at least one of the genes differs from any other gene by at least 2 base pairs in the gene library. In some embodiments, each of the genes differs from any other gene by at least 2 base pairs in the gene library. In some embodiments, at least 90% of the deliverable genes are error free. In some embodiments, the deliverable genes comprises an error rate of less than 1/3000 resulting in the generation of a sequence that deviates from the sequence of a gene in the joint list of genes. In some embodiments, at least 90% of the deliverable genes comprise an error rate of less than 1 in 3000 bp resulting in the generation of a sequence that deviates from the sequence of a gene in the joint list of genes. In some embodiments, genes in a subset of the deliverable genes are covalently linked together. In some embodiments, a first subset of the joint list of genes encode for components of a first metabolic pathway with one or more metabolic end products. In some embodiments, any of the methods of constructing a gene library as described herein further comprises selecting of the one or more metabolic end products, thereby constructing the first, the second or the joint list of genes. In some embodiments, the one or more metabolic end products comprise a biofuel. In some embodiments, a second subset of the joint list of genes encode for components of a second metabolic pathway with one or more metabolic end products. In some embodiments, the joint list of genes comprises at least 500 genes. In some embodiments, the joint list of genes comprises at least 5000 genes. In some embodiments, the joint list of genes comprises at least 10000 genes. In some embodiments, the genes can be at least 1 kb. In some embodiments, the genes are at least 2 kb. In some embodiments, the genes are at least 3 kb. In some embodiments, the second timepoint is less than 25 days apart from the first timepoint. In some embodiments, the second timepoint is less than 5 days apart from the first timepoint. In some embodiments, the second timepoint is less than 2 days apart from the first timepoint. It is noted that any of the embodiments described herein can be combined with any of the methods, devices or systems provided in the current invention.

In another aspect, a method of constructing a gene library is provided herein. The method comprises the steps of: entering at a first timepoint, in a computer readable non-transient medium a list of genes; synthesizing more than 90% of the list of genes, thereby constructing a gene library with deliverable genes; and delivering the deliverable genes at a second timepoint. In some embodiments, the list comprises at least 100 genes and the genes can be at least 500 bp. In still yet some embodiments, the second timepoint is less than a month apart from the first timepoint.

In practicing any of the methods of constructing a gene library as provided herein, in some embodiments, the method as described herein further comprises delivering at least one gene at a second timepoint. In some embodiments, at least one of the genes differs from any other gene by at least 0.1% in the gene library. In some embodiments, each of the genes differs from any other gene by at least 0.1% in the gene library. In some embodiments, at least one of the genes differs from any other gene by at least 10% in the gene library. In some embodiments, each of the genes differs from any other gene by at least 10% in the gene library. In some embodiments, at least one of the genes differs from any other gene by at least 2 base pairs in the gene library. In some embodiments, each of the genes differs from any other gene by at least 2 base pairs in the gene library. In some embodiments, at least 90% of the deliverable genes are error free. In some embodiments, the deliverable genes comprises an error rate of less than 1/3000 resulting in the generation of a sequence that deviates from the sequence of a gene in the list of genes. In some embodiments, at least 90% of the deliverable genes comprise an error rate of less than 1 in 3000 bp resulting in the generation of a sequence that deviates from the sequence of a gene in the list of genes. In some embodiments, genes in a subset of the deliverable genes are covalently linked together. In some embodiments, a first subset of the list of genes encode for components of a first metabolic pathway with one or more metabolic end products. In some embodiments, the method of constructing a gene library further comprises selecting of the one or more metabolic end products, thereby constructing the list of genes. In some embodiments, the one or more metabolic end products comprise a biofuel. In some embodiments, a second subset of the list of genes encode for components of a second metabolic pathway with one or more metabolic end products. It is noted that any of the embodiments described herein can be combined with any of the methods, devices or systems provided in the current invention.

In practicing any of the methods of constructing a gene library as provided herein, in some embodiments, the list of genes comprises at least 500 genes. In some embodiments, the list comprises at least 5000 genes. In some embodiments, the list comprises at least 10000 genes. In some embodiments, the genes are at least 1 kb. In some embodiments, the genes are at least 2 kb. In some embodiments, the genes are at least 3 kb. In some embodiments, the second timepoint as described in the methods of constructing a gene library is less than 25 days apart from the first timepoint. In some embodiments, the second timepoint is less than 5 days apart from the first timepoint. In some embodiments, the second timepoint is less than 2 days apart from the first timepoint. It is noted that any of the embodiments described herein can be combined with any of the methods, devices or systems provided in the current invention.

In another aspect, the present invention also provides a method of synthesizing n-mer oligonucleotides on a substrate. The method comprises a) providing a substrate with resolved loci that are functionalized with a chemical moiety suitable for nucleotide coupling; and b) coupling at least two building blocks to a plurality of growing oligonucleotide chains each residing on one of the resolved loci at a rate of at least 12 nucleotides per hour according to a locus specific predetermined sequence, thereby synthesizing a plurality of oligonucleotides that are n basepairs long. Various embodiments related to the method of synthesizing n-mer oligonucleotides on a substrate are described herein.

In any of the methods of synthesizing n-mer oligonucleotides on a substrate as provided herein, in some embodiments, the methods further comprise coupling at least two building blocks to a plurality of growing oligonucleotide chains each residing on one of the resolved loci at a rate of at least 15 nucleotides per hour. In some embodiments, the method further comprises coupling at least two building blocks to a plurality of growing oligonucleotide chains each residing on one of the resolved loci at a rate of at least 20 nucleotides per hour. In some embodiments, the method further comprises coupling at least two building blocks to a plurality of growing oligonucleotide chains each residing on one of the resolved loci at a rate of at least 25 nucleotides per hour. In some embodiments, at least one resolved locus comprises n-mer oligonucleotides deviating from the locus specific predetermined sequence with an error rate of less than 1/500 bp. In some embodiments, at least one resolved locus comprises n-mer oligonucleotides deviating from the locus specific predetermined sequence with an error rate of less than 1/1000 bp. In some embodiments, at least one resolved locus comprises n-mer oligonucleotides deviating from the locus specific predetermined sequence with an error rate of less than 1/2000 bp. In some embodiments, the plurality of oligonucleotides on the substrate deviate from respective locus specific predetermined sequences at an error rate of less than 1/500 bp. In some embodiments, the plurality of oligonucleotides on the substrate deviate from respective locus specific predetermined sequences at an error rate of less than 1/1000 bp. In some embodiments, the plurality of oligonucleotides on the substrate deviate from respective locus specific predetermined sequences at an error rate of less than 1/2000 bp.

In practicing any of the methods of synthesizing n-mer oligonucleotides on a substrate as provided herein, in some embodiments, the building blocks comprise an adenine, guanine, thymine, cytosine, or uridine group, or a modified nucleotide. In some embodiments, the building blocks comprise a modified nucleotide. In some embodiments, the building blocks comprise dinucleotides or trinucleotides. In some embodiments, the building blocks comprise phosphoramidite. In some embodiments, n of the n-mer oligonucleotides is at least 100. In some embodiments, n is at least 200. In some embodiments, n is at least 300. In some embodiments, n is at least 400. In some embodiments, the surface comprises at least 100,000 resolved loci and at least two of the plurality of growing oligonucleotides can be different from each other.

In some embodiments, the method of synthesizing n-mer oligonucleotides on a substrate as described herein further comprises vacuum drying the substrate before coupling. In some embodiments, the building blocks comprise a blocking group. In some embodiments, the blocking group comprises an acid-labile DMT. In some embodiments, the acid-labile DMT comprises 4,4'-dimethoxytrityl. In some embodiments, the method of synthesizing n-mer oligonucleotides on a substrate as described herein further comprises oxidation or sulfurization. In some embodiments, the method of synthesizing n-mer oligonucleotides on a substrate as described herein further comprises chemically capping uncoupled oligonucleotide chains. In some embodiments, the method of synthesizing n-mer oligonucleotides on a substrate as described herein further comprises removing the blocking group, thereby deblocking the growing oligonucleotide chain. In some embodiments, the position of the substrate during the coupling step is within 10 cm of the position of the substrate during the vacuum drying step. In some embodiments, the position of the substrate during the coupling step is within 10 cm of the position of the substrate during the oxidation step. In some embodiments, the position of the substrate during the coupling step is within 10 cm of the position of the substrate during the capping step. In some embodiments, the position of the substrate during the coupling step is within 10 cm of the position of the substrate during the deblocking step. In some embodiments, the substrate comprises at least 10,000 vias providing fluid communication between a first surface of the substrate and a second surface of the substrate. In some embodiments, the substrate comprises at least 100,000 vias providing fluid communication between a first surface of the substrate and a second surface of the substrate. In some embodiments, the substrate comprises at least 1,000,000 vias providing fluid communication between a first surface of the substrate and a second surface of the substrate. It is noted that any of the embodiments described herein can be combined with any of the methods, devices or systems provided in the current invention.

In another aspect of the present invention, a system for conducting a set of parallel reactions is provided herein. The system comprises: a first surface with a plurality of resolved loci; a capping element with a plurality of resolved reactor caps. In some embodiments, the system aligns the plurality of resolved reactor caps with the plurality of resolved loci on the first surface forming a temporary seal between the first surface and the capping element, thereby physically dividing the loci on the first surface into groups of at least two loci into a reactor associated with each reactor cap. In some embodiments, each reactor holds a first set of reagents.

In some embodiments related to any of the systems for conducting a set of parallel reactions as described herein, upon release from the first surface, the reactor caps retain at least a portion of the first set of reagents. In some embodiments, the portion is about 30%. In some embodiments, the portion is about 90%. In some embodiments, the plurality of resolved loci resides on microstructures fabricated into a support surface. In some embodiments, the plurality of resolved loci is at a density of at least 1 per $mm^2$. In some embodiments, the plurality of resolved loci is at a density of at least 10 per $mm^2$. In some embodiments, the plurality of resolved loci are at a density of at least 100 per $mm^2$. In some embodiments, the microstructures comprise at least two channels in fluidic communication with each other. In some embodiments, the at least two channels comprise two channels with different width. In some embodiments, at least two channels comprise two channels with different length. In some embodiments, at least one of the channels is longer than 100 µm. In some embodiments, at least one of the channels is shorter than 1000 µm. In some embodiments, at least one of the channels is wider than 50 µm in diameter. In some embodiments, at least one of the channels is narrower than 100 µm in diameter. In some embodiments, the system further comprises a second surface with a plurality of resolved loci at a density of at least 0.1 per $mm^2$. In some embodiments, the system further comprises a second surface with a plurality of resolved loci at a density of at least 1 per $mm^2$. In some embodiments, the system further comprises a second surface with a plurality of resolved loci at a density of at least 10 per $mm^2$.

In some embodiments related to any of the systems for conducting a set of parallel reactions as described herein, the resolved loci of the first surface comprise a coating of reagents. In some embodiments, the resolved loci of the second surface comprise a coating of reagents. In some embodiments, the coating of reagents is covalently linked to the first or second surface. In some embodiments, the coating of reagents comprises oligonucleotides. In some embodiments, the coating of reagents has a surface area of at least 1.45 $µm^2$ per 1.0 $µm^2$ of planar surface area. In some embodiments, the coating of reagents has a surface area of at least 1.25 $µm^2$ per 1.0 $µm^2$ of planar surface area. In some embodiments, the coating of reagents has a surface area of at least 1 $µm^2$ per 1.0 $µm^2$ of planar surface area. In some embodiments, the resolved loci in the plurality of resolved loci comprise a nominal arclength of the perimeter at a density of at least 0.001 $µm/µm^2$. In some embodiments, the resolved loci in the plurality of resolved loci comprise a nominal arclength of the perimeter at a density of at least 0.01 $µm/µm^2$. In some embodiments, the resolved loci in the plurality of resolved loci of the first surface comprise a high energy surface. In some embodiments, the first and second surfaces comprise a different surface tension with a given liquid. In some embodiments, the high surface energy corresponds to a water contact angle of less than 20 degree. In some embodiments, the plurality of resolved loci are located on a solid substrate comprising a material selected from the group consisting of silicon, polystyrene, agarose, dextran, cellulosic polymers, polyacrylamides, PDMS, and glass. In some embodiments, the capping elements comprise a material selected from the group consisting of silicon, polystyrene, agarose, dextran, cellulosic polymers, polyacrylamides, PDMS, and glass. It is noted that any of the embodiments described herein can be combined with any of the methods, devices or systems provided in the current invention.

In yet another aspect, the present invention also provides an array of enclosures. The array of enclosures comprise: a plurality of resolved reactors comprising a first substrate and a second substrate comprising reactor caps; at least 2 resolved loci in each reactor. In some cases, the resolved reactors are separated with a releasable seal. In some cases, the reactor caps retain at least a part of the contents of the reactors upon release of the second substrate from the first substrate. In some embodiments, the reactor caps on the second substrate have a density of at least 0.1 per $mm^2$. In some embodiments, reactor caps on the second substrate have a density of at least 1 per $mm^2$. In some embodiments, reactor caps on the second substrate have a density of at least 10 per $mm^2$.

In some embodiments related to the array of enclosures as provided herein, the reactor caps retain at least 30% of the contents of the reactors. In some embodiments, the reactor caps retain at least 90% of the contents of the reactors. In some embodiments, the resolved loci are at a density of at least 2/$mm^2$. In some embodiments, the resolved loci are at a density of at least 100/$mm^2$. In some embodiments, the array of enclosures further comprises at least 5 resolved loci in each reactor. In some embodiments, the array of enclosures as described herein further comprises at least 20 resolved loci in each reactor. In some embodiments, the array of enclosures as described herein further comprises at least 50 resolved loci in each reactor. In some embodiments, the array of enclosures as described herein further comprises at least 100 resolved loci in each reactor.

In some embodiments related to the array of enclosures as described herein, the resolved loci reside on microstructures fabricated into a support surface. In some embodiments, the microstructures comprise at least two channels in fluidic communication with each other. In some embodiments, the at least two channels comprise two channels with different width. In some embodiments, the at least two channels comprise two channels with different length. In some embodiments, at least one of the channels is longer than 100 µm. In some embodiments, at least one of the channels is shorter than 1000 µm. In some embodiments, at least one of the channels is wider than 50 µm in diameter. In some embodiments, at least one of the channels is narrower than 100 µm in diameter. In some embodiments, the microstructures comprise a nominal arclength of the perimeter of the at least two channels that has a density of at least 0.01/square µm. In some embodiments, the microstructures comprise a nominal arclength of the perimeter of the at least two channels that has a density of at least 0.001 µm/square µm. In some embodiments, the resolved reactors are separated with a releasable seal. In some embodiments, the seal comprises a capillary burst valve.

In some embodiments related to the array of enclosures as described herein, the plurality of resolved loci of the first substrate comprise a coating of reagents. In some embodiments, the plurality of resolved loci of the second substrate comprises a coating of reagents. In some embodiments, the coating of reagents is covalently linked to the first or second surface. In some embodiments, the coating of reagents comprises oligonucleotides. In some embodiments, the coating of reagents has a surface area of at least 1 $µm^2$ per 1.0 $µm^2$ of planar surface area. In some embodiments, the coating of reagents has a surface area of at least 1.25 $µm^2$ per 1.0 $µm^2$ of planar surface area. In some embodiments, the coating of reagents has a surface area of at least 1.45 $µm^2$ per 1.0 $µm^2$ of planar surface area. In some embodiments, the plurality of resolved loci of the first substrate comprises a high energy surface. In some embodiments, the first and second substrates comprise a different surface tension with a given liquid. In some embodiments, the surface energy corresponds to a water contact angle of less than 20 degree. In some embodiments, the plurality of resolved loci or the reactor caps are located on a solid substrate comprising a material selected from the group consisting of silicon, polystyrene, agarose, dextran, cellulosic polymers, polyacrylamides, PDMS, and glass. It is noted that any of the embodiments described herein can be combined with any of the methods, devices, arrays or systems provided in the current invention.

In still yet another aspect, the present invention also provides a method of conducting a set of parallel reactions. The method comprises: (a) providing a first surface with a plurality of resolved loci; (b) providing a capping element with a plurality of resolved reactor caps; (c) aligning the plurality of resolved reactor caps with the plurality of resolved loci on the first surface and forming a temporary seal between the first surface and the capping element, thereby physically dividing the loci on the first surface into groups of at least two loci; (d) performing a first reaction, thereby forming a first set of reagents; and (e) releasing the capping element from the first surface, wherein each reactor cap retains at least a portion of the first set of reagents in a first reaction volume. In some embodiments, the portion is about 30%. In some embodiments, the portion is about 90%.

In some embodiments, the method of conducting a set of parallel reactions as described herein further comprises the steps of: (0 providing a second surface with a plurality of resolved loci; (g) aligning the plurality of resolved reactor caps with the plurality of resolved loci on the second surface and forming a temporary seal between the second surface and the capping element, thereby physically dividing the loci on the second surface; (h) performing a second reaction using the portion of the first set of reagents, thereby forming a second set of reagents; and (i) releasing the capping element from the second surface, wherein each reactor cap can retain at least a portion of the second set of reagents in a second reaction volume. In some embodiments, the portion is about 30%. In some embodiments, the portion is about 90%.

In practicing any of the methods of conducting a set of parallel reactions as described herein, the plurality of resolved loci can have a density of at least 1 per $mm^2$ on the first surface. In some embodiments, the plurality of resolved loci have a density of at least 10 per $mm^2$ on the first surface. In some embodiments, the plurality of resolved loci have a density of at least 100 per $mm^2$ on the first surface. In some embodiments, the plurality of resolved reactor caps have a density of at least 0.1 per $mm^2$ on the capping element. In some embodiments, the plurality of resolved reactor caps have a density of at least 1 per $mm^2$ on the capping element. In some embodiments, the plurality of resolved reactor caps have a density of at least 10 per $mm^2$ on the capping element. In some embodiments, the plurality of resolved loci have a density of more than 0.1 per $mm^2$ on the second surface. In some embodiments, the plurality of resolved loci have a density of more than 1 per $mm^2$ on the second surface. In some embodiments, the plurality of resolved loci have a density of more than 10 per $mm^2$ on the second surface.

In practicing any of the methods of conducting a set of parallel reactions as described herein, the releasing of the capping elements from the surface steps such as the releasing steps in (e) and (i) as described herein can be performed at a different velocity. In some embodiments, the resolved loci of the first surface comprise a coating of reagents for the first reaction. In some embodiments, the resolved loci of the second surface comprise a coating of reagents for the second reaction. In some embodiments, the coating of reagents is covalently linked to the first or second surface. In some embodiments, the coating of reagents comprises oligonucleotides. In some embodiments, the coating of reagents has a surface area of at least 1 $\mu m^2$ per 1.0 $\mu m^2$ of planar surface area. In some embodiments, the coating of reagents has a surface area of at least 1.25 $\mu m^2$ per 1.0 $\mu m^2$ of planar surface area. In some embodiments, the coating of reagents has a surface area of at least 1.45 $\mu m^2$ per 1.0 $\mu m^2$ of planar surface area. In some embodiments, the oligonucleotides are at least 25 bp. In some embodiments, the oligonucleotides are at least 200 bp. In some embodiments, the oligonucleotides are at least 300 bp. In some embodiments, the resolved loci of the first surface comprise a high energy surface. In some embodiments, the first and second surfaces comprise a different surface tension with a given liquid. In some embodiments, the surface energy corresponds to a water contact angle of less than 20 degree.

In some embodiments related to the method of conducting a set of parallel reactions as described herein, the plurality of resolved loci or the resolved reactor caps are located on a solid substrate comprising a material selected from the group consisting of silicon, polystyrene, agarose, dextran, cellulosic polymers, polyacrylamides, PDMS, and glass. In some embodiments, the first and second reaction volumes are different. In some embodiments, the first or second reaction comprises polymerase cycling assembly. In some embodiments, the first or second reaction comprises enzymatic gene synthesis, annealing and ligation reaction, simultaneous synthesis of two genes via a hybrid gene, shotgun ligation and co-ligation, insertion gene synthesis, gene synthesis via one strand of DNA, template-directed ligation, ligase chain reaction, microarray-mediated gene synthesis, solid-phase assembly, Sloning building block technology, or RNA ligation mediated gene synthesis. In some embodiments, the methods of conducting a set of parallel reactions as described herein further comprises cooling the capping element. In some embodiments, the method of conducting a set of parallel reactions as described herein further comprises cooling the first surface. In some embodiments, the method of conducting a set of parallel reactions as described herein further comprises cooling the second surface. It is noted that any of the embodiments described herein can be combined with any of the methods, devices, arrays or systems provided in the current invention.

In another aspect, the present invention provides a substrate having a functionalized surface. The substrate having a functionalized surface can comprise a solid support having a plurality of resolved loci. In some embodiments, the resolved loci are functionalized with a moiety that increases the surface energy of the solid support. In some embodiments, the resolved loci are localized on microchannels.

In some embodiments related to the substrate having a functionalized surface as described herein, the moiety is a chemically inert moiety. In some embodiments, the microchannels comprise a volume of less than 1 nl. In some embodiments, the microchannels comprise a density of the nominal arclength of the perimeter of 0.036 μm/square μm. In some embodiments, the functionalized surface comprises a nominal surface area of at least 1 $\mu m^2$ per 1.0 $\mu m^2$ of planar surface area of the substrate. In some embodiments, the functionalized surface comprises a nominal surface area of at least 1.25 $\mu m^2$ per 1.0 $\mu m^2$ of planar surface area of the substrate. In some embodiments, the functionalized surface comprises a nominal surface area of at least 1.45 $\mu m^2$ per 1.0 $\mu m^2$ of planar surface area of the substrate. In some embodiments, the resolved loci in the plurality of resolved loci comprise a coating of reagents. In some embodiments, the coating of reagents is covalently linked to the substrate. In some embodiments, the coating of reagents comprises oligonucleotides. In some embodiments, at least one of the microchannels is longer than 100 μm. In some embodiments, at least one of the microchannels is shorter than 1000 μm. In some embodiments, at least one of the microchannels is wider than 50 μm in diameter. In some embodiments, at least one of the microchannels is narrower than 100 μm in diameter. In some embodiments, the surface energy corresponds to a water contact angle of less than 20 degree. In some embodiments, the solid support comprises a material selected from the group consisting of silicon, polystyrene, agarose, dextran, cellulosic polymers, polyacrylamides, PDMS, and glass. In some embodiments, the plurality of resolved loci is at a density of at least 1/$mm^2$. In some embodiments, the plurality of resolved loci is at a density of at least 100/mm². It is noted that any of the embodiments described herein can be combined with any of the methods, devices, arrays, substrates or systems provided in the current invention.

In another aspect, the present invention also provides a method for synthesizing oligonucleotides on a substrate having a functionalized surface. The method comprises: (a) applying through at least one inkjet pump at least one drop of a first reagent to a first locus of a plurality of loci; (b) applying negative pressure to the substrate; and (c) applying through at least one inkjet pump at least one drop of a second reagent to the first locus.

In practicing any of the methods for synthesizing oligonucleotides on a substrate having a functionalized surface as described herein, the first and second reagents can be different. In some embodiments, the first locus is functionalized with a moiety that increases their surface energy. In some embodiments, the moiety is a chemically inert moiety. In some embodiments, the plurality of loci resides on microstructures fabricated into the substrate surface. In some embodiments, the microstructures comprise at least two channels in fluidic communication with each other. In some embodiments, the at least two channels comprise two channels with different width. In some embodiments, the at least two channels comprise two channels with different length. In some embodiments, at least one of the channels is longer than 100 μm. In some embodiments, at least one of the channels is shorter than 1000 μm. In some embodiments, at least one of the channels is wider than 50 μm in diameter. In some embodiments, at least one of the channels is narrower than 100 μm in diameter. In some embodiments, the substrate surface comprises a material selected from the group consisting of silicon, polystyrene, agarose, dextran, cellulosic polymers, polyacrylamides, PDMS, and glass.

In some embodiments related to the methods for synthesizing oligonucleotides on a substrate having a functionalized surface as described herein, the volume of the drop of the first and/or the second reagents is at least 2 pl. In some embodiments, the volume of the drop is about 40 pl. In some embodiments, the volume of the drop is at most 100 pl. In some embodiments, the microchannels comprise a density of the nominal arclength of the perimeter of at least 0.01 μm/μm². In some embodiments, the microchannels comprise a density of the nominal arclength of the perimeter of at least 0.001 μm/μm². In some embodiments, the functionalized surface comprises a nominal surface area of at least 1 μm² per 1.0 μm² of planar surface area of the substrate. In some embodiments, the functionalized surface comprises a nominal surface area of at least 1.25 μm² per 1.0 μm² of planar surface area of the substrate. In some embodiments, the functionalized surface comprises a nominal surface area of at least 1.45 μm² per 1.0 μm² of planar surface area of the substrate. In some embodiments, the pressure surrounding the substrate is reduced to less than 1 mTorr. It is noted that any of the embodiments described herein can be combined with any of the methods, devices, arrays, substrates or systems provided in the current invention.

In some embodiments, the method for synthesizing oligonucleotides on a substrate having a functionalized surface as described herein further comprises coupling at least a first building block originating from the first drop to a growing oligonucleotide chain on the first locus. In some embodiments, the building blocks comprise a blocking group. In some embodiments, the blocking group comprises an acid-labile DMT. In some embodiments, the acid-labile DMT comprises 4,4'-dimethoxytrityl. In some embodiments, the method for synthesizing oligonucleotides on a substrate having a functionalized surface as described herein further comprises oxidation or sulfurization. In some embodiments, the method for synthesizing oligonucleotides on a substrate having a functionalized surface as described herein further comprises chemically capping uncoupled oligonucleotide chains. In some embodiments, the method for synthesizing oligonucleotides on a substrate having a functionalized surface as described herein further comprises removing the blocking group, thereby deblocking the growing oligonucleotide chain. In some embodiments, the position of the substrate during the negative pressure application is within 10 cm of the position of the substrate during the coupling step. In some embodiments, the position of the substrate during the negative pressure application is within 10 cm of the position of the substrate during the oxidation step. In some embodiments, the position of the substrate during the negative pressure application is within 10 cm of the position of the substrate during the capping step. In some embodiments, the position of the substrate during the negative pressure application is within 10 cm of the position of the substrate during the deblocking step. In some embodiments, the first locus resides on a microstructure fabricated into the substrate surface. In some embodiments, at least one reagent for the oxidation step is provided by flooding the microstructure with a solution comprising the at least one reagent. In some embodiments, at least one reagent for the capping step is provided by flooding the microstructure with a solution comprising the at least one reagent. In some embodiments, the first locus resides on a microstructure fabricated into the substrate surface and at least one reagent for the deblocking step can be provided by flooding the microstructure with a solution comprising the at least one reagent. In some embodiments, the method for synthesizing oligonucleotides on a substrate having a functionalized surface as described herein further comprises enclosing the substrate within a sealed chamber. In some embodiments, the sealed chamber allows for purging of liquids from the first locus. In some embodiments, the method for synthesizing oligonucleotides on a substrate having a functionalized surface as described herein further comprises draining a liquid through a drain that is operably linked to the first locus. In some embodiments, after applying the negative pressure to the substrate, the moisture content on the substrate is less than 1 ppm. In some embodiments, the surface energy is increased corresponding to a water contact angle of less than 20 degree. It is noted that any of the embodiments described herein can be combined with any of the methods, devices, arrays, substrates or systems provided in the current invention.

In yet another aspect, the present invention provides a method of depositing reagents to a plurality of resolved loci. The method comprises applying through an inkjet pump at least one drop of a first reagent to a first locus of the plurality of loci; applying through an inkjet pump at least one drop of a second reagent to a second locus of the plurality of resolved loci. In some embodiments, the second locus is adjacent to the first locus. In still some embodiments, the first and second reagents are different. In still yet some embodiments, the first and second loci reside on microstructures fabricated into a support surface. In yet some embodiments, the microstructures comprise at least one channel that is more than 100 μm deep.

In practicing any of the methods of depositing reagents to a plurality of resolved loci as described herein, in some embodiments, the microstructures comprise at least two channels in fluidic communication with each other. In some embodiments, the at least two channels comprise two channels with different width. In some embodiments, the at least two channels comprise two channels with different length. In some embodiments, the first locus receives less than 0.1% of the second reagent and the second locus receives less than 0.1% of the first reagent. In some embodiments, the loci comprise a density of the nominal arclength of the perimeter of at least 0.01 µm/square µm. In some embodiments, the loci comprise a density of the nominal arclength of the perimeter of at least 0.001 µm/square µm. In some embodiments, the first and second loci comprise a coating of reagents. In some embodiments, the coating of reagents is covalently linked to the substrate. In some embodiments, the coating of reagents comprises oligonucleotides. In some embodiments, at least one of the channels is longer than 100 µm. In some embodiments, at least one of the channels is shorter than 1000 µm. In some embodiments, at least one of the channels is wider than 50 µm in diameter. In some embodiments, at least one of the channels is narrower than 100 µm in diameter. In some embodiments, the support surface comprises a material selected from the group consisting of silicon, polystyrene, agarose, dextran, cellulosic polymers, polyacrylamides, PDMS, and glass. In some embodiments, the plurality of resolved loci is at a density of at least $1/mm^2$. In some embodiments, the plurality of resolved loci is at a density of at least $100/mm^2$. In some embodiments, the volume of the drop is at least 2 pl. In some embodiments, the volume of the drop is about 40 pl. In some embodiments, the volume of the drop is at most 100 pl. It is noted that any of the embodiments described herein can be combined with any of the methods, devices, arrays, substrates or systems provided in the current invention.

In still yet another aspect, the present invention provides a microfluidic system. The microfluidic system comprises a first surface with a plurality of microwells at a density of at least 10 per $mm^2$; and a droplet inside one of the plurality of microwells. In some embodiments, the droplet inside one of the plurality of microwells has a Reynolds number at a range of about 1-1000. In some embodiments, the plurality of microwells is at a density of at least 1 per $mm^2$. In some embodiments, plurality of microwells is at a density of at least 10 per $mm^2$.

In some embodiments related to the microfluidic system as provided herein, the microfluidic system further comprises an inkjet pump. In some embodiments, the droplet is deposited by the inkjet pump. In some embodiments, the droplet is moving in the lower half of a first microwell dimension. In some embodiments, the droplet is moving in the middle third of a first microwell dimension. In some embodiments, the plurality of microwells is at a density of at least 100 per $mm^2$. In some embodiments, the first microwell dimension is larger than the droplet. In some embodiments, the microwell is longer than 100 µm. In some embodiments, the microwell is shorter than 1000 µm. In some embodiments, the microwell is wider than 50 µm in diameter. In some embodiments, the microwell is narrower than 100 µm in diameter. In some embodiments, the volume of the droplet is at least 2 pl. In some embodiments, the volume of the droplet is about 40 pl. In some embodiments, the volume of the droplet is at most 100 pl. In some embodiments, each of the plurality of microwells is fluidically connected to at least one microchannel. In some embodiments, the at least one microchannel is coated with a moiety that increases surface energy. In some embodiments, the moiety is a chemically inert moiety. In some embodiments, the surface energy corresponds to a water contact angle of less than 20 degree. In some embodiments, the microwells are formed on a solid support comprising a material selected from the group consisting of silicon, polystyrene, agarose, dextran, cellulosic polymers, polyacrylamides, PDMS, and glass. In some embodiments, the microchannels comprise a density of the nominal arclength of the perimeter of at least 0.01 µm/square µm. In some embodiments, the microchannels comprise a density of the nominal arclength of the perimeter of 0.001 µm/µm². In some embodiments, the surface coated with the moiety comprises a nominal surface area of at least 1 µm² per 1.0 µm² of planar surface area of the first surface. In some embodiments, the surface coated with the moiety comprises a nominal surface area of at least 1.25 µm² per 1.0 µm² of planar surface area of the first surface. In some embodiments, the surface coated with the moiety comprises a nominal surface area of at least 1.45 µm² per 1.0 µm² of planar surface area of the first surface. It is noted that any of the embodiments described herein can be combined with any of the methods, devices, arrays, substrates or systems provided in the current invention. In some embodiments, the droplet comprises a reagent that enables oligonucleotide synthesis. In some embodiments, the reagent is a nucleotide or nucleotide analog.

In another aspect, the present invention provides a method of depositing droplets to a plurality of microwells. The method comprises applying through an inkjet pump at least one droplet to a first microwell of the plurality of microwells. In some cases, the droplet inside one of the plurality of microwells has a Reynolds number at a range of about 1-1000. In some embodiments, the plurality of microwells has a density of at least $1/mm^2$. In yet some cases, the plurality of microwells has a density of at least $10/mm^2$.

In practicing any of the methods of depositing droplets to a plurality of microwells as provided herein, the plurality of microwells can have a density of at least $100/mm^2$. In some embodiments, the microwell is longer than 100 µm. In some embodiments, the microwell is shorter than 1000 µm. In some embodiments, the microwell is wider than 50 µm in diameter. In some embodiments, the microwell is narrower than 100 µm in diameter. In some embodiments, the droplet is applied at a velocity of at least 2 m/sec. In some embodiments, the volume of the droplet is at least 2 pl. In some embodiments, the volume of the droplet is about 40 pl. In some embodiments, the volume of the droplet is at most 100 pl. In some embodiments, each of the plurality of microwells is fluidically connected to at least one microchannel. In some embodiments, the at least one microwell is coated with a moiety that increases surface energy. In some embodiments, the moiety is a chemically inert moiety. In some embodiments, the surface energy corresponds to a water contact angle of less than 20 degree. In some embodiments, the microwells are formed on a solid support comprising a material selected from the group consisting of silicon, polystyrene, agarose, dextran, cellulosic polymers, polyacrylamides, PDMS, and glass. In some embodiments, the microchannels comprise a density of the nominal arclength of the perimeter of at least 0.01 µm/square µm. In some embodiments, the microchannels comprise a density of the nominal arclength of the perimeter of at least 0.001 µm²m/µm². In some embodiments, the surface coated with the moiety comprises a nominal surface area of at least 1 µm² per 1.0 µm² of planar surface area of the first surface. In some embodiments, the surface coated with the moiety comprises a nominal surface area of at least 1.25 µm² per 1.0 µm² of planar surface area of the first surface. In some embodiments, the surface coated with the moiety comprises a nominal surface area of at least 1.45 µm² per 1.0 µm² of planar surface area of the first surface. In some embodiments, a droplet inside a microwell is traveling in the middle third of the microwell. In some embodiments, a droplet inside a microwell is traveling in the bottom half of the microwell. In some embodiments, droplet comprises a reagent that enables oligonucleotide synthesis. In some embodiments, the reagent is a nucleotide or nucleotide analog. It is noted that any of the embodiments described herein can be combined with any of the methods, devices, arrays, substrates or systems provided in the current invention.

In another aspect, the present invention also provides a method of partitioning. The method of partitioning comprises contacting a first surface comprising a liquid at a first plurality of resolved loci with a second surface comprising a second plurality of resolved loci; determining a velocity of release such that a desired fraction of the liquid can be transferred from the first plurality of resolved loci to the second plurality of resolved loci; and detaching the second surface from the first surface at said velocity. In some embodiments, the first surface comprises a first surface tension with the liquid, and the second surface can comprise a second surface tension with the liquid.

In practicing any of the methods of partitioning as provided herein, a portion of the first surface can be coated with a moiety that increases surface tension. In some embodiments, the moiety is a chemically inert moiety. In some embodiments, the surface tension of the first surface corresponds to a water contact angle of less than 20 degree. In some embodiments, the surface tension of the second surface corresponds to a water contact angle of more than 90 degree. In some embodiments, the first surface comprises a material selected from the group consisting of silicon, polystyrene, agarose, dextran, cellulosic polymers, polyacrylamides, PDMS, and glass. In some embodiments, the plurality of resolved loci comprises a density of the nominal arclength of the perimeter of at least 0.01 $\mu m/\mu m^2$. In some embodiments, the plurality of resolved loci comprises a density of the nominal arclength of the perimeter of at least 0.001 $\mu m/\mu m^2$. In some embodiments, the surface coated with the moiety comprises a nominal surface area of at least 1 $\mu m^2$ per 1.0 $\mu m^2$ of planar surface area of the first surface. In some embodiments, the surface coated with the moiety comprises a nominal surface area of at least 1.25 $\mu m^2$ per 1.0 $\mu m^2$ of planar surface area of the first surface. In some embodiments, the surface coated with the moiety comprises a nominal surface area of at least 1.45 $\mu m^2$ per 1.0 $\mu m^2$ of planar surface area of the first surface. In some embodiments, the first plurality of resolved loci is at a density of at least $1/mm^2$. In some embodiments, the first plurality of resolved loci is at a density of at least $100/mm^2$. In some embodiments, the first or the second surface comprises microchannels holding at least a portion of the liquid. In some embodiments, the first or the second surface comprises nanoreactors holding at least a portion of the liquid. In some embodiments, the method of partitioning as described herein further comprises contacting a third surface with a third plurality of resolved loci. In some embodiments, the liquid comprises a nucleic acid. In some embodiments, the desired fraction is more than 30%. In some embodiments, the desired fraction is more than 90%. It is noted that any of the embodiments described herein can be combined with any of the methods, devices, arrays, substrates or systems provided in the current invention.

In yet another aspect, the present invention also provides a method of mixing as described herein. The method comprises: (a) providing a first substrate comprising a plurality of microstructures fabricated thereto; (b) providing a second substrate comprising a plurality of resolved reactor caps; (c) aligning the first and second substrates such that a first reactor cap of the plurality can be configured to receive liquid from n microstructures in the first substrate; and (d) delivering liquid from the n microstructures into the first reactor cap, thereby mixing liquid from the n microstructures forming a mixture.

In practicing any of the methods of mixing as described herein, the plurality of resolved reactor caps can be at a density of at least $0.1/mm^2$. In some embodiments, the plurality of resolved reactor caps are at a density of at least $1/mm^2$. In some embodiments, plurality of resolved reactor caps are at a density of at least $10/mm^2$. In some embodiments, each of the plurality of microstructures can comprise at least two channels of different width. In some embodiments, the at least one of the channels is longer than 100 $\mu m$. In some embodiments, the at least one of the channels is shorter than 1000 $\mu m$. In some embodiments, the at least one of the channels is wider than 50 $\mu m$ in diameter. In some embodiments, the at least one of the channels is narrower than 100 $\mu m$ in diameter. In some embodiments, the at least one of the channels is coated with a moiety that increases surface energy. In some embodiments, the moiety is a chemically inert moiety. In some embodiments, the microstructures are formed on a solid support comprising a material selected from the group consisting of silicon, polystyrene, agarose, dextran, cellulosic polymers, polyacrylamides, PDMS, and glass. In some embodiments, the microchannels comprise a density of the nominal arclength of the perimeter of at least 0.01 $\mu m/square \mu m$. In some embodiments, the microchannels comprise a density of the nominal arclength of the perimeter of at least 0.001 $\mu m/\mu m^2$. In some embodiments, the surface coated with the moiety comprises a nominal surface area of at least 1 $\mu m^2$ per 1.0 $\mu m^2$ of planar surface area of the first surface. In some embodiments, the surface coated with the moiety comprises a nominal surface area of at least 1.25 $\mu m^2$ per 1.0 $\mu m^2$ of planar surface area of the first surface. In some embodiments, the surface coated with the moiety comprises a nominal surface area of at least 1.45 $\mu m^2$ per 1.0 $\mu m^2$ of planar surface area of the first surface. In some embodiments, the plurality of microstructures comprises a coating of reagents. In some embodiments, the coating of reagents is covalently linked to the first surface. In some embodiments, the coating of reagents comprises oligonucleotides. In some embodiments, the microstructures are at a density of at least $1/mm^2$. In some embodiments, the microstructures are at a density of at least $100/mm^2$.

In some embodiments related to the methods of mixing as described herein, after step (c), which is aligning the first and second substrates such that a first reactor cap of the plurality can be configured to receive liquid from n microstructures in the first substrate, there is a gap of less than 100 $\mu m$ between the first and the second substrates. In some embodiments, after step (c), there is a gap of less than 50 $\mu m$ between the first and the second substrates. In some embodiments, after step (c), there is a gap of less than 20 $\mu m$ between the first and the second substrates. In some embodiments, after step (c), there is a gap of less than 10 $\mu m$ between the first and the second substrates. In some embodiments, the mixture partially spreads into the gap. In some embodiments, the method of mixing further comprises sealing the gap by bringing the first and the second substrate closer together. In some embodiments, one of the two channels is coated with a moiety that increases surface energy corresponding to a water contact angle of less than 20 degree. In some embodiments, the moiety is a chemically inert moiety. In some embodiments, the delivering is performed by pressure. In some embodiments, the volume of the mixture is greater than the volume of the reactor cap. In some embodiments, the liquid comprises a nucleic acid. In some embodiments, n is at least 10. In some embodiments, n is at least 25. In some embodiments, n, the number of microstructures from which the liquid is mixed forming a mixture, can be at least 50. In some embodiments, n is at least 75. In some embodiments, n is at least 100. It is noted that any of the embodiments described herein can be combined with any of the methods, devices, arrays, substrates or systems provided in the current invention.

In yet another aspect, the present invention also provides a method of synthesizing n-mer oligonucleotides on a substrate as described herein. The method comprises: providing a substrate with resolved loci that are functionalized with a chemical moiety suitable for nucleotide coupling; and coupling at least two building blocks to a plurality of growing oligonucleotide chains each residing on one of the resolved loci according to a locus specific predetermined sequence without transporting the substrate between the couplings of the at least two building blocks, thereby synthesizing a plurality of oligonucleotides that are n basepairs long.

In practicing any of the methods of synthesizing n-mer oligonucleotides on a substrate as described herein, the method can further comprise coupling at least two building blocks to a plurality of growing oligonucleotide chains each residing on one of the resolved loci at a rate of at least 12 nucleotides per hour. In some embodiments, the method further comprises coupling at least two building blocks to a plurality of growing oligonucleotide chains each residing on one of the resolved loci at a rate of at least 15 nucleotides per hour. In some embodiments, the method further comprises coupling at least two building blocks to a plurality of growing oligonucleotide chains each residing on one of the resolved loci at a rate of at least 20 nucleotides per hour. In some embodiments, the method further comprises coupling at least two building blocks to a plurality of growing oligonucleotide chains each residing on one of the resolved loci at a rate of at least 25 nucleotides per hour. In some embodiments, at least one resolved locus comprises n-mer oligonucleotides deviating from the locus specific predetermined sequence with an error rate of less than 1/500 bp. In some embodiments, at least one resolved locus comprises n-mer oligonucleotides deviating from the locus specific predetermined sequence with an error rate of less than 1/1000 bp. In some embodiments, at least one resolved locus comprises n-mer oligonucleotides deviating from the locus specific predetermined sequence with an error rate of less than 1/2000 bp. In some embodiments, the plurality of oligonucleotides on the substrate deviate from respective locus specific predetermined sequences at an error rate of less than 1/500 bp. In some embodiments, the plurality of oligonucleotides on the substrate deviate from respective locus specific predetermined sequences at an error rate of less than 1/1000 bp. In some embodiments, the plurality of oligonucleotides on the substrate deviate from respective locus specific predetermined sequences at an error rate of less than 1/2000 bp.

In some embodiments related to the method of synthesizing n-mer oligonucleotides on a substrate as described herein, the building blocks comprise an adenine, guanine, thymine, cytosine, or uridine group, or a modified nucleotide. In some embodiments, the building blocks comprise a modified nucleotide. In some embodiments, the building blocks comprise dinucleotides. In some embodiments, the building blocks comprise phosphoramidite. In some embodiments, n is at least 100. In some embodiments, wherein n is at least 200. In some embodiments, n is at least 300. In some embodiments, n is at least 400. In some embodiments, the substrate comprises at least 100,000 resolved loci and at least two of the plurality of growing oligonucleotides are different from each other. In some embodiments, the method further comprise vacuum drying the substrate before coupling. In some embodiments, the building blocks comprise a blocking group. In some embodiments, the blocking group comprises an acid-labile DMT. In some embodiments, the acid-labile DMT comprises 4,4'-dimethoxytrityl. In some embodiments, the method further comprise oxidation or sulfurization. In some embodiments, the method further comprise chemically capping uncoupled oligonucleotide chains. In some embodiments, the method further comprise removing the blocking group, thereby deblocking the growing oligonucleotide chain. In some embodiments, the substrate comprises at least 10,000 vias providing fluid communication between a first surface of the substrate and a second surface of the substrate. In some embodiments, the substrate comprises at least 100,000 vias providing fluid communication between a first surface of the substrate and a second surface of the substrate. In some embodiments, the substrate comprises at least 1,000,000 vias providing fluid communication between a first surface of the substrate and a second surface of the substrate. It is noted that any of the embodiments described herein can be combined with any of the methods, devices, arrays, substrates or systems provided in the current invention.

In yet another aspect, the present invention also provides a method of constructing a gene library as described herein. The method comprises: entering at a first timepoint, in a computer readable non-transient medium a list of genes, wherein the list comprises at least 100 genes and wherein the genes are at least 500 bp; synthesizing more than 90% of the list of genes, thereby constructing a gene library with deliverable genes; preparing a sequencing library that represents the gene library; obtaining sequence information; selecting at least a subset of the deliverable genes based on the sequence information; and delivering the selected deliverable genes at a second timepoint, wherein the second timepoint is less than a month apart from the first timepoint.

In practicing any of the methods of constructing a gene library as described herein, the sequence information can be obtained via next-generation sequencing. The sequence information can be obtained by Sanger sequencing. In some embodiments, the method further comprises delivering at least one gene at a second timepoint. In some embodiments, at least one of the genes differ from any other gene by at least 0.1% in the gene library. In some embodiments, each of the genes differ from any other gene by at least 0.1% in the gene library. In some embodiments, at least one of the genes differ from any other gene by at least 10% in the gene library. In some embodiments, each of the genes differ from any other gene by at least 10% in the gene library. In some embodiments, at least one of the genes differ from any other gene by at least 2 base pairs in the gene library. In some embodiments, each of the genes differ from any other gene by at least 2 base pairs in the gene library. In some embodiments, at least 90% of the deliverable genes are error free. In some embodiments, the deliverable genes comprise an error rate of less than 1/3000 resulting in the generation of a sequence that deviates from the sequence of a gene in the list of genes. In some embodiments, at least 90% of the deliverable genes comprise an error rate of less than 1 in 3000 bp resulting in the generation of a sequence that deviates from the sequence of a gene in the list of genes. In some embodiments, a subset of the deliverable genes are covalently linked together. In some embodiments, a first subset of the list of genes encode for components of a first metabolic pathway with one or more metabolic end products. In some embodiments, the method further comprises selecting of the one or more metabolic end products, thereby constructing the list of genes. In some embodiments, the one or more metabolic end products comprise a biofuel. In some embodiments, a second subset of the list of genes encode for components of a second metabolic pathway with one or more metabolic end products. In some embodiments, the list comprises at least 500, genes. In some embodiments, the list comprises at least 5000 genes. In some embodiments, the list comprises at least 10000 genes. In some embodiments, the genes are at least 1 kb. In some embodiments, the genes are at least 2 kb. In some embodiments, the genes are at least 3 kb. In some embodiments, the second timepoint is less than 25 days apart from the first timepoint. In some embodiments, the second timepoint is less than 5 days apart from the first timepoint. In some embodiments, the second timepoint is less than 2 days apart from the first timepoint. It is noted that any of the embodiments described herein can be combined with any of the methods, devices, arrays, substrates or systems provided in the current invention.

Provided herein, in some embodiments, is a microfluidic device for nucleic acid synthesis, comprising a substantially planar substrate portion comprising n groupings of m microfluidic connections between opposite surfaces, wherein each one of the n*m microfluidic connections comprises a first channel and a second channel, and wherein the first channel within each of the n groupings is common to all m microfluidic connections, wherein the plurality of microfluidic connections span the substantially planar substrate portion along the smallest dimension of the substrate, and wherein n and m are at least 2. In some embodiments, the second channel is functionalized with a coating that is capable of facilitating the attachment of an oligonucleotide to the device. In some embodiments, the device further comprises a first oligonucleotide that is attached to the second channels in k of the n groupings. In some embodiments, k is 1. In some embodiments, the device further comprises a second oligonucleotide that is attached to 1 of then groupings. In some embodiments, 1 is 1. In some embodiments, the none of the groupings in the 1 groupings are in the k groupings.

In some embodiments, the oligonucleotide is at least 10 nucleotides, 25 nucleotides, 50 nucleotides, 75 nucleotides, 100 nucleotides, 125 nucleotides, 150 nucleotides, or 200 nucleotides long.

In some embodiments, the first and the second oligonucleotides differ by at least 2 nucleotides, 3 nucleotides, 4 nucleotides, 5 nucleotides, or 10 nucleotides.

In some embodiments, the n*m microfluidic connections are at most 5 mm, 1.5 mm, 1.0 mm, or 0.5 mm long. In some embodiments, the first channel within each of the n groupings is at most 5 mm, 1.5 mm, 1.0 mm, or 0.5 mm long. In some embodiments, the first channel within each of then groupings is at least 0.05 mm, 0.75 mm, 0.1 mm, 0.2 mm, 0.3 mm, or 0.4 mm long. In some embodiments, the second channel in each of the n*m microfluidic connections is at most 0.2 mm, 0.1 mm, 0.05 mm, 0.04 mm, or 0.03 mm long. In some embodiments, the second channel in each of the n*m microfluidic connections is at least 0.001 mm, 0.005 mm, 0.01 mm, 0.02 mm, or 0.03 mm long. In some embodiments, the cross section of the first channel within each of the n groupings is at least 0.01 mm, 0.025 mm, 0.05 mm, or 0.075 mm. In some embodiments, the cross section of the first channel within each of the n groupings is at most 1 mm, 0.5 mm, 0.25 mm, 0.1 mm, or 0.075 mm. In some embodiments, the cross section of the second channel in each of the n*m microfluidic connections is at least 0.001 mm, 0.05 mm, 0.01 mm, 0.015 mm, or 0.02 mm. In some embodiments, the cross section of the second channel in each of the n*m microfluidic connections is at most 0.25 mm, 0.125 mm, 0.050 mm, 0.025 mm, 0.02 mm. In some embodiments, the standard deviation in the cross section of the second channels in each of the n*m microfluidic connections is less than 25%, 20%, 15%, 10%, 5%, or 1% of the mean of the cross section. In some embodiments, the variation in the cross section within at least 90% of the second channels of the n*m microfluidic connections is at most 25%, 20%, 15%, 10%, 5%, or 1%.

In some embodiments, n is at least 10, 25, 50, 100, 1000, or 10000. In some embodiments, m is at least 3, 4, or 5.

In some embodiments, the substrate comprises at least 5%, 10%, 25%, 50%, 80%, 90%, 95%, or 99% silicon.

In some embodiments, at least 90% of the second channels of the n*m microfluidic connections is functionalized with a moiety that increases surface energy. In some embodiments, the surface energy is increased to a level corresponding to a water contact angle of less than 75, 50, 30, or 20 degrees.

In some embodiments, the aspect ratio for at least 90% of the second channels of the n*m microfluidic connections is less than 1, 0.5, or 0.3. In some embodiments, the aspect ratio for at least 90% of the first channels in the n groupings is less than 0.5, 0.3, or 0.2.

In some embodiments, the total length of at least 10%, 25%, 50%, 75%, 90%, or 95% of the n*m fluidic connections are within 10%, 20%, 30%, 40%, 50%, 100%, 200%, 500%, or 1000% of the smallest dimension of the substantially planar substrate.

In some embodiments, the substantially planar portion of the device is fabricated from a SOI wafer.

In another aspect, the invention relates to a method of nucleic acid amplification, comprising: (a) providing a sample comprising n circularized single stranded nucleic acids, each comprising a different target sequence; (b) providing a first adaptor that is hybridizable to at least one adaptor hybridization sequence on m of the n circularized single stranded nucleic acids; (c) providing conditions suitable for extending the first adaptor using the m circularized single stranded nucleic acids as a template, thereby generating m single stranded amplicon nucleic acids, wherein each of the m single stranded amplicon nucleic acids comprises a plurality of replicas of the target sequence from its template; (d) providing a first auxiliary oligonucleotide that is hybridizable to the first adaptor; and (e) providing a first agent under conditions suitable for the first agent to cut the m single stranded amplicon nucleic acids at a plurality of cutting sites, thereby generating a plurality of single stranded replicas of the target sequences in the m circularized single stranded nucleic acids. In some embodiments, n or m is at least 2. In some embodiments, n or m is at least 3, 4, 5, 6, 7, 8, 9, 10, 15, 20, 25, 50, 75, 100, 150, 200, 300, 400, or 500. In some embodiments, m is less than n. In some embodiments, the sample comprising the n circularized single stranded nucleic acid is formed by providing at least n linear single stranded nucleic acids, each comprising one of the different target sequences and circularizing the n linear single stranded nucleic acids, thereby generating the n circularized single stranded nucleic acids. In some embodiments, the first adaptor is hybridizable to both ends of the n linear single stranded nucleic acids concurrently. In some embodiments, the different target sequences in the n linear single stranded nucleic acids are flanked by a first and a second adaptor hybridization sequence. In some embodiments, the at least n linear single stranded nucleic acids are generated by de novo oligonucleotide synthesis. In some embodiments, the first adaptor hybridization sequence in each of the n linear single stranded nucleic acids differ by no more than two nucleotide bases. In some embodiments, the first or the second adaptor hybridization sequence is at least 5 nucleotides long. In some embodiments, the first or the second adaptor hybridization sequence is at most 75, 50, 45, 40, 35, 30, or 25 nucleotides long. In some embodiments, the ends of the n linear single stranded nucleic acids pair with adjacent bases on the first adaptor when the first adaptor is hybridized to the both ends of the linear single stranded nucleic acid concurrently. In some embodiments, the locations of the plurality of cutting sites are such that the adaptor hybridization sequence is severed from at least 5% of a remainder sequence portion of the m circularized single stranded nucleic acid replicas. In some embodiments, at least 5% of the sequence of the m circularized single stranded nucleic acid replicas other than the at least one adaptor hybridization sequence remains uncut. In some embodiments, the locations of the plurality of cutting sites are outside the at least one adaptor hybridization sequence. In some embodiments, the locations of the plurality of cutting sites are independent of the target sequences. In some embodiments, the locations of the plurality of cutting sites are determined by at least one sequence element within the sequence of the first adaptor or the first auxiliary oligonucleotide. In some embodiments, the sequence element comprises a recognition site for a restriction endonuclease. In some embodiments, the first auxiliary oligonucleotide or the first adaptor oligonucleotide comprises a recognition site for a Type IIS restriction endonuclease. In some embodiments, the recognition sites are at least 1, 2, 3, 4, 5, 6, 7, 8, 9, or 10 nucleotides away from the cutting sites. In some embodiments, the plurality of cutting sites are at junctures of single and double stranded nucleic acids. In some embodiments, the double stranded nucleic acids comprise the first adaptor and the first auxiliary oligonucleotide. In some embodiments, the single stranded nucleic acids consists essentially of the m different target sequences. In some embodiments, the m different target sequences have at most 95% pairwise similarity. In some embodiments, the m different target sequences have at most 90% pairwise similarity. In some embodiments, the m different target sequences have at most 80% pairwise similarity. In some embodiments, the m different target sequences have at most 50% pairwise similarity. In some embodiments, generating the m single stranded amplicon nucleic acid comprises strand displacement amplification. In some embodiments, the first auxiliary oligonucleotide comprises an affinity tag. In some embodiments, the affinity tag comprises biotin or biotin derivative. In some embodiments, the method further comprises isolating double stranded nucleic acids from the sample. In some embodiments, the isolating comprises affinity purification, chromatography, or gel purification. In some embodiments, the first agent comprises a restriction endonuclease. In some embodiments, the first agent comprises at least two restriction endonucleases. In some embodiments, the first agent comprises a Type IIS restriction endonuclease. In some embodiments, the first agent comprises a nicking endonuclease. In some embodiments, the first agent comprises at least two nicking endonucleases. In some embodiments, the first agent comprises at least one enzyme selected from the group consisting of MlyI, SchI, AlwI, BccI, BceAI, BsmAI, BsmFI, FokI, HgaI, PleI, SfaNI, BfuAI, BsaI, BspMI, BtgZI, EarI, BspQI, SapI, SgeI, BceFI, BslFI, BsoMAI, Bst71I, FaqI, AceIII, BbvII, BveI, LguI, BfuCI, DpnII, FatI, MboI, MluCI, Sau3AI, Tsp509I, BssKI, PspGI, StyD4I, Tsp45I, AoxI, BscFI, Bsp143I, BssMI, BseENII, BstMBI, Kzo9I, NedII, Sse9I, TasI, TspEI, AjnI, BstSCI, EcoRII, MaeIII, NmuCI, Psp6I, Mn1I, BspCNI, BsrI, BtsCI, HphI, HpyAV, MboII, AcuI, BciVI, BmrI, BpmI, BpuEI, BseRI, BsgI, BsmI, BsrDI, BtsI, EciI, MmeI, NmeAIII, Hin4II, TscAI, Bce83I, BmuI, BsbI, BscCI, NlaIII, Hpy99I, TspRI, FaeI, Hin1III, Hsp92II, SetI, TaiI, TscI, TscAI, TseFI, Nb.BsrDI, Nb.BtsI, AspCNI, BscGI, BspNCI, EcoHI, FinI, TsuI, UbaF11I, UnbI, Vpak11AI, BspGI, DrdII, Pfl1108I, UbaPI, Nt.AlwI, Nt.BsmAI, Nt.BstNBI, and Nt.BspQI, and variants thereof. In some embodiments, the first agent comprises essentially the same function, recognizes the same or essentially the same recognition sequence, or cuts at the same or essentially same cutting site, as any of the listed first agents and variants. In some embodiments, the at least two restriction enzymes comprise MlyI and BciVI or BfuCI and MlyI. In some embodiments, the method further comprises (a) partitioning the sample into a plurality of fractions; (b) providing at least one fraction with a second adaptor that is hybridizable to at least one adaptor hybridization sequence on k of the n different circularized single stranded nucleic acids; (c) providing conditions suitable for extending the second adaptor using the k circularized single stranded nucleic acids as a template, thereby generating k single stranded amplicon nucleic acids, wherein the second single stranded amplicon nucleic acid comprises a plurality of replicas of the target sequence from its template; (d) providing a second auxiliary oligonucleotide that is hybridizable to the second adaptor; and (e) providing a second agent under conditions suitable for the agent to cut the k single stranded amplicon nucleic acids at a second plurality of cutting sites, thereby generating a plurality of single stranded replicas of the target sequences in the k circularized single stranded nucleic acids. In some embodiments, the first and the second adaptors are the same. In some embodiments, the first and the second auxiliary oligonucleotides are the same. In some embodiments, the first and the second agents are the same. In some embodiments, k+m is less than n. In some embodiments, k is at least 2. In some embodiments, the sample comprising the n circularized single stranded nucleic acid is formed by single stranded nucleic acid amplification. In some embodiments, the single stranded nucleic acid amplification comprises: (a) providing a sample comprising at least m circularized single stranded precursor nucleic acids; (b) providing a first precursor adaptor that is hybridizable to the m circularized single stranded precursor nucleic acids; (c) providing conditions suitable for extending the first precursor adaptor using the m circularized single stranded precursor nucleic acids as a template, thereby generating m single stranded precursor amplicon nucleic acids, wherein the single stranded amplicon nucleic acid comprises a plurality of replicas of the m circularized single stranded precursor nucleic acid; (d) providing a first precursor auxiliary oligonucleotide that is hybridizable to the first precursor adaptor; and (e) providing a first precursor agent under conditions suitable for the first precursor agent to cut the first single stranded precursor amplicon nucleic acid at a plurality of cutting sites, thereby generating the m linear precursor nucleic acids. In some embodiments, the method further comprises circularizing the m linear precursor nucleic acids, thereby forming replicas of the m circularized single stranded precursor nucleic acids. In some embodiments, the m circularized single stranded precursor nucleic acid is amplified by at least 10, 100, 250, 500, 750, 1000, 1500, 2000, 3000, 4000, 5000, 10000-fold, or more in single stranded replicas. In some embodiments, at least one of the m circularized single stranded nucleic acids is at a concentration of about or at most about 100 nM, 10 nM, 1 nM, 50 pM, 1 pM, 100 fM, 10 fM, 1 fM, or less. In some embodiments, circularizing comprises ligation. In some embodiments, ligation comprises the use of a ligase selected from the group consisting of T4 DNA ligase, T3 DNA ligase, T7 DNA ligase, E. coli DNA ligase, Taq DNA ligase, and 9N DNA ligase.

In yet a further aspect, the invention, in various embodiments relates to a kit comprising: (a) a first adaptor; (b) a first auxiliary oligonucleotide that is hybridizable to the adaptor; (c) a ligase; and (d) a first cleaving agent, comprising at least one enzyme selected from the group consisting of MlyI, SchI, AlwI, BccI, BceAI, BsmAI, BsmFI, FokI, HgaI, PleI, SfaNI, BfuAI, BsaI, BspMI, BtgZI, EarI, BspQI, SapI, SgeI, BceFI, BslFI, BsoMAI, Bst71I, FaqI, AceIII, BbvII, BveI, LguI, BfuCI, DpnII, FatI, MboI, MluCI, Sau3AI, Tsp509I, BssMI, PspGI, StyD4I, Tsp45I, AoxI, BscFI, Bsp143I, BssMI, BseENII, BstMBI, Kzo9I, NedII, Sse9I, TasI, TspEI, AjnI, BstSCI, EcoRII, MaeIII, NmuCI, Psp6I, Mn1I, BspCNI, BsrI, BtsCI, HphI, HpyAV, MboII, AcuI, BciVI, BmrI, BpmI, BpuEI, BseRI, BsgI, BsmI, BsrDI, BtsI, EciI, MmeI, NmeAIII, Hin4II, TscAI, Bce83I, BmuI, BsbI, BscCI, NlaIII, Hpy99I, TspRI, FaeI, Hin1II, Hsp92II, SetI, TaiI, TscI, TscAI, TseFI, Nb.BsrDI, Nb.BtsI, AspCNI, BscGI, BspNCI, EcoHI, FinI, TsuI, UbaF11I, UnbI, Vpak11AI, BspGI, DrdII, Pfl1108I, UbaPI, Nt.AlwI, Nt.BsmAI, Nt.BstNBI, and Nt.BspQI, and variants thereof. In some embodiments, the first agent comprises essentially the same function, recognizes the same or essentially the same recognition sequence, or cuts at the same or essentially same cutting site as any of the listed first agents and variants. In some embodiments, the kit further comprises a second cleaving agent. In some embodiments, the second cleaving agent comprises and enzyme selected from the group consisting of MlyI, SchI, AlwI, BccI, BceAI, BsmAI, BsmFI, FokI, HgaI, PleI, SfaNI, BfuAI, BsaI, BspMI, BtgZI, EarI, BspQI, SapI, SgeI, BceFI, BslFI, BsoMAI, Bst71I, FaqI, AceIII, BbvII, BveI, LguI, BfuCI, DpnII, FatI, MboI, MluCI, Sau3AI, Tsp509I, BssMI, PspGI, StyD4I, Tsp45I, AoxI, BscFI, Bsp143I, BssMI, BseENII, BstMBI, Kzo9I, NedII, Sse9I, TasI, TspEI, AjnI, BstSCI, EcoRII, MaeIII, NmuCI, Psp6I, Mn1I, BspCNI, BsrI, BtsCI, HphI, HpyAV, MboII, AcuI, BciVI, BmrI, BpmI, BpuEI, BseRI, BsgI, BsmI, BsrDI, BtsI, EciI, MmeI, NmeAIII, Hin4II, TscAI, Bce83I, BmuI, BsbI, BscCI, NlaIII, Hpy99I, TspRI, FaeI, Hin1II, Hsp92II, SetI, TaiI, TscI, TscAI, TseFI, Nb.BsrDI, Nb.BtsI, AspCNI, BscGI, BspNCI, EcoHI, FinI, TsuI, UbaF11I, UnbI, Vpak11AI, BspGI, DrdII, Pfl1108I, UbaPI, Nt.AlwI, Nt.BsmAI, Nt.BstNBI, and Nt.BspQI, and variants thereof. In some embodiments, the second agent comprises essentially the same function, recognizes the same or essentially the same recognition sequence, or cuts at the same or essentially same cutting site as any of the listed second agents and variants. In some embodiments, the first cleaving agents comprises MlyI. In some embodiments, the second cleaving agent comprises BciVI or BfuCI.

In yet another aspect, the invention relates to a method of nucleic acid amplification, comprising: (a) providing a sample comprising n circularized single stranded nucleic acids, each comprising a different target sequence; (b) providing a first adaptor that is hybridizable to at least one adaptor hybridization sequence on m of the n circularized single stranded nucleic acids; (c) providing conditions suitable for extending the first adaptor using the m circularized single stranded nucleic acids as a template, thereby generating m single stranded amplicon nucleic acids, wherein each of the m single stranded amplicon nucleic acids comprises a plurality of replicas of the target sequence from its template; (d) generating double stranded recognition sites for a first agent on the m single stranded amplicon nucleic acids; and (e) providing the first agent under conditions suitable for the first agent to cut the m single stranded amplicon nucleic acids at a plurality of cutting sites, thereby generating a plurality of single stranded replicas of the target sequences in the m circularized single stranded nucleic acids. In some embodiments, the double stranded recognition sites comprise a first portion of the first adaptor on a first strand of the double stranded recognition sites and a second strand of the first adaptor on the second strand of the double stranded recognition sites. In some embodiments, the adaptor comprises a palindromic sequence. In some embodiments, the double stranded recognition sites are generated by hybridizing the first and second portions of the first adaptor to each other. In some embodiments, the m single stranded amplicon nucleic acids comprise a plurality of double stranded self-hybridized regions.

In a yet further aspect, the invention relates to a method for generating a long nucleic acid molecule, the method comprising the steps of: (a) providing a plurality of nucleic acids immobilized on a surface, wherein said plurality of nucleic acids comprises nucleic acids having overlapping complementary sequences; (b) releasing said plurality of nucleic acids into solution; and (c) providing conditions promoting: i) hybridization of said overlapping complementary sequences to form a plurality of hybridized nucleic acids; and ii) extension or ligation of said hybridized nucleic acids to synthesize the long nucleic acid molecule.

In another aspect, the invention relates to an automated system capable of processing one or more substrates, comprising: an inkjet print head for spraying a microdroplet comprising a chemical species on a substrate; a scanning transport for scanning the substrate adjacent to the print head to selectively deposit the microdroplet at specified sites; a flow cell for treating the substrate on which the microdroplet is deposited by exposing the substrate to one or more selected fluids; an alignment unit for aligning the substrate correctly relative to the print head each time when the substrate is positioned adjacent to the print head for deposition; and not comprising a treating transport for moving the substrate between the print head and the flow cell for treatment in the flow cell, wherein said treating transport and said scanning transport are different elements.

In yet another aspect, the invention relates to an automated system for synthesizing oligonucleotides on a substrate, said automated system capable of processing one or more substrates, comprising: an inkjet print head for spraying a solution comprising a nucleoside or activated nucleoside on a substrate; a scanning transport for scanning the substrate adjacent to the print head to selectively deposit the nucleoside at specified sites; a flow cell for treating the substrate on which the monomer is deposited by exposing the substrate to one or more selected fluids; an alignment unit for aligning the substrate correctly relative to the print head each time when the substrate is positioned adjacent to the print head for deposition; and not comprising a treating transport for moving the substrate between the print head and the flow cell for treatment in the flow cell, wherein said treating transport and said scanning transport are different elements.

In yet a further aspect, the invention relates to an automated system comprising: an inkjet print head for spraying a microdroplet comprising a chemical species on a substrate; a scanning transport for scanning the substrate adjacent to the print head to selectively deposit the microdroplet at specified sites; a flow cell for treating the substrate on which the microdroplet is deposited by exposing the substrate to one or more selected fluids; and an alignment unit for aligning the substrate correctly relative to the print head each time when the substrate is positioned adjacent to the print head for deposition; and wherein the system does NOT comprise a treating transport for moving the substrate between the print head and the flow cell for treatment in the flow cell.

With the above in mind, reference is made more specifically to the drawings which, for illustrative purposes, show the present invention embodied in compositions, systems and methods in FIGS. 1A-1C and 2A-2C. It will be appreciated that the methods, systems, and compositions may vary in configuration and in the details of the individual parts in various embodiments of the invention. Further, the methods may vary in detail and the order of the events or acts. In various embodiments, the invention is described primarily in terms of use with nucleic acids, in particular, DNA oligomers and polynucleotides. It should be understood, however, that the invention may be used with a variety of different types of molecules, including RNA or other nucleic acids, peptides, proteins, or other molecules of interest. Suitable building blocks for each of these larger molecules of interest are known in the art.

The present invention provides compositions, systems, and methods useful in the preparation and the synthesis of libraries of molecules of interest, including nucleic acids, polypeptides, proteins and combinations thereof. In various embodiments, the invention contemplates the use of static and dynamic wafers, e.g. those that are manufactured from silicon substrates, for performing micro-, nano-, or picoliter scale reactions in parallel. In addition, the same can be applied to micro-, nano-, or picoliter manipulation of fluids in parallel to allow for linking a plurality of reactions in resolved volumes. The manipulation of fluids may comprise flowing, combining, mixing, fractionation, generation of drops, heating, condensation, evaporation, sealing, stratification, pressurizing, drying, or any other suitable fluid manipulation known in the art. In various embodiments, the wafers provide architectures for fluid manipulation that are built into the surface. Features of varying shape and size may be architected inside or through a wafer substrate. The methods and compositions of the invention, in various embodiments, make use of specifically architected devices exemplified in further detail herein, for the synthesis of biological molecules. In particular, the invention provides for the de novo synthesis of large, high-density libraries comprising long, high-quality oligonucleotides and polynucleotides, e.g. using standard phosphoramidite chemistry and suitable gene assembly techniques, by precisely controlling reaction conditions such as time, dosage and temperature.

Figure 1C:
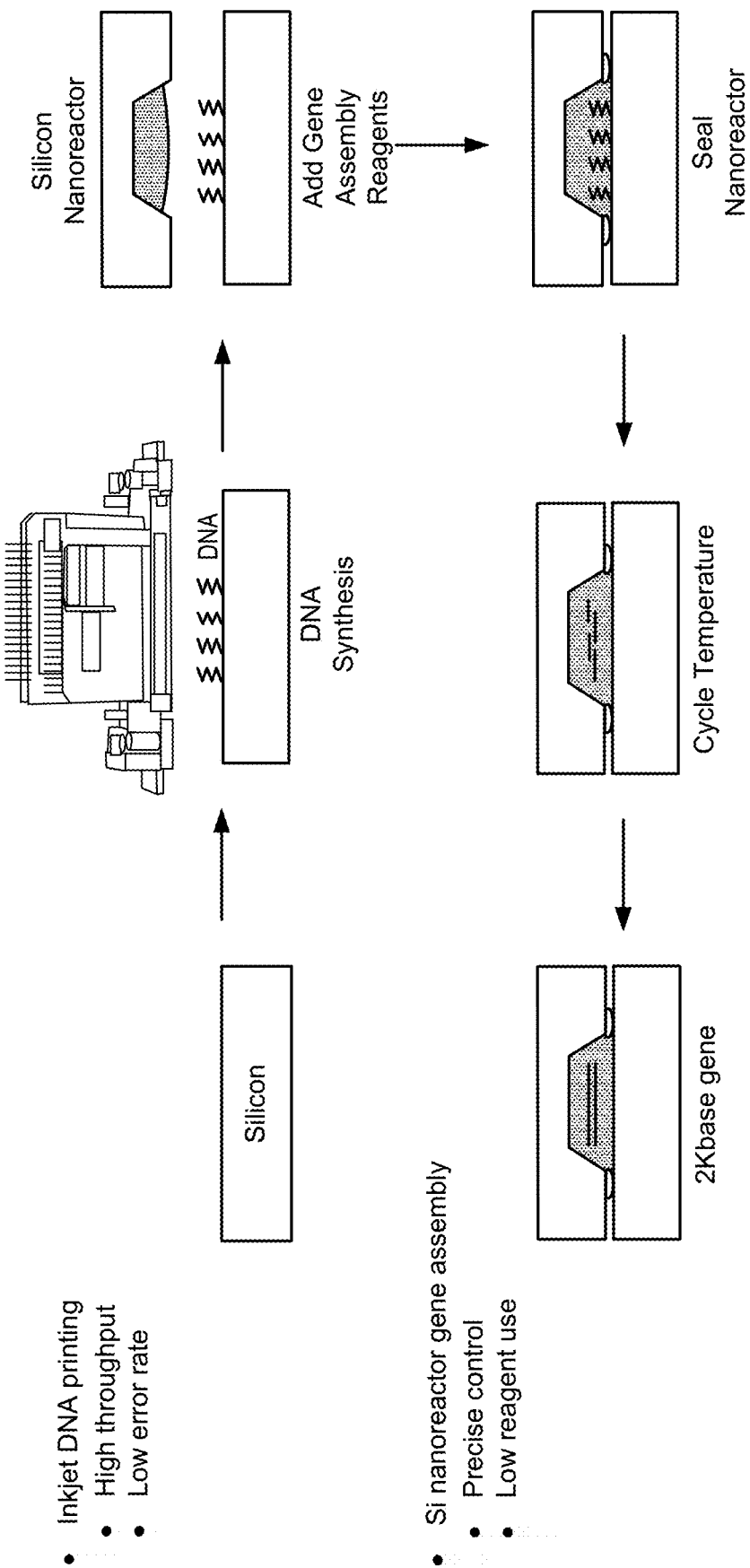

Referring now to FIG. 1C, the invention in various embodiments contemplates the use of one or more static or dynamic wafers for fluid manipulation. The wafers may be constructed from a number of suitable materials as further described herein, e.g. silicon. Nanoreactor wafers may be configured to receive and hold liquids in a plurality of features. Additional wafers, for example those that are used for in situ synthesis reactions, maybe contacted with nanoreactor wafers to collect and/or mix liquids. The nanoreactors may collect liquids from a plurality of additional wafers. Typically, nanoreactors are aligned with one or more resolved loci on additional wafers when the nanoreactor wafer is contacted. Reagents and solvents may be provided within the nanoreactor prior to contact. Alternatively, nanoreactors may be empty prior to contacting an additional wafer. In some embodiments, nanoreactors collect oligonucleotides synthesized in one or more resolved locus of a DNA synthesis wafer. These oligonucleotides can be assembled into a longer gene within the nanoreactor. The nanoreactors may be sealed upon alignment and contact of an additional wafer by any suitable means, e.g. capillary burst valves, pressure, adhesives, or any other suitable sealing means known the art. The seal may be releasable. Reactions within the nanoreactor wafer may be carried out in sealed volumes and may comprise temperature cycling, e.g. as applied in PCR or PCA. Isothermal reactions, such as isothermal amplification, are further within the bounds of the invention. The DNA synthesis wafers may be configured to perform in situ synthesis of oligonucleotides at resolved loci on or inside the surface with precise control. An inkjet printhead may be utilized to deliver drops of reagents for synthesis, e.g. standard phosphoramidite synthesis onto the resolved loci of the synthesis wafer. Other reagents that are common to a plurality of resolved loci may be passed through them in bulk. In some embodiments, DNA synthesis wafers are replaced with synthesis wafers for the in situ synthesis of molecules other than DNA oligonucleotides as further described elsewhere herein. Thus, the invention contemplates fast synthesis of large libraries of oligonucleotides and long genes with high-quality through the precise control of reaction conditions in a plurality of small volumes. A further benefit of the invention is a reduced reagent use in comparison to the traditional synthesis methods known in the art.

Figure 2A:
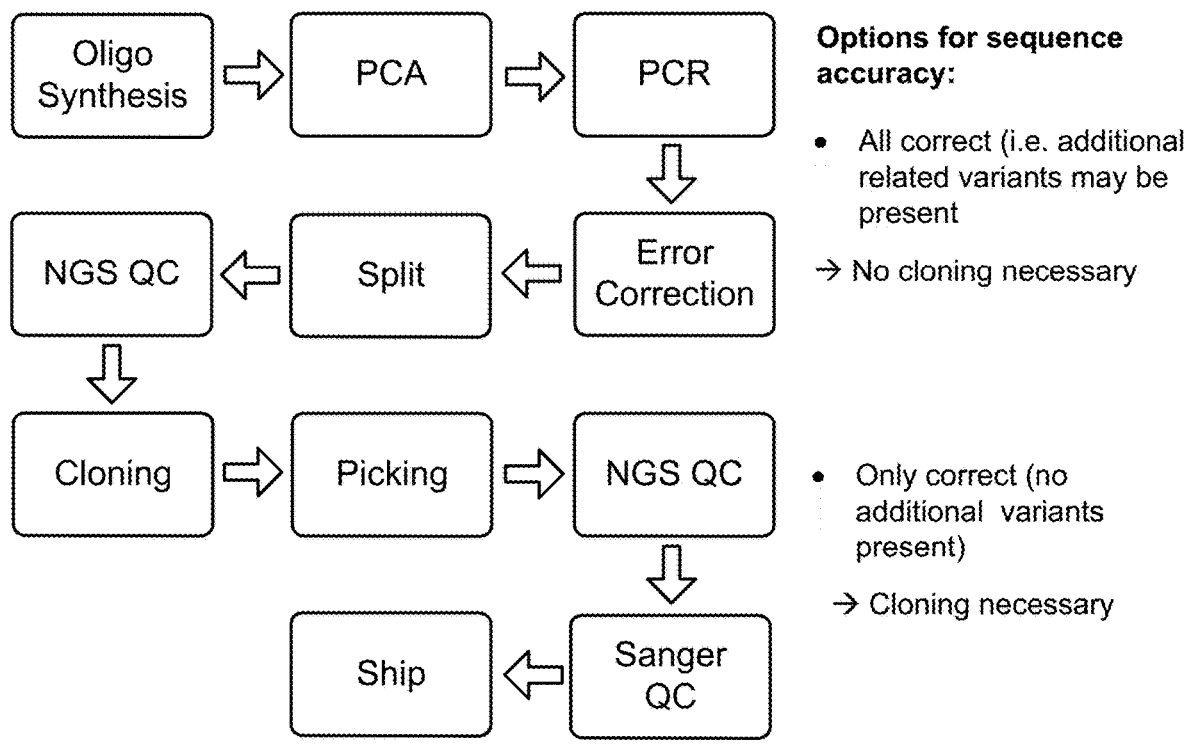
FIGS. 2A-2C are block diagrams demonstrating exemplary business process flows. Cloning of the synthesized genes may be skipped (FIG. 2B).
Figure 2B:
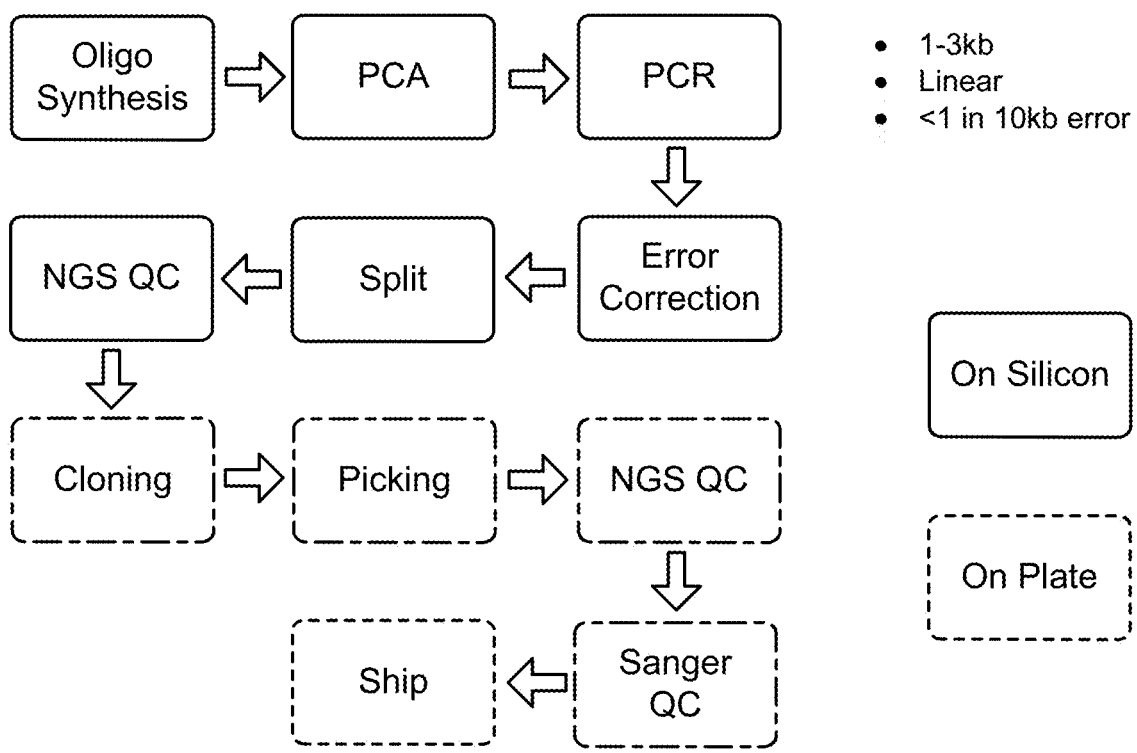
Figure 2C:
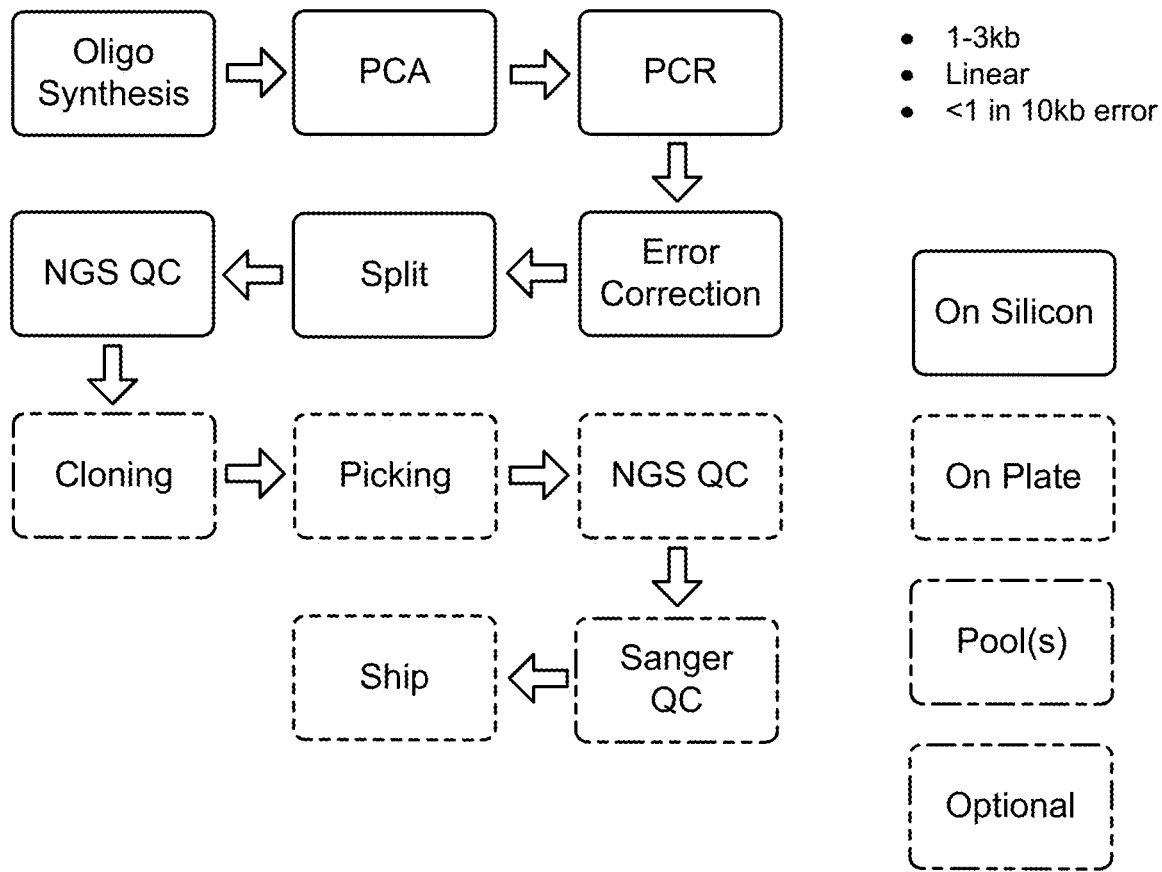

Various methods are contemplated for the de novo synthesis of gene libraries with low error rates. FIGS. 2A-2C illustrates exemplary applications of the methods and compositions of the invention for the synthesis of large, high quality gene libraries with long sequences in parallel. In various embodiments, static and dynamic wafers enable a plurality of reactions in a process flow. For example, oligonucleotide synthesis typically in situ on a DNA synthesis wafer, may be followed by a gene assembly reaction, such as polymerase cycling assembly (PCA), of the synthesized oligonucleotides into longer sequences. The assembled sequences may be amplified, e.g. through PCR. Suitable error correction reactions described herein or known in the art can be used to minimize the number of assembled sequences that deviate from a target sequence. Sequencing libraries may be built and a fraction of the product may be aliquoted for sequencing, such as next generation sequencing (NGS).

The gene synthesis processes as exemplified in FIGS. 2A-2C may be adjusted according to the needs of a requester. According to the results obtained from an initial sequencing step, e.g. NGS, the assembled genes with acceptable error rates may be shipped, e.g. on a plate, to a requester (FIG. 2B). The methods and compositions of the invention allow for error rates less than about 1/10 kb to be easily achieved, although alternative error thresholds may be set as described in further detail elsewhere herein. To achieve higher degrees of purity, de novo synthesized/assembled sequences may be cloned purified from single colonies. The identity of a correct desired sequence may be tested through sequencing, e.g. NGS. Optionally, a higher confidence for the accuracy of the sequencing information may be obtained, e.g. via another sequencing method such as Sanger sequencing. Verified sequences may be shipped, e.g. on a plate, to a requester (FIG. 2C) Methods for generation of sequencing libraries are described in further detail elsewhere herein.

Substrates/Wafers

In an aspect, a substrate having a functionalized surface made by any of the methods described herein and methods of synthesizing oligonucleotides on the substrate having a functionalized surface are described herein. The substrate can comprise a solid support having a plurality of resolved loci. The plurality of resolved loci may have any geometry, orientation or organization. The resolved loci may be in any scale (e.g., micro-scale or nano-scale), or contain microstructures fabricated into the substrate surface. The resolved loci can be localized on microchannels with at least one dimension. Individual resolved loci of a substrate may be fluidically disconnected from each other, e.g. a first resolved locus for the synthesis of a first oligonucleotide may be on a first via between the two surfaces of a substrate and a second resolved locus for the synthesis of a second oligonucleotide may be on a second via between the two surfaces of a substrate, the first and second vias not being fluidically connected within the substrate, but starting and ending from the same two surfaces of the substrate. In some cases, the microstructure of resolved loci can be microchannels or microwells in 2-D or 3-D. A "3-D" microchannel means the cavity of the microchannel can be interconnected or extend within the solid support. Within the microchannels or microwells, there can be secondary microstructures or features with any geometry, orientation or organization. The surface of the secondary features may be functionalized with a moiety that can decrease the surface energy of the surface of the secondary features. Droplets of reagents for synthesizing oligonucleotides can be deposited into the microchannels or microwells. A microwell, as used herein, refers to a structure of microfluidic scale that can hold a liquid. In various embodiments, microwells allow liquid flow between a top and a bottom end, through a fluidic opening on each end, therefore acting like a microchannel. In these contexts, the terms microwell and microchannel are used interchangeably throughout the specification.

Figure 3:
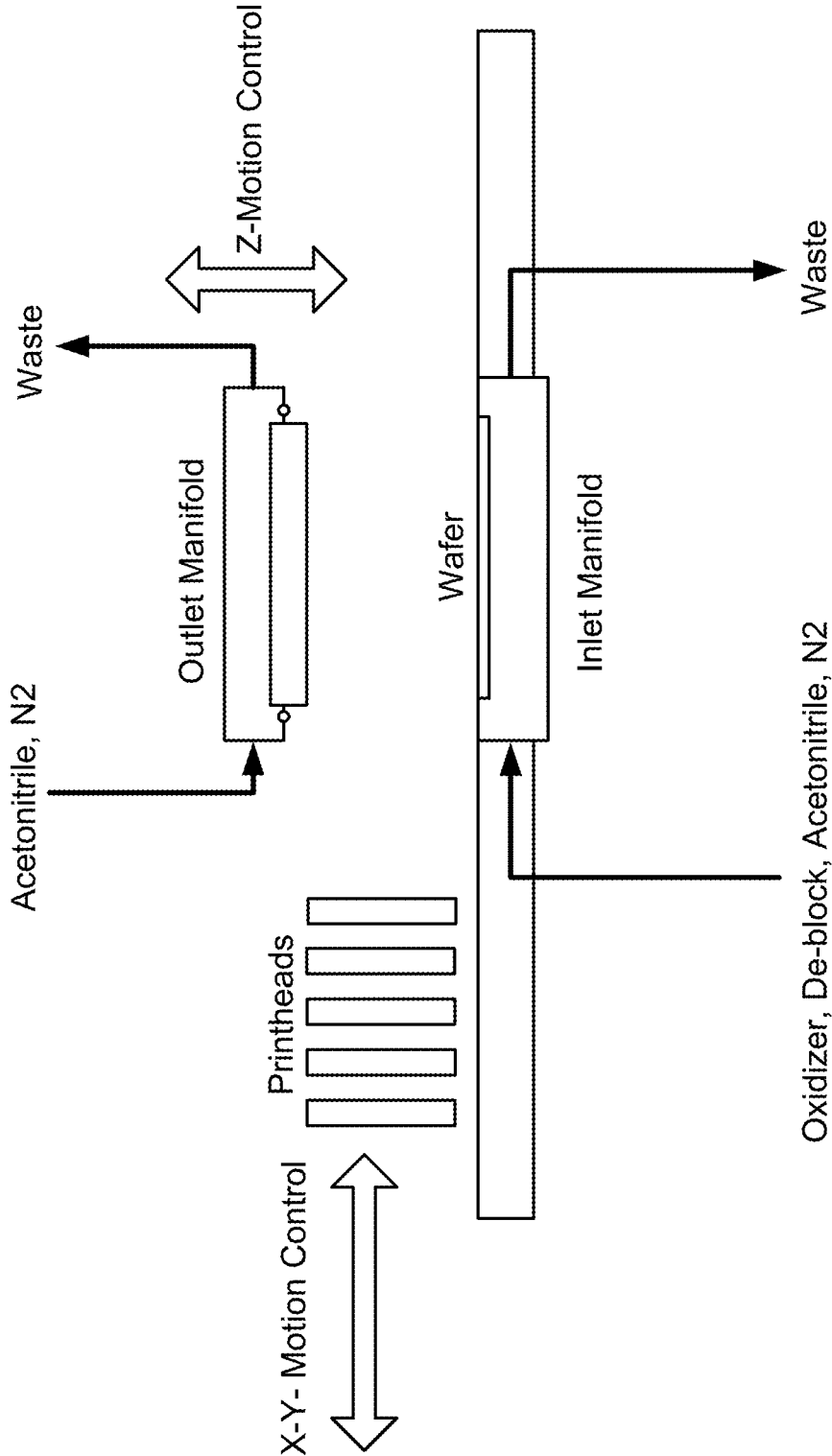
FIG. 3 demonstrates an exemplary outline of a system for oligonucleotide synthesis, including a printer, e.g. inkjet printer, for reagent deposition, a substrate (wafer), schematics outlining the alignment of the system elements in multiple directions, and exemplary setups for reagent flow.
Figure 4:
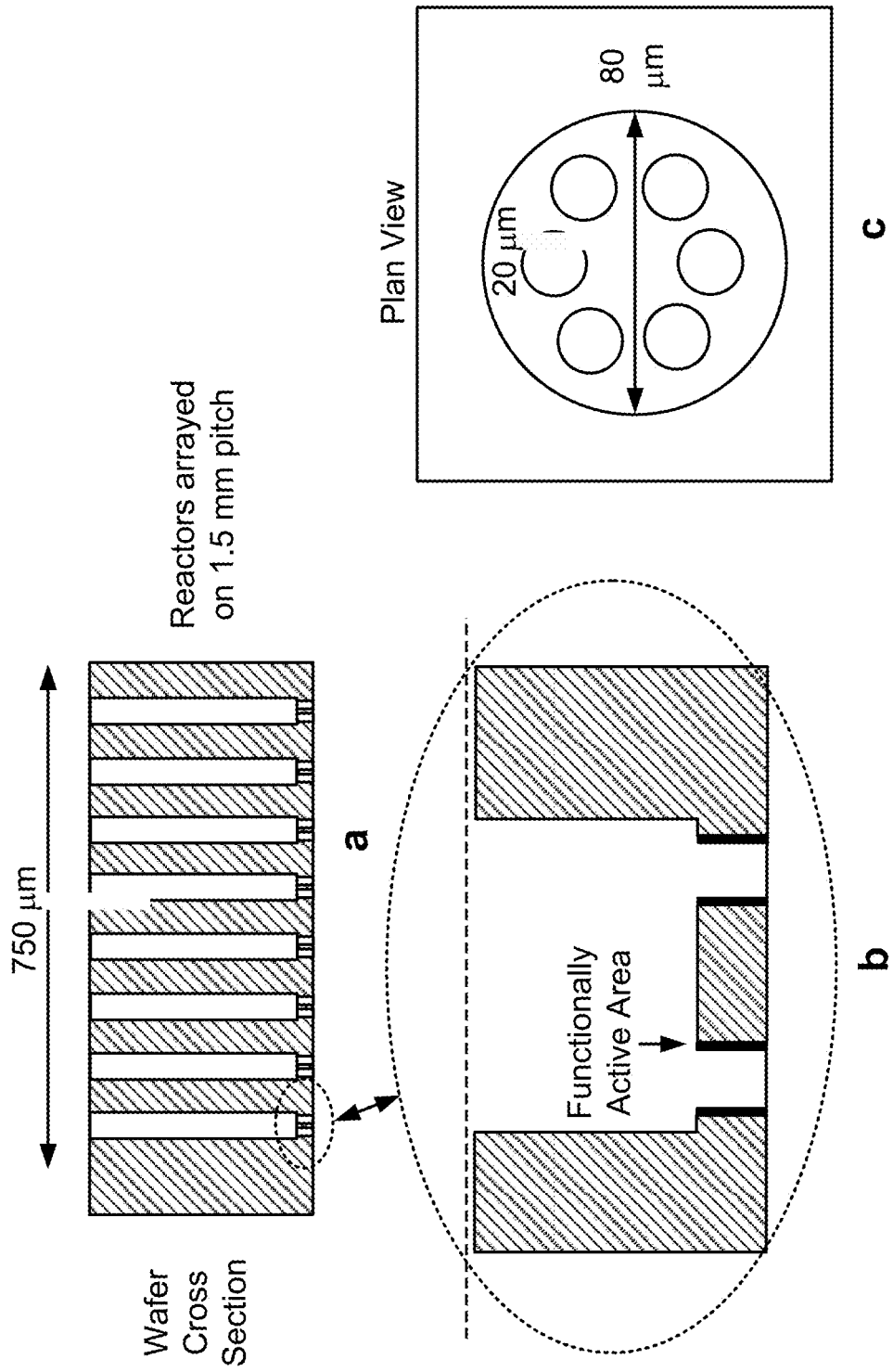
FIG. 4 illustrates an example of the design microstructures built into a substrate (oligonucleotide wafer reactor).
Figure 5:
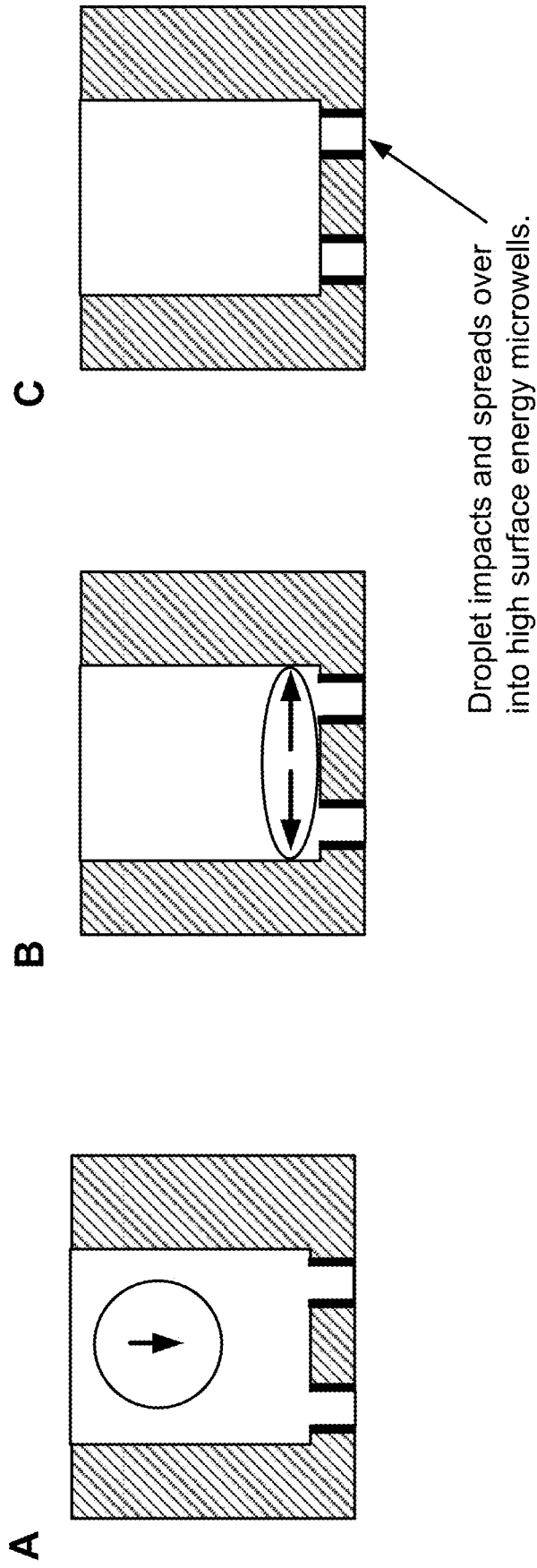
FIG. 5 is a diagram demonstrating an exemplary process for reagent deposition into the microstructures illustrated in FIG. 4. The selected area for surface functionalization allows reagent spreading into the smaller functionalized wells under wetting conditions.

FIG. 3 illustrates an example of the system for oligonucleotide synthesis comprising a first substrate and, optionally, a second substrate as described herein. The inkjet printer printheads can move in X-Y direction to the location of the first substrate. A second substrate can move in Z direction to seal with the first substrate, forming a resolved reactor. The synthesized oligonucleotides can be delivered from the first substrate to the second substrate. In another aspect, current invention also concerns a system for oligonucleotide assembly. The system for oligonucleotide assembly can comprise a system for wafer handling. FIG. 4 illustrates an example for the layout design of a substrate, according to various embodiments of the invention. The substrate can comprise a plurality of microwells and the microwells can be arrayed on a uniform pitch, e.g. a 1.5 mm pitch. Alternatively, multiple pitches may be picked in different directions of the layout, for example, rows of microstructures can be defined by a first pitch and within each row, the microstructures may be separated by a second pitch. The pitch may comprise any suitable size, e.g. 0.1, 0.2, 0.3, 0.4, 0.5, 0.6, 0.7, 0.75, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.5, 4, 4.5, or 5 mm. The microwell can be designed having any suitable dimensions, for example a diameter of 80 μm as exemplified in FIG. 4, or any suitable diameter, including 10, 20, 30, 40, 50, 60, 70, 80, 90, 100, 110, 120, 130, 140, 150, 160, 170, 180, 190, 200, 300, 400 or 500 μm, and the microwells can be connected to a plurality of smaller microwells. The surface of the smaller microwells can be functionalized at selected regions facilitating liquid of reagents to flow into, for example via a high energy surface functionalization. As illustrated in FIG. 4, the diameter of the smaller microwells can be about 20 μm, or any suitable diameter, including 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, 55, 60, 65, 70, 75 or 80 μm. FIG. 5 illustrates a case when a droplet of reagent is deposited into a microwell by an inkjet printer. The liquid droplet can spread over and fill the smaller microwells, in some cases facilitated by a high energy surface modification of the surface of the microwells in comparison adjacent surfaces.

Figure 6A:
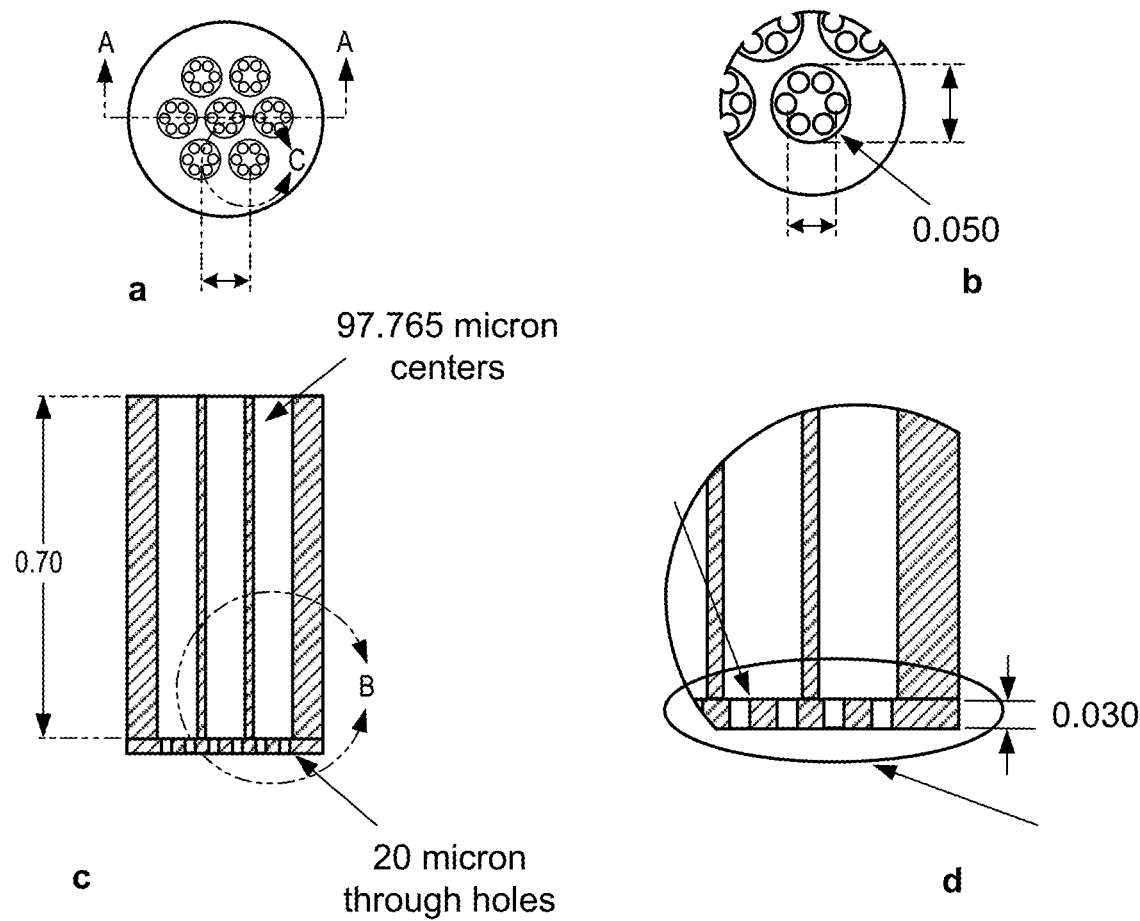
FIG. 6A are illustrations further exemplifying the microstructures illustrated in FIG. 4.
Figure 6B:
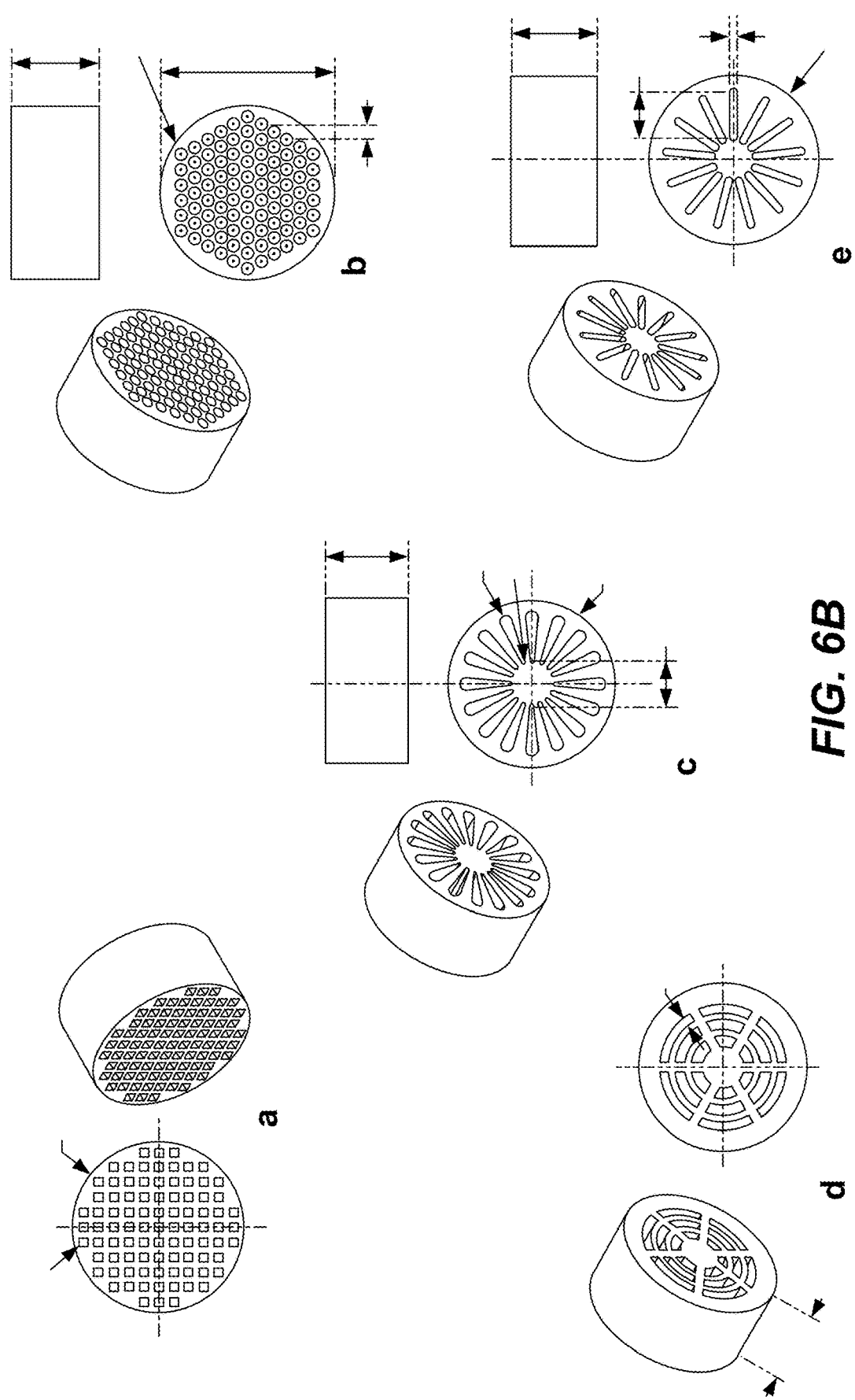
FIG. 6B are illustrations of various alternative designs for the microstructures.
Figure 6C:
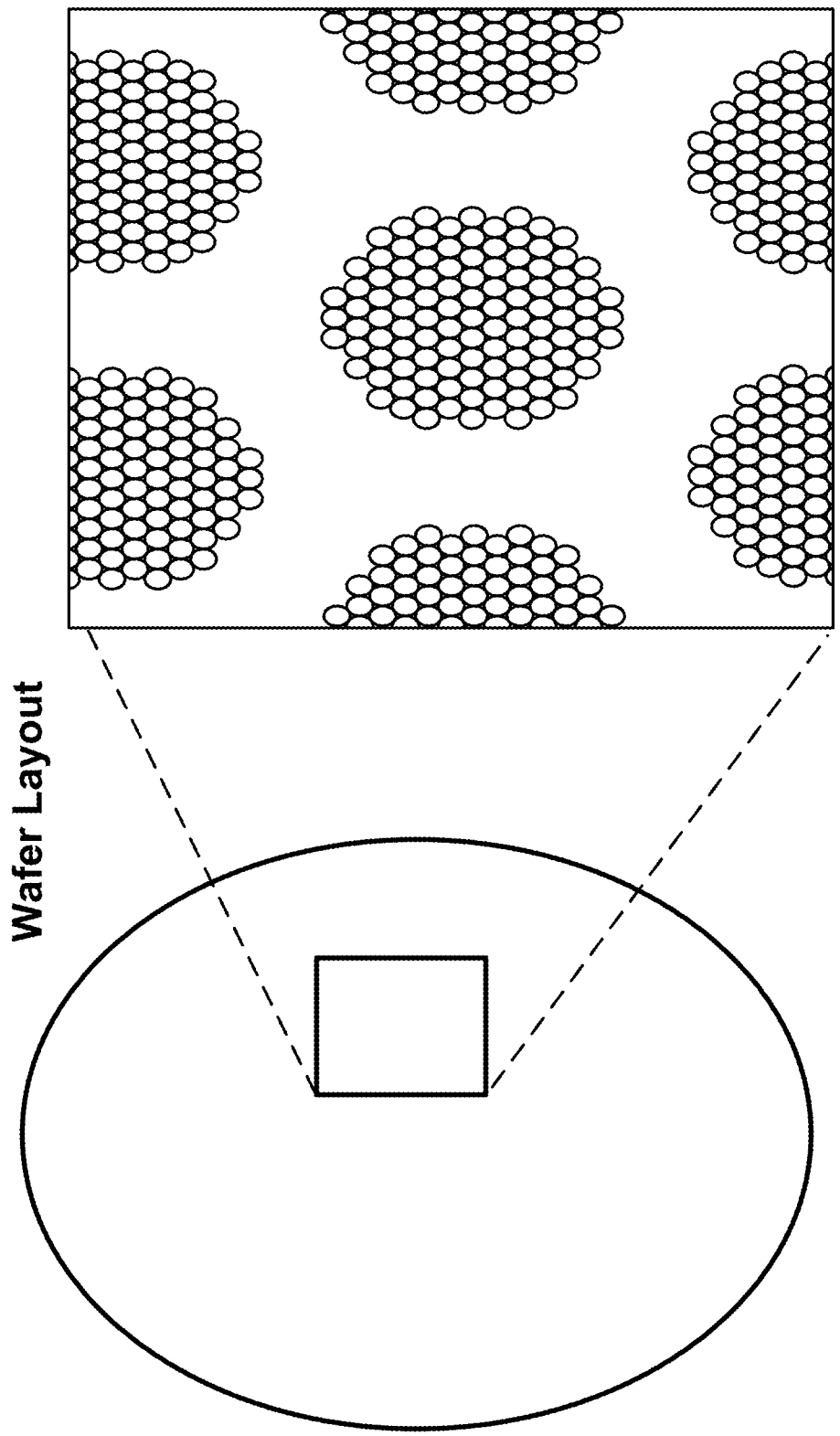
FIG. 6C illustrates a layout design for the microstructures on the substrate (wafer).

Having a high density of resolved loci on the substrate having a functionalized surface may be desirable for having a small device and/or synthesizing a large number of molecules with a small device and/or synthesizing a large number of different molecules. The functionalized surface of the substrate may comprise any suitable density of resolved loci (e.g., a density suitable for synthesizing oligonucleotides with a given number of total different oligonucleotides to be synthesized, given amount of time for the synthesis process, or for a given cost per oligonucleotide, gene, or library). In some embodiments, the surface has a density of resolved loci of about 1, about 2, about 3, about 4, about 5, about 6, about 7, about 8, about 9, about 10, about 15, about 20, about 25, about 30, about 35, about 40, about 50, about 75, about 100, about 200, about 300, about 400, about 500, about 600, about 700, about 800, about 900, about 1000, about 1500, about 2000, about 3000, about 4000, about 5000, about 6000, about 7000, about 8000, about 9000, about 10000, about 20000, about 40000, about 60000, about 80000, about 100000, or about 500000 sites per 1 $mm^2$. In some embodiments, the surface has a density of resolved loci of at least about 50, at least 75, at least about 100, at least about 200, at least about 300, at least about 400, at least about 500, at least about 600, at least about 700, at least about 800, at least about 900, at least about 1000, at least about 1500, at least about 2000, at least about 3000, at least about 4000, at least about 5000, at least about 6000, at least about 7000, at least about 8000, at least about 9000, at least about 10000, at least about 20000, at least about 40000, at least about 60000, at least about 80000, at least about 100000, or at least about 500000 sites per 1 $mm^2$. The resolved loci on the substrate can have any different organization. For example without limitations, the resolved loci can be clustered in close proximity to form one or more circular region, rectangular region, elliptical region, irregular region and the like. In an aspect, the resolved loci are closely packed and have a low amount or no amount of cross-contamination (e.g., the droplets of reagents that are deposited into one resolved locus will not substantially mix with the droplets of reagents that are deposited into another nearest resolved locus). The organization of the resolved loci on the substrate can be designed such that it allows each sub-region or the entire region to be covered together creating a sealed cavity with controlled humidity, pressure or gas content in the sealed cavity so that the each sub-region or the entire region can have the same humidity, pressure or gas content, or substantially similar humidity, pressure or gas content as allowed under fluidically connected conditions. Some examples of different designs for the resolved loci on the substrate are illustrated in FIG. 6. For example, FIG. 6B part b is a design of a layout referred to as Array of Holes; FIG. 6B part c is a design of a layout referred to as Flowers; FIG. 6B part d is a design of a layout referred to as Gunsight; and FIG. 6B part e is a design of a layout referred to as Radial Flower. FIG. 6C exemplifies a design of the substrate covered with a series of microwells on a 97.765 μm stencil. The microwells as exemplified in FIG. 6C are clustered into islands. The microwells can be filled with reagents from the inkjet head.

Each of the resolved loci on the substrate can have any shape that is known in the art, or the shapes that can be made by methods known in the art. For example, each of the resolved loci can have an area that is in a circular shape, a rectangular shape, elliptical shape, or irregular shape. In some embodiments, the resolved loci can be in a shape that allows liquid to easily flow through without creating air bubbles. In some embodiments, the resolved loci can have a circular shape, with a diameter that can be about, at least about, or less than about 1 micrometers (μm), 2 μm, 3 μm, 4 μm, 5 μm, 6 μm, 7 μm, 8 μm, 9 μm, 10 μm, 11 μm, 12 μm, 13 μm, 14 μm, 15 μm, 16 μm, 17 μm, 18 μm, 19 μm, 20 μm, 25 μm, 30 μm, 35 μm, 40 μm, 45 μm, 50 μm, 55 μm, 60 μm, 65 μm, 70 μm, 75 μm, 80 μm, 85 μm, 90 μm, 95 μm, 100 μm, 110 μm, 120 μm, 130 μm, 140 μm, 150 μm, 160 μm, 170 μm, 180 μm, 190 μm, 200 μm, 250 μm, 300 μm, 350 μm, 400 μm, 450 μm, 500 μm, 550 μm, 600 μm, 650 μm, 700 μm or 750 μm. The resolved loci may have a monodisperse size distribution, i.e. all of the microstructures may have approximately the same width, height, and/or length. Alternatively, the resolved loci of may have a limited number of shapes and/or sizes, for example the resolved loci may be represented in 2, 3, 4, 5, 6, 7, 8, 9, 10, 12, 15, 20, or more distinct shapes, each having a monodisperse size. In some embodiments, the same shape can be repeated in multiple monodisperse size distributions, for example, 2, 3, 4, 5, 6, 7, 8, 9, 10, 12, 15, 20, or more monodisperse size distributions. A monodisperse distribution may be reflected in a unimodular distribution with a standard deviation of less than 25%, 20%, 15%, 10%, 5%, 3%, 2%, 1%, 0.1%, 0.05%, 0.01%, 0.001% of the mode or smaller.

A substrate having a high density of resolved loci typically results in a resolved locus within a small area. Consequently, it can result in a small microchannel. The microchannels can contain deposited droplets of reagents in different volumes. The microchannels can have any suitable dimensions that allow sufficiently large surface areas and/or volumes for the various embodiments of the invention. In an aspect, the volume of the microchannel is suitably large such that a reagent in a droplet that is deposited in the microchannel is not fully depleted during the oligonucleotide synthesis. In these aspects, amongst others, the volume of a well structure can guide the time period or density with which oligonucleotides can be synthesized.

Each of the resolved loci can have any suitable area for carrying out the reactions according to various embodiments of the invention described herein. In some cases, the plurality of resolved loci can occupy any suitable percentage of the total surface area of the substrate. In some cases, the area of the resolved loci can be the cross-sectional area of microchannels or microwells built into a substrate. In some embodiments, the plurality of the microstructures or resolved loci directly can occupy about, at least about, or less than about 1%, 2%, 3%, 4%, 5%, 6%, 7%, 8%, 9%, 10%, 11%, 12%, 13%, 14%, 15%, 16%, 17%, 18%, 19%, 20%, 25%, 30%, 35%, 40%, 45%, 50%, 55%, 60%, 65%, 70%, 75%, 80%, 85%, 90%, or 95% of the surface of the substrate. In some embodiments, the plurality of resolved loci can occupy about, at least about, or less than about 10 $mm^2$, 11 $mm^2$, 12 $mm^2$, 13 $mm^2$, 14 $mm^2$, 15 $mm^2$, 16 $mm^2$, 17 $mm^2$, 18 $mm^2$, 19 $mm^2$, 20 $mm^2$, 25 $mm^2$, 30 $mm^2$, 35 $mm^2$, 40 $mm^2$, 50 $mm^2$, 75 $mm^2$, 100 $mm^2$, 200 $mm^2$, 300 $mm^2$, 400 $mm^2$, 500 $mm^2$, 600 $mm^2$, 700 $mm^2$, 800 $mm^2$, 900 $mm^2$, 1000 $mm^2$, 1500 $mm^2$, 2000 $mm^2$, 3000 $mm^2$, 4000 $mm^2$, 5000 $mm^2$, 7500 $mm^2$, 10000 $mm^2$, 15000 $mm^2$, 20000 $mm^2$, 25000 $mm^2$, 30000 $mm^2$, 35000 $mm^2$, 40000 $mm^2$, 50000 $mm^2$, 60000 $mm^2$, 70000 $mm^2$, 80000 $mm^2$, 90000 $mm^2$, 100000 $mm^2$, 200000 $mm^2$, 300000 $mm^2$, or more of total area.

The microstructures built into a substrate may comprise microchannels or microwells, wherein the microstructures start from a top or bottom surface of the substrate and in some cases are fluidically connected to a typically opposing surface (e.g. bottom or top). The terms "top" and "bottom" do not necessarily relate to the position of the substrate with respect to gravity at any given time, but are generally used for convenience and clarity. The microchannels or microwells can have any suitable depth or length. In some cases, the depth or length of the microchannel or microwell is measured from the surface of the substrate (and/or bottom of the solid support) to the top of the solid support. In some cases, the depth or length of the microchannel or microwell is approximately equal to the thickness of the solid support. In some embodiments, the microchannels or microwells are about, less than about, or greater than about 1 micrometer (μm), 2 μm, 3 μm, 4 μm, 5 μm, 6 μm, 7 μm, 8 μm, 9 μm, 10 μm, 15 μm, 20 μm, 25 μm, 30 μm, 35 μm, 40 μm, 45 μm, 50 μm, 55 μm, 60 μm, 65 μm, 70 μm, 75 μm, 80 μm, 85 μm, 90 μm, 95 μm, 100 μm, 125 μm, 150 μm, 175 μm, 200 μm, 300 μm, 400 μm or 500 μm deep or long. The microchannels or microwells can have any length of perimeter that is suitable for the embodiments of the invention described herein. In some cases, the perimeter of the microchannel or microwell is measured as the perimeter of a cross-sectional area, e.g. a cross sectional area that is perpendicular to fluid flow direction through said microchannel or microwell. In some embodiments, the microchannels or microwells have about, less than about, or at least about 1 micrometer (μm), 2 μm, 3 μm, 4 μm, 5 μm, 6 μm, 7 μm, 8 μm, 9 μm, 10 μm, 15 μm, 20 μm, 25 μm, 30 μm, 31 μm, 35 μm, 40 μm, 45 μm, 50 μm, 55 μm, 60 μm, 65 μm, 70 μm, 75 μm, 80 μm, 85 μm, 90 μm, 95 μm, 100 μm, 125 μm, 150 μm, 175 μm, 200 μm, 300 μm, 400 μm or 500 μm in perimeter. In some embodiments, the nominal arclength density of the microchannels or microwells can have any suitable arclength per $μm^2$ of the planar substrate area. As described herein, the arclength density refers to the length of the perimeters of the cross-sections of the microchannels or microwells per surface area of the planar substrate. For example, without limitation, the nominal arclength density of the microchannels or microwells can be at least 0.001, 0.002, 0.003, 0.004, 0.005, 0.006, 0.007, 0.008, 0.009, 0.01, 0.015, 0.02, 0.025, 0.03, 0.035, 0.04, 0.045, 0.05, 0.055, 0.06, 0.065, 0.07, 0.075, 0.08, 0.085, 0.09, 0.095, 0.1, 0.2, 0.3, 0.4, 0.5, 0.6, 0.7, 0.8, 0.9, 1 $μm/μm^2$, or more. In some embodiments, the nominal arclength density of the microchannels or microwells can be 0.036 $μm/μm^2$. In some embodiments, the nominal arclength density of the microchannels or microwells can be at least 0.001 $μm/μm^2$. In some embodiments, the nominal arclength density of the microchannels or microwells can be at least 0.01 $μm/μm^2$. Further, the nominal surface area of the microchannels or microwells that is suitable for reactions described herein, e.g. through surface coating with a suitable moiety, can be maximized. The surface area of the microchannels or microwells that is coated with suitable moieties as described herein can facilitate the attachment of oligonucleotides to the surface. In some embodiments, the nominal surface area of the microchannels or microwells suitable for reactions described herein, such as oligonucleotide synthesis, is at least 0.05, 0.1, 0.2, 0.3, 0.4, 0.5, 0.6, 0.7, 0.8, 0.9, 1, 1.05, 1.1, 1.15, 1.2, 1.25, 1.3, 1.35, 1.4, 1.45, 1.5, 1.55, 1.6, 1.65, 1.7, 1.75, 1.8, 1.85, 1.9, 1.95, 2, 2.1, 2.2, 2.3, 2.4, 2.5, 2.6, 2.7, 2.8, 2.9, 3, 3.5, 4, 4.5 or 5 µm$^2$ of the planar substrate area.

The microchannels or microwells can have any volume that is suitable for the methods and compositions described herein. In some embodiments, the microchannels or microwells have a volume that is less than about 10, 20, 30, 40, 50, 60, 70, 80, 90, 100, 150, 200, 250, 300, 350, 400, 450, 500, 550, 600, 650, 700, 750, 800, 850, 900 or 950 picoliter (pl), less than about 1, 2, 3, 4, 5, 6, 7, 8, 9, 10, 15, 20, 25, 30, 35, 40, 50, 60, 70, 80, 90, 100, 110, 120, 130, 140, 150, 160, 170, 180, 190, 200, 250, 300, 350, 400, 450, 500, 550, 600, 650, 700, 750, 800, 850, 900, 950 or 990 nanoliter (nl), less than about 0.5 microliters (µl), less than about 1 µl, less than about 1.5 µl, less than about 2 µl, less than about 2.5 µl, less than about 3 µl, less than about 3.5 µl, less than about 4 µl, less than about 4.5 µl, less than about 5 µl, less than about 5.5 µl, less than about 6 µl, less than about 6.5 µl, less than about 7 µl, less than about 7.5 µl, less than about 8 µl, less than about 8.5 µl, less than about 9 µl, less than about 9.5 µl, less than about 10 µl, less than about 11 µl, less than about 12 µl, less than about 13 µl, less than about 14 µl, less than about 15 µl, less than about 16 µl, less than about 17 µl, less than about 18 µl, less than about 19 µl, less than about 20 µl, less than about 25 µl, less than about 30 µl, less than about 35 µl, less than about 40 µl, less than about 45 µl, less than about 50 µl, less than about 55 µl, less than about 60 µl, less than about 65 µl, less than about 70 µl, less than about 75 µl, less than about 80 µl, less than about 85 µl, less than about 90 µl, less than about 95 µl or less than about 100 pl. In some embodiments, the microchannels or microwells have a volume that is equal to or greater than about 10, 20, 30, 40, 50, 60, 70, 80, 90, 100, 150, 200, 250, 300, 350, 400, 450, 500, 550, 600, 650, 700, 750, 800, 850, 900 or 950 picoliter (pl), equal or greater than about 1, 2, 3, 4, 5, 6, 7, 8, 9, 10, 15, 20, 25, 30, 35, 40, 50, 60, 70, 80, 90, 100, 110, 120, 130, 140, 150, 160, 170, 180, 190, 200, 250, 300, 350, 400, 450, 500, 550, 600, 650, 700, 750, 800, 850, 900, 950 or 990 nanoliter (nl), equal or greater than about 0.5 microliters (µl), about 1 µl, about 1.5 µl, about 2 µl, about 2.5 µl, about 3 µl, about 3.5 µl, about 4 µl, about 4.5 µl, about 5 µl, about 5.5 µl, about 6 µl, about 6.5 µl, about 7 µl, about 7.5 µl, about 8 µl, about 8.5 µl, about 9 µl, about 9.5 µl, about 10 µl, about 11 µl, about 12 µl, about 13 µl, about 14 µl, about 15 µl, about 16 µl, about 17 µl, about 18 µl, about 19 µl, about 20 µl, about 25 µl, about 30 µl, about 35 µl, about 40 µl, about 45 µl, about 50 µl, about 55 µl, about 60 µl, about 65 µl, about 70 µl, about 75 µl, about 80 µl, about 85 µl, about 90 µl, about 95 µl or about 100 pl.

The microchannels or microwells can have an aspect ratio of less than 1. As used herein, the term "aspect ratio," refers to the ratio of a channel's width to that channel's depth. Thus, a channel having an aspect ratio of less than 1, is deeper than it is wide, while a channel having an aspect ratio greater than 1 is wider than it is deep. In some aspects, the aspect ratio of the microchannels or microwells can be less than or equal to about 0.5, about 0.2, about 0.1, about 0.05 or less. In some embodiments, the aspect ratio of the microchannels or microwells can be about 0.1. In some embodiments, the aspect ratio of the microchannels or channels can be about 0.05. The microstructures described herein, e.g., microchannels or microwells having aspect ratios less than 1, 0.1 or 0.05, may include channels having one, two, three, four, five, six or more corners, turns, and the like. The microstructures described herein may include the aspect ratios described, e.g., less than 1, 0.1 or 0.05, with respect to all microchannels or microwells contained within a particular resolved locus, e.g., one or more intersecting channels, some of these channels, a single channel and even a portion or portions of one or more microchannels or microwells. Other designs and methods of fabricating the microchannels with low aspect ratios are described in U.S. Pat. No. 5,842,787, which is incorporated herein by reference.

The microstructures such as microchannels or microwells on a substrate having a plurality of resolved loci can be manufactured by any method that is described herein or otherwise known in the art (e.g., microfabrication processes). Microfabrication processes that may be used in making the substrate disclosed herein include without limitation lithography; etching techniques such as wet chemical, dry, and photoresist removal; microelectromechanical (MEMS) techniques including microfluidics/lab-on-a-chip, optical MEMS (also called MOEMS), RF MEMS, Power-MEMS, and BioMEMS techniques and deep reactive ion etching (DRIE); nanoelectromechanical (NEMS) techniques; thermal oxidation of silicon; electroplating and electroless plating; diffusion processes such as boron, phosphorus, arsenic, and antimony diffusion; ion implantation; film deposition such as evaporation (filament, electron beam, flash, and shadowing and step coverage), sputtering, chemical vapor deposition (CVD), epitaxy (vapor phase, liquid phase, and molecular beam), electroplating, screen printing, and lamination. See generally Jaeger, Introduction to Microelectronic Fabrication (Addison-Wesley Publishing Co., Reading Mass. 1988); Runyan, et al., Semiconductor Integrated Circuit Processing Technology (Addison-Wesley Publishing Co., Reading Mass. 1990); Proceedings of the IEEE Micro Electro Mechanical Systems Conference 1987-1998; Rai-Choudhury, ed., Handbook of Microlithography, Micromachining & Microfabrication (SPIE Optical Engineering Press, Bellingham, Wash. 1997).

In an aspect, a substrate having a plurality of resolved loci can be manufactured using any method known in the art. In some embodiments, the material of the substrate having a plurality of resolved loci can be a semiconductor substrate such as silicon dioxide. The materials of the substrate can also be other compound III-V or II-VI materials, such as Gallium arsenide (GaAs), a semiconductor produced via the Czochralski process (Grovenor, C. (1989). *Microelectronic Materials*. CRC Press. pp. 113-123). The material can present a hard, planar surface that exhibits a uniform covering of reactive oxide (—OH) groups to a solution in contact with its surface. These oxide groups can be the attachment points for subsequent silanization processes. Alternatively, a lipophillic and hydrophobic surface material can be deposited that mimics the etching characteristics of silicon oxide. Silicon nitride and silicon carbide surfaces may also be utilized for the manufacturing of suitable substrates according to the various embodiments of the invention.

In some embodiments, a passivation layer can be deposited on the substrate, which may or may not have reactive oxide groups. The passivation layer can comprise silicon nitride ($Si_3N_4$) or polymide. In some instances, a photolithographic step can be used to define regions where the resolved loci form on the passivation layer.

The method for producing a substrate having a plurality of resolved loci can start with a substrate. The substrate (e.g., silicon) can have any number of layers disposed upon it, including but not limited to a conducting layer such as a metal. The conducting layer can be aluminum in some instances. In some cases, the substrate can have a protective layer (e.g., titanium nitride). In some cases, the substrate can have a chemical layer with a high surface energy. The layers can be deposited with the aid of various deposition techniques, such as, for example, chemical vapor deposition (CVD), atomic layer deposition (ALD), plasma enhanced CVD (PECVD), plasma enhanced ALD (PEALD), metal organic CVD (MOCVD), hot wire CVD (HWCVD), initiated CVD (iCVD), modified CVD (MCVD), vapor axial deposition (VAD), outside vapor deposition (OVD) and physical vapor deposition (e.g., sputter deposition, evaporative deposition).

In some cases, an oxide layer is deposited on the substrate. In some instances, the oxide layer can comprise silicon dioxide. The silicon dioxide can be deposited using tetraethyl orthosilicate (TEOS), high density plasma (HDP), or any combination thereof.

In some instances, the silicon dioxide can be deposited using a low temperature technique. In some cases, the process is low-temperature chemical vapor deposition of silicon oxide. The temperature is generally sufficiently low such that pre-existing metal on the chip is not damaged. The deposition temperature can be about 50° C., about 100° C., about 150° C., about 200° C., about 250° C., about 300° C., about 350° C., and the like. In some embodiments, the deposition temperature is below about 50° C., below about 100° C., below about 150° C., below about 200° C., below about 250° C., below about 300° C., below about 350° C., and the like. The deposition can be performed at any suitable pressure. In some instances, the deposition process uses RF plasma energy.

In some cases, the oxide is deposited by a dry thermally grown oxide procedure (e.g., those that may use temperatures near or exceeding 1,000° C.). In some cases, the silicon oxide is produced by a wet steam process.

The silicon dioxide can be deposited to a thickness suitable for the manufacturing of suitable microstructures described in further detail elsewhere herein.

The silicon dioxide can be deposited to any suitable thickness. In some embodiments, the silicon dioxide layer may have a thickness of at least or at least about 1 nm, 2 nm, 3 nm, 4 nm, 5 nm, 6 nm, 7 nm, 8 nm, 9 nm, 10 nm, 15 nm, 20 nm, 25 nm, 30 nm, 35 nm, 40 nm, 45 nm, 50 nm, 55 nm, 60 nm, 65 nm, 70 nm, 75 nm, 80 nm, 85 nm, 90 nm, 95 nm, 100 nm, 125 nm, 150 nm, 175 nm, 200 nm, 300 nm, 400 nm or 500 nm, 1 µm, 1.1 µm, 1.2 µm, 1.3 µm, 1.4 µm, 1.5 µm, 1.6 µm, 1.7 µm, 1.8 µm, 1.9 µm, 2.0 µm, or more. The silicon dioxide layer may have a thickness of at most or at most about 2.0 µm, 1.9 µm, 1.8 µm, 1.7 µm, 1.6 µm, 1.5 µm, 1.4 µm, 1.3 µm, 1.2 µm, 1.1 µm, 1.0 µm, 500 nm, 400 nm, 300 nm, 200 nm, 175 nm, 150 nm, 125 nm, 100 nm, 95 nm, 90 nm, 85 nm, 80 nm, 75 nm, 70 nm, 65 nm, 60 nm, 55 nm, 50 nm, 45 nm, 40 nm, 35 nm, 30 nm, 25 nm, 20 nm, 15 nm, 10 nm, 9 nm, 8, nm, 7 nm, 6 nm, 5 nm, 4 nm, 3 nm, 2 nm, 1 nm, or less. The silicon dioxide layer may have a thickness that is between 1.0 nm-2.0 µm, 1.1-1.9 µm, 1.2-1.8 nm, 1.3-1.7 µm, 1.4-1.6 µm. Those of skills in the art will appreciate that The silicon dioxide layer may have a thickness that falls within any range bound by any of these values, for example (1.5-1.9 µm). The silicon dioxide may have a thickness that falls within any range defined by any of the values serving as endpoints of the range. The resolved loci (e.g., microchannels or microwells) can be created in a silicon dioxide substrate using various manufacturing techniques that are known in the art. Such techniques may include semiconductor fabrication techniques. In some cases, the resolved loci are created using photolithographic techniques such as those used in the semiconductor industry. For example, a photo-resist (e.g., a material that changes properties when exposed to electromagnetic radiation) can be coated onto the silicon dioxide (e.g., by spin coating of a wafer) to any suitable thickness. The substrate including the photo-resist can be exposed to an electromagnetic radiation source. A mask can be used to shield radiation from portions of the photo-resist in order to define the area of the resolved loci. The photo-resist can be a negative resist or a positive resist (e.g., the area of the resolved loci can be exposed to electromagnetic radiation or the areas other than the resolved loci can be exposed to electromagnetic radiation as defined by the mask). The area overlying the location in which the resolved loci are to be created is exposed to electromagnetic radiation to define a pattern that corresponds to the location and distribution of the resolved loci in the silicon dioxide layer. The photoresist can be exposed to electromagnetic radiation through a mask defining a pattern that corresponds to the resolved loci. Next, the exposed portion of the photoresist can be removed, such as, e.g., with the aid of a washing operation (e.g., deionized water). The removed portion of the mask can then be exposed to a chemical etchant to etch the substrate and transfer the pattern of resolved loci into the silicon dioxide layer. The etchant can include an acid, such as, for example, sulfuric acid ($H_2SO_4$). The silicon dioxide layer can be etched in an anisotropic fashion. Using the methods described herein, high anisotropy manufacturing methods, such as DRIE can be applied to fabricate microstructures, such as microwells or microchannels comprising loci of synthesis, on or within a substrate with side walls that deviate less than about ±3°, 2°, 1°, 0.5°, 0.1°, or less from the vertical with respect to the surface of the substrate. Undercut values of less than about 10, 9, 8, 7, 6, 5, 4, 3, 2, 1, 0.5, 0.1 µm or less can be achieved resulting in highly uniform microstructures.

Various etching procedures can be used to etch the silicon dioxide in the area where the resolved loci are to be formed. The etch can be an isotropic etch (i.e., the etch rate alone one direction substantially equal or equal to the etch rate along an orthogonal direction), or an anisotropic etch (i.e., the etch rate along one direction is less than the etch rate along an orthogonal direction), or variants thereof. The etching techniques can be both wet silicon etches such as KOH, TMAH, EDP and the like, and dry plasma etches (for example DRIE). Both may be used to etch micro structures wafer through interconnections.

In some cases, an anisotropic etch removes the majority of the volume of the resolved loci. Any suitable percentage of the volume of the resolved loci can be removed including about 60%, about 70%, about 80%, about 90%, or about 95%. In some cases, at least about 60%, at least about 70%, at least about 80%, at least about 90%, or at least about 95% of the material is removed in an anisotropic etch. In some cases, at most about 60%, at most about 70%, at most about 80%, at most about 90%, or at most about 95% of the material is removed in an anisotropic etch. In some embodiments, the anisotropic etch does not remove silicon dioxide material all of the way through the substrate. An isotropic etch is used to remove material all of the way through the substrate creating a hole, according to some embodiments.

In some cases, the wells are etched using a photo-lithographic step to define the resolved loci followed by a hybrid dry-wet etch. The photo-lithographic step can comprise coating the silicon dioxide with a photo-resist and exposing the photo-resist to electromagnetic radiation through a mask (or reticle) having a pattern that defines the resolved loci. In some instances, the hybrid dry-wet etch comprises: (a) dry etching to remove the bulk of the silicon dioxide in the regions of the resolved loci defined in the photoresist by the photo-lithographic step; (b) cleaning the substrate; and (c) wet etching to remove the remaining silicon dioxide from the substrate in the regions of the resolved loci.

The substrate can be cleaned with the aid of a plasma etching chemistry, or exposure to an oxidizing agent, such as, for example, $H_2O_2$, $O_2$, $O_3$, $H_2SO_4$, or a combination thereof, such as a combination of $H_2O_2$ and $H_2SO_4$. The cleaning can comprise removing residual polymer, removing material that can block the wet etch, or a combination thereof. In some instances, the cleaning is plasma cleaning. The cleaning step can proceed for any suitable period of time (e.g., 15 to 20 seconds). In an example, the cleaning can be performed for 20 seconds with an Applied Materials eMAx-CT machine with settings of 100 mT, 200 W, 20 G, 20 $O_2$.

The dry etch can be an anisotropic etch that etches substantially vertically (e.g., toward the substrate) but not laterally or substantially laterally (e.g., parallel to the substrate). In some instances, the dry etch comprises etching with a fluorine based etchant such as $CF_4$, $CHF_3$, $C_2F_6$, $C_3F_6$, or any combination thereof. In one instance, the etching is performed for 400 seconds with an Applied Materials eMax-CT machine having settings of 100 mT, 1000 W, 20 G, and 50 CF4. The substrates described herein can be etched by deep reactive-ion etching (DRIE). DRIE is a highly anisotropic etch process used to create deep penetration, steep-sided holes and trenches in wafers/substrates, typically with high aspect ratios. The substrates can be etched using two main technologies for high-rate DRIE: cryogenic and Bosch. Methods of applying DRIE are described in the U.S. Pat. No. 5,501,893, which is herein incorporated by reference in its entirety.

The wet etch can be an isotropic etch that removes material in all directions. In some instances, the wet etch undercuts the photo-resist. Undercutting the photo-resist can make the photo-resist easier to remove in a later step (e.g., photo-resist "lift off"). In an embodiment, the wet etch is buffered oxide etch (BOE). In some cases, the wet oxide etches are performed at room temperature with a hydrofluoric acid base that can be buffered (e.g., with ammonium fluoride) to slow down the etch rate. Etch rate can be dependent on the film being etched and specific concentrations of HF and/or $NH_4F$. The etch time needed to completely remove an oxide layer is typically determined empirically. In one example, the etch is performed at 22° C. with 15:1 BOE (buffered oxide etch).

The silicon dioxide layer can be etched up to an underlying material layer. For example, the silicon dioxide layer can be etched until a titanium nitride layer.

In an aspect, a method for preparing a substrate having a plurality of resolved loci comprises etching the resolved loci such as microwells or microchannels into a substrate, such as a silicon substrate comprising a silicon dioxide layer coated thereon using (a) a photo-lithographic step to define the resolved loci; (b) a dry etch to remove the bulk of the silicon dioxide in the regions of the resolved loci defined by the photo-lithographic step; and (c) a wet etch to remove the remaining silicon dioxide from the substrate in the regions of the resolved loci. In some cases, the method further comprises removing residual polymer, removing material that can block the wet etch, or a combination thereof. The method can include a plasma cleaning step.

In some embodiments, the photo-resist is not removed from the silicon dioxide following the photo-lithographic step or the hybrid wet-dry etch in some cases. Leaving the photo-resist can be used to direct metal selectively into the resolved loci and not onto the upper surface of the silicon dioxide layer in later steps. In some cases, the substrate is coated with a metal (e.g., aluminum) and the wet etch does not remove certain components on the metal, e.g. those that protect the metal from corrosion (e.g., titanium nitride (TiN)). In some cases, however, the photoresist layer can be removed, such as with the aid of chemical mechanical planarization (CMP).

Differential Functionalization of Substrates

As described herein, functionalization of a surface, for example the surface of a silicon wafer, may refer to any process by which the surface properties of a material are modified by the deposition of a chemical species on the surface. A common method for achieving functionalization is deposition of an organosilane molecule by chemical vapor deposition. It can also be done in a wet silanization process.

Differential functionalization, also commonly referred to as "selective area deposition" or "selective area functionalization," may refer to any process that produces two or more distinct areas on a monolithic structure where at least one area has different surface or chemical properties than other areas on the same structure. The properties include but are not limited to surface energy, chemical termination, surface concentration of a chemical moiety, etc. The different areas may be contiguous.

Active functionalization may refer to the functionalization of surfaces that will take part in some downstream production step such as DNA synthesis, or DNA or protein binding. Thus, a suitable functionalization method as described elsewhere herein or otherwise known in the art, is selected to allow for the particular downstream production step to take place on the surface.

Passive functionalization may refer to the functionalization of surfaces that will render those areas ineffective at the principle function of the active areas. For example, if the active functionalization is designed to bind DNA, the passive functionalized areas will not bind DNA.

Photoresist typically refers to a light-sensitive material commonly used in standard industrial processes, such as photolithography, to form patterned coatings. It is applied as a liquid, but it solidifies on the substrate as volatile solvents in the mixture evaporate. It may be applied in a spin coating process as a thin film (1 μm to 100 μm) to a planar substrate. It may be patterned by exposing it to light through a mask or reticle, changing its dissolution rate in a developer. It may be "positive" (light exposure increases dissolution) or "negative" (light exposure decreases dissolution). It may be used as a sacrificial layer that serves as a blocking layer for subsequent steps that modify the underlying substrate (such as etching). Once that modification is complete, the resist is removed.

Photolithography may refer to a process for patterning substrates. A common basic process comprises 1) applying a photoresist to a substrate, 2) exposing the resist to light through a binary mask that is opaque in some areas and clear in other areas, and then 3) developing the resist which results in patterning the resist based on what areas were exposed. After development, the patterned resist serves as a mask for subsequent processing steps, such as etching, ion implantation, or deposition. After the processing steps, the resist is typically removed, for example via plasma stripping or wet chemical removal.

In various embodiments, methods using photoresist are employed wherein photoresist facilitates manufacturing of substrates with differential functionalization.

A series of manufacturing steps may form the baseline of a differential functionalization process, wherein the individual steps may be modified, removed, or supplemented with additional steps to achieve the desired functionalization pattern on a surface, according to the various embodiments of the invention. First, an initial preparation of the target surface may be achieved, for example, by a chemical clean and may include an initial active or passive surface functionalization.

Second, the application of photoresist may be achieved by a variety of different techniques. In various embodiments, the flow of resist into different parts of the structure is controlled by the design of the structure, for example by taking advantage of the intrinsic pinning properties of fluids at various points of the structure, such as at sharp step edges. The photoresist leaves behind a solid film once the transporting solvents of the resist evaporate.

Third, photolithography may be optionally used to remove the resist in certain specific regions of the substrate so that those regions can be further modified.

Fourth, plasma descum, a, typically, short plasma cleaning step using, for example, an oxygen plasma, may be used to facilitate the removal of any residual organic contaminants in the resist cleared areas.

Fifth, the surface may be functionalized while the areas covered in resist are protected from any active or passive functionalization. Any suitable process that changes the chemical properties of the surface described herein or known in the art may be used to functionalize the surface, for example chemical vapor deposition of an organosilane. Typically, this results in the deposition of a self-assembled monolayer (SAM) of the functionalization species.

Sixth, the resist may be stripped and removed, for example by dissolving it in suitable organic solvents, plasma etching, exposure and development, etc., thereby exposing the areas of the substrate that had been covered by the resist. In some embodiments, a method that will not remove functionalization groups or otherwise damage the functionalized surfaces is selected for the resist strip.

Seventh, a second functionalization step involving active or passive functionalization may optionally be performed. In some embodiments, the areas functionalized by the first functionalization step block the deposition of the functional groups used in the second functionalization step.

In various embodiments, differential functionalization facilitates spatial control of the regions on the chip where DNA is synthesized. In some embodiments, differential functionalization provides improved flexibility to control the fluidic properties of the chip. In some embodiments, the process by which oligos are transferred from a oligonucleotide synthesis device to a nanowell device is therefore improved by differential functionalization. In some embodiments, differential functionalization provides for the manufacturing of devices, for example nanoreactor or oligonucleotide syntheses devices, where the walls of wells or channels are relatively hydrophilic, as described elsewhere herein, and the external surfaces are relatively hydrophobic, as described elsewhere herein.

Figure 36:
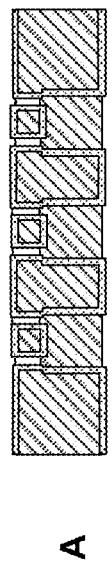
FIG. 36 parts A-F illustrates various configurations for differential functionalization. In each figure, the light shaded line indicates an active surface, while a dark line indicates a passive surface.
Figure 36:
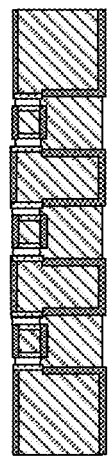
Figure 36:
Figure 36:
Figure 36:
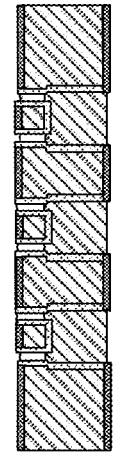
Figure 36:

FIG. 36 parts A-F illustrates exemplary applications of differential functionalization on the microfluidic devices according to the various embodiments of the invention. The active and passive functionalization areas are shaded differently as denoted. In particular, first channels (vias) and second channels that connect to them forming a so called revolver pattern are used in these examples to illustrate differential functionalization in three dimensions. The specific layout of the three-dimensional features within these exemplary substrates is largely unimportant for the functionalization process, with the exception of a few guidelines that help control the application of resist.

Figure 37:
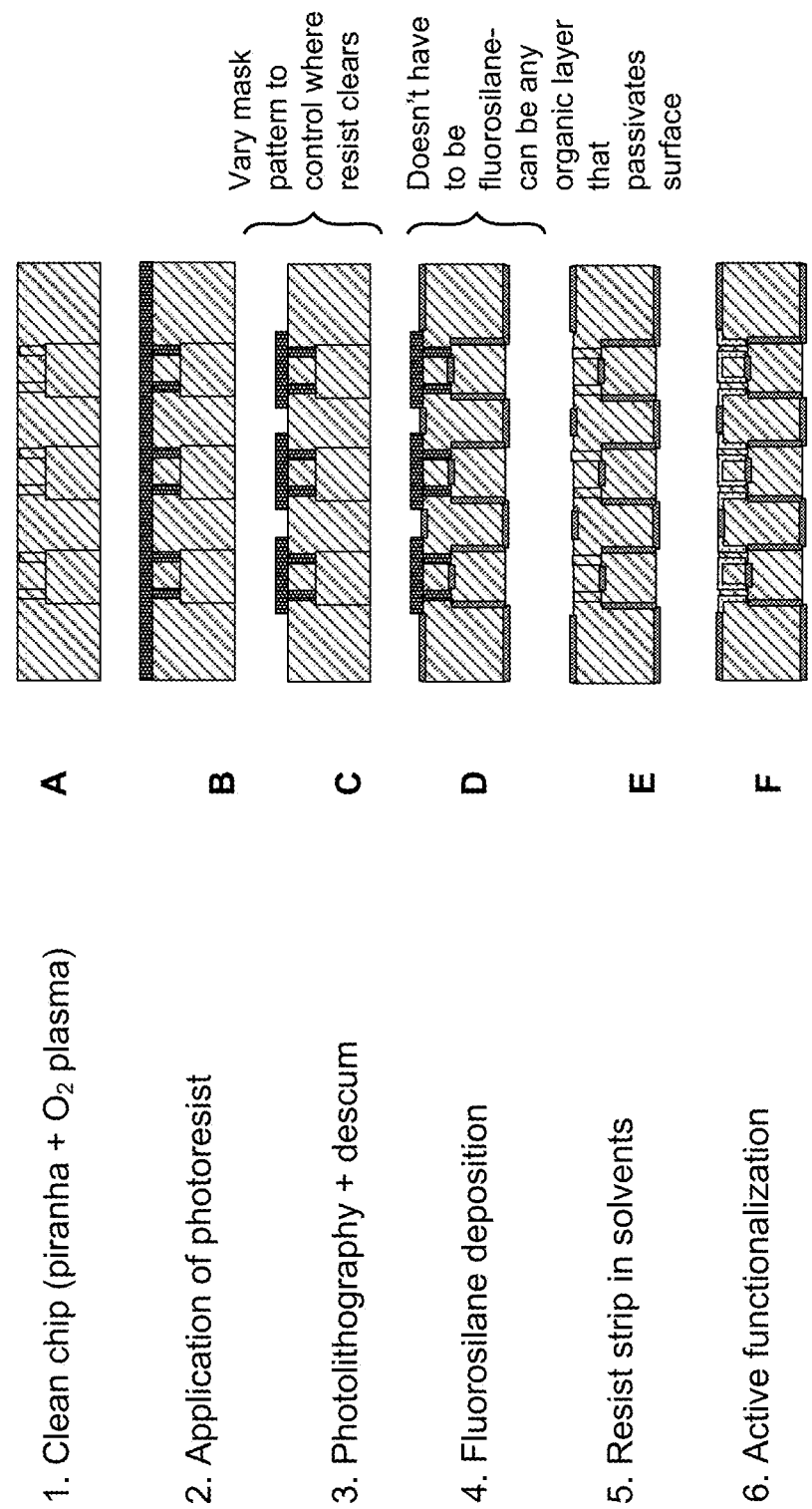
FIG. 37 parts A-F illustrate a process flow for device functionalization.

FIG. 37 parts A-F illustrates an exemplary workflow for the generation of differential functionalization patterns illustrated in FIG. 37 part B-D. Accordingly, the substrate may first be cleaned, for example using a piranha solution, followed by $O_2$ plasma exposure (FIG. 37 part A). Photoresist may be applied to the device layer embedding the second channels (aka revolvers; FIG. 37 part B). A photolithography and/or a plasma descum step may be used to generate a desired pattern of photoresist on the substrate, using a suitable mask for the pattern (FIG. 37 part C). The mask pattern may be varied to control where the photoresist stays and where it is cleared. A functionalization step, for example with a fluorosilane, a hydrocarbon silane, or any group forming an organic layer that may passivate the surface, may be performed to define the passively functionalized areas on the device (FIG. 37 part D). The resist may be stripped using a suitable method described elsewhere herein or otherwise known in the art (FIG. 37 part E). Once the resist is removed, the exposed areas may be subject to active functionalization leaving the desired differential functionalization pattern (FIG. 37 part F).

Figure 38:
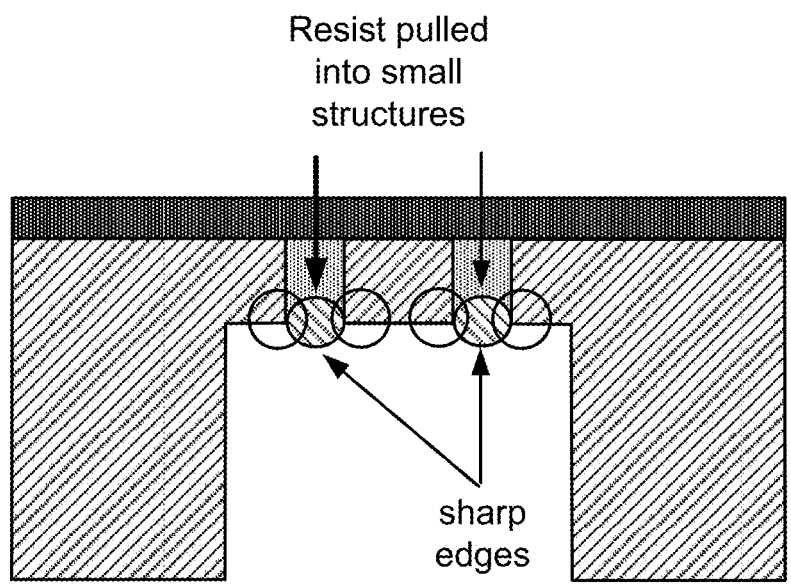
FIG. 38 depicts an exemplary illustration of resist application, wherein resist is pulled into small structures and stopped by sharp edges.

In various embodiments, the methods and compositions described herein relate to the application of photoresist for the generation of modified surface properties in selective areas, wherein the application of the photoresist relies on the fluidic properties of the substrates defining the spatial distribution of the photoresist. Without being bound by theory, surface tension effects related to the applied fluid may define the flow of the photoresist. For example surface tension and/or capillary action effects may facilitate drawing of the photoresist into small structures in a controlled fashion before the resist solvents evaporate (FIG. 38). In one embodiment, resist contact points get pinned by sharp edges, thereby controlling the advance of the fluid. The underlying structures may be designed based on the desired flow patterns that are used to apply photoresist during the manufacturing and functionalization processes. A solid organic layer left behind after solvents evaporate may be used to pursue the subsequent steps of the manufacturing process.

Substrates may be designed to control the flow of fluids by facilitating or inhibiting wicking effects into neighboring fluidic paths. For example, FIG. 39 part A illustrates a design avoiding overlap between top and bottom edges, which facilitates the keeping of the fluid in top structures allowing for a particular disposition of the resist. In contrast, FIG. 39 part B illustrates an alternative design, wherein the top and bottom edges do overlap, leading to the wicking of the applied fluid into bottom structures. Appropriate designs may be selected accordingly, depending on the desired application of the resist.

Figure 40:
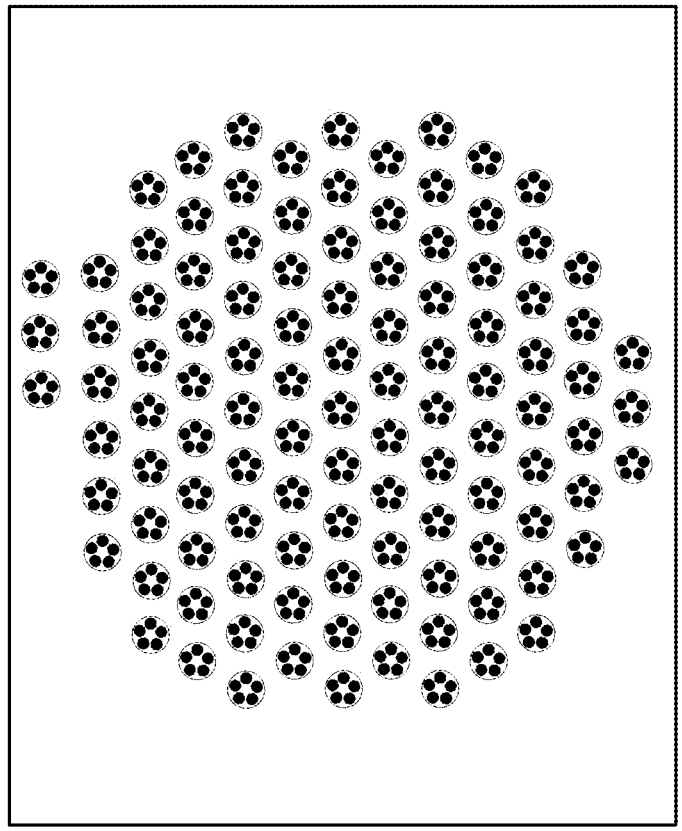
FIG. 40 parts A-C illustrate post-lithographic resist patterns in an exemplary differential functionalization configuration.
Figure 40:
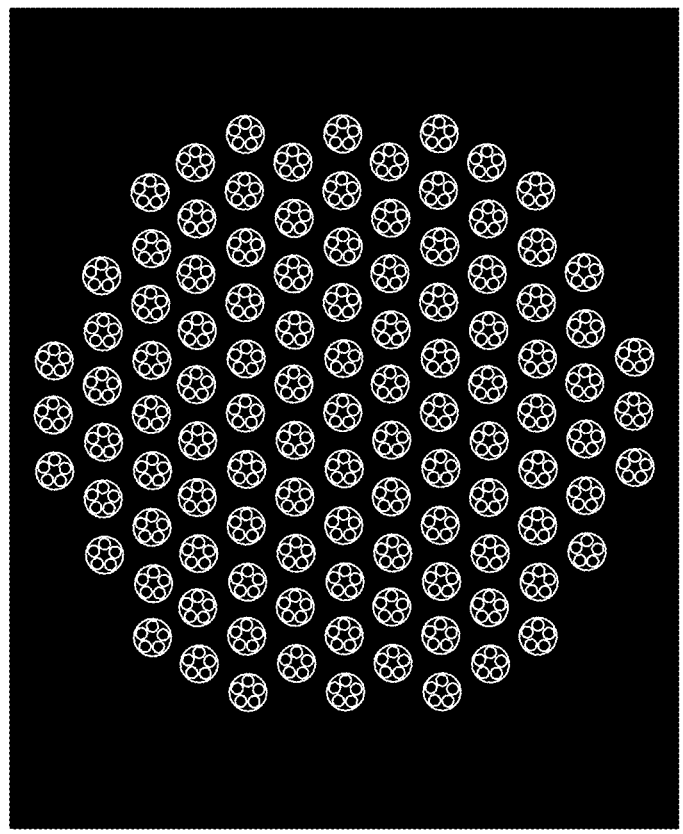
Figure 40:
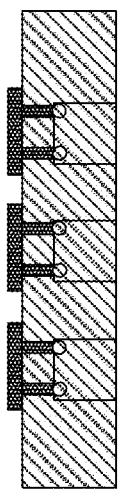

FIG. 40 illustrates bright field (part A) and dark field (part B) images of a device that is subjected to resist according to the illustrated small disk photoresist pattern in FIG. 40 part C after photolithography.

Figure 41:
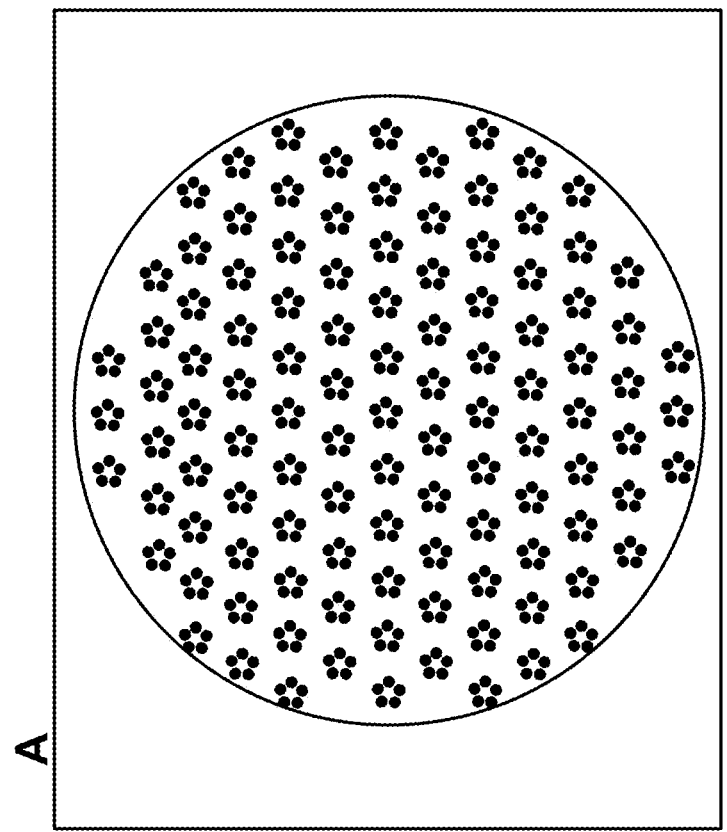
FIG. 41 parts A-C illustrate post-lithographic resist patterns in another exemplary differential functionalization configuration.
Figure 41:
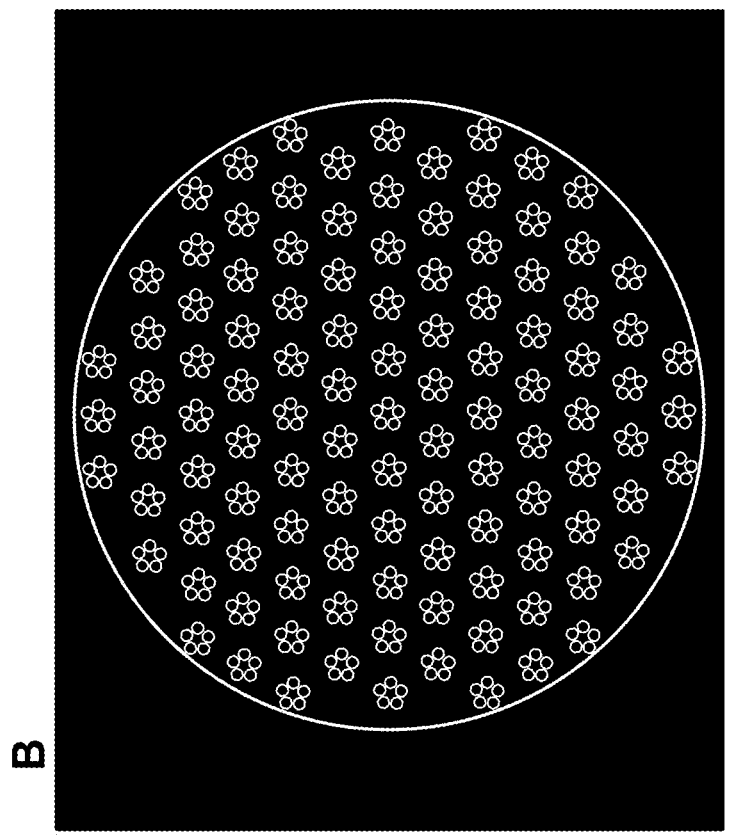
Figure 41:
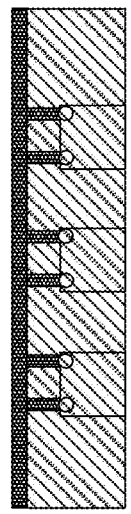

FIG. 41 illustrates bright field (part A) and dark field (part B) images of a device that is subjected to resist according to the illustrated full disk photoresist pattern in FIG. 41 part 41C after photolithography.

Figure 42:
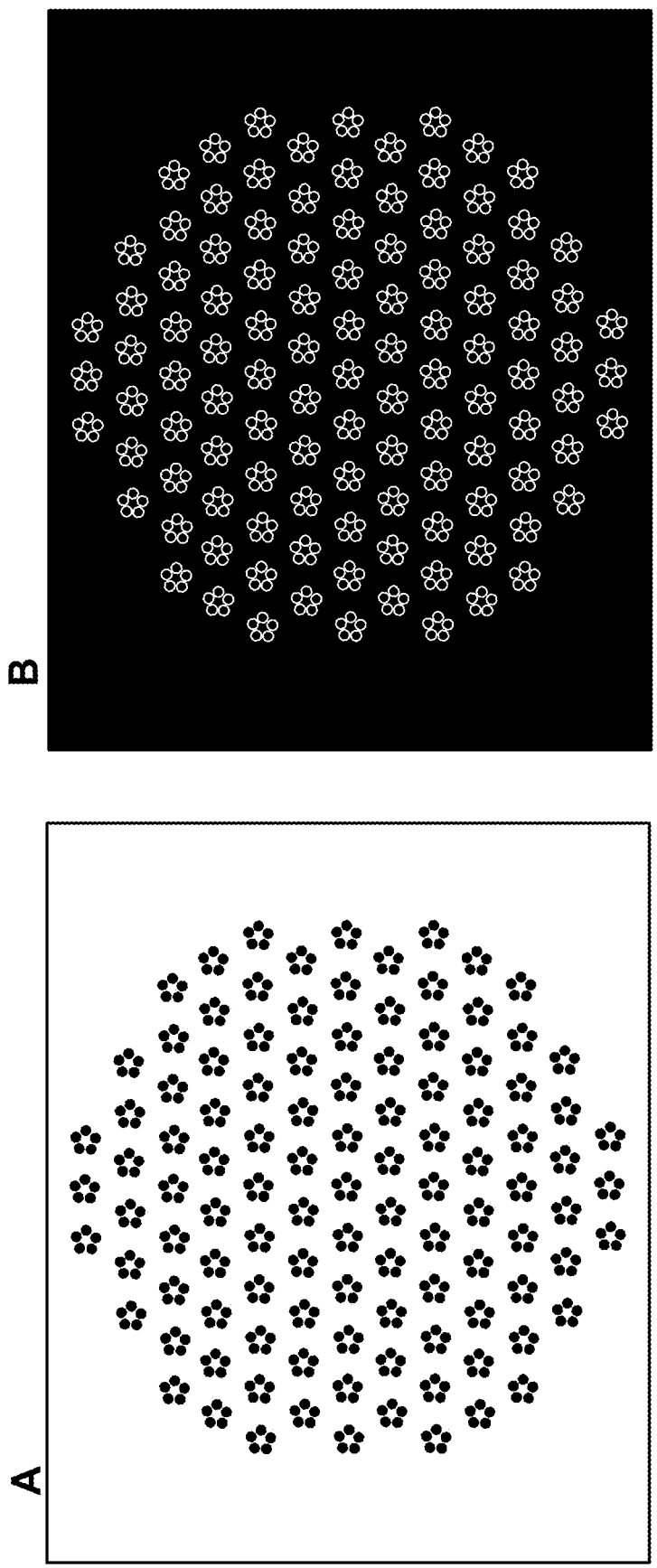
FIG. 42 parts A-C illustrate a post resist strip after functionalization with a fluorosilane.
Figure 42:
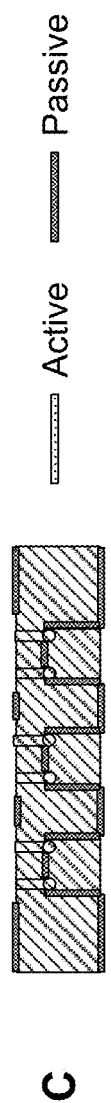

FIG. 42 illustrates bright field (part A) and dark field (part B) images of a device that is functionalized according to the pattern in FIG. 42 part C after passive functionalization and stripping of the resist.

Figure 43:
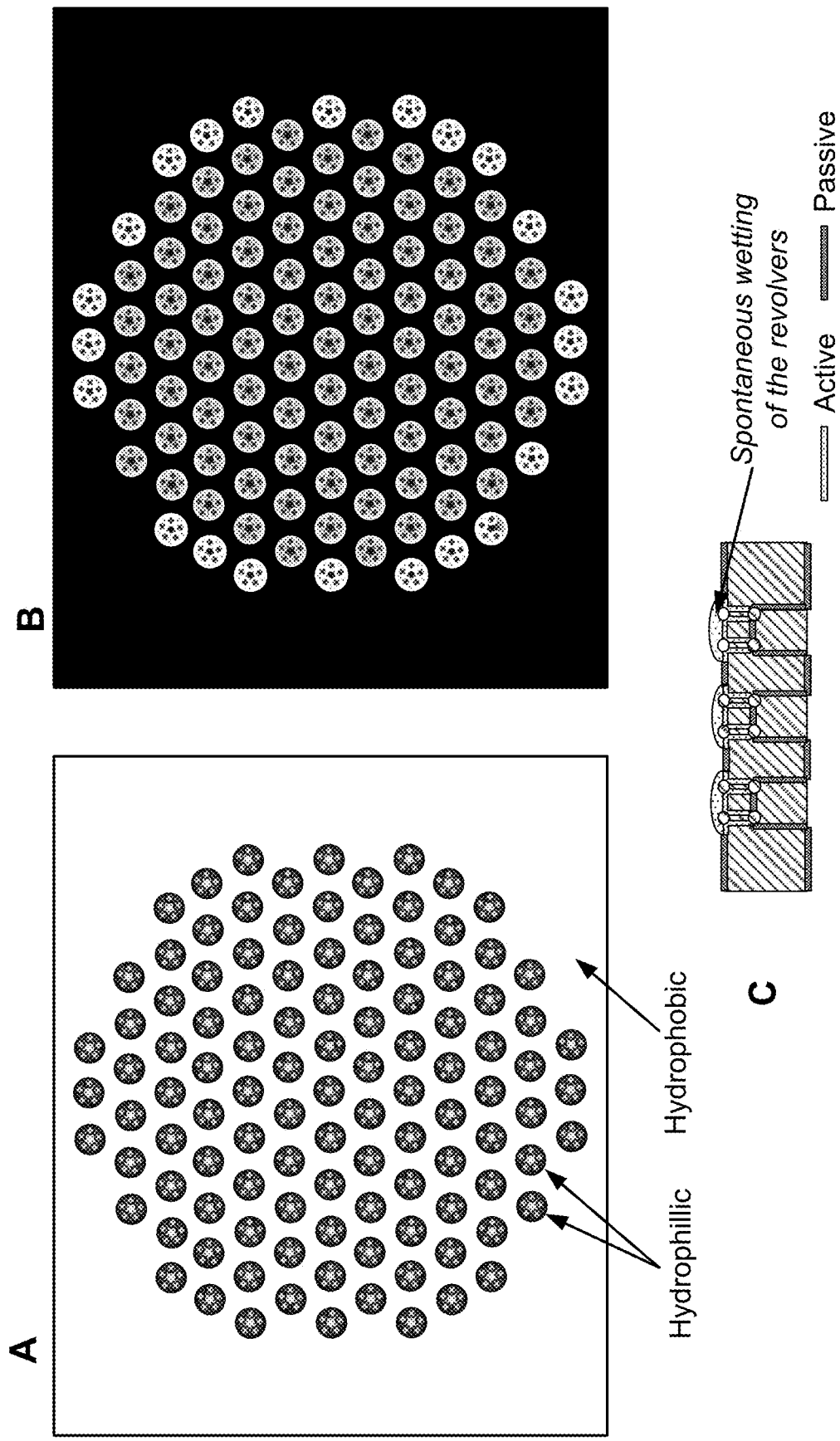
FIG. 43 parts A-C illustrate an exemplary oligonucleotide synthesis device ("Keratin chip"), fully loaded with DMSO.

FIG. 43 illustrates the differing fluidic properties of the differentially functionalized surfaces in bright field (part A) and dark field (part B) images according to the pattern in FIG. 43 part C using dimethylsulfoxide (DMSO) as a fluid. Spontaneous wetting of the revolvers was achieved using the hydrophilic surfaces within the revolvers surrounded by the hydrophobic areas.

Figure 44:
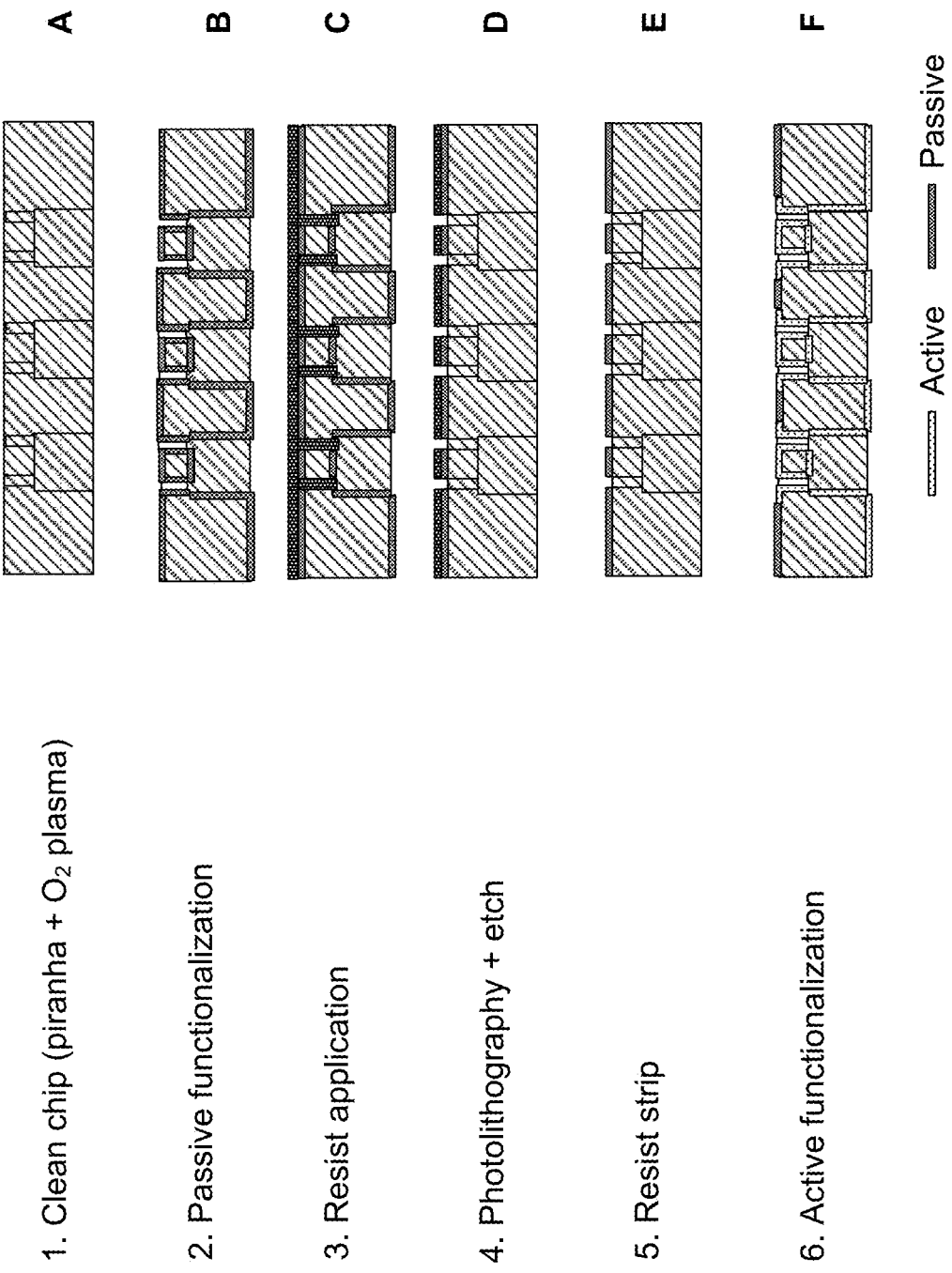
FIG. 44 parts A-F outline an exemplary process flow for configuration 6 illustrated in FIG. 36.

FIG. 44 illustrates another exemplary workflow for the generation of differential functionalization patterns illustrated in FIG. 36 part F. Accordingly, the substrate may first be cleaned, for example using a piranha solution, followed by $O_2$ plasma exposure (FIG. 44 part 44A). A functionalization step, for example with a fluorosilane, a hydrocarbon silane, or any group that can form an organic layer that may passivate the surface, may be performed to define the passively functionalized areas on the device (FIG. 44 part B). Photoresist may be applied to the device layer embedding the second channels (aka revolvers; FIG. 44 part C). A photolithography and/or an etch step may be used to generate a desired pattern of photoresist on the substrate, using a suitable mask for the pattern (FIG. 44 part D). The mask pattern may be varied to control where the photoresist stays and where it is cleared. The resist may be stripped using a suitable method described elsewhere herein or otherwise known in the art (FIG. 44 part E). Once the resist is removed, the exposed areas may be subject to active functionalization leaving the desired differential functionalization pattern (FIG. 44 part F).

In another embodiment, the functionalization workflow is designed such that the resist is applied from the via (bottom) side and flown into the vias and the revolvers. The exposed areas on the outer surfaces may be subjected to functionalization. The resist may be removed, for example from the back (bottom) side of the device using lithography or etching, allowing active functionalization in the exposed areas leading to the pattern described in FIG. 36 part E.

Figure 39:
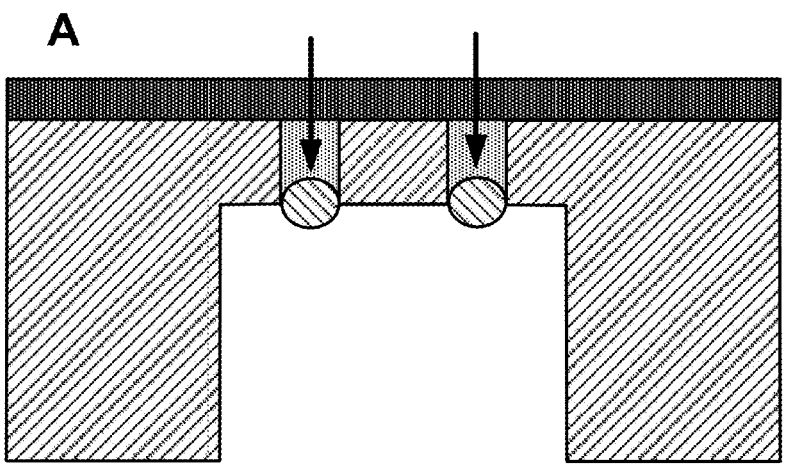
FIG. 39 parts A-B illustrate use of underlying structures to either stop or wick the resist application in an exemplary embodiment.
Figure 39:
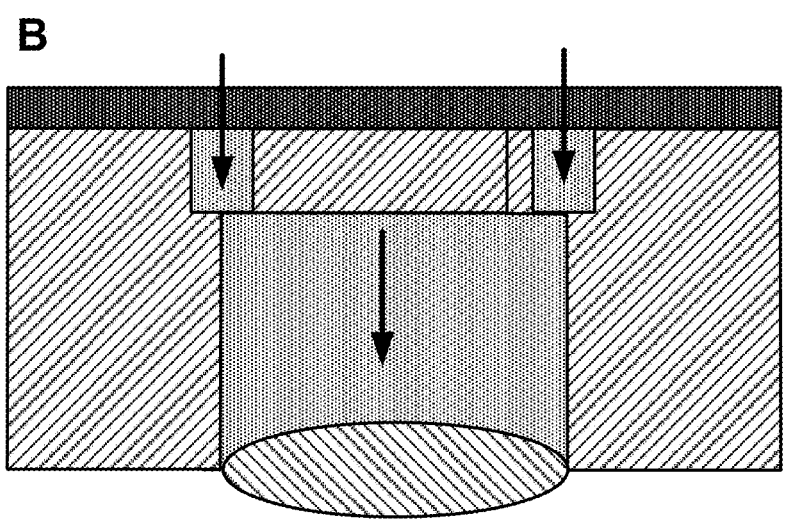

In yet another embodiment, an overlap design may be chosen between the vias and the revolver channel edges as shown in FIG. 39 part B. The resist may be applied from the front (top) side wicking the fluid into the vias. Passive functionalization, stripping of the resist, followed by active functionalization would lead to the manufacturing of the pattern illustrated in FIG. 36 part E.

An exemplary microfluidic device comprising a substantially planar substrate portion is shown as a diagram in FIG. 25 part D. A cross-section of the diagram is shown in FIG. 25 part E. The substrate comprises a plurality of clusters, wherein each cluster comprises a plurality of groupings of fluidic connections. Each grouping comprises a plurality of second channels extending from a first channel. FIG. 25 part A is a device view of a cluster comprising a high density of groupings. FIG. 25 part C is a handle view of the cluster of FIG. 25A. FIG. 25 part B is a section view of FIG. 25 part A.

A cluster of groupings may be arranged in any number of conformations. In FIG. 25 part A, the groupings are arranged in offset rows to form a cluster in a circle-like pattern. FIG. 25 part C depicts arrangement of a plurality of such clusters on an exemplary microfluidic device. In some embodiments, individual clusters are contained within individual cluster regions whose interior forms a convex set. In some embodiments, the individual cluster regions are non-overlapping with each other. The individual cluster regions may be a circle or any other suitable polygon, e.g. a triangle, a square, a rectangle, a, a parallelogram, a hexagon etc. As represented by 2503, an exemplary distance between three rows of groupings may be from about 0.05 mm to about 1.25 mm, as measured from the center of each grouping. The distance between 2, 3, 4, 5, or more rows of groupings may be about or at least about 0.05 mm, 0.1 mm, 0.15 mm, 0.2 mm, 0.25 mm, 0.3 mm, 0.35 mm, 0.4 mm, 0.45 mm, 0.5 mm, 0.55 mm, 0.6 mm, 0.65 mm, 0.7 mm, 0.75 mm, 0.8 mm, 0.9 mm, 1 mm, 1.1 mm, 1.2 mm, 1.2 mm, or 1.3 mm. The distance between 2, 3, 4, 5, or more rows of groupings may be about or at most about 1.3 mm, 1.2 mm, 1.1 mm, 1 mm, 0.9 mm, 0.8 mm, 0.75 mm, 0.65 mm, 0.6 mm, 0.55 mm, 0.5 mm, 0.45 mm, 0.4 mm, 0.35 mm, 0.3 mm, 0.25 mm, 0.2 mm, 0.15 mm, 0.1 mm, 0.05 mm or less. The distance between 2, 3, 4, 5, or more rows of groupings may range between 0.05-1.3 mm, 0.1-1.2 mm, 0.15-1.1 mm, 0.2-1 mm, 0.25-0.9 mm, 0.3-0.8 mm, 0.35-0.8 mm, 0.4-0.7 mm, 0.45-0.75 mm, 0.5-0.6 mm, 0.55-0.65 mm, or 0.6-0.65 mm. Those of skill in the art appreciate that the distance may fall within any range bound by any of these values, for example 0.05 mm-0.8 mm. As shown by 2506, an exemplary distance between two groupings in a row of groupings may be from about 0.02 mm to about 0.5 mm, as measured from the center of each grouping. The distance between two groupings in a row of groupings may be about or at least about 0.02 mm, 0.04 mm, 0.06 mm, 0.08 mm, 0.1 mm, 0.12 mm, 0.14 mm, 0.16 mm, 0.18 mm, 0.2 mm, 0.22 mm, 0.24 mm, 0.26 mm, 0.28 mm, 0.3 mm, 0.32 mm, 0.34 mm, 0.36 mm, 0.38 mm, 0.4 mm, 0.42 mm, 0.44 mm, 0.46 mm, 0.48 mm or 0.5 mm. The distance between two groupings in a row of groupings may be about or at most about 0.5 mm, 0.48 mm, 0.46 mm, 0.44 mm, 0.42 mm, 0.4 mm, 0.38 mm, 0.36 mm, 0.34 mm, 0.32 mm, 0.3 mm, 0.28 mm, 0.26 mm, 0.24 mm, 0.22 mm, 0.2 mm, 0.18 mm, 0.16 mm, 0.14 mm, 0.12 mm, 0.1 mm, 0.08 mm, 0.06 mm, 0.04 mm, or 0.2 mm or less. The distance between two groupings may range between 0.02-0.5 mm, 0.04-0.4 mm, 0.06-0.3 mm, or 0.08-0.2 mm. Those of skill in the art appreciate that the distance may fall within any range bound by any of these values, for example 0.04 mm-0.2 mm.

The length and width of the first and second channels of each grouping may be optimized according to experimental conditions. In some embodiments, the cross-section of a first channel in a grouping, represented by 2504, is about or at least about 0.01 mm, 0.015 mm, 0.02 mm, 0.025 mm, 0.03 mm, 0.035 mm, 0.04 mm, 0.045 mm, 0.05 mm, 0.055 mm, 0.06 mm, 0.065 mm, 0.07 mm, 0.075 mm, 0.08 mm, 0.085 mm, 0.09 mm, 0.1 mm, 0.15 mm, 0.2 mm, 0.25 mm, 0.3 mm, 0.35 mm, 0.4 mm, 0.45 mm, or 0.5 mm. In some embodiments, the cross-section of a first channel in a grouping is about or at most about 0.5 mm, 0.45 mm, 0.4 mm, 0.35 mm, 0.3 mm, 0.25 mm, 0.2 mm, 0.15 mm, 0.1 mm, 0.09 mm, 0.085 mm, 0.08 mm, 0.075 mm, 0.07 mm, 0.065 mm, 0.06 mm, 0.055 mm, 0.05 mm, 0.045 mm, 0.04 mm, 0.035 mm, 0.03 mm, 0.025 mm, 0.02 mm, 0.015 mm, or 0.01 mm or less. The cross-section of a first channel in a grouping may range between 0.01-0.5 mm, 0.02-0.45 mm, 0.03-0.4 mm, 0.04-0.35 mm, 0.05-0.3 mm, 0.06-0.25 mm, or 0.07-0.2 mm. Those of skill in the art appreciate that the distance may fall within any range bound by any of these values, for example 0.04 mm-0.2 mm. In some embodiments, the cross-section of a second channel in a grouping, represented by 2505, is about or at least about 0.001 mm, 0.002 mm, 0.004 mm, 0.006 mm, 0.008 mm, 0.01 mm, 0.012 mm, 0.014 mm, 0.016 mm, 0.018 mm, 0.02 mm, 0.025 mm, 0.03 mm, 0.035 mm, 0.04 mm, 0.045 mm, 0.05 mm, 0.055 mm, 0.06 mm, 0.065 mm, 0.07 mm, 0.075 mm, or 0.08 mm. In some embodiments, the cross-section of a second channel in a grouping, is about or at most about 0.08 mm, 0.075 mm, 0.07 mm, 0.065 mm, 0.06 mm, 0.055 mm, 0.05 mm, 0.045 mm, 0.04 mm, 0.035 mm, 0.03 mm, 0.025 mm, 0.02 mm, 0.018 mm, 0.016 mm, 0.014 mm, 0.012 mm, 0.01 mm, 0.008 mm, 0.006 mm, 0.004 mm, 0.002 mm, 0.001 mm or less. The cross-section of a second channel in a grouping may range between 0.001-0.08 mm, 0.004-0.07 mm, 0.008-0.06 mm, 0.01-0.05 mm, 0.015-0.04 mm, 0.018-0.03 mm, or 0.02-0.025 mm. Those of skill in the art appreciate that the distance may fall within any range bound by any of these values, for example 0.008 mm-0.04 mm. FIG. 25 part B depicts an exemplary cross-section of a cluster comprising a row of 11 groupings. In some embodiments, the height of the second channel in each grouping is about or at least about 0.005 mm, 0.008 mm, 0.01 mm, 0.015 mm, 0.02 mm, 0.025 mm, 0.03 mm, 0.04 mm, 0.05 mm, 0.06 mm, 0.07 mm, 0.08 mm, 0.1 mm, 0.12 mm, 0.14 mm, 0.16 mm, 0.18 mm, or 0.2 mm long. In some embodiments, the height of the second channel, shown as 2501, in each grouping is about or at most about 0.2 mm, 0.18 mm, 0.16 mm, 0.14 mm, 0.12 mm, 0.1 mm, 0.08 mm, 0.07 mm, 0.06 mm, 0.05 mm, 0.04 mm, 0.03 mm, 0.025 mm, 0.02 mm, 0.015 mm, 0.01 mm, 0.008 mm, or 0.005 mm long. The height of the second channel in each grouping may range between 0.005-0.2 mm, 0.008-0.018 mm, 0.01-0.16 mm, 0.015-0.1 mm, 0.02-0.08 mm, or 0.025-0.04 mm. Those of skill in the art appreciate that the distance may fall within any range bound by any of these values, for example 0.01 mm-0.04 mm. In some embodiments, the height of the first channel within each grouping, shown as 2502, is about or at most about 5 mm, 4.5 mm, 4 mm, 3.5 mm, 3 mm, 2.5 mm, 2 mm, 1.5 mm, 1.0 mm, 0.8 mm, 0.5 mm, 0.4 mm, 0.375 mm, 0.35 mm, 0.3 mm, 0.275 mm, 0.25 mm, 0.225 mm, 0.2 mm, 0.175 mm, 0.15 mm, 0.125 mm, 0.1 mm, 0.075 mm, or 0.05 mm. In some embodiments, the height of the first channel within each grouping, shown as 2502, is about or at least about 0.05 mm, 0.075 mm, 0.1 mm, 0.125 mm, 0.15 mm, 0.175 mm, 0.2 mm, 0.225 mm, 0.25 mm, 0.275 mm, 0.3 mm, 0.325 mm, 0.35 mm, 0.375 mm, 0.4 mm, 0.5 mm, 0.8 mm, 1.0 mm, 1.5 mm, 2 mm, 2.5 mm, 3 mm, 3.5 mm, 4 mm, 4.5 mm, or 5 mm. The height of the first channel within each grouping may range between 0.05-5 mm, 0.075-4 mm, 0.1-3 mm, 0.15-2 mm, 0.2-1 mm, or 0.3-0.8 mm. Those of skill in the art appreciate that the distance may fall within any range bound by any of these values, for example 0.1 mm-1 mm.

The cluster of groupings may be arranged in a conformation suitable for placement in a single reaction well of the substantially planar substrate portion of a microfluidic device, as shown in FIG. 25 part D. FIG. 25 part D is a diagram of a substantially planar substrate portion of a microfluidic device comprising 108 reaction wells, wherein each reaction well comprises a plurality of groupings. A substrate may comprise any number of wells, including but not limited to, any number between about 2 and about 250. In some embodiments, the number of wells includes from about 2 to about 225 wells, from about 2 to about 200 wells, from about 2 to about 175 wells, from about 2 to about 150 wells, from about 2 to about 125 wells, from about 2 to about 100 wells, from about 2 to about 75 wells, from about 2 to about 50 wells, from about 2 to about 25 wells, from about 25 to about 250 wells, from about 50 to about 250 wells, from about 75 to about 250 wells, from about 100 to about 250 wells, from about 125 to about 250 wells, from about 150 to about 250 wells, from about 175 to about 250 wells, from about 200 to about 250 wells, or from about 225 to about 250 wells. Those of skill in the art appreciate that the well number may fall within any range bound by any of these values, for example 25-125. In addition, each well can comprise a cluster of any number groupings, including, but not limited to, any number between about 2 and about 250 groupings. In some embodiments, a cluster comprises from about 2 to about 225 groupings, from about 2 to about 200 groupings, from about 2 to about 175 groupings, from about 2 to about 150 groupings, from about 2 to about 125 groupings, from about 2 to about 100 groupings, from about 2 to about 75 groupings, from about 2 to about 50 groupings, from about 2 to about 25 groupings, from about 25 to about 250 groupings, from about 50 to about 250 groupings, from about 75 to about 250 groupings, from about 100 to about 250 groupings, from about 125 to about 250 groupings, from about 150 to about 250 groupings, from about 175 to about 250 groupings, from about 200 to about 250 groupings, or from about 225 to about 250 groupings. Those of skill in the art appreciate that the number of groupings may fall within any range bound by any of these values, for example 25-125. As an example, each of the 108 wells of the substrate shown in FIG. 25 part D, can comprise a cluster of 109 groupings shown in FIG. 25 part A, resulting in 11,772 groupings present in the substantially planar substrate portion of the microfluidic device.

FIG. 25 part D includes an origin of reference indicated by a 0,0 (X,Y) axis, wherein the bottom left corner of an exemplary substantially planar substrate portion of a microfluidic device is diagramed. In some embodiments, the width of the substantially planar substrate, represented as 2508, is from about 5 mm to about 150 mm along one dimension, as measured from the origin. In some embodiments, the width of a substantially planar substrate, represented as 2519, is from about 5 mm to about 150 mm along another dimension, as measured from the origin. In some embodiments, the width of a substrate in any dimension is from about 5 mm to about 125 mm, from about 5 mm to about 100 mm, from about 5 mm to about 75 mm, from about 5 mm to about 50 mm, from about 5 mm to about 25 mm, from about 25 mm to about 150 mm, from about 50 mm to about 150 mm, from about 75 mm to about 150 mm, from about 100 mm to about 150 mm, or from about 125 mm to about 150 mm. Those of skill in the art appreciate that the width may fall within any range bound by any of these values, for example 25-100 mm. The substantially planar substrate portion shown in FIG. 25 part D comprises 108 clusters of groupings. The clusters may be arranged in any configuration. In FIG. 25 part D, the clusters are arranged in rows forming a square shape. Regardless of arrangement, the clusters may start at a distance of about 0.1 mm to about 149 mm from the origin, as measured on the X- or Y-axis. Lengths 2518 and 2509 represent the furthest distances of the center of a cluster on the X- and Y-axis, respectively. Lengths 2517 and 2512 represent the closest distances of the center of a cluster on the X- and Y-axis, respectively. In some embodiments, the clusters are arranged so that there exists a repeated distance between two clusters. As shown by 2507 and 2522, the distance between two clusters may be from about 0.3 mm to about 9 mm apart. In some embodiments, the distance between two clusters is about or at least about 0.3 mm, 0.4 mm, 0.5 mm, 0.6 mm, 0.7 mm, 0.8 mm. 0.9 mm, 1 mm, 1.2 mm, 1.4 mm, 1.6 mm, 1.8 mm, 2 mm, 2.2 mm, 2.4 mm, 2.6 mm, 2.8 mm, 3 mm, 3.2 mm, 3.4 mm, 3.6 mm, 3.8 mm, 4 mm, 4.2 mm, 4.4 mm, 4.6 mm, 4.8 mm, 5 mm, 5.2 mm, 5.4 mm, 5.6 mm, 5.8 mm, 6 mm, 6.2 mm, 6.4 mm, 6.6 mm, 6.8 mm, 7 mm, 7.2 mm, 7.4 mm, 7.6 mm, 7.8 mm, 8 mm, 8.2 mm, 8.4 mm, 8.6 mm, 8.8 mm, or 9 mm. In some embodiments, the distance between two clusters is about or at most about 9 mm, 8.8 mm, 8.6 mm, 8.4 mm, 8.2 mm, 8 mm, 7.8 mm, 7.6 mm, 7.4 mm, 7.2 mm, 7 mm, 6.8 mm, 6.6 mm, 6.4 mm, 6.2 mm, 6 mm, 5.8 mm, 5.6 mm, 5.4 mm, 5.2 mm, 5 mm, 4.8 mm, 4.6 mm, 4.4 mm, 4.2 mm, 4 mm, 3.8 mm, 3.6 mm, 3.4 mm, 3.2 mm, 3 mm, 2.8 mm, 2.6 mm, 2.4 mm, 2.2 mm, 2 mm, 1.8 mm, 1.6 mm, 1.4 mm, 1.2 mm, 1 mm, 0.9 mm, 0.8 mm, 0.7 mm, 0.6 mm, 0.5 mm, 0.4 mm, or 0.3 mm. The distance between two clusters may range between 0.3-9 mm, 0.4-8 mm, 0.5-7 mm, 0.6-6 mm, 0.7-5 mm, 0.7-4 mm, 0.8-3 mm, or 0.9-2 mm. Those of skill in the art appreciate that the distance may fall within any range bound by any of these values, for example 0.8 mm-2 mm.

Fiducial marks may be placed on microfluidic devices described herein to facilitate alignment of such devices with other components of a system. Microfluidic devices of the invention may have one or more fiducial marks, e.g. 2, 3, 4, 5, 6, 7, 8, 9, 10, or more fiducial marks. The substantially planar substrate portion of an exemplary microfluidic device shown in FIG. 25 part D comprises three fiducial marks useful for aligning the device with other components of a system. A fiducial mark may be located at any position within the substantially planar substrate portion of the microfluidic device. As shown by 2513 and 2516, a fiducial mark may be located near the origin, where the fiducial mark is closer to the origin than any one cluster. In some embodiments, a fiducial mark is located near an edge of the substrate portion, as shown by 2511 and 2521, where the distance from the edge is indicated by 2510 and 2520, respectively. The fiducial mark may be located from about 0.1 mm to about 10 mm from the edge of the substrate portion. In some embodiments, the fiducial mark is located about or at least about 0.1 mm, 0.2 mm, 0.3 mm, 0.4 mm, 0.5 mm, 0.6 mm, 0.7 mm, 0.8 mm. 0.9 mm, 1 mm, 1.2 mm, 1.4 mm, 1.6 mm, 1.8 mm, 2 mm, 2.2 mm, 2.4 mm, 2.6 mm, 2.8 mm, 3 mm, 3.2 mm, 3.4 mm, 3.6 mm, 3.8 mm, 4 mm, 4.2 mm, 4.4 mm, 4.6 mm, 4.8 mm, 5 mm, 5.2 mm, 5.4 mm, 5.6 mm, 5.8 mm, 6 mm, 6.2 mm, 6.4 mm, 6.6 mm, 6.8 mm, 7 mm, 7.2 mm, 7.4 mm, 7.6 mm, 7.8 mm, 8 mm, 8.2 mm, 8.4 mm, 8.6 mm, 8.8 mm, 9 mm, or 10 mm from the edge of the substrate portion. In some embodiments, the fiducial mark is located about or at most about 10 mm, 9 mm, 8.8 mm, 8.6 mm, 8.4 mm, 8.2 mm, 8 mm, 7.8 mm, 7.6 mm, 7.4 mm, 7.2 mm, 7 mm, 6.8 mm, 6.6 mm, 6.4 mm, 6.2 mm, 6 mm, 5.8 mm, 5.6 mm, 5.4 mm, 5.2 mm, 5 mm, 4.8 mm, 4.6 mm, 4.4 mm, 4.2 mm, 4 mm, 3.8 mm, 3.6 mm, 3.4 mm, 3.2 mm, 3 mm, 2.8 mm, 2.6 mm, 2.4 mm, 2.2 mm, 2 mm, 1.8 mm, 1.6 mm, 1.4 mm, 1.2 mm, 1 mm, 0.9 mm, 0.8 mm, 0.7 mm, 0.6 mm, 0.5 mm, 0.4 mm, 0.3 mm, 0.2 mm, or 0.1 mm from the substrate portion. The fiducial mark may be located between 0.1-10 mm, 0.2-9 mm, 0.3-8 mm, 0.4-7 mm, 0.5-6 mm, 0.1-6 mm, 0.2-5 mm, 0.3-4 mm, 0.4-3 mm, or 0.5-2 mm from the edge of the substrate. Those of skill in the art appreciate that the distance may fall within any range bound by any of these values, for example 0.1 mm-5 mm. The fiducial mark may be located close in distance to a cluster, where exemplary X- and Y-axis distances are indicated by 2515 and 2514, respectively. In some embodiments, a distance between a cluster and a fiducial mark is about or at least about 0.001 mm, 0.005 mm, 0.01 mm, 0.02 mm, 0.03 mm, 0.04 mm, 0.05 mm, 0.06 mm, 0.07 mm, 0.08 mm, 0.09 mm, 0.1 mm, 0.2 mm, 0.3 mm, 0.4 mm, 0.5 mm, 0.6 mm, 0.7 mm, 0.8 mm, 0.9 mm, 1 mm, 1.2 mm, 1.5 mm, 1.7 mm, 2 mm, 2.2 mm, 2.5 mm, 2.7 mm, 3 mm, 3.5 mm, 4 mm, 4.5 mm, 5 mm, 5.5 mm, 6 mm, 6.5 mm, or 8 mm. In some embodiments, a distance between a cluster and a fiducial mark is about or at most about 8 mm, 6.5 mm, 6 mm, 5.5 mm, 5 mm, 4.5 mm, 4 mm, 3.5 mm, 3 mm, 2.7 mm, 2.5 mm, 2.2 mm, 2 mm, 1.7 mm, 1.5 mm, 1.2 mm, 1 mm, 0.9 mm, 0.8 mm, 0.7 mm, 0.6 mm, 0.5 mm, 0.4 mm, 0.3 mm, 0.2 mm, 0.1 mm, 0.09 mm, 0.08 mm, 0.07 mm, 0.06 mm, 0.05 mm, 0.04 mm, 0.03 mm, 0.02 mm, 0.01 mm, 0.005 mm, or 0.001 mm. The distance between a cluster and a fiducial mark may be in a range between 0.001-8 mm, 0.01-7 mm, 0.05-6 mm, 0.1-5 mm, 0.5-4 mm, 0.6-3 mm, 0.7-2 mm, or 0.8-1.7 mm. Those of skill in the art appreciate that the distance may fall within any range bound by any of these values, for example 0.5-2 mm.

FIG. 25 part E depicts a cross section of the substantially planar substrate portion of an exemplary microfluidic device shown in FIG. 25 part D. The section shows a row of 11 groupings, each comprising a cluster of groupings, wherein each grouping comprises a plurality of second channels extending from a first channel. As exemplified by 2523, the total length of a grouping may be from about 0.05 mm to about 5 mm long. In some embodiments, the total length of a grouping is about or at least about 0.05 mm, 0.06 mm, 0.07 mm, 0.08 mm, 0.09 mm, 0.1 mm, 0.2 mm, 0.3 mm, 0.4 mm, 0.5 mm, 0.6 mm, 0.7 mm, 0.8 mm, 0.9 mm, 1 mm, 1.2 mm, 1.5 mm, 1.7 mm, 2 mm, 2.2 mm, 2.5 mm, 2.7 mm, 3 mm, 3.2 mm, 3.5 mm, 3.7 mm, 4 mm, 4.2 mm, 4.5 mm, 4.7 mm, or 5 mm. In some embodiments, the total length of a grouping is about or at most about 5 mm, 4.7 mm, 4.5 mm, 4.2 mm, 4 mm, 3.7 mm, 3.5 mm, 3.2 mm, 3 mm, 2.7 mm, 2.5 mm, 2.2 mm, 2 mm, 1.7 mm, 1.5 mm, 1.2 mm, 1 mm, 0.9 mm, 0.8 mm, 0.7 mm, 0.6 mm, 0.5 mm, 0.4 mm, 0.3 mm, 0.2 mm, 0.1 mm, 0.09 mm, 0.08 mm, 0.07 mm, 0.06 mm, or 0.05 mm or less. The total length of a grouping may be in a range between 0.05-5 mm, 0.06-4 mm, 0.07-3 mm, 0.08-2 mm, 0.09-1 mm, 0.1-0.9 mm, 0.2-0.8 mm, or 0.3-0.7 mm. Those of skill in the art appreciate that the distance may fall within any range bound by any of these values, for example 0.1-0.7 mm. In some embodiments, the microfluidic device may have a location for a label or a serial label, as exemplified in FIG. 25 part F depicting an exemplary layout of clusters in a microfluidic device. The label may be located near an edge of the substrate, as exemplified by the distance 2603. In some embodiments, the label is located from about 0.1 mm to about 10 mm from the edge of the substrate. In some embodiments, the label is located about or at least about 0.1 mm, 0.2 mm, 0.3 mm, 0.4 mm, 0.5 mm, 0.6 mm, 0.7 mm, 0.8 mm. 0.9 mm, 1 mm, 1.2 mm, 1.4 mm, 1.6 mm, 1.8 mm, 2 mm, 2.2 mm, 2.4 mm, 2.6 mm, 2.8 mm, 3 mm, 3.2 mm, 3.4 mm, 3.6 mm, 3.8 mm, 4 mm, 4.2 mm, 4.4 mm, 4.6 mm, 4.8 mm, 5 mm, 5.2 mm, 5.4 mm, 5.6 mm, 5.8 mm, 6 mm, 6.2 mm, 6.4 mm, 6.6 mm, 6.8 mm, 7 mm, 7.2 mm, 7.4 mm, 7.6 mm, 7.8 mm, 8 mm, 8.2 mm, 8.4 mm, 8.6 mm, 8.8 mm, 9 mm, or 10 mm from the edge of a substrate. In some embodiments, the label is located about or at most about 10 mm, 9 mm, 8.8 mm, 8.6 mm, 8.4 mm, 8.2 mm, 8 mm, 7.8 mm, 7.6 mm, 7.4 mm, 7.2 mm, 7 mm, 6.8 mm, 6.6 mm, 6.4 mm, 6.2 mm, 6 mm, 5.8 mm, 5.6 mm, 5.4 mm, 5.2 mm, 5 mm, 4.8 mm, 4.6 mm, 4.4 mm, 4.2 mm, 4 mm, 3.8 mm, 3.6 mm, 3.4 mm, 3.2 mm, 3 mm, 2.8 mm, 2.6 mm, 2.4 mm, 2.2 mm, 2 mm, 1.8 mm, 1.6 mm, 1.4 mm, 1.2 mm, 1 mm, 0.9 mm, 0.8 mm, 0.7 mm, 0.6 mm, 0.5 mm, 0.4 mm, 0.3 mm, 0.2 mm, or 0.1 mm from the edge of a substrate. The distance may be in a range between 0.1-10 mm, 0.2-9 mm, 0.3-8 mm, 0.4-7 mm, 0.5-6 mm, 0.6-5 mm, 0.7-4 mm, 0.8-3 mm, 0.9-2 mm or 1.5 mm. Those of skill in the art appreciate that the distance may fall within any range bound by any of these values, for example 0.5-2 mm. The label may start at a position from about 0.1 mm to about 20 mm from the origin as exemplified by 2602. The label may have a length from about 1 mm to about 32 mm as exemplified by 2601.

Wafers with Large Sized Vias for High Mass Oligonucleotide Synthesis

In some embodiments, the invention provides for methods and systems for controlled flow and mass transfer paths for oligonucleotide synthesis on a surface. The advantages of the systems and methods provided herein allow for improved levels of structure for the controlled and even distribution of mass transfer paths, chemical exposure times, and wash efficacy during oligonucleotide synthesis. Further, the methods and systems described herein allow for increased sweep efficiency, such as by providing sufficient volume for a growing oligonucleotide such that the excluded volume by the growing oligonucleotide does not take up more than 50, 45, 40, 35, 30, 25, 20, 15, 14, 13, 12, 11, 10, 9, 8, 7, 6, 5, 4, 3, 2, 1%, or less of the initially available volume that is available or suitable for growing oligonucleotides. In addition, the methods and systems described herein allow for an sufficient structure for the growth of oligomers beyond 80 mer to 100, 120, 150, 175, 200, 225, 250, 275, 300, 325, 350, 375, 400, 425, 450, 475, 500-mer or longer.

Accordingly, the methods and systems described herein provide solutions to achieve these advantages, such as collections of small parallel passages. Structures, such as small vias may be used to feed smaller structures, such as those found in the "revolver pattern" (FIG. 56B). Structures having a low surface energy surface on the inner surface may cause gas to hang up on the walls. Gas bubbles may impede the flow rate and flow uniformity during oligonucleotide synthesis cycles or subsequent aqueous steps used for gene assembly. Accordingly, structures that are adapted for oligonucleotide synthesis may comprise a surface with increased surface energy as described elsewhere herein.

In some embodiments, the methods and systems of the invention exploit silicon wafer processes for manufacturing substrates for oligonucleotide synthesis. Such substrates may have a series of sites accessible to material deposition via a deposition device such as an inkjet. Substrates manufactured according to the various embodiments of the invention may support flood chemistry steps that are shared among a plurality of such sites through their plane. In various embodiments, devices allow aqueous reagents to be injected and pooled in a large relief (FIG. 61 parts A-B).

In various embodiments, such oligonucleotide synthesis devices with large vias are created on a standard Silicon on Insulator (SOI) silicon wafer. The oligonucleotide synthesis device may have a total width of at least or at least about 10 micrometer (μm), 11 μm, 12 μm, 13 μm, 14 μm, 15 μm, 16 μm, 17 μm, 18 μm, 19 μm, 20 μm, 25 μm, 30 μm, 35 μm, 40 μm, 45 μm, 50 μm, 55 μm, 60 μm, 65 μm, 70 μm, 75 μm, 80 μm, 85 μm, 90 μm, 95 μm, 100 μm, 110 μm, 120 μm, 130 μm, 140 μm, 150 μm, 160 μm, 170 μm, 180 μm, 190 μm, 200 μm, 250 μm, 300 μm, 350 μm, 400 μm, 450 μm, 500 μm, 550 μm, 600 μm, 650 μm, 700 μm, 750 μm, 800 μm, 850 μm, 900 μm, 950 μm, 1000 μm, or more. The oligonucleotide synthesis device may have a total width of at most or at most about 1000 μm, 900 μm, 850 μm, 750 μm, 700 μm, 650 μm, 600 μm, 550 μm, 500 μm, 450 μm, 400 μm, 350 μm, 300 μm, 250 μm, 200 μm, 190 μm, 180 μm, 170 μm, 160 μm, 150 μm, 140 μm, 130 μm, 120 μm, 110 μm, 100 μm, 95 μm, 90 μm, 85 μm, 80 μm, 75 μm, 70 μm, 65 μm, 60 μm, 55 μm, 50 μm, 45 μm, 40 μm, 35 μm, 30 μm, 25 μm, 20 μm, 19 μm, 18 μm, 17 μm, 16 μm, 15 μm, 14 μm, 13 μm, 12 μm, 11 μm, 10 μm, or less. The oligonucleotide synthesis device may have a total width that is between 10-1000 μm, 11-950 μm, 12-900 μm, 13-850 μm, 14-800 μm, 15-750 μm, 16-700 μm, 17-650 μm, 18-600 μm, 19-550 μm, 20-500 μm, 25-450 μm, 30-400 μm, 35-350 μm, 40-300 μm, 45-250 μm, 50-200 μm, 55-150 μm, 60-140 μm, 65-130 μm, 70-120 μm, 75-110 μm, 70-100 μm, 75-80 μm, 85-90 μm or 90-95 μm. Those of skill in the art appreciate that the total width of the oligonucleotide synthesis device may fall within any range bound by any of these values, for example 20-80 μm. The total width of the oligonucleotide device may fall within any range defined by any of the values serving as endpoints of the range. It may be subdivided into a handle layer and a device layer. All or portions of the device may be covered with a silicon dioxide layer. The silicon dioxide layer may have a thickness of at least or at least about 1 nm, 2 nm, 3 nm, 4 nm, 5 nm, 6 nm, 7 nm, 8 nm, 9 nm, 10 nm, 15 nm, 20 nm, 25 nm, 30 nm, 35 nm, 40 nm, 45 nm, 50 nm, 55 nm, 60 nm, 65 nm, 70 nm, 75 nm, 80 nm, 85 nm, 90 nm, 95 nm, 100 nm, 125 nm, 150 nm, 175 nm, 200 nm, 300 nm, 400 nm, 500 nm, 1 μm, 1.1 μm, 1.2 μm, 1.3 μm, 1.4 μm, 1.5 μm, 1.6 μm, 1.7 μm, 1.8 μm, 1.9 μm, 2.0 μm, or more. The silicon dioxide layer may have a thickness of at most or at most about 2.0 μm, 1.9 μm, 1.8 μm, 1.7 μm, 1.6 μm, 1.5 μm, 1.4 μm, 1.3 μm, 1.2 μm, 1.1 μm, 1.0 μm, 500 nm, 400 nm, 300 nm, 200 nm, 175 nm, 150 nm, 125 nm, 100 nm, 95 nm, 90 nm, 85 nm, 80 nm, 75 nm, 70 nm, 65 nm, 60 nm, 55 nm, 50 nm, 45 nm, 40 nm, 35 nm, 30 nm, 25 nm, 20 nm, 15 nm, 10 nm, 9 nm, 8, nm, 7 nm, 6 nm, 5 nm, 4 nm, 3 nm, 2 nm, 1 nm, or less. The silicon dioxide layer may have a thickness that is between 1.0 nm-2.0 μm, 1.1-1.9 μm, 1.2-1.8 nm, 1.3-1.7 μm, 1.4-1.6 μm. Those of skills in the art will appreciate that the silicon dioxide layer may have a thickness that falls within any range bound by any of these values, for example (1.5-1.9 μm). The silicon dioxide may have a thickness that falls within any range defined by any of the values serving as endpoints of the range.

Figure 61:
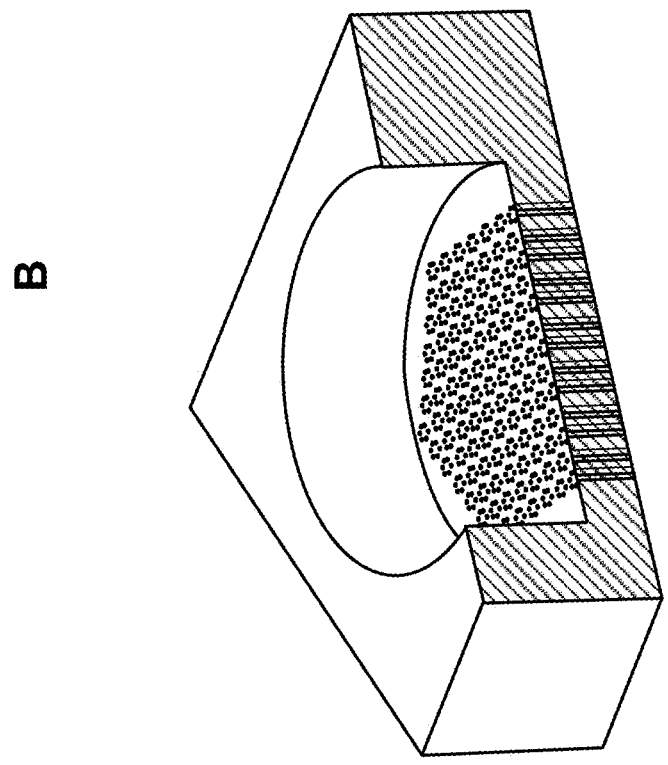
FIG. 61 parts A-B present block views of a high capacity oligonucleotide synthesis device consistent with the disclosure herein.
Figure 61:
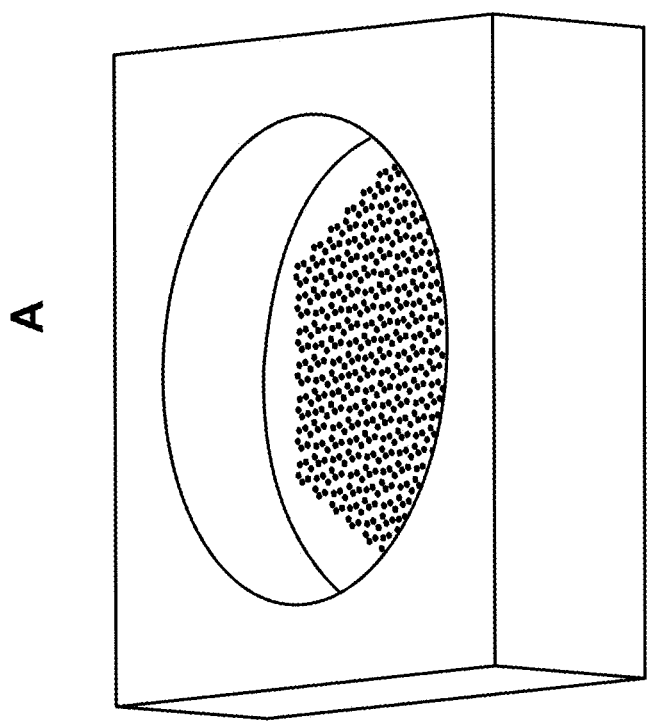

The device layer may comprise a plurality of structures suitable for oligonucleotide growth, as described elsewhere herein, such as a plurality of small holes (FIG. 61 parts A-B). The device layer may have a thickness of at least or at least about 1 micrometer (μm), 2 μm, 3 μm, 4 μm, 5 μm, 6 μm, 7 μm, 8 μm, 9 μm, 10 μm, 11 μm, 12 μm, 13 μm, 14 μm, 15 μm, 16 μm, 17 μm, 18 μm, 19 μm, 20 μm, 25 μm, 30 μm, 35 μm, 40 μm, 45 μm, 50 μm, 55 μm, 60 μm, 65 μm, 70 μm, 75 μm, 80 μm, 85 μm, 90 μm, 95 μm, 100 μm, 200 μm, 300 μm, 400 μm, 500 μm, or more. The device layer may have a thickness of at most or at most about 500 μm, 400 μm, 300 μm, 200 μm, 100 μm, 95 μm, 90 μm, 85 μm, 80 μm, 75 μm, 70 μm, 65 μm, 60 μm, 55 μm, 50 μm, 45 μm, 40 μm, 35 μm, 30 μm, 25 μm, 20 μm, 19 μm, 18 μm, 17 μm, 16 μm, 15 μm, 14 μm, 13 μm, 12 μm, 11 μm, 10 μm, 9 μm, 8 μm, 7 μm, 6 μm, 5 μm, 4 μm, 3 μm, 2 μm, 1 μm, or less. The device layer may have a thickness that is between 1-100 μm, 2-95 μm, 3-90 μm, 4-85 μm, 5-80 μm, 6-75 μm, 7-70 μm, 8-65 μm, 9-60 μm, 10-55 μm, 11-50 μm, 12-45 μm, 13-40 μm, 14-35 μm, 15-30 μm, 16-25 μm, 17-20 μm, 18-19 μm. Those of skill in the art appreciate that the thickness of the device layer may fall within any range bound by any of these values, for example (20-60 μm). The thickness of the device layer may fall within any range defined by any of the values serving as endpoints of the range. The handle and/or the device layer may comprise deep features. Such deep features may be manufactured using a suitable MEMS technique, such as deep reactive ion etching. A series of etches may be used to construct the desired device geometry. One of the etches may be allowed to last longer and penetrate the insulator layer. Accordingly, passages that span the entire width of the device may be constructed. Such passages may be used to pass fluid from one surface of a substrate, such as a substantially planar substrate, to another.

In some embodiments, the device layer has at least two and up to 500 sites, from at least 2 to about 250 sites, from at least 2 to about 200 sites, from at least 2 to about 175 sites, from at least 2 to about 150 sites, from at least 2 to about 125 sites, from at least 2 to about 100 sites, from at least 2 to about 75 sites, from at least 2 to about 50 sites, from at least 2 to about 25 sites, or from at least 2 to about 250 sites that penetrate through the device layer. In some embodiments, the device layer has at least or at least about 2, 3, 4, 5, 6, 7, 8, 9, 10, 15, 20, 30, 50, 75, 100, 125, 150, 175, 200, 225, 250, 275, 300, 350, 400, 450, 500, or more sites. Those of skill in the art appreciate that the number of sites that penetrate through the device layer may fall within any range bound by any of these values, for example 75-150 sites. The device layer may be at least or at least about 2 µm, 3 µm, 4 µm, 5 µm, 6 µm, 7 µm, 8 µm, 9 µm, 10 µm, 11 µm, 12 µm, 13 µm, 14 µm, 15 µm, 16 µm, 17 µm, 18 µm, 19 µm, 20 µm, 25 µm, 30 µm, 35 µm, 40 µm, 45 µm, 50 µm, 55 µm, 60 µm, 65 µm, 70 µm, 75 µm, 80 µm, 85 µm, 90 µm, 95 µm, 100 µm thick, or more. The device layer may be at most or at most about 100 µm, 95 µm, 90 µm, 85 µm, 80 µm, 75 µm, 70 µm, 65 µm, 60 µm, 55 µm, 50 µm, 45 µm, 40 µm, 35 µm, 30 µm, 25 µm, 20 µm, 19 µm, 18 µm, 17 µm, 16 µm, 15 µm, 14 µm, 13 µm, 12 µm, 11 µm, 10 µm, 9 µm, 8 µm, 7 µm, 6 µm, 5 µm, 4 µm, 3 µm, 2 µm, 1 µm, thick, or less. The device layer can have any thickness that fall between 1-100 µm, 2-95 µm, 3-90 µm, 4-85 µm, 5-80 µm, 6-75 µm, 7-70 µm, 8-65 µm, 9-60 µm, 10-55 µm, 11-50 µm, 12-45 µm, 13-40 µm, 14-35 µm, 15-30 µm, 16-25 µm, 17-20 µm, 18-19 µm. Those skilled in the art appreciate that the device layer can have any thickness that may fall within any range bound by any of these values bound by any of these values, for example, 4-100 µm.

The thickness of the device layer may fall within any range defined by any of the values serving as endpoints of the range. The handle layer may have a larger area etched into the wafer that neighbors the features in the device layer. The handle layer may have a thickness of at least or at least about 10 µm, 11 µm, 12 µm, 13 µm, 14 µm, 15 µm, 16 µm, 17 µm, 18 µm, 19 µm, 20 µm, 25 µm, 30 µm, 35 µm, 40 µm, 45 µm, 50 µm, 55 µm, 60 µm, 65 µm, 70 µm, 75 µm, 80 µm, 85 µm, 90 µm, 95 µm, 100 µm, 110 µm, 120 µm, 130 µm, 140 µm, 150 µm, 160 µm, 170 µm, 180 µm, 190 µm, 200 µm, 250 µm, 300 µm, 350 µm, 400 µm, 450 µm, 500 µm, 550 µm, 600 µm, 650 µm, 700 µm, 750 µm, 800 µm, 850 µm, 900 µm, 950 µm, 1000 µm, or more. The handle layer may have a thickness of at most or at most about 1000 µm, 950 µm, 900 µm, 850 µm, 800 µm, 750 µm, 700 µm, 650 µm, 600 µm, 550 µm, 500 µm, 450 µm, 400 µm, 350 µm, 300 µm, 250 µm, 200 µm, 150 µm, 100 µm, 95 µm, 90 µm, 85 µm, 80 µm, 75 µm, 70 µm, 65 µm, 60 µm, 55 µm, 50 µm, 45 µm, 40 µm, 30 µm, 25 µm, 20 µm, 19 µm, 18 µm, 17 µm, 16 µm, 15 µm, 14 µm, 13 µm, 12 µm, 11 µm, 10 µm, 9 µm, 8 µm, 7 µm, 6 µm, 5 µm, 4 µm, 3 µm, 2 µm, 1 µm, or less. The handle layer can have any thickness that is between 10-1000 µm, 11-950 µm, 12-900 µm, 13-850 µm, 14-800 µm, 15-750 µm, 16-700 µm, 17-650 µm, 18-600 µm, 19-550 µm, 20-500 µm, 25-450 µm, 30-400 µm, 35-350 µm, 40-300 µm, 45-250 µm, 50-200 µm, 55-150 µm, 60-140 µm, 65-130 µm, 70-120 µm, 75-110 µm, 70-100 µm, 75-80 µm, 85-90 µm or 90-95 µm. Those of skill in the art appreciate that handle layer may have a thickness that falls within any range bound by any of these values, for example 20-350 µm. The thickness of the handle layer fall within any range defined by any of the values serving as endpoints of the range Etched regions in the handle layer may form well-like structures embedded in the substrate. In some embodiments, etched regions within the handle layer may have a thickness of at least or about at least 100 µm, 101 µm, 102 µm, 103 µm, 104 µm, 105 µm, 106 µm, 107 µm, 108 µm, 109 µm, 110 µm, 120 µm, 130 µm, 140 µm, 150 µm, 160 µm, 170 µm, 180 µm, 190 µm, 200 µm, 250 µm, 300 µm, 350 µm, 400 µm, 450 µm, 500 µm, 550 µm, 600 µm, 650 µm, 700 µm, 750 µm, 800 µm, 850 µm, 900 µm, 950 µm, or 1000 µm, or more. The etched region within the handle layer may have any thickness of at most or about at most 1000 µm, 950 µm, 900 µm, 850 µm, 800 µm, 750 µm, 700 µm, 650 µm, 600 µm, 550 µm, 500 µm, 450 µm, 400 µm, 350 µm, 300 µm, 250 µm, 200 µm, 190 µm, 180 µm, 170 µm, 160 µm, 150 µm, 140 µm, 130 µm, 120 µm, 110 µm, 109 µm, 108 µm, 107 µm, 106 µm, 105 µm, 104 µm, 103 µm, 102 µm, 101 µm, 100 µm, or less. The etched region within the handle layer may have any thickness that is between 100-1000 µm, 101-950 µm, 102-900 µm, 103-850 µm, 104-800 µm, 105-750 µm, 106-700 µm, 105-650 µm, 106-600 µm, 107-550 µm, 108-500 µm, 109-450 µm, 110-400 µm, 120-350 µm, 130-300 µm, 140-250 µm, 150-200 µm, 160-190 µm, 170-180 µm. Those of skill in the art appreciate that handle layer may have a thickness that falls within any range bound by any of these values, for example 200-300 µm.

The shape of the etched regions within the handle layer may be rectangular or curvilinear.

In some embodiments, large etched regions within the handle layer allow for easy transition from a gas phase to a liquid phase during the oligonucleotide synthesis cycle, and/or during oligonucleotide release, such as oligonucleotide release into gas phase.

Substrates with High Surface Area Synthesis Sites

In various embodiments, the methods and systems described herein relate to oligonucleotide synthesis devices for the synthesis of high masses of oligonucleotides. The synthesis may be in parallel. For example at least or about at least 2, 3, 4, 5, 6, 7, 8, 9, 10, 11, 12, 13, 14, 15, 16, 17, 18, 19, 20, 21, 22, 23, 24, 25, 30, 35, 40, 45, 50, 100, 150, 200, 250, 300, 350, 400, 450, 500, 550, 600, 650, 700, 750, 800, 850, 900, 1000, 10000, 50000, 100000, 100000 or more oligonucleotides can be synthesized in parallel. The total number oligonucleotides that may be synthesized in parallel may be between 2-100000, 3-50000, 4-10000, 5-1000, 6-900, 7-850, 8-800, 9-750, 10-700, 11-650, 12-600, 13-550, 14-500, 15-450, 16-400, 17-350, 18-300, 19-250, 20-200, 21-150, 22-100, 23-50, 24-45, 25-40, 30-35. Those of skill in the art appreciate that the total number of oligonucleotides synthesized in parallel may fall within any range bound by any of these values, for example 25-100. The total number of oligonucleotides synthesized in parallel may fall within any range defined by any of the values serving as endpoints of the range. Total molar mass of oligonucleotides synthesized within the device or the molar mass of each of the oligonucleotides may be at least or at least about 10, 20, 30, 40, 50, 100, 250, 500, 750, 1000, 2000, 3000, 4000, 5000, 6000, 7000, 8000, 9000, 10000, 25000, 50000, 75000, 100000 picomoles, or more. The length of each of the oligonucleotides or average length of the oligonucleotides within the device may be at least or about at least 10, 15, 20, 25, 30, 35, 40, 45, 50, 100, 150, 200, 300, 400, 500 nucleotides, or more. The length of each of the oligonucleotides or average length of the oligonucleotides within the device may be at most or about at most 500, 400, 300, 200, 150, 100, 50, 45, 35, 30, 25, 20, 19, 18, 17, 16, 15, 14, 13, 12, 11, 10 nucleotides, or less. The length of each of the oligonucleotides or average length of the oligonucleotides within the device may fall between 10-500, 9-400, 11-300, 12-200, 13-150, 14-100, 15-50, 16-45, 17-40, 18-35, 19-25. Those of skill in the art appreciate that the length of each of the oligonucleotides or average length of the oligonucleotides within the device may fall within any range bound by any of these values, for example 100-300. The length of each of the oligonucleotides or average length of the oligonucleotides within the device may fall within any range defined by any of the values serving as endpoints of the range.

Figure 62:
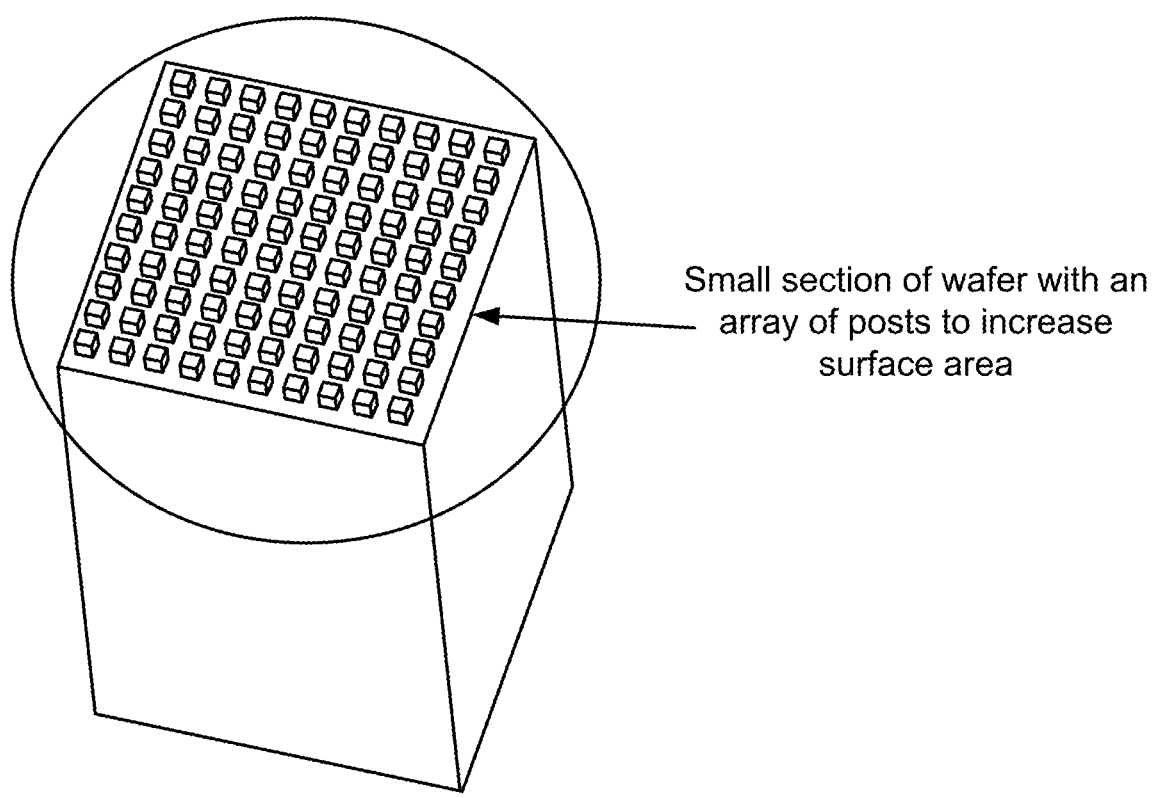
FIG. 62 depicts a block view of another high capacity oligonucleotide synthesis device consistent with the disclosure herein, having an array of posts on its surface, which increase surface area.

In various embodiments, high surface areas are achieved by structuring the surface of a substrate with raised and/or lower features as exemplified in FIG. 62. The raised or lowered features may have sharp or rounded edges and may have cross-sections (widths) of any desired geometric shape, such as rectangular, circular, etc. They may form channels along the entire substrate surface or a portion of it. The raised or lowered features may have an aspect ratio of at least or about at least 1:20, 2:20, 3:20, 4:20, 5:20, 6:20, 10:20, 15:20, 20:20, 20:10, 20:5, 20:1, or more. The raised or lowered features may have an aspect ratio of at most or about at most 20:1, 20:5, 20:10, 20:20, 20:15, 20:10, 20:10, 6:20, 5:20, 4:20, 3:20, 2:20, 1:20, or less. The raised or lowered features may have an aspect ratio that falls between 1:20-20:1, 2:20-20:5, 3:20-20:10, 4-20:20:15, 5:20-20:20, 6:20-20:20. Those of skill in the art appreciate that the raised or lowered features may have an aspect ratio that may fall within any range bound by any of these values, for example 3:20-4:20. The raised or lowered features may have an aspect ratio that falls within any range defined by any of the values serving as endpoints of the range.

The raised or lowered features may have cross-sections of at least or about at least 10 nanometers (nm), 11 nm, 12 nm, 20 nm, 30 nm, 100 nm, 500 nm, 1000 nm, 10000 nm, 100000 nm, 1000000 nm, or more. The raised or lowered features may have cross-sections of at least or most or about at most 1000000 nm, 100000 nm, 10000 nm, 1000 nm, 500 nm, 100 nm, 30 nm, 20 nm, 12 nm, 11 nm, 10 nm, or less. The raised or lowered features may have cross-sections that fall between 10 nm-1000000 nm, 11 nm-100000 nm, 12 nm-10000 nm, 20 nm-1000 nm, 30 nm-500 nm. Those of skill in the art appreciate that the raised or lowered features may have cross-sections that may fall within any range bound by any of these values, for example 10 nm-100 nm. The raised or lowered features may have cross-sections that fall within any range defined by any of the values serving as endpoints of the range.

The raised or lowered features may have heights of at least or about at least 10 nanometers (nm), 11 nm, 12 nm, 20 nm, 30 nm, 100 nm, 500 nm, 1000 nm, 10000 nm, 100000 nm, 1000000 nm, or more. The raised or lowered features may have heights of at most or about at most 1000000 nanometers (nm), 100000 nm, 10000 nm, 1000 nm, 500 nm, 100 nm, 30 nm, 20 nm, 12 nm, 11 nm, 10 nm, or less. The raised or lowered features may have heights that fall between 10 nm-1000000 nm, 11 nm-100000 nm, 12 nm-10000 nm, 20 nm-1000 nm, 30 nm-500 nm. Those of skill in the art appreciate that the raised or lowered features may have heights that may fall within any range bound by any of these values, for example 100 nm-1000 nm. The raised or lowered features may have heights that fall within any range defined by any of the values serving as endpoints of the range. The individual raised or lowered features may be separated from a neighboring raised or lowered feature by a distance of at least or at least about 5 nanometers (nm), 10 nm, 11 nm, 12 nm, 20 nm, 30 nm, 100 nm, 500 nm, 1000 nm, 10000 nm, 100000 nm, 1000000 nm, or more. The individual raised or lowered features may be separated from a neighboring raised or lowered feature by a distance of at most or about at most 1000000 nanometers (nm), 100000 nm, 10000 nm, 1000 nm, 500 nm, 100 nm, 30 nm, 20 nm, 12 nm, 11 nm, 10 nm, 5 nm, or less. The raised or lowered features may have heights that fall between 5-1000000 nm, 10-100000 nm, 11-10000 nm, 12-1000 nm, 20-500 nm, 30-100 nm. Those of skill in the art appreciate that the individual raised or lowered features may be separated from a neighboring raised or lowered feature by a distance that may fall within any range bound by any of these values, for example 100-1000 nm. The individual raised or lowered features may be separated from a neighboring raised or lowered feature by a distance that falls within any range defined by any of the values serving as endpoints of the range. In some embodiments, the distance between two raised or lowered features is at least or about at least 0.1, 0.2, 0.5, 1.0, 2.0, 3.0, 5.0, 10.0 times, or more, the cross-section (width) or average cross-section of the raised or lowered features. The distance between the two raised or lowered features is at most or about at most 10.0, 5.0, 3.0, 2.0, 1.0, 0.5, 0.2, 0.1 times, or less, the cross-section (width) or average cross-section of the raised or lowered features. The distance between the two raised or lowered features may be between 0.1-10, 0.2-5.0, 1.0-3.0 times, the cross-section (width) or average cross-section of the raised or lowered features. Those of skill in the art appreciate that the distance between the two raised or lowered features may be between any times the cross-section (width) or average cross-section of the raised or lower features within any range bound by any of these values, for example 5-10 times. The distance between the two raised or lowered features may be within any range defined by any of the values serving as endpoints of the range.

In some embodiments, groups of raised or lowered features are separated from each other. Perimeters of groups of raised or lowered features may be marked by a different type of structural feature or by differential functionalization. A group of raised or lowered features may be dedicated to the synthesis of a single oligonucleotide. A group of raised of lowered features may span an area that is at least or about at least 10 µm, 11 µm, 12 µm, 13 µm, 14 µm, 15 µm, 20 µm, 50 µm, 70 µm, 90 µm, 100 µm, 150 µm, 200 µm, or wider in cross section. A group of raised of lowered features may span an area that is at most or about at most 200 µm, 150 µm, 100 µm, 90 µm, 70 µm, 50 µm, 20 µm, 15 µm, 14 µm, 13 µm, 12 µm, 11 µm, 10 µm, or narrower in cross section. A group of raised of lowered features may span an area that is between 10-200 µm, 11-150 µm, 12-100 µm, 13-90 µm, 14-70 µm, 15-50 µm, 13-20 µm, wide in cross-section. Those of skill in art appreciate that a group of raised of lowered features may span an area that falls within any range bound by any of these values, for example 12-200 µm. A group of raised of lowered features may span an area that fall within any range defined by any of the values serving as endpoints of the range.

In various embodiments, the raised or lowered features on a substrate increase the total available area for oligonucleotide synthesis by at least or at least about 1.1, 1.2, 1.3, 1.4, 2, 5, 10, 50, 100, 200, 500, 1000 fold, or more. The raised or lowered features on a substrate increase the total available area for oligonucleotide synthesis between 1.1-1000, 1.2-500, 1.3-200, 1.4-100, 2-50, 5-10, fold. Those of skill in art appreciate that the raised or lowered features on a substrate may increase the total available area for oligonucleotide synthesis between any fold bound by any of these values, for example 20-80 fold. The raised or lowered features on a substrate increase the total available area for oligonucleotide synthesis by a factor that may fall within any range defined by any of the values serving as endpoints of the range.

The methods and systems of the invention using large oligonucleotide synthesis surfaces allow for the parallel synthesis of a number of oligonucleotides with nucleotide addition cycles times of at most or about at most 20 min, 15 min, 14 min, 13 min, 12 min, 11 min, 10 min, 1 min, 40 sec, 30 sec, or less. The methods and systems of the invention using large oligonucleotide synthesis surfaces allow for the parallel synthesis of a number of oligonucleotides with nucleotide addition cycles times between 30 sec-20 min, 40 sec-10 min, 1 min-10 min. Those of skill in art appreciate that the methods and systems of the invention using large oligonucleotide synthesis surfaces allow for the parallel synthesis of a number of oligonucleotides with nucleotide addition cycles times between any of these values, for example 30 sec-10 min. The methods and systems of the invention using large oligonucleotide synthesis surfaces allow for the parallel synthesis of a number of oligonucleotides with nucleotide addition cycles times that may be fall between any range defined by any of the values serving as endpoints of the range.

The overall error rate or error rates for individual types of errors such as deletions, insertions, or substitutions for each oligonucleotide synthesized on the substrate, for at least 10%, 20%, 30%, 40%, 50%, 60%, 70%, 80%, 90%, 95%, 98%, 99%, 99.5%, or more of the oligonucleotides synthesized on the substrate, or for the substrate average may be at most or at most about 1:100, 1:500, 1:1000, 1:10000, 1:20000, 1:30000, 1:40000, 1:50000, 1:60000, 1:70000, 1:80000, 1:90000, 1:1000000, or less. The overall error rate or error rates for individual types of errors such as deletions, insertions, or substitutions for each oligonucleotide synthesized on the substrate, for at least 10%, 20%, 30%, 40%, 50%, 60%, 70%, 80%, 90%, 95%, 98%, 99%, 99.5%, or more of the oligonucleotides synthesized on the substrate, or the substrate average may fall between 1:100 and 1:10000, 1:500 and 1:30000. Those of skill in art, appreciate that the overall error rate or error rates for individual types of errors such as deletions, insertions, or substitutions for each oligonucleotide synthesized on the substrate, for at least 10%, 20%, 30%, 40%, 50%, 60%, 70%, 80%, 90%, 95%, 98%, 99%, 99.5%, or more of the oligonucleotides synthesized on the substrate, or the substrate average may fall between any of these values, for example 1:500 and 1:10000. The overall error rate or error rates for individual types of errors such as deletions, insertions, or substitutions for each oligonucleotide synthesized on the substrate, for at least 10%, 20%, 30%, 40%, 50%, 60%, 70%, 80%, 90%, 95%, 98%, 99%, 99.5%, or more of the oligonucleotides synthesized on the substrate, or the substrate average may fall between any range defined by any of the values serving as endpoints of the range.

Standard silicon wafer processes can be employed to create a substrate that will have a high surface area as described above and a managed flow, allowing rapid exchange of chemical exposure. The oligonucleotide synthesis substrate can be created with a series of structures with sufficient separation to allow oligomer chains greater than at least or about at least 20 mer, 25 mer, 30 mer, 50 mer, 100 mer, 200 mer, 250 mer, 300 mer, 400 mer, 500 mer, or more to be synthesized without substantial influence on the overall channel or pore dimension, for example due to excluded volume effects, as the oligonucleotide grows. The oligonucleotide synthesis substrate can be created with a series of structures with sufficient separation to allow oligomer chains greater than at most or about at most 500 mer, 200 mer, 100 mer, 50 mer, 30 mer, 25 mer, 20 mer, or less to be synthesized without substantial influence on the overall channel or pore dimension, for example due to excluded volume effects, as the oligonucleotide grows. The oligonucleotide synthesis substrate can be created with a series of structures with sufficient separation to allow oligomer chains that are at least or at least about 20 mer, 50 mer, 75 mer, 100 mer, 125 mer, 150 mer, 175 mer, 200 mer, 250 mer, 300 mer, 350 mer, 400 mer, 500 mer, or more to be synthesized without substantial influence on the overall channel or pore dimension, for example due to excluded volume effects, as the oligonucleotide grows. Those of skill in the art appreciate that the oligonucleotide synthesis substrate can be created with a series of structures with sufficient separation to allow oligomer chains greater than between any of these values, for example, 20-300 mer 200 mer to be synthesized without substantial influence on the overall channel or pore dimension, for example due to excluded volume effects, as the oligonucleotide grows.

FIG. 62 shows an exemplary substrate according to the embodiments of the invention with an array of structures. The distance between the features may be greater than at least or about at least 5 nm, 10 nm, 20 nm, 100 nm, 1000 nm, 10000 nm, 100000 nm, 1000000 nm, or more. The distance between the features may be greater than at most or about at most 1000000 nm, 100000 nm, 10000 nm, 1000 nm, 100 nm, 20 nm, 10 nm, 5 nm, or less. The distance between the features may fall between 5-1000000 nm, 10-100000 nm, 20-10000 nm, 100-1000 nm. Those of skill in the art appreciate that the distance between the features may fall between any of these values, for example, 20-1000 nm. The distance between the features may fall between any range defined by any of the values serving as endpoints of the range. In one embodiment, the distance between the features is greater than 200 nm. The features may be created by any suitable MEMS processes described elsewhere herein or otherwise known in the art, such as a process employing a timed reactive ion etch process. Such semiconductor manufacturing processes can typically create feature sizes smaller than 200 nm, 100 nm, 50 nm, 40 nm, 30 nm, 25 nm, 20 nm, 10 nm, 5 nm, or less. Those of skill in the art appreciate that the feature size smaller than 200 nm can be between any of these values, for example, 20-100 nm. The feature size can fall within any range defined by any of these values serving as endpoints of the range. In one embodiment, an array of 40 µm wide posts are etched with 30 µm depth, which about doubles the surface area available for synthesis.

The arrays of raised or lowered features may be segregated allowing material deposition of a phosphoramidite chemistry for highly complex and dense library generation. The segregation may be achieved by larger structures or by differential functionalization of the surface generating active and passive regions for oligonucleotide synthesis. Alternatively, the locations for the synthesis of individual oligonucleotides may be separated from each other by creating regions of cleavable and non-cleavable oligonucleotide attachments to the surface under a certain condition. A device, such as an inkjet printer, may be used to deposit reagents to the individual oligonucleotide synthesis locations. Differential functionalization can also achieve alternating the hydrophobicity across the substrate surface, thereby creating water contact angle effects that may cause beading or wetting of the deposited reagents. Employing larger structures can decrease splashing and cross-contamination of individual oligonucleotide synthesis locations with reagents of the neighboring spots.

Reactors

In another aspect, an array of enclosures is described herein. The array of enclosures can comprise a plurality of resolved reactors comprising a first substrate and a second substrate comprising reactor caps. In some cases, at least two resolved loci are contained in each reactor. The resolved reactors may be separated with a releasable seal. The reactors caps may retain the contents of the reactors upon release of the second substrate from the first substrate. The plurality of resolved reactors can be any suitable density at a density of at least 1 per mm$^2$. The plurality of reactor caps can be coated with a moiety. The moiety can be a chemically inert or chemically active moiety. The moiety that is coated onto the reactor caps can be a moiety that can minimize the attachment of the oligonucleotides. The types of chemical moieties are described in further detail elsewhere herein.

Figure 7:
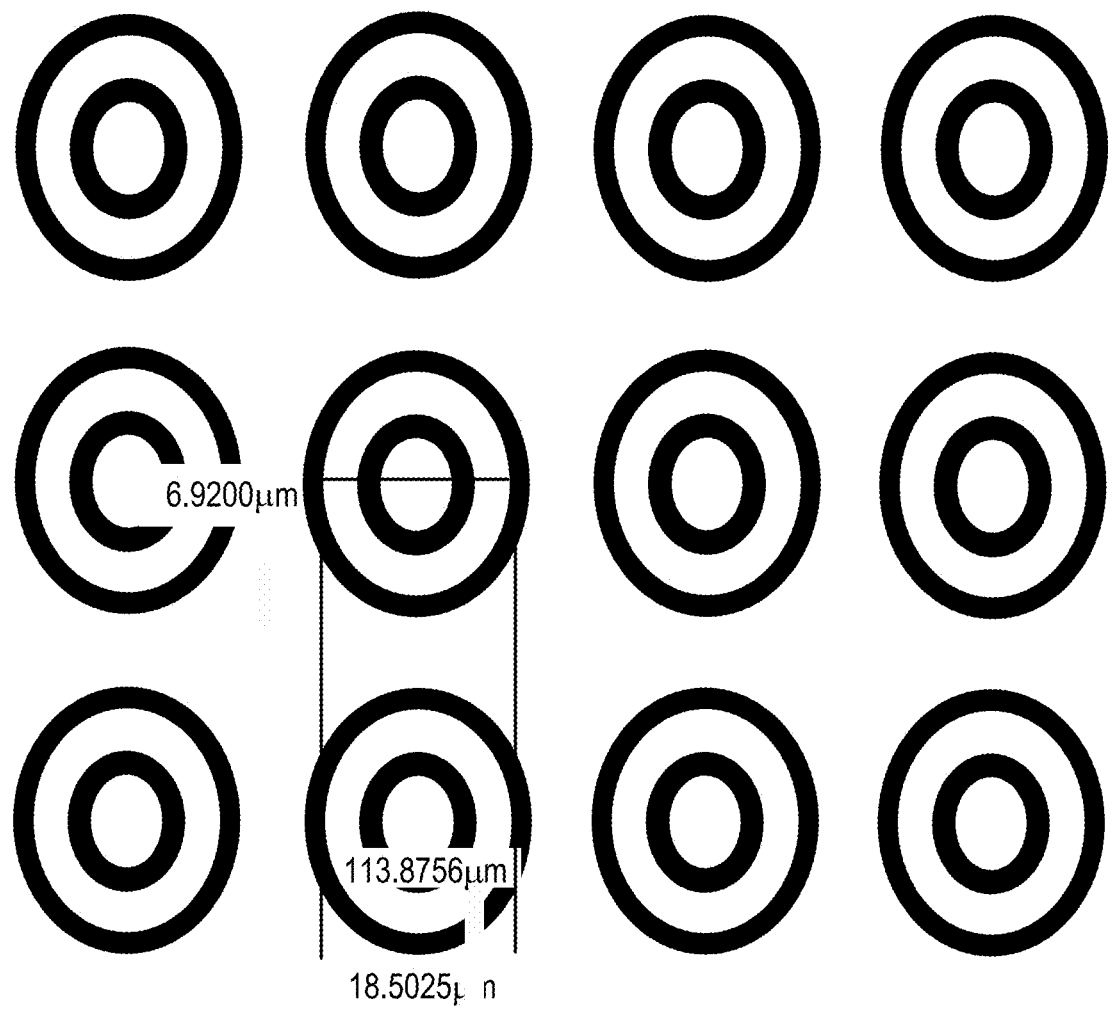
FIG. 7 illustrates an exemplary layout of reactor caps on a capping element.

In some embodiments, the reactor caps described herein may relate to enclosures with an open top on the surface of a capping element substrate. For example, the reactor caps may resemble cylinders sticking out on top of the substrate surface. The inner diameter of the reactor caps can be about, at least about, or less than about 10, 20, 30, 40, 50, 60, 70, 80, 90, 100, 110, 115, 125, 150, 175, 200, 225, 250, 275, 300, 325, 350, 375, 400, 425, 450, 475 or 500 μm. The outer diameter of the reactor caps can be about, at least about, or less than about 10, 20, 30, 40, 50, 60, 70, 80, 90, 100, 110, 115, 125, 150, 175, 200, 225, 250, 275, 300, 325, 350, 375, 400, 425, 450, 475, 500, or 600 μm. The rim of the cylinder can have a width of about, at least about, or less than about 0.1, 0.5, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 40, 50, 60, 70, 80, 90, 100, 200, 300, or 400 μm. The height of the reactor cap measured inside can be about, at least about, or less than about 0.1, 0.5, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 50, 60, 70, 80, 90 or 100 μm. FIG. 7 illustrates an exemplary embodiment of reactor caps on a capping element.

All or part of the reactor cap surfaces, such as the rim surface, may be modified using suitable surface modification methods described in further detail elsewhere herein and otherwise known in the art. In some cases, surface irregularities are engineered. Chemical surface modifications and irregularities may serve to adjust the water contact angle of the rim. Similar surface treatments may also be applied on the surface of a substrate that is brought in close proximity to the reactor caps forming a seal, e.g. a reversible seal. A capillary burst valve may be utilized between the two surfaces as described in further detail elsewhere herein. The surface treatments can be useful in precise control of such seals comprising capillary burst valves.

The reactor caps comprised in a substrate may be in any shape or design that is known in the art. The reactor cap may contain a volume of cavity that is capable of enclosing the contents of the reactors. The contents of the reactors may stem from a plurality of resolved loci on an adjacent substrate. The reactor cap can be in circular, elliptical, rectangular or irregular shapes. The reactor cap may have sharp corners. In some cases, the reactor cap may have round corners to minimize retaining any air bubble and to facilitate better mixing of the contents of the reactors. The reactor cap can be fabricated in any shape, organization or design that allows controlled transfer or mixing of the contents of the reactors. The reactor cap can be in similar design as the resolved loci on the substrate as described in the instant application. In some embodiments, the reactor caps can be in a shape that allows liquid to easily flow in without creating air bubbles. In some embodiments, the reactor caps can have a circular shape, with a diameter that can be about, at least about, or less than about 1 micrometers (μm), 2 μm, 3 μm, 4 μm, 5 μm, 6 μm, 7 μm, 8 μm, 9 μm, 10 μm, 11 μm, 12 μm, 13 μm, 14 μm, 15 μm, 16 μm, 17 μm, 18 μm, 19 μm, 20 μm, 25 μm, 30 μm, 35 μm, 40 μm, 45 μm, 50 μm, 55 μm, 60 μm, 65 μm, 70 μm, 75 μm, 80 μm, 85 μm, 90 μm, 95 μm, 100 μm, 110 μm, 120 μm, 130 μm, 140 μm, 150 μm, 160 μm, 170 μm, 180 μm, 190 μm, 200 μm, 250 μm, 300 μm, 350 μm, 400 μm, 450 μm, 500 μm, 550 μm, 600 μm, 650 μm, 700 μm or 750 μm. The reactor caps may have a monodisperse size distribution, i.e. all of the microstructures may have approximately the same width, height, and/or length. Alternatively, the reactor caps of may have a limited number of shapes and/or sizes, for example the reactor caps may be represented in 2, 3, 4, 5, 6, 7, 8, 9, 10, 12, 15, 20, or more distinct shapes, each having a monodisperse size. In some embodiments, the same shape can be repeated in multiple monodisperse size distributions, for example, 2, 3, 4, 5, 6, 7, 8, 9, 10, 12, 15, 20, or more monodisperse size distributions. A monodisperse distribution may be reflected in a unimodular distribution with a standard deviation of less than 25%, 20%, 15%, 10%, 5%, 3%, 2%, 1%, 0.1%, 0.05%, 0.01%, 0.001% of the mode or smaller.

Each of the reactor caps can have any suitable area for carrying out the reactions according to various embodiments of the invention described herein. In some cases, the plurality of reactor caps can occupy any suitable percentage of the total surface area of the substrate. In some embodiments, the plurality of the reactor caps can occupy about, at least about, or less than about 1%, 2%, 3%, 4%, 5%, 6%, 7%, 8%, 9%, 10%, 11%, 12%, 13%, 14%, 15%, 16%, 17%, 18%, 19%, 20%, 25%, 30%, 35%, 40%, 45%, 50%, 55%, 60%, 65%, 70%, 75%, 80%, 85%, 90%, or 95% of the surface of the substrate. In some embodiments, the reactor caps can occupy about, at least about, or less than about 0.1 mm$^2$, 0.15 mm$^2$, 0.2 mm$^2$, 0.25 mm$^2$, 0.3 mm$^2$, 0.35 mm$^2$, 0.4 mm$^2$, 0.45 mm$^2$, 0.5 mm$^2$, 0.55 mm$^2$, 0.6 mm$^2$, 0.65 mm$^2$, 0.7 mm$^2$, 0.75 mm$^2$, 0.8 mm$^2$, 0.85 mm$^2$, 0.9 mm$^2$, 0.95 mm$^2$, 1 mm$^2$, 2 mm$^2$, 3 mm$^2$, 4 mm$^2$, 5 mm$^2$, 6 mm$^2$, 7 mm$^2$, 8 mm$^2$, 9 mm$^2$, 10 mm$^2$, 11 mm$^2$, 12 mm$^2$, 13 mm$^2$, 14 mm$^2$, 15 mm$^2$, 16 mm$^2$, 17 mm$^2$, 18 mm$^2$, 19 mm$^2$, 20 mm$^2$, 25 mm$^2$, 30 mm$^2$, 35 mm$^2$, 40 mm$^2$, 50 mm$^2$, 75 mm$^2$, 100 mm$^2$, 200 mm$^2$, 300 mm$^2$, 400 mm$^2$, 500 mm$^2$, 600 mm$^2$, 700 mm$^2$, 800 mm$^2$, 900 mm$^2$, 1000 mm$^2$, 1500 mm$^2$, 2000 mm$^2$, 3000 mm$^2$, 4000 mm$^2$, 5000 mm$^2$, 7500 mm$^2$, 10000 mm$^2$, 15000 mm$^2$ 20000 mm$^2$, 25000 mm$^2$, 30000 mm$^2$, 35000 mm$^2$, 40000 mm$^2$, 50000 mm$^2$, 60000 mm$^2$, 70000 mm$^2$, 80000 mm$^2$, 90000 mm$^2$, 100000 mm$^2$, 200000 mm$^2$, 300000 mm$^2$ of total area, or more. The resolved reactors, the resolved loci and the reactor caps can be in any density. In some embodiments, the surface can have a density of resolved reactors, resolved loci or reactor caps of about 1, about 2, about 3, about 4, about 5, about 6, about 7, about 8, about 9, about 10, about 15, about 20, about 25, about 30, about 35, about 40, about 50, about 75, about 100, about 200, about 300, about 400, about 500, about 600, about 700, about 800, about 900, about 1000, about 1500, about 2000, about 3000, about 4000, about 5000, about 6000, about 7000, about 8000, about 9000, about 10000, about 20000, about 40000, about 60000, about 80000, about 100000, or about 500000 sites per 1 mm$^2$. In some embodiments, the surface has a density of resolved reactors, resolved loci or reactor caps of at least about 50, at least 75, at least about 100, at least about 200, at least about 300, at least about 400, at least about 500, at least about 600, at least about 700, at least about 800, at least about 900, at least about 1000, at least about 1500, at least about 2000, at least about 3000, at least about 4000, at least about 5000, at least about 6000, at least about 7000, at least about 8000, at least about 9000, at least about 10000, at least about 20000, at least about 40000, at least about 60000, at least about 80000, at least about 100000, or at least about 500000 sites per 1 mm$^2$.

Taken in account the density of the resolved loci on an adjacent substrate surface, the density, distribution, and shape of the reactor caps can be designed accordingly to be configured to align with a preferred number of resolved loci in each reactor. Each of the plurality of resolved reactors can comprise a number of resolved loci. For example, without limitation, each reactor can comprise about, at least about, less than about 2, 3, 4, 5, 6, 7, 8, 9, 10, 20, 30, 40, 50, 60, 70, 80, 90, 100, 110, 120, 130, 140, 150, 160, 170, 180, 190, 200, 225, 250, 275, 300, 350, 400, 450, 500, 550, 600, 650, 700, 750, 800, 850, 900, 950, or 1000 resolved loci. In some cases, each reactor can comprise at least 100 resolved loci.

Comprised within the array of the plurality of enclosures, the resolved loci or reactor caps can reside on microstructures that are fabricated into a support surface. The microstructures can be fabricated by any known methods in the art, as described in other paragraphs herein. The microstructures can be microchannels or microwells that have any shape and design in 2D or 3D. The microstructures (e.g., microchannels or microwells) may comprise at least two channels in fluidic communication with each other. For example, the microchannels can be interconnected, allowing fluid to perfuse through with given condition, such as vacuum suction. Individual microstructures may be individually addressable and resolved, such that the contents of two resolved loci are kept unmixed. The microchannels can comprise at least 2, 3, 4, 5, 6, 7, 8, 9 or 10 channels in fluidic communications in any combinations, allowing controlled mixing, communicating or distributing of the fluid. The connectivity of microchannels can be controlled by valve systems that are known in the art of microfluidic design. For example, a fluid control layer of substrate can be fabricated directly on top of the fluidic communicating layer of the substrate. Different microfluidic valves systems are described in Marc A. Unger et al, "Monolithic Microfabricated Valves and Pumps by Multilayer Soft Lithography," Science, vol. 288, no. 7, pp. 113-116, April 2000, and David C. Duffy et al., "Rapid Prototyping of Microfluidic Systems in Poly(dimethylsiloxane)," Analytical Chemistry, vol. 70, no. 23, pp. 4974-4984, December 1998.

Comprised within the array of the plurality of enclosures, the resolved loci or reactor caps can reside on microstructures such as microchannels or channels. The dimensions and designs of the microchannels of the resolved loci on the adjacent substrate surface are described elsewhere herein. The microstructures may comprise at least two channels that are in fluidic communications, wherein the at least two channels can comprise at least two channels with different width. In some cases, the at least two channels can have the same width, or a combination of the same or different width. For example, without limitation, the width of the channels or microchannels can be about, at least about, or less than about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, 55, 60, 65, 70, 75, 80, 85, 90, 95 or 100 µm. The channels or microchannels can have any length that allows fluidic communications of the resolved loci. At least one channel can comprise a ratio of surface area to length, or a perimeter, of about, at least about, less than about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, 55, 60, 65, 70, 75, 80, 85, 90, 95 or 100 µm. At least one channel can have a cross-sectional area that is in a circular shape and can comprise a radius of the cross-sectional area of about, at least about, less than about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, 55, 60, 65, 70, 75, 80, 85, 90, 95 or 100 µm.

As described herein, an array of enclosures can comprise a plurality of resolved reactors comprising a first substrate and a second substrate comprising reactor caps. The resolved reactors can be formed by combining or capping the second substrate onto the first substrate, and sealed together. The seal can be reversible or irreversible. In preferred embodiments, the seal is reversible or releasable. Upon sealing the resolved reactors, the content of reactors such as oligonucleotides or reagents needed for amplification or other downstream reactions can be released and mixed within the resolved reactors. The resolved reactors can be separated with a releasable seal and wherein the reactors caps can retain all or a portion of the contents of the reactors upon release of the second substrate from the first substrate. Depending on the materials of the first substrate and the second substrate, the seal can be designed differently to allow reversible seal in between the first substrate and the second substrate, and forming the resolved reactors. The first substrate and the second substrate can come in direct physical contact when forming the seal. In some cases, the first substrate and the second substrate can come in close proximity without their respective surfaces immediately around a nanoreactor or between two nanoreactors making a direct physical contact. The seal can comprise a capillary burst valve. The distance in between the first substrate and the second substrate when forming the seal can be about, at least about, less than about 0.1 µm, 0.2 µm, 0.3 µm, 0.4 µm, 0.5 µm, 0.6 µm, 0.7 µm, 0.8 µm, 0.9 µm, 1 µm, 1.1 µm, 1.2 µm, 1.3 µm, 1.4 µm, 1.5 µm, 1.6 µm, 1.7 µm, 1.8 µm, 1.9 µm, 2 µm, 2.5 µm, 3 µm, 3.5 µm, 4 µm, 4.5 µm, 5 µm, 5.5 µm, 6 µm, 6.5 µm, 7 µm, 7.5 µm, 8 µm, 8.5 µm, 9 µm, 9.5 µm or 10 µm. The seal can comprise a capillary burst valve.

In some cases, the resolved enclosures may comprise pressure release holes. The pressure release holes may allow separation of the first substrate and the second substrate. Design of microfluidic systems with pressure release system are described in European Patent No. EP 1987275 A1, which is herein incorporated by reference in its entirety.

The plurality of resolved reactor caps on a substrate can be manufactured by any method that is described herein or otherwise known in the art (e.g., microfabrication processes). Microfabrication processes that may be used in making the substrate with the plurality of reactor caps or reactors disclosed herein include without limitation lithography; etching techniques such as wet chemical, dry, and photoresist removal; microelectromechanical (MEMS) techniques including microfluidics/lab-on-a-chip, optical MEMS (also called MOEMS), RF MEMS, PowerMEMS, and BioMEMS techniques and deep reactive ion etching (DRIE); nanoelectromechanical (NEMS) techniques; thermal oxidation of silicon; electroplating and electroless plating; diffusion processes such as boron, phosphorus, arsenic, and antimony diffusion; ion implantation; film deposition such as evaporation (filament, electron beam, flash, and shadowing and step coverage), sputtering, chemical vapor deposition (CVD), epitaxy (vapor phase, liquid phase, and molecular beam), electroplating, screen printing, and lamination. See generally Jaeger, Introduction to Microelectronic Fabrication (Addison-Wesley Publishing Co., Reading Mass. 1988); Runyan, et al., Semiconductor Integrated Circuit Processing Technology (Addison-Wesley Publishing Co., Reading Mass. 1990); Proceedings of the IEEE Micro Electro Mechanical Systems Conference 1987-1998; Rai-Choudhury, ed., Handbook of Microlithography, Micromachining & Microfabrication (SPIE Optical Engineering Press, Bellingham, Wash. 1997).

In an aspect, a substrate having a plurality of resolved reactor caps can be manufactured using any method known in the art. In some embodiments, the material of the substrate having a plurality of reactor caps can be a semiconductor substrate such as silicon dioxide. The materials of the substrate can also be other compound III-V or II-VI materials, such as (GaAs), a semiconductor produced via the Czochralski process (Grovenor, C. (1989). *Microelectronic Materials*. CRC Press. pp. 113-123). The material can present a hard, planar surface that exhibits a uniform covering of reactive oxide (—OH) groups to a solution in contact with its surface. These oxide groups can be the attachment points for subsequent silanization processes. Alternatively, a lipophillic and hydrophobic surface material can be deposited that mimics the etching characteristics of silicon oxide. Silicon nitride and silicon carbide surfaces may also be utilized for the manufacturing of suitable substrates according to the various embodiments of the invention.

In some embodiments, a passivation layer can be deposited on the substrate, which may or may not have reactive oxide groups. The passivation layer can comprise silicon nitride ($Si_3N_4$) or polyimide. In some instances, a photolithographic step can be used to define regions where the resolved loci form on the passivation layer.

The method for producing a substrate having a plurality of reactor caps can start with a substrate. The substrate (e.g., silicon) can have any number of layers disposed upon it, including but not limited to a conducting layer such as a metal. The conducting layer can be aluminum in some instances. In some cases, the substrate can have a protective layer (e.g., titanium nitride). In some cases, the substrate can have a chemical layer with a high surface energy. The layers can be deposited with the aid of various deposition techniques, such as, for example, chemical vapor deposition (CVD), atomic layer deposition (ALD), plasma enhanced CVD (PECVD), plasma enhanced ALD (PEALD), metal organic CVD (MOCVD), hot wire CVD (HWCVD), initiated CVD (iCVD), modified CVD (MCVD), vapor axial deposition (VAD), outside vapor deposition (OVD) and physical vapor deposition (e.g., sputter deposition, evaporative deposition).

In some cases, an oxide layer is deposited on the substrate. In some instances, the oxide layer can comprise silicon dioxide. The silicon dioxide can be deposited using tetraethyl orthosilicate (TEOS), high density plasma (HDP), or any combination thereof.

In some instances, the silicon dioxide can be deposited using a low temperature technique. In some cases, the process is low-temperature chemical vapor deposition of silicon oxide. The temperature is generally sufficiently low such that pre-existing metal on the chip is not damaged. The deposition temperature can be about 50° C., about 100° C., about 150° C., about 200° C., about 250° C., about 300° C., about 350° C., and the like. In some embodiments, the deposition temperature is below about 50° C., below about 100° C., below about 150° C., below about 200° C., below about 250° C., below about 300° C., below about 350° C., and the like. The deposition can be performed at any suitable pressure. In some instances, the deposition process uses RF plasma energy.

In some cases, the oxide is deposited by a dry thermally grown oxide procedure (e.g., those that may use temperatures near or exceeding 1,000° C.). In some cases, the silicon oxide is produced by a wet steam process.

The silicon dioxide can be deposited to a thickness suitable for the formation of reactor caps that can form a plurality of resolved reactors comprising a volume for reagents to be deposited and mixed that can be suitable for amplifying any desired amount of oligonucleotide or other downstream reactions as described in other paragraphs of the current invention.

The silicon dioxide can be deposited to any suitable thickness. In some embodiments, the silicon dioxide is about, at least about or less than about 1 nanometer (nm), about 2 nm, about 3 nm, about 4 nm, about 5 nm, about 6 nm, about 7 nm, about 8 nm, about 9 nm, about 10 nm, about 15 nm, about 20 nm, about 25 nm, about 30 nm, about 35 nm, about 40 nm, about 45 nm, about 50 nm, about 55 nm, about 60 nm, about 65 nm, about 70 nm, about 75 nm, about 80 nm, about 85 nm, about 90 nm, about 95 nm, about 100 nm, about 125 nm, about 150 nm, about 175 nm, about 200 nm, about 300 nm, about 400 nm or about 500 nm thick.

The reactor caps can be created in a silicon dioxide substrate using various manufacturing techniques that are known in the art. Such techniques may include semiconductor fabrication techniques. In some cases, the reactor caps are created using photolithographic techniques such as those used in the semiconductor industry. For example, a photo-resist (e.g., a material that changes properties when exposed to electromagnetic radiation) can be coated onto the silicon dioxide (e.g., by spin coating of a wafer) to any suitable thickness. The substrate including the photo-resist can be exposed to an electromagnetic radiation source. A mask can be used to shield radiation from portions of the photo-resist in order to define the area of the resolved loci. The photo-resist can be a negative resist or a positive resist (e.g., the area of the reactor caps can be exposed to electromagnetic radiation or the areas other than the reactor caps can be exposed to electromagnetic radiation as defined by the mask). The area overlying the location in which the reactor caps are to be created is exposed to electromagnetic radiation to define a pattern that corresponds to the location and distribution of the reactor caps in the silicon dioxide layer. The photoresist can be exposed to electromagnetic radiation through a mask defining a pattern that corresponds to the reactor caps. Next, the exposed portion of the photo-resist can be removed, such as, e.g., with the aid of a washing operation (e.g., deionized water). The removed portion of the mask can then be exposed to a chemical etchant to etch the substrate and transfer the pattern of reactor caps into the silicon dioxide layer. The etchant can include an acid, such as, for example, sulfuric acid ($H_2SO_4$). The silicon dioxide layer can be etched in an anisotropic fashion. Using the methods described herein, high anisotropy manufacturing methods, such as DRIE can be applied to fabricate microstructures, such as reactor caps, on or within a substrate with side walls that deviate less than about ±3°, 2°, 1°, 0.5°, 0.1°, or less from the vertical with respect to the surface of the substrate. Undercut values of less than about 10, 9, 8, 7, 6, 5, 4, 3, 2, 1, 0.5, 0.1 μm or less can be achieved resulting in highly uniform microstructures.

Various etching procedures can be used to etch the silicon dioxide in the area where the reactor caps are to be formed. The etch can be an isotropic etch (i.e., the etch rate alone one direction is equal to the etch rate along an orthogonal direction), or an anisotropic etch (i.e., the etch rate along one direction is less than the etch rate alone an orthogonal direction), or variants thereof. The etching techniques can be both wet silicon etches such as KOH, TMAH, EDP and the like, and dry plasma etches (for example DRIE). Both may be used to etch micro structures wafer through interconnections.

In some cases, an anisotropic etch removes the majority of the volume of the reactor caps. Any suitable percentage of the volume of the reactor caps can be removed including about 60%, about 70%, about 80%, about 90%, or about 95%. In some cases, at least about 60%, at least about 70%, at least about 80%, at least about 90%, or at least about 95% of the material is removed in an anisotropic etch. In some cases, at most about 60%, at most about 70%, at most about 80%, at most about 90%, or at most about 95% of the material is removed in an anisotropic etch. In some embodiments, the anisotropic etch does not remove silicon dioxide material all of the way through the substrate. An isotropic etch removes the silicon dioxide material all of the way through the substrate creating a hole in some instances.

In some cases, the reactor caps are etched using a photo-lithographic step to define the reactor caps followed by a hybrid dry-wet etch. The photo-lithographic step can comprise coating the silicon dioxide with a photo-resist and exposing the photo-resist to electromagnetic radiation through a mask (or reticle) having a pattern that defines the reactor caps. In some instances, the hybrid dry-wet etch comprises: (a) dry etching to remove the bulk of the silicon dioxide in the regions of the reactor caps defined in the photoresist by the photo-lithographic step; (b) cleaning the substrate; and (c) wet etching to remove the remaining silicon dioxide from the substrate in the regions of the reactor caps.

The substrate can be cleaned with the aid of a plasma etching chemistry, or exposure to an oxidizing agent, such as, for example, $H_2O_2$, $O_2$, $O_3$, $H_2SO_4$, or a combination thereof, such as a combination of $H_2O_2$ and $H_2SO_4$. The cleaning can comprise removing residual polymer, removing material that can block the wet etch, or a combination thereof. In some instances, the cleaning is plasma cleaning. The cleaning step can proceed for any suitable period of time (e.g., 15 to 20 seconds). In an example, the cleaning can be performed for 20 seconds with an Applied Materials eMAx-CT machine with settings of 100 mT, 200 W, 20 G, 20 $O_2$.

The dry etch can be an anisotropic etch that etches substantially vertically (e.g., toward the substrate) but not laterally or substantially laterally (e.g., parallel to the substrate). In some instances, the dry etch comprises etching with a fluorine based etchant such as $CF_4$, $CHF_3$, $C_2F_6$, $C_3F_6$, or any combination thereof. In one instance, the etching is performed for 400 seconds with an Applied Materials eMax-CT machine having settings of 100 mT, 1000 W, 20 G, and 50 CF4. The substrates described herein can be etched by deep reactive-ion etching (DRIE). DRIE is a highly anisotropic etching process used to create deep penetration, steep-sided holes and trenches in wafers/substrates, typically with high aspect ratios. The substrates can be etched using two main technologies for high-rate DRIE: cryogenic and Bosch. Methods of applying DRIE are described in the U.S. Pat. No. 5,501,893, which is herein incorporated by reference in its entirety.

The wet etch can be an isotropic etch that removes material in all directions. In some instances, the wet etch undercuts the photo-resist. Undercutting the photo-resist can make the photo-resist easier to remove in a later step (e.g., photo-resist "lift off"). In an embodiment, the wet etch is buffered oxide etch (BOE). In some cases, the wet oxide etches are performed at room temperature with a hydrofluoric acid base that can be buffered (e.g., with ammonium fluoride) to slow down the etch rate. Etch rate can be dependent on the film being etched and specific concentrations of HF and/or $NH_4F$. The etch time needed to completely remove an oxide layer is typically determined empirically. In one example, the etch is performed at 22° C. with 15:1 BOE (buffered oxide etch).

The silicon dioxide layer can be etched up to an underlying material layer. For example, the silicon dioxide layer can be etched until a titanium nitride layer.

In an aspect, a method for preparing a substrate having a plurality of reactor caps comprises etching the cavity of the reactor caps into a substrate, such as a silicon substrate comprising a silicon dioxide layer coated thereon using (a) a photo-lithographic step to define the resolved loci; (b) a dry etch to remove the bulk of the silicon dioxide in the regions of the reactor caps defined by the photo-lithographic step; and (c) a wet etch to remove the remaining silicon dioxide from the substrate in the regions of the reactor caps. In some cases, the method further comprises removing residual polymer, removing material that can block the wet etch, or a combination thereof. The method can include a plasma cleaning step.

In some embodiments, the photo-resist is not removed from the silicon dioxide following the photo-lithographic step or the hybrid wet-dry etch in some cases. Leaving the photo-resist can be used to direct metal selectively into the reactor caps and not onto the upper surface of the silicon dioxide layer in later steps. In some cases, the substrate is coated with a metal (e.g., aluminum) and the wet etch does not remove certain components on the metal, e.g. those that protect the metal from corrosion (e.g., titanium nitride (TiN)). In some cases, however, the photoresist layer can be removed, such as with the aid of chemical mechanical planarization (CMP).

Figure 25A:
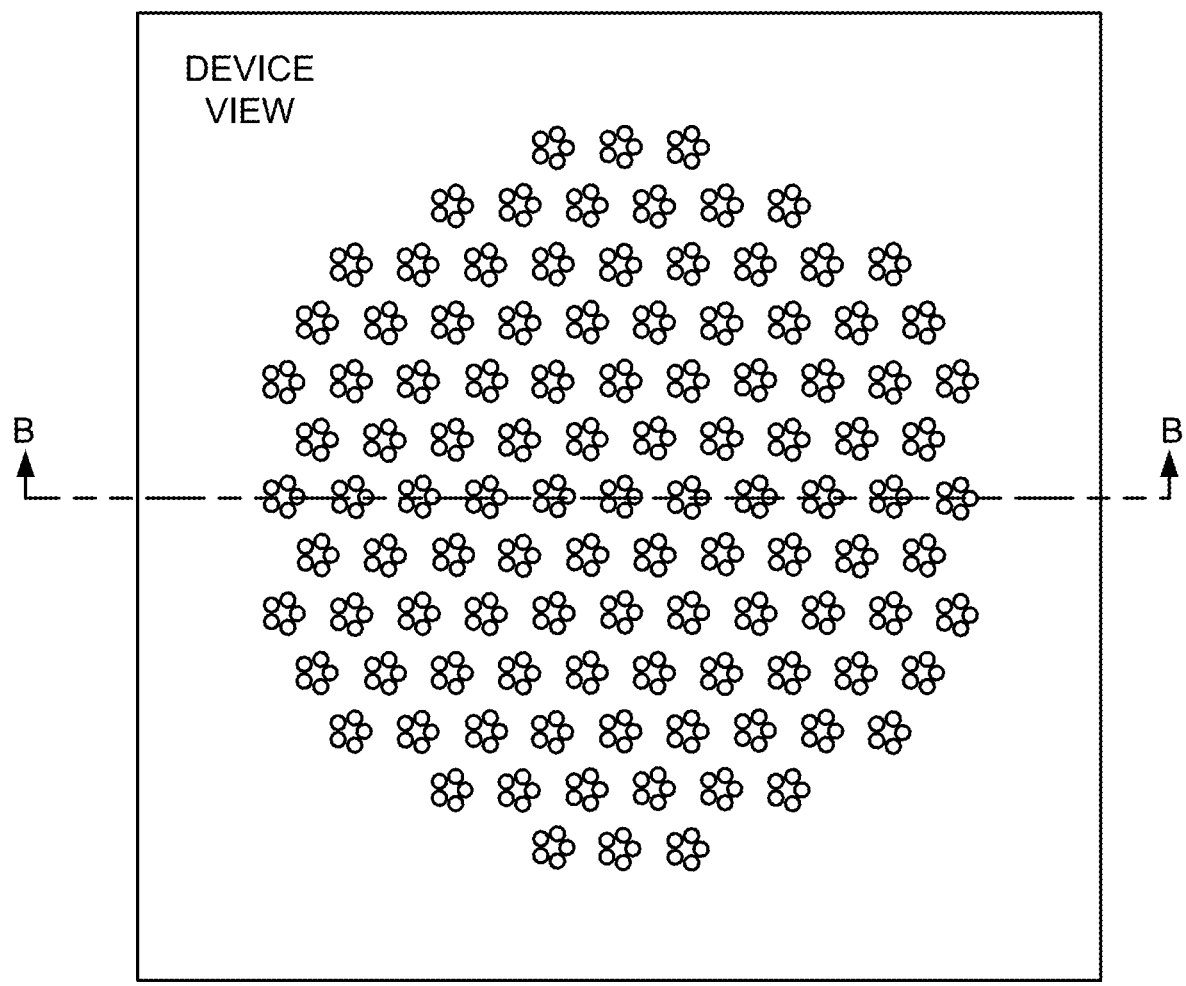
FIGS. 25A-25C depict different views of a cluster comprising a high density of groupings.
Figure 25B:
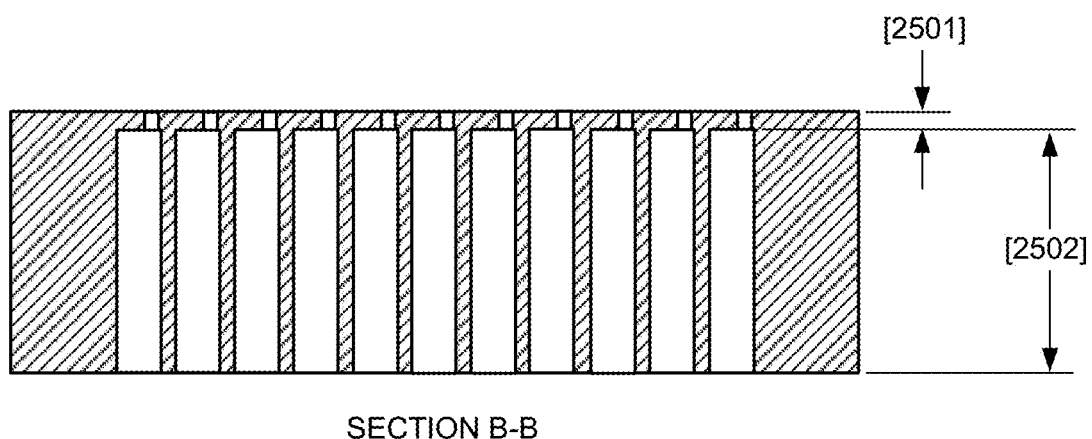
Figure 25C:
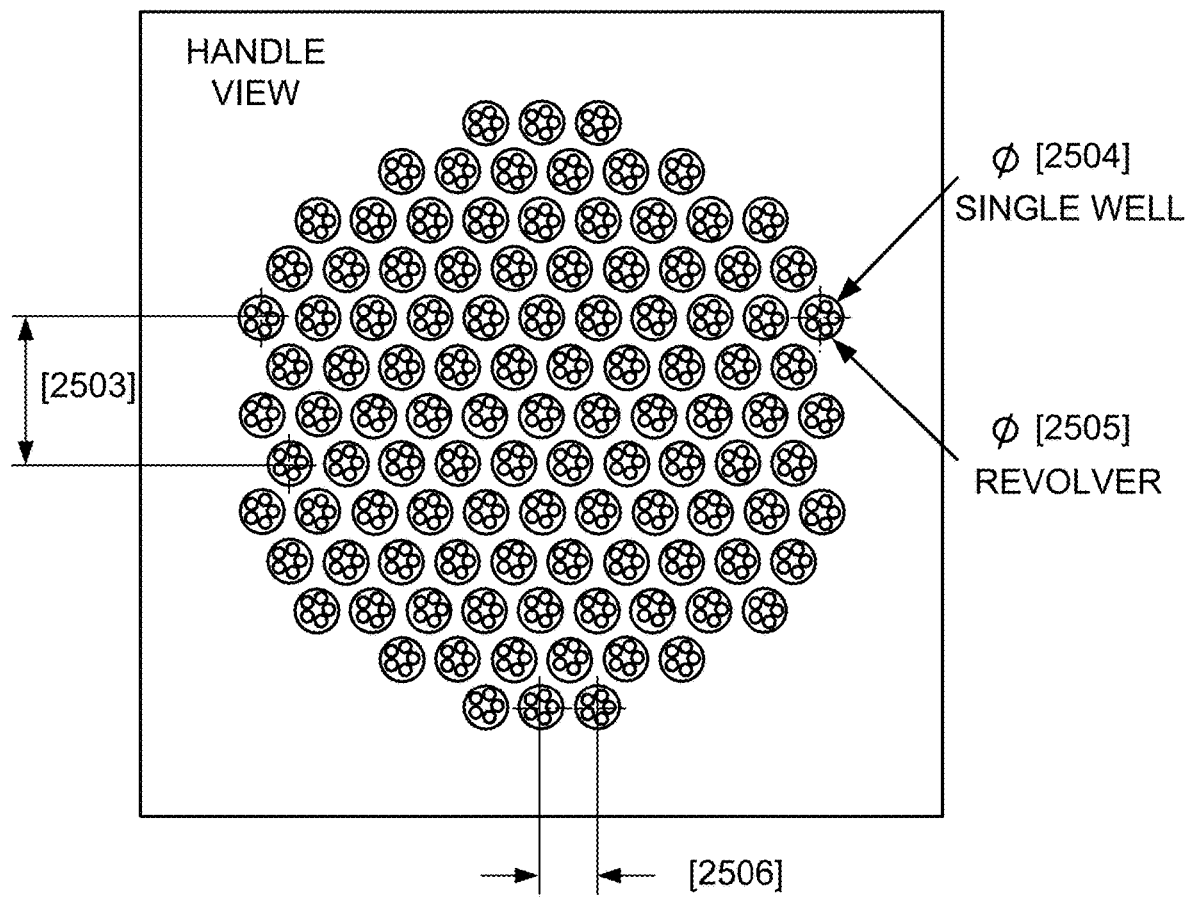
Figure 25D:
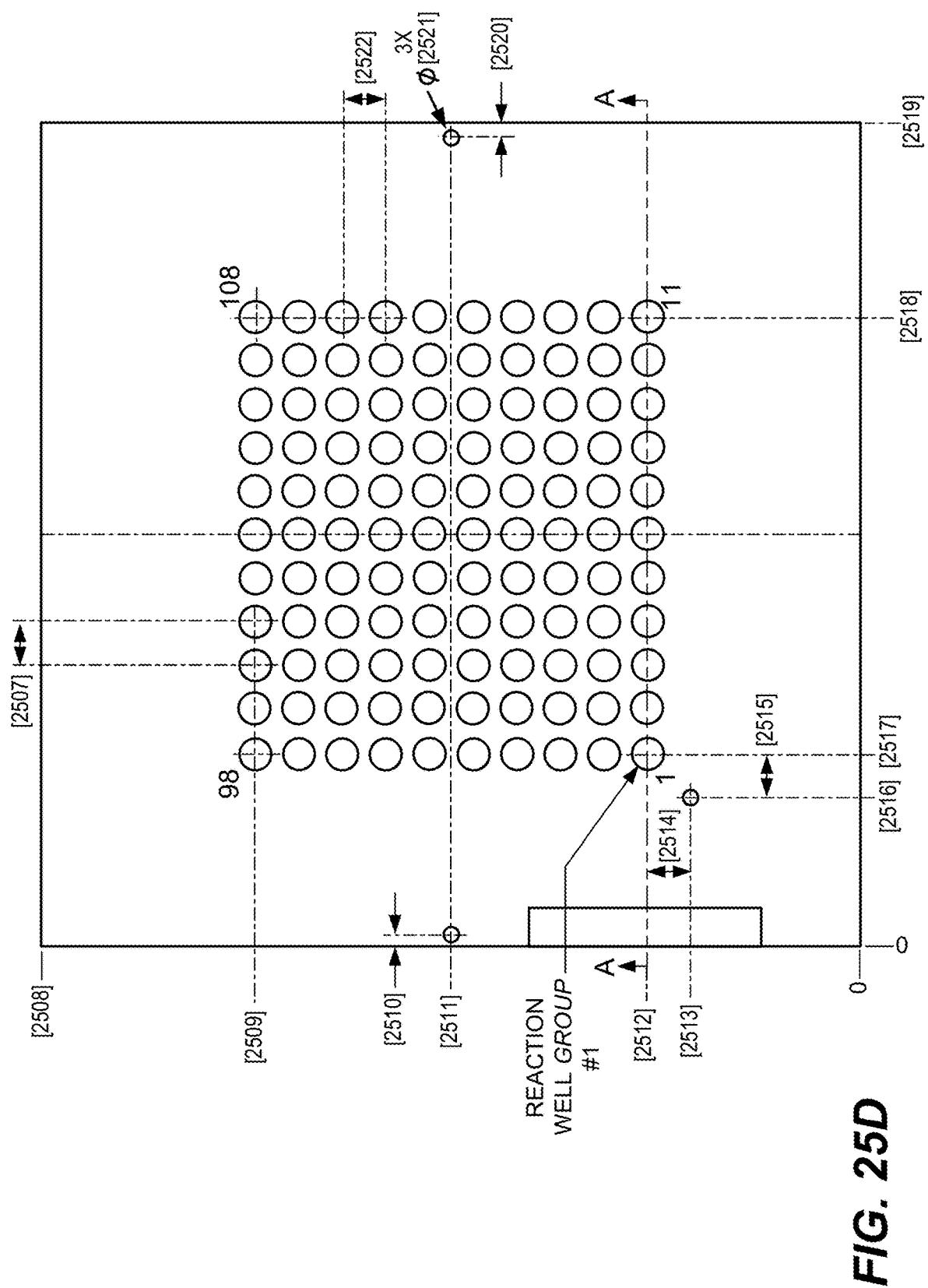
FIGS. 25D-25E depict different views of a diagram of a microfluidic device comprising a substantially planar substrate portion.
Figure 25E:
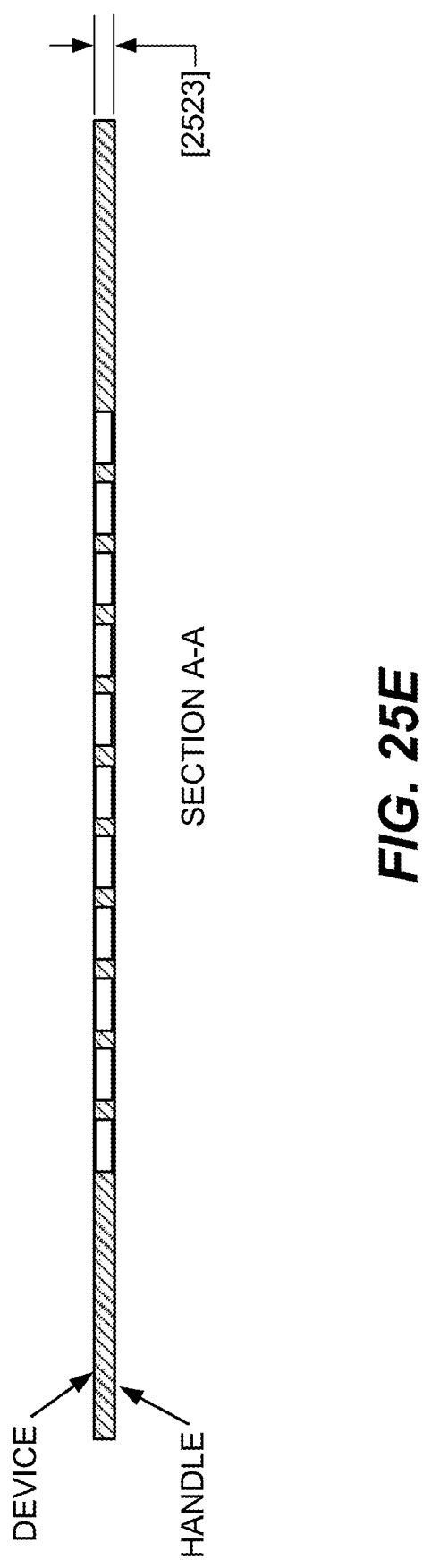
Figure 25F:
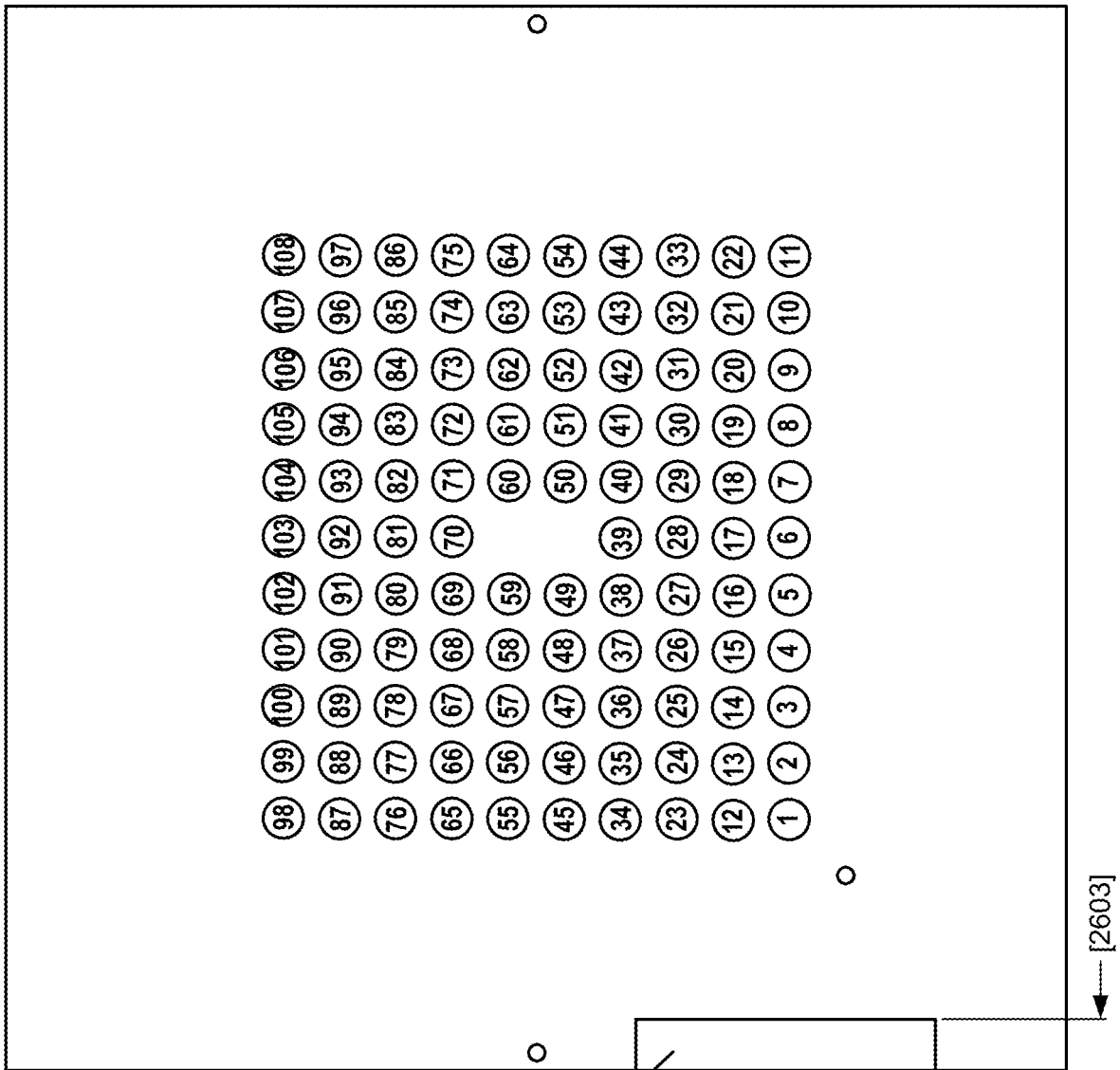
FIG. 25F depicts the device view of a diagram of a microfluidic device comprising a substantially planar substrate portion having 108 reaction wells and a designated area for a label.
Figure 25G:
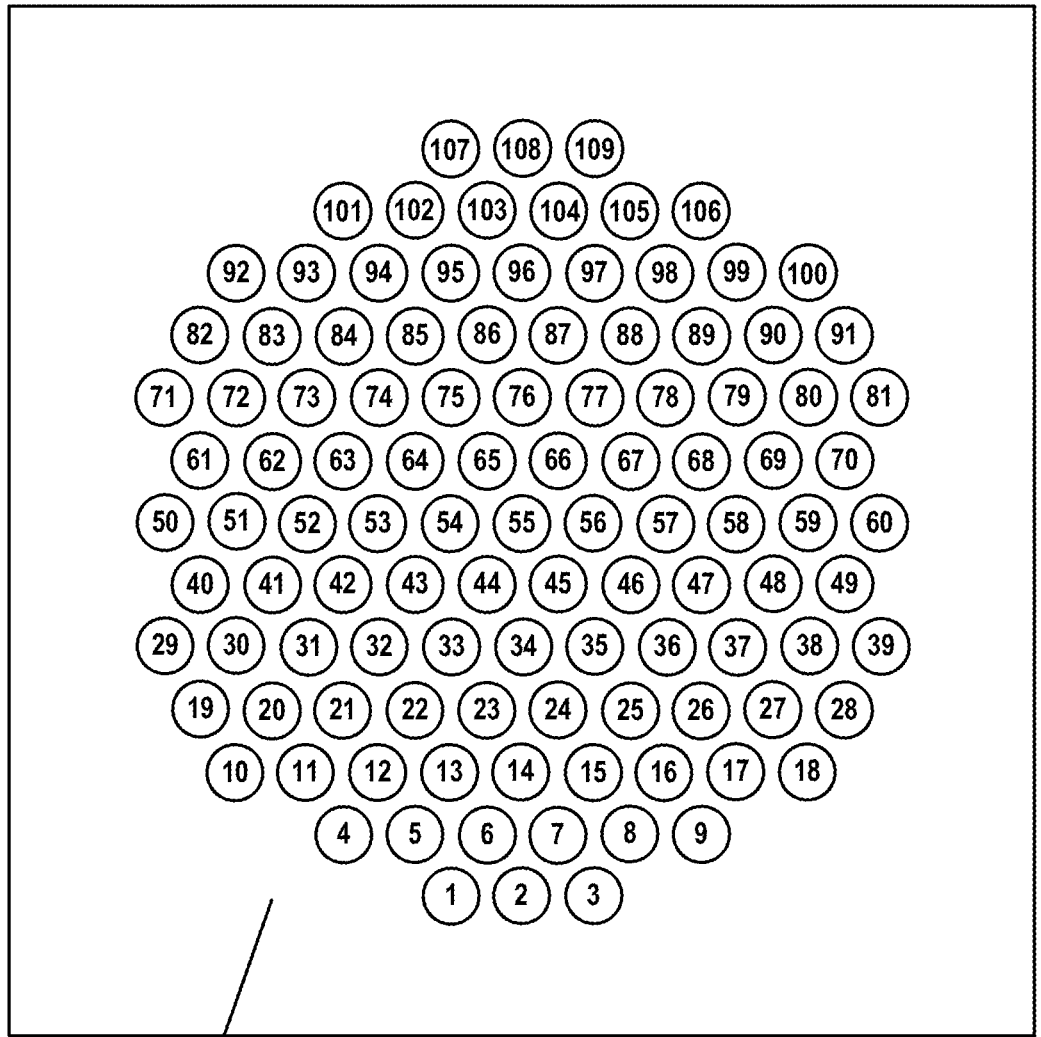
FIG. 25G depicts the device view of a cluster comprising 109 groupings.
Figure 26A:
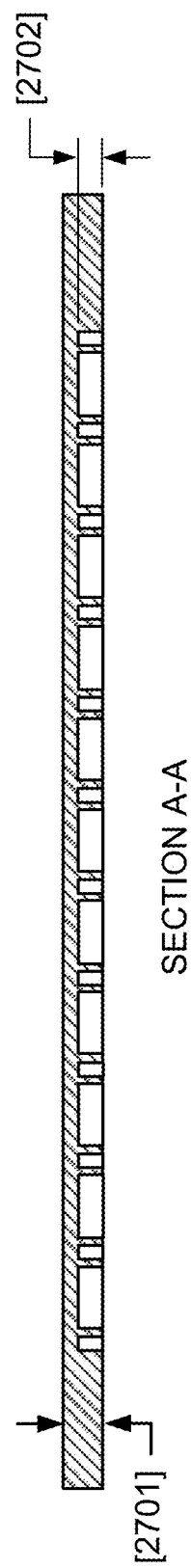
FIG. 26A depicts a cross-section view of a diagram of a nanoreactor, where the view shows a row of the nanoreactor comprising 11 wells.
Figure 26B:
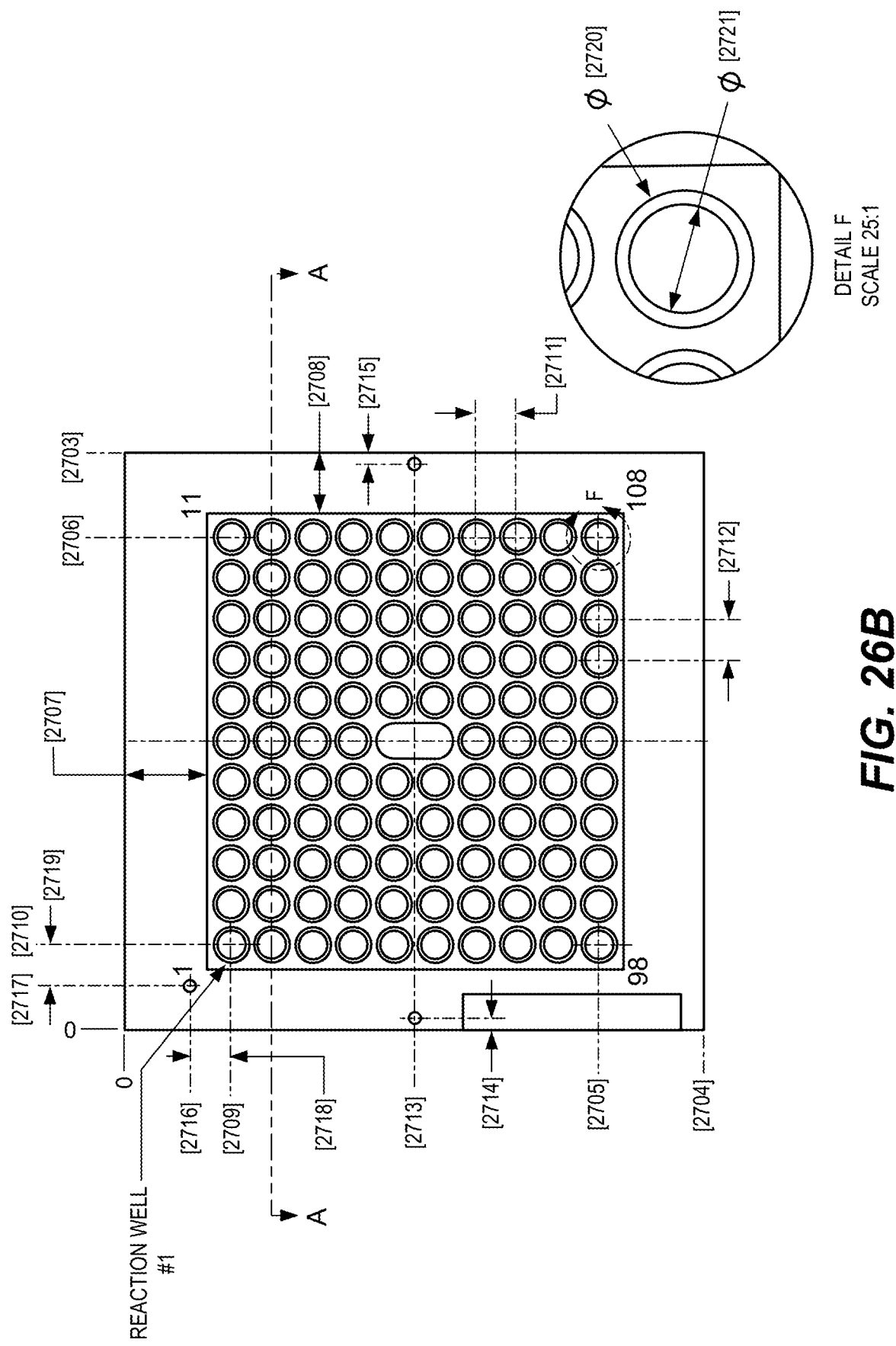
FIG. 26B depicts a device view of a diagram of a nanoreactor comprising 108 raised wells. The detail F depicts a detailed view of one well of the nanoreactor.
Figure 26C:
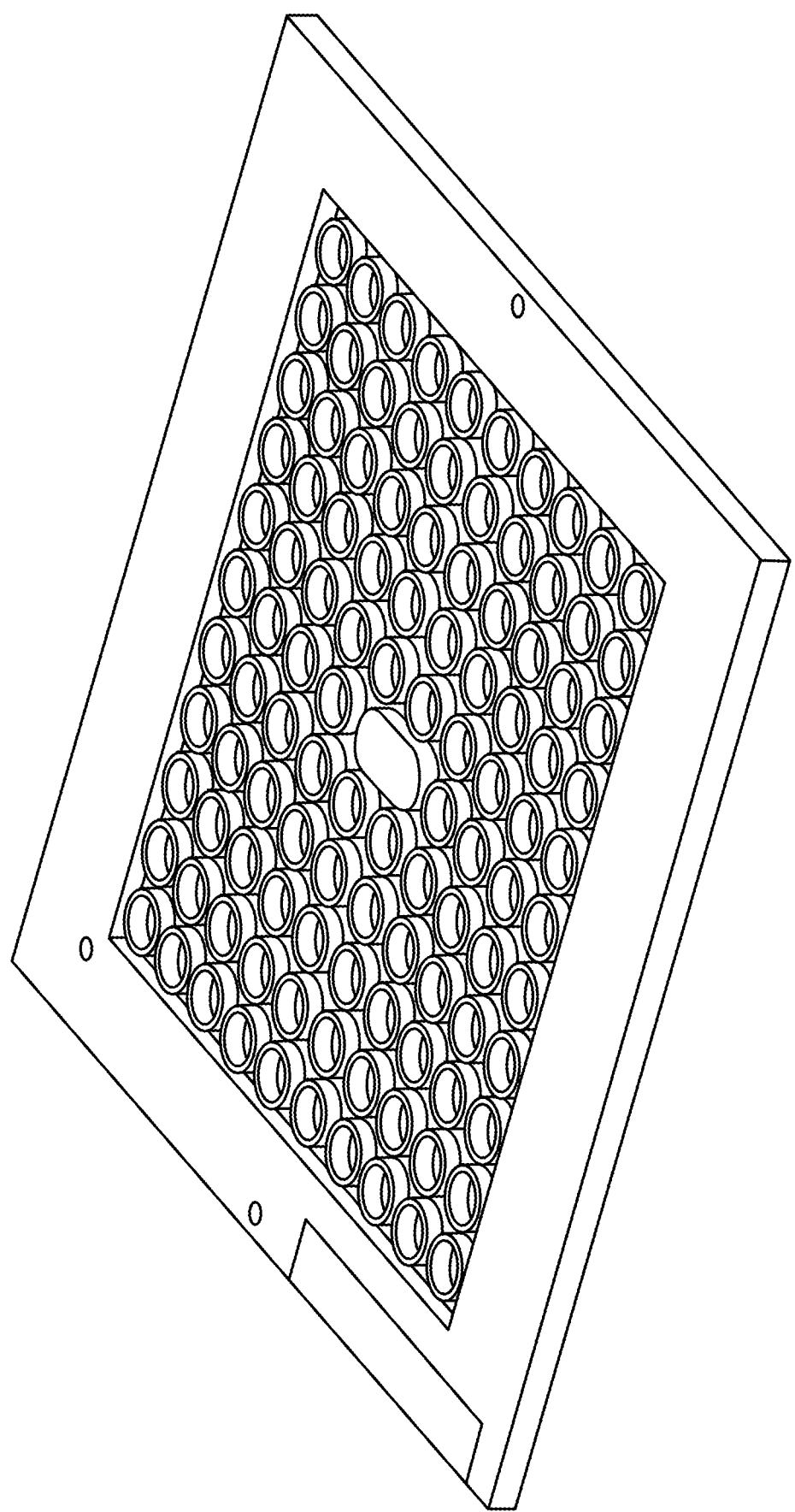
FIG. 26C depicts an angled device view of the nanoreactor diagram shown in FIG. 26B.
Figure 26D:
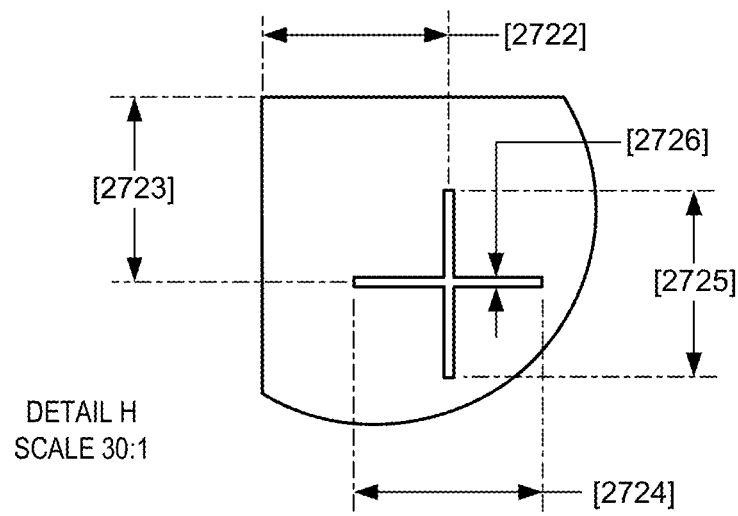
FIG. 26D depicts a handle view of a diagram of a nanoreactor. The detail H depicts a detailed view of a fiducial marking on the handle side of the nanoreactor.
Figure 26D:
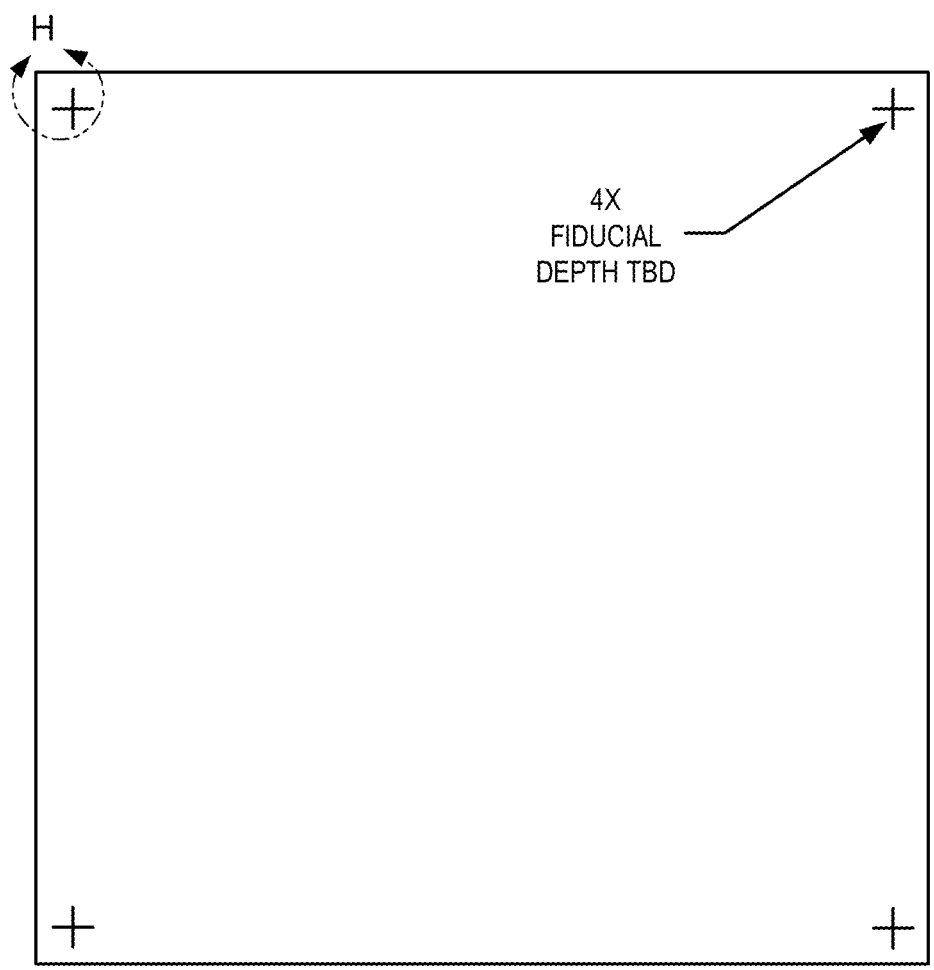

An exemplary nanoreactor is shown in various views in FIGS. 26A-D. This nanoreactor comprises 108 wells which are individually raised from a base of the nanoreactor. A cross-section of the nanoreactor is shown in FIG. 26A. A device view of the nanoreactor is shown in FIGS. 26B and 26C. A handle view of the nanoreactor is shown in FIG. 26D. A nanoreactor can be configured to receive and hold liquids in a plurality of features. The nanoreactor of FIGS. 26A-D is designed to hold liquids in any number of the 108 wells. A nanoreactor may be contacted and/or aligned with a substrate, such as that exemplified in FIG. 25. The wells of a nanoreactor are not limited to the configuration shown in FIG. 26A-D, as any number of wells in any configuration may be arranged within a nanoreactor. In some embodiments, the nanoreactor wells are arranged in a configuration which aligns with a substrate configuration. As represented by 2701, the height of a nanoreactor may be about or at least about 0.1 mm, 0.2 mm, 0.3 mm, 0.4 mm, 0.5 mm, 0.6 mm, 0.7 mm, 0.8 mm, 0.9 mm, 1 mm, 1.5 mm, 2 mm, 2.5 mm, 3 mm, 3.5 mm, 4 mm, 4.5 mm, 5 mm, 5.5 mm, 6 mm, 6.5 mm, 7 mm, 7.5 mm, 8 mm, 8.5 mm, 9 mm, 9.5 mm, or 10 mm. In some embodiments, the height of a nanoreactor may be about or at most about 10 mm, 9.5 mm, 9 mm, 8.5 mm, 8 mm, 7.5 mm, 7 mm, 6.5 mm, 6 mm, 5.5 mm, 5 mm, 4.5 mm, 4 mm, 3.5 mm, 3 mm, 2.5 mm, 2 mm, 1.5 mm, 1 mm, 0.9 mm, 0.8 mm, 0.7 mm, 0.6 mm, 0.5 mm, 0.4 mm, 0.3 mm, 0.2 mm, or 0.1 mm or less. In some embodiments, the height of a nanoreactor may range between 0.1-10 mm, 0.2-9 mm, 0.3-8 mm, 0.4-7 mm, 0.5-6 mm, 0.6-5 mm, 0.7-4 mm, 0.8-3 mm, or 0.9-2 mm. Those of skill in the art appreciate that the distance may fall within any range bound by any of these values, for example 0.2 mm-0.8 mm. As represented by 2702, the height of a well of a nanoreactor may be about or at least about 0.1 mm, 0.2 mm, 0.3 mm, 0.4 mm, 0.5 mm, 0.6 mm, 0.7 mm, 0.8 mm, 0.9 mm, 1 mm, 1.5 mm, 2 mm, 2.5 mm, 3 mm, 3.5 mm, 4 mm, 4.5 mm, 5 mm, 5.5 mm, 6 mm, 6.5 mm, 7 mm, 7.5 mm, 8 mm, 8.5 mm, 9 mm, 9.5 mm, or 10 mm. In some embodiments, the height of a well of a nanoreactor may be about or at most about 10 mm, 9.5 mm, 9 mm, 8.5 mm, 8 mm, 7.5 mm, 7 mm, 6.5 mm, 6 mm, 5.5 mm, 5 mm, 4.5 mm, 4 mm, 3.5 mm, 3 mm, 2.5 mm, 2 mm, 1.5 mm, 1 mm, 0.9 mm, 0.8 mm, 0.7 mm, 0.6 mm, 0.5 mm, 0.4 mm, 0.3 mm, 0.2 mm, or 0.1 mm or less. In some embodiments, the height of a well of a nanoreactor may range between 0.1-10 mm, 0.2-9 mm, 0.3-8 mm, 0.4-7 mm, 0.5-6 mm, 0.6-5 mm, 0.7-4 mm, 0.8-3 mm, or 0.9-2 mm. Those of skill in the art appreciate that the distance may fall within any range bound by any of these values, for example 0.1 mm-0.6 mm.

FIG. 26B includes an origin of reference indicated by a 0,0 (X,Y) axis, wherein the top left corner of an exemplary nanoreactor is diagramed. In some embodiments, the width of the nanoreactor, represented as 2703, is from about 5 mm to about 150 mm along one dimension, as measured from the origin. In some embodiments, the width of a nanoreactor, represented as 2704, is from about 5 mm to about 150 mm along another dimension, as measured from the origin. In some embodiments, the width of a nanoreactor in any dimension is from about 5 mm to about 125 mm, from about 5 mm to about 100 mm, from about 5 mm to about 75 mm, from about 5 mm to about 50 mm, from about 5 mm to about 25 mm, from about 25 mm to about 150 mm, from about 50 mm to about 150 mm, from about 75 mm to about 150 mm, from about 100 mm to about 150 mm, or from about 125 mm to about 150 mm. Those of skill in the art appreciate that the width may fall within any range bound by any of these values, for example 5-25 mm. In some embodiments, the width of a nanoreactor in any dimension is about or at least about 5 mm, 10 mm, 15 mm, 20 mm, 25 mm, 30 mm, 40 mm, 50 mm, 60 mm, 70 mm, 80 mm, 90 mm, 100 mm, 110 mm, 120 mm, 130 mm, 140 mm, or 150 mm. In some embodiments, the width of a nanoreactor in any dimension is about or at most about 150 mm, 140 mm, 130 mm, 120 mm, 110 mm, 100 mm, 90 mm, 80 mm, 70 mm, 60 mm, 50 mm, 50 mm, 40 mm, 30 mm, 25 mm, 20 mm, 15 mm, 10 mm, or 5 mm or less.

The nanoreactor shown in FIG. 26B comprises 108 wells. The wells may be arranged in any configuration. In FIG. 26B, the wells are arranged in rows forming a square shape. Regardless of arrangement, the wells may start at a distance of about 0.1 mm to about 149 mm from the origin, as measured on the X- or Y-axis and end at a distance of about 1 mm to about 150 mm from the origin. Lengths 2706 and 2705 represent the furthest distances of the center of a well on the X- and Y-axis from the origin, respectively. Lengths 2710 and 2709 represent the closest distances of the center of a well on the X- and Y-axis from the origin, respectively. In some embodiments, the furthest distance of the center of a well in any dimension from the origin is about or at least about 1 mm, 5 mm, 10 mm, 15 mm, 20 mm, 25 mm, 30 mm, 40 mm, 50 mm, 60 mm, 70 mm, 80 mm, 90 mm, 100 mm, 110 mm, 120 mm, 130 mm, 140 mm, or 150 mm. In some embodiments, the furthest distance of the center of a well in any dimension is about or at most about 150 mm, 140 mm, 130 mm, 120 mm, 110 mm, 100 mm, 90 mm, 80 mm, 70 mm, 60 mm, 50 mm, 50 mm, 40 mm, 30 mm, 25 mm, 20 mm, 15 mm, 10 mm, 5 mm, 1 mm or less. In some embodiments, the furthest distance of the center of a well in any dimension is from about 5 mm to about 125 mm, from about 5 mm to about 100 mm, from about 5 mm to about 75 mm, from about 5 mm to about 50 mm, from about 5 mm to about 25 mm, from about 25 mm to about 150 mm, from about 50 mm to about 150 mm, from about 75 mm to about 150 mm, from about 100 mm to about 150 mm, or from about 125 mm to about 150 mm. Those of skill in the art appreciate that the distance may fall within any range bound by any of these values, for example 5-25 mm. In some embodiments, the closest distance of the center of a well in any dimension from the origin is about or at least about 0.1 mm, 0.2 mm, 0.3 mm, 0.4 mm, 0.5 mm, 0.6 mm, 0.7 mm, 0.8 mm, 0.9 mm, 1 mm, 2 mm, 3 mm, 4 mm, 5 mm, 10 mm, 15 mm, 20 mm, 25 mm, 30 mm, 40 mm, 50 mm, 60 mm, 70 mm, 80 mm, 90 mm, 100 mm, 110 mm, 120 mm, 130 mm, 140 mm, or 149 mm. In some embodiments, the closest distance of the center of a well in any dimension is about or at most about 149 mm, 140 mm, 130 mm, 120 mm, 110 mm, 100 mm, 90 mm, 80 mm, 70 mm, 60 mm, 50 mm, 50 mm, 40 mm, 30 mm, 25 mm, 20 mm, 15 mm, 10 mm, 5 mm, 4 mm, 3 mm, 2 mm, 1 mm, 0.9 mm, 0.8 mm, 0.7 mm, 0.6 mm, 0.5 mm, 0.4 mm, 0.3 mm, 0.2 mm, 0.1 mm or less. In some embodiments, the closest distance of the center of a well in any dimension is from about 0.1 mm to about 125 mm, from about 0.5 mm to about 100 mm, from about 0.5 mm to about 75 mm, from about 0.5 mm to about 50 mm, from about 0.5 mm to about 25 mm, from about 1 mm to about 50 mm, from about 1 mm to about 40 mm, from about 1 mm to about 30 mm, from about 1 mm to about 20 mm, or from about 1 mm to about 5 mm. Those of skill in the art appreciate that the distance may fall within any range bound by any of these values, for example 0.1-5 mm.

The wells of a nanoreactor may be located at any distance from the edge of a nanoreactor. Exemplary distances between a well and an edge of a nanoreactor are shown by 2707 and 2708. In some embodiments, the distance between the center of a well and an edge of a nanoreactor in any dimension is about or at least about 0.1 mm, 0.2 mm, 0.3 mm, 0.4 mm, 0.5 mm, 0.6 mm, 0.7 mm, 0.8 mm, 0.9 mm, 1 mm, 2 mm, 3 mm, 4 mm, 5 mm, 10 mm, 15 mm, 20 mm, 25 mm, 30 mm, 40 mm, 50 mm, 60 mm, 70 mm, 80 mm, 90 mm, 100 mm, 110 mm, 120 mm, 130 mm, 140 mm, or 149 mm. In some embodiments, the distance between the center of well and an edge of a nanoreactor in any dimension is about or at most about 149 mm, 140 mm, 130 mm, 120 mm, 110 mm, 100 mm, 90 mm, 80 mm, 70 mm, 60 mm, 50 mm, 50 mm, 40 mm, 30 mm, 25 mm, 20 mm, 15 mm, 10 mm, 5 mm, 4 mm, 3 mm, 2 mm, 1 mm, 0.9 mm, 0.8 mm, 0.7 mm, 0.6 mm, 0.5 mm, 0.4 mm, 0.3 mm, 0.2 mm, 0.1 mm or less. In some embodiments, the distance between the center of well and an edge of a nanoreactor in any dimension is from about 0.1 mm to about 125 mm, from about 0.5 mm to about 100 mm, from about 0.5 mm to about 75 mm, from about 0.5 mm to about 50 mm, from about 0.5 mm to about 25 mm, from about 1 mm to about 50 mm, from about 1 mm to about 40 mm, from about 1 mm to about 30 mm, from about 1 mm to about 20 mm, or from about 1 mm to about 5 mm. Those of skill in the art appreciate that the distance may fall within any range bound by any of these values, for example 0.1-5 mm.

In some embodiments, the wells are arranged so that there exists a repeated distance between two wells. As shown by 2711 and 2712, the distance between two wells may be from about 0.3 mm to about 9 mm apart. In some embodiments, the distance between two wells is about or at least about 0.3 mm, 0.4 mm, 0.5 mm, 0.6 mm, 0.7 mm, 0.8 mm. 0.9 mm, 1 mm, 1.2 mm, 1.4 mm, 1.6 mm, 1.8 mm, 2 mm, 2.2 mm, 2.4 mm, 2.6 mm, 2.8 mm, 3 mm, 3.2 mm, 3.4 mm, 3.6 mm, 3.8 mm, 4 mm, 4.2 mm, 4.4 mm, 4.6 mm, 4.8 mm, 5 mm, 5.2 mm, 5.4 mm, 5.6 mm, 5.8 mm, 6 mm, 6.2 mm, 6.4 mm, 6.6 mm, 6.8 mm, 7 mm, 7.2 mm, 7.4 mm, 7.6 mm, 7.8 mm, 8 mm, 8.2 mm, 8.4 mm, 8.6 mm, 8.8 mm, or 9 mm. In some embodiments, the distance between two wells is about or at most about 9 mm, 8.8 mm, 8.6 mm, 8.4 mm, 8.2 mm, 8 mm, 7.8 mm, 7.6 mm, 7.4 mm, 7.2 mm, 7 mm, 6.8 mm, 6.6 mm, 6.4 mm, 6.2 mm, 6 mm, 5.8 mm, 5.6 mm, 5.4 mm, 5.2 mm, 5 mm, 4.8 mm, 4.6 mm, 4.4 mm, 4.2 mm, 4 mm, 3.8 mm, 3.6 mm, 3.4 mm, 3.2 mm, 3 mm, 2.8 mm, 2.6 mm, 2.4 mm, 2.2 mm, 2 mm, 1.8 mm, 1.6 mm, 1.4 mm, 1.2 mm, 1 mm, 0.9 mm, 0.8 mm, 0.7 mm, 0.6 mm, 0.5 mm, 0.4 mm, or 0.3 mm. The distance between two wells may range between 0.3-9 mm, 0.4-8 mm, 0.5-7 mm, 0.6-6 mm, 0.7-5 mm, 0.7-4 mm, 0.8-3 mm, or 0.9-2 mm. Those of skill in the art appreciate that the distance may fall within any range bound by any of these values, for example 0.8 mm-2 mm.

In some embodiments, the cross-section of the inside of a well, as shown by 2721, is about or at least about 0.3 mm, 0.4 mm, 0.5 mm, 0.6 mm, 0.7 mm, 0.8 mm. 0.9 mm, 1 mm, 1.2 mm, 1.4 mm, 1.6 mm, 1.8 mm, 2 mm, 2.2 mm, 2.4 mm, 2.6 mm, 2.8 mm, 3 mm, 3.2 mm, 3.4 mm, 3.6 mm, 3.8 mm, 4 mm, 4.2 mm, 4.4 mm, 4.6 mm, 4.8 mm, 5 mm, 5.2 mm, 5.4 mm, 5.6 mm, 5.8 mm, 6 mm, 6.2 mm, 6.4 mm, 6.6 mm, 6.8 mm, 7 mm, 7.2 mm, 7.4 mm, 7.6 mm, 7.8 mm, 8 mm, 8.2 mm, 8.4 mm, 8.6 mm, 8.8 mm, or 9 mm. In some embodiments, the cross-section of the inside of a well is about or at most about 9 mm, 8.8 mm, 8.6 mm, 8.4 mm, 8.2 mm, 8 mm, 7.8 mm, 7.6 mm, 7.4 mm, 7.2 mm, 7 mm, 6.8 mm, 6.6 mm, 6.4 mm, 6.2 mm, 6 mm, 5.8 mm, 5.6 mm, 5.4 mm, 5.2 mm, 5 mm, 4.8 mm, 4.6 mm, 4.4 mm, 4.2 mm, 4 mm, 3.8 mm, 3.6 mm, 3.4 mm, 3.2 mm, 3 mm, 2.8 mm, 2.6 mm, 2.4 mm, 2.2 mm, 2 mm, 1.8 mm, 1.6 mm, 1.4 mm, 1.2 mm, 1 mm, 0.9 mm, 0.8 mm, 0.7 mm, 0.6 mm, 0.5 mm, 0.4 mm, or 0.3 mm. The cross-section of the inside of a well may range between 0.3-9 mm, 0.4-8 mm, 0.5-7 mm, 0.6-6 mm, 0.7-5 mm, 0.7-4 mm, 0.8-3 mm, or 0.9-2 mm. Those of skill in the art appreciate that the cross-section may fall within any range bound by any of these values, for example 0.8 mm-2 mm. In some embodiments, the cross-section of a well, including the rim of the well, as shown by 2720, is about or at least about 0.3 mm, 0.4 mm, 0.5 mm, 0.6 mm, 0.7 mm, 0.8 mm. 0.9 mm, 1 mm, 1.2 mm, 1.4 mm, 1.6 mm, 1.8 mm, 2 mm, 2.2 mm, 2.4 mm, 2.6 mm, 2.8 mm, 3 mm, 3.2 mm, 3.4 mm, 3.6 mm, 3.8 mm, 4 mm, 4.2 mm, 4.4 mm, 4.6 mm, 4.8 mm, 5 mm, 5.2 mm, 5.4 mm, 5.6 mm, 5.8 mm, 6 mm, 6.2 mm, 6.4 mm, 6.6 mm, 6.8 mm, 7 mm, 7.2 mm, 7.4 mm, 7.6 mm, 7.8 mm, 8 mm, 8.2 mm, 8.4 mm, 8.6 mm, 8.8 mm, or 9 mm. In some embodiments, the cross-section of a well, including the rim of the well, is about or at most about 9 mm, 8.8 mm, 8.6 mm, 8.4 mm, 8.2 mm, 8 mm, 7.8 mm, 7.6 mm, 7.4 mm, 7.2 mm, 7 mm, 6.8 mm, 6.6 mm, 6.4 mm, 6.2 mm, 6 mm, 5.8 mm, 5.6 mm, 5.4 mm, 5.2 mm, 5 mm, 4.8 mm, 4.6 mm, 4.4 mm, 4.2 mm, 4 mm, 3.8 mm, 3.6 mm, 3.4 mm, 3.2 mm, 3 mm, 2.8 mm, 2.6 mm, 2.4 mm, 2.2 mm, 2 mm, 1.8 mm, 1.6 mm, 1.4 mm, 1.2 mm, 1 mm, 0.9 mm, 0.8 mm, 0.7 mm, 0.6 mm, 0.5 mm, 0.4 mm, or 0.3 mm. The cross-section of a well, including the rim of the well, may range between 0.3-9 mm, 0.4-8 mm, 0.5-7 mm, 0.6-6 mm, 0.7-5 mm, 0.7-4 mm, 0.8-3 mm, or 0.9-2 mm. Those of skill in the art appreciate that the cross-section may fall within any range bound by any of these values, for example 0.8 mm-2 mm.

A nanoreactor may comprise any number of wells, including but not limited to, any number between about 2 and about 250. In some embodiments, the number of wells includes from about 2 to about 225 wells, from about 2 to about 200 wells, from about 2 to about 175 wells, from about 2 to about 150 wells, from about 2 to about 125 wells, from about 2 to about 100 wells, from about 2 to about 75 wells, from about 2 to about 50 wells, from about 2 to about 25 wells, from about 25 to about 250 wells, from about 50 to about 250 wells, from about 75 to about 250 wells, from about 100 to about 250 wells, from about 125 to about 250 wells, from about 150 to about 250 wells, from about 175 to about 250 wells, from about 200 to about 250 wells, or from about 225 to about 250 wells. Those of skill in the art appreciate that the well number may fall within any range bound by any of these values, for example 25-125.

Fiducial marks may be placed on a nanoreactor described herein to facilitate alignment of the nanoreactor with other components of a system, for example a microfluidic device or a component of a microfluidic device. Nanoreactors of the invention may have one or more fiducial marks, e.g. 2, 3, 4, 5, 6, 7, 8, 9, 10, or more fiducial marks. The device view of the nanoreactor shown in FIG. 25B comprises three fiducial marks useful for aligning the device with other components of a system. A fiducial mark may be located at any position within the nanoreactor. As shown by 2716 and 2717, a fiducial mark may be located near the origin, where the fiducial mark is closer to the origin than any one well. In some embodiments, a fiducial mark is located near an edge of the nanoreactor, as shown by 2713, where the distance from the edge is exemplified by 2714 and 2715. The fiducial mark may be located from about 0.1 mm to about 10 mm from the edge of the nanoreactor. In some embodiments, the fiducial mark is located about or at least about 0.1 mm, 0.2 mm, 0.3 mm, 0.4 mm, 0.5 mm, 0.6 mm, 0.7 mm, 0.8 mm. 0.9 mm, 1 mm, 1.2 mm, 1.4 mm, 1.6 mm, 1.8 mm, 2 mm, 2.2 mm, 2.4 mm, 2.6 mm, 2.8 mm, 3 mm, 3.2 mm, 3.4 mm, 3.6 mm, 3.8 mm, 4 mm, 4.2 mm, 4.4 mm, 4.6 mm, 4.8 mm, 5 mm, 5.2 mm, 5.4 mm, 5.6 mm, 5.8 mm, 6 mm, 6.2 mm, 6.4 mm, 6.6 mm, 6.8 mm, 7 mm, 7.2 mm, 7.4 mm, 7.6 mm, 7.8 mm, 8 mm, 8.2 mm, 8.4 mm, 8.6 mm, 8.8 mm, 9 mm, or 10 mm from the edge of the nanoreactor. In some embodiments, the fiducial mark is located about or at most about 10 mm, 9 mm, 8.8 mm, 8.6 mm, 8.4 mm, 8.2 mm, 8 mm, 7.8 mm, 7.6 mm, 7.4 mm, 7.2 mm, 7 mm, 6.8 mm, 6.6 mm, 6.4 mm, 6.2 mm, 6 mm, 5.8 mm, 5.6 mm, 5.4 mm, 5.2 mm, 5 mm, 4.8 mm, 4.6 mm, 4.4 mm, 4.2 mm, 4 mm, 3.8 mm, 3.6 mm, 3.4 mm, 3.2 mm, 3 mm, 2.8 mm, 2.6 mm, 2.4 mm, 2.2 mm, 2 mm, 1.8 mm, 1.6 mm, 1.4 mm, 1.2 mm, 1 mm, 0.9 mm, 0.8 mm, 0.7 mm, 0.6 mm, 0.5 mm, 0.4 mm, 0.3 mm, 0.2 mm, or 0.1 mm from the edge of the nanoreactor. The fiducial mark may be located between 0.1-10 mm, 0.2-9 mm, 0.3-8 mm, 0.4-7 mm, 0.5-6 mm, 0.1-6 mm, 0.2-5 mm, 0.3-4 mm, 0.4-3 mm, or 0.5-2 mm from the edge of the nanoreactor. Those of skill in the art appreciate that the distance may fall within any range bound by any of these values, for example 0.1 mm-5 mm. The fiducial mark may be located close in distance to a well, where exemplary X- and Y-axis distances are indicated by 2719 and 2718, respectively. In some embodiments, a distance between a well and a fiducial mark is about or at least about 0.001 mm, 0.005 mm, 0.01 mm, 0.02 mm, 0.03 mm, 0.04 mm, 0.05 mm, 0.06 mm, 0.07 mm, 0.08 mm, 0.09 mm, 0.1 mm, 0.2 mm, 0.3 mm, 0.4 mm, 0.5 mm, 0.6 mm, 0.7 mm, 0.8 mm, 0.9 mm, 1 mm, 1.2 mm, 1.5 mm, 1.7 mm, 2 mm, 2.2 mm, 2.5 mm, 2.7 mm, 3 mm, 3.5 mm, 4 mm, 4.5 mm, 5 mm, 5.5 mm, 6 mm, 6.5 mm, or 8 mm. In some embodiments, a distance between a well and a fiducial mark is about or at most about 8 mm, 6.5 mm, 6 mm, 5.5 mm, 5 mm, 4.5 mm, 4 mm, 3.5 mm, 3 mm, 2.7 mm, 2.5 mm, 2.2 mm, 2 mm, 1.7 mm, 1.5 mm, 1.2 mm, 1 mm, 0.9 mm, 0.8 mm, 0.7 mm, 0.6 mm, 0.5 mm, 0.4 mm, 0.3 mm, 0.2 mm, 0.1 mm, 0.09 mm, 0.08 mm, 0.07 mm, 0.06 mm, 0.05 mm, 0.04 mm, 0.03 mm, 0.02 mm, 0.01 mm, 0.005 mm, or 0.001 mm. The distance between a well and a fiducial mark may be in a range between 0.001-8 mm, 0.01-7 mm, 0.05-6 mm, 0.1-5 mm, 0.5-4 mm, 0.6-3 mm, 0.7-2 mm, or 0.8-1.7 mm. Those of skill in the art appreciate that the distance may fall within any range bound by any of these values, for example 0.5-2 mm.

The handle view of the nanoreactor shown in FIG. 26D comprises four fiducial marks useful for aligning the device with other components of a system. A fiducial mark may be located at any position within the nanoreactor. As shown by 2722 and 2723 on the detailed view of the fiducial mark H, a fiducial mark may be located near a corner of a nanoreactor on the handle side. The fiducial mark may be located from about 0.1 mm to about 10 mm from the corner of the nanoreactor. In some embodiments, the fiducial mark is located about or at least about 0.1 mm, 0.2 mm, 0.3 mm, 0.4 mm, 0.5 mm, 0.6 mm, 0.7 mm, 0.8 mm. 0.9 mm, 1 mm, 1.2 mm, 1.4 mm, 1.6 mm, 1.8 mm, 2 mm, 2.2 mm, 2.4 mm, 2.6 mm, 2.8 mm, 3 mm, 3.2 mm, 3.4 mm, 3.6 mm, 3.8 mm, 4 mm, 4.2 mm, 4.4 mm, 4.6 mm, 4.8 mm, 5 mm, 5.2 mm, 5.4 mm, 5.6 mm, 5.8 mm, 6 mm, 6.2 mm, 6.4 mm, 6.6 mm, 6.8 mm, 7 mm, 7.2 mm, 7.4 mm, 7.6 mm, 7.8 mm, 8 mm, 8.2 mm, 8.4 mm, 8.6 mm, 8.8 mm, 9 mm, or 10 mm from the corner of the nanoreactor. In some embodiments, the fiducial mark is located about or at most about 10 mm, 9 mm, 8.8 mm, 8.6 mm, 8.4 mm, 8.2 mm, 8 mm, 7.8 mm, 7.6 mm, 7.4 mm, 7.2 mm, 7 mm, 6.8 mm, 6.6 mm, 6.4 mm, 6.2 mm, 6 mm, 5.8 mm, 5.6 mm, 5.4 mm, 5.2 mm, 5 mm, 4.8 mm, 4.6 mm, 4.4 mm, 4.2 mm, 4 mm, 3.8 mm, 3.6 mm, 3.4 mm, 3.2 mm, 3 mm, 2.8 mm, 2.6 mm, 2.4 mm, 2.2 mm, 2 mm, 1.8 mm, 1.6 mm, 1.4 mm, 1.2 mm, 1 mm, 0.9 mm, 0.8 mm, 0.7 mm, 0.6 mm, 0.5 mm, 0.4 mm, 0.3 mm, 0.2 mm, or 0.1 mm from the corner of the nanoreactor. The fiducial mark may be located between 0.1-10 mm, 0.2-9 mm, 0.3-8 mm, 0.4-7 mm, 0.5-6 mm, 0.1-6 mm, 0.2-5 mm, 0.3-4 mm, 0.4-3 mm, or 0.5-2 mm from the corner of the nanoreactor. Those of skill in the art appreciate that the distance may fall within any range bound by any of these values, for example 0.1 mm-5 mm. The fiducial mark may have any width suitable for function. In some embodiments, as exemplified by 2724 and 2725, the width of a fiducial mark is about or at least about 0.1 mm, 0.2 mm, 0.3 mm, 0.4 mm, 0.5 mm, 0.6 mm, 0.7 mm, 0.8 mm. 0.9 mm, 1 mm, 1.2 mm, 1.4 mm, 1.6 mm, 1.8 mm, 2 mm, 2.2 mm, 2.4 mm, 2.6 mm, 2.8 mm, 3 mm, 3.2 mm, 3.4 mm, 3.6 mm, 3.8 mm, 4 mm, 4.2 mm, 4.4 mm, 4.6 mm, 4.8 mm, 5 mm, 5.2 mm, 5.4 mm, 5.6 mm, 5.8 mm, 6 mm, 6.2 mm, 6.4 mm, 6.6 mm, 6.8 mm, 7 mm, 7.2 mm, 7.4 mm, 7.6 mm, 7.8 mm, 8 mm, 8.2 mm, 8.4 mm, 8.6 mm, 8.8 mm, 9 mm, or 10 mm. In some embodiments, the width of a fiducial mark is about or at most about 10 mm, 9 mm, 8.8 mm, 8.6 mm, 8.4 mm, 8.2 mm, 8 mm, 7.8 mm, 7.6 mm, 7.4 mm, 7.2 mm, 7 mm, 6.8 mm, 6.6 mm, 6.4 mm, 6.2 mm, 6 mm, 5.8 mm, 5.6 mm, 5.4 mm, 5.2 mm, 5 mm, 4.8 mm, 4.6 mm, 4.4 mm, 4.2 mm, 4 mm, 3.8 mm, 3.6 mm, 3.4 mm, 3.2 mm, 3 mm, 2.8 mm, 2.6 mm, 2.4 mm, 2.2 mm, 2 mm, 1.8 mm, 1.6 mm, 1.4 mm, 1.2 mm, 1 mm, 0.9 mm, 0.8 mm, 0.7 mm, 0.6 mm, 0.5 mm, 0.4 mm, 0.3 mm, 0.2 mm, or 0.1 mm. The fiducial mark width may range between 0.1-10 mm, 0.2-9 mm, 0.3-8 mm, 0.4-7 mm, 0.5-6 mm, 0.1-6 mm, 0.2-5 mm, 0.3-4 mm, 0.4-3 mm, or 0.5-2 mm long. Those of skill in the art appreciate that the width may fall within any range bound by any of these values, for example 0.1 mm-5 mm. A cross-section of a fiducial mark may be of any suitable size, as shown in by 2726. In some embodiments, the cross-section of a fiducial mark is about or at least about 0.001 mm, 0.002 mm, 0.004 mm, 0.006 mm, 0.008 mm, 0.01 mm, 0.012 mm, 0.014 mm, 0.016 mm, 0.018 mm, 0.02 mm, 0.025 mm, 0.03 mm, 0.035 mm, 0.04 mm, 0.045 mm, 0.05 mm, 0.055 mm, 0.06 mm, 0.065 mm, 0.07 mm, 0.075 mm, 0.08 mm, 0.1 mm, 0.2 mm, 0.3 mm, 0.4 mm, or 0.5 mm. In some embodiments, the cross-section of a fiducial mark is about or at most about 0.5 mm, 0.4 mm, 0.3 mm, 0.2 mm, 0.1 mm, 0.08 mm, 0.075 mm, 0.07 mm, 0.065 mm, 0.06 mm, 0.055 mm, 0.05 mm, 0.045 mm, 0.04 mm, 0.035 mm, 0.03 mm, 0.025 mm, 0.02 mm, 0.018 mm, 0.016 mm, 0.014 mm, 0.012 mm, 0.01 mm, 0.008 mm, 0.006 mm, 0.004 mm, 0.002 mm, 0.001 mm or less. The cross-section of a fiducial mark may range between 0.001-0.5 mm, 0.004-0.4 mm, 0.008-0.3 mm, 0.01-0.2 mm, 0.015-0.1 mm, 0.018-0.1 mm, or 0.02-0.05 mm. Those of skill in the art appreciate that the cross-section may fall within any range bound by any of these values, for example 0.02 mm-0.1 mm.

Figure 26E:
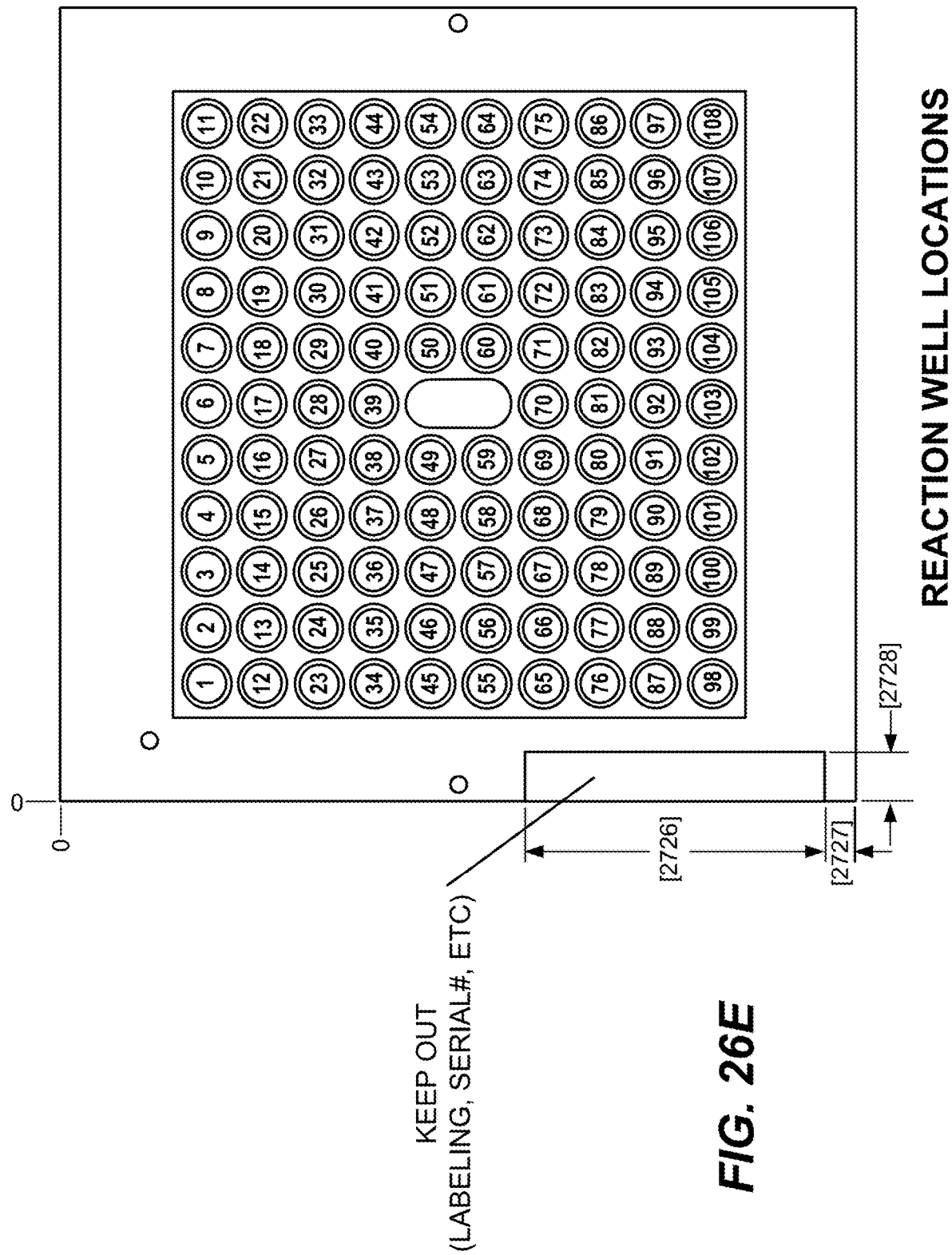
FIG. 26E depicts a device view of a diagram of nanoreactor comprising 108 wells and a label.

In some embodiments, the nanoreactor may have a location for a label or a serial label, as exemplified in FIG. 26E depicting an exemplary layout of wells in a nanoreactor. In some embodiments, the label is a serial number. The label may be located near an edge of the nanoreactor, as exemplified by the distances 2728 and 2727. In some embodiments, any portion of the label is located from about 0.1 mm to about 10 mm from the edge of the nanoreactor. In some embodiments, any portion of the label is located about or at least about 0.1 mm, 0.2 mm, 0.3 mm, 0.4 mm, 0.5 mm, 0.6 mm, 0.7 mm, 0.8 mm. 0.9 mm, 1 mm, 1.2 mm, 1.4 mm, 1.6 mm, 1.8 mm, 2 mm, 2.2 mm, 2.4 mm, 2.6 mm, 2.8 mm, 3 mm, 3.2 mm, 3.4 mm, 3.6 mm, 3.8 mm, 4 mm, 4.2 mm, 4.4 mm, 4.6 mm, 4.8 mm, 5 mm, 5.2 mm, 5.4 mm, 5.6 mm, 5.8 mm, 6 mm, 6.2 mm, 6.4 mm, 6.6 mm, 6.8 mm, 7 mm, 7.2 mm, 7.4 mm, 7.6 mm, 7.8 mm, 8 mm, 8.2 mm, 8.4 mm, 8.6 mm, 8.8 mm, 9 mm, or 10 mm from the edge of a nanoreactor. In some embodiments, the any portion of the label is located about or at most about 10 mm, 9 mm, 8.8 mm, 8.6 mm, 8.4 mm, 8.2 mm, 8 mm, 7.8 mm, 7.6 mm, 7.4 mm, 7.2 mm, 7 mm, 6.8 mm, 6.6 mm, 6.4 mm, 6.2 mm, 6 mm, 5.8 mm, 5.6 mm, 5.4 mm, 5.2 mm, 5 mm, 4.8 mm, 4.6 mm, 4.4 mm, 4.2 mm, 4 mm, 3.8 mm, 3.6 mm, 3.4 mm, 3.2 mm, 3 mm, 2.8 mm, 2.6 mm, 2.4 mm, 2.2 mm, 2 mm, 1.8 mm, 1.6 mm, 1.4 mm, 1.2 mm, 1 mm, 0.9 mm, 0.8 mm, 0.7 mm, 0.6 mm, 0.5 mm, 0.4 mm, 0.3 mm, 0.2 mm, or 0.1 mm from the edge of a nanoreactor. The distance may be in a range between 0.1-10 mm, 0.2-9 mm, 0.3-8 mm, 0.4-7 mm, 0.5-6 mm, 0.6-5 mm, 0.7-4 mm, 0.8-3 mm, 0.9-2 mm or 1.5 mm. Those of skill in the art appreciate that the distance may fall within any range bound by any of these values, for example 0.5-2 mm. The label may have any length, including from about 1 mm to about 25 mm as exemplified by 2726. In some embodiments, the length of a label is about or at least about 1 mm, 5 mm, 10 mm, 15 mm, 20 mm, 25 mm, 30 mm, 40 mm, 50 mm, 60 mm, 70 mm, 80 mm, 90 mm, 100 mm, 110 mm, 120 mm, 130 mm, 140 mm, or 150 mm. In some embodiments, the length of a label is about or at most about 150 mm, 140 mm, 130 mm, 120 mm, 110 mm, 100 mm, 90 mm, 80 mm, 70 mm, 60 mm, 50 mm, 50 mm, 40 mm, 30 mm, 25 mm, 20 mm, 15 mm, 10 mm, 5 mm, 1 mm or less. In some embodiments, the length of a label is from about 5 mm to about 125 mm, from about 5 mm to about 100 mm, from about 5 mm to about 75 mm, from about 5 mm to about 50 mm, from about 5 mm to about 25 mm, from about 25 mm to about 150 mm, from about 50 mm to about 150 mm, from about 75 mm to about 150 mm, from about 100 mm to about 150 mm, or from about 125 mm to about 150 mm. Those of skill in the art appreciate that the length may fall within any range bound by any of these values, for example 5-25 mm.

Materials

The substrates, the solid support or the microstructures or reactors therein may be fabricated from a variety of materials, suitable for the methods and compositions of the invention described herein. In certain embodiments, the materials from which the substrates/solid supports of the comprising the invention are fabricated exhibit a low level of oligonucleotide binding. In some situations, material that are transparent to visible and/or UV light can be employed. Materials that are sufficiently conductive, e.g. those that can form uniform electric fields across all or a portion of the substrates/solids support described herein, can be utilized. In some embodiments, such materials may be connected to an electric ground. In some cases, the substrate or solid support can be heat conductive or insulated. The materials can be chemical resistant and heat resistant to support chemical or biochemical reactions such as a series of oligonucleotide synthesis reaction. For flexible materials, materials of interest can include: nylon, both modified and unmodified, nitrocellulose, polypropylene, and the like. For rigid materials, specific materials of interest include: glass; fuse silica; silicon, plastics (for example polytetraflouroethylene, polypropylene, polystyrene, polycarbonate, and blends thereof, and the like); metals (for example, gold, platinum, and the like). The substrate, solid support or reactors can be fabricated from a material selected from the group consisting of silicon, polystyrene, agarose, dextran, cellulosic polymers, polyacrylamides, polydimethylsiloxane (PDMS), and glass. The substrates/solid supports or the microstructures, reactors therein may be manufactured with a combination of materials listed herein or any other suitable material known in the art.

Surface Modifications

In various embodiments, surface modifications are employed for the chemical and/or physical alteration of a surface by an additive or subtractive process to change one or more chemical and/or physical properties of a substrate surface or a selected site or region of a substrate surface. For example, surface modification may involve (1) changing the wetting properties of a surface, (2) functionalizing a surface, i.e., providing, modifying or substituting surface functional groups, (3) defunctionalizing a surface, i.e., removing surface functional groups, (4) otherwise altering the chemical composition of a surface, e.g., through etching, (5) increasing or decreasing surface roughness, (6) providing a coating on a surface, e.g., a coating that exhibits wetting properties that are different from the wetting properties of the surface, and/or (7) depositing particulates on a surface.

The substrate surface, or the resolved loci, onto which the oligonucleotides or other moieties are deposited may be smooth or substantially planar, or have irregularities, such as depressions or elevations. The surface may be modified with one or more different layers of compounds that serve to modify the properties of the surface in a desirable manner. Such modification layers of interest include: inorganic and organic layers such as metals, metal oxides, polymers, small organic molecules and the like. Polymeric layers of interest include layers of: peptides, proteins, nucleic acids or mimetics thereof (for example, peptide nucleic acids and the like); polysaccharides, phospholipids, polyurethanes, polyesters, polycarbonates, polyureas, polyamides, polyetheyleneamines, polyarylene sulfides, polysiloxanes, polyimides, poly- acetates, and the like, or any other suitable compounds described herein or otherwise known in the art, where the polymers may be hetero- or homopolymeric, and may or may not have separate functional moieties attached thereto (for example, conjugated). Other materials and methods for surface modification of the substrate or coating of the solid support are described in U.S. Pat. No. 6,773,888 and U.S. Pub. No. 2007/0054127, which are herein incorporated by reference in their entirety.

The resolved loci can be functionalized with a moiety that can increase or decrease the surface energy of the solid support. The moiety can be chemically inert or alternatively, be a moiety that is suited to support a desired chemical reaction. The surface energy, or hydrophobicity, of a surface can determine the affinity of an oligonucleotide to attach onto the surface. A method for preparing a substrate can comprise: (a) providing a substrate having a surface that comprises silicon dioxide; and (b) silanizing the surface using, a suitable silanizing agent described herein or otherwise known in the art, for example, an organofunctional alkoxysilane molecule. In some cases, the organofunctional alkoxysilane molecule can be dimethylchloro-octodecyl-silane, methyldichloro-octodecyl-silane, trichloro-octodecyl-silane, trimethyl-octodecyl-silane, triethyl-octodecyl-silane or any combination thereof.

The surface of the substrate can also be prepared to have a low surface energy using any method that is known in the art. Lowering the surface energy can facilitate oligonucleotides to attach to the surface. The surface can be functionalized to enable covalent binding of molecular moieties that can lower the surface energy so that wettability can be reduced. In some embodiments, the functionalization of surfaces enables an increase in surface energy and wettability.

In some embodiments, the surface of the substrate is contacted with a derivatizing composition that contains a mixture of silanes, under reaction conditions effective to couple the silanes to the substrate surface, typically via reactive hydrophilic moieties present on the substrate surface. Silanization generally can be used to cover a surface through self-assembly with organofunctional alkoxysilane molecules. A variety of siloxane functionalizing reagents can further be used as currently known in the art, e.g. for lowering or increasing surface energy. The organofunctional alkoxysilanes are classified according to their organic functions. Non-limiting examples of siloxane functionalizing reagents include hydroxyalkyl siloxanes (silylate surface, functionalizing with diborane and oxidizing the alcohol by hydrogen peroxide), diol (dihydroxyalkyl) siloxanes (silylate surface, and hydrolyzing to diol), aminoalkyl siloxanes (amines require no intermediate functionalizing step), glycidoxysilanes (3-glycidoxypropyl-dimethyl-ethoxysilane, glycidoxy-trimethoxysilane), mercaptosilanes (3-mercaptopropyl-trimethoxysilane, 3-4 epoxycyclohexyl-ethyltrimethoxysilane or 3-mercaptopropyl-methyl-dimethoxysilane), bicyclohepthenyl-trichlorosilane, butyl-aldehyde-trimethoxysilane, or dimeric secondary aminoalkyl siloxanes. The hydroxyalkyl siloxanes can include allyl trichlorochlorosilane turning into 3-hydroxypropyl, or 7-oct-1-enyl trichlorochlorosilane turning into 8-hydroxyoctyl. The diol (dihydroxyalkyl) siloxanes include glycidyl trimethoxysilane-derived (2,3-dihydroxypropyloxy)propyl. The aminoalkyl siloxanes include 3-aminopropyl trimethoxysilane turning into 3-aminopropyl (3-aminopropyl-tri-ethoxysilane, 3-aminopropyl-diethoxy-methylsilane, 3-aminopropyl-dimethyl-ethoxysilane, or 3-aminopropyl-trimethoxysilane). The dimeric secondary aminoalkyl siloxanes can be bis (3-trimethoxysilylpropyl) amine turning into bis(silyloxylpropyl)amine. In addition, a number of alternative functionalized surfaces can be used in the present invention. Non-limiting examples include the following: 1. polyethylene/polypropylene (functionalized by gamma irradiation or chromic acid oxidation, and reduction to hydroxyalkyl surface); 2. highly crosslinked polystyrene-divinylbenzene (derivatized by chloromethylation, and aminated to benzylamine functional surface); 3. nylon (the terminal aminohexyl groups are directly reactive); or 4. etched, reduced polytetrafluoroethylene. Other methods and functionalizing agents are described in U.S. Pat. No. 5,474,796, which is herein incorporated by reference in its entirety. The mixture of functionalization groups, e.g. silanes, can be in any different ratios. For example, without limitation, the mixture can comprise at least two different types of functionalization agents, e.g. silanes. The ratio of the at least two types of surface functionalization agents, e.g. silanes, in a mixture can be about 1:1, 1:2, 1:3, 1:4, 1:5, 1:6, 1:7, 1:8, 1:9, 1:10, 2:3, 2:5, 2:7, 2:9, 2:11, 2:13, 2:15, 2:17, 2:19, 3:5, 3:7, 3:8, 3:10, 3:11, 3:13, 3:14, 3:16, 3:17, 3:19, 4:5, 4:7, 4:9, 4:11, 4:13, 4:15, 4:17, 4:19, 5:6, 5:8, 5:9, 5:11, 5:12, 5:13, 5:14, 5:16, 5:17, 5:18, 5:19, 6:7, 6:11, 6:13, 6:17, 6:19, 7:8, 7:9, 7:10, 7:11, 7:12, 7:13, 7:15, 7:16, 7:18, 7:19, 8:9, 8:11, 8:13, 8:15, 8:17, 8:19, 9:10, 9:11, 9:13, 9:14, 9:16, 9:17, 9:19, 10:11, 10:13, 10:17, 10:19, 11:12, 11:13, 11:14, 11:15, 11:16, 11:17, 11:18, 11:19, 11:20, 12:13, 12:17, 12:19, 13:14, 13:15, 13:16, 13:17, 13:18, 13:19, 13:20, 14:15, 14:17, 14:19, 15:16, 15:17, 15:19, 16:17, 16:19, 17:18, 17:19, 17:20, 18:19, 19:20, or any other ratio to achieve a desired surface representation of two groups. Without being bound by theory, it is understood that surface representation will be highly proportional to the ration of two groups in a mixture. Desired surface tensions, wettabilities, water contact angles, or contact angles for other suitable solvents according to the methods and compositions of the invention can be achieved by providing a ratio of functionalization agents. Further, the agents in the mixture maybe chosen from suitable reactive and inert moieties for downstream reactions, diluting the surface density of reactive groups to a desired level according to the methods and compositions of the invention. In some embodiments, the density of the fraction of a surface functional group that reacts to form a growing oligonucleotide in an oligonucleotide synthesis reaction is about, less than about, or greater than about 0.005, 0.01, 0.05, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 3.0, 3.5, 4.0, 4.5, 5.0, 7.0, 10.0, 15.0, 20.0, 50.0, 75.0, 100.0 μMol/m$^2$.

In various embodiments, the surface is modified to have a higher surface energy, or become more hydrophilic with a coating of reactive hydrophilic moieties. By altering the surface energy of different parts of the substrate surface, the spreading of the deposited reagent liquid can be adjusted, in some cases facilitated. For example, FIG. 5A-C illustrates a case when a droplet of reagent is deposited into a microwell by an inkjet printer. The liquid droplet can spread over and fill the smaller microwells because the surface of the microwells has higher surface energy compared to the other surface nearby in this case. The reactive hydrophilic moieties on the substrate surface can be hydroxyl groups, carboxyl groups, thiol groups, and/or substituted or unsubstituted amino groups. Suitable materials include, but are not limited to, supports that can be used for solid phase chemical synthesis, e.g., cross-linked polymeric materials (e.g., divinylbenzene styrene-based polymers), agarose (e.g., Sepharose®), dextran (e.g., Sephadex®), cellulosic polymers, polyacrylamides, silica, glass (particularly controlled pore glass, or "CPG"), ceramics, and the like. The supports may be obtained commercially and used as is, or they may be treated or coated prior to functionalization.

Hydrophilic and Hydrophobic Surfaces

The surface energy, or hydrophobicity of a surface, can be evaluated or measured by measuring a water contact angle. Water contact angle is the angle between the drop surface and a solid surface where a water droplet meets the solid surface. The solid surface can be a smooth, flat or planar surface. It can quantify the wetting of a solid surface by a liquid (e.g., water) via the Young equation. In some cases, water contact angle hysteresis can be observed, ranging from the so-called advancing (maximal) water contact angle to the receding (minimal) water contact angle. The equilibrium water contact can be found within those values, and can be calculated from them. Hydrophobicity and hydrophilicity can be expressed in relative quantitative terms using water contact angle. A surface with a water contact angle of smaller than 90°, the solid surface can be considered hydrophilic or polar. A surface with a water contact angle of greater than 90°, the solid surface can be considered hydrophobic or apolar. Highly hydrophobic surfaces with low surface energy can have water contact angle that is greater than 120°.

Surface characteristics of coated surfaces can be adjusted in various ways suitable for oligonucleotide synthesis. The surface can be selected to be inert to the conditions of ordinary oligonucleotide synthesis; e.g. the solid surface may be devoid of free hydroxy, amino, or carboxyl groups to the bulk solvent interface during monomer addition, depending on the selected chemistry. Alternatively, the surface may comprise reactive moieties prior to the start of the first cycle, or first few cycles of the oligonucleotide synthesis and these reactive moieties can be quickly depleted to unmeasurable densities after one, two, three, four, five, or more cycles of the oligonucleotide synthesis reaction. The surface can further be optimized for well or poor wetting, e.g. by common organic solvents such as acetonitrile and the glycol ethers or aqueous solvents, relative to surrounding surfaces.

Without being bound by theory, the wetting phenomenon is understood to be a measure of the surface tension or attractive forces between molecules at a solid-liquid interface, and is expressed in dynes/cm2. For example, fluorocarbons have very low surface tension, which is typically attributed to the unique polarity (electronegativity) of the carbon-flourine bond. In tightly structured Langmuir-Blodgett type films, surface tension of a layer can be primarily determined by the percent of fluorine in the terminus of the alkyl chains. For tightly ordered films, a single terminal trifluoromethyl group can render a surface nearly as lipophobic as a perfluoroalkyl layer. When fluorocarbons are covalently attached to an underlying derivatized solid (e.g. a highly crosslinked polymeric) support, the density of reactive sites can be lower than Langmuir-Blodgett and group density. For example, surface tension of a methyltrimethoxysilane surface can be about 22.5 mN/m and aminopropyltriethoxysilane surface can be about 35 mN/m. Other examples of silane surfaces are described in Arkles B et al., "The role of polarity in the structure of silanes employed in surface modification", Silanes and Other Coupling Agents, Vol. 5, which is herein incorporated by reference in its entirety. Briefly, hydrophilic behavior of surfaces is generally considered to occur when critical surface tensions are greater than 45 mN/m. As the critical surface tension increases, the expected decrease in contact angle is accompanied with stronger adsorptive behavior. Hydrophobic behavior of surfaces is generally considered to occur when critical surface tensions are less than 35 mN/m.

At first, the decrease in critical surface tension is associated with oleophilic behavior, i.e. the wetting of the surfaces by hydrocarbon oils. As the critical surface tensions decrease below 20 mN/m, the surfaces resist wetting by hydrocarbon oils and are considered both oleophobic as well as hydrophobic. For example, silane surface modification can be used to generate a broad range of critical surface tensions. Accordingly, the methods and compositions of the invention may use surface coatings, e.g. those involving silanes, to achieve surface tensions of less than 5, 6, 7, 8, 9, 10, 12, 15, 20, 25, 30, 35, 40, 45, 50, 60, 70, 80, 90, 100, 110, 115, 120 mN/m, or higher. Further, the methods and compositions of the invention may use surface coatings, e.g. those involving silanes, to achieve surface tensions of more than 115, 110, 100, 90, 80, 70, 60, 50, 45, 40, 35, 30, 25, 20, 15, 12, 10, 9, 8, 7, 6 mN/m or less. The water contact angle and the surface tension of non-limiting examples of surface coatings, e.g., those involving silanes, are described in Table 1 and Table 2 of Arkles et al. (Silanes and Other Coupling Agents, Vol. 5v: The Role of Polarity in the Structure of Silanes Employed in Surface Modification. 2009), which is incorporated herein by reference in its entirety. The tables are replicated below.

TABLE 1

Contact angles of water (degrees) on smooth surfaces

| | |
|---|---|
| Heptadecafluorodecyltrimethoxysilane | 113-115 |
| Poly(tetrafluoroethylene) | 108-112 |
| Polypropylene | 108 |
| Octadecyldimethylchlorosilane | 110 |
| Octadecyltrichlorosilane | 102-109 |
| Tris(trimethylsiloxy)silylethyldimethylchlorosilane | 103-104 |
| Octyldimethylchlorosilane | 104 |
| Butyldimethylchlorosilane | 100 |
| Trimethylchlorosilane | 90-100 |
| Polyethylene | 88-103 |
| Polystyrene | 94 |
| Poly(chlorotrifluoroethylene) | 90 |
| Human skin | 75-90 |
| Diamond | 87 |
| Graphite | 86 |
| Silicon (etched) | 86-88 |
| Talc | 82-90 |
| Chitosan | 80-81 |
| Steel | 70-75 |
| Methoxyethoxyundecyltrichlorosilane | 73-74 |
| Methacryloxypropyltrimethoxysilane | 70 |
| Gold, typical (see gold, clean) | 66 |
| Intestinal mucosa | 50-60 |
| Kaolin | 42-46 |
| Platinum | 40 |
| Silicon nitride | 28-30 |
| Silver iodide | 17 |
| [Methoxy(polyethyleneoxy)propyl]trimethoxysilane | 15-16 |
| Sodalime glass | <15 |
| Gold, clean | <10 |
| Trimethoxysilylpropyl substituted poly(ethyleneimine), hydrochloride | <10 |

Note:
In Table 1, contact angles for silanes refer to hydrolytic deposition of the silane onto smooth surfaces. The data here are drawn from various literature sources and from the authors' work. Exact comparisons between substrates do not take into account differences in test methods or whether advancing, receding or equilibrium contact angles were reported.

TABLE 2

Critical surface tensions (mN/m)

| | |
|---|---|
| Heptadecafluorodecyltrichlorosilane | 12 |
| Poly(tetrafluoroethylene) | 18.5 |
| Octadecyltrichlorosilane | 20-24 |
| Methyltrimethoxysilane | 22.5 |
| Nonafluorohexyltrimethoxysilane | 23 |
| Vinyltriethoxysilane | 25 |
| Paraffin wax | 25.5 |
| Ethyltrimethoxysilane | 27.0 |
| Propyltrimethoxysilane | 28.5 |
| Glass, sodalime (wet) | 30.0 |
| Poly(chlorotrifluoroethylene) | 31.0 |
| Polypropylene | 31.0 |
| Poly(propylene oxide) | 32 |
| Polyethylene | 33.0 |
| Trifluoropropyltrimethoxysilane | 33.5 |
| 3-(2-Aminoethyl)aminopropyltrimethoxysilane | 33.5 |
| Polystyrene | 34 |
| p-Tolyltrimethoxysilane | 34 |
| Cyanoethyltrimethoxysilane | 34 |
| Aminopropyltriethoxysilane | 35 |
| Acetoxypropyltrimethoxysilane | 37.5 |
| Poly(methyl methacrylate) | 39 |
| Poly(vinyl chloride) | 39 |
| Phenyltrimethoxysilane | 40.0 |
| Chloropropyltrimethoxysilane | 40.5 |
| Mercaptopropyltrimethoxysilane | 41 |
| Glycidoxypropyltrimethoxysilane | 42.5 |
| Poly(ethylene terephthalate) | 43 |
| Copper (dry) | 44 |
| Poly(ethylene oxide) | 43-45 |
| Aluminum (dry) | 45 |
| Nylon 6/6 | 45-46 |
| Iron (dry) | 46 |
| Glass, sodalime (dry) | 47 |
| Titanium oxide (anatase) | 91 |
| Ferric oxide | 107 |
| Tin oxide | 111 |

Methods to measure water contact angle can use any method that is known in the art, including the static sessile drop method, the dynamic sessile drop method, dynamic Wilhelmy method, single-fiber Wilhelmy method, powder contact angle method, and the like. In some cases, the surface of the substrate, or a portion of the surface of the substrate as described herein in the current invention can be functionalized or modified to be hydrophobic, to have a low surface energy, or to have a water contact angle that would be measured to be greater than about 90°, 95°, 100°, 105°, 110°, 115°, 120°, 125°, 130°, 135°, 140°, 145° or 150° on an uncurved, smooth, or planar equivalent of the relevant functionalized surface of the substrate, as described herein. The water contact angle of a functionalized surface described herein can refer to the contact angle of a water droplet on the functionalized surface in an uncurved, smooth, flat and planar geometry. In some cases, the surface of the substrate, or a portion of the surface of the substrate as described herein in the current invention can be functionalized or modified to be hydrophilic, to have a high surface energy, or to have a water contact angle that would be measured to be less than about 90°, 85°, 80°, 75°, 70°, 65°, 60°, 55°, 50°, 45°, 40°, 35°, 30°, 25°, 20°, 15° or 10° on an uncurved, smooth or planar equivalent of the relevant functionalized surface of the substrate, as described herein. The surface of the substrate or a portion of the surface of the substrate can be functionalized or modified to be more hydrophilic or hydrophobic as compared to the surface or the portion of the surface prior to the functionalization or modification.

In some cases, one or more surfaces can be modified to have a difference in water contact angle of greater than 90°, 85°, 80°, 75°, 70°, 65°, 60°, 55°, 50°, 45°, 40°, 35°, 30°, 25°, 20°, 15° or 10° as measured on one or more uncurved, smooth or planar equivalent surfaces. In some cases, the surface of the microstructures, channels, resolved loci, resolved reactor caps or other parts of the substrate may be modified to have a differential hydrophobicity corresponding to a difference in water contact angle that is greater than 90°, 85°, 80°, 75°, 70°, 65°, 60°, 55°, 50°, 45°, 40°, 35°, 30°, 25°, 20°, 15° or 10° as measured on uncurved, smooth or planar equivalent surfaces of such structures. Unless otherwise stated, water contact angles mentioned herein correspond to measurements that would be taken on uncurved, smooth or planar equivalents of the surfaces in question.

Other methods for functionalizing the surface are described in U.S. Pat. No. 6,028,189, which is herein incorporated by reference in its entirety. For example, hydrophilic resolved loci can be generated by first applying a protectant, or resist, over each loci within the substrate. The unprotected area can be then coated with a hydrophobic agent to yield an unreactive surface. For example, a hydrophobic coating can be created by chemical vapor deposition of (tridecafluorotetrahydrooctyl)-triethoxysilane onto the exposed oxide surrounding the protected circles. Finally, the protectant, or resist, can be removed exposing the loci regions of the substrate for further modification and oligonucleotide synthesis. In some embodiments, the initial modification of such unprotected regions may resist further modification and retain their surface functionalization, while newly unprotected areas can be subjected to subsequent modification steps.

Multiple Parallel Microfluidic Reactions

In another aspect, systems and methods for conducting a set of parallel reactions are described herein. The system may comprise two or more substrates that can be sealed, e.g. releasably sealed, with each other, forming a plurality of individually addressable reaction volumes or reactors upon sealing. New sets of reactors may be formed by releasing a first substrate from a second substrate and aligning it with a third substrate. Each substrate can carry reagents, e.g. oligonucleotides, enzymes, buffers, or solvents, for desired reactions. In some embodiments, the system comprises a first surface with a plurality of resolved loci at a first suitable density and a capping element with a plurality of resolved reactor caps at a second suitable density. The system can align the plurality of resolved reactor caps with the plurality of resolved loci on the first surface forming a temporary seal between the first surface and the capping element. The temporary seal between the aligned substrates may physically divide the loci on the first surface into groups of about at least about, or less than about 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, 100, 125, 150, 200 loci, or more. A set of parallel reactions described herein can be conducted according to the methods and compositions of the invention. A first surface with a plurality of resolved loci at a first density and a capping element with a plurality of resolved reactor caps at a second density can be aligned, such that the plurality of resolved reactor caps with the plurality of resolved loci on the first surface form a temporary seal between the first surface and the capping element and thereby physically divide the loci on the first surface into groups of about at least about, or less than about 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, 100, 125, 150, 200 loci, or more. A first reaction can be performed, forming a first set of reagents. The capping element may be released from the first surface. Upon release, the reactor caps may each retain at least a portion of the first set of reagents in the previously sealed reaction volumes. The plurality of resolved loci can be at a density of about, at least about or less than about 1, about 2, about 3, about 4, about 5, about 6, about 7, about 8, about 9, about 10, about 15, about 20, about 25, about 30, about 35, about 40, about 50, about 75, about 100, about 200, about 300, about 400, about 500, about 600, about 700, about 800, about 900, about 1000, about 1500, about 2000, about 3000, about 4000, about 5000, about 6000, about 7000, about 8000, about 9000, about 10000, about 20000, about 40000, about 60000, about 80000, about 100000, or about 500000 per 1 $mm^2$. In some embodiments, the plurality of resolved loci can be at a density of about, at least about, less than about 100 per $mm^2$. The plurality of resolved reactor caps can be at a density of about, at least about, less than about 1 per $mm^2$. In some embodiments, the plurality of resolved reactor caps can be at a density of about, at least about or less than about 2, about 3, about 4, about 5, about 6, about 7, about 8, about 9, about 10, about 15, about 20, about 25, about 30, about 35, about 40, about 50, about 75, about 100, about 200, about 300, about 400, about 500, about 600, about 700, about 800, about 900, about 1000, about 1500, about 2000, about 3000, about 4000, about 5000, about 6000, about 7000, about 8000, about 9000, about 10000, about 20000, about 40000, about 60000, about 80000, about 100000, or about 500000 per 1 $mm^2$. The methods described herein can further comprise providing a second surface with a plurality of resolved loci at a third density and aligning the plurality of resolved reactor caps with the plurality of resolved loci on the second surface. and forming a seal, typically a temporary or releasable seal, between the second surface and the capping element. The newly formed sealed may physically divide the loci on the second surface into groups of about at least about, or less than about 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, 100, 125, 150, 200 loci, or more. A second reaction may be performed, optionally using a portion of the first set of reagents, thereby forming a second set of reagents. The capping element may be released from the second surface. Upon release, the reactor caps may each retain at least a portion of the second set of reagents in the previously sealed second reaction volumes. In some cases, the second surface with a plurality of resolved loci can have a locus density of at least about 1, about 2, about 3, about 4, about 5, about 6, about 7, about 8, about 9, about 10, about 15, about 20, about 25, about 30, about 35, about 40, about 50, about 75, about 100, about 200, about 300, about 400, about 500, about 600, about 700, about 800, about 900, about 1000, about 1500, about 2000, about 3000, about 4000, about 5000, about 6000, about 7000, about 8000, about 9000, about 10000, about 20000, about 40000, about 60000, about 80000, about 100000, or about 500000 per 1 $mm^2$. Various aspects of the embodiments of the systems, methods and instrumentations are described herein.

The system assembly can comprise any number of static wafers and any number of dynamic wafers. For example, the system can comprise three substrates in a column and four substrates in a row. The transport system can comprise three static wafers (or substrates) and one dynamic wafer (or substrate). The dynamic wafers can move or transport in between a plurality of static wafers. A dynamic wafer can be transported between three statically mounted wafers. In some embodiments, the dynamic wafer can have a diameter that is about 50, 100, 150, 200 or 250 mm or 2, 4, 6, or 8 in or higher. The dynamic wafers can be mounted in a temperature controlled vacuum chuck. The systems of the invention allow for configurations, wherein the dynamic wafers can move in Z direction, which may be the direction that is perpendicular to the surface of a wafer that is to face a surface of a second wafer, with about or less than about 0.01, 0.05, 0.1, 0.5, 1, 1.5, 2, 2.5 or 3 µm control of z-position, and can align theta_z of wafers, the angle between the normals of the surfaces of two wafers that are to face each other, e.g. by matching a pattern on the dynamic wafer with another pattern on the static wafer within a range of tolerance. The wafer positioning tolerances can be about or less than about 1, 5, 10, 20, 30, 40, 50, 60, 70, 80, 90, 100, 150, 200, 250, 300 350, 400, 450 or 500 micro radians in difference in angle of rotation in x-y plane. In some embodiments, the wafer positioning tolerances can be about or less than about 50 micro radians in difference in angle of rotation in x-y plane. The wafer positioning tolerances can be about or less than about 0.01, 0.05, 0.1, 0.5, 1, 2, 3, 4, 5, 6, 7, 8, 9, 10, 11, 12, 13, 14 or 15 µm of distance in x-direction. The wafer positioning tolerances can be about or less than about 0.01, 0.05, 0.1, 0.5, 1, 2, 3, 4, 5, 6, 7, 8, 9, 10, 11, 12, 13, 14 or 15 µm of distance in y-direction. The wafer positioning tolerances can be about or less than about 1, 2, 3, 4, 5, 6, 7, 8, 9 or 10 micro radians in rotations of x-y plane in z-direction. In some embodiments, the wafer positioning tolerances can be about or less than about 5 micro radians in rotations of x-y plane in z-direction. In some embodiments, the wafer positioning tolerances can be about or less than about 0.01, 0.05, 0.1, 0.5, 1, 1.5, 2, 2.5, 3, 3.5, 4, 4.5 or 5 µm of distance in z-direction. In some embodiments, the wafer positioning tolerances can be about or less than about 0.5 µm of distance in z-direction.

In some cases, the systems and methods for conducting a set of parallel reactions can further comprise a third, a four, a fifth, a sixth, a seventh, a eighth, a ninth or a tenth surface with a plurality of resolved loci and/or a capping element with a plurality of resolved reactor caps. The third, the four, the fifth, the sixth, the seventh, the eighth, the ninth or the tenth surfaces can be aligned and can form a temporary seal between the two surfaces and the corresponding capping element, thereby physically dividing the loci and/or reactor caps on the surfaces. A third, a four, a fifth, a sixth, a seventh, a eighth, a ninth or a tenth reaction can be performed using a portion of the reagents that is retained from the previous reaction, namely, the second, a third, a four, a fifth, a sixth, a seventh, a eighth or a ninth set of reagents, thereby forming the third, the four, the fifth, the sixth, the seventh, the eighth, the ninth or the tenth set of reagents. Each of the capping elements described herein can be released from its corresponding surface, wherein the reactor caps can retain at least a portion of the previous set of reagents of another reaction volume. In some cases, the second surface with a plurality of resolved loci can be at a density of at least 2/mm². In some embodiments, the second surface with a plurality of resolved loci can have a locus density of at least about 1, about 2, about 3, about 4, about 5, about 6, about 7, about 8, about 9, about 10, about 15, about 20, about 25, about 30, about 35, about 40, about 50, about 75, about 100, about 200, about 300, about 400, about 500, about 600, about 700, about 800, about 900, about 1000, about 1500, about 2000, about 3000, about 4000, about 5000, about 6000, about 7000, about 8000, about 9000, about 10000, about 20000, about 40000, about 60000, about 80000, about 100000, or about 500000 per 1 mm². The portion of the reagents retained each time can be different and controlled to be at a desirable portion depending on the reactions to be performed.

The invention, in various embodiments, contemplates a system for conducting a set of parallel reactions comprising a first surface with a plurality of resolved loci and a capping element with a plurality of resolved reactor caps. The plurality of resolved loci and the capping element with a plurality of resolved reactor caps can be combined to form a plurality of resolved reactors, as described in further detail elsewhere herein. In some cases, the resolved loci of the first surface of the first substrate can comprise a coating of reagents. The resolved loci of the second surface of the second substrate can comprise a coating of reagents. In some embodiments, the coating of reagents can be covalently linked to the first or second surface. In the cases when there is a third, a four, a fifth, a sixth, a seventh, a eighth, a ninth or a tenth surface, each surface may comprise a coating of reagents.

The coating of reagents on the first surface or the second surface may comprise oligonucleotides. The oligonucleotides can be any length as further described elsewhere herein, for example at least 25, 50, 75, 100, 125, 150, 175, 200, 225, 250, 275, 300 bp, or longer. Upon sealing the resolved loci with the resolved reactor caps, the oligonucleotides that are comprised within the coating of reagents may be released. A variety of reactions can be conducted, for example, the oligonucleotide amplification reaction, PCA, generation of sequencing libraries, or error correction, inside of the plurality of resolved reactors.

The oligonucleotides can be released from the coated surface by a variety of suitable methods as described in further details elsewhere herein and known in the art, for example by enzymatic cleavage, as is well known in that art. Examples of such enzymatic cleavage include, but are not limited to, the use of restriction enzymes such as MlyI, or other enzymes or combinations of enzymes capable of cleaving single or double-stranded DNA such as, but not limited to, Uracil DNA glycosylase (UDG) and DNA Endonuclease IV. Other methods of cleavage known in the art may also be advantageously employed in the present invention, including, but not limited to, chemical (base labile) cleavage of DNA molecules or optical (photolabile) cleavage from the surface. PCR or other amplification reactions can also be employed to generate building material for gene synthesis by copying the oligonucleotides while they are still anchored to the substrate. Methods of releasing oligonucleotides are described in P.C.T. Patent Publication No. WO2007137242, and U.S. Pat. No. 5,750,672 which is herein incorporated by reference in its entirety.

In some cases, the releasing in the releasing the capping element from the first surface, and the releasing the capping element from the second surface can be performed at a different velocity. The amount of the portion of reagents that is retained upon releasing the capping element from the corresponding surface can be controlled by the velocity or the surface energy of the capping element and the corresponding surface. In some cases, the first or second surface comprises a different surface tension, surface energy, or hydrophobicity with a given liquid, such as water. In some cases, the resolved loci of the first surface can comprise a high surface energy, surface tension or hydrophobicity. The difference in the surface energy, or hydrophobicity, of the capping element and the corresponding surface can be a parameter to control the portion of the reagents that is retained upon release. The volume of the first and the second reactions can be different.

In some cases, the air pressure outside of the resolved reactors may be greater than the pressure inside the resolved reactors. In other cases, the air pressure outside of the resolved reactors may be less than the pressure inside of the resolved reactors. The difference in the air pressure outside of the resolved reactors and the inside of the resolved reactors (or the differential pressure) can affect the sealing of the resolved reactors. By modifying the surface energy or hydrophobicity of the first surface and the second surface, the differential pressure may result in a curve or straight air/liquid interface within a gap between the first surface and the reactor cap of the second surface. Furthermore, the force needed to release the capping element from the surface can be controlled by the differential pressure, and the differential surface energy. In some cases, the surface can be modified to have a differential surface energy and differential pressure such that the capping element is capable of being released from the surface easily.

The first or second reaction, or any reaction after the second reaction may comprise various molecular or biochemical assays as described herein or any suitable reaction known in the art. In some cases, the first or second reaction can comprise polymerase cycling assembly. In some cases, the first or second reaction can comprise enzymatic gene synthesis, annealing and ligation reaction, simultaneous synthesis of two genes via a hybrid gene, shotgun ligation and co-ligation, insertion gene synthesis, gene synthesis via one strand of DNA, template-directed ligation, ligase chain reaction, microarray-mediated gene synthesis, solid-phase assembly, Sloning building block technology, or RNA ligation mediated gene synthesis. The reactions or the method for conducting a set of parallel reactions may further comprise cooling the capping element, or cooling the first surface (second surface).

Figure 8:
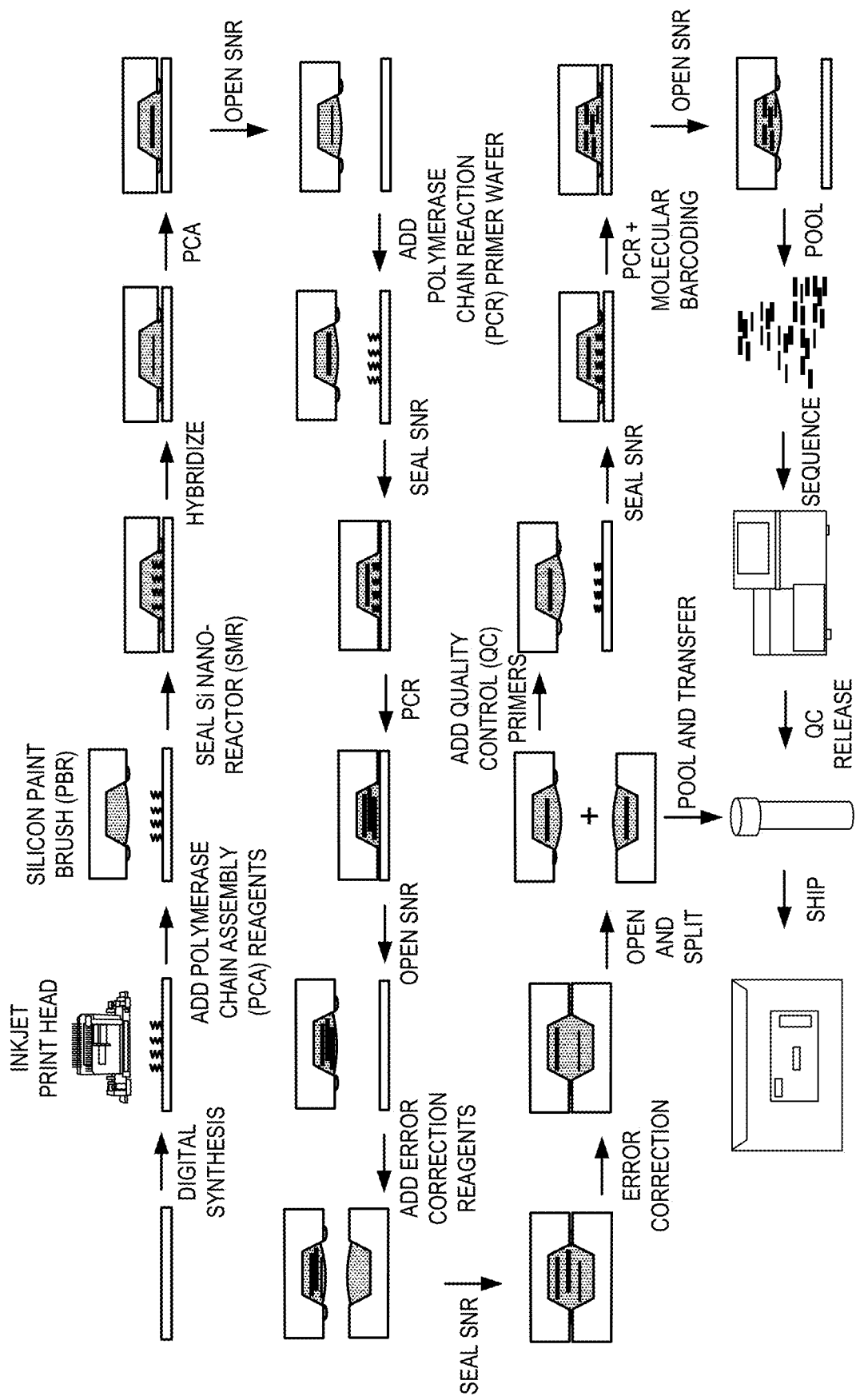
FIG. 8 is a diagram demonstrating an exemplary process workflow for gene synthesis to shipment.

The general process work flow of the methods and compositions of the present invention using the systems described herein is illustrated in FIG. 8.

Auxiliary Instrumentation

In one aspect, the current invention concerns systems and methods for oligonucleotide synthesis. The system for oligonucleotide synthesis may comprise a scanning deposition system. The systems for oligonucleotide synthesis can comprise a first substrate (e.g. oligonucleotide synthesis wafer) having a functionalized surface and a plurality of resolved loci and a inkjet printer, typically comprising a plurality of printheads. Each printhead is typically configured to deposit one of a variety of building blocks for reactions that are performed in the resolved loci of a first substrate, e.g. nucleotide building blocks for phosphoramidite synthesis. The resolved loci of the oligonucleotide synthesis wafer may reside in microchannels as described in further detail elsewhere herein. The substrate may be sealed within a flow cell, e.g. by providing continuous flow of liquids such as those containing necessary reagents for the reactions within the resolved loci (e.g. oxidizer in toluene) or solvents (e.g. acetonitrile) allowing precise control of dosage and concentration of reagents at the sites of synthesis, e.g. the resolved loci of an oligonucleotide synthesis wafer. Flow of an inert gas, such as nitrogen, may be used to dry the substrate, typically through enhanced evaporation of a volatile substrate. A variety of means, for example a vacuum source/a depressurizing pump or a vacuum tank, can be used to create reduced relative pressure (negative pressure) or vacuum to improve drying and reduce residual moisture amounts and any liquid droplets on the surface. Accordingly, the pressure immediately surrounding the substrates or the resolved loci thereof may measure to be about or less than about 100, 75, 50, 40, 30, 20, 15, 10, 5, 4, 3, 2, 1, 0.5, 0.1, 0.05, 0.01 mTorr, or less.

FIG. 3 illustrates an example of a system for oligonucleotide synthesis. Accordingly, an oligonucleotide synthesis wafer is configured to provide the resolved loci for oligonucleotide synthesis with necessary bulk reagents through an inlet manifold and, optionally an outlet manifold. for the bulk reagents can include any suitable reagents, carriers, solvents, buffers, or gasses for oligonucleotide synthesis that is commonly needed among a plurality of resolved loci in various embodiments, such as oxidizer, de-block, acetonitrile or nitrogen gas. The inkjet printer printheads can move in X-Y direction to the addressable locations of the first substrate. A second substrate, such as a capping element, as described in further detail elsewhere herein, can move in the Z direction, and if needed, in the X and Y directions, to seal with the first substrate, forming a plurality of resolved reactors. Alternatively, the second substrate may be stationary. In such cases, the synthesis substrate may move in the Z direction, and if necessary in X and Y directions, to align and seal with the second substrate. The synthesized oligonucleotides can be delivered from the first substrate to the second substrate. Suitable amounts of fluids may be passed through an inlet manifold and the resolved loci of a first substrate, into a second substrate to facilitate the delivery of reagents from the first substrate/the resolved loci thereof into the second substrate. In another aspect, current invention relates to a system for oligonucleotide assembly comprising wafer handling.

In various embodiments, the present invention makes use of systems for scanning deposition. The scanning deposition systems can comprise an inkjet that can be used to deposit reagents to the resolved loci or microwells etched into a substrate. In some embodiments, the scanning deposition system can use organic solvents or inks. In some cases, the scanning deposition system can comprise a plurality of wafers, such as silicon wafers, typically about 200 mm in diameter. In some cases, the entire system can be place and function in an atmospherically controlled enclosure. The scanning deposition system can comprise a work envelope, a printhead assembly, a flowcell assembly, and/or a service envelope. In some cases, the printhead assembly can move while the flowcell assembly remains stationary. The scanning deposition system can comprise one or more flowcells, such as 2, 3, 4, 5, 6, 7, 8, 9, 10, 15, 20, 30, 40, 50, or more flowcells servicing one or more substrates/wafers, such as 2, 3, 4, 5, 6, 7, 8, 9, 10, 15, 20, 30, 40, 50, or more substrates/wafers. Wafers can stay fixed within the flowcells. In some cases, the system can facilitate alignment of substrates through theta_z automation. The work envelope can include area comprising scanning direction travel, e.g. about (n−1) Printhead Pitch+Wafer Diameter=9*20 mm+200 mm=380 mm, in one particular embodiment. Suitable working envelopes can be envisioned with equivalent setups. The service envelope may comprise printheads that are parked for servicing. In some cases, the service envelope can be environmentally isolated from a larger box. In various embodiments, the systems for the methods and compositions described herein comprise scanning deposition systems for oligonucleotide synthesis, oligonucleotide assembly, or more generally for the manufacturing of reagents.

Figure 9:
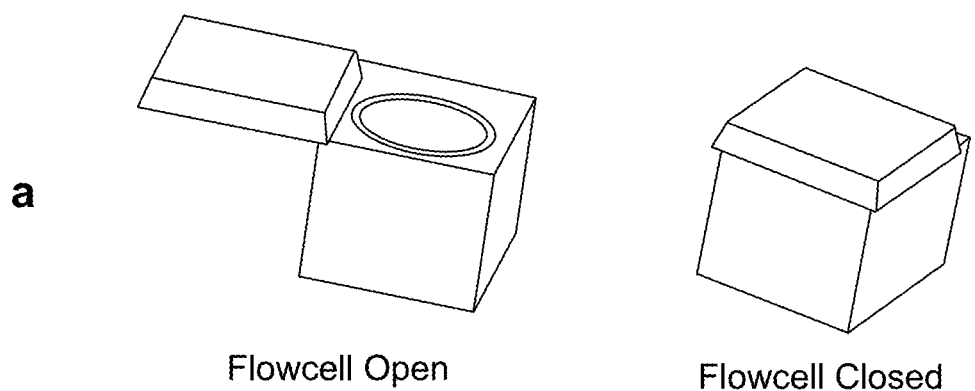
FIG. 9 part A show illustrations of an exemplary flowcell with lid opened or closed.
Figure 9:
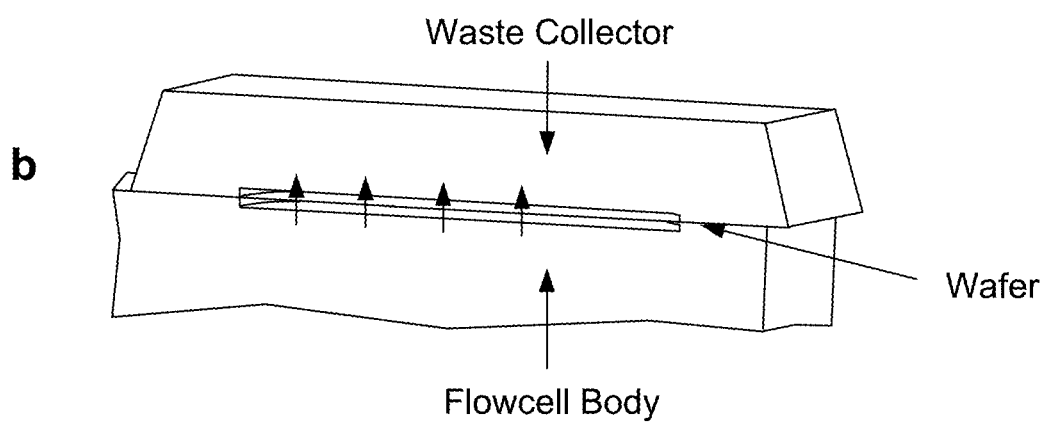
Figure 9:
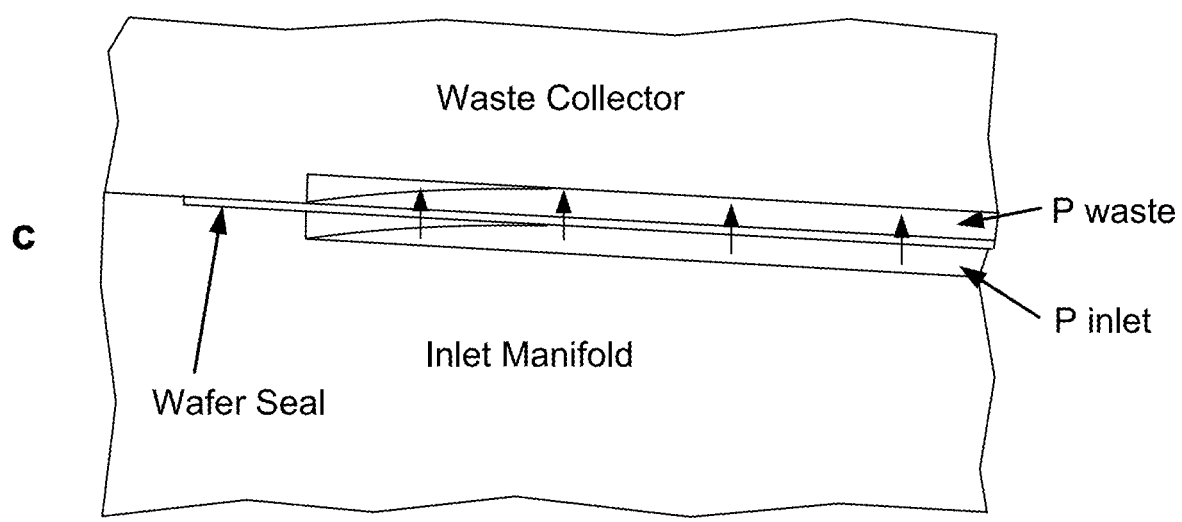
Figure 10:
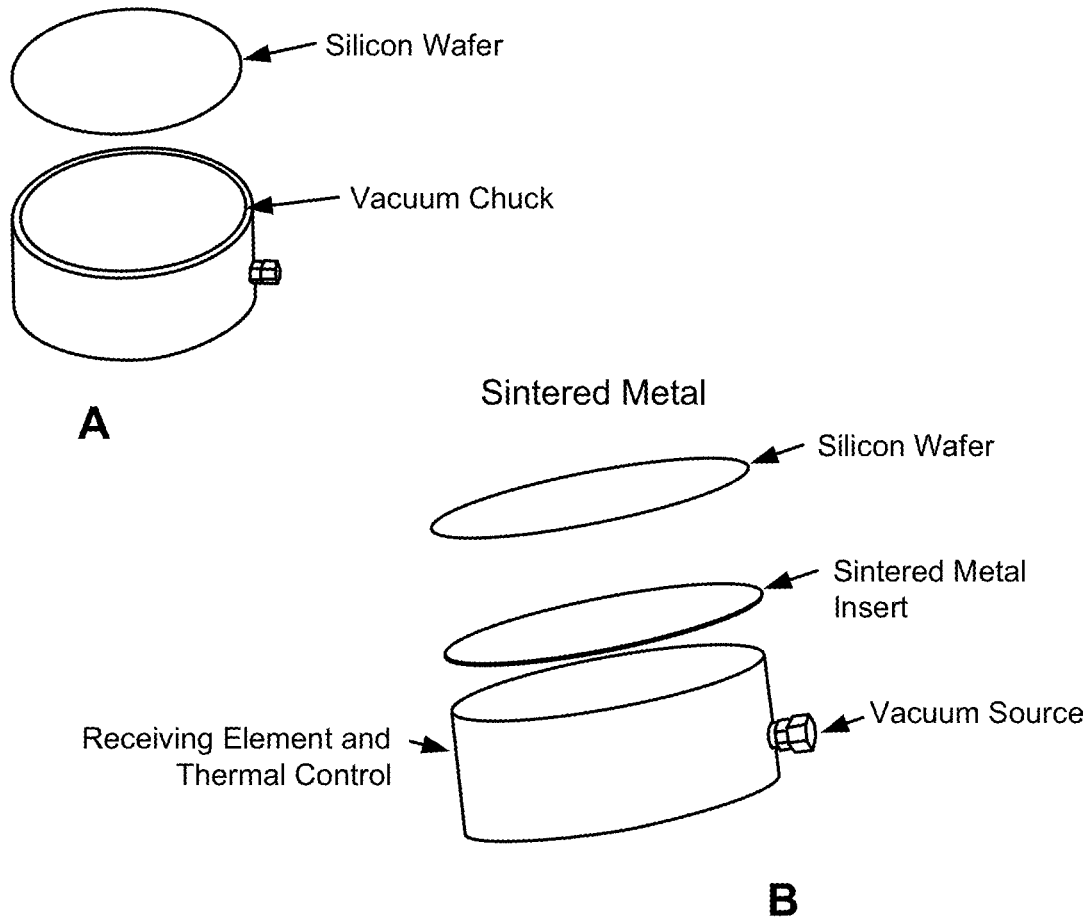
FIG. 10 part A illustrates an example of a single groove vacuum chuck with a single 1-5 mm groove, 198 mm diameter.
Figure 10:
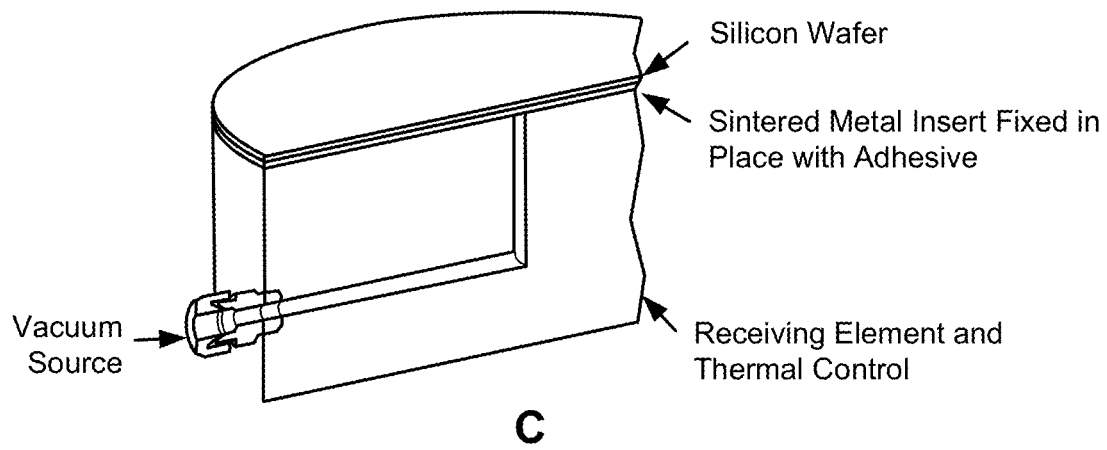

The plurality of resolved loci and the plurality of resolved reactor caps may be located on microstructures that have interconnectivity or fluidic communications. Such fluidic communications allow washing and perfusing new reagents as droplets or using continuous flow, for different steps of reactions. The fluid communication microchannels may contain inlets and outlets to and/or from the plurality of resolved loci and the plurality of resolved reactors. The inlets and/or outlets can be made with any known methods in the art. For example, the inlets and/or outlets can be provided on a front side and the back side of the substrate. Methods of creating the inlets and/or outlets are described in U.S. Patent Publication No. US 20080308884 A1, which is herein incorporated by reference in its entirety, an may comprise making suitable microstructural components by lithographic and etching processes on a front side; drilling holes from the back side of said substrate in precise alignment with the microstructures on the front side, to provide inlets and/or outlets to and/or from said micromechanical structure. The inlets and/or outlets may be Hele-Shaw type flowcells, with fluid flowing in a thin gap fed by a manifold. As illustrated in FIG. 9 part A, the substrates described herein, may form part of a flowcell. The flowcell can be closed by sliding a lid over the top of the substrate (i.e. wafer) and can be clamped into place forming a pressure tight seal around the edge of the substrate. In some embodiments, the seal may be adequate to seal against vacuum or about 1, 2, 3, 4, 5, 6, 7, 8, 9 or 10 atmospheres of pressure. Reagents can be introduced into a thin gap underneath the substrate (i.e. wafer) and flow up through the substrate. Reagents can then be collected in the tapered waste collector as illustrated in FIG. 9 part B. After a final solvent wash step, in some embodiments, the wafer can be drained out, e.g. through the bottom of the assembly and then purged with nitrogen. The chamber can be then pulled down to a vacuum to dry out the remaining solvent in any microstructures reducing the residual liquids or moisture to less than 50%, 30%, 30%, 20%, 10%, 9%, 8%, 7%, 6%, 5%, 4%, 3%, 2%, 1%, 0.1%, 0.01%, 0.001%, 0.0001%, 0.00001%, or less by volume. The chamber can be then pulled down to a vacuum to reduce the pressure surrounding the substrate to be less than 0.1, 0.5, 1, 2, 3, 4, 5, 6, 7, 8, 9, 10, 25, 50, 75, 100, 200, 300, 400, 500 or 1000 mTorr. In some cases, the chamber can be filled with nitrogen subsequent to the vacuum step and the roof can be slid open again to allow access by auxiliary parts of the system, for example a printer. In some cases, the flowcell can be opened. The substrate/wafer can be mounted with the waste manifold displaced sideways, as illustrated in FIG. 9 part B. This set-up can allow easier inkjet access to the wafer. At this point the reagents can be deposited into the microwells. In some embodiments, the lids of the resolved enclosures (i.e. flowcells) can serve as a waste collector, and the liquid of reagents may flow thereto. The arrows in FIG. 9 parts B and C represent an exemplary flow direction for the reagents. In some cases, reagents can enter through the thin gap on the bottom, passing through the holes in the substrate (e.g. a silicon wafer), and being collected in the waste collector as illustrated in FIG. 9 part C. In some cases, gas may be purged through an upper or bottom manifold to drive liquid out, e.g. through the bottom or top of the flowcell. An exit or inlet port can be connected to vacuum to complete drying. The vacuum port can be connected to the waste side or the inlet side, as illustrated in FIG. 10 parts A-C. In some embodiments, there can be a plurality of pressure release holes that pass through the substrate (i.e. wafer). The plurality of holes can be more than a about 1000, 5000, 10,000, 50,000, 100,000, 500,000, 1,000,000 or 2,000,000. In some cases, the plurality of holes can be more than 5 millions. In some cases, the microstructures for synthesis as described in further detail elsewhere herein serve as pressure release holes. These holes can allow gas to pass through from one side of the wafer as the resolved enclosures are evacuated to dry down the substrate. In some cases, for example if the air is driven out of the waste collector side, the air pressure of the waste collector side, $P_{waste}$, may be maintained at substantially the same level as the air pressure of the inlet side, $P_{inlet}$. In some embodiments, a port that connects the inlet manifold to the waste collector can be used. Thus, a plurality of the steps described herein, such as scanning, depositing, flooding, washing, purging, and/or drying, can be performed without transporting the wafer substrates.

The resolved reactors formed by sealing the first substrate and the second substrate may be enclosed in chambers with controlled humidity, air content, vapor pressure, and/or pressure forming an assembly with a controlled environment. In some embodiments, the humidity of the chambers can be saturated or about 100% to prevent liquid evaporation from the resolved reactors during the reactions. For example, the humidity can be controlled to about, less than about, or more than about 100%, 99.5%, 99%, 98.5%, 98%, 97.5%, 97%, 96.5%, 96%, 95.5%, 95%, 94%, 93%, 92%, 91%, 90%, 89%, 88%, 87%, 86%, 85%, 84%, 83%, 82%, 81%, 80%, 75%, 70%, 65%, 60%, 55%, 50%, 45%, 40%, 35%, 30% or 25%.

Systems described herein, such as those with controlled environment assemblies described above may include a vacuum device/chuck and/or a temperature control system operatively connected with the plurality of resolved reactors. The substrates may be positioned on a vacuum chuck. The vacuum chuck may include surface irregularities positioned directly underneath the substrate. In various embodiments, the surface irregularities may comprise channels or recesses. The vacuum chuck may be in fluid communication with the substrate for drawing gas out of the spaces defined by the channels. Methods of maintaining the substrate on vacuum device are described in further detail in U.S. Pat. No. 8,247,221, which is herein incorporated by reference in its entirety.

In various embodiments, the substrate (e.g. a silicon wafer) may be positioned onto a chuck, such as the vacuum chuck described above. FIG. 10 parts A-C exemplifies a system assembly of a single groove vacuum chuck and a sintered metal piece in between the substrate and the temperature control device. The vacuum chuck can comprise a single groove with suitable dimensions to hold a substrate. In some embodiments, the vacuum chuck is designed such that a substrate can be held in place during one or more of the methods described herein. The vacuum chuck, illustrated in FIG. 10 part A as an example, comprises a single 1-5 mm groove with approximately 198 mm in diameter. In some cases, single groove vacuum chuck designs can be used to provide improved heat transfer to the substrate. FIG. 10 part B illustrates a sintered metal insert that is situated in between the substrate (e.g. silicon wafer) and the vacuum chuck, being fixed in place with adhesives. In some embodiments, the chuck can be an electrostatic chuck, as further described in U.S. Pat. No. 5,530,516, which is herein incorporated by reference in its entirety.

The plurality of resolved reactor caps can be aligned with the plurality of resolved loci on the first surface forming a temporary seal between the first surface and the capping element using any methods that are known in the art, as described in the U.S. Pat. No. 8,367,016 and European Patent No. EP 0126621 B 1, both of which are herein incorporated by reference in their entirety. For example, for a substrate with a plurality of resolved loci having x, y, and z dimensions and a locus depth center point located along the z dimension, the locus depth center point can be located a known z dimension distance from a fiducial marking embedded within the substrate. The substrate can be placed within an imaging system that can include an optical device capable of detecting the fiducial marking. The optical device can define an optical path axially aligned with the z dimension and can have a focal plane perpendicular to the optical path. When the focal plane is moved along the optical path, the fiducial marking can be maximally detected when the focal plane is at the z depth in comparison to when the focal plane is not substantially in-plane with the z depth. Fiducial markings can be selectively placed in a suitable spatial arrangement on a first substrate, for example a synthesis wafer comprising a plurality of resolved loci, and/or the second substrate, for example a reactor element comprising a plurality of capping elements. In some embodiments, the global alignment fiducial marking can be formed close to a resolved locus. Depending upon the application, there may be variations, alternatives, and modifications. For example, two of the fiducial markings may be within a vicinity of the resolve loci and the third fiducial marking may be at the edge of the substrate. For another example, the pattern of the microstructures in substrates described herein may itself be selected in a recognizable fashion suitable for alignment, for example in an asymmetric pattern, and can be used for alignment. In some cases, the fiducial marking serves as an alignment point to correct for depth of field or other optical characteristics. U.S. Pat. No. 4,123,661, which is herein incorporated by reference in its entirety discloses electronic beam alignment make on a substrate, the marks being adjacent each other but separated by a distance so that the rising and falling slopes of the marks can be detected by a video signal, hence allowing alignments.

The system may comprise a heating component, a cooling component, or a temperature controlled element (e.g., a thermal cycling device). In various embodiments, a thermal cycling device for use with a plurality of resolved reactors may be configured to perform nucleic acid amplification or assembly, such as PCR or PCA or any other suitable nucleic acid reaction described herein or known in the art. The temperature can be controlled such that the temperatures within the reactors can be uniform and heat can be conducted quickly. In various embodiments, the systems described herein may have detection components for endpoint or real-time detection from the reactors or the individual microstructures within substrates, for example during oligonucleotide synthesis, gene assembly or nucleic acid amplification.

Any of the systems described herein, may be operably linked to a computer and may be automated through a computer either locally or remotely. Computers and computer systems for the control of the system components described herein are further described elsewhere herein.

Primary Compositions—Oligonucleotides

As used herein, the terms "preselected sequence", "predefined sequence" or "predetermined sequence" are used interchangeably. The terms mean that the sequence of the polymer is known and chosen before synthesis or assembly of the polymer. In particular, various aspects of the invention are described herein primarily with regard to the preparation of nucleic acids molecules, the sequence of the oligonucleotide or polynucleotide being known and chosen before the synthesis or assembly of the nucleic acid molecules. In one embodiment, oligonucleotides are short nucleic acid molecules. For example, oligonucleotides may be from about 10 to about 300 nucleotides, from about 20 to about 400 nucleotides, from about 30 to about 500 nucleotides, from about 40 to about 600 nucleotides, or more than about 600 nucleotides long. Those of skill in the art appreciate that the oligonucleotide lengths may fall within any range bounded by any of these values (e.g., from about 10 to about 400 nucleotides or from about 300 to about 400 nucleotides etc.). Suitably short or long oligonucleotides may be used as necessitated by the specific application. Individual oligonucleotides may be designed to have a different length from another in a library. Oligonucleotides can be relatively short, e.g. shorter than 200, 100, 80, 60, 50, 40, 30, 25, 20, 15, 12, 10, 9, 8, 7, 6, 5, or 4 nucleotides, more particularly. Relatively longer oligonucleotides are also contemplated; in some embodiments, oligonucleotides are longer than or equal to 7, 8, 9, 10, 11, 12, 13, 14, 15, 16, 17, 18, 19, 20, 25, 30, 35, 40, 50, 60, 70, 80, 90, 100, 125, 150, 200, 250, 300, 350, 400, 500, 600 nucleotides, or longer. Typically, oligonucleotides are single-stranded DNA or RNA molecules.

In one aspect of the invention, a device for synthesizing a plurality of nucleic acids having a predetermined sequence is provided. The device can include a support having a plurality of features, each feature having a plurality of oligonucleotides. In some embodiments, the plurality oligonucleotides having a predefined sequence are immobilized at different discrete features of a solid support. In some embodiments, the oligonucleotides are single-stranded. In some embodiments, the plurality of oligonucleotide sequences may comprise degenerate sequences. In some embodiments, the oligonucleotides are support-bound. In some embodiments, the device comprises a solid support having a plurality of spots or features, and each of the plurality of spots includes a plurality of support-bound oligonucleotides. In some embodiments, the oligonucleotides are covalently linked through their 3' end to the solid support. Yet, in other embodiments the oligonucleotides are covalently linked through their 5' end to the solid support.

In some embodiments, the surface or support-bound oligonucleotides are immobilized through their 3' end. It should be appreciated that by 3' end, it is meant the sequence downstream to the 5' end, for example 2, 3, 4, 5, 6, 7, 10, 15, 20 nucleotides or more downstream from the 5' end, for another example on the 3' half, third, or quarter of the sequence, for yet another example, less than 2, 3, 4, 5, 6, 7, 10, 15, or 20 nucleotides away from the absolute 3' end and by 5' end it is meant the sequence upstream to the 3' end, for example 2, 3, 4, 5, 6, 7, 10, 15, 20 nucleotides or more upstream from the 3' end, for another example on the 5' half, third, or quarter of the sequence, for yet another example, less than 2, 3, 4, 5, 6, 7, 10, 15, or 20 nucleotides away from the absolute 5' end. For example, an oligonucleotide may be immobilized on the support via a nucleotide sequence (e.g., a degenerate binding sequence), a linker or spacer (e.g., a moiety that is not involved in hybridization). In some embodiments, the oligonucleotide comprises a spacer or linker to separate the oligonucleotide sequence from the support. Useful spacers or linkers include photocleavable linkers, or other traditional chemical linkers. In one embodiment, oligonucleotides may be attached to a solid support through a cleavable linkage moiety. For example, the solid support may be functionalized to provide cleavable linkers for covalent attachment to the oligonucleotides. The linker moiety may be of six or more atoms in length. Alternatively, the cleavable moiety may be within an oligonucleotide and may be introduced during in situ synthesis. A broad variety of cleavable moieties are available in the art of solid phase and microarray oligonucleotide synthesis (see e.g., Pon, R., Methods Mol. Biol. 20:465-496 (1993); Verma et al, Annu. Rev. Biochem. 67:99-134 (1998); U.S. Pat. Nos. 5,739,386, 5,700,642 and 5,830,655; and U.S. Patent Publication Nos. 2003/0186226 and 2004/0106728). A suitable cleavable moiety may be selected to be compatible with the nature of the protecting group of the nucleoside bases, the choice of solid support, and/or the mode of reagent delivery, among others. In an exemplary embodiment, the oligonucleotides cleaved from the solid support contain a free 3'-OH end. Alternatively, the free 3'-OH end may also be obtained by chemical or enzymatic treatment, following the cleavage of oligonucleotides. In various embodiments, the invention relates to methods and compositions for release of support or surface bound oligonucleotides into solution. The cleavable moiety may be removed under conditions which do not degrade the oligonucleotides. Preferably the linker may be cleaved using two approaches, either simultaneously under the same conditions as the deprotection step or subsequently utilizing a different condition or reagent for linker cleavage after the completion of the deprotection step.

In other embodiments, the oligonucleotides are in solution. For example, oligonucleotides may be provided within a discrete volume such as a droplet or microdroplet at different discrete features. In some embodiments, discrete microvolumes of between about 0.5 pL and about 100 nL may be used. However, smaller or larger volumes may be used. In some embodiments, a suitable dispenser or continuous flow, such as flow through microstructures that is actuated by a pump, may be used for transferring volumes of less than 100 nL, less than 10 nL, less than 5 nL, less than 100 pL, less than 10 pL, or less than 0.5 pL to and between microstructures of substrates described herein. For example, small volumes from one or more microstructures of an oligonucleotide synthesis wafer may be dispensed into a reactor cap of a capping element by pushing a fluid through the oligonucleotide synthesis wafer.

In some embodiments, a plurality of nucleotide acid constructs are provided at different features of the support. In some embodiments, the nucleic acid constructs, including short oligonucleotides and longer/assembled polynucleotides, are partially double-stranded or duplex oligonucleotides. As used herein, the term "duplex" refers to a nucleic acid molecule that is at least partially double-stranded. The terms "nucleoside" or "nucleotide" are intended to include those moieties which contain not only the known purine and pyrimidine bases, but also other heterocyclic bases that have been modified. Such modifications include methylated purines or pyrimidines, acylated purines or pyrimidines, alkylated riboses or other heterocycles or any other suitable modifications described herein or otherwise known in the art. In addition, the terms "nucleoside" and "nucleotide" include those moieties that contain not only conventional ribose and deoxyribose sugars, but other sugars as well. Modified nucleosides or nucleotides also include modifications on the sugar moiety, e.g., wherein one or more of the hydroxyl groups are replaced with halogen atoms or aliphatic groups, or are functionalized as ethers, amines, or the like.

It will be appreciated that, as used herein, the terms "nucleoside" and "nucleotide" refer to nucleosides and nucleotides containing not only the conventional purine and pyrimidine bases, i.e., adenine (A), thymine (T), cytosine (C), guanine (G) and uracil (U), but also protected forms thereof, e.g., wherein the base is protected with a protecting group such as acetyl, difluoroacetyl, trifluoroacetyl, isobutyryl or benzoyl, and purine and pyrimidine analogs. Suitable analogs will be known to those skilled in the art and are described in the pertinent texts and literature. Common analogs include, but are not limited to, 1-methyladenine, 2-methyladenine, N6-methyladenine, N6-isopentyladenine, 2-methylthio-N6-isopentyladenine, N,N-dimethyladenine, 8-bromoadenine, 2-thiocytosine, 3-methylcytosine, 5-methylcytosine, 5-ethylcytosine, 4-acetylcytosine, 1-methylguanine, 2-methylguanine, 7-methylguanine, 2,2-dimethylguanine, 8-bromoguanine, 8-chloroguanine, 8-aminoguanine, 8-methylguanine, 8-thioguanine, 5-fluorouracil, 5-bromouracil, 5-chlorouracil, 5-iodouracil, 5-ethyluracil, 5-propyluracil, 5-methoxyuracil, 5-hydroxymethyluracil, 5-(carboxyhydroxymethyl)uracil, 5-(methylanminomethyl)uracil, 5-(carboxymethylaminomethyl)-uracil, 2-thiouracil, 5-methyl-2-thiouracil, 5-(2-bromovinyl)uracil, uracil-5-oxyacetic acid, uracil-5-oxyacetic acid methyl ester, pseudouracil, 1-methylpseudouracil, queosine, inosine, 1-methylinosine, hypoxanthine, xanthine, 2-aminopurine, 6-hydroxyaminopurine, 6-thiopurine and 2,6-diaminopurine. In addition, the terms "nucleoside" and "nucleotide" include those moieties that contain not only conventional ribose and deoxyribose sugars, but other sugars as well. Modified nucleosides or nucleotides also include modifications on the sugar moiety, e.g., wherein one or more of the hydroxyl groups are replaced with halogen atoms or aliphatic groups, or are functionalized as ethers, amines, or the like.

As used herein, the term "oligonucleotide" shall be generic to polydeoxynucleotides (containing 2-deoxy-D-ribose), to polyribonucleotides (containing D-ribose), to any other type of polynucleotide that is an N-glycoside of a purine or pyrimidine base, and to other polymers containing nonnucleotidic backbones (for example PNAs), providing that the polymers contain nucleobases in a configuration that allows for base pairing and base stacking, such as is found in DNA and RNA. Thus, these terms include known types of oligonucleotide modifications, for example, substitution of one or more of the naturally occurring nucleotides with an analog, internucleotide modifications such as, for example, those with uncharged linkages (e.g., methyl phosphonates, phosphotriesters, phosphoramidates, carbamates, etc.), with negatively charged linkages (e.g., phosphorothioates, phosphorodithioates, etc.), and with positively charged linkages (e.g., aminoalkylphosphoramidates, aminoalkylphosphotriesters), those containing pendant moieties, such as, for example, proteins (including nucleases, toxins, antibodies, signal peptides, poly-L-lysine, etc.), those with intercalators (e.g., acridine, psoralen, etc.), those containing chelators (e.g., metals, radioactive metals, boron, oxidative metals, etc.). There is no intended distinction in length between the term "polynucleotide" and "oligonucleotide," and these terms will be used interchangeably.

The term "attached," as in, for example, a substrate surface having a moiety "attached" thereto, includes covalent binding, adsorption, and physical immobilization. The terms "binding" and "bound" are identical in meaning to the term "attached."

In various embodiments, the invention relates to the synthesis, such as chemical synthesis, of molecules other than nucleic acids. The terms "peptide," "peptidyl" and "peptidic" as used throughout the specification and claims are intended to include any structure comprised of two or more amino acids. For the most part, the peptides in the present arrays comprise about 5 to 10,000 amino acids, preferably about 5 to 1000 amino acids. The amino acids forming all or a part of a peptide may be any of the twenty conventional, naturally occurring amino acids, i.e., alanine (A), cysteine (C), aspartic acid (D), glutamic acid (E), phenylalanine (F), glycine (G), histidine (H), isoleucine (I), lysine (K), leucine (L), methionine (M), asparagine (N), proline (P), glutamine (Q), arginine (R), serine (S), threonine (T), valine (V), tryptophan (W), and tyrosine (Y). Any of the amino acids in the peptidic molecules forming the present arrays may be replaced by a non-conventional amino acid. In general, conservative replacements are preferred. Conservative replacements substitute the original amino acid with a non-conventional amino acid that resembles the original in one or more of its characteristic properties (e.g., charge, hydrophobicity, stearic bulk; for example, one may replace Val with Nval). The term "non-conventional amino acid" refers to amino acids other than conventional amino acids, and include, for example, isomers and modifications of the conventional amino acids (e.g., D-amino acids), non-protein amino acids, post-translationally modified amino acids, enzymatically modified amino acids, constructs or structures designed to mimic amino acids (e.g., α,α-disubstituted amino acids, N-alkyl amino acids, lactic acid, β-alanine, naphthylalanine, 3-pyridylalanine, 4-hydroxyproline, O-phosphoserine, N-acetylserine, N-formylmethionine, 3-methylhistidine, 5-hydroxylysine, and norleucine), and peptides having the naturally occurring amide —CONH— linkage replaced at one or more sites within the peptide backbone with a non-conventional linkage such as N-substituted amide, ester, thioamide, retropeptide (—NHCO—), retrothioamide (—NHCS—), sulfonamido (—SO2NH—), and/or peptoid (N-substituted glycine) linkages. Accordingly, the peptidic molecules of the array include pseudopeptides and peptidomimetics. The peptides of this invention can be (a) naturally occurring, (b) produced by chemical synthesis, (c) produced by recombinant DNA technology, (d) produced by biochemical or enzymatic fragmentation of larger molecules, (e) produced by methods resulting from a combination of methods (a) through (d) listed above, or (f) produced by any other means for producing peptides.

The term "oligomer" is meant to encompass any polynucleotide or polypeptide or other chemical compound with repeating moieties such as nucleotides, amino acids, carbohydrates and the like.

In some examples, the device has at least 2, 3, 4, 5, 6, 7, 8, 9, 10, 12, 15, 18, 20, 25, 30, 40, 50, 100, 1,000, 4,000, 10,000, 100,000, 1,000,000, or more different features (or "regions" or "spots") at a particular location (i.e., an "address"). It should be appreciated that a device may comprise one or more solid supports. Each addressable location of a device may hold a different composition, such as a different oligonucleotide. Alternatively, groups of addressable location of a device may hold wholly or substantially similar compositions, e.g. oligonucleotides, that are different from those held in other groups of microstructures of a device.

The number of each oligonucleotide, which may be prepared by methods of the invention in individually addressable locations and/or in mixed populations can range from five to 500,000, from 500 to 500,000, from 1,000 to 500,000, from 5,000 to 500,000, from 10,000 to 500,000, from 20,000 to 500,000, from 30,000 to 500,000, from 5,000 to 250,000, from 5,000 to 100,000, from five to 5,000, from five to 50,000, from 5,000 to 800,000, from 5,000 to 1,000,000, from 5,000 to 2,000,000, from 10,000 to 2,000,000, from 20,000 to 1,000,000, from 30,000 to 2,000,000, etc. In various embodiments, about or more than about 5, 10, 20, 50, 100, 500, 1000, 10000, 100000, 1000000, 10000000, 100000000, or more copies of each oligonucleotide can be synthesized. In some cases, less than 100000000, 10000000, 1000000, 100000, 10000, 1000, 100, or fewer copies of an oligonucleotide may be synthesized.

Oligonucleotide phosphorothioates (OPS) are modified oligonucleotides where one of the oxygen atoms in the phosphate moiety is replaced by sulfur. Phosphorothioates having sulfur at a non-bridging position are widely used. OPS are substantially more stable towards hydrolysis by nucleases. This property renders OPS to be an advantageous candidate to be used as antisense oligonucleotides in in vitro and in vivo applications comprising extensive exposure to nucleases. Similarly, to improve the stability of siRNA, at least one phosphorothioate linkage is often introduced at the 3'-terminus of sense and/or antisense strands. In some embodiments, methods and compositions of the invention relate to the de novo/chemical synthesis of OPSs. The synthesis of a large number of OPSs may be carried out in parallel using the methods and compositions described herein.

Amplification of Single Stranded Nucleic Acids

In various embodiments, the methods and systems relate to amplification of single stranded nucleic acids. Accordingly, single stranded nucleic acids, e.g. single stranded DNA (ssDNA), can be amplified in an isolated sample, in a plurality of samples in parallel or in a multiplexed format having a plurality of different single stranded nucleic acids within the same sample. The plurality of samples that can be amplified in parallel format may be at least or about at least 1, 2, 3, 4, 5, 10, 20, 25, 50, 55, 100, 150, 200, 250, 300, 350, 500, 550, 600, 650, 700, 750, 800, 850, 900, 950, 1000, or more. The plurality of samples that can be amplified in parallel format may be between 1-1000, 2-950, 3-900, 4-850, 5-800, 10-800, 20-750, 25-700, 30-650, 35-600, 40-550, 45-500, 50-450, 55-400, 60-350, 65-250, 70-200, 75-150, 80-100. Those of skill in the art will appreciate that the plurality of samples that can be amplified in parallel format may fall between any ranges, bound by any of these values, for example 3-800. The number of multiplexed amplification reactions may be at least or about at least 1, 2, 3, 4, 5, 10, 20, 25, 50, 100, or more. The number of multiplexed amplification reactions may be between 1-100, 2-50, 3-25, 4-20, 5-10. Those of skill in the art will appreciate that the number of multiplexed amplification reactions may fall within any range bound by any of these values, for example 3-100.

The number of different single stranded nucleic acids within the same sample can be at least or about at least 1, 2, 3, 10, 50, 100, 150, 200, 1000, 10000, 100000, or more. The number of different single stranded nucleic acid within the same sample can be at most or about at most 10000, 10000, 1000, 200, 150, 100, 50, 10, 3, 2, 1, or less. The number of different single stranded nucleic acids within the same sample can be between 1-100000, 2-10000, 3-1000, 10-200, 50-100. Those of skill in the art appreciate that the number of different single stranded nucleic acid within the same sample can be between any of these ranges, bound by any of these values, for example 3-100.

The single stranded target nucleic acids may be at least or about at least 10, 20, 50, 100, 200, 500, 1000, 3000, or more nucleotides long. The single stranded target nucleic acids may be at most or about at most 3000, 1000, 500, 200, 100, 50, 20, 10, or less, nucleotides long. The single stranded target nucleic acids may be between 50-500, 75-450, or 100-400 nucleotides long. Those of skill in the art appreciate that length of the single stranded target nucleic acids may fall within any range bound by any of these values, for example between 50-1000.

Figure 64:
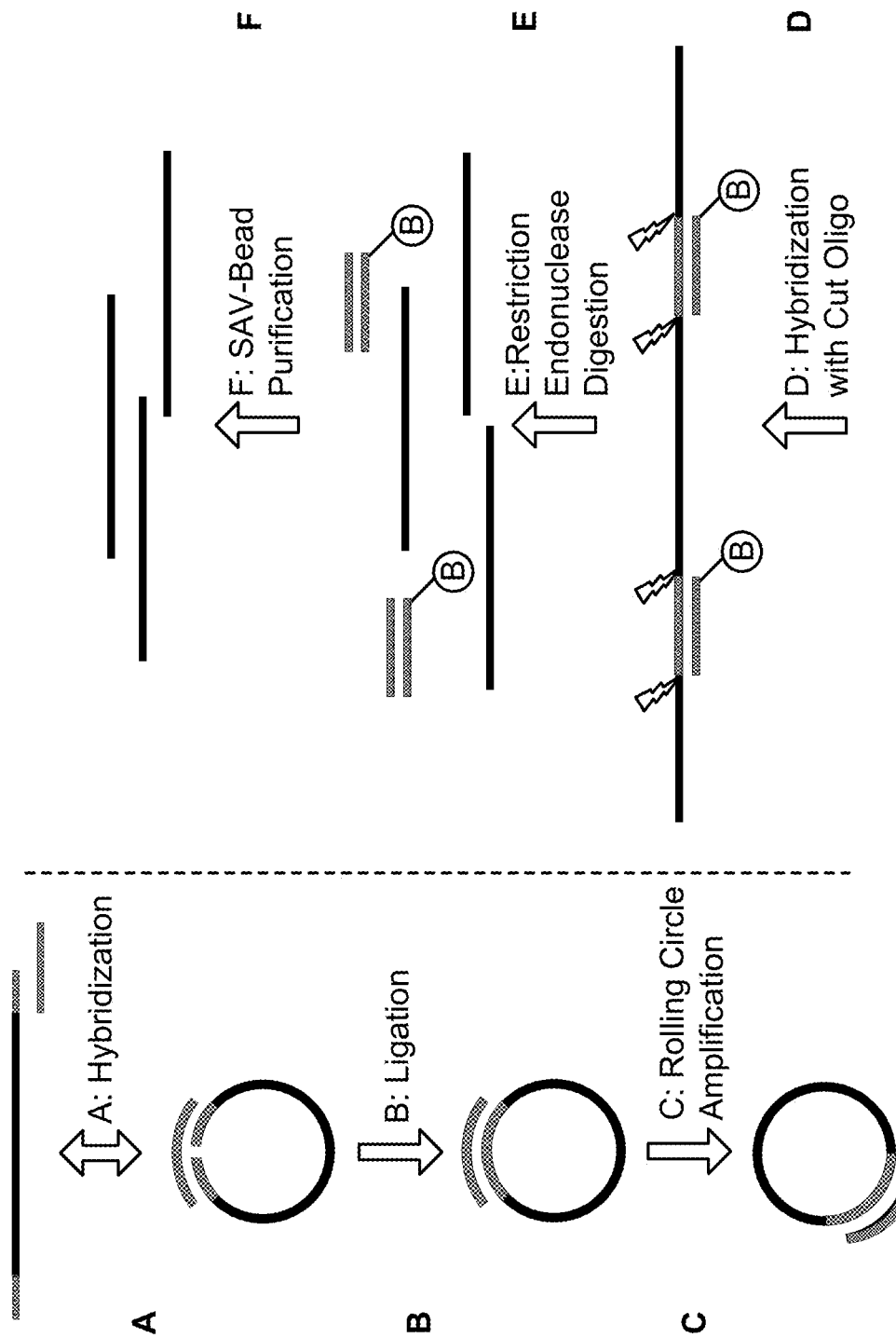
FIG. 64 parts A-F represent a method for the amplification of single stranded nucleic acids.

Referring now to FIG. 64, a single stranded target nucleic acid may be flanked with one or more adaptor hybridization sequences. These adaptor hybridization sequences may be at least or about at least 12, 13, 14, 15, 16, 17, 18, 19, 20, or more nucleotides long. These adaptor hybridization sequences may be at least or about at least 20, 19, 18, 17, 16, 15, 14, 13, 12, or fewer nucleotides long. The adaptor hybridization sequences may be between 15-20, 16-19, 17-18 nucleotides long. Those of skill in the art appreciate that length the adaptor hybridization sequences may fall between a range bound by any of these values, for example between 15-17, 12-20, or 13, 25. The adaptor hybridization sequences may be shared by a plurality of nucleic acids within a sample, wherein such plurality of single stranded nucleic acids have varying single stranded target nucleic acid regions. Multiple groups of single stranded nucleic acids, each group having different adaptor hybridization sequences, may coexist within a sample and be subjected to the amplification methods described herein. The different adaptor hybridization sequences may differ from each other by at least or at least about 1, 2, 5, 10, 15, 20, 25, 30, 35, 40, 45, 50, or more, nucleotides. The different adaptor hybridization sequences may differ from each other by at most or at most about 50, 45, 40, 35, 30, 25, 20, 15, 10, 5, 2, 1, or fewer nucleotides. The different adaptor hybridization sequences may differ from each other by a number of nucleotides between 1-50, 2-45, 5-40, 10-35, 15-25, or 20-30. Those of skill in the art appreciate that, the different adaptor hybridization sequences may differ from each other by a number of nucleotides that falls in any ranges bound by any of these values, for example between 2-50. Thus, a single universal adaptor may be used for a number of single stranded nucleic acids sharing end sequences such that the universal adaptor is hybridizable to all of them. A plurality of adaptors may be used in a sample with a plurality of groups of single stranded nucleic acids, wherein each of the adaptors is hybridizable to the end sequences in one or more of the groups. At least or at least about 1, 2, 3, 4, 5, 10, 20, 25, 30, 50, 100, or more adaptors may be used in a multiplexed fashion. At most or about at most 100, 50, 30, 25, 20, 10, 5, 4, 3, 21, 1 or fewer adaptors may be used in a multiplexed fashion. Between 1-100, 2-50, 3-30, 4-25, 5-20, adaptors may be used in a multiplexed fashion. Those of skill in the art appreciate that the number of adaptors that may be used in a multiplexed fashion may fall within any ranges, bound by any of these values, for example between 2-30. A first sequence on an adaptor may hybridize to the 5' end of a single stranded nucleic acid and a second sequence on the adaptor may hybridize to the 3' end of the same single stranded nucleic acid, facilitating the circularization of the single stranded nucleic acid.

The single stranded nucleic acids may be circularized upon hybridization with an adaptor. The circularized single stranded nucleic acid may be joined at its 5' and 3' ends, forming a contiguous circle. Various ligation methods and enzymes are suitable for the reaction as described elsewhere herein and otherwise known in the art.

The adaptor can be extended using the circularized single stranded nucleic acid as a template. Alternatively, one or more different primers may be used to anneal elsewhere on the circle in addition or instead of the adaptor and can be extended with a polymerase enzyme. The extension reaction, such as rolling circle amplification, multi-primer rolling circle amplification or any other suitable extension reaction, can facilitate the creation of one long and linear single stranded amplicon nucleic acids comprising alternating replicas of the single stranded template nucleic acid and the adaptor hybridization sequences. In some embodiments, the combined replicas of the adaptor hybridization sequences are copies of the adaptor sequence, or differ by less than 8, 7, 6, 5, 4, 3, or 2 nucleotides. These sequences will together be referred to as "adaptor copies" for ease, but it is understood that they may refer to a number of different types of sequences generated from the extension reaction using the circle as a template.

One or more auxiliary oligonucleotides may be provided to anneal to the single stranded amplicon nucleic acids. The auxiliary oligonucleotides may be partially or completely complementary to the adaptor copies. The hybridization of the auxiliary oligonucleotide to the single stranded amplicon nucleic acid can form alternating single and double stranded regions. The single stranded regions may correspond to replicas of the single stranded template nucleic acid sequence. The hybridization of the auxiliary oligonucleotide to the single stranded amplicon nucleic acid, e.g. at adaptor copies, can generate recognition sites for a cleaving agent, such as a restriction endonucleases, e.g. a Type IIS restriction endonucleases. The sequences can be designed in such a way that the cutting site for the cleaving agent falls at or near the juncture of the single and double stranded regions. In some cases, upon cleavage with one or more cleaving agents, a plurality of single stranded replicas of the single stranded target nucleic acids will be formed, wherein the single stranded target nucleic acids do not contain any portions from the adaptor copies, or contain less than 15, 14, 13, 12, 11, 10, 9, 8, 7, 6, 5, 4, 3, 2, or 1 nucleotides from the adaptor copies.

The auxiliary oligonucleotides may have an affinity tag, such as biotin or a biotin derivative. The affinity tag may be at the 5' end, 3' end, or in the middle of the oligonucleotide. Purification of the auxiliary oligonucleotides from the sample may be facilitated using an affinity binding partner on a purification medium, such as streptavidin coated beads surfaces, or any other suitable affinity purification method. Cleaved adaptor copies or portion thereof may also be purified along with the auxiliary oligonucleotides, facilitated by their hybridization with the auxiliary oligonucleotides. In multiplexed reactions using a plurality of adaptors, a plurality of auxiliary oligonucleotides may be used, each hybridizing to a different group of single stranded amplicon nucleic acids, for example at the locations of the adaptor copies. Alternative purification methods, such as HPLC or PAGE purification, may be used with or without affinity tagged oligonucleotides.

Figure 65:
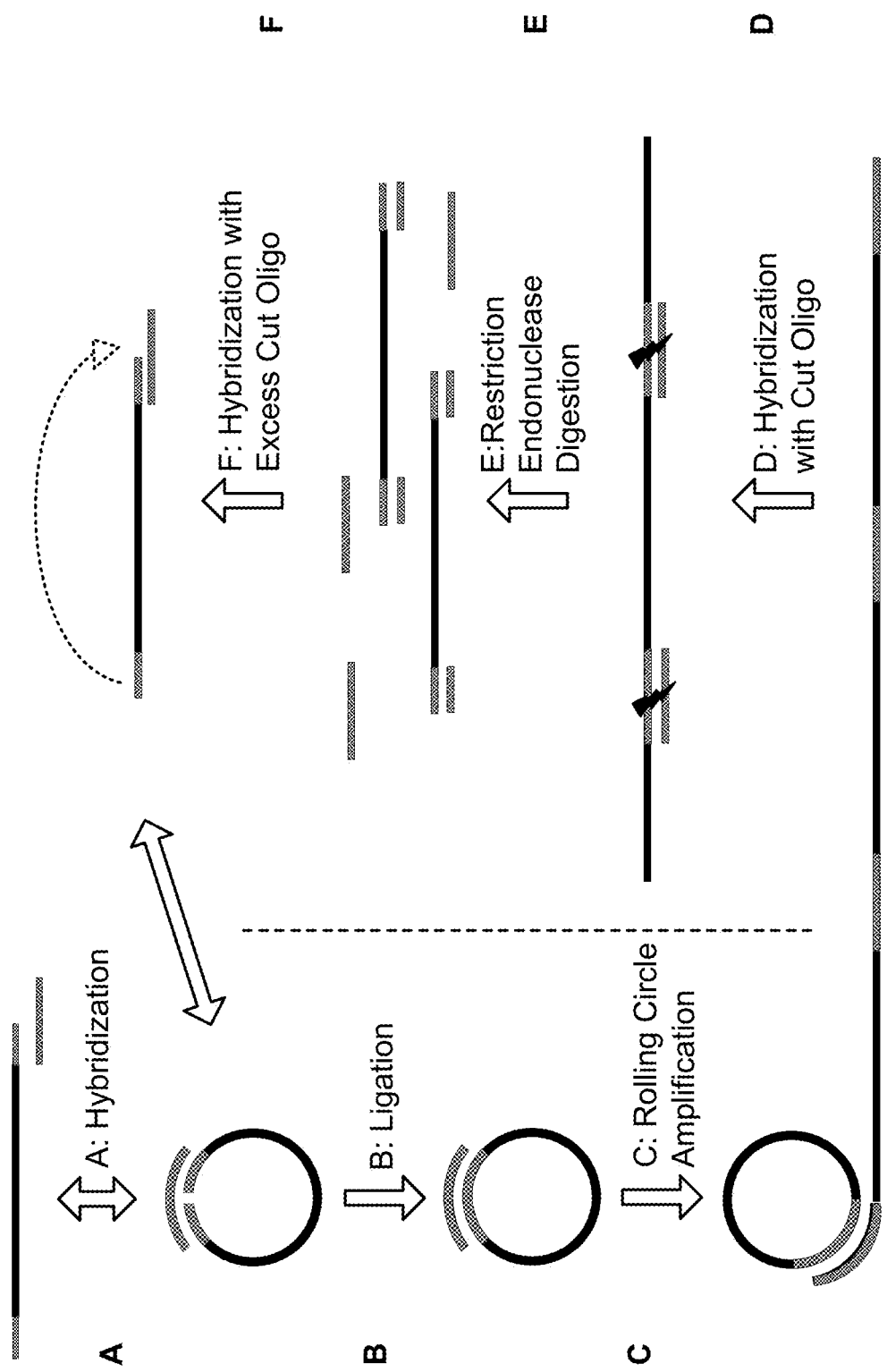
FIG. 65 parts A-F represent method for the amplification of single stranded nucleic acids, which may be coupled to the method illustrated in FIG. 64.

Referring now to FIG. 65 parts A-F, single stranded nucleic acids may also be amplified in a similar way to the method described for FIG. 64 parts A-F, with the exception that the sequences and the cleaving agent is selected such that the cutting site falls within the adaptor copies such that single stranded replicas of the single stranded target nucleic acid sequence are formed with flanking regions. Such flanking regions may be reverse complements of the flanking regions of the original single stranded target nucleic acid sequence. Alternatively, depending on the exact location of the cutting site, they may "shift" nucleotides from one flanking region to the other. In such cases, a reverse complementary oligonucleotide to the adaptor nucleotide can still effectively hybridize to the both ends facilitating another round of circularization. Thus, the method illustrated in FIG. 65 parts A-F can be repeated a plurality of times, such as at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 or more times, alone or as a precursor reaction to the method illustrated in FIG. 64 parts A-F, to amplify the single stranded target nucleic acid. The method illustrated in FIG. 64 parts A-F can be used as a last round to get rid of the flanking regions, leaving behind amplified single stranded copies or replicas of the single stranded target nucleic acids.

The extension reaction product, such as a rolling cycle amplification product, comprising single-stranded repeating units of amplified desired oligonucleotides and adaptor oligonucleotides, may be cleaved within or near the adaptor oligonucleotides to generate released desired oligonucleotides, wherein the released desired oligonucleotides may or may not comprise adaptor nucleotides at the 5' or 3' ends of the desired oligonucleotide. In some embodiments, the cleaving is accomplished at the very juncture of the single-stranded repeating units of amplified desired oligonucleotides and adaptor sequences. In some embodiments, one or more regions of an adaptor sequence comprise a molecular barcode, protein binding site, restriction endonuclease site, or any combination thereof. In some embodiments, the amplification product is cleaved with one or more restriction endonucleases at or near a restriction endonuclease recognition site, wherein the recognition site is located within an adaptor oligonucleotide sequence. Prior to cleavage with an endonuclease, the amplification product can be hybridized with an auxiliary oligonucleotide comprising a sequence complementary to the adaptor oligonucleotide sequence comprising the restriction endonuclease recognition site.

The amplification product may be cleaved at the 5' end of a recognition site by Type II endonucleases. The cutting site may be 1, 2, 3, 4, 5, 6, 7, 8, 9, 10, 11, 12, 13, 14, 15, 16, 17, 18, 19, 20, 21, 22, 23, 24, 25 nucleotides or more upstream from the first nucleotide of the recognition site. The 5' or 3' end of a recognition site may form a 0, 1, 2, 3, 4, or 5 nucleotide overhang. Blunt Type II endonucleases which cleave with a 0 nucleotide overhang include MlyI and SchI. Exemplary Type IIS endonucleases which generate 5' overhangs (e.g., 1, 2, 3, 4, 5 nucleotides overhangs) include, but are not limited to, AlwI, BccI, BceAI, BsmAI, BsmFI, FokI, HgaI, PleI, SfaNI, BfuAI, BsaI, BspMI, BtgZI, EarI, BspQI, SapI, SgeI, BceFI, BslFI, BsoMAI, Bst71I, FaqI, AceIII, BbvII, BveI, and LguI. Nicking endonucleases which remove the recognition site and cleave on the 5' site of the recognition site include, but are not limited to Nb.BsrDI, Nb.BtsI, AspCNI, BscGI, BspNCI, EcoHI, FinI, TsuI, UbaF11I, UnbI, Vpak11AI, BspGI, DrdII, Pfl1108I, and UbaPI.

The amplification product may be cleaved by non-Type IIS endonucleases which cleave at the 5' end of the recognition site on both strands to generate a blunt end. The amplification product may be cleaved by non-Type IIS endonucleases which cleave at the 5' end of the recognition site on one strand and in the middle of the recognition site on the other strand, generating a 5' overhang. Examples of endonucleases which generate a 5' overhang include, but are not limited to, BfuCI, DpnII, FatI, MboI, MluCI, Sau3AI, Tsp509I, BssMI, PspGI, StyD4I, Tsp45I, AoxI, BscFI, Bsp143I, BssMI, BseENII, BstMBI, Kzo9I, NedII, Sse9I, TasI, TspEI, AjnI, BstSCI, EcoRII, MaeIII, NmuCI, and Psp6I.

The amplification product may be cleaved by nicking endonucleases which cleave at the 5' end of a recognition site to produce a nick. The nicking site may be 1, 2, 3, 4, 5, 6, 7, 8, 9, 10, 11, 12, 13, 14, 15, 16, 17, 18, 19, 20, 21, 22, 23, 24, 25 nucleotides or more upstream from the first nucleotide of the recognition site. Exemplary nicking endonucleases include, but are not limited to, Nb.BsrDI, Nb.BtsI, AspCNI, BscGI, BspNCI, EcoHI, FinI, TsuI, UbaF11I, UnbI, Vpak11AI, BspGI, DrdII, Pfl1108I, and UbaPI.

The amplification product may be cleaved at the 3' end of a recognition site by Type IIS endonucleases. The 5' or 3' end of a recognition site may form a 0, 1, 2, 3, 4, or 5 nucleotide overhang. The cutting site may be 1, 2, 3, 4, 5, 6, 7, 8, 9, 10, 11, 12, 13, 14, 15, 16, 17, 18, 19, 20, 21, 22, 23, 24, 25 nucleotides or more downstream from the last nucleotide of the recognition site. Type IIS endonucleases which cleave at 0 nucleotides downstream of the last nucleotide of the recognition site include MlyI and SchI. Exemplary Type IIS endonucleases which generate 3' overhangs (e.g., 1, 2, 3, 4, 5 nucleotide overhangs) include, but are not limited to, Mn1I, BspCNI, BsrI, BtsCI, HphI, HpyAV, MboII, AcuI, BciVI, BmrI, BpmI, BpuEI, BseRT, BsgI, BsmI, BsrDI, BtsI, EciI, MmeI, NmeAIII, Hin4II, TscAI, Bce83I, BmuI, BsbI, and BscCI. Non-Type II endonucleases which remove the recognition site on one strand and generate a 3' overhang or blunt end on the other strand include, but are not limited to NlaIII, Hpy99I, TspRT, FaeI, Hin1II, Hsp92II, SetI, TaiI, TscI, TscAI, and TseFI. Nicking endonucleases which remove the recognition site and cut on the 3' end of the recognition site include Nt.AlwI, Nt.BsmAI, Nt.BstNBI, and Nt.BspQI.

The distance between the recognition site and the cleavage site may depend on the restriction endonuclease used for cleavage. For example, restriction endonucleases with cutting sites located 1 base pair downstream or upstream from a recognition site which may efficiently cleave under optimal reaction conditions include, but are not limited to, AgeI, ApaI, AscI, BmtI, BsaI, BsmBI, BsrGI, DdeI, DraIII, HpaI, MseI, PacI, PciI, PmeI, PvuI, SacII, SapI, Sau3AI, ScaI, SfiI, SmaI, SphI, StuI, and XmaI. Restriction endonucleases with cutting sites located 2 base pairs downstream or upstream from a recognition site which may efficiently cleave under optimal reaction conditions include, but are not limited to, AgeI, AluI, ApaI, AscI, BglII, BmtI, BsaI, BsiWI, BsmBI, BsrGI, BssHII, DdeI, DraIII, EagI, HpaI, KpnI, MseI, NlaIII, PacI, PciI, PmeI, PstI, PvuI, RsaI, SacII, SapI, Sau3AI, SbfI, ScaI, SfiI, SmaI, SphI, SspI, StuI, StyI, and XmaI. Restriction endonucleases with cutting sites located 3 base pairs downstream or upstream from a recognition site which may efficiently cleave under optimal reaction conditions include, but are not limited to, AgeI, AluI, ApaI, AscI, AvrII, BamHI, BglII, BmtI, BsaI, BsiWI, BsmBI, BsrGI, BssHII, DdeI, DraIII, EagI, FseI, HindIII, HpaI, KpnI, MfeI, MluI, MseI, NcoI, NdeI, NheI, NlaIII, NsiI, PacI, PciI, PmeI, PstI, RsaI, SacI, SacII, SalI, SapI, Sau3AI, SbfI, ScaI, SfiI, SmaI, SphI, SspI, StuI, StyI, and XmaI. Restriction endonucleases with cutting sites located 4 base pairs downstream or upstream from a recognition site which may efficiently cleave under optimal reaction conditions include, but are not limited to, AgeI, AluI, ApaI, AscI, AvrII, BamHI, BglII, BmtI, BsaI, BsiWI, BsmBI, BsrGI, BssHII, ClaI, DdeI, DraIII, EagI, EcoRI, FseI, HindIII, HpaI, KpnI, MfeI, MluI, MseI, NcoI, NdeI, NheI, NlaIII, NsiI, PacI, PciI, PmeI, PstI, PvuI, PvuII, RsaI, SacI, SacII, SalI, SapI, Sau3AI, SbfI, ScaI, SfiI, SmaI, SphI, SspI, StuI, StyI, XhoI, and XmaI. Restriction endonucleases with cutting sites located 5 base pairs downstream or upstream from a recognition site which may efficiently cleave under optimal reaction conditions include, but are not limited to, AgeI, AluI, ApaI, AscI, AvrII, BamHI, BglII, BmtI, BsaI, BsiWI, BsmBI, BsrGI, BssHII, ClaI, DdeI, DraIII, EagI, EcoRI, EcoRV, FseI, HindIII, HpaI, KpnI, MfeI, MluI, MseI, NcoI, NdeI, NheI, NlaIII, NsiI, NspI, PacI, PciI, PmeI, PstI, PvuI, PvuII, RsaI, SacI, SacII, SalI, SapI, Sau3AI, SbfI, ScaI, SfiI, SmaI, SphI, SspI, StuI, StyI, XhoI, and XmaI.

The adaptor sequence may comprise one or more restriction recognition sites. In some embodiments, the recognition site is at least 4, 5, or 6 base pairs long. In some embodiments, the recognition site is non-palindromic. In some embodiments, the adaptor oligonucleotide comprises two or more recognition sites. Two or more recognition sites may be cleaved with one or more restriction enzymes. It will be known to one of skill in the art that the cleavage of two or more recognition sites with two or more restriction enzymes may be achieved and/or perfected by buffer and reaction temperature optimization. Exemplary pairs of recognition sites in an adaptor sequence include, but are not limited to, MlyI-MlyI, MlyI-Nt.AlwI, BsaI-MlyI, MlyI-BciVI, and BfuCI-MlyI.

Genes

The methods and compositions of the invention in various embodiments allow for the construction of gene libraries comprising a collection of individually accessible polynucleotides of interest. The polynucleotides can be linear, can be maintained in vectors (e. g., plasmid or phage), cells (e. g., bacterial cells), as purified DNA, or in other suitable forms known in the art. Library members (variously referred to as clones, constructs, polynucleotides, etc.) can be stored in a variety of ways for retrieval and use, including for example, in multiwell culture or microtiter plates, in vials, in a suitable cellular environment (e.g., E. coli cells), as purified DNA compositions on suitable storage media (e.g., the Storage IsoCodeD ID™ DNA library card; Schleicher & Schuell BioScience), or a variety of other suitable library forms known in the art. A gene library may comprise at least about 10, 100, 200, 300, 400, 500, 600, 750, 1000, 1500, 2000, 3000, 4000, 5000, 6000, 7500, 10000, 15000, 20000, 30000, 40000, 50000, 60000, 75000, 100000 members, or more. Nucleic acid molecules described herein may be produced in microscale quantities (e.g., femtomoles to nanomoles quantities, such as from about 0.001 femtomole to about 1.0 nanomole, from about 0.01 femtomole to about 1.0 nanomole, from about 0.1 femtomole to about 1.0 nanomole, from about 0.001 femtomole to about 0.1 nanomole, from about 0.001 femtomole to about 0.01 nanomole, from about 0.001 femtomole to about 0.001 nanomole, from about 1.0 femtomole to about 1.0 nanomole, from about 1.0 femtomole to about 0.1 nanomole, from about 1.0 femtomole to about 0.01 nanomole, from about 1.0 femtomole to about 0.001 nanomole, from about 10 femtomoles to about 1.0 nanomole, from about 10 femtomoles to about 0.001 nanomole, from about 20 femtomoles to about 1.0 nanomole, from about 100 femtomoles to about 1.0 nanomole, from about 500 femtomoles to about 1.0 nanomole, from about 1 nanomole to about 800 nanomoles, from about 40 nanomoles to about 800 nanomoles, from about 100 nanomoles to about 800 nanomoles, from about 200 nanomoles to about 800 nanomoles, from about 500 nanomoles to about 800 nanomoles, from about 100 nanomoles to about 1,000 nanomoles, etc.). Those of skill in the art appreciate that the nucleic acid quantity may fall within any range bounded by any of these values (e.g., from about 0.001 femtomole to about 1000 nanomoles or from about 0.001 femtomole to about 0.01 femtomole). In general, nucleic acid molecules may be produced at quantities of about or more than about 0.001, 0.01, 0.1, 1, 10, 100, femtomoles, 1, 10, 100 picomoles, 1, 10, 100 nanomoles, 1 micromole, or more. In some embodiments, nucleic acid molecules may be produced at quantities of less than about 1 micromole, 100, 10, 1 nanomoles, 100, 10, 1 picomoles, 100, 10, 1, 0.1, 0.001, 0.001 femtomoles or less. In some embodiments, nucleic acid molecules may be produced at concentrations of about or more than about 0.01, 0.05, 0.1, 0.2, 0.3, 0.4, 0.5, 1, 2, 3, 4, 5, 6, 7, 8, 9, 10, 15, 20, 25, 30, 40, 50, 60, 70, 80, 90, 100, 150, 200, 250, 500, 750, 1000 nM. In some embodiments, the gene library is synthesized/assembled and/or held in a space that is less than 1000, 100, 10, 1 m$^3$, 100, 10, 1 dm$^3$, 100, 10, 1 cm$^3$, or less.

The location of individually accessible members can be available or easily determined. Individually accessible members may be easily retrieved from the library.

In various embodiments, the methods and compositions of the invention allow for production of synthetic (i.e. de novo synthesized) genes. Libraries comprising synthetic genes may be constructed by a variety of methods described in further detail elsewhere herein, such as PCA, non-PCA gene assembly methods or hierarchical gene assembly, combining ("stitching") two or more double-stranded polynucleotides (referred to here as "synthons") to produce larger DNA units (i.e., multisynthons or chassis). Libraries of large constructs may involve polynucleotides that are at least 1, 1.5, 2, 3, 4, 5, 6, 7, 8, 9, 10, 15, 20, 30, 40, 50, 60, 70, 80, 90, 100, 125, 150, 175, 200, 250, 300, 400, 500 kb long or longer. The large constructs can be bounded by an independently selected upper limit of about 5000, 10000, 20000 or 50000 base pairs. The synthesis of any number of polypeptide-segment encoding nucleotide sequences, including sequences encoding non-ribosomal peptides (NRPs), sequences encoding non-ribosomal peptide-synthetase (NRPS) modules and synthetic variants, polypeptide segments of other modular proteins, such as antibodies, polypeptide segments from other protein families, including non-coding DNA or RNA, such as regulatory sequences e.g. promoters, transcription factors, enhancers, siRNA, shRNA, RNAi, miRNA, small nucleolar RNA derived from micro-RNA, or any functional or structural DNA or RNA unit of interest. The term "gene" as used herein refers broadly to any type of coding or non-coding, long polynucleotide or polynucleotide analog.

In various embodiments, the methods and compositions of the invention relate to a library of genes. The gene library may comprise a plurality of subsegments. In one or more subsegments, the genes of the library may be covalently linked together. In one or more subsegments, the genes of the library may encode for components of a first metabolic pathway with one or more metabolic end products. In one or more subsegments, genes of the library may be selected based on the manufacturing process of one or more targeted metabolic end products. The one or more metabolic end products comprise a biofuel. In one or more subsegments, the genes of the library may encode for components of a second metabolic pathway with one or more metabolic end products. The one or more end products of the first and second metabolic pathways may comprise one or more shared end products. In some cases, the first metabolic pathway comprises an end product that is manipulated in the second metabolic pathway.

In some embodiments, a subsegment of the library may comprise, consists of, or consists essentially of genes encoding for a part or all of the genome of a synthetic organism, e.g. a virus or a bacterium. Thus, the terms "gene", "polynucleotide", "nucleotide", "nucleotide sequence", "nucleic acid" and "oligonucleotide" are used interchangeably and refer to a nucleotide polymer. Unless otherwise limited, the same include known analogs of natural nucleotides that can function in a similar manner (e.g., hybridize) to naturally occurring nucleotides. They can be of polymeric form of nucleotides of any length, either deoxyribonucleotides or ribonucleotides, or analogs thereof. Polynucleotides may have any three dimensional structure, and may perform any function, known or unknown. The following are non limiting examples of polynucleotides: coding or non-coding regions of a gene or gene fragment, intergenic DNA, loci (locus) defined from linkage analysis, exons, introns, messenger RNA (mRNA), transfer RNA, ribosomal RNA, short interfering RNA (siRNA), short-hairpin RNA (shRNA), micro-RNA (miRNA), small nucleolar RNA, ribozymes, complementary DNA (cDNA), which is a DNA representation of mRNA, usually obtained by reverse transcription of messenger RNA (mRNA) or by amplification; DNA molecules produced synthetically or by amplification, genomic DNA, recombinant polynucleotides, branched polynucleotides, plasmids, vectors, isolated DNA of any sequence, isolated RNA of any sequence, nucleic acid probes, and primers. A polynucleotide may comprise modified nucleotides, such as methylated nucleotides and nucleotide analogs. If present, modifications to the nucleotide structure may be imparted before or after assembly of the polymer. The sequence of nucleotides may be interrupted by non nucleotide components. A polynucleotide may be further modified after polymerization, such as by conjugation with a labeling component. Polynucleotide sequences, when provided, are listed in the 5' to 3' direction, unless stated otherwise.

The term nucleic acid encompasses double- or triple-stranded nucleic acids, as well as single-stranded molecules. In double- or triple-stranded nucleic acids, the nucleic acid strands need not be coextensive (i.e., a double-stranded nucleic acid need not be double-stranded along the entire length of both strands).

The term nucleic acid also encompasses any chemical modification thereof, such as by methylation and/or by capping. Nucleic acid modifications can include addition of chemical groups that incorporate additional charge, polarizability, hydrogen bonding, electrostatic interaction, and functionality to the individual nucleic acid bases or to the nucleic acid as a whole. Such modifications may include base modifications such as 2'-position sugar modifications, 5-position pyrimidine modifications, 8-position purine modifications, modifications at cytosine exocyclic amines, substitutions of 5-bromo-uracil, backbone modifications, unusual base pairing combinations such as the isobases isocytidine and isoguanidine, and the like.

More particularly, in certain embodiments, nucleic acids, can include polydeoxyribonucleotides (containing 2-deoxy-D-ribose), polyribonucleotides (containing D-ribose), and any other type of nucleic acid that is an N- or C-glycoside of a purine or pyrimidine base, as well as other polymers containing nonnucleotidic backbones, for example, poly-amide (e.g., peptide nucleic acids (PNAs)) and polymorpholino (commercially available from the Anti-Virals, Inc., Corvallis, Oreg., as Neugene) polymers, and other synthetic sequence-specific nucleic acid polymers providing that the polymers contain nucleobases in a configuration which allows for base pairing and base stacking, such as is found in DNA and RNA. The term nucleic acid also encompasses linked nucleic acids (LNAs), which are described in U.S. Pat. Nos. 6,794,499, 6,670,461, 6,262,490, and 6,770,748, which are incorporated herein by reference in their entirety for their disclosure of LNAs.

As used herein, the term "complementary" refers to the capacity for precise pairing between two nucleotides. If a nucleotide at a given position of a nucleic acid is capable of hydrogen bonding with a nucleotide of another nucleic acid, then the two nucleic acids are considered to be complementary to one another at that position. Complementarity between two single-stranded nucleic acid molecules may be "partial", in which only some of the nucleotides bind, or it may be complete when total complementarity exists between the single-stranded molecules. The degree of complementarity between nucleic acid strands has significant effects on the efficiency and strength of hybridization between nucleic acid strands.

"Hybridization" and "annealing" refer to a reaction in which one or more polynucleotides react to form a complex that is stabilized via hydrogen bonding between the bases of the nucleotide residues. The hydrogen bonding may occur by Watson Crick base pairing, Hoogstein binding, or in any other sequence specific manner. The complex may comprise two strands forming a duplex structure, three or more strands forming a multi stranded complex, a single self hybridizing strand, or any combination of these. A hybridization reaction may constitute a step in a more extensive process, such as the initiation of a PCR or other amplification reactions, or the enzymatic cleavage of a polynucleotide by a ribozyme. A first sequence that can be stabilized via hydrogen bonding with the bases of the nucleotide residues of a second sequence is said to be "hybridizable" to said second sequence. In such a case, the second sequence can also be said to be hybridizable to the first sequence.

The term "hybridized" as applied to a polynucleotide refers to a polynucleotide in a complex that is stabilized via hydrogen bonding between the bases of the nucleotide residues. The hydrogen bonding may occur by Watson Crick base pairing, Hoogstein binding, or in any other sequence specific manner. The complex may comprise two strands forming a duplex structure, three or more strands forming a multi stranded complex, a single self hybridizing strand, or any combination of these. The hybridization reaction may constitute a step in a more extensive process, such as the initiation of a PCR reaction, or the enzymatic cleavage of a polynucleotide by a ribozyme. A sequence hybridized with a given sequence is referred to as the "complement" of the given sequence.

"Specific hybridization" refers to the binding of a nucleic acid to a target nucleotide sequence in the absence of substantial binding to other nucleotide sequences present in the hybridization mixture under defined stringency conditions. Those of skill in the art recognize that relaxing the stringency of the hybridization conditions allows sequence mismatches to be tolerated.

In general, a "complement" of a given sequence is a sequence that is fully or substantially complementary to and hybridizable to the given sequence. In general, a first sequence that is hybridizable to a second sequence or set of second sequences is specifically or selectively hybridizable to the second sequence or set of second sequences, such that hybridization to the second sequence or set of second sequences is preferred (e.g. thermodynamically more stable under a given set of conditions, such as stringent conditions commonly used in the art) to hybridization with non-target sequences during a hybridization reaction. Typically, hybridizable sequences share a degree of sequence complementarity over all or a portion of their respective lengths, such as between 25%-100% complementarity, including at least about 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99%, and 100% sequence complementarity.

The term "primer" refers to an oligonucleotide that is capable of hybridizing (also termed "annealing") with a nucleic acid and serving as an initiation site for nucleotide (RNA or DNA) polymerization under appropriate conditions (i.e., in the presence of four different nucleoside triphosphates and an agent for polymerization, such as DNA or RNA polymerase or reverse transcriptase) in an appropriate buffer and at a suitable temperature. The appropriate length of a primer depends on the intended use of the primer, but primers are typically at least 7 nucleotides long and, more typically range from 10 to 30 nucleotides, or even more typically from 15 to 30 nucleotides, in length. Other primers can be somewhat longer, e.g., 30 to 50 or 40-70 nucleotides long. Those of skill in the art appreciate that the primer length may fall within any range bounded by any of these values (e.g., from 7 to 70 or from 50 to 70). Oligonucleotides of various lengths as further described herein can be used as primers or building blocks for amplification and/or gene assembly reactions. In this context, "primer length" refers to the portion of an oligonucleotide or nucleic acid that hybridizes to a complementary "target" sequence and primes nucleotide synthesis. Short primer molecules generally require cooler temperatures to form sufficiently stable hybrid complexes with the template. A primer need not reflect the exact sequence of the template but must be sufficiently complementary to hybridize with a template. The term "primer site" or "primer binding site" refers to the segment of the target nucleic acid to which a primer hybridizes. A construct presenting a primer binding site is often referred to as a "priming ready construct" or "amplification ready construct".

A primer is said to anneal to another nucleic acid if the primer, or a portion thereof, hybridizes to a nucleotide sequence within the nucleic acid. The statement that a primer hybridizes to a particular nucleotide sequence is not intended to imply that the primer hybridizes either completely or exclusively to that nucleotide sequence.

Oligonucleotide Synthesis

Oligonucleotides synthesized on the substrates described herein may comprise greater than about 100, preferably greater than about 1000, more preferably greater than about 16,000, and most preferably greater than 50,000 or 250,000 or even greater than about 1,000.000 different oligonucleotide probes, preferably in less than 20, 10, 5, 1, 0.1 cm$^2$, or smaller surface area.

A method of quickly synthesizing n-mer, such as about or at least about 100-, 150-, 200, 250-, 300, 350-, or longer nucleotide, oligonucleotides on a substrate is further described herein in various embodiments. The method can use a substrate with resolved loci that are functionalized with a chemical moiety suitable for nucleotide coupling. Standard phosphoramidite chemistry can be used in some cases. Accordingly, at least two building blocks are coupled to a plurality of growing oligonucleotide chains each residing on one of the resolved loci at a fast rate, such as a rate of at least 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, 55, 60, 70, 80, 90, 100, 125, 150, 175, 200 nucleotides per hour, or more. In some embodiments, adenine, guanine, thymine, cytosine, or uridine building blocks, or analogs/ modified versions thereof are used as described in further detail elsewhere herein. In some cases, the added building blocks comprise dinucleotides, trinucleotides, or longer nucleotide based building blocks, such as building blocks containing about or at least about 4, 5, 6, 7, 8, 9, 10, 11, 12, 13, 14, 15, 16, 17, 18, 19, 20, 25, 30, 35, 40, 45, 50, or more nucleotides. In some embodiments, large libraries of n-mer oligonucleotides are synthesized in parallel on substrate, e.g. a substrate with about or at least about 100, 1000, 10000, 100000, 1000000, 2000000, 3000000, 4000000, 5000000 resolved loci hosting oligonucleotide synthesis. Individual loci may host synthesis of oligonucleotides that are different from each other. In some embodiments, during the flow of phosphoramidite chemistry, e.g. a process with coupling, capping, oxidation, and deblocking steps, reagent dosage can be accurately controlled through cycles of continuous/ displacing flow of liquids and vacuum drying steps, such as a vacuum drying step prior to coupling of new building blocks. The substrate may comprise vias, such as at least about 100, 1000, 10000, 100000, 1000000, or more vias providing fluid communication between a first surface of the substrate and a second surface of the substrate. Substrates may be kept in place during one or all of the steps within a phosphoramidite chemistry cycle and flow reagents may be passed through the substrate.

A common method for the preparation of synthetic nucleic acids is based on the fundamental work of Caruthers and is known as the phosphoramidite method (M. H. Caruthers, Methods in Enzymology 154, 287-313, 1987; incorporated herein by reference in its entirety). The sequence of the resultant molecules can be controlled by the order of synthesis. Other methods, such as the H-phosphonate method, serve the same purpose of successive synthesis of a polymer from its subunits.

Typically, the synthesis of DNA oligomers by the methods of the invention may be achieved through traditional phosphoramidite chemistry. Phosphoramidite based chemical synthesis of nucleic acids is well known to those of skill in the art, being reviewed in Streyer, Biochemistry (1988) pp 123-124 and U.S. Pat. No. 4,415,732, herein incorporated by reference. Phosporamidite reagents, including B-cyanoethyl (CE) phosphoramidite monomers and CPG (controlled porous glass) reagents usable with the invention may be purchased from numerous commercial sources, including American International Chemical (Natick Mass.), BD Biosciences (Palo Alto Calif.), and others.

In various embodiments, the chemical synthesis of nucleic acids is overwhelmingly performed using variations of the phosphoramidite chemistry on solid surfaces (Beaucage S L, Caruthers M H. Deoxynucleoside phosphoramidites—a new class of key intermediates for deoxypolynucleotide synthesis. Tetrahedron Lett. 1981; 22:1859-1862; Caruthers M H. Gene synthesis machines—DNA chemistry and its uses. Science. 1985; 230:281-285.), both of which are incorporated herein by reference in their entirety.

For instance, phosphoramidite based methods can be used to synthesize abundant base, backbone and sugar modifications of deoxyribo- and ribonucleic acids, as well as nucleic acid analogs (Beaucage S L, Iyer R P. Advances in the synthesis of oligonucleotides by the phosphoramidite approach. Tetrahedron. 1992; 48:2223-2311; Beigelman L, Matulic-Adamic J, Karpeisky A, Haeberli P, Sweedler D. Base-modified phosphoramidite analogs of pyrimidine ribonucleosides for RNA structure-activity studies. Methods Enzymol. 2000; 317:39-65; Chen X, Dudgeon N, Shen L, Wang J H. Chemical modification of gene silencing oligonucleotides for drug discovery and development. Drug Discov. Today. 2005; 10:587-593; Pankiewicz K W. Fluorinated nucleosides. Carbohydrate Res. 2000; 327:87-105; Lesnikowski Z J, Shi J, Schinazi R F. Nucleic acids and nucleosides containing carboranes. J. Organometallic Chem. 1999; 581:156-169; Foldesi A, Trifonova A, Kundu M K, Chattopadhyaya J. The synthesis of deuterionucleosides. Nucleosides Nucleotides Nucleic Acids. 2000; 19:1615-1656; Leumann C J. DNA Analogues: from supramolecular principles to biological properties. Bioorg. Med. Chem. 2002; 10:841-854; Petersen M, Wengel J. LNA: a versatile tool for therapeutics and genomics. Trends Biotechnol. 2003; 21:74-81; De Mesmaeker A, Altmann K-H, Waldner A, Wendeborn S. Backbone modifications in oligonucleotides and peptide nucleic acid systems. Curr. Opin. Struct. Biol. 1995; 5:343-355), all of which are incorporated herein by reference in their entirety.

The phosphoramidite chemistry has been adapted for in situ synthesis of DNA on solid substrates, e.g. microarrays. Such synthesis is typically achieved by spatial control of one step of the synthesis cycle, which results in thousands to hundreds of thousands of unique oligonucleotides distributed in a small area, e.g. an area of a few square centimeters. The areas and substrates architectures for the synthesis of oligonucleotides are further described elsewhere herein in greater detail. Suitable methods used to achieve spatial control can include (i) control of the coupling step by inkjet printing (Agilent, Protogene; Hughes T R, Mao M, Jones A R, Burchard J, Marton M J, Shannon K W, Lefkowitz S M, Ziman M, Schelter J M, Meyer M R, et al. Expression profiling using microarrays fabricated by an ink-jet oligonucleotide synthesizer. Nat. Biotechnol. 2001; 19:342-347; Butler J H, Cronin M, Anderson K M, Biddison G M, Chatelain F, Cummer M, Davi D J, Fisher L, Frauendorf A W, Frueh F W, et al. In situ synthesis of oligonucleotide arrays by using surface tension. J. Am. Chem. Soc. 2001; 123:8887-8894) or physical masks (Southern E M, Maskos U, Elder J K. Analyzing and comparing nucleic acid sequences by hybridization to arrays of oligonucleotides: evaluation using experimental models. Genomics. 1992; 13:1008-1017.), (ii) control of the 5'-hydroxyl deblock step by classical (Affymetrix; Pease A C, Solas D, Sullivan E J, Cronin M T, Holmes C P, Fodor S P A. Light-generated oligonucleotide arrays for rapid dna-sequence analysis. Proc. Natl Acad. Sci. USA. 1994; 91:5022-5026.) and maskless (Nimblegen; Singh-Gasson S, Green R D, Yue Y J, Nelson C, Blattner F, Sussman M R, Cerrina F. Maskless fabrication of light-directed oligonucleotide microarrays using a digital micromirror array. Nat. Biotechnol. 1999; 17:974-978) photolithographic deprotection of photolabile monomers or (iii) digital activation of photogenerated acids to carry out standard detritylation (Xeotron/Atactic; Gao X L, LeProust E, Zhang H, Srivannavit O, Gulari E, Yu P L, Nishiguchi C, Xiang Q, Zhou X C. A flexible light-directed DNA chip synthesis gated by deprotection using solution photogenerated acids. Nucleic Acids Res. 2001; 29:4744-4750), all of which are herein incorporated by reference in their entirety.

Oligonucleotides made on substrates can be cleaved from their solid surface and optionally pooled to enable new applications such as, gene assembly, nucleic acid amplification, sequencing libraries, shRNA libraries etc. (Cleary M A, Kilian K, Wang Y Q, Bradshaw J, Cavet G, Ge W, Kulkarni A, Paddison P J, Chang K, Sheth N, et al. Production of complex nucleic acid libraries using highly parallel in situ oligonucleotide synthesis. Nature Methods. 2004; 1:241-248), gene synthesis (Richmond K E, Li M H, Rodesch M J, Patel M, Lowe A M, Kim C, Chu L L, Venkataramaian N, Flickinger S F, Kaysen J, et al. Amplification and assembly of chip-eluted DNA (AACED): a method for high-throughput gene synthesis. Nucleic Acids Res. 2004; 32:5011-5018; Tian J D, Gong H, Sheng N J, Zhou X C, Gulari E, Gao X L, Church G. Accurate multiplex gene synthesis from programmable DNA microchips. Nature. 2004; 432:1050-1054) and site-directed mutagenesis (Saboulard D, Dugas V, Jaber M, Broutin J, Souteyrand E, Sylvestre J, Delcourt M. High-throughput site-directed mutagenesis using oligonucleotides synthesized on DNA chips. BioTechniques. 2005; 39:363-368), all of which are herein incorporated by reference in their entirety.

Successful synthesis of long high-quality oligonucleotides is strongly supported by high stepwise coupling yields, for example stepwise coupling yields that are at least about 99.5%. In various embodiments, the methods and compositions of the invention contemplate a coupling yield of more than 98%, 98.5%, 99%, 99.5%, 99.6%, 99.7%, 99.8%, 99.9%, 99.95%, 99.96%, 99.97%, 99.98%, 99.99% or higher. Without being bound by theory, if the coupling efficiency is lower, e.g. below 99%, the impact on sequence integrity typically follows one of two scenarios. If capping is used, the low coupling efficiency will be evidenced by short, truncated sequences. If capping is not used, or if capping is unsuccessful, single base deletions will occur in the oligonucleotide and as a consequence, a large number of failure sequences lacking one or two nucleotides will be formed. Efficient removal of the 5'-hydroxyl protecting group further supports the synthesis of long, high-quality oligonucleotides at desirably high yields, such as at very high efficiencies approaching 100% within each cycle, e.g. greater than or equal to 98%, 98.5%, 99%, 99.5%, 99.6%, 99.7%, 99.8%, 99.9%, 99.95%, 99.96%, 99.97%, 99.98%, 99.99% or higher. This step can be optimized with precise control of the dosage of reagents as well as other environmental parameters, using the methods and compositions described herein, avoiding final product mixtures comprising a family of oligomers with single base deletions in addition to the desired product.

Further, for synthesis of long oligonucleotides, it is important to minimize the most prevalent side reaction—depurination (Carr P A, Park J S, Lee Y J, Yu T, Zhang S G, Jacobson J M. Protein-mediated error correction for de novo dna synthesis. Nucleic Acids Res. 2004; 32:e162). Depurination results in the formation of an abasic site that typically does not interfere with chain extension. Critical DNA damage occurs during the final nucleobase deprotection under basic conditions, which also cleaves oligonucleotide chains at abasic sites. Without being bound by theory, depurination may affect sequence integrity by generating short, truncated sequences that can typically be mapped to purine nucleobases. Thus, high yield, high quality synthesis of oligonucleotides is supported by control of depurination combined with highly efficient coupling and 5'-hydroxyl deprotection reactions. With high coupling yields and low depurination, long, high quality oligonucleotides can be synthesized without the need for extensive purification and/or PCR amplification to compensate for the low yield. The methods and compositions of the invention in various embodiments provide conditions to achieve such high coupling yields, low depurination, and effective removal of protecting groups.

Figure 11:
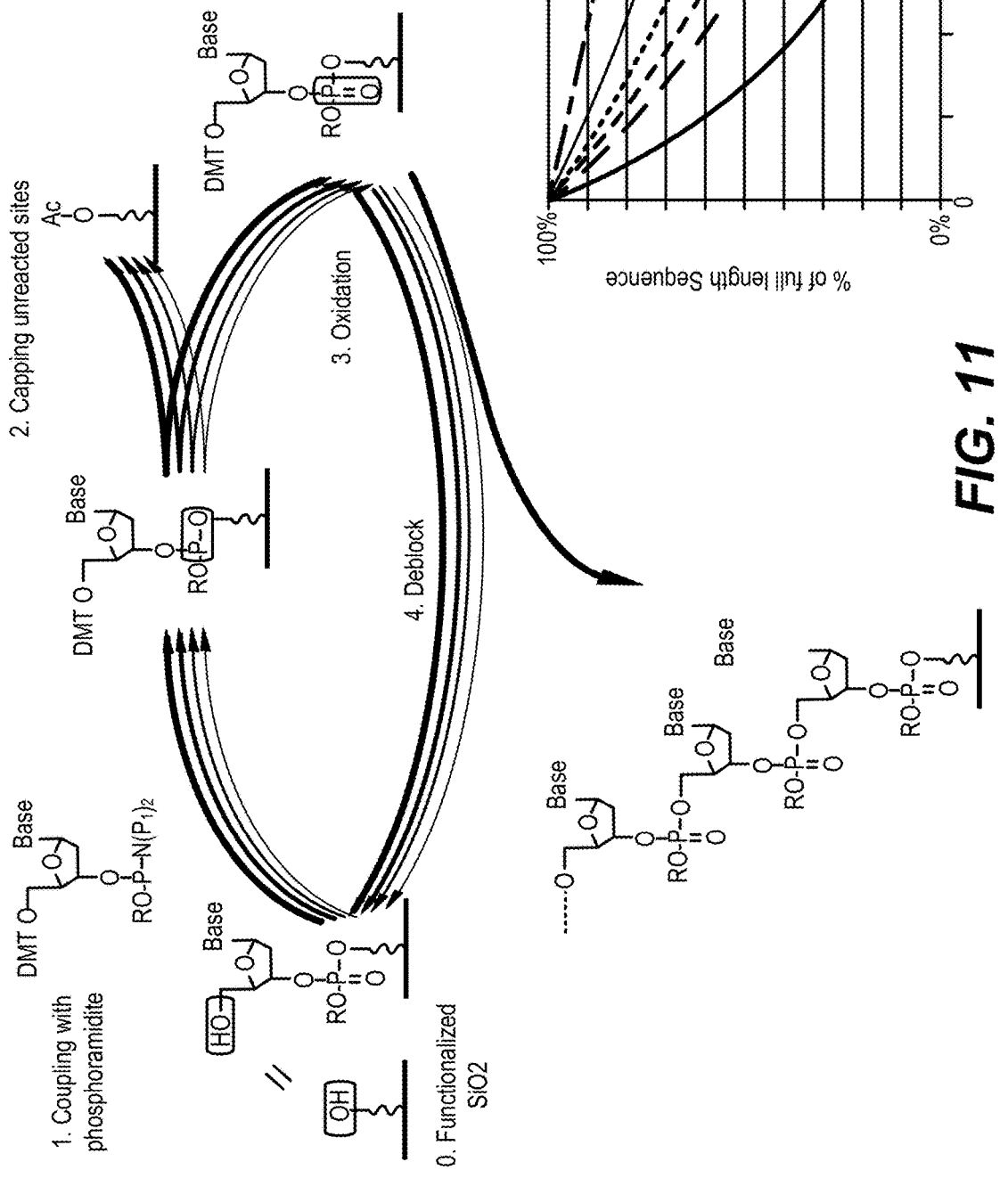
FIG. 11 illustrates exemplary application standard phosphoramidite chemistry for oligonucleotide synthesis.

In various embodiments, the methods and compositions of the invention described herein rely on standard phosphoramidite chemistry on a functionalized substrate, e.g. a silylated wafer optionally using suitable modifications, known in the art, Typically, after the deposition of a monomer, e.g. a mononucleotide, a dinucleotide, or a longer oligonucleotide with suitable modifications for phosphoramidite chemistry one or more of the following steps may be performed at least once to achieve the step-wise synthesis of high-quality polymers in situ: 1) Coupling, 2) Capping, 3) Oxidation, 4) Sulfurization, 5) Deblocking (detritylation), and 6) Washing. Typically, either oxidation or sulfurization will be used as one of the steps, but not both. FIG. 11 exemplifies a four-step phosphoramidite synthesis method comprising coupling, capping, oxidation and deblocking steps.

Elongation of a growing oligodeoxynucleotide may be achieved through subsequent additions of phosphoramidite building blocks typically via the formation of a phosphate triester internucleotide bond. During the coupling step, a solution of phosphoramidite building blocks, e.g. nucleoside phosphoramidite (or a mixture of several phosphoramidites), typically at 0.02-0.2 M concentration, in acetonitrile may be activated, e.g. by a solution of an acidic azole catalyst, 1H-tetrazole, 2-ethylthiotetrazole (Sproat et al., 1995, "An efficient method for the isolation and purification of oligoribonucleotides". Nucleosides & Nucleotides 14 (1&2): 255-273), 2-benzylthiotetrazole (Stutz et al., 2000, "Novel fluoride-labile nucleobase-protecting groups for the synthesis of 3'(2')-O-amino-acylated RNA sequences", Helv. Chim. Acta 83 (9): 2477-2503; Welz et al., 2002, "5-(Benzylmercapto)-1H-tetrazole as activator for 2'-O-TB-DMS phosphoramidite building blocks in RNA synthesis", Tetrahedron Lett., 43 (5): 795-797), 4,5-dicyanoimidazole (Vargeese et al., 1998, "Efficient activation of nucleoside phosphoramidites with 4,5-dicyanoimidazole during oligonucleotide synthesis", Nucl. Acids Res., 26 (4): 1046-1050) or a number of similar compounds, typically at 0.2-0.7 M concentration. The mixing may be achieved in fluid lines of an inkjet while the components are being delivered to selected spots of a suitable substrate described in further detail elsewhere herein. The phosphoramidite building blocks, such as those activated as described above, are typically provided in 1.5, 2, 3, 4, 5, 6, 7, 8, 9, 10, 11, 12, 13, 14, 15, 16, 17, 18, 19, 20, 25, 30, 35, 40, 50, 60, 70, 80, 90, 100-fold excess or more over the substrate-bound material is then brought in contact with the starting solid support (first coupling) or a support-bound oligonucleotide precursor (following couplings). In 3' to 5' synthesis, 5'-hydroxy group of the precursor may be set to react with the activated phosphoramidite moiety of the incoming nucleoside phosphoramidite to form a phosphite triester linkage. The reaction is also highly sensitive to the presence of water, particularly when dilute solutions of phosphoramidites are used, and is typically carried out in anhydrous acetonitrile. Upon the completion of the coupling, any unbound reagents and byproducts may be removed by a wash step.

The product of the coupling reaction may be treated with a capping agent that can e.g. esterify failure sequences and/or cleave phosphate reaction products on the heterocyclic bases. The capping step may be performed by treating the solid support-bound material with a mixture of acetic anhydride and 1-methylimidazole or DMAP as catalysts and may serve two purposes: After the completion of the coupling reaction, a fraction of the solid support-bound 5'-OH groups (e.g. 0.1 to 1%) may remain unreacted. These unreacted groups can be permanently blocked from further chain elongation to prevent the formation of oligonucleotides with an internal base deletion commonly referred to as (n−1) shortmers. The unreacted 5'-hydroxy groups can be acetylated by the capping mixture. Further, phosphoramidites activated with 1H-tetrazole are understood to react, to a small extent, with the 6 position of guanosine. Without being bound by theory, upon oxidation with $I_2$/water, this side product, possibly via 06-N7 migration, may undergo depurination. The apurinic sites may end up being cleaved in the course of the final deprotection of the oligonucleotide thus reducing the yield of the full-length product. The 06 modifications may be removed by treatment with the capping reagent prior to oxidation with $I_2$/water.

The synthesis of oligonucleotide phosphorothioates (OPS; described in further detail elsewhere herein) typically does not involve the oxidation with $I_2$/water, and, to that extent, does not suffer from the side reaction described above. On the other hand, the capping mixture may interfere with the sulfur transfer reaction. Without being bound by theory, the capping mixture my cause extensive formation of the phosphate triester internucleosidic linkages in place of the desired PS triesters. Therefore, for the synthesis of OPS, the sulfurization step may be performed prior to any capping steps.

The support-bound material may be treated with iodine and water, typically in the presence of a weak base (e.g. pyridine, lutidine, or collidine) to affect oxidation of the phosphite triester into a tetracoordinated phosphate triester, a protected precursor of the naturally occurring phosphate diester internucleosidic linkage. Oxidation may be carried out under anhydrous conditions using, e.g. tert-Butyl hydroperoxide or (1S)-(+)-(10-camphorsulfonyl)-oxaziridine (CSO). The step of oxidation may be substituted with a sulfurization step to obtain oligonucleotide phosphorothioates.

Synthesis of oligonucleotide phosphorothioates (OPS) can be achieved similar to that of natural oligonucleotides using the methods and compositions of the invention in various embodiments. Briefly, the oxidation step can be replaced by the sulfur transfer reaction (sulfurization) and any capping steps can be performed after the sulfurization. Many reagents are capable of the efficient sulfur transfer, including but not limited to 3-(Dimethylaminomethylidene) amino)-3H-1,2,4-dithiazole-3-thione, DDTT, 3H-1,2-benzodithiol-3-one 1,1-dioxide, also known as Beaucage reagent, and N,N,N'N'-Tetraethylthiuram disulfide (TETD).

A deblocking (or detritylation) step may serve to remove blocking groups, such as the DMT group, e.g. with a solution of an acid, such as 2% trichloroacetic acid (TCA) or 3% dichloroacetic acid (DCA), in an inert solvent (dichloromethane or toluene). A washing step may be performed. The solid support-bound oligonucleotide precursor is affected to bear a free 5'-terminal hydroxyl group. Conducting detritylation for an extended time or with stronger than recommended solutions of acids may lead to increased depurination of solid support-bound oligonucleotide and thus reduces the yield of the desired full-length product. Methods and compositions of the invention described herein provide for controlled deblocking conditions limiting undesired depurination reactions.

In some embodiments, an oxidation solution comprising about 0.02 M $I_2$ in THF/pyridine/H2O or any suitable variations obvious to one skilled in the art may be used. The detritylation solution may be 3% dichloroacetic acid (DCA) or 2% tricholoroacetic acid (TCA) in toluene or dichloromethane or any other suitable inert solvent. Suitable variations of the detritylation solution are understood to be obvious to one skilled in the art. The methods and compositions of the invention allow for the displacement of the detritylation solution without allowing for significant evaporation of the solvent, preventing concentrated spots of the depurinating components, e.g. DCA or TCA. For example, a chasing solution may be run after the detritylation solution. The density of the chasing solution may be adjusted to achieve a first in first out process. A slightly denser chasing solution may be used to achieve this outcome. For example, the detritylation solution may be chased with the oxidation solution. The chasing solution may comprise a quenching agent, such as pyridine. In some embodiments, continuous liquid conditions are used until the deblocking solution is substantially removed from the oligonucleotide synthesis loci on a substrate. The concentration of the depurinating components may be tightly controlled, e.g. limiting their values on oligonucleotide synthesis loci of a substrate to be less than 3-, 2.5-, 2-, 1.5-, 1.4-, 1.3-, 1.25-, 1.2-, 1.15-, 1.1-, 1.05-, 1.04-, 1.03-, 1.02-, 1.01-, 1.005-fold or less of the original concentration.

The displacement process can be optimized to adequately control the chemical dosage on the oligonucleotide synthesis loci within a useful range. The dosage may collectively refer to the summed kinetic effects of time, concentration and temperature on both the completion of the intended reaction (detritylation) and the extent of the side reaction (depurination).

Further, detritylation, by virtue of being reversible, may result in the synthesis of a series of oligomers lacking one or more of the correct nucleotides. A two-step chemistry proposed by Sierzchala et al. (Solid-phase oligodeoxynucleotide synthesis: A two-step cycle using peroxy anion deprotection. J. Am. Chem. Soc. 2003; 125:13427-13441) can address the issue of depurination by eliminating the use of acid deprotection of the 5' or 3' ends of the growing chain. The two-step synthesis cycle makes use of aqueous peroxy anions buffered under mildly basic conditions, e.g. about pH 9.6, to remove an aryloxycarbonyl group, which substitutes the DMT group commonly used in the four-step phosphormidite synthesis. Accordingly, the peroxy anion solution, or any suitable variation with strong nucleophylic and mildly oxidizing properties permits consolidating deblocking and oxidization steps into one. Further, high cyclical yields allows for the elimination of capping steps.

Deprotection and cleavage of the DNA from the substrate may be performed as described by Cleary et al. (Production of complex nucleic acid libraries using highly parallel in situ oligonucleotide synthesis. Nature Methods. 2004; 1:241-248), for example by treatment with $NH_4OH$, by applying ultraviolet light to a photocleavable linker, by targeting, e.g. heat treating, apurinic sites, such as those generated by uracil-DNA glycosylase treatment of incorporated dU-residues, or any suitable cleavage method known in the art. Oligonucleotides may be recovered after cleavage by lyophylization.

In order to host phosphoramidite chemistry, the surface of the oligonucleotide synthesis loci of a substrate can be chemically modified to provide a proper site for the linkage of the growing nucleotide chain to the surface. Various types of surface modification chemistry exist which allow a nucleotide to attached to the substrate surface. Surface modifications may vary in their implementation depending on whether the oligonucleotide chain is to be cleaved from the surface concomitant with deprotection of the nucleic acid bases, or left attached to the surface after deprotection. Various types of suitable surface modification chemistries are known in the art and are described at www.glenresearch.com, which is incorporated herein by reference in its entirety. One surface modification technique that allows for the exocyclic N atoms of the A, G and C bases to be deprotected while having the oligonucleotide chain remain attached to the substrate.

Another scheme comprises reacting a trialkoxysilyl amine (e.g. $(CH_3CH_2O)_3Si-(CH_2)_2-NH_2$) with the glass or silica surface SiOH groups, followed by reaction with succinic anhydride with the amine to create and amide linkage and a free OH on which the nucleotide chain growth could commence.

A third type of linker group may be based on photocleavable primers. This type of linker allows for oligonucleotide to be removed from the substrate (by irradiation with light, e.g. ~350 nm light) without cleaving the protecting groups on the nitrogenous functionalities on each base. The typical ammonia or $NH_3$ treatment deprotects everything when used as the reagent to cleave the oligomers from the substrate. The use of photocleavable linkers of this sort is described at www.glenresearch.com. Various other suitable cleavable linker groups are known in the art and may alternatively be used.

Time frames for oxidation and detritylation may typically be about 30 s and 60 s, respectively. The reagents may be drained, followed by washes of acetonitrile (ACN). In the depurination controlled detritylation processes, the detritylation solution may be driven out using a continuous inflow of oxidation solution without a drain step in between.

Precise control of the flow of reagents during the in situ synthesis steps allows for improved yield, uniformity and quality of the products. For example, the acid concentration and detritylation times can be precisely controlled. A water contact angle for the substrate, in particular, for regions of in situ synthesis and/or surrounding areas, may be chosen in order to reduce depurination and/or speed of synthesis. Proper desired values of water contact angle are described elsewhere herein. In some embodiments, lower amount of depurination may be achieved on surfaces of higher surface energy, i.e. lower contact angle.

The methods and compositions of the invention allow for a reduced rate of depurination during oligonucleotide synthesis, e.g. at a rate of less than 0.1%, 0.09%, %, 0.08%, 0.07%, 0.06%, 0.05%, 0.04%, 0.03%, 0.02%, 0.01%, 0.009%, 0.008%, 0.007%, 0.006%, 0.005%, 0.004%, 0.003%, 0.002%, 0.001%, 0.0009%, 0.0008%, 0.0007%, 0.0006%, 0.0005%, 0.0004%, 0.0003%, 0.0002%, 0.0001% per cycle or less. Further, methods and compositions of the invention described herein allow for the reduction or elimination of a depurination gradient across the surface of a substrate supporting in situ synthesis of oligonucleotides. Thus, highly uniform, high quality, and high-yield oligonucleotide synthesis can be achieved on substrates that can host a high density of resolved oligonucleotide loci.

In situ synthesis of oligonucleotides typically starts with the solid support being relatively hydrophobic, and subsequently growing increasingly more hydrophylic with the synthesis of oligonucleotide features affecting its surface energy. Oligonucleotide features can gain substantial surface energy with increasing oligonucleotide length. Generally, these sites or features consisting of protected oligonucleotide acquire enough surface energy to become spontaneously wetting to high surface tension organic solvents commonly used in phosphoramidite synthesis, such as acetonitrile or propylene carbonate, after about 10-20 synthesis cycles. The methods and compositions of the invention allow for varying parameters, such as time, flow rate, temperature, volume, viscosity, or reagent concentration, during the synthesis of a growing oligonucleotide as a function of length to account for the changing surface properties on loci of oligonucleotide synthesis. Such a variation may be applied by continuously changing parameters in constant or varying increments at repeating cycles of the synthesis. Alternatively, parameters may be changed at only selected cycles of the synthesis and can optionally follow a pattern, such as every other cycle, every third, fourth, fifth, sixth, seventh, eighth, ninth, tenth cycle etc.

In various embodiments, the methods and compositions of the invention contemplate a library of oligonucleotides synthesized on a substrate, wherein the library comprises oligonucleotides of varying sizes, as described in further detail elsewhere herein. Further, the methods and compositions of the invention allow for the synthesis of substantially similar amounts of oligonucleotides, or in some cases varying preselected amounts of oligonucleotides, of varying size, sequence or nucleotide composition on a substrate. The variation in amounts may be limited to less than 50%, 40%, 30%, 25%, 20%, 15%, 10%, 5%, 3%, 2%, 1%, 0.5%, 0.1% or less between any two synthesized oligonucleotides, or alternatively, as relative error or percent deviation across the library. The methods and compositions of the invention described herein contemplate synthesized oligonucleotides on a substrate at desired amounts as described in further detail elsewhere herein.

In some embodiments, the methods and compositions of the invention permit the synthesis of libraries of oligonucleotides on substrates, in which the stoichiometry of each oligonucleotide is tightly controlled and tunable by varying the relative number of features synthesized. Suitable surface functionalizations and coatings to finetune the density of growing oligonucleotides on resolved loci of substrates are described in further detail elsewhere herein and can be uniformly applied to all microstructures of a substrate, or alternatively, can be applied at selected amounts and ratios to individual microstructures.

The in situ synthesis methods include those described in U.S. Pat. No. 5,449,754 for synthesizing peptide arrays, as well as WO 98/41531 and the references cited therein for synthesizing polynucleotides (specifically, DNA) using phosphoramidite or other chemistry. Additional patents describing in situ nucleic acid array synthesis protocols and devices include U.S. Pub. No. 2013/0130321 and U.S. Pub. No. 2013/0017977, and the references cited therein, incorporated herein by reference in their entirety.

Such in situ synthesis methods can be basically regarded as iterating the sequence of depositing droplets of: a protected monomer onto predetermined locations on a substrate to link with either a suitably activated substrate surface (or with previously deposited deprotected monomer); deprotecting the deposited monomer so that it can react with a subsequently deposited protected monomer; and depositing another protected monomer for linking. Different monomers may be deposited at different regions on the substrate during any one cycle so that the different regions of the completed array will carry the different biopolymer sequences as desired in the completed array. One or more intermediate further steps may be required in each iteration, such as oxidation, sulfurization, and/or washing steps.

Various methods which can be used to generate an array of oligonucleotides on a single substrate are described in U.S. Pat. Nos. 5,677,195, 5,384,261, and in PCT Publication No. WO 93/09668. In the methods disclosed in these applications, reagents are delivered to the substrate by either (1) flowing within a channel defined on predefined regions or (2) "spotting" on predefined regions, or (3) through the use of photoresist. However, other approaches, as well as combinations of spotting and flowing, can be employed. In each instance, certain activated regions of the substrate are mechanically separated from other regions when the monomer solutions are delivered to the various reaction sites. Thus, in situ synthesis of oligonucleotides can be achieved applying various suitable methods of synthesis known in the art to the methods and compositions described herein. One such method is based on a photolithographic technique which involves direct in situ synthesis of oligonucleotides at resolved pre-determined sites on the solid or polymeric surface, using photolabile protecting groups (Kumar et al., 2003). The hydroxyl groups can be generated on the surface and blocked by photolabile-protecting groups. When the surface is exposed to ~UV light, e.g. through a photolithographic mask, a pattern of free hydroxyl groups on the surface may be generated. These hydroxyl groups can react with photoprotected nucleosidephosphoramidites, according to phosphoramidite chemistry. A second photolithographic mask can be applied and the surface can be exposed to UV light to generate second pattern of hydroxyl groups, followed by coupling with 5'-photoprotected nucleosidephosphoramidite. Likewise, patterns can be generated and oligomer chains can be extended. Several photolabile-protecting groups, which can be removed cleanly and rapidly from the 5'-hydroxyl functionalities are known in the art. Without being bound by theory, the lability of a photocleavable group depends on the wavelength and polarity of a solvent employed and the rate of photocleavage may be affected by the duration of exposure and the intensity of light. This method can leverage a number of factors, e.g. accuracy in alignment of the masks, efficiency of removal of photo-protecting groups, and the yields of the phosphoramidite coupling step. Further, unintended leakage of light into neighboring sites can be minimized. The density of synthesized oligomer per spot can be monitored by adjusting loading of the leader nucleoside on the surface of synthesis.

It is understood that the methods and compositions of the invention can make use of a number of suitable techniques of construction that are well known in the art e.g., maskless array synthesizers, light directed methods utilizing masks, flow channel methods, spotting methods etc. In some embodiments, construction and/or selection oligonucleotides may be synthesized on a solid support using maskless array synthesizer (MAS). Maskless array synthesizers are described, for example, in PCT application No. WO 99/42813 and in corresponding U.S. Pat. No. 6,375,903. Other examples are known of maskless instruments which can fabricate a custom DNA microarray in which each of the features in the array has a single-stranded DNA molecule of desired sequence. Other methods for synthesizing construction and/or selection oligonucleotides include, for example, light-directed methods utilizing masks, flow channel methods, spotting methods, pin-based methods, and methods utilizing multiple supports. Light directed methods utilizing masks (e.g., VLSIPS™ methods) for the synthesis of oligonucleotides is described, for example, in U.S. Pat. Nos. 5,143,854, 5,510,270 and 5,527,681. These methods involve activating predefined regions of a solid support and then contacting the support with a preselected monomer solution. Selected regions can be activated by irradiation with a light source through a mask much in the manner of photolithography techniques used in integrated circuit fabrication. Other regions of the support remain inactive because illumination is blocked by the mask and they remain chemically protected. Thus, a light pattern defines which regions of the support react with a given monomer. By repeatedly activating different sets of predefined regions and contacting different monomer solutions with the support, a diverse array of polymers is produced on the support. Other steps, such as washing unreacted monomer solution from the support, can be optionally used. Other applicable methods include mechanical techniques such as those described in U.S. Pat. No. 5,384,261. Additional methods applicable to synthesis of construction and/or selection oligonucleotides on a single support are described, for example, in U.S. Pat. No. 5,384,261. For example, reagents may be delivered to the support by flowing within a channel defined on predefined regions or "spotting" on predefined regions. Other approaches, as well as combinations of spotting and flowing, may be employed as well. In each instance, certain activated regions of the support are mechanically separated from other regions when the monomer solutions are delivered to the various reaction sites. Flow channel methods involve, for example, microfluidic systems to control synthesis of oligonucleotides on a solid support. For example, diverse polymer sequences may be synthesized at selected regions of a solid support by forming flow channels on or in a surface of the support through which appropriate reagents flow or in which appropriate reagents are placed. Spotting methods for preparation of oligonucleotides on a solid support involve delivering reactants in relatively small quantities by directly depositing them in selected regions or structures fluidically connected to the same. In some steps, the entire support surface can be sprayed or otherwise coated with a solution. Precisely measured aliquots of monomer solutions may be deposited dropwise by a dispenser that moves from region to region. Pin-based methods for synthesis of oligonucleotides on a solid support are described, for example, in U.S. Pat. No. 5,288,514. Pin-based methods utilize a support having a plurality of pins or other extensions. The pins are each inserted simultaneously into individual reagent containers in a tray.

In an alternative approach, light directed synthesis of high density microarrays can be achieved in 5'-3' direction (Albert et al., 2003). This approach allows for downstream reactions, such as parallel genotyping or sequencing, to be done on the synthesis surface, because 3'-end is available for enzymatic reactions, such as sequence specific primer extension and ligation reactions. Complete or substantially complete deprotection of photoprotected 5'-OH groups, base-assisted photo-deprotection of NPPOC (2-(2-nitrophenyl) propoxy carbonyl) can be used (Beier et al., 2002).

The methods and compositions described herein may facilitate the production of synthetic nucleic acids using in situ synthesis on substrates of various geometries, including planar or irregular surfaces. Various materials suitable for these substrates, e.g. silicon, are described herein are otherwise known in the art. A substrate may be loaded with a multiplicity of different sequences during the synthesis. In situ synthesis methods on substrates allows for the preparation of a multiplicity of oligomers of different and defined sequences at addressable locations on a common support. The methods and compositions described herein allow for the in situ synthesis of oligonucleotides that are longer and higher quality as further described elsewhere herein. The synthesis steps can incorporate various sets of feed materials, in the case of oligonucleotide synthesis, as a rule the 4 bases A, G, T and C, as well as suitable modified bases known in the art some of which are described herein, may be used building up desired sequences of nucleic acid polymers in a resolved manner on a support or substrate.

The fabrication and application of high density oligonucleotides on solid support, e.g. arrays, have been further disclosed previously in, for example, PCT Publication No's WO 97/10365, WO 92/10588, U.S. Pat. No. 6,309,822 filed Dec. 23, 1996; U.S. Pat. No. 6,040,138 filed on Sep. 15, 1995; Ser. No. 08/168,904 filed Dec. 15, 1993; Ser. No. 07/624,114 filed on Dec. 6, 1990, Ser. No. 07/362,901 filed Jun. 7, 1990, and in U.S. Pat. No. 5,677,195, all incorporated herein for all purposes by reference. In some embodiments using high density arrays, high density oligonucleotide arrays are synthesized using methods such as the Very Large Scale Immobilized Polymer Synthesis (VLSIPS) disclosed in U.S. Pat. Nos. 5,445,934 and 6,566,495, both incorporated herein for all purposes by reference. Each oligonucleotide occupies a known location on a substrate.

Various other suitable methods of forming high density arrays of oligonucleotides, peptides and other polymer sequences with a minimal number of synthetic steps are known in the art. The oligonucleotide analogue array can be synthesized on a solid substrate by a variety of methods, including, but not limited to, light-directed chemical coupling and mechanically directed coupling. See Pirrung et al., U.S. Pat. No. 5,143,854 (see also PCT Application No. WO 90/15070) and Fodor et al., PCT Publication Nos. WO 92/10092 and WO 93/09668 and U.S. Ser. No. 07/980,523, which disclose methods of forming vast arrays of peptides, oligonucleotides and other molecules using, for example, light-directed synthesis techniques. See also, Fodor et al., Science, 251, 767-77 (1991). These procedures for synthesis of polymer arrays are now referred to as VLSIPS procedures. Using the VLSIPS approach, one heterogeneous array of polymers is converted, through simultaneous coupling at a number of reaction sites, into a different heterogeneous array. See, U.S. application Ser. Nos. 07/796,243 and 07/980,523.

In the event that an oligonucleotide analogue with a polyamide backbone is used in the VLSIPS procedure, it is often unsuitable to use phosphoramidite chemistry to perform the synthetic steps, since the monomers do not attach to one another via a phosphate linkage. Instead, peptide synthetic methods can be substituted e. g., as described by Pirrung et al. in U.S. Pat. No. 5,143,854, which is herein incorporated by reference in its entirety.

The individual molecular species can be demarcated by separate fluidic compartments for addition of the synthesis feed materials, as is the case e.g. in the so-called in situ spotting method or piezoelectric techniques, based on inkjet printing technology (A. Blanchard, in Genetic Engineering, Principles and Methods, Vol. 20, Ed. J. Sedlow, 111-124, Plenum Press; A. P. Blanchard, R. J. Kaiser, L. E. Hood, High-Density Oligonucleotide Arrays, Biosens. & Bioelectronics 11, 687, 1996). Resolved in situ synthesis of oligonucleotides can further be achieved by the spatially-resolved activation of synthesis sites, which is possible through selective illumination, through selective or spatially-resolved generation of activation reagents (deprotection reagents) or through selective addition of activation reagents (deprotection reagents).

Examples of the methods known to date for the in situ synthesis of arrays are photolithographic light-based synthesis (McGall, G. et al.; J. Amer. Chem. Soc. 119; 5081-5090; 1997), projector-based light-based synthesis (PCT/EP99/06317), fluidic synthesis by means of physical separation of the reaction spaces (known by a person skilled in the art from the work of Prof. E. Southern, Oxford, UK, and of the company Oxford Gene Technologies, Oxford, UK), indirect projector-based light-controlled synthesis by light-activated photo-acids and suitable reaction chambers or physically separated reaction spaces in a reaction support, electronically induced synthesis by spatially-resolved deprotection on individual electrodes on the support using proton production induced by the electrodes, and fluidic synthesis by spatially-resolved deposition of the activated synthesis monomers (known from A. Blanchard, in Genetic Engineering, Principles and Methods, Vol. 20, Ed. J. Sedlow, 111-124, Plenum Press; A. P. Blanchard, R. J. Kaiser, L. E. Hood, High-Density Oligonucleotide Arrays, Biosens. & Bioelectronics 11, 687, 1996).

Methods of preparation of synthetic nucleic acids, in particular nucleic acid double strands on a common solid support, are also known from PCT Publications WO 00/49142 and WO 2005/051970, both of which are herein incorporated by reference in their entirety.

In situ preparation of nucleic acid arrays, can be achieved, 3' to 5', as well as the more traditional 5' to 3' direction. Addition of reagents may be achieved by pulse-jet depositing, e.g. an appropriate nucleotide phosphoramidite and an activator to each resolved locus on or in a substrate surface, e.g., a coated silicon wafer surface. The resolved loci of the substrate may further be subjected to additional reagents of the other phosphoramidite cycle steps (deprotection of the 5'-hydroxyl group, oxidation, sulfurization and/or sulfurization), which may be performed in parallel. The deposition and common phosphoramidite cycle steps may be performed without moving the oligonucleotide synthesis wafer. For example, the reagents may be passed over resolved loci within a substrate, by flowing them through the substrate from one surface to the opposite surface of the substrate. Alternatively, the substrate may be moved, e.g. to a flow cell, for some of the phosphoramidite cycle steps. The substrate can then be repositioned, re-registered, and/or re-aligned before printing a next layer of monomers.

Substrates with oligonucleotides can be fabricated using drop deposition from pulsejets of either polynucleotide precursor units (such as monomers) in the case of in situ fabrication, or a previously synthesized polynucleotide. Such methods are described in detail in, for example, the U.S. Pub. No. 2013/0130321 and U.S. Pub. No. 2013/0017977, and the references cited therein, incorporated herein by reference in their entirety. These references are incorporated herein by reference. Other drop deposition methods can be used for fabrication, as described elsewhere herein. Also, instead of drop deposition methods, light directed fabrication methods may be used, as are known in the art. Interfeature areas need not be present particularly when the arrays are made by light directed synthesis protocols.

A variety of known in situ fabrication devices can be adapted, where representative pulse-jet devices include, but are not limited to, those described in U.S. Pub. No. US2010/0256017, U.S. Pat. Pub. No. US20120050411, and U.S. Pat. No. 6,446,682, the disclosures of which patents are herein incorporated by reference in their entirety.

In various embodiments, biopolymer arrays on or inside substrates can be fabricated using either deposition of the previously obtained biopolymers or in situ synthesis methods. The deposition methods typically involve depositing biopolymers at predetermined locations on or in a substrate which are suitably activated such that the biopolymers can link thereto. Biopolymers of different sequences may be deposited at different regions on or in a substrate. Typical procedures known in the art for deposition of previously obtained polynucleotides, particularly DNA, such as whole oligomers or cDNA, includes, but is not limited to loading the polynucleotide into a drop dispenser in the form of a pulse jet head and fired onto the substrate. Such a technique has been described in WO 95/25116 and WO 98/41531, both of which are herein incorporated by reference in their entirety. Various suitable forms of inkjets for drop depositions to resolved sites of a substrate are known in the art.

In some embodiments, the invention may rely on the use of pre-synthesized oligonucleotides within an entire oligonucleotide library or parts thereof, for example, an oligonucleotide library immobilized on a surface. Substrates supporting a high density of nucleic acid arrays can be fabricated by depositing presynthesized or natural nucleic acids in predetermined positions on, in, or through a substrate. Synthesized or natural nucleic acids may be deposited on specific locations of a substrate by light directed targeting, oligonucleotide directed targeting, or any other suitable method known in the art. Nucleic acids can also be directed to specific locations. A dispenser that moves from region to region to deposit nucleic acids in specific spots can be used. The dispenser may deposit the nucleic acid through microchannels leading to selected regions. Typical dispensers include a micropipette or capillary pin to deliver nucleic acid to the substrate and a robotic system to control the position of the micropipette with respect to the substrate. In other embodiments, the dispenser includes a series of tubes, a manifold, an array of pipettes or capillary pins, or the like so that various reagents can be delivered to the reaction regions simultaneously.

Attachment of pre-synthesized oligonucleotide and/or polynucleotide sequences to a support and in situ synthesis of the same using light-directed methods, flow channel and spotting methods, inkjet methods, pin-based methods and bead-based methods are further set forth in the following references: McGall et al. (1996) Proc. Natl. Acad. Sci. U.S.A. 93: 13555; Synthetic DNA Arrays In Genetic Engineering, Vol. 20: 111, Plenum Press (1998); Duggan et al. (1999) Nat. Genet. S21: 10; Microarrays: Making Them and Using Them In Microarray Bioinformatics, Cambridge University Press, 2003; U.S. Patent Application Publication Nos. 2003/0068633 and 2002/0081582; U.S. Pat. Nos. 6,833,450, 6,830,890, 6,824,866, 6,800,439, 6,375,903 and 5,700,637; and PCT Publication Nos. WO 04/031399, WO 04/031351, WO 04/029586, WO 03/100012, WO 03/066212, WO 03/065038, WO 03/064699, WO 03/064027, WO 03/064026, WO 03/046223, WO 03/040410 and WO 02/24597; the disclosures of which are incorporated herein by reference in their entirety for all purposes. In some embodiments, pre-synthesized oligonucleotides are attached to a support or are synthesized using a spotting methodology wherein monomers solutions are deposited dropwise by a dispenser that moves from region to region (e.g., inkjet). In some embodiments, oligonucleotides are spotted on a support using, for example, a mechanical wave actuated dispenser.

The systems described herein can further include a member for providing a droplet to a first spot (or feature) having a plurality of support-bound oligonucleotides. In some embodiments, the droplet can include one or more compositions comprising nucleotides or oligonucleotides (also referred herein as nucleotide addition constructs) having a specific or predetermined nucleotide to be added and/or reagents that allow one or more of hybridizing, denaturing, chain extension reaction, ligation, and digestion. In some embodiments, different compositions or different nucleotide addition constructs may be deposited at different addresses on the support during any one iteration so as to generate an array of predetermined oligonucleotide sequences (the different features of the support having different predetermined oligonucleotide sequences). One particularly useful way of depositing the compositions is by depositing one or more droplet, each droplet containing the desired reagent (e.g. nucleotide addition construct) from a pulse jet device spaced apart from the support surface, onto the support surface or features built into the support surface.

To make it possible to automate the chemical method of polymer synthesis from subunits, solid phases are often employed, on which the growing molecular chain is anchored. On completion of synthesis it may be split off, which may be achieved by breaking a suitable linker between the actual polymer and the solid phase. For automation, the method may employ a substrate surface directly or the method may employ a substrate surface of solid phases in the form of activated particles, which are packed in a column or microchannel in a substrate, e.g. controlled pore glass (CPG). The substrate surface at times can carry one specifically removable type of oligo with a predetermined sequence. The individual synthesis reagents can be then added in a controllable manner. The quantity of molecules synthesized can be controlled by various factors, including but not limited to the size of the dedicated substrate surface, amount of support material, the size of the reaction batches, available functionalized substrate area for synthesis, the degree of functionalization, or the duration of the synthesis reaction.

Thus, various embodiments of the invention relate to the manufacturing and use of substrates holding a library of compositions, typically oligonucleotides. A substrate with resolved features is "addressable" when it has multiple regions of different moieties (e.g., different polynucleotide sequences) such that a region (i.e., a "feature" or "spot" of the substrate) at a particular predetermined location (i.e., an "address") on the substrate will detect a particular target or class of targets (although a feature may incidentally detect non-targets of that location). Substrate features are typically, but need not be, separated by intervening spaces. In some cases, features may be built into a substrate and may create one-, two-, or three-dimensional microfluidic geometries. A "substrate layout" refers to one or more characteristics of the features, such as feature positioning on the substrate, one or more feature dimensions, and an indication of a moiety at a given location.

Synthesis of Other Molecules

The subject methods and compositions can be used to synthesize other types of molecules of interest. The synthesis of peptides at selected grid regions is one such case. Various suitable chemistries used in stepwise growth of peptides on an array surface are known in the art. The peptide synthesis techniques described in U.S. Pat. No. 5,449,754, incorporated herein by reference in its entirety, may be used with the present invention. The methods and compositions of the invention described herein also find uses in chemical synthesis of drugs, protein inhibitors or any chemical synthesis in which the rapid synthesis of a plurality of compounds is desired.

Gene Assembly

In various embodiments, the present invention relates to the preparation of a polynucleotide sequence (also called "gene") using assembly of overlapping shorter oligonucleotides synthesized or spotted on substrate surfaces or alternatively, substrates housing suitable surfaces for the synthesis or spotting of oligonucleotides, e.g. beads. The shorter oligonucleotides may be patchworked together on the same strand using annealing oligonucleotides with complementary regions to consecutive assembled oligonucleotides, e.g. using a polymerase lacking strand displacement activity, a ligase, Click chemistry, or any other suitable assembly method known in the art. In this fashion, the sequence of the annealing nucleotide may be replicated between the consecutive oligonucleotides of the opposing strand. In some cases, consecutive oligonucleotides of the same strand may be stitched together without the introduction of sequence elements from the annealing oligonucleotide, for example using a ligase, Click chemistry, or any other suitable assembly chemistry known in the art. In some cases, longer polynucleotides can be synthesized hierarchically through rounds of assembly involving shorter polynucleotides/oligonucleotides.

Genes or genomes can be synthesized de novo from oligonucleotides by assembling large polynucleotides as described in the synthesis of a viral genome (7.5 kb; Cello et al, Science, 2002, 297, 1016), bacteriophage genome (5.4 kb; Smith et al, Proc. Natl. Acad. Sci. USA, 2003, 100, 15440), and a gene cluster as large as 32 kb (Kodumal et al, Proc. Natl. Acad. Sci. USA, 2004, 101, 15573), all of which are herein incorporated by reference in their entirety. Libraries of long synthetic DNA sequence can be manufactured, following the methods described in the 582 kb the genome assembly of a bacterium (*Mycoplasma genitalium*) by Venter and co-workers (Gibson et al, Science, 2008, 319, 1215), which is incorporated herein by reference in its entirety. Furthermore, large DNA biomolecules can be constructed with oligonucleotides, as described for the case of a 15 kb nucleic acid (Tian et al, Nature, 2004, 432, 1050; incorporated herein by reference in its entirety). The methods and compositions of the invention contemplate large libraries of de novo synthesized polynucleotide sequences using gene assembly methods described herein or known in the art. The synthesis of such sequences are typically performed in parallel in high densities on suitable regions of substrates that are described in further detail elsewhere herein. Further, these large libraries may be synthesized with very low error rates, described in further detail elsewhere herein.

Genes may be assembled from large numbers of synthesized oligonucleotides that are pooled. For example, gene synthesis using a pool of 600 distinct oligonucleotides can be applied as described by Tian et al. (Tian et al. Nature, 432:1050, 2004). The length of the assembled genes can be further extended by using longer oligonucleotides. For even larger genes and DNA fragments, for example larger than about 0.5, 1, 1.5, 2, 3, 4, 5 kb, or more, more than one rounds of synthesis may be applied, typically within a hierarchical gene assembly process. PCR assembly and synthesis from oligonucleotides as disclosed herein may be adapted for use in series, as described below.

A variety of gene assembly methods can be used according to the methods and compositions of the invention, ranging from methods such as ligase-chain reaction (LCR) (Chalmers and Curnow, Biotechniques, 30(2), 249-52, 2001; Wosnick et al, Gene, 60(1), 115-27, 1987) to suites of PCR strategies (Stemmer et al, 164, Gene, 49-53, 1995; Prodromou and L. H. Pearl, 5(8), Protein Engineering, 827-9, 1992; Sandhu et al, 12(1), BioTechniques, 14-6, 1992; Young and Dong, Nucleic Acids Research, 32(7), e59, 2004; Gao et al, Nucleic Acids Res., 31, e143, 2003; Xiong et al, Nucleic Acids Research, 32(12), e98, 2004) (FIG. 11). While most assembly protocols start with pools of overlapping synthesized oligos and end with PCR amplification of the assembled gene, the pathway between those two points can be quite different. In the case of LCR, the initial oligo population has phosphorylated 5' ends that allow a ligase, e.g. Pfu DNA ligase, to covalently connect these "building blocks" together to form the initial template. PCR assembly, however, typically makes use of unphosphorylated oligos, which undergo repetitive PCR cycling to extend and create a full length template. Additionally, the LCR processes may require oligo concentrations in the μM range, whereas both single stranded and double stranded PCR options have concentration requirements that are much lower (e.g. nM range).

Published synthesis attempts have used oligos ranging in size from 20-70 bp, assembling through hybridization of overlaps (6-40 bp). Since many factors are determined by the length and composition of oligos (Tm, secondary structure, etc.), the size and heterogeneity of this population could have a large effect on the efficiency of assembly and quality of assembled genes. The percentage of correct final DNA product relies on the quality and number of "building block" oligos. Shorter oligos have lower mutated rate compared with that of longer oligos, but more oligos are required to build the DNA product. In addition, the reduced overlaps of shorter oligos results in lower $T_m$ of the annealing reaction, which promotes non-specific annealing, and reduce the efficiency of the assembly process. Methods and compositions of the invention address this problem by delivering long oligonucleotides with low error rates.

A time varying thermal field refers to the time regulated heating of the microfluidic device to allow PCR amplification or PCA reactions to occur. The time varying thermal field may be applied externally, for example by placing a device substrate with reactors, e.g. nanoreactors on top of a thermal heating block, or integrated within a microfluidic device, for example as a thin film heater located immediately below the PCA and PCR chambers. A temperature controller can vary the temperature of the heating element in conjunction with a temperature sensor linked to a heater element, or integrated into the reaction chamber. A timer can vary the duration of heat applied to the reaction chambers.

The temperature of the thermal field may vary according to the denaturation, annealing and extension steps of PCR or PCA reactions. Typically, nucleic acids are denatured at about 95° C. for 2 min, followed by 30 or more cycles of denaturation at 95° C. for 30 sec, annealing at 40-60° C. for 30 sec and extension at about 72° C. for 30 sec, and a last extension of 72° C. for 10 min. The duration and temperatures used may vary depending on the composition of the oligonucleotides, PCR primers, amplified product size, template, and the reagents used, for example the polymerase.

Polymerases are enzymes that incorporate nucleoside triphosphates, or deoxynucleoside triphosphates, to extend a 3' hydroxyl terminus of a PCR primer, an oligonucleotide or a DNA fragment. For a general discussion concerning polymerases, see Watson, J. D. et al, (1987) Molecular Biology of the Gene, 4th Ed., W. A. Benjamin, Inc., Menlo Park, Calif. Suitable polymerases include, but are not limited to, KOD polymerase; Pfu polymerase; Taq-polymerase; E. coli DNA polymerase I, "Klenow" fragment, T7 polymerase, T4 polymerase, T5 polymerase and reverse transcriptase, all of which are known in the art. A polymerase having proof-reading capability, such as Pfu and Pyrobest may be used to replicate DNA with high fidelity. Pfu DNA polymerase possesses 3' to 5' exonuclease proof-reading activity, thus it may correct nucleotide misincorporation errors. In various embodiments of the invention, the nucleic acid fragments are joined together preferably by a specific hybridization reaction between overlapping regions of mutually complementary segments of the nucleic acid fragments, thereby obtaining longer synthetic double-stranded nucleic acids. The individual sequence segments used for building up longer nucleic acids can have a length of, e.g. 20-200, 50-300, 75-350 or 100-400 nucleotide building blocks. Those of skill in the art appreciate that the sequence segment length may fall within any range bounded by any of these values (e.g., 20-350 or 200-350).

The sequence segments are preferably selected in such a way that they at least partially overlap a sequence segment of the antisense strand of the complementary nucleic acid that is to be synthesized, so that the nucleic acid strand to be synthesized can be built up by hybridization of individual sequence segments. In an alternative embodiment, the sequence segments are preferably selected so that the sequence segments on both strands of the nucleic acid to be synthesized completely overlap, and accordingly preparation of a more or less complete double strand now only requires covalent linkage of the phosphodiester backbone. The length of the complementary regions or overlaps between individual fragments can be e.g. 10-50, 10-100, 12-25, 20-80, 15-20, or 15-25 nucleotide building blocks. Those of skill in the art appreciate that the sequence segment length may fall within any range bounded by any of these values (e.g., 25-100 or 10-25). If the overlapping or complementarity region between two nucleic acid fragments has a high AT content, e.g. an AT content of greater than 50%, 60%, 65%, or higher the binding constant is lower in comparison with GC-richer sequences. Accordingly, for thermodynamic reasons, hybridization between these fragments may be of comparatively low efficiency. This can have an influence on the assembly of 2 or more fragments. A possible sequence-dependent consequence is a reduced yield of nucleic acid double strands with the correct target sequence. Accordingly, sequence segments to assemble genes can be designed with desired levels of GC content in overlapping regions, for example GC content of more than 35, 40, 45, 50, 55, 60, 65%, or higher. A more detailed discussion of exemplary gene assembly methods can be found in U.S. Pat. No. 8,367,335, which is herein incorporated by reference in its entirety.

In various embodiments, polymerase chain reaction (PCR)-based and non-polymerase-cycling-assembly (PCA)-based strategies can be used for chemical gene synthesis. In addition, non-PCA-based chemical gene synthesis using different strategies and methods, including enzymatic gene synthesis, annealing and ligation reaction, simultaneous synthesis of two genes via a hybrid gene, shotgun ligation and co-ligation, insertion gene synthesis, gene synthesis via one strand of DNA, template-directed ligation, ligase chain reaction, microarray-mediated gene synthesis, Blue Heron solid support technology, Sloning building block technology, RNA-mediated gene assembly, the PCR-based thermodynamically balanced inside-out (TBIO) (Gao et al., 2003), two-step total gene synthesis method that combines dual asymmetrical PCR (DA-PCR) (Sandhu et al., 1992), overlap extension PCR (Young and Dong, 2004), PCR-based two-step DNA synthesis (PTDS) (Xiong et al., 2004b), successive PCR method (Xiong et al., 2005, 2006a), or any other suitable method known in the art can be used in connection with the methods and compositions described herein, for the assembly of longer polynucleotides from shorter oligonucleotides.

The DNA sequences that have been chemically synthesized using the methods and compositions of the invention may extend to long polynucleotide sequences, for example, polynucleotide sequences of more than 500, 750, 1000, 1250, 1500, 1750, 2000, 2500, 3000, 4000, 5000, 6000, 7500, 10000, 20000, 30000, 40000, 50000, 75000, 100000 base pairs or longer. The methods and compositions of the invention also allow for chemically synthesized polynucleotide sequences with very low error rates, as further described elsewhere herein.

In various embodiments, variations of the polymerase-mediated assembly techniques, collectively termed polymerase construction and amplification, are used for chemical synthesis of polynucleotides. Some of the commonly used technologies known in the art for custom gene synthesis are based on polymerase cycling assembly and may achieve de novo synthesis of longer polynucleotides through the assembly of a pool of oligonucleotides. The pool of oligonucleotides may be synthesized as building blocks for use in various gene synthesis techniques. The sequence, length and precise distribution of the oligonucleotides, as well as any sequence overlaps within the pool, may be designed according to the desired polynucleotide sequence and the assembly method used. The desired full-length DNA may be obtained, for example, by a few steps of PCR with necessary temperature conditions for denaturing, annealing, and elongating overlapping oligonucleotides.

PCR Assembly (PCA)

PCR assembly uses polymerase-mediated chain extension in combination with at least two oligonucleotides having complementary ends which can anneal such that at least one of the polynucleotides has a free 3'-hydroxyl capable of polynucleotide chain elongation by a polymerase (e.g., a thermostable polymerase such as Taq polymerase, VENT™ polymerase (New England Biolabs), KOD (Novagen) and the like). Overlapping oligonucleotides may be mixed in a standard PCR reaction containing dNTPs, a polymerase, and buffer. The overlapping ends of the oligonucleotides, upon annealing, create regions of double-stranded nucleic acid sequences that serve as primers for the elongation by polymerase in a PCR reaction. Products of the elongation reaction serve as substrates for formation of a longer double-strand nucleic acid sequences, eventually resulting in the synthesis of full-length target sequence. The PCR conditions may be optimized to increase the yield of the target long DNA sequence.

Various PCR based methods can be used to synthesize genes from oligonucleotides. These methods include, but are not limited to, the thermodynamically balanced inside-out (TBIO) method (Gao et al, Nucleic Acids Research, 31:e143, 2003), successive PCR (Xiong et al, Nucleic Acids Research, 32:e98, 2004), dual asymmetrical PCR (DA-PCR) (Sandhu et al, Biotechniques, 12:14, 1992), overlap extension PCR (OE-PCR) (Young and Dong, Nucleic Acids Research, 32:e59, 2004; Prodromou and Pearl, Protein Eng., 5:827, 1992) and PCR-based two step DNA synthesis (PTDS) (Xiong et al, Nucleic Acids Research, 32:e98, 2004), all of which are incorporated by reference herein in their entirety and can be adapted to assemble a PCR template in a microfluidic device.

DA-PCR is a one-step process for constructing synthetic genes. In one example, four adjacent oligonucleotides of, e.g. 17-100 bases in length with overlaps of, e.g. 15-17 bases are used as primers in a PCR reaction. Other suitable oligonucleotide and overlap sizes are within the bounds of the invention as further described herein. The quantity of the two internal primers is highly limited, and the resultant reaction causes an asymmetric single-stranded amplification of the two halves of the total sequence due to an excess of the two flanking primers. In subsequent PCR cycles, these dual asymmetrically amplified fragments, which overlap each other, yield a double-stranded, full-length product.

TBIO synthesis requires only sense-strand primers for the amino-terminal half and only antisense-strand primers for the carboxy-terminal half of a gene sequence. In addition, the TBIO primers may contain identical regions of temperature-optimized primer overlaps. The TBIO method involves complementation between the next pair of outside primers with the termini of a fully synthesized inside fragment. TBIO bidirectional elongation is completed for a given outside primer pair before the next round of bidirectional elongation takes place.

Successive PCR is a single step PCR approach in which half the sense primers correspond to one half of the template to be assembled, and the antisense primers correspond to the second half of the template to be assembled. With this approach, bidirectional amplification with an outer primer pair will not occur until amplification using an inner primer pair is complete.

PDTS typically involves two steps. First individual fragments of the DNA of interest are synthesized: In some embodiments of the invention, 10-12 oligonucleotides, such as oligonucleotides of length of about 60, 80, 100, 125, 150, 175, 200, 250, 300, 350, or more nucleotides, with about 20 bp overlap are mixed and a PCR reaction is carried out with a polymerase, such as pfu DNA, to produce longer DNA fragments. And second, the entire sequence of the DNA of interest is synthesized: 5-10 PCR products from the first step are combined and used as the template for a second PCR reaction with a polymerase, such as pyrobest DNA polymerase with two outermost oligonucleotides as primers.

Although PCR assembly using short oligonucleotides work well for relatively shorter nucleic acids, there may be a limit to the maximum number of oligonucleotides that can be assembled within a single reaction. This may impose a size limit on the double stranded DNA product. A solution to this problem is to make the DNA in series. In this scheme, multiple smaller DNA segments are synthesized in parallel in separate chambers, in multiple chips, or in series and then introduced together as precursors for the PCA reaction for assembly into a "larger" DNA fragment for subsequent PCR amplification. In other words, PCR assembly using oligonucleotides would result in a template (a first-run template) for PCR amplification. A number of first-run templates so produced may serve as precursors for PCA assembly of DNA fragments larger than the first-run templates, thus producing second-run templates. In turn, the second-run templates may serve as the precursors for the assembly of a third-run template, and so on. The approach may be repeated until the desired DNA is obtained.

Figure 12:
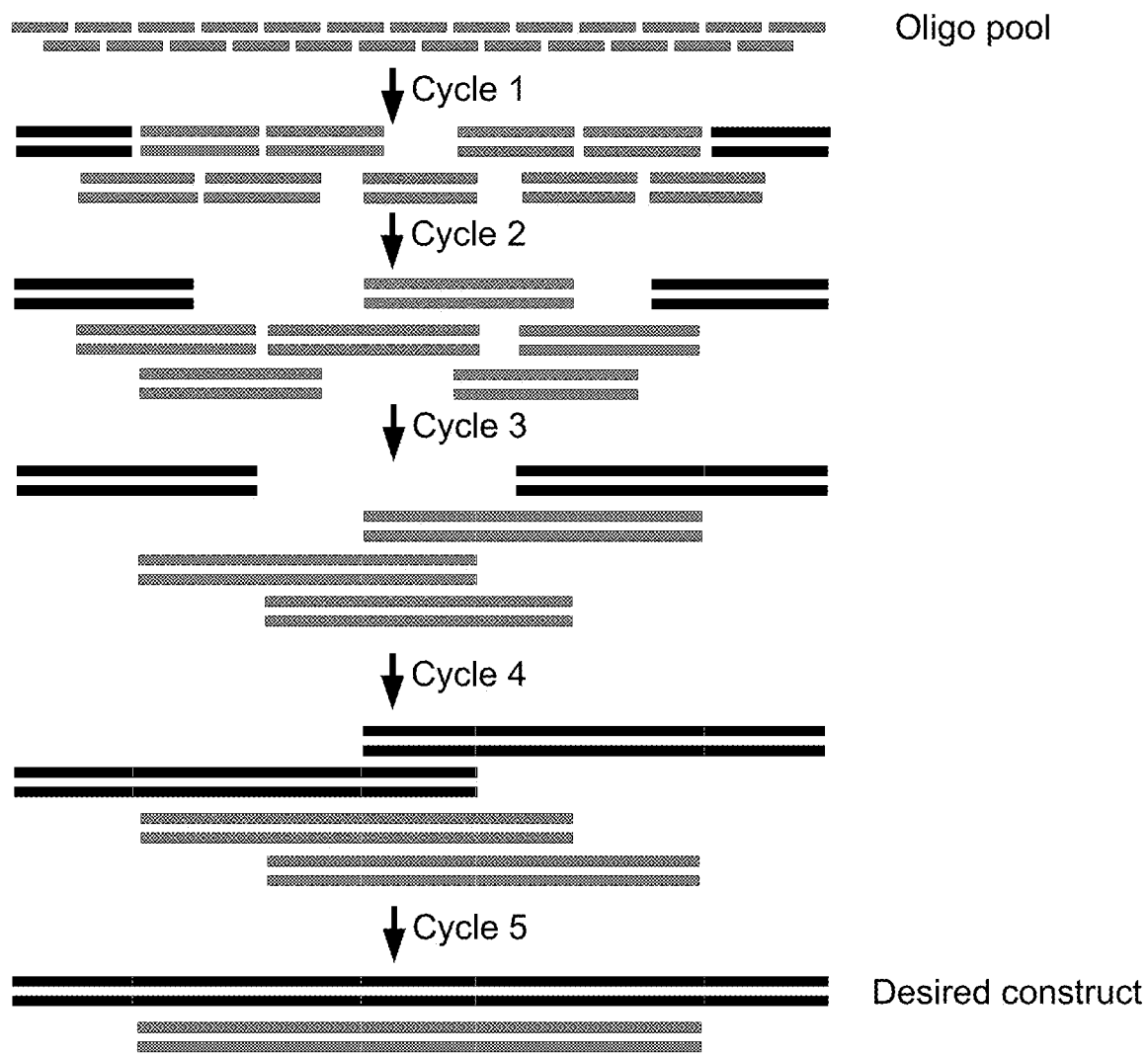
FIG. 12 illustrates an exemplary application of the polymerase chain assembly (PCA).

The oligonucleotides used in the synthesis reactions are typically single stranded molecules for assembling nucleic acids that are longer than the oligonucleotide itself. An oligonucleotide may be e.g. 20-200, 50-300, 75-350 or 100-400 nucleotide building blocks. Those of skill in the art appreciate that the sequence segment length may fall within any range bounded by any of these values (e.g., 20-350 or 200-350). A PCA chamber containing a plurality of oligonucleotides refers to the pool of oligonucleotides necessary to produce a template corresponding to a gene or to a DNA fragment. When the synthesis reactions and devices are used in series, the PCA chamber in the subsequent series of reactions would contain a pool of DNA fragments instead of the starting oligonucleotides for assembly into templates for PCR. FIG. 12 demonstrates the polymerase cycling assembly of longer constructs from a pool of overlapping oligonucleotides into gradually longer constructs through multiple cycles of the reaction.

Figure 13:
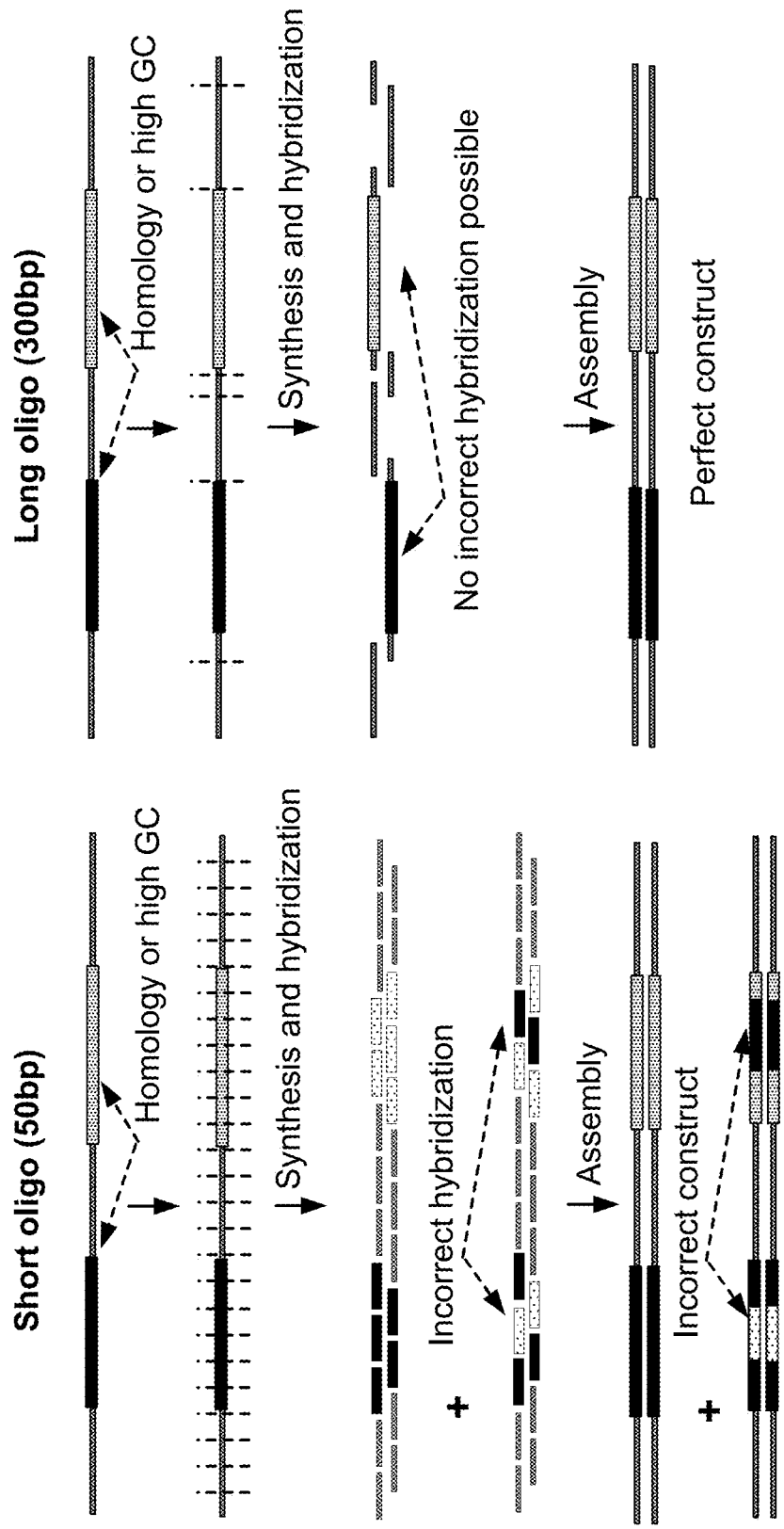
FIG. 13 are diagrams demonstrating the advantage of using longer oligonucleotides (e.g. about 300 bp) vs. shorter oligonucleotides (e.g. about 50 kb). Longer oligonucleotides can be used in the assembly of gene products with reduced error.

It is understood that longer oligonucleotides as described herein can be used advantageously in a variety of gene assembly methods to avoid assembly errors and increase the quality of synthesized genes (FIG. 13). Homologous repeats or high GC regions in a sequence to be assembled may introduce errors associated with the correct order and hybridization of smaller oligonucleotides. Longer oligonucleotides can circumvent these problems by reducing the number of oligonucleotides to be ordered and aligned, by avoiding problematic sequences, such as homology repeats or high GC regions from sites of alignment, and/or by reducing the number of assembly cycles required to assemble the desired gene.

Figure 14:
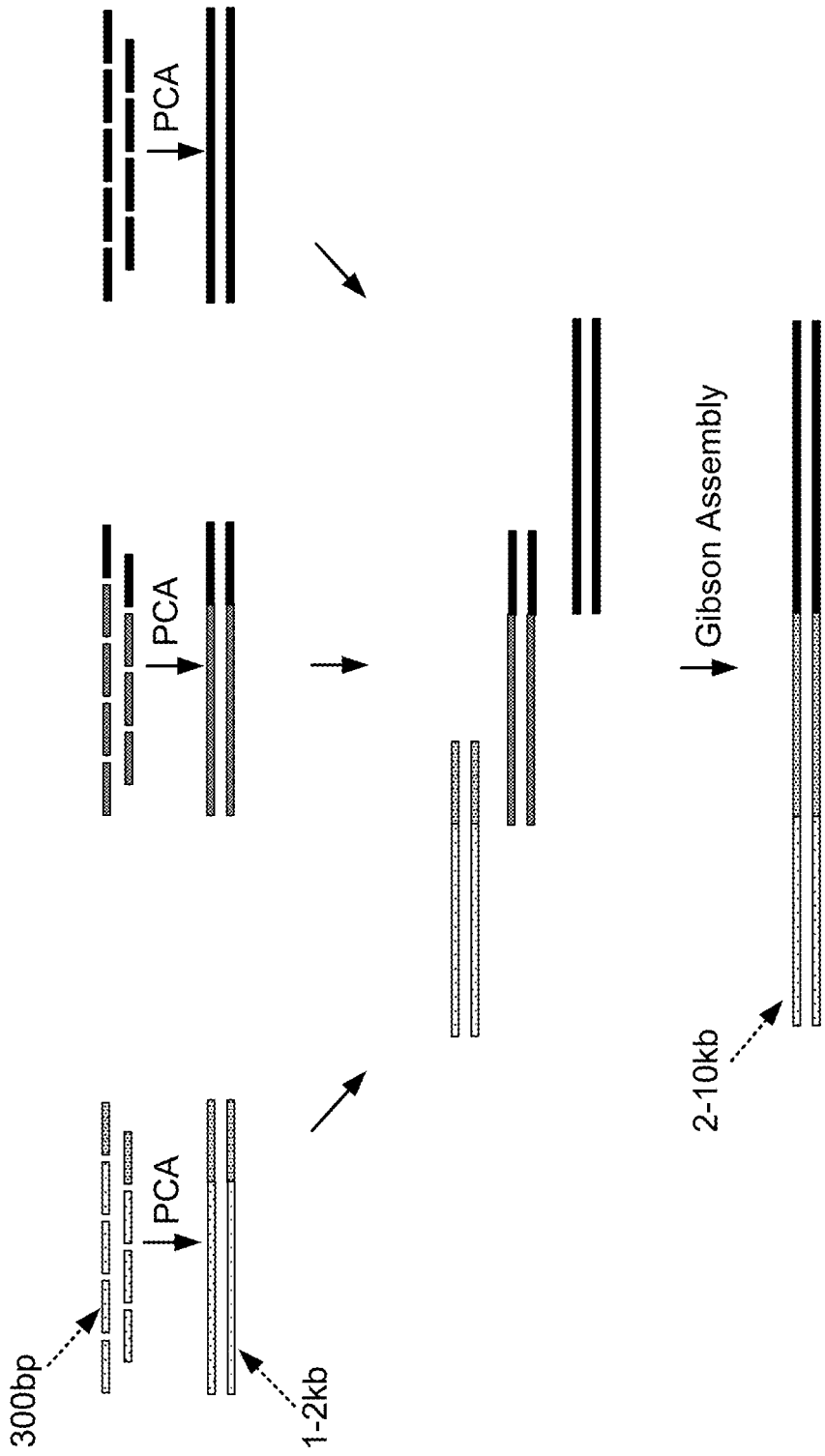
FIG. 14 are diagrams demonstrating an exemplary combined application of PCA and Gibson methods for assembly of oligonucleotides into gene products.

Larger genes may be synthesized combining gene assembly methods hierarchically as exemplified in FIG. 14. Accordingly, a number of genes of intermediary length, for example about 2 kb, can be assembled using a first gene assembly method, such as PCA. A second gene assembly method, e.g. Gibson Assembly (Gibson et al, Science, 2008, 319, 1215) may be utilized to combine the genes of intermediary length into larger genes, e.g. about 5 or 10 kb. Hierarchical assembly can be applied in stages. In vitro recombination techniques may be used to assemble cassettes of gene of intermediary length into increasingly longer sequences, e.g. more than 5, 10, 15, 20, 25, 30, 40, 50, 60, 70, 80, 90, 100, 125, 150, 175, 200, 250, 300, 400, 500, 600, 700, 800, 900, 1000 kb or longer.

Oligonucleotides useful for the assembly of genes de novo may be synthesized on one or more solid supports. Exemplary solid supports include, for example, slides, beads, chips, particles, strands, gels, sheets, tubing, spheres, containers, capillaries, pads, slices, films, plates, polymers, or a microfluidic device. Further, the solid supports may be biological, nonbiological, organic, inorganic, or combinations thereof. On supports that are substantially planar, the support may be physically separated into regions, for example, with trenches, grooves, wells, or chemical barriers (e.g., hydrophobic coatings, etc.). Supports may also comprise physically separated regions built into a surface, optionally spanning the entire width of the surface. Suitable supports for improved oligonucleotide synthesis are further described herein.

In one aspect, the oligonucleotides may be provided on a solid support for use in a microfluidic device, for example, as part of the PCA reaction chamber. Alternatively, oligonucleotides may be synthesized and subsequently introduced into a microfluidic device.

Generally, the complete gene sequence is broken down into variable or fixed length (N) oligonucleotides as appropriate. A suitable oligonucleotide length can be chosen, e.g. 20-200, 50-300, 75-350 or 100-400 nucleotide building blocks. Those of skill in the art appreciate that the sequence segment length may fall within any range bounded by any of these values (e.g., 20-350 or 200-350). The length of the overlap between sub-sequences is about or less than about N/2, but may be chosen as the needs of the assembly reaction dictates, e.g. 6-40 bp, 10-20 bp and 20-30 bp of overlap. Those of skill in the art appreciate that the sequence segment length may fall within any range bounded by any of these values (e.g., 20-40 or 6-30). The amount of partial base complementarity may vary depending on the assembly method used. For various overlapping gene assembly methods, the PCA oligonucleotides may overlap at both the 5' and 3' ends, except those forming the ends of the resulting PCR template. Base pair mismatches between oligonucleotides may affect hybridization depending on the nature of the mismatch. Mismatches at or near the 3' end of the oligonucleotide may inhibit extension. However, a G/C rich region of overlap may overcome mismatches thus resulting in templates containing errors. Accordingly, consideration of the overlap sequence, melting temperature, potential for cross-hybridization and secondary structure in oligonucleotide design can be taken into consideration.

Nucleic acid sequences resulting from a PCR assembly reaction may be referred as templates and serve as the target nucleic acid for the reproduction of a complementary strand by PCR. Typically, following an assembly reaction, the PCR assembly products may be double stranded DNA of variable sizes due perhaps to incomplete assembly and/or concatamers. In some embodiments, a first-run template is assembled from oligo-nucleotides. In other embodiments, a second-run template is assembled from DNA fragments comprising at least two first-run templates, the two templates being the PCR reaction products, optionally purified and/or error-filtered, obtained from the first two runs. A third-run template is assembled from DNA fragments comprising at least two second-run templates, which may be similarly error-filtered and so on.

Non-polymerase-cycling-assembly-based strategies, such as annealing and ligation reaction (Climie and Santi, 1990; Smith et al., 1990; Kalman et al., 1990), insertion gene synthesis (IGS) (Ciccarelli et al., 1990), gene synthesis via one strand (Chen et al., 1990), template-directed ligation (TDL) (Strizhov et al., 1996), ligase chain reaction (Au et al., 1998), or any suitable assembly method known in the art may also be used for chemical synthesis of polynucleotides. Other non-polymerase-cycling-assembly-based gene synthesis strategies include, but are not limited to microarray-based gene synthesis technology (Zhou et al., 2004), Blue Heron solid support technology, Sloning building block technology (Ball, 2004; Schmidt, 2006; Bugl et al., 2007), and RNA-mediated gene assembly from DNA arrays (Wu et al., 2012).

Enzymatic Gene Synthesis

Enzymes that repair single-stranded breaks in double-stranded DNA, first discovered in the 1960s in *E. coli* and in T4 bacteriophage infected *E. coli* cells (Meselson, 1964; Weiss and Richardson, 1967; Zimmerman et al., 1967), can be used to join chemically synthesized oligonucleotides, such as deoxyribopolynucleotides, to form continuous bihelical structures (Gupta et al., 1968a). In another example, DNA polymerase I (Klenow) can be used to join oligonucleotides to longer polynucleotides. Oligonucleotides can further be joined together via ligation, for example using a ligase, such as using phage T4 polynucleotide ligase. In some cases, oligonucleotides can be ligated hierarchically, forming longer and longer polynucleotides in each step.

Annealing and Ligation Reaction

Another approach for the facile synthesis of genes comprises assembly of a polynucleotide from many oligonucleotides through annealing and ligation reaction (Climie and Santi, 1990; Smith et al., 1990; Kalman et al., 1990). In the first, both strands of the desired sequences can be divided with short cohesive ends so that adjacent pairs of complementary oligonucleotides can anneal. The synthesized oligonucleotides can be phosphorylated, for example using a kinase, and annealed before ligation into a duplex.

Shotgun Ligation and Co-Ligation

The shotgun ligation approach comprises the assembly of a full gene from several synthesized blocks (Eren and Swenson, 1989). Accordingly, a gene may be sub-assembled in several sections, each constructed by the enzymatic ligation of several complementary pairs of chemically synthesized oligonucleotides with short single strands complementary to that of an adjacent pair. Co-ligation of the sections can achieve the synthesis of the final polynucleotide.

Insertion Gene Synthesis

Insertion gene synthesis (IGS) (Ciccarelli et al., 1990) can be used to assemble a DNA sequence in a stepwise manner within a plasmid containing a single-stranded DNA phage origin of replication. The IGS method is based upon consecutive targeted insertions of long DNA oligonucleotides within a plasmid by oligonucleotide-directed mutagenesis.

Gene Synthesis Via One Strand

Gene synthesis via one strand refers to a method to synthesize a gene via one stand (Chen et al.; 1990). A plus-stranded DNA of the target gene can be assembled by a stepwise or single-step T4 DNA ligase reaction with several, for example six, oligonucleotides in the presence of multiple, for example two, terminal complementary oligonucleotides and multiple, for example three, short interfragment complementary oligonucleotides. The use of fewer synthesized bases, in comparison to the double-strand or overlap methods can reduce costs.

Template-Directed Ligation

Template-directed ligation refers to a method to construct large synthetic genes by ligation of oligonucleotide modules, by partial annealing with a single-stranded DNA template derived from a wild-type gene (Strizhov et al.; 1996). Oligonucleotides comprising only one strand can be synthesized, in contrast to other technologies that require synthesis of two strands. A ligase, such as the Pfu DNA ligase, can be used to perform thermal cycling for assembly, selection and ligation of full-length oligonucleotides as well as for linear amplification of the template-directed ligation (TDL) product. Due to its reliance on a homologous template, this method is suitable to the synthesis of only a limited number of sequences with similarity to an existing polynucleotide molecule.

Ligase Chain Reaction

A ligase chain reaction (LCR) can be used method for synthesis of polynucleotides (Au et al.; 1998). Fragments can be assembled from several oligonucleotides via ligation, using a ligase, for example Pfu DNA ligase. After LCR, the full-length gene can be amplified with the mixture of fragments which shared an overlap by denaturation and extension using the outer two oligonucleotides.

Microarray-Mediated Gene Synthesis

Microarray-mediated gene synthesis, as a general concept, is based on the capacity to immobilize tens of thousands of specific probes on a small solid surface (Lockhart and Barlow, 2001). For the production of arrays, DNA can either be synthesized directly on the solid support (Lipshutz et al., 1999; Hughes et al., 2001) or can be deposited in a pre-synthesized form onto the surface, for example with pins or ink-jet printers (Goldmann and Gonzalez, 2000). The oligonucleotides obtained can be used in ligation under thermal cycling conditions to generate DNA constructs of several hundreds of base-pairs. Another microchip-based technology for accurate multiplex gene synthesis, the modified array-mediated gene synthesis technology (Tian et al., 2004), is similar to amplification and assembly of chip-eluted DNA AACED), a method developed for high-throughput gene synthesis (Richmond et al., 2004). Pools of thousands of 'construction' oligonucleotides and tagged complementary 'selection' oligonucleotides can be synthesized on photo-programmable microfluidic chips, released, ligation amplified, and selected by hybridization to reduce synthesis errors (Tian et al., 2004).

Blue Heron Technology

The Blue Heron technology, developed by Blue Heron Biotechnology, is based on a solid-phase support strategy based on the GeneMaker platform and enables automation (Parker and Mulligan, 2003; Mulligan and Tabone, 2003; Mulligan et al., 2007). The GeneMaker protocol may generally comprise a user sequence data entry, an algorithm designing suitable oligonucleotides for the assembly of entered sequence, oligonucleotides synthesis and hybridization into duplexes, automated ligation based solid-phase assembly through automated sequential additions inside a column on a solid support matrix, and/or cloning and sequence verification. The Blue Heron technology relies on the sequential addition of building blocks to lower errors that occur with other gene assembly methods based on non-serial pools of building blocks, such as PCR methods.

Various embodiments of the invention make use of serial and hierarchical assembly methods as exemplified in the implementation of the Blue Heron technology.

Sloning Building Block Technology

Sloning building block technology (Slonomics™; Sloning Biotechnology GmbH, Puchheim, Germany) is another method using a ligation-based strategy for chemical gene synthesis (Adis International, 2006). The Sloning synthesis method consists of a series of parallel iterative and standardized reaction steps (pipetting, mixing, incubation, washing) (Schatz and O'Connell, 2003; Schatz et al., 2004; Schatz, 2006). In contrast to ligating oligonucleotides specifically designed and synthesized for a given gene construct, Sloning technology uses a library of standardized building blocks that can be combined to form any desired sequence with a series of standardized, fully automated, cost-effective reaction steps (Schatz and O'Connell, 2003; Schatz, 2006).

Golden Gate Assembly

The Golden-gate method (see, e.g., Engler et al. (2008) PLoS ONE, 3(11): e3647; Engler et al. (2009) PLoS ONE 4(5): e5553) offers standardized, multi-part DNA assembly. The Golden-gate method can use Type IIs endonucleases, whose recognition sites are distal from their cutting sites. There are several different Type IIs endonucleases to choose from, for example BsaI. The Golden-gate method can be advantageous by the use of a single Type IIs endonuclease. The Golden-gate method is further described in U.S. Patent Pub. 2012/025848 which is incorporated heroin by reference in its entirety.

In some cases, the methods and compositions for gene assembly may involve a combination of specifically synthesized building blocks and presynthesized building blocks. Libraries of presynthesized oligonucleotides may be stored and assembly processes for desired target nucleic acids may be optimized for maximum use of presynthesized oligonucleotides, minimizing the need for new synthesis. Specifically synthesized oligonucleotides may fill in parts of a target nucleic acid, for which there is no coverage in libraries of presynthesized oligonucleotides.

RNA-Mediated Gene Assembly

In various embodiments, RNA-mediated gene assembly is used to assemble RNA transcripts from DNA elements, optionally immobilized to a surface forming an immobilized DNA array. DNA elements are designed to include an RNA polymerase (RNAP) promoter sequence, such as a T& RNA polymerase promoter sequence, toward the 5' end. Hybridization of an oligonucleotide encoding the promoter sequence, such as the T7 RNAP promoter sequence, to a DNA element can yield a double-stranded promoter. Addition of RNAP may affect the transcription from these optionally surface-bound promoters yielding many RNA copies. These amplified RNA molecules can be designed to allow self-assembly to yield a longer RNA. Briefly, the DNA elements can be designed to encode "segment sequences", which are the sections of the desired full-length RNA transcript, and "splint sequences", which are complementary RNAs that serve as templates to direct the correct assembly of the RNA segments. The DNA elements encoding RNA segments or splints may be chosen to optimize one or more reactions during the synthesis of assembled polynucleotides. For example, the DNA elements may be constructed such that that the 5' end of each RNA transcript corresponds to a GG dinucleotide, which is believed to affect higher efficiency of transcription exhibited by T7 RNA polymerase (T7 RNAP). GGG trinucleotide sequences at the 5' terminus may in turn be avoided, to avoid giving rise to a ladder of poly G transcripts in which the number of G residues can range from 1-3, attributed to "slippage" of the enzyme during coupling of GTP. Assembly can be affected via RNA:RNA hybridization of the segments to the splints. Nicks can be sealed chemically or enzymatically, using a suitable enzyme known in the art. In one example, the assembly of the RNA segment sequences into the full-length RNA transcript includes ligation with T4 RNA ligase 2. Triphosphorylated transcripts, such as those generated by T7 RNA polymerase can be "trimmed" to their monophosphorylated analogues before ligation. Trimming can be accomplished by treatment of the transcript pool with RNA 5' pyrophosphohydrolase removing a pyrophosphate group from the 5' end of each RNA. The transcript, once synthesized, can be copied by reverse transcription polymerase chain reaction (RT-PCR) to yield the corresponding gene. The assembled RNA sequence or its DNA equivalent may be amplified using a suitable nucleic acid amplification method, including those described elsewhere herein. The method is further described in Wu et al. (Cheng-Hsien Wu, Matthew R. Lockett, and Lloyd M. Smith, RNA-Mediated Gene Assembly from DNA Arrays, 2012, Angew. Chem. Int. Ed. 51, 4628-4632), which is herein incorporated by reference in its entirety.

Nonenzymatic Chemical Ligation of DNA

Other approaches include, nonenzymatic chemical ligation of DNA, for example with cyanogen bromide as a condensing agent, as described for the synthesis of a 183 bp biologically active mini-gene (Shabarova et al., 1991).

In some embodiments, assembly of oligonucleotides comprises the use of CLICK chemistry. Suitable methods to link various molecules using CLICK chemistry are known in the art (for CLICK chemistry linkage of oligonucleotides, see, e.g. El-Sagheer et al. (PNAS, 108:28, 11338-11343, 2011). Click chemistry may be performed in the presence of CuI.

Error Rates and Corrections

A critical limitation of current gene synthesis technology is the low sequence fidelity of the process: gene clones created from chemically synthesized DNA often contain sequence errors. These errors can be introduced at many stages of the process: during chemical synthesis of the component oligonucleotides, during assembly of the double-stranded oligonucleotides, and by chemical damage occurring during the manipulation and isolation of the DNA or during the cloning process.

Known methods generating chemically-synthesized DNA fragments have very high sequence error rates, e.g. every 200 to 500 bp on average. The methods described herein allow for the initial de novo synthesis of oligonucleotides and longer polynucleotide with very low error rates. Common mutations in oligonucleotides comprise deletions that can come from capping, oxidation and/or deblocking failure. Other prominent side reactions include modification of guanosine (G) by ammonia to give 2,6-diaminopurine, which codes as an adenosine (A). Deamination is also possible with cytidine (C) forming uridine (U) and adenosine forming inosine (I).

Without being bound by theory, non limiting examples of base modifications typically produced during the synthesis of an oligonucleotide using the phosphoramidite method include transamination of the 06-oxygen of deoxyguanosine to form a 2,6-diaminopurine residue, deamination of the N4-amine of deoxycytidine to form a uridine residue (Eadie, J. S. and Davidson, D. S., Nucleic Acids Res. 15:8333, 1987), depurination of N6-benzoyldeoxyadenosine yielding an apurinic site (Shaller, H. and Khorana, H. G., J. Am. Chem. Soc. 85:3828, 1963; Matteucci, M. D. and Caruthers, M. H., J. Am. Chem. Soc. 103:3185, 1981), and incomplete removal of the N2-isobutyrlamide protecting group on deoxyguanosine. Each of these side products (byproducts) can contribute to sequence errors in cloned synthetic polynucleotides.

In addition, common methods of oligonucleotide synthesis are prone to the formation of truncated products that are less than the full length of the desired oligonucleotide. The solid phase approach to oligonucleotide synthesis involves building an oligomer chain that is anchored to a solid support typically through its 3'-hydroxyl group, and is elongated by coupling of building blocks to its 5' end. The yield of each coupling step in a given chain-elongation cycle will generally be <100%. For an oligonucleotide of length n, there are n–1 linkages and the maximum yield estimation will typically be governed by [coupling efficiency]$^{n-1}$. For a 25-mer, assuming a coupling efficiency of 98%, the calculated maximum yield of full-length product will be around 61%. The final product therefore would contain decreasing amounts of n–1, n–2, n–3 etc. failure sequences.

Another class of synthetic failures is the formation of "n+" products that are longer than the full length of the desired oligonucleotide. Without being bound by theory, these products may originate from the branching of the growing oligonucleotide, in which a phosphoramidite monomer reacts through the bases, especially the N-6 of adenosine and the O-6 of guanosine. Another source of n+ products is the initiation and propagation from unwanted reactive sites on the solid support. The n+ products may also form if the 5'-trityl protecting group is inadvertently deprotected during the coupling step. This premature exposure of the 5'-hydroxyl allows for a double addition of a phosphoramidite. This type of synthetic failure of the oligonucleotide synthesis process can also contribute to sequence errors in synthetic genes. Methods and compositions of the invention, in various embodiments, allow for reducing errors during de novo synthesis of oligonucleotides through precise control of reaction parameters as described in further detail elsewhere herein.

Other types of errors maybe introduced during the assembly of oligonucleotides into longer constructs during PCR-based as well as non-PCR-based assembly methods. For example, ligation of synthetic double-stranded oligonucleotides to other synthetic double-stranded oligonucleotides to form larger synthetic double-stranded oligonucleotides may be prone to errors. For example, T4 DNA ligase exhibits poor fidelity, sealing nicks with 3' and 5' A/A or T/T mismatches (Wu, D. Y., and Wallace, R. B., Gene 76:245-54, 1989), 5' G/T mismatches (Harada, K. and Orgel, L. Nucleic Acids Res. 21:2287-91, 1993) or 3' C/A, C/T, T/G, T/T, T/C, A/C, G/G or G/T mismatches (Landegren, U., Kaiser, R., Sanders, J., and Hood, L., Science 241:1077-80, 1988).

The error rate also limits the value of gene synthesis for the production of libraries of gene variants. With an error rate of 1/300, about 0.7% of the clones in a 1500 base pair gene will be correct. As most of the errors from oligonucleotide synthesis result in frame-shift mutations, over 99% of the clones in such a library will not produce a full-length protein. Reducing the error rate by 75% would increase the fraction of clones that are correct by a factor of 40. The methods and compositions of the invention allow for fast de novo synthesis of large oligonucleotide and gene libraries with error rates that are lower than commonly observed gene synthesis methods both due to the improved quality of synthesis and the applicability of error correction methods that are enabled in a massively parallel and time-efficient manner. Accordingly, libraries may be synthesized with base insertion, deletion, substitution, or total error rates that are under 1/300, 1/400, 1/500, 1/600, 1/700, 1/800, 1/900, 1/1000, 1/1250, 1/1500, 1/2000, 1/2500, 1/3000, 1/4000, 1/5000, 1/6000, 1/7000, 1/8000, 1/9000, 1/10000, 1/12000, 1/15000, 1/20000, 1/25000, 1/30000, 1/40000, 1/50000, 1/60000, 1/70000, 1/80000, 1/90000, 1/100000, 1/125000, 1/150000, 1/200000, 1/300000, 1/400000, 1/500000, 1/600000, 1/700000, 1/800000, 1/900000, 1/1000000, or less, across the library, or across more than 80%, 85%, 90%, 93%, 95%, 96%, 97%, 98%, 99%, 99.5%, 99.8%, 99.9%, 99.95%, 99.98%, 99.99%, or more of the library. The methods and compositions of the invention further relate to large synthetic oligonucleotide and gene libraries with low error rates associated with at least 30%, 40%, 50%, 60%, 70%, 75%, 80%, 85%, 90%, 93%, 95%, 96%, 97%, 98%, 99%, 99.5%, 99.8%, 99.9%, 99.95%, 99.98%, 99.99%, or more of the oligonucleotides or genes in at least a subset of the library to relate to error free sequences in comparison to a predetermined/preselected sequence. In some embodiments, at least 30%, 40%, 50%, 60%, 70%, 75%, 80%, 85%, 90%, 93%, 95%, 96%, 97%, 98%, 99%, 99.5%, 99.8%, 99.9%, 99.95%, 99.98%, 99.99%, or more of the oligonucleotides or genes in an isolated volume within the library have the same sequence. In some embodiments, at least 30%, 40%, 50%, 60%, 70%, 75%, 80%, 85%, 90%, 93%, 95%, 96%, 97%, 98%, 99%, 99.5%, 99.8%, 99.9%, 99.95%, 99.98%, 99.99%, or more of any oligonucleotides or genes related with more than 95%, 96%, 97%. 98%, 99%, 99.5%, 99.6%, 99.7%, 99.8%, 99.9% or more similarity or identity have the same sequence. In some embodiments, the error rate related to a specified locus on an oligonucleotide or gene is optimized. Thus, a given locus or a plurality of selected loci of one or more oligonucleotides or genes as part of a large library may each have an error rate that is less than 1/300, 1/400, 1/500, 1/600, 1/700, 1/800, 1/900, 1/1000, 1/1250, 1/1500, 1/2000, 1/2500, 1/3000, 1/4000, 1/5000, 1/6000, 1/7000, 1/8000, 1/9000, 1/10000, 1/12000, 1/15000, 1/20000, 1/25000, 1/30000, 1/40000, 1/50000, 1/60000, 1/70000, 1/80000, 1/90000, 1/100000, 1/125000, 1/150000, 1/200000, 1/300000, 1/400000, 1/500000, 1/600000, 1/700000, 1/800000, 1/900000, 1/1000000, or less. In various embodiments, such error optimized loci may comprise at least 1, 2, 3, 4, 5, 6, 7, 8, 9, 10, 11, 12, 13, 14, 15, 16, 17, 18, 19, 20, 25, 30, 35, 40, 45, 50, 60, 70, 80, 90, 100, 200, 300, 400, 500, 600, 700, 800, 900, 1000, 1500, 2000, 2500, 3000, 4000, 5000, 6000, 7000, 8000, 9000, 10000, 100000, 500000, 1000000, 2000000, 3000000 or more loci. The error optimized loci may be distributed to at least 1, 2, 3, 4, 5, 6, 7, 8, 9, 10, 11, 12, 13, 14, 15, 16, 17, 18, 19, 20, 25, 30, 35, 40, 45, 50, 60, 70, 80, 90, 100, 200, 300, 400, 500, 600, 700, 800, 900, 1000, 1500, 2000, 2500, 3000, 4000, 5000, 6000, 7000, 8000, 9000, 10000, 100000, 500000, 1000000, 2000000, 3000000 or more oligonucleotides or genes.

The error rates can be achieved with or without error correction. The error rates can be achieved across the library, or across more than 80%, 85%, 90%, 93%, 95%, 96%, 97%, 98%, 99%, 99.5%, 99.8%, 99.9%, 99.95%, 99.98%, 99.99%, or more of the library.

The library may comprise more than 100, 200, 300, 400, 500, 600, 750, 1000, 15000, 20000, 30000, 40000, 50000, 60000, 75000, 100000, 200000, 300000, 400000, 500000, 600000, 750000, 1000000, 2000000, 3000000, 4000000, 5000000, or more different oligonucleotides or genes. The different oligonucleotides or genes may be related to predetermined/preselected sequences. The library may comprise oligonucleotides or genes that are over 500 bp, 600 bp, 700 bp, 800 bp, 900 bp, 1000 bp, 1250 bp, 1500 bp, 1750 bp, 2000 bp, 2500 bp, 3000 bp, 4000 bp, 5000 bp, 6000 bp, 7000 bp, 8000 bp, 9000 bp, 10 kb, 20 kb, 30 kb, 40 kb, 50 kb, 60 kb, 80 kb, 90 kb, 100 kb long, or longer. It is understood that the library may comprise of a plurality of different subsections, such as 2, 3, 4, 5, 6, 7, 8, 9, 10 subsections or more, that are governed by different error rates and/or construct sizes. Compositions and methods of the invention further allow construction of the above mentioned large synthetic libraries of oligonucleotides or genes with low error rates described above in short time frames, such us in less than three months, two months, one month, three weeks, 15, 14, 13, 12, 11, 10, 9, 8, 7, 6, 5, 4, 3, 2 days or less. Genes of the above mentioned libraries maybe synthesized by assembling de novo synthesized oligonucleotides by suitable gene assembly methods further described in detail elsewhere herein or otherwise known in the art.

Figure 15:
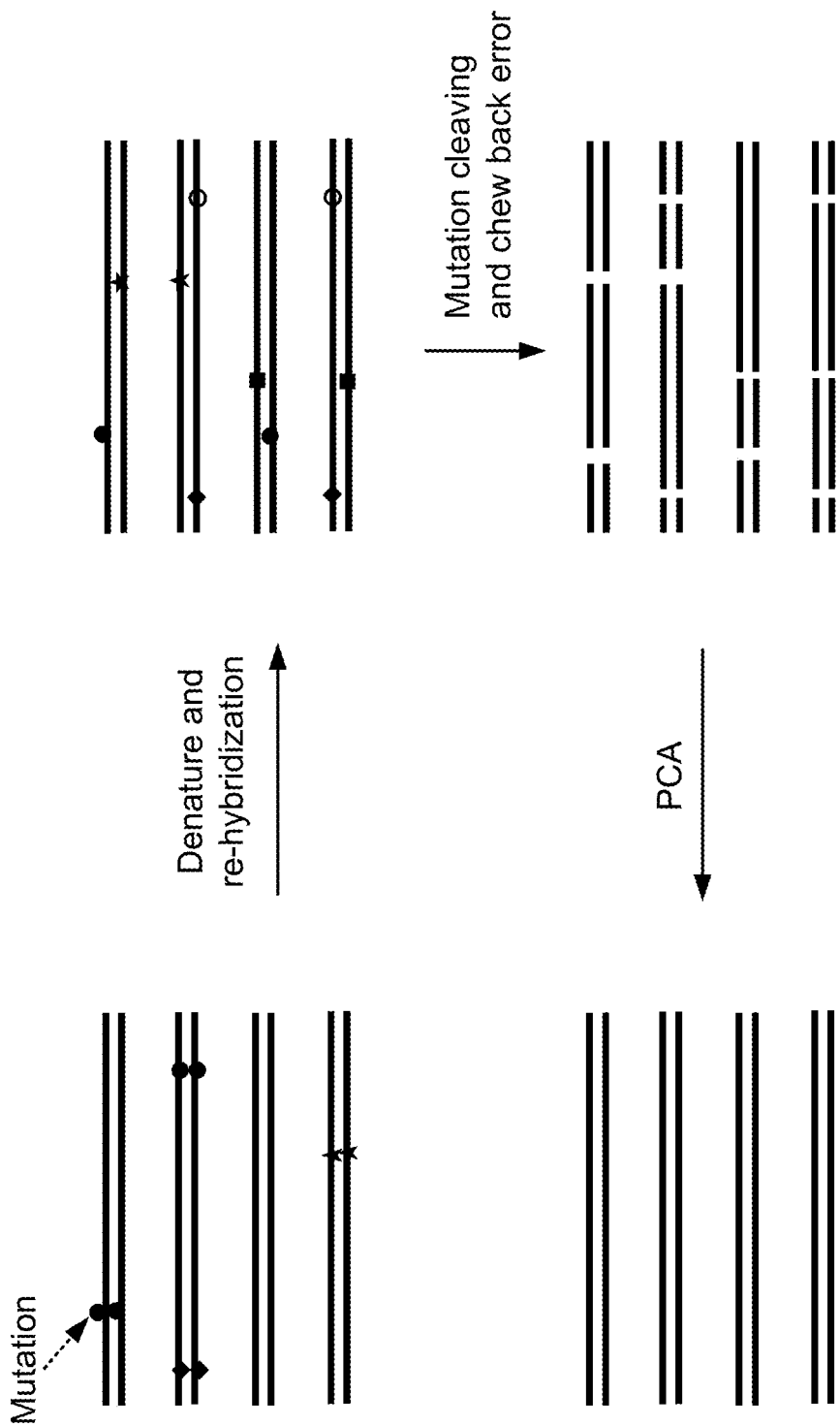
FIG. 15 is a diagram demonstrating an error correction method especially suited for application to gene synthesis products with higher error rates.
Figure 16:
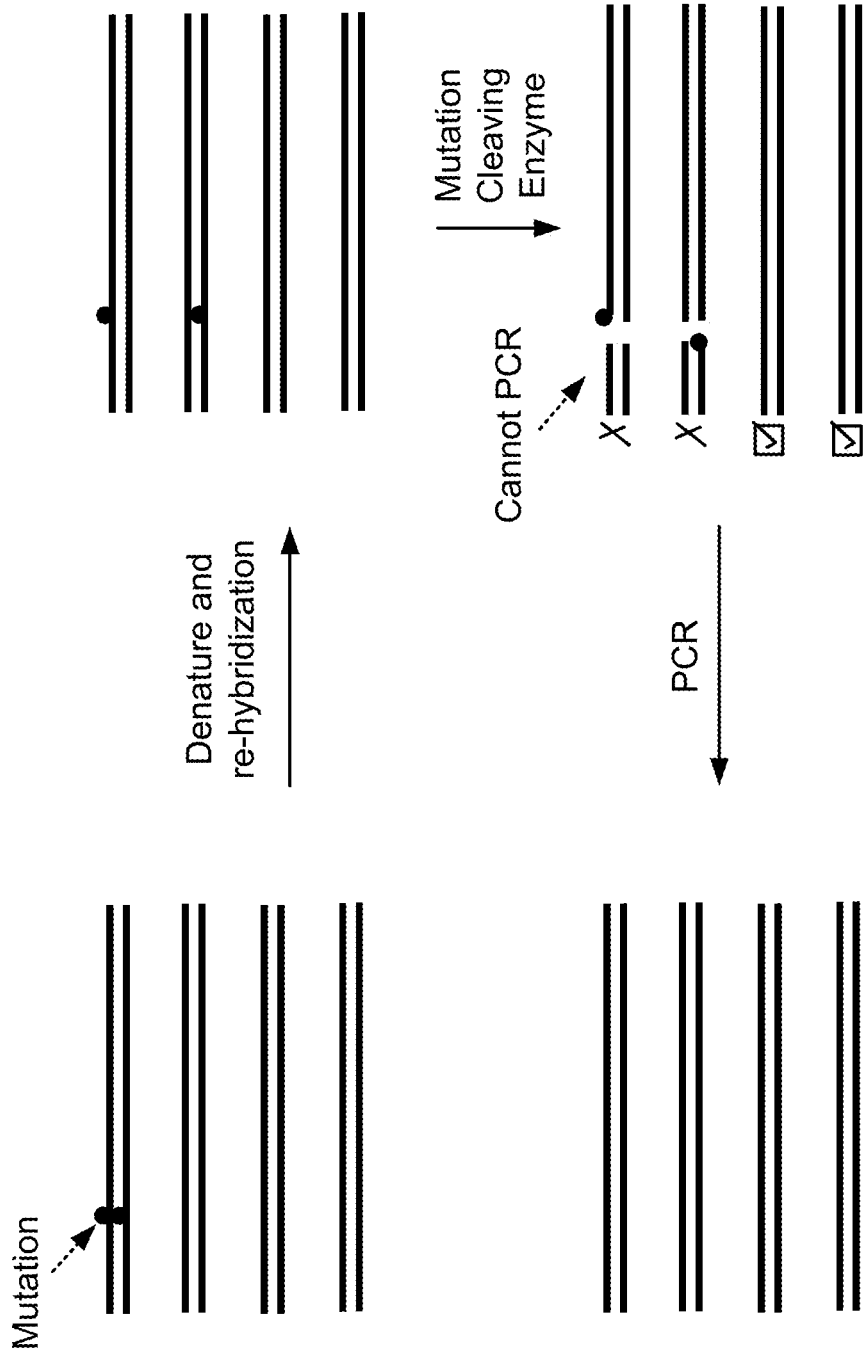
FIG. 16 is a diagram demonstrating an error correction method especially suited for application to gene synthesis products with lower error rates.

Several methods are known in the art for removal of error-containing sequences in a synthesized gene. A DNA mismatch-binding protein, MutS (from *Thermus aquaticus*), can be employed to remove failure products from synthetic genes using different strategies (Schofield and Hsieh, 2003; Carr et al., 2004; Binkowski et al., 2005). Some other strategies (Pogulis et al., 1996; Ling and Robinson, 1997; An et al., 2005; Peng et al., 2006b) use site-directed mutagenesis by overlap extension PCR to correct mistakes, and can be coupled with two or more rounds of cloning and sequencing, as well as additional synthesis of oligonucleotides. Functional selection and identification after gene synthesis is another approach (Xiong et al., 2004b; Smith et al., 2003). Another approach to error correction uses SURVEYOR endonuclease (Transgenomic), a mismatch-specific DNA endonuclease to scan for known and unknown mutations and polymorphisms in heteroduplex DNA. SURVEYOR technology is based on a mismatch-specific DNA endonuclease from celery, Surveyor nuclease, which is a member of the CEL nuclease family of plant DNA endonucleases (Qiu et al., 2004). Surveyor nuclease cleaves with high specificity at the 3' side of any base-substitution mismatch and other distortion site in both DNA strands, including all base substitutions and insertion/deletions up to at least 12 nucleotides. Insertion/deletion mismatches and all base-substitution mismatches can be recognized, with varying efficiency of cleavage based on the mismatch sequence. In one example, Surveyor nuclease technology can be used for mismatch detection in a method involving four steps: (i) optional polynucleotide amplification, e.g. PCR, of desired polynucleotide targets with both mutant/variant and wild-type/desired sequences; (ii) hybridization resulting heteroduplexes comprising mismatches; (iii) treatment of heteroduplexes with Surveyor nuclease to cleave at mismatch sites; and (iv) optional analysis of digested polynucleotide products using the detection/separation platform of choice (FIGS. 15-16). The cleavage products resulting from the treatment of heteroduplexes may be subjected to PCA after the error at the cleavage site is chewed out, e.g. by an exonuclease, to generate error depleted products (FIG. 15). The mismatch bases can be substantially or in some cases completely removed to produce error-free strands. In some embodiments, the cleaved strands can be reannealed to targets in a pool of polynucleotides and extended. As the frequency of error containing polynucleotides is very low after the initial annealing and cleavage of heteroduplexes removing mismatches, most cleaved strands will anneal to targets with sequences free of error at the site of the initial mismatch. Through extension along the targets, polynucleotides can be resynthesized free of the initial mismatch. Various examples of gene assembly incorporate error correction. For example, the PCR-based accurate synthesis (PAS) protocol can incorporate: design of the gene and oligonucleotides, purification of the oligonucleotides, a first PCR to synthesize segments, a second PCR to assemble the full-length gene, and sequencing and error correction (Xiong et al., 2006). Alternatively, the sample by be subjected to PCR, wherein the cleaved products are not able to participate, thereby diluting the abundance of the error in the sample (FIG. 16).

In certain embodiments, the present invention provides methods that selectively remove double-stranded oligonucleotides, such as DNA molecules, with mismatches, bulges and small loops, chemically altered bases and other heteroduplexes arising during the process of chemical synthesis of DNA, from solutions containing perfectly matched synthetic DNA fragments. The methods separate specific protein-DNA complexes formed directly on heteroduplex DNA or through an affinity system comprising an incorporated nucleotide analog, e.g. one that is based on avidin-biotin-DNA complexes formed following the introduction of a biotin molecule or a biotin analog, into heteroduplex containing DNA and subsequent binding by any member of the avidin family of proteins, including streptavidin. The avidin may be immobilized on a solid support.

Central to the method are enzymes that recognize and bind specifically to mismatched, or unpaired bases within a double-stranded oligonucleotide (e.g., DNA) molecule and remain associated at or near to the site of the heteroduplex, create a single or double strand break or are able to initiate a strand transfer transposition event at or near to the heteroduplex site. The removal of mismatched, mispaired and chemically altered heteroduplex DNA molecules from a synthetic solution of DNA molecules results in a reduced concentration of DNA molecules that differ from the expected synthesized DNA sequence.

The mismatch recognition proteins typically bind on or within the vicinity of a mismatch. Reagents for mismatch recognition protein based error correction may comprise proteins that are endonucleases, restriction enzymes, ribonucleases, mismatch repair enzymes, resolvases, helicases, ligases, antibodies specific for mismatches, and their variants. The enzymes can be selected, for example, from T4 endonuclease 7, T7 endonuclease 1, S1, mung bean endonuclease, MutY, MutS, MutH, MutL, cleavase, and HINF1. In certain embodiments of the invention, a mismatch recognition protein cleaves at least one strand of the mismatched DNA in the vicinity of the mismatch site.

In the case of proteins that recognize and cleave heteroduplex DNA forming a single strand nick, for example the CELI endonuclease enzyme, the resultant nick can be used as substrate for DNA polymerase to incorporate modified nucleotides suitable for affinity partnerships, e.g. ones containing a biotin moiety or an analog thereof. There are many examples of proteins that recognize mismatched DNA and produce a single strand nick, including resolvase endonucleases, glycosylases and specialized MutS-like proteins that possess endonuclease activity. In some cases the nick is created in a heteroduplex DNA molecule after further processing, for example thymine DNA glycosylases can be used to recognize mismatched DNA and hydrolyze the bond between deoxyribose and one of the bases in DNA, generating an abasic site without necessarily cleaving the sugar phosphate backbone of DNA. The abasic site can be converted by an AP endonuclease to a nicked substrate suitable for DNA polymerase extension. Protein-heteroduplex DNA complexes can thus be formed directly, in the example of MutS proteins, or indirectly, following incorporation of nucleotide analogs, e.g. biotin or analogs thereof, into the heteroduplex containing strand and subsequent binding of biotin or biotin analogs with streptavidin or avidin proteins.

Other error correction methods may rely on transposase enzymes, such as the MuA transposase, preferentially inserting labeled DNA, e.g. biotin or biotin-analog labeled DNA, containing a precleaved version of the transposase DNA binding site into or near to the site of mismatched DNA in vitro via a strand transfer reaction. The in vitro MuA transposase directed strand transfer is known by those skilled in the art and familiar with transposase activity to be specific for mismatched DNA. In this method, the precleaved MuA binding site DNA may be biotinylated at the 5' end of the molecule enabling the formation of a protein-biotin-DNA complex with streptavidin or avidin protein following strand transfer into heteroduplex containing DNA.

Separation of protein-DNA complexes in vitro can be achieved by incubation of the solution containing protein-DNA complexes with a solid matrix that possesses high affinity and capacity for binding of protein and low affinity for binding of DNA. In some cases, such matrices can be embedded within microfluidic devices in connection with the various embodiments of the invention described herein.

Several large classes of enzymes preferentially digest heteroduplex polynucleotides, such as DNA substrates, containing mismatches, deletions or damaged bases. Typically, these enzymes act to convert their damaged or mismatched substrates into nicks or single base pair gaps (in some cases with the help of an AP endonuclease that converts abasic sites into nicks). DNA glycosylases, mismatch endonucleases, and the MutSLH mismatch repair proteins are especially useful for their utility in modifying synthetic fragments which contain errors. Methods and compositions of the present invention may rely on these nicks or small gaps to identify the error-containing DNA molecules and remove them from the cloning process.

A combination of techniques can be used for removing the treated polynucleotides containing errors. DNA glycosylases are a class of enzymes that remove mismatched bases and, in some cases, cleave at the resulting apurinic/apyrimidimic (AP) site. Thymine DNA glycosylases (TDGs) can be used to enrich mismatch-containing or perfectly-matched DNA populations from complex mixtures (X. Pan and S. Weissman, "An approach for global scanning of single nucleotide variations" 2002 PNAS 99:9346-9351). DNA glycosylases can be used to hydrolyze the bond between deoxyribose and one of the bases in DNA, generating an abasic site without necessarily cleaving the sugar phosphate backbone of DNA. All four groups of single base mismatches and some other mismatches could be hydrolyzed by a mixture of two TDGs. In addition, the enzymes' high affinity for abasic sites in the absence of magnesium can be utilized to separate DNA molecules into populations enriched or depleted for heteroduplexes. A very large number of DNA glycosylases have been identified, and non-limiting examples can be found in US Pat. Pub. 2006/0134638, which is incorporated herein by reference in its entirety. DNA glycosylases typically act on a subset of unnatural, damaged or mismatched bases, removing the base and leaving a substrate for subsequent repair. As a class, the DNA glycosylases have broad, distinct and overlapping specificities for the chemical substrates that they will remove from DNA. Glycosylase treatment may be especially useful in reducing the error rates of base substitutions to low levels. Glycosylases that leave AP sites are combined with an AP endonuclease such as E. coli Endonuclease IV or Exo III to generate a nick in the DNA.

Non-limiting examples of mismatch endonuclease enzymes for nicking DNA in the region of mismatches or damaged DNA include T7 Endonuclease I, E. coli Endonuclease V, T4 Endonuclease VII, mung bean nuclease, Cell, E. coli Endonuclease IV, and UVDE.

The use of the MutSLH complex to remove the majority of errors from PCR fragments is described by Smith et al. (J. Smith and P. Modrich, "Removal of polymerase-produced mutant sequences from PCR products." 1997, PNAS 94:6847-6850), incorporated herein by reference in its entirety. In the absence of DAM methylation, the MutSLH complex can be used to catalyze double-stranded cleavage at (GATC) sites. PCR products can be treated with MutSLH in the presence of ATP.

A more detailed disclosure regarding error correction in synthetic polynucleotides can be found in US. Pat. Pub. 2006/0134638 and U.S. Pat. No. 6,664,112, both of which are herein incorporated in their entirety.

Enzymes, binding partners and other reagents used in error correction of synthesized polynucleotides according to the methods and compositions of the invention may be immobilized on surfaces, such as coated or functionalized surfaces, on supports and substrates described herein. Reactions can be carried out in situ with one or more components immobilized. Purification schemes enriching polynucleotides with fewer or no errors utilizing such components on appropriate surfaces are understood to be within the bounds of the invention.

Ultimately, strategies for gene assembly rely on high-quality oligonucleotides to achieve the de novo synthesis of polynucleotides with low error rates. Methods and compositions described herein allow for the synthesis of such high-quality oligonucleotides in various embodiments.

Amplification of Nucleic Acids

In some embodiments, the nucleic acids described herein are amplified. Amplification can be performed by any means known in the art. In some cases, the nucleic acids are amplified by polymerase chain reaction (PCR). Various PCR methods are known in the art, as described in, for example, U.S. Pat. Nos. 5,928,907 and 6,015,674, the complete disclosures of which are hereby incorporated by reference for any purpose. Other methods of nucleic acid amplification include, for example, ligase chain reaction, oligonucleotide ligations assay, and hybridization assay. These and other methods are described in greater detail in U.S. Pat. Nos. 5,928,907 and 6,015,674. Real-time optical detection systems are known in the art, as also described in greater detail in, for example, U.S. Pat. Nos. 5,928,907 and 6,015,674, incorporated herein above. Other amplification methods that can be used herein include those described in U.S. Pat. Nos. 5,242,794; 5,494,810; 4,988,617; and 6,582,938, all of which are incorporated herein in their entirety.

In some aspects of the invention, exponential amplification of nucleic acids or polynucleotides is used. These methods often depend on the product catalyzed formation of multiple copies of a nucleic acid or polynucleotide molecule or its complement. The amplification products are sometimes referred to as "amplicons." One such method for the enzymatic amplification of specific double stranded sequences of DNA is polymerase chain reaction (PCR). This in vitro amplification procedure is based on repeated cycles of denaturation, oligonucleotide primer annealing, and primer extension by thermophilic template dependent polynucleotide polymerase, resulting in the exponential increase in copies of the desired sequence of the polynucleotide analyte flanked by the primers. The two different PCR primers, which anneal to opposite strands of the DNA, are positioned so that the polymerase catalyzed extension product of one primer can serve as a template strand for the other, leading to the accumulation of a discrete double stranded fragment whose length is defined by the distance between the 5' ends of the oligonucleotide primers. Other amplification techniques that can be used in the methods of the provided invention include, e.g., AFLP (amplified fragment length polymorphism) PCR (see e.g.: Vos et al. 1995. AFLP: a new technique for DNA fingerprinting. Nucleic Acids Research 23: 4407-14), allele-specific PCR (see e.g., Saiki R K, Bugawan T L, Horn G T, Mullis K B, Erlich H A (1986). Analysis of enzymatically amplified beta-globin and HLA-DQ alpha DNA with allele-specific oligonucleotide probes Nature 324: 163-166), Alu PCR, assembly PCR (see e.g., Stemmer W P, Crameri A, Ha K D, Brennan T M, Heyneker H L (1995). Single-step assembly of a gene and entire plasmid from large numbers of oligodeoxyribonucleotides Gene 164: 49-53), assymetric PCR (see e.g., Saiki R K supra), colony PCR, helicase dependent PCR (see e.g., Myriam Vincent, Yan Xu and Huimin Kong (2004). Helicase-dependent isothermal DNA amplification EMBO reports 5 (8): 795-800), hot start PCR, inverse PCR (see e.g., Ochman H, Gerber A S, Hartl D L. Genetics. 1988 November; 120(3):621-3), in situ PCR, intersequence-specific PCR or IS SR PCR, digital PCR, linear-after-the-exponential-PCR or Late PCR (see e.g., Pierce K E and Wangh L T (2007). Linear-after-the-exponential polymerase chain reaction and allied technologies Real-time detection strategies for rapid, reliable diagnosis from single cells Methods Mol. Med. 132: 65-85), long PCR, nested PCR, real-time PCR, duplex PCR, multiplex PCR, quantitative PCR, quantitative fluorescent PCR (QF-PCR), multiplex fluorescent PCR (MF-PCR), restriction fragment length polymorphism PCR (PCR-RFLP), PCK-RFLPIRT-PCR-IRFLP, polonony PCR, in situ rolling circle amplification (RCA), bridge PCR, picotiter PCR and emulsion PCR, or single cell PCR. Other suitable amplification methods include, transcription amplification, self-sustained sequence replication, selective amplification of target polynucleotide sequences, consensus sequence primed polymerase chain reaction (CP-PCR), arbitrarily primed polymerase chain reaction (AP-PCR), and degenerate oligonucleotide-primed PCR (DOP-PCR). Another method for amplification involves amplification of a single stranded polynucleotide using a single oligonucleotide primer. The single stranded polynucleotide that is to be amplified contains two non-contiguous sequences that are substantially or completely complementary to one another and, thus, are capable of hybridizing together to form a stem-loop structure. This single stranded polynucleotide already may be part of a polynucleotide analyte or may be created as the result of the presence of a polynucleotide analyte.

Another method for achieving the result of an amplification of nucleic acids is known as the ligase chain reaction (LCR). This method uses a ligase enzyme to join pairs of preformed nucleic acid probes. The probes hybridize with each complementary strand of the nucleic acid analyte, if present, and ligase is employed to bind each pair of probes together resulting in two templates that can serve in the next cycle to reiterate the particular nucleic acid sequence.

Another method for achieving nucleic acid amplification is the nucleic acid sequence based amplification (NASBA). This method is a promoter-directed, enzymatic process that induces in vitro continuous, homogeneous and isothermal amplification of a specific nucleic acid to provide RNA copies of the nucleic acid. The reagents for conducting NASBA include a first DNA primer with a 5'-tail comprising a promoter, a second DNA primer, reverse transcriptase, RNase-H, T7 RNA polymerase, NTPs and dNTPs.

Another method for amplifying a specific group of nucleic acids is the Q-beta-replicase method, which relies on the ability of Q-beta-replicase to amplify its RNA substrate exponentially. The reagents for conducting such an amplification include "midi-variant RNA" (amplifiable hybridization probe), NTP's, and Q-beta-replicase.

Another method for amplifying nucleic acids is known as 3SR and is similar to NASBA except that the RNase-H activity is present in the reverse transcriptase. Amplification by 3SR is an RNA specific target method whereby RNA is amplified in an isothermal process combining promoter directed RNA polymerase, reverse transcriptase and RNase H with target RNA. See for example Fahy et al. PCR Methods Appl. 1:25-33 (1991).

Another method for amplifying nucleic acids is the Transcription Mediated Amplification (TMA) used by Gen- Probe. The method is similar to NASBA in utilizing two enzymes in a self-sustained sequence replication. See U.S. Pat. No. 5,299,491 herein incorporated by reference.

Another method for amplification of nucleic acids is Strand Displacement Amplification (SDA) (Westin et al 2000, Nature Biotechnology, 18, 199-202; Walker et al 1992, Nucleic Acids Research, 20, 7, 1691-1696), which is an isothermal amplification technique based upon the ability of a restriction endonuclease such as HincII or BsoBI to nick the unmodified strand of a hemiphosphorothioate form of its recognition site, and the ability of an exonuclease deficient DNA polymerase such as Klenow exo minus polymerase, or Bst polymerase, to extend the 3'-end at the nick and displace the downstream DNA strand. Exponential amplification results from coupling sense and antisense reactions in which strands displaced from a sense reaction serve as targets for an antisense reaction and vice versa.

Another method for amplification of nucleic acids is Rolling Circle Amplification (RCA) (Lizardi et al. 1998, Nature Genetics, 19:225-232). RCA can be used to amplify single stranded molecules in the form of circles of nucleic acids. In its simplest form, RCA involves the hybridization of a single primer to a circular nucleic acid. Extension of the primer by a DNA polymerase with strand displacement activity results in the production of multiple copies of the circular nucleic acid concatenated into a single DNA strand.

In some embodiments of the invention, RCA is coupled with ligation. For example, a single oligonucleotide can be used both for ligation and as the circular template for RCA. This type of polynucleotide can be referred to as a "padlock probe" or a "RCA probe." For a padlock probe, both termini of the oligonucleotide contain sequences complementary to a domain within a nucleic acid sequence of interest. The first end of the padlock probe is substantially complementary to a first domain on the nucleic acid sequence of interest, and the second end of the padlock probe is substantially complementary to a second domain, adjacent to the first domain near the first domain. Hybridization of the oligonucleotide to the target nucleic acid results in the formation of a hybridization complex. Ligation of the ends of the padlock probe results in the formation of a modified hybridization complex containing a circular polynucleotide. In some cases, prior to ligation, a polymerase can fill in the gap by extending one end of the padlock probe. The circular polynucleotide thus formed can serve as a template for RCA that, with the addition of a polymerase, results in the formation of an amplified product nucleic acid. The methods of the invention described herein can produce amplified products with defined sequences on both the 5'- and 3'-ends. Such amplified products can be used as padlock probes.

Some aspects of the invention utilize the linear amplification of nucleic acids or polynucleotides. Linear amplification generally refers to a method that involves the formation of one or more copies of the complement of only one strand of a nucleic acid or polynucleotide molecule, usually a nucleic acid or polynucleotide analyte. Thus, the primary difference between linear amplification and exponential amplification is that in the latter process, the product serves as substrate for the formation of more product, whereas in the former process the starting sequence is the substrate for the formation of product but the product of the reaction, i.e. the replication of the starting template, is not a substrate for generation of products. In linear amplification the amount of product formed increases as a linear function of time as opposed to exponential amplification where the amount of product formed is an exponential function of time.

In some embodiments, amplification methods can be solid-phase amplification, polony amplification, colony amplification, emulsion PCR, bead RCA, surface RCA, surface SDA, etc., as will be recognized by one of skill in the art. In some embodiments, amplification methods that results in amplification of free DNA molecules in solution or tethered to a suitable matrix by only one end of the DNA molecule can be used. Methods that rely on bridge PCR, where both PCR primers are attached to a surface (see, e.g., WO 2000/018957 and Adessi et al., Nucleic Acids Research (2000): 28(20): E87) can be used. In some cases the methods of the invention can create a "polymerase colony technology," or "polony," referring to a multiplex amplification that maintains spatial clustering of identical amplicons (see Harvard Molecular Technology Group and Lipper Center for Computational Genetics website). These include, for example, in situ polonies (Mitra and Church, Nucleic Acid Research 27, e34, Dec. 15, 1999), in situ rolling circle amplification (RCA) (Lizardi et al., Nature Genetics 19, 225, July 1998), bridge PCR (U.S. Pat. No. 5,641,658), picotiter PCR (Leamon et al., Electrophoresis 24, 3769, November 2003), and emulsion PCR (Dressman et al., PNAS 100, 8817, Jul. 22, 2003). The methods of the invention provide new methods for generating and using polonies.

Amplification may be achieved through any process by which the copy number of a target sequence is increased, e.g. PCR. Conditions favorable to the amplification of target sequences by PCR are known in the art, can be optimized at a variety of steps in the process, and depend on characteristics of elements in the reaction, such as target type, target concentration, sequence length to be amplified, sequence of the target and/or one or more primers, primer length, primer concentration, polymerase used, reaction volume, ratio of one or more elements to one or more other elements, and others, some or all of which can be altered. In general, PCR involves the steps of denaturation of the target to be amplified (if double stranded), hybridization of one or more primers to the target, and extension of the primers by a DNA polymerase, with the steps repeated (or "cycled") in order to amplify the target sequence. Steps in this process can be optimized for various outcomes, such as to enhance yield, decrease the formation of spurious products, and/or increase or decrease specificity of primer annealing. Methods of optimization are well known in the art and include adjustments to the type or amount of elements in the amplification reaction and/or to the conditions of a given step in the process, such as temperature at a particular step, duration of a particular step, and/or number of cycles. In some embodiments, an amplification reaction comprises at least 5, 10, 15, 20, 25, 30, 35, 50, or more cycles. In some embodiments, an amplification reaction comprises no more than 5, 10, 15, 20, 25, 35, 50, or more cycles. Cycles can contain any number of steps, such as 1, 2, 3, 4, 5, 6, 7, 8, 9, 10 or more steps. Steps can comprise any temperature or gradient of temperatures, suitable for achieving the purpose of the given step, including but not limited to, 3' end extension (e.g. adaptor fill-in), primer annealing, primer extension, and strand denaturation. Steps can be of any duration, including but not limited to about, less than about, or more than about 1, 5, 10, 15, 20, 25, 30, 35, 40, 45, 50, 55, 60, 70, 80, 90, 100, 120, 180, 240, 300, 360, 420, 480, 540, 600, or more seconds, including indefinitely until manually interrupted. Cycles of any number comprising different steps can be combined in any order. In some embodiments, different cycles comprising different steps are combined such that the total number of cycles in the combination is about, less that about, or more than about 5, 10, 15, 20, 25, 30, 35, 50, or more cycles.

Amplification can be performed at any point during a multi reaction procedure using the methods and compositions of the invention, e.g. before or after pooling of sequencing libraries from independent reaction volumes and may be used to amplify any suitable target molecule described herein.

Ligation Reactions

In some embodiments, the oligonucleotides can be ligated or linked to adaptors or barcodes. The linking agent can be a ligase. In some embodiments the ligase is T4 DNA ligase, using well known procedures (Maniatis, T. in Molecular Cloning, Cold Spring Harbor Laboratory (1982)). Other DNA ligases may also be used. With regard to ligation, other ligases, such as those derived from thermophilic organisms may be used thus permitting ligation at higher temperatures allowing the use of longer oligonucleotides (with increased specificity) which could be annealed and ligated simultaneously under the higher temperatures normally permissible for annealing such oligonucleotides.

The terms "joining" and "ligation" as used herein, with respect to two polynucleotides, refers to the covalent attachment of two separate polynucleotides to produce a single larger polynucleotide with a contiguous backbone. Methods for joining two polynucleotides are known in the art, and include without limitation, enzymatic and non-enzymatic (e.g. chemical) methods. Examples of ligation reactions that are non-enzymatic include the non-enzymatic ligation techniques described in U.S. Pat. Nos. 5,780,613 and 5,476,930, which are herein incorporated by reference. In some embodiments, an adaptor oligonucleotide is joined to a target polynucleotide by a ligase, for example a DNA ligase or RNA ligase. Multiple ligases, each having characterized reaction conditions, are known in the art, and include, without limitation NAD$^+$-dependent ligases including tRNA ligase, Taq DNA ligase, *Thermus filiformis* DNA ligase, *Escherichia coli* DNA ligase, Tth DNA ligase, *Thermus scotoductus* DNA ligase (I and II), thermostable ligase, Ampligase thermostable DNA ligase, VanC-type ligase, 9° N DNA Ligase, Tsp DNA ligase, and novel ligases discovered by bioprospecting; ATP-dependent ligases including T4 RNA ligase, T4 DNA ligase, T3 DNA ligase, T7 DNA ligase, Pfu DNA ligase, DNA ligase 1, DNA ligase III, DNA ligase IV, and novel ligases discovered by bioprospecting; and wild-type, mutant isoforms, and genetically engineered variants thereof. Ligation can be between polynucleotides having hybridizable sequences, such as complementary overhangs. Ligation can also be between two blunt ends. Generally, a 5' phosphate is utilized in a ligation reaction. The 5' phosphate can be provided by the target polynucleotide, the adaptor oligonucleotide, or both. 5' phosphates can be added to or removed from polynucleotides to be joined, as needed. Methods for the addition or removal of 5' phosphates are known in the art, and include without limitation enzymatic and chemical processes. Enzymes useful in the addition and/or removal of 5' phosphates include kinases, phosphatases, and polymerases. In some embodiments, both of the two ends joined in a ligation reaction (e.g. an adaptor end and a target polynucleotide end) provide a 5' phosphate, such that two covalent linkages are made in joining the two ends. In some embodiments, only one of the two ends joined in a ligation reaction (e.g. only one of an adaptor end and a target polynucleotide end) provides a 5' phosphate, such that only one covalent linkage is made in joining the two ends. In some embodiments, only one strand at one or both ends of a target polynucleotide is joined to an adaptor oligonucleotide. In some embodiments, both strands at one or both ends of a target polynucleotide are joined to an adaptor oligonucleotide. In some embodiments, 3' phosphates are removed prior to ligation. In some embodiments, an adaptor oligonucleotide is added to both ends of a target polynucleotide, wherein one or both strands at each end are joined to one or more adaptor oligonucleotides. When both strands at both ends are joined to an adaptor oligonucleotide, joining can be followed by a cleavage reaction that leaves a 5' overhang that can serve as a template for the extension of the corresponding 3' end, which 3' end may or may not include one or more nucleotides derived from the adaptor oligonucleotide. In some embodiments, a target polynucleotide is joined to a first adaptor oligonucleotide on one end and a second adaptor oligonucleotide on the other end. In some embodiments, the target polynucleotide and the adaptor to which it is joined comprise blunt ends. In some embodiments, separate ligation reactions are carried out for each sample, using a different first adaptor oligonucleotide comprising at least one barcode sequence for each sample, such that no barcode sequence is joined to the target polynucleotides of more than one sample. A target polynucleotide that has an adaptor/primer oligonucleotide joined to it is considered "tagged" by the joined adaptor.

In some embodiments, nucleic acids described herein are linked making use of CLICK chemistry. Suitable methods to link various molecules using CLICK chemistry are known in the art (for CLICK chemistry linkage of oligonucleotides, see, e.g. El-Sagheer et al. (PNAS, 108:28, 11338-11343, 2011). Click chemistry may be performed in the presence of CuI.

Barcodes

Barcodes are typically known nucleic acid sequences that allow some feature of a polynucleotide with which the barcode is associated to be identified. In some embodiments, a barcode comprises a nucleic acid sequence that when joined to a target polynucleotide serves as an identifier of the sample from which the target polynucleotide was derived.

Barcodes can be designed at suitable lengths to allow sufficient degree of identification, e.g. at least 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, or more nucleotides in length. Multiple barcodes, such as 2, 3, 4, 5, 6, 7, 8, 9, 10, or more barcodes, may be used on the same molecule, optionally separated by non-barcode sequences. In some embodiments, barcodes are shorter than 10, 9, 8, 7, 6, 5, or 4 nucleotides in length. In some embodiments, barcodes associated with some polynucleotides are of different length than barcodes associated with other polynucleotides. In general, barcodes are of sufficient length and comprise sequences that are sufficiently different to allow the identification of samples based on barcodes with which they are associated. In some embodiments, a barcode, and the sample source with which it is associated, can be identified accurately after the mutation, insertion, or deletion of one or more nucleotides in the barcode sequence, such as the mutation, insertion, or deletion of 1, 2, 3, 4, 5, 6, 7, 8, 9, 10, or more nucleotides. In some embodiments, each barcode in a plurality of barcodes differ from every other barcode in the plurality at at least three nucleotide positions, such as at least 3, 4, 5, 6, 7, 8, 9, 10, or more positions.

Sequencing

De novo synthesized oligonucleotide and longer polynucleotide products described herein may be subject to quality control prior to proceeding with subsequent steps of a procedure, such as a multireaction procedure. Quality control may be applied while keeping individual products in separate volumes, such as on resolved features of a substrate as described herein. A fraction may be aliquoted for quality control, while the rest of the volumes compartmentalizing each product remain individually accessible.

Figure 17:
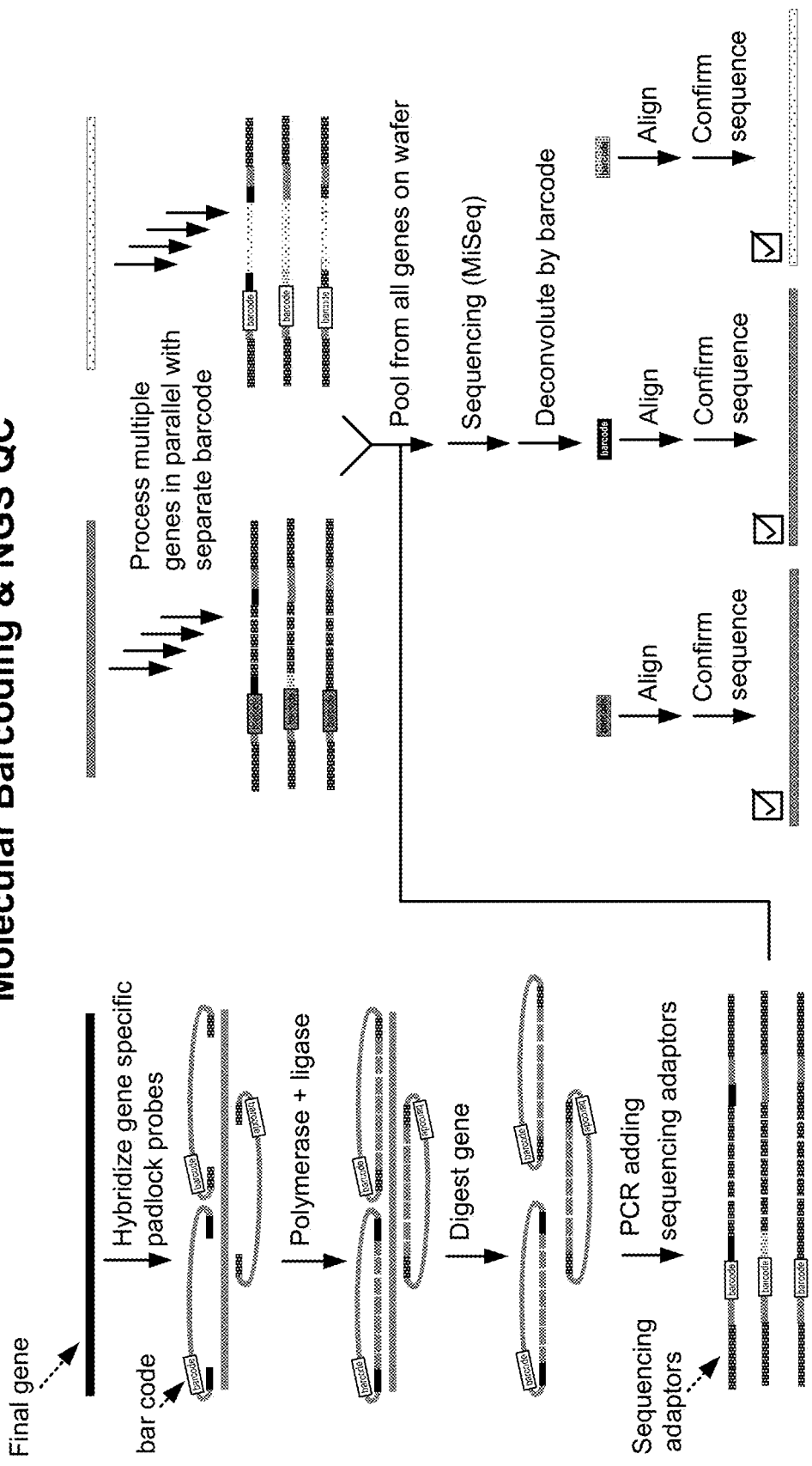
FIG. 17 is a diagram demonstrating the use of padlock probes for the generation of molecularly barcoded sequencing libraries and quality control (QC) processes comprising next generation sequencing (NGS).

FIG. 17 illustrates an example quality control procedure comprising next generation sequencing. Gene specific padlock probes targeting a specific product are designed to cover overlapping sequence segments of the product that is being tested. The ends of the individual padlock probes specific for a gene product may be designed to be hybridizable to regions scattered along the gene product for proper coverage during sequencing. All probes specific for the same gene product may comprise a barcode sequence associated with that gene product. A suitable polymerase and/or ligase may be used to fill between the ends of the padlock probes along the gene product target. In some cases, the padlock probes will form circular single stranded DNA. The typically linear gene product may be digested, for example after aliquoting a fraction of the gene product volume. Alternatively, a fraction of the gene product volume may be aliquoted prior to the addition of padlock probes. The padlock probes carrying segments of the gene product may be amplified, e.g. using PCR. Universal or specific primer binding regions on the padlock probes may be targeted during amplification. Sequencing primer binding regions may be originally present in the padlock probes or may be added during subsequent steps, e.g. by utilizing sequencing adaptors prior to, during, or after amplification.

In various embodiments, the gene product specific padlock probes will be pooled after the initial sequencing library steps. In those cases, the gene product specific barcodes may be utilized to track sequence information back to the individual gene products. The sequencing information obtained by any suitable means described herein or otherwise known in the art may be deconvoluted, e.g. by binning into individual sequence pool based on the barcode information. Suitable alignment and sequence confirmation algorithms known in the art can be utilized to finalize quality control. Error rates and locations can be analyzed by sequence locus, by gene product, by library, or by library subsegment. The error analysis may inform acceptance or rejection of products for subsequent steps or for delivery to a requester.

In any of the embodiments, the detection or quantification analysis of the oligonucleotides can be accomplished by sequencing. The subunits or entire synthesized oligonucleotides can be detected via full sequencing of all oligonucleotides by any suitable methods known in the art, e.g., Illumina HiSeq 2500, including the sequencing methods described herein.

Sequencing can be accomplished through classic Sanger sequencing methods which are well known in the art. Sequencing can also be accomplished using high-throughput systems some of which allow detection of a sequenced nucleotide immediately after or upon its incorporation into a growing strand, i.e., detection of sequence in red time or substantially real time. In some cases, high throughput sequencing generates at least 1,000, at least 5,000, at least 10,000, at least 20,000, at least 30,000, at least 40,000, at least 50,000, at least 100,000 or at least 500,000 sequence reads per hour; with each read being at least 50, at least 60, at least 70, at least 80, at least 90, at least 100, at least 120 or at least 150 bases per read.

In some embodiments, high-throughput sequencing involves the use of technology available by Illumina's Genome Analyzer IIX, MiSeq personal sequencer, or HiSeq systems, such as those using HiSeq 2500, HiSeq 1500, HiSeq 2000, or HiSeq 1000. These machines use reversible terminator-based sequencing by synthesis chemistry. These machines can do 200 billion DNA or more reads in eight days. Smaller systems may be utilized for runs within 3, 2, 1 days or less time. Short synthesis cycles may be used to minimize the time it takes to obtain sequencing results.

In some embodiments, high-throughput sequencing involves the use of technology available by ABI Solid System. This genetic analysis platform that enables massively parallel sequencing of clonally-amplified DNA fragments linked to beads. The sequencing methodology is based on sequential ligation with dye-labeled oligonucleotides.

The next generation sequencing can comprise ion semiconductor sequencing (e.g., using technology from Life Technologies (Ion Torrent)). Ion semiconductor sequencing can take advantage of the fact that when a nucleotide is incorporated into a strand of DNA, an ion can be released. To perform ion semiconductor sequencing, a high density array of micromachined wells can be formed. Each well can hold a single DNA template. Beneath the well can be an ion sensitive layer, and beneath the ion sensitive layer can be an ion sensor. When a nucleotide is added to a DNA, H+ can be released, which can be measured as a change in pH. The H+ ion can be converted to voltage and recorded by the semiconductor sensor. An array chip can be sequentially flooded with one nucleotide after another. No scanning, light, or cameras can be required. In some cases, an ION-PROTON™ Sequencer is used to sequence nucleic acid. In some cases, an IONPGM™ Sequencer is used. The Ion Torrent Personal Genome Machine (PGM) can do 10 million reads in two hours.

In some embodiments, high-throughput sequencing involves the use of technology available by Helicos BioSciences Corporation (Cambridge, Mass.) such as the Single Molecule Sequencing by Synthesis (SMSS) method. SMSS is unique because it allows for sequencing the entire human genome in up to 24 hours. Finally, SMSS is powerful because, like the MIP technology, it does not require a pre amplification step prior to hybridization. In fact, SMSS does not require any amplification. SMSS is described in part in US Publication Application Nos. 2006002471 I; 20060024678; 20060012793; 20060012784; and 20050100932.

In some embodiments, high-throughput sequencing involves the use of technology available by 454 Lifesciences, Inc. (Branford, Conn.) such as the Pico Titer Plate device which includes a fiber optic plate that transmits chemiluminescent signal generated by the sequencing reaction to be recorded by a CCD camera in the instrument. This use of fiber optics allows for the detection of a minimum of 20 million base pairs in 4.5 hours.

Methods for using bead amplification followed by fiber optics detection are described in Marguiles, M., et al. "Genome sequencing in microfabricated high-density picolitre reactors", Nature, doi: 10.1038/nature03959; and well as in US Publication Application Nos. 20020012930; 20030058629; 20030100102; 20030148344; 20040248161; 20050079510, 20050124022; and 20060078909.

In some embodiments, high-throughput sequencing is performed using Clonal Single Molecule Array (Solexa, Inc.) or sequencing-by-synthesis (SBS) utilizing reversible terminator chemistry. These technologies are described in part in U.S. Pat. Nos. 6,969,488; 6,897,023; 6,833,246; 6,787,308; and US Publication Application Nos. 20040106130; 20030064398; 20030022207; and Constans, A., The Scientist 2003, 17(13):36. High-throughput sequencing of oligonucleotides can be achieved using any suitable sequencing method known in the art, such as those commercialized by Pacific Biosciences, Complete Genomics, Genia Technologies, Halcyon Molecular, Oxford Nanopore Technologies and the like. Other high-throughput sequencing systems include those disclosed in Venter, J., et al. Science 16 Feb. 2001; Adams, M. et al, Science 24 Mar. 2000; and M. J, Levene, et al. Science 299:682-686, January 2003; as well as US Publication Application No. 20030044781 and 2006/0078937. Overall such systems involve sequencing a target oligonucleotide molecule having a plurality of bases by the temporal addition of bases via a polymerization reaction that is measured on a molecule of oligonucleotide, i e., the activity of a nucleic acid polymerizing enzyme on the template oligonucleotide molecule to be sequenced is followed in real time. Sequence can then be deduced by identifying which base is being incorporated into the growing complementary strand of the target oligonucleotide by the catalytic activity of the nucleic acid polymerizing enzyme at each step in the sequence of base additions. A polymerase on the target oligonucleotide molecule complex is provided in a position suitable to move along the target oligonucleotide molecule and extend the oligonucleotide primer at an active site. A plurality of labeled types of nucleotide analogs are provided proximate to the active site, with each distinguishably type of nucleotide analog being complementary to a different nucleotide in the target oligonucleotide sequence. The growing oligonucleotide strand is extended by using the polymerase to add a nucleotide analog to the oligonucleotide strand at the active site, where the nucleotide analog being added is complementary to the nucleotide of the target oligonucleotide at the active site. The nucleotide analog added to the oligonucleotide primer as a result of the polymerizing step is identified. The steps of providing labeled nucleotide analogs, polymerizing the growing oligonucleotide strand, and identifying the added nucleotide analog are repeated so that the oligonucleotide strand is further extended and the sequence of the target oligonucleotide is determined.

The next generation sequencing technique can comprises real-time (SMRT™) technology by Pacific Biosciences. In SMRT, each of four DNA bases can be attached to one of four different fluorescent dyes. These dyes can be phospho linked. A single DNA polymerase can be immobilized with a single molecule of template single stranded DNA at the bottom of a zero-mode waveguide (ZMW). A ZMW can be a confinement structure which enables observation of incorporation of a single nucleotide by DNA polymerase against the background of fluorescent nucleotides that can rapidly diffuse in an out of the ZMW (in microseconds). It can take several milliseconds to incorporate a nucleotide into a growing strand. During this time, the fluorescent label can be excited and produce a fluorescent signal, and the fluorescent tag can be cleaved off. The ZMW can be illuminated from below. Attenuated light from an excitation beam can penetrate the lower 20-30 nm of each ZMW. A microscope with a detection limit of 20 zepto liters ($10^{"}$ liters) can be created. The tiny detection volume can provide 1000-fold improvement in the reduction of background noise. Detection of the corresponding fluorescence of the dye can indicate which base was incorporated. The process can be repeated.

In some cases, the next generation sequencing is nanopore sequencing {See e.g., Soni G V and Meller A. (2007) Clin Chem 53: 1996-2001). A nanopore can be a small hole, of the order of about one nanometer in diameter. Immersion of a nanopore in a conducting fluid and application of a potential across it can result in a slight electrical current due to conduction of ions through the nanopore. The amount of current which flows can be sensitive to the size of the nanopore. As a DNA molecule passes through a nanopore, each nucleotide on the DNA molecule can obstruct the nanopore to a different degree. Thus, the change in the current passing through the nanopore as the DNA molecule passes through the nanopore can represent a reading of the DNA sequence. The nanopore sequencing technology can be from Oxford Nanopore Technologies; e.g., a GridlON system. A single nanopore can be inserted in a polymer membrane across the top of a microwell. Each microwell can have an electrode for individual sensing. The microwells can be fabricated into an array chip, with 100,000 or more microwells (e.g., more than 200,000, 300,000, 400,000, 500,000, 600,000, 700,000, 800,000, 900,000, or 1,000,000) per chip. An instrument (or node) can be used to analyze the chip. Data can be analyzed in real-time. One or more instruments can be operated at a time. The nanopore can be a protein nanopore, e.g., the protein alpha-hemolysin, a heptameric protein pore. The nanopore can be a solid-state nanopore made, e.g., a nanometer sized hole formed in a synthetic membrane (e.g., SiNx, or $SiO_2$). The nanopore can be a hybrid pore (e.g., an integration of a protein pore into a solid-state membrane). The nanopore can be a nanopore with an integrated sensors (e.g., tunneling electrode detectors, capacitive detectors, or graphene based nano-gap or edge state detectors (see e.g., Garaj et al. (2010) Nature vol. 67, doi: 10.1038/nature09379)). A nanopore can be functionalized for analyzing a specific type of molecule (e.g., DNA, RNA, or protein). Nanopore sequencing can comprise "strand sequencing" in which intact DNA polymers can be passed through a protein nanopore with sequencing in real time as the DNA translocates the pore. An enzyme can separate strands of a double stranded DNA and feed a strand through a nanopore. The DNA can have a hairpin at one end, and the system can read both strands. In some cases, nanopore sequencing is "exonuclease sequencing" in which individual nucleotides can be cleaved from a DNA strand by a processive exonuclease, and the nucleotides can be passed through a protein nanopore. The nucleotides can transiently bind to a molecule in the pore (e.g., cyclodextran). A characteristic disruption in current can be used to identify bases.

Nanopore sequencing technology from GENIA can be used. An engineered protein pore can be embedded in a lipid bilayer membrane. "Active Control" technology can be used to enable efficient nanopore-membrane assembly and control of DNA movement through the channel. In some cases, the nanopore sequencing technology is from NABsys. Genomic DNA can be fragmented into strands of average length of about 100 kb. The 100 kb fragments can be made single stranded and subsequently hybridized with a 6-mer probe. The genomic fragments with probes can be driven through a nanopore, which can create a current-versus-time tracing. The current tracing can provide the positions of the probes on each genomic fragment. The genomic fragments can be lined up to create a probe map for the genome. The process can be done in parallel for a library of probes. A genome-length probe map for each probe can be generated. Errors can be fixed with a process termed "moving window Sequencing By Hybridization (mwSBH)." In some cases, the nanopore sequencing technology is from IBM/Roche. An electron beam can be used to make a nanopore sized opening in a microchip. An electrical field can be used to pull or thread DNA through the nanopore. A DNA transistor device in the nanopore can comprise alternating nanometer sized layers of metal and dielectric. Discrete charges in the DNA backbone can get trapped by electrical fields inside the DNA nanopore. Turning off and on gate voltages can allow the DNA sequence to be read.

The next generation sequencing can comprise DNA nanoball sequencing (as performed, e.g., by Complete Genomics; see e.g., Drmanac et al. (2010) Science 327: 78-81). DNA can be isolated, fragmented, and size selected. For example, DNA can be fragmented (e.g., by sonication) to a mean length of about 500 bp. Adaptors (Ad1) can be attached to the ends of the fragments. The adaptors can be used to hybridize to anchors for sequencing reactions. DNA with adaptors bound to each end can be PCR amplified. The adaptor sequences can be modified so that complementary single strand ends bind to each other forming circular DNA. The DNA can be methylated to protect it from cleavage by a type IIS restriction enzyme used in a subsequent step. An adaptor (e.g., the right adaptor) can have a restriction recognition site, and the restriction recognition site can remain non-methylated. The non-methylated restriction recognition site in the adaptor can be recognized by a restriction enzyme (e.g., AcuI), and the DNA can be cleaved by AcuI 13 bp to the right of the right adaptor to form linear double stranded DNA. A second round of right and left adaptors (Ad2) can be ligated onto either end of the linear DNA, and all DNA with both adapters bound can be PCR amplified (e.g., by PCR). Ad2 sequences can be modified to allow them to bind each other and form circular DNA. The DNA can be methylated, but a restriction enzyme recognition site can remain non-methylated on the left Ad1 adapter. A restriction enzyme (e.g., AcuI) can be applied, and the DNA can be cleaved 13 bp to the left of the Ad1 to form a linear DNA fragment. A third round of right and left adaptor (Ad3) can be ligated to the right and left flank of the linear DNA, and the resulting fragment can be PCR amplified. The adaptors can be modified so that they can bind to each other and form circular DNA. A type III restriction enzyme (e.g., EcoP15) can be added; EcoP15 can cleave the DNA 26 bp to the left of Ad3 and 26 bp to the right of Ad2. This cleavage can remove a large segment of DNA and linearize the DNA once again. A fourth round of right and left adaptors (Ad4) can be ligated to the DNA, the DNA can be amplified (e.g., by PCR), and modified so that they bind each other and form the completed circular DNA template.

Rolling circle replication (e.g., using Phi 29 DNA polymerase) can be used to amplify small fragments of DNA. The four adaptor sequences can contain palindromic sequences that can hybridize and a single strand can fold onto itself to form a DNA nanoball (DNB™) which can be approximately 200-300 nanometers in diameter on average. A DNA nanoball can be attached (e.g., by adsorption) to a microarray (sequencing flowcell). The flow cell can be a silicon wafer coated with silicon dioxide, titanium and hexamethyldisilazane (HMDS) and a photoresist material. Sequencing can be performed by unchained sequencing by ligating fluorescent probes to the DNA. The color of the fluorescence of an interrogated position can be visualized by a high resolution camera. The identity of nucleotide sequences between adaptor sequences can be determined.

Inkjet Deposits

The methods and compositions of the invention, in some embodiments, make use of depositing, positioning, or placing a composition at a specific location on or in the surface of a support. Depositing may comprise contacting one composition with another. Depositing may be manual or automatic, e.g., depositing may be accomplished by automated robotic devices. Pulse jets or inkjets may be used to dispense drops of a fluid composition onto a support. Pulse jets typically operate by delivering a pulse of pressure (such as by a piezoelectric or thermoelectric element) to liquid adjacent to an outlet or orifice such that a drop can be dispensed therefrom.

Liquids of reagents can be deposited to resolved loci of a substrate described in further detail elsewhere herein using various methods or systems known in the art. Microdroplets of fluid can be delivered to a surface or resolved loci on or within a substrate described in the current invention at submicron precision. Commercially available dispensing equipments using inkjet technology as the microdispensing method for fluid volume below can be employed. The droplets produced using ink-jet technology are highly reproducible and can be controlled so that a droplet may be placed on a specific location at a specific time according to digitally stored image data. Typical droplet diameters for demand mode ink-jet devices can be 30-100 µm, which translates to droplet volumes of 14-520 pl. Droplet creation rates for demand mode ink-jet devices can be 2000-5000 droplets per second. Demand mode ink-jet microdispensing can be utilized at suitable resolutions and throughputs to service substrates with high densities of resolved loci described in further detail elsewhere herein. Methods and systems for depositing or delivering reagents are described in further detail in U.S. Pat. Nos. 5,843,767 and 6,893,816, both of which are incorporated by reference in their entirety.

The systems for depositing or delivering the reagents to resolved loci can comprise one or more subsystems including but not limited to: a microjet dispense head, a fluid delivery system or an inkjet pump, a X-Y positioning system, a vision system, or a system controller. The microjet dispense head can be an assembly of a plurality of MicroJet devices (e.g., 8 MicroJet devices) and the required drive electronics. The system complexity can be minimized by using a single channel of drive electronics to multiplex the 8 or 10 dispensing devices. Drive waveform requirements for each individual device can be downloaded from the system controller. The drive electronics can be constructed using conventional methods that are known in the art. The fluid delivery system, or the inkjet pump, can be a Beckman Biomec that is modified to act as the multiple reagent input system. Between it and the MicroJet dispense head can be a system of solenoid valves, controlled by the system controller. They provide pressurized flushing fluid and air to purge reagent from the system and vacuum to load reagent into the system. The X-Y positioning system can be any commercially available precision X-Y positioning system with a controller. The positioning system can be sized to accommodate a plurality of sensors. The vision system can be used to calibrate the "landing zone" of each MicroJet device relative to the positioning system. Calibration may occur after each reagent loading cycle. Also, the vision system can locate each dispensing site on each sensor when the sensor tray is first loaded via fiducial marks on the sensors. A software based system or a hardware based vision system can be used. The system controller can be a standard computer system that is used as the overall system controller. The vision system image capture and processing also reside on the system controller. Systems for depositing or delivering the reagents to resolved loci are described in further detail in PCT Pub. No. WO2000039344, which is incorporated herein by reference in its entirety.

Figure 18:
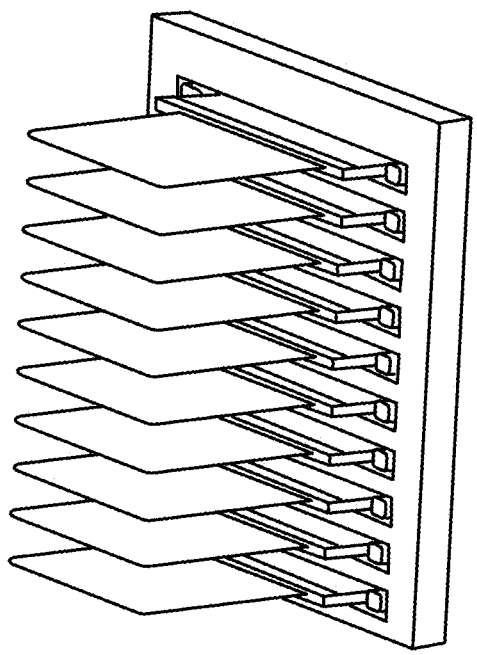
FIG. 18 illustrates an example for an inkjet assembly, with 10 inkjet heads that have silicon orifice plates with 256 nozzles on 254 µm centers, and 100 µm fly height.
Figure 18:
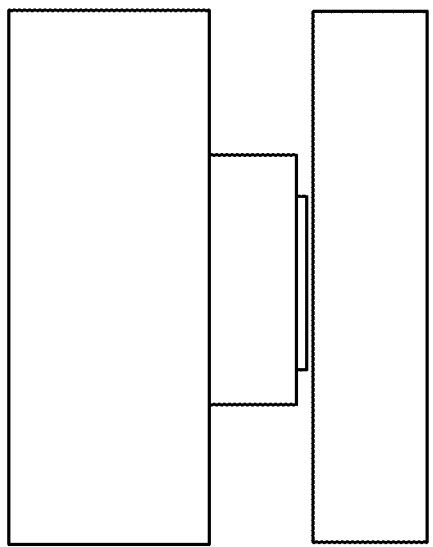

FIG. 18 illustrates an example of an inkjet assembly. In some embodiments, the inkjet assembly can comprise at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 32, 34, 36, 38, 40, 45, 48, 50, 56, 60, 64, 72, 75, 80, 85, 90, 95, 100 or more inkjet heads. The inkjets heads may each deposit a different codon (trinucleotide) building blocks. In an exemplary embodiment, inkjet heads can have Silicon orifice plates with 256 nozzles on 254 µm centers and 100 µm fly height. Each head can have access to each well that traverses. The inkjet assembly can have a scan speed about 100 mm/s with precision in the traveling (x,y) plane that is about 2 µm. In some cases, the scan height over wafer of the inkjet assembly can be about 100 µm with a flatness runout of about 1, 2, 3, 4, 5, 6, 7, 8, 9, 10, 11, 12, 13, 14, 15, 16, 17, 18, 19 or 20 µm. In some cases, the inkjet assembly can comprise a vision system to align inkjet with substrates, e.g. silicon wafers, chucked on a vacuum chuck, in some cases as part of a flowcell assembly.

In some cases, methods and systems of depositing reagents to a plurality of resolved loci described herein can comprise applying through an inkjet pump at least one microdrop of a first reagent to a first locus of the plurality of loci and applying through an inkjet pump at least one microdrop of a second reagent to a second locus of the plurality of resolved loci. In some embodiments, the second locus can be adjacent to the first locus, and the first and second reagents can be different. The first and second loci can reside on microstructures fabricated into a support surface and the microstructures can comprise at least one channel. In some cases, the at least one channel is more than 100 µm deep. In some embodiments, the first and the second reagents can be the same. In some cases, the microstructures comprise a large microchannel and one or more microchannels that are fluidically connected to the first microchannel. The large initial microchannel initially receives a deposited liquid, typically reducing any cross contamination of reagents to and from adjacent microstructures. The contents of the droplet can subsequently flow into the one or more smaller microchannels, which may host suitable surfaces for the reactions described herein, such as oligonucleotide synthesis.

The at least one channel can have a depth that can be about, at least about, or less than about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, 55, 60, 65, 70, 75, 80, 85, 90, 95, 100, 110, 120, 130, 140, 150, 160, 170, 180, 190, 200, 225, 250, 275, 300, 325, 350, 375, 400, 425, 450, 475, 500, 550, 600, 650, 700, 750, 800, 850, 900, 950 or 1000 µm. In some embodiments, the at least one channel can have a depth that can be between about 50-100, 50-150, 50-200, 100-200, 100-300, 20-300 or 20-100 µm. In some embodiments, the at least one channel can be more than 100 µm deep.

Each of the droplets of reagents can have a suitable volume that can traverse through the depth of the microchannel without losing momentum. The suitable volume can comprise a desired amount of reagents for oligonucleotide synthesis. For example, without limitation, each of the droplets comprising reagents can have a volume that is about or at least about 4, 5, 10, 20, 30, 40, 50, 60, 70, 80, 90, 100, 110, 120, 130, 140, 150, 160, 170, 180, 190, 200, 250, 300, 400, 500 pl, 1, 1.5, 2, 2.5, 3, 4, 5, 6, 7, 8, 9, 10, 15, 20, 30, 40, 50, 75, 100, 200, 500 nl, or more. In various embodiments, the system is adjusted such that any satellite droplets trailing a deposited droplet is small enough to minimize cross-contamination. In the case of an inkjet, the printheads can be brought sufficiently close to a substrate e.g. within 100 µm, such that a deposited droplet and its satellite drops are substantially within a channel of the substrate before aerosol movement. The satellite droplets may have a diameter of less than 0.5, 1, 1.5 or 2 µm. In various embodiments, the by volume fraction of satellite droplets that engage in aerosol movement is less than 5, 4, 3, 2, 1, 0.5, 0.1, 0.05, 0.01% of a deposited droplet, or less.

As described elsewhere herein, the microstructures can comprise multiple channels in fluidic communication with each other. In some cases, the microstructures can comprise at least three, four, five, six, seven, eight, nine or ten channels in fluid communications. The channels can have different dimensions, e.g. widths or lengths, as described in further detail elsewhere herein. In some embodiments, the fluidically connected channels of the microstructures can comprise two or more channels with the same width, length, and/or other dimensions.

The microdroplets of fluid can be delivered to a surface or resolved loci within a substrate as described elsewhere herein at a high precision with minimal cross-contamination. In some cases, the first locus can receive less than 0.1% of a second reagent that is intended to be deposited to a second locus and similarly the second locus can receive less than 0.1% of the first reagent. In some cases, the first locus can receive less than about 0.5%, 0.45%, 0.4%, 0.35%, 0.3%, 0.25%, 0.2%, 0.15%, 0.1%, 0.05%, 0.04%, 0.03%, 0.02% or 0.01% of the second reagent. The second locus can receive less than about 0.5%, 0.45%, 0.4%, 0.35%, 0.3%, 0.25%, 0.2%, 0.15%, 0.1%, 0.05%, 0.04%, 0.03%, 0.02% or 0.01% of the first reagent.

In some cases, the reagents can be delivered in droplets that have a diameter of about 2, 3, 4, 5, 6, 7, 8, 9, 10, 11, 12, 13, 14, 15, 16, 17, 18, 19, 20, 25, 30, 40, 50, 60, 70, 80, 90, 100, 110, 120, 130, 140, 150, 160, 170, 180, 190 or 200 µm. The droplets of reagent can have a diameter that is at least about 2 µm. The reagents can be delivered in droplets that have a diameter of less than about 5, 10, 20, 30, 40, 50, 60, 70, 80, 90, 100, 110, 120, 130, 140, 150, 160, 170, 180, 190 or 200 µm. The reagents can be delivered in droplets that have a diameter of between 2-10, 2-5, 10-200, 10-150, 10-100, 10-500, 20-200, 20-150, 20-100, 30-100, 30-200, 30-150, 40-100, 40-80 or 50-60 µm.

The droplets of reagents can be deposited in a rate of about or at least about 1000, 1500, 2000, 2500, 3000, 3500, 4000, 4500 or 5000 droplets per second.

Soft Landing

Systems and methods for depositing droplets to a plurality of microwells are also described herein. In one aspect, droplets can be deposited into a microwell of a microfluidic system comprising a first surface with a plurality of microwells. The droplet can have a suitable Reynolds number, such as about 1-1000, 1-2000, 1-3000, 0.5-1000, 0.5-2000, 0.5-3000, 0.5-4000, 0.5-5000, 1-500, 2-500, 1-100, 2-100, 5-100, 1-50, 2-50, 5-50 or 10-50, such that bouncing of liquids is minimized upon reaching the bottom of the microwell. Those of skill in the art appreciate that the Reynolds number may fall within any range bounded by any of these values (e.g., about 0.5 to about 500). Suitable methods for accurate estimation of Reynolds numbers in fluid systems are described in Clift et al. (Clift, Roland, John R. Grace, and Martin E. Weber, Bubbles, Drops and Particles, 2005. Dover Publications) and Happel et al. (Happel, John and Howard Brenner, 1965. Prentice-Hall), both of which are herein incorporated by reference in their entirety.

The density of the plurality of microwells can be more than 1, 2, 3, 4, 5, 6, 7, 8, 9, 10, 20, 30, 40, 50, 75, 100, 200, 300, 400, 500, 1000 or more per $mm^2$. Following the methods described herein, the droplet of the liquid can flow through the microwell smoothly and land on the bottom of the microwell softly.

The liquid droplets can be deposited using any methods and systems known in the art. In some embodiments, the microfluidic system can further comprise an inkjet pump. The inkjet pump can be used to deposit the liquid droplet to one of the plurality of microwells. Various embodiments of the liquid deposit systems are described elsewhere in the specification.

In some cases, the microwells can be in different width, the same width, or a combination of the same or different width within subregions of a substrate. The microwells can have any different width. For example, without limitation, the width of the microwells can be about, wider than about, or narrower than about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, 55, 60, 65, 70, 75, 80, 85, 90, 95 or 100 μm.

The microwells can have any different length. For example, without limitation, the length of the microwells can be about, longer than about, or shorter than about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, 55, 60, 65, 70, 75, 80, 85, 90, 95, 100, 110, 120, 130, 140, 150, 160, 170, 180, 190, 200, 210, 220, 230, 240, 250, 260, 270, 280, 290, 300, 325, 350, 375, 400, 425, 450, 475, 500, 600, 700, 800, 900 or 1000 μm.

The microwells can be fluidically connected to at least one microchannel. The microwells can comprise a ratio of surface area to length, or a perimeter, of about, at least about, or less than about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, 55, 60, 65, 70, 75, 80, 85, 90, 95 or 100 μm.

The droplets of the liquid can have a volume that is suitable for the methods described herein. In some embodiments, the droplet can have a volume that is less than about 0.5 microliters (μl), less than about 1 μl, less than about 1.5 μl, less than about 2 μl, less than about 2.5 μl, less than about 3 μl, less than about 3.5 μl, less than about 4 μl, less than about 4.5 μl, less than about 5 μl, less than about 5.5 μl, less than about 6 μl, less than about 6.5 μl, less than about 7 μl, less than about 7.5 μl, less than about 8 μl, less than about 8.5 μl, less than about 9 μl, less than about 9.5 μl, less than about 10 μl, less than about 11 μl, less than about 12 μl, less than about 13 μl, less than about 14 μl, less than about 15 μl, less than about 16 μl, less than about 17 μl, less than about 18 μl, less than about 19 μl, less than about 20 μl, less than about 25 μl, less than about 30 μl, less than about 35 μl, less than about 40 μl, less than about 45 μl, less than about 50 μl, less than about 55 μl, less than about 60 μl, less than about 65 μl, less than about 70 μl, less than about 75 μl, less than about 80 μl, less than about 85 μl, less than about 90 μl, less than about 95 μl or less than about 100 μl. In some embodiments, the droplet can have a volume that is about 0.5 microliters (μl), about 1 μl, about 1.5 μl, about 2 μl, about 2.5 μl, about 3 μl, about 3.5 μl, about 4 μl, about 4.5 μl, about 5 μl, about 5.5 μl, about 6 μl, about 6.5 μl, about 7 μl, about 7.5 μl, about 8 μl, about 8.5 μl, about 9 μl, about 9.5 μl, about 10 μl, about 11 μl, about 12 μl, about 13 μl, about 14 μl, about 15 μl, about 16 μl, about 17 μl, about 18 μl, about 19 μl, about 20 μl, about 25 μl, about 30 μl, about 35 μl, about 40 μl, about 45 μl, about 50 μl, about 55 μl, about 60 μl, about 65 μl, about 70 μl, about 75 μl, about 80 μl, about 85 μl, about 90 μl, about 95 μl or about 100 μl.

In some cases, the microchannels can be coated with a moiety, such as a chemically inert moiety, that increases surface energy. The types of suitable chemically inert or reactive moieties are described elsewhere in the current specification.

The Reynolds number of the droplet can be at a range of Reynolds number that allows the liquid to flow smoothly through microwells and/or microchannels as described herein. In some embodiments, the Reynolds number of the droplet can be less than about 1, 5, 10, 15, 20, 25, 30, 35, 40, 45, 50, 60, 70, 80, 90, 100, 200, 300, 400, 500, 600, 700, 800, 900, or 1000. In some embodiments, the Reynolds number of the droplet can be more than about 0.1, 0.5, 1, 2, 5, 10, 15, 20, 25, 30, 35, 40, 45, 50, 60, 70, 80, 90, 100, 200, 300, 400, 500, 600, 700, 800, 900, or 1000. In some cases, the droplets can flow through the microwells in a laminar flow or near-laminar flow.

The droplet can be applied or deposited at a velocity of at least 0.1, 0.2, 0.3, 0.4, 0.5, 0.6, 0.7, 0.8, 0.9, 1, 2, 3, 4, 5, 6, 7, 8, 9, 10, 15, 20, 25, 30, 35, 40, 45, 50, 60, 70, 80, 90, 100 m/sec or higher.

Programmable Split

The system as described herein can comprise a plurality of resolved loci and a plurality of resolved reactor caps that can be sealed together to form a plurality of resolved reactors. The plurality of resolved reactors can contain reagents. The sealing may be reversible or loose, and the plurality of resolved reactor caps can be released from the plurality of resolved loci. Upon release from the first surface comprising the plurality of resolved loci, the reactor caps can retain at least a portion of the reagents. By controlling the release of the reactor caps from the plurality of resolved loci, the partitioning of the liquid or the reagents can be controlled. In one aspect of the instant invention, a method of partitioning is described herein. The method may comprise contacting a first surface comprising a liquid at a first plurality of resolved loci with a second surface comprising a second plurality of resolved loci, such as reactor caps, wherein the first surface can comprise a first surface tension with the liquid, the second surface can comprise a second surface tension with the liquid and determining a velocity of release such that a desired fraction of the liquid can be transferred from the first plurality of resolved loci to the second plurality of resolved loci Upon detaching the second surface from the first surface at this calculated velocity, a desired fraction of the contents of the reactors may be retained in reactors. The first surface comprising the first plurality of resolved loci may comprise the plurality of resolved loci that are coated with oligonucleotides. The second surface comprising the second plurality of resolved loci may be a capping element comprising a plurality of reactor caps. In some cases, the method can further comprise contacting a third surface with a third plurality of resolved loci. Various aspects or embodiments are described herein.

The liquid that is retained in the second surface may be held by any methods known in the art. In some cases, the first or the second surface can comprise microchannels holding at least a portion of the liquid. In some cases, the first or the second surface can comprise nanoreactors holding at least a portion of the liquid. In some cases, the liquid can be retained due to the surface tension differences between the first and the second surface. Without being bound by theory, for water based liquids, a higher portion of the liquid may be retained on the surface having higher surface energy, or less hydrophobic.

The liquid may be partitioned such that a desired fraction of the reagents can be retained onto the first or the second surface upon releasing. For example, without limitation, the desired fraction may be about, at least about, or more than about 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98% or 99%.

Parallel Microfluidic Mixing Methods

In another aspect of the current invention, methods of mixing liquid are described herein. The methods can comprise providing a first substrate comprising a plurality of microstructures fabricated thereto; providing a second substrate comprising a plurality of resolved reactor caps; aligning the first and second substrates such that a first reactor cap of the plurality is configured to receive liquid from n microstructures in the first substrate; and delivering liquid from the n microstructures into the first reactor cap, thereby mixing liquid from the n microstructures forming a mixture. Various embodiments and variations are described herein.

The density of the resolved reactor caps can be any suitable density that allows desired alignment of the microstructures of a first substrate and the reactor caps of a second substrate. In some cases, the density of the resolved reactor caps can be at least $1/mm^2$. In some cases, the density of the resolved reactors can be about 1, about 2, about 3, about 4, about 5, about 6, about 7, about 8, about 9, about 10, about 15, about 20, about 25, about 30, about 35, about 40, about 50, about 75, about 100, about 200, about 300, about 400, about 500, about 600, about 700, about 800, about 900, about 1000, about 1500, or about 2000 sites per 1 $mm^2$. In some embodiments, the density of the resolved reactors can be at least about 1, at least about 2, at least about 3, at least about 4, at least about 5, at least about 6, at least about 7, at least about 8, at least about 9, at least about 10, at least about 20, at least about 30, at least about 40, at least about 50, at least about 75, at least about 100, at least about 200, at least about 300, at least about 400, at least about 500, at least about 600, at least about 700, at least about 800, at least about 900, at least about 1000, at least about 1500, at least about 2000, or at least about 3000 sites per 1 $mm^2$.

The microstructures can be at any density practicable according to the methods and compositions of the invention. In some cases, the microstructures can be at a density of about, at least about, or less than about 1, about 2, about 3, about 4, about 5, about 6, about 7, about 8, about 9, about 10, about 15, about 20, about 25, about 30, about 35, about 40, about 50, about 75, about 100, about 200, about 300, about 400, about 500, about 600, about 700, about 800, about 900, about 1000, about 1500, about 2000, or about 3000 sites per 1 $mm^2$. In some embodiments, the microstructures can be at a density of at least 100 per 1 $mm^2$. In some cases, the microstructures can have a surface density that is about the same as the density of the resolved reactors.

In some cases, there can be a gap, e.g. a gap of less than about 1, 2, 3, 4, 5, 6, 7, 8, 9, 10, 15, 20, 25, 30, 35, 40, 45, 50, 55, 60, 65, 70, 75, 80, 85, 90, 95, 100, 110, 120, 130, 140, 150, 160, 170, 180, 190, or 200 µm between the first and the second substrates after aligning the first and the second substrates such that a first reactor cap of the plurality is configured to receive liquid from n microstructures in the first substrate.

In some cases, the mixture or the liquid can partially spread into the gap between the first and the second substrates after aligning the first and the second substrates such that a first reactor cap of the plurality is configured to receive liquid from n microstructures in the first substrate. The liquid or mixture that partially spreads into the gap may form a capillary burst valve. The methods of mixing can further comprise sealing the gap by bringing the first and the second substrate closer together. In some cases, the first and the second substrate can be in direct physical contact.

The plurality of microstructures and reactor caps can have any suitable design or dimensions as described in further detail elsewhere herein. At least one channel can have a cross-sectional area that is in a circular shape and can comprise a radius of the cross-sectional area of about, at least about, less than about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, 55, 60, 65, 70, 75, 80, 85, 90, 95 or 100 µm.

In some cases, the channels may be coated with a moiety, such as a chemically inert moiety, that increases surface energy corresponding to a water contact angle of less than 90°. The surface energy, or hydrophobicity of a surface, can be evaluated or measured by measuring a water contact angle. A water contact angle of smaller than 90° may functionalize the solid surface in a relatively hydrophilic manner. A water contact angle of greater than 90° may functionalize the solid surface in a relatively hydrophobic manner. Highly hydrophobic surfaces with low surface energy can have water contact angles that are greater than 120°. In some cases, the surface of the channels, or one of the two channels as described herein can be functionalized or modified to be hydrophobic, to have a low surface energy, or to have a water contact angle that can be greater than about 90°, 95°, 100°, 105°, 110°, 115°, 120°, 125°, 130°, 135°, 140°, 145° or 150° as measured on an uncurved surface. In some cases, the surface of the channels, or one of the two channels as described herein in the current invention can be functionalized or modified to be hydrophilic, to have a high surface energy, or to have a water contact angle that can be less than about 90°, 85°, 80°, 75°, 70°, 65°, 60°, 55°, 50°, 45°, 40°, 35°, 30°, 25°, 20°, 15° or 10° as measured on an uncurved surface. The surface of the channels or one of the two channels can be functionalized or modified to be more hydrophilic or hydrophobic. In some cases, the surfaces of the first and the second substrate can comprise a different surface energy with a given liquid, such as water. In some cases, the surfaces of the first and the second substrates can comprise a differential water contact angle of between about 5°, 10°, 20°, 30°, 40°, 50°, 60°, 70°, 80°, 90°. Other methods for functionalizing the surface are described in U.S. Pat. No. 6,028,189, which is herein incorporated by reference in its entirety.

In some embodiments, the delivering can be performed by pressure. The delivering liquid from the n microstructures into the first reactor cap can result in mixing liquid from the n microstructures and forming a mixture.

In some cases, the volume of the total mixture liquid can be greater than the volume of the reactor cap. All or part of the reactor cap surfaces, such as the rim surface, may be modified using suitable surface modification methods described in further detail elsewhere herein and otherwise known in the art. In some cases, surface irregularities are engineered. Chemical surface modifications and irregularities may serve to adjust the water contact angle of the rim. Similar surface treatments may also be applied on the surface of a substrate that is brought in close proximity to the reactor caps forming a seal, e.g. a reversible seal. A capillary burst valve may be utilized between the two surfaces as described in further detail elsewhere herein. The surface treatments can be useful in precise control of such seals comprising capillary burst valves.

In some cases, the releasing of the capping element from the first surface, and the releasing of the capping element from the second surface can be performed at a different velocity. The amount of the portion of reagents that is retained upon releasing the capping element from the corresponding surface can be controlled by the velocity or the surface energy of the capping element and the corresponding surface. The difference in the surface energy, or hydrophobicity, of the capping element and the corresponding surface can be a parameter to control the portion of the reagents that is retained upon release. The volume of the first and the second reactions can be different.

Downstream Applications

The methods and compositions of the invention may be used for nucleic acid hybridization studies such as gene expression analysis, genotyping, heteroduplex analysis, nucleic acid sequencing determinations based on hybridization, synthesis of DNA, RNA, peptides, proteins or other oligomeric or non-oligomeric molecules, combinatorial libraries for evaluation of candidate drugs.

DNA and RNA synthesized in accordance with the invention may be used in any application including, by way of example, probes for hybridization methods such as gene expression analysis, genotyping by hybridization (competitive hybridization and heteroduplex analysis), sequencing by hybridization, probes for Southern blot analysis (labeled primers), probes for array (either microarray or filter array) hybridization, "padlock" probes usable with energy transfer dyes to detect hybridization in genotyping or expression assays, and other types of probes. The DNA and RNA prepared in accordance with the invention may also be used in enzyme-based reactions such as polymerase chain reaction (PCR), as primers for PCR, templates for PCR, allele-specific PCR (genotyping/haplotyping) techniques, realtime PCR, quantitative PCR, reverse transcriptase PCR, and other PCR techniques. The DNA and RNA may be used for various ligation techniques, including ligation-based genotyping, oligo ligation assays (OLA), ligation-based amplification, ligation of adapter sequences for cloning experiments, Sanger dideoxy sequencing (primers, labeled primers), high throughput sequencing (using electrophoretic separation or other separation method), primer extensions, mini-sequencings, and single base extensions (SBE). The DNA and RNA produced in accordance with the invention may be used in mutagenesis studies, (introducing a mutation into a known sequence with an oligo), reverse transcription (making a cDNA copy of an RNA transcript), gene synthesis, introduction of restriction sites (a form of mutagenesis), protein-DNA binding studies, and like experiments. Various other uses of DNA and RNA produced by the subject methods will suggest themselves to those skilled in the art, and such uses are also considered to be within the scope of this disclosure.

Computer Systems

In various embodiments, the methods and systems of the invention may further comprise software programs on computer systems and use thereof. Accordingly, computerized control for the synchronization of the dispense/vacuum/refill functions such as orchestrating and synchronizing the printhead movement, dispense action and vacuum actuation are within the bounds of the invention. The computer systems may be programmed to interface between the user specified base sequence and the position of a dispenser head to deliver the correct reagents to specified regions of the substrate.

Figure 19:
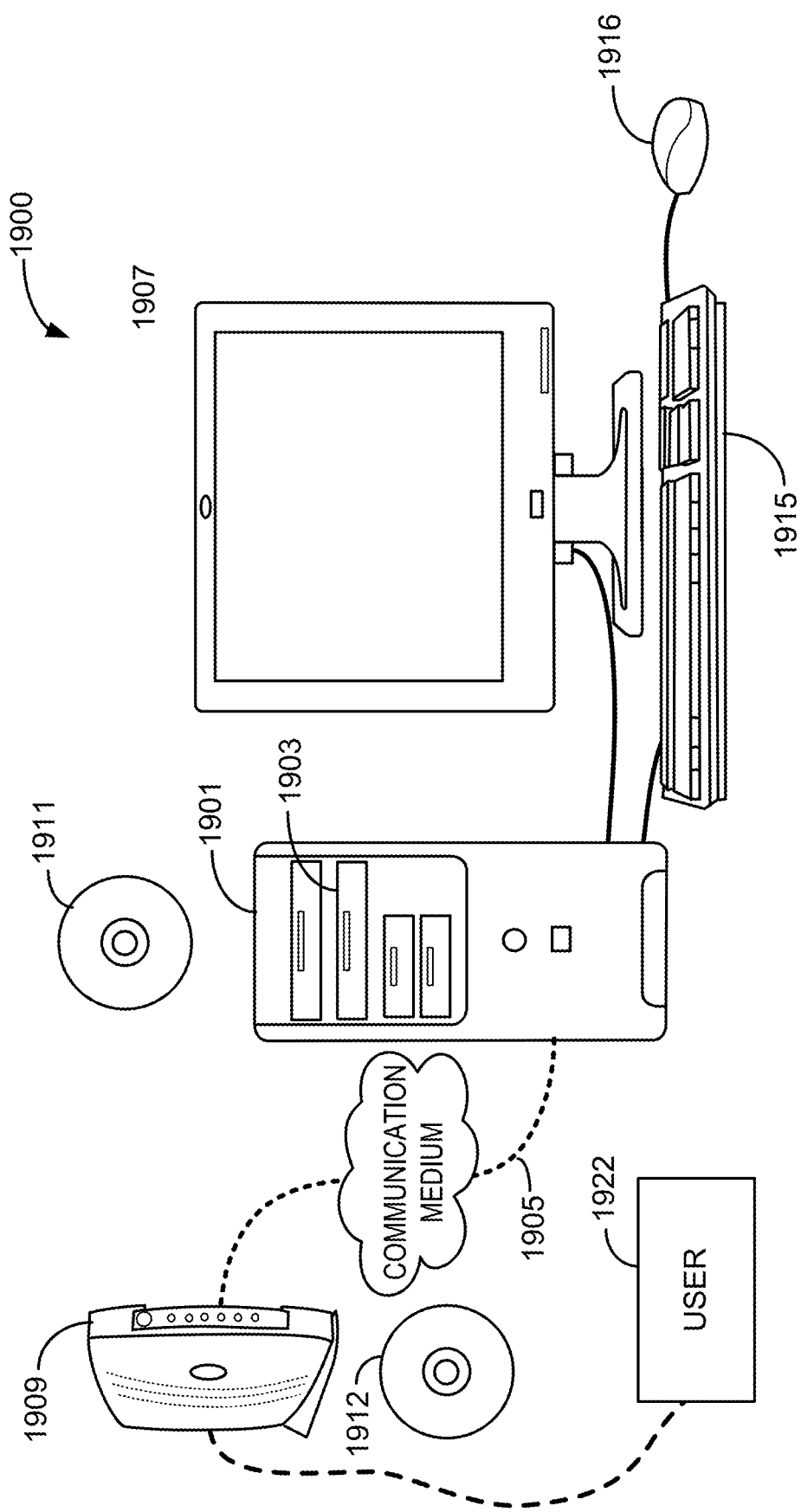
FIG. 19 illustrates an example of a computer system that can be used in connection with example embodiments of the present invention.

The computer system 1900 illustrated in FIG. 19 may be understood as a logical apparatus that can read instructions from media 1911 and/or a network port 1905, which can optionally be connected to server 1909 having fixed media 1912. The system, such as shown in FIG. 19 can include a CPU 1901, disk drives 1903, optional input devices such as keyboard 1915 and/or mouse 1916 and optional monitor 1907. Data communication can be achieved through the indicated communication medium to a server at a local or a remote location. The communication medium can include any means of transmitting and/or receiving data. For example, the communication medium can be a network connection, a wireless connection or an internet connection. Such a connection can provide for communication over the World Wide Web. It is envisioned that data relating to the present disclosure can be transmitted over such networks or connections for reception and/or review by a party 1922 as illustrated in FIG. 19.

Figure 20:
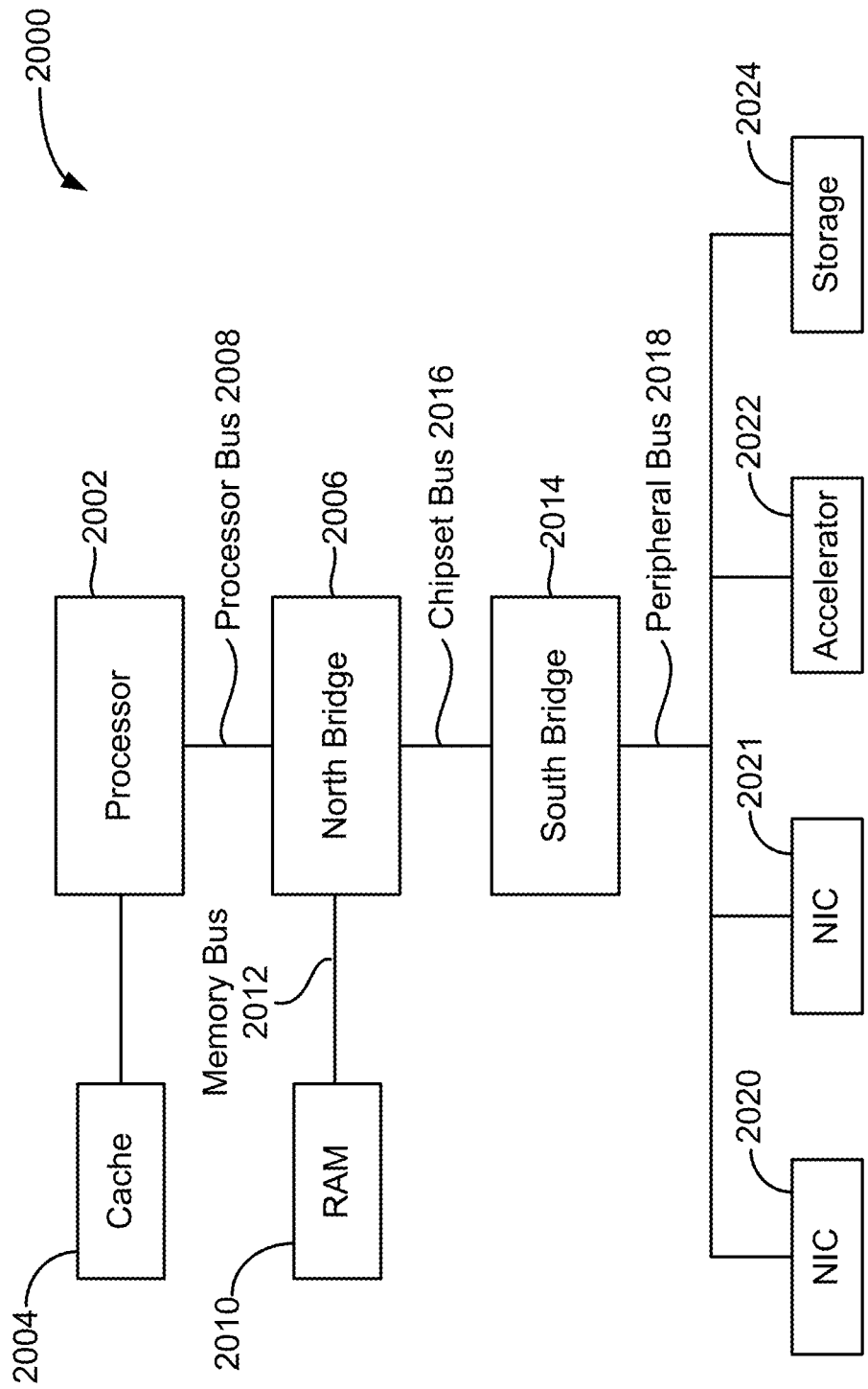
FIG. 20 is a block diagram illustrating a first example architecture of a computer system 2000 that can be used in connection with example embodiments of the present invention.

FIG. 20 is a block diagram illustrating a first example architecture of a computer system 2000 that can be used in connection with example embodiments of the present invention. As depicted in FIG. 20, the example computer system can include a processor 2002 for processing instructions. Non-limiting examples of processors include: Intel Xeon™ processor, AMD Opteron™ processor, Samsung 32-bit RISC ARM 1176JZ(F)-S v1.0™ processor, ARM Cortex-A8 Samsung S5PC100™ processor, ARM Cortex-A8 Apple A4™ processor, Marvell PXA 930™ processor, or a functionally-equivalent processor. Multiple threads of execution can be used for parallel processing. In some embodiments, multiple processors or processors with multiple cores can also be used, whether in a single computer system, in a cluster, or distributed across systems over a network comprising a plurality of computers, cell phones, and/or personal data assistant devices.

As illustrated in FIG. 20, a high speed cache 2004 can be connected to, or incorporated in, the processor 2002 to provide a high speed memory for instructions or data that have been recently, or are frequently, used by processor 2002. The processor 2002 is connected to a north bridge 2006 by a processor bus 2008. The north bridge 2006 is connected to random access memory (RAM) 2010 by a memory bus 2012 and manages access to the RAM 2010 by the processor 2002. The north bridge 2006 is also connected to a south bridge 2014 by a chipset bus 2016. The south bridge 2014 is, in turn, connected to a peripheral bus 2018. The peripheral bus can be, for example, PCI, PCI-X, PCI Express, or other peripheral bus. The north bridge and south bridge are often referred to as a processor chipset and manage data transfer between the processor, RAM, and peripheral components on the peripheral bus 2018. In some alternative architectures, the functionality of the north bridge can be incorporated into the processor instead of using a separate north bridge chip.

In some embodiments, system 2000 can include an accelerator card 2022 attached to the peripheral bus 2018. The accelerator can include field programmable gate arrays (FPGAs) or other hardware for accelerating certain processing. For example, an accelerator can be used for adaptive data restructuring or to evaluate algebraic expressions used in extended set processing.

Software and data are stored in external storage 2024 and can be loaded into RAM 2010 and/or cache 2004 for use by the processor. The system 2000 includes an operating system for managing system resources; non-limiting examples of operating systems include: Linux, Windows™, MACOS™, BlackBerry OS™, iOS™, and other functionally-equivalent operating systems, as well as application software running on top of the operating system for managing data storage and optimization in accordance with example embodiments of the present invention.

In this example, system 2000 also includes network interface cards (NICs) 2020 and 2021 connected to the peripheral bus for providing network interfaces to external storage, such as Network Attached Storage (NAS) and other computer systems that can be used for distributed parallel processing.

Figure 21:
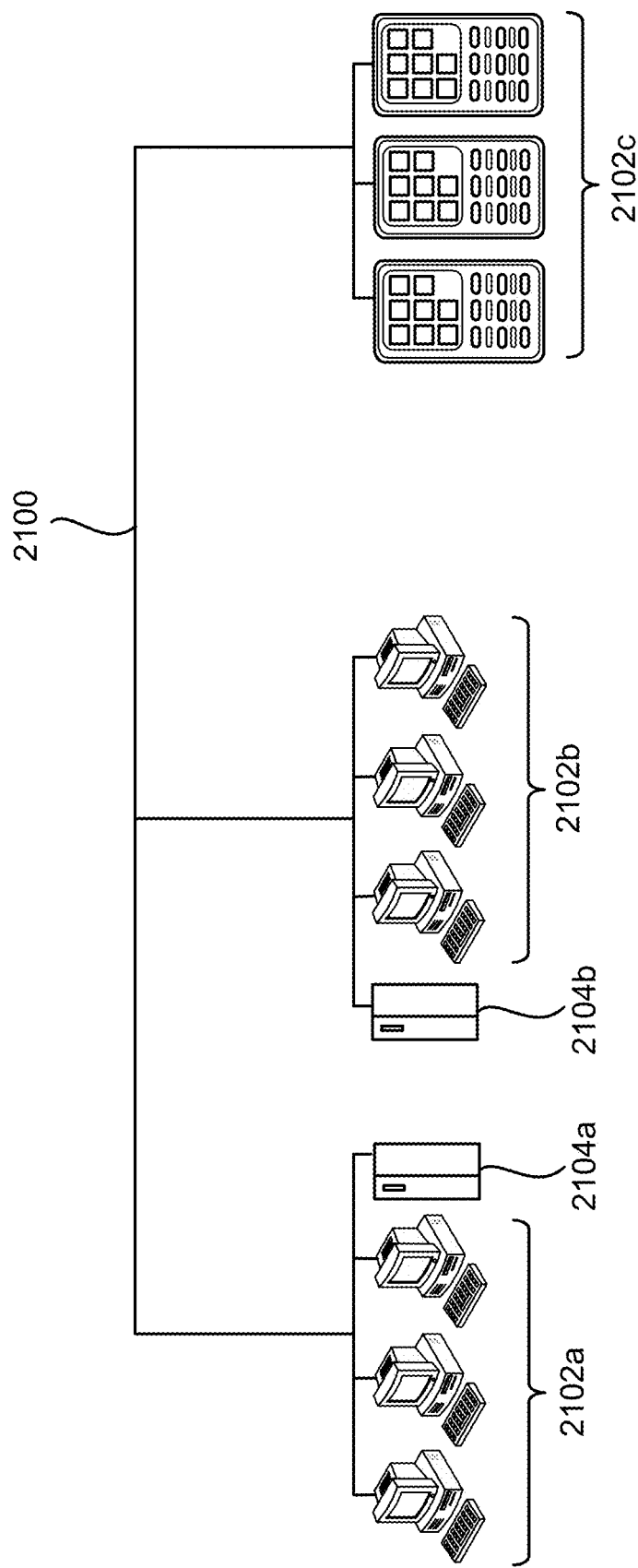
FIG. 21 is a diagram demonstrating a network 2100 configured to incorporate a plurality of computer systems, a plurality of cell phones and personal data assistants, and Network Attached Storage (NAS) that can be used in connection with example embodiments of the present invention.

FIG. 21 is a diagram showing a network 2100 with a plurality of computer systems 2102a, and 2102b, a plurality of cell phones and personal data assistants 2102c, and Network Attached Storage (NAS) 2104a, and 2104b. In example embodiments, systems 2102a, 2102b, and 2102c can manage data storage and optimize data access for data stored in Network Attached Storage (NAS) 2104a and 2104b. A mathematical model can be used for the data and be evaluated using distributed parallel processing across computer systems 2102a, and 2102b, and cell phone and personal data assistant systems 2102c. Computer systems 2102a, and 2102b, and cell phone and personal data assistant systems 2102c can also provide parallel processing for adaptive data restructuring of the data stored in Network Attached Storage (NAS) 2104a and 2104b. FIG. 21 illustrates an example only, and a wide variety of other computer architectures and systems can be used in conjunction with the various embodiments of the present invention. For example, a blade server can be used to provide parallel processing. Processor blades can be connected through a back plane to provide parallel processing. Storage can also be connected to the back plane or as Network Attached Storage (NAS) through a separate network interface.

In some example embodiments, processors can maintain separate memory spaces and transmit data through network interfaces, back plane or other connectors for parallel processing by other processors. In other embodiments, some or all of the processors can use a shared virtual address memory space.

Figure 22:
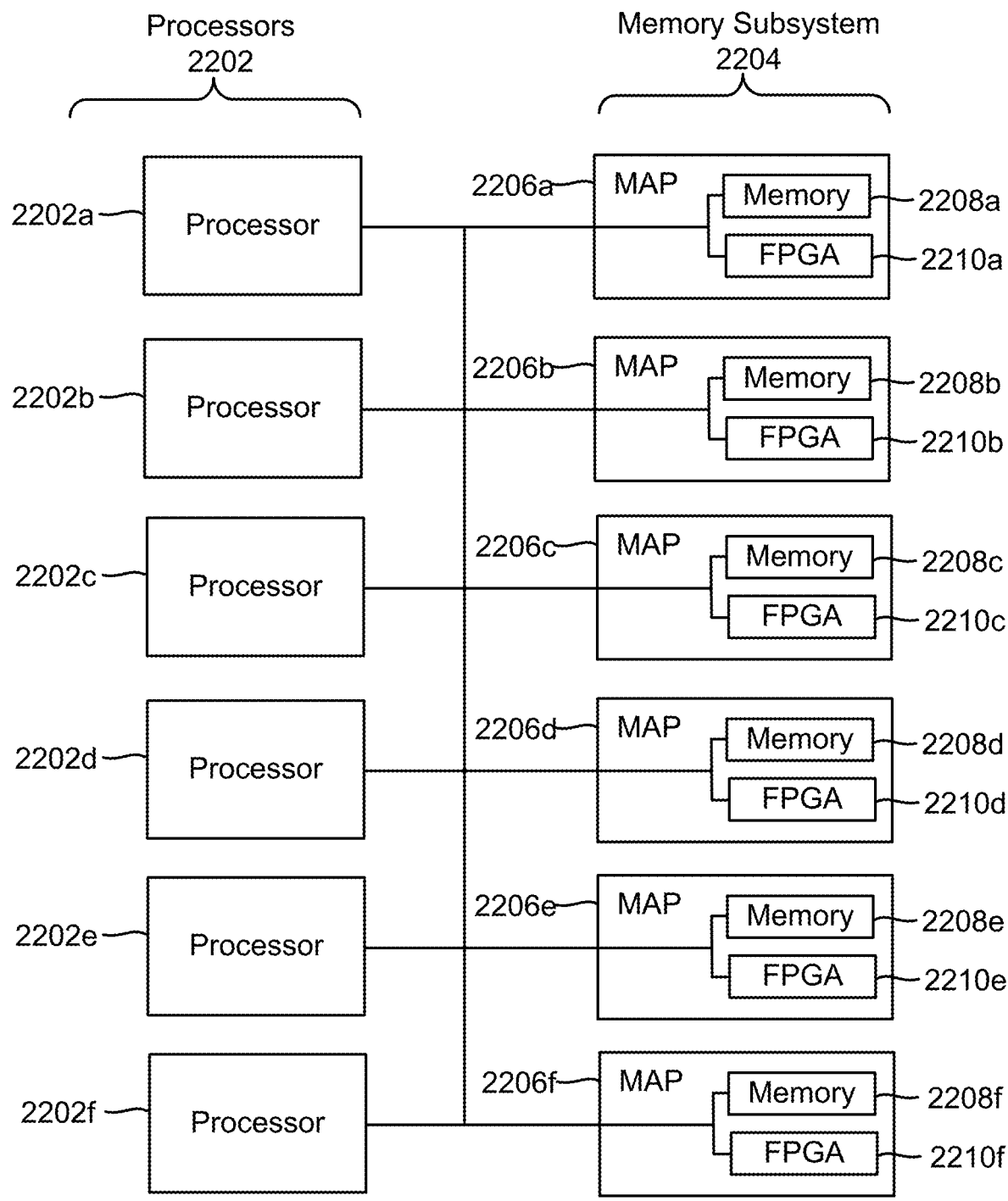
FIG. 22 is a block diagram of a multiprocessor computer system 2200 using a shared virtual address memory space that can be used in connection with example embodiments of the present invention.

FIG. 22 is a block diagram of a multiprocessor computer system 2200 using a shared virtual address memory space in accordance with an example embodiment. The system includes a plurality of processors 2202a-f that can access a shared memory subsystem 2204. The system incorporates a plurality of programmable hardware memory algorithm processors (MAPs) 2206a-f in the memory subsystem 2204. Each MAP 2206a-f can comprise a memory 2208a-f and one or more field programmable gate arrays (FPGAs) 2210a-f. The MAP provides a configurable functional unit and particular algorithms or portions of algorithms can be provided to the FPGAs 2210a-f for processing in close coordination with a respective processor. For example, the MAPs can be used to evaluate algebraic expressions regarding the data model and to perform adaptive data restructuring in example embodiments. In this example, each MAP is globally accessible by all of the processors for these purposes. In one configuration, each MAP can use Direct Memory Access (DMA) to access an associated memory 2208a-f, allowing it to execute tasks independently of, and asynchronously from, the respective microprocessor 2202a-f. In this configuration, a MAP can feed results directly to another MAP for pipelining and parallel execution of algorithms.

The above computer architectures and systems are examples only, and a wide variety of other computer, cell phone, and personal data assistant architectures and systems can be used in connection with example embodiments, including systems using any combination of general processors, co-processors, FPGAs and other programmable logic devices, system on chips (SOCs), application specific integrated circuits (ASICs), and other processing and logic elements. In some embodiments, all or part of the computer system can be implemented in software or hardware. Any variety of data storage media can be used in connection with example embodiments, including random access memory, hard drives, flash memory, tape drives, disk arrays, Network Attached Storage (NAS) and other local or distributed data storage devices and systems.

In example embodiments, the computer system can be implemented using software modules executing on any of the above or other computer architectures and systems. In other embodiments, the functions of the system can be implemented partially or completely in firmware, programmable logic devices such as field programmable gate arrays (FPGAs) as referenced in FIG. 22, system on chips (SOCs), application specific integrated circuits (ASICs), or other processing and logic elements. For example, the Set Processor and Optimizer can be implemented with hardware acceleration through the use of a hardware accelerator card, such as accelerator card 122 illustrated in FIG. 20.

Example 1: Front-End Processing of a Silicon Wafer to Create a Microwell

Figure 23:
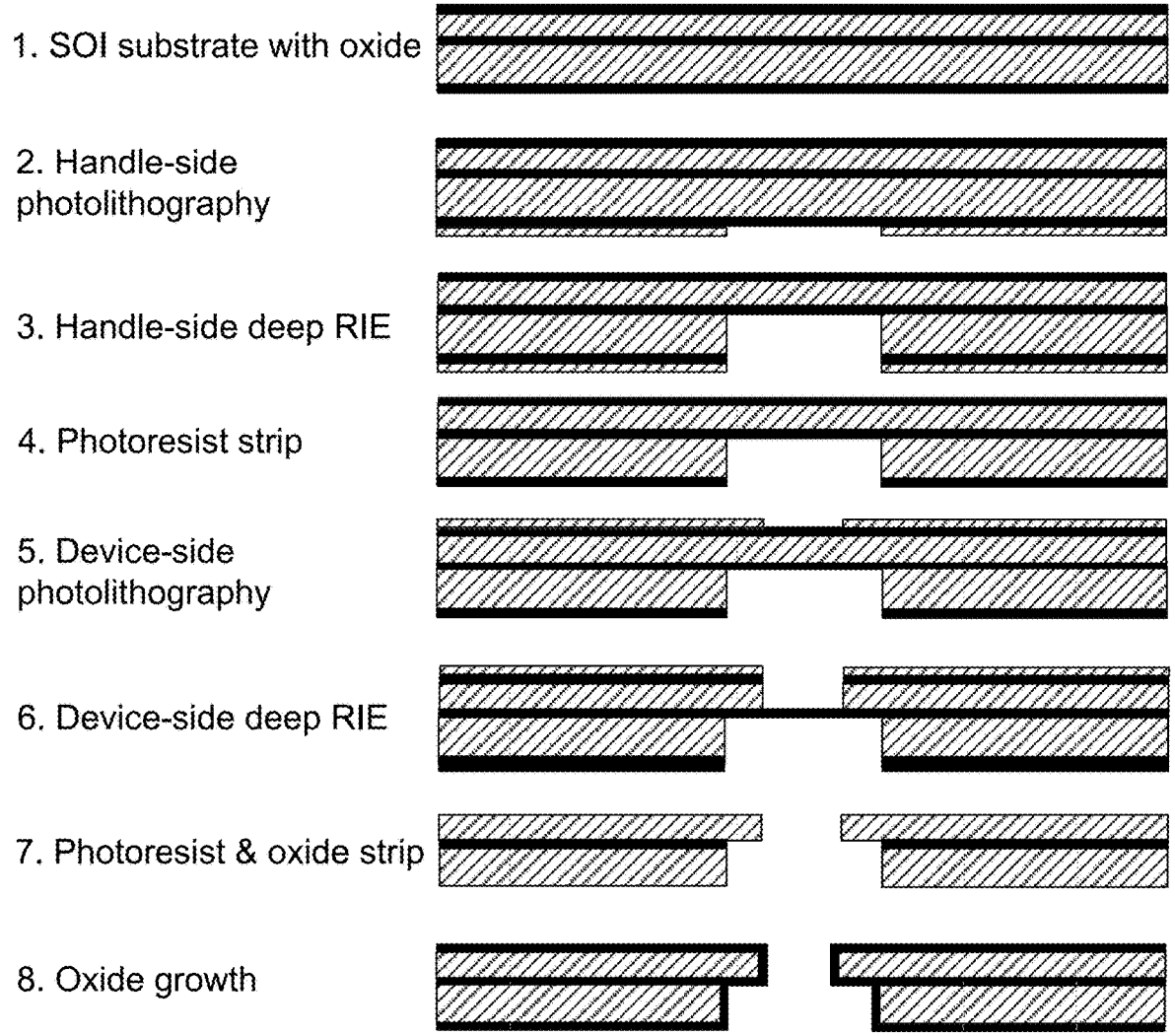
FIG. 23 is a diagram demonstrating exemplary steps constituting the front end processing for the manufacturing of microstructures on a substrate (e.g. silicon wafer).

Silicon wafers are etched to create an exemplary substrate comprising a plurality of microwells using a front-end processing method as illustrated in FIG. 23. Starting with a SOI substrate with a layer of oxide on both surfaces of the substrate, a layer of photo-resist is coated using photolithography method on the handle-side of the substrate at preferred locations. Following the coating of the photo-resist, DRIE is performed on the handle side until reaching to the layer of oxide in the middle of the wafer. Then, the coating of the photo-resist is stripped away exposing the layer of oxide underneath. Similarly, a second layer of photo-resist is coated using photolithography method on the device-side of the substrate at preferred locations, with suitable diameters. Following the coating of the second layer of photo-resist, DRIE is performed again on the device-side of the silicon wafer until reaching the layer of oxide in the middle of the silicon wafer. Then, the photo-resist and the layer of oxide in the middle of the wafer is stripped away. Lastly, oxide is coated on all surface of the wafer, creating a silicon wafer with a plurality of microstructures, each comprising a larger microwell and one or more microchannels fluidically connected to the microwell.

Figure 24:
FIG. 24 is a diagram demonstrating exemplary steps constituting the back end processing for the functionalizing of the microstructure surfaces on a substrate (e.g. silicon wafer).
Figure 24:
Figure 24:
Figure 24:
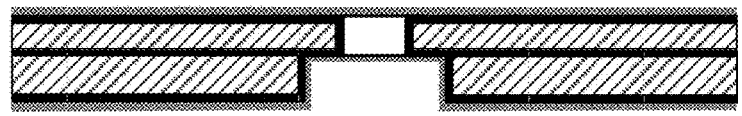
Figure 24:
Figure 24:
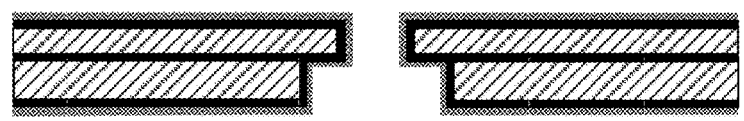

Example 2: Back-End Processing of a Silicon Wafer to Functionalize Selected Surface of the Microwell The silicon wafer with etched microwells is further processed to functionalize selected portions of the microwells using a back-end processing method as illustrated in FIG. 24. To coat only the surface of a smaller microwell within a microwell with an active functionalization agent that increases surface energy, the product from Example 1 is used as the starting material. A droplet of photo-resist is deposited into the microchannel using an inkjet printer as described herein. The droplet of photo-resist is spread into the microchannel in fluidic connection to the microwell. Following the photoresist deposition, oxygen plasma etch is performed to etch back excess photoresist, leaving a smoother surface of photo-resist as illustrated in FIG. 24. A layer of a chemically inert moiety is coated onto all exposed surfaces of the silicon wafer to create a passive functionalization layer with low surface energy. Afterwards, the photo-resist is stripped away, exposing the surface of the smaller microchannel in fluidic communication with the microwell. Upon removal of the photo-resist, a layer of active functionalization agent is coated onto the surface of the smaller microchannel to increase the surface energy of the surface of the microwell and/or to provide surface chemistries for oligonucleotide growth. The previously functionalized surfaces remain substantially unaffected by the second application of surface functionalization. As a result, a plurality of microwell with a first surface functionalization each in fluidic communication with one or more microchannels with a second surface functionalization is manufactured on a solid substrate.

Example 3: Microfluidic Device

A microfluidic device comprising a substantially planar substrate portion was manufactured according to the methods and compositions of the invention as shown in FIG. 25D. A cross-section of the substrate is shown in FIG. 25E. The substrate comprises 108 clusters, wherein each cluster comprises 109 groupings of fluidic connections. Each grouping comprises 5 second channels extending from a first channel. FIG. 25A is a device view of each cluster comprising the 109 groupings. FIG. 25C is a handle view of the cluster of FIG. 25 part 25A. FIG. 25B is a section view of FIG. 25A showing a row of 11 groupings. FIG. 25F is another view of the substrate shown in FIG. 25D, wherein the position of a label is visualized. FIG. 25G is an expanded view of FIG. 25A, indicating the 109 groupings of the cluster.

As shown in FIGS. 25A and 25C, the 109 groupings are arranged in offset rows to form a cluster in a circle-like pattern, where the individual regions are non-overlapping with each other. The individual groupings form a circle. As represented by 2503, the distance between three rows of these groupings is 0.254 mm. As shown by 2506, the distance between two groupings in a row of groupings is 0.0978 mm. The cross-section of the first channel in a grouping, as shown by 2504, is 0.075 mm. The cross-section of each second channel in a grouping, as shown by 2505, is 0.020 mm. The length of the first channel in a grouping, as shown by 2502, is 0.400 mm. The length of each second channel in a grouping, as shown by 2501, is 0.030 mm.

The cluster of 109 groupings shown in FIGS. 25A and 25C are arranged in a conformation suitable for placement in a single reaction well that may be placed adjacent to the cluster in FIGS. 25A and 25C. The remainder of the clusters in FIG. 25D are similarly arranged in a way that facilitates delivery into a number of reaction wells, such as the nanoreactor plate described in FIG. 26A-26E and Example 4. The substrate comprises 108 reaction wells, providing 11,772 groupings.

The width of the substrate along one dimension, as indicated by 2508, is 32.000 mm. The width of the substrate along another dimension, as indicated by 2519, is 32.000 mm.

The substantially planar substrate portion, as shown in FIG. 25D, comprises 108 clusters of groupings. The clusters are arranged in rows forming a square shape. The furthest distance from the center of a cluster to the origin in one dimension, as indicated by 2518, is 24.467 mm. The furthest distance from the center of a cluster to the origin in another dimension, as indicated by 2509, is 23.620 mm. The closest distance from the center of a cluster to the origin in one dimension, as shown by 2517, is 7.533. The closest distance from the center of a cluster to the origin in another dimension, as shown by 2512, is 8.380. The distance between the centers of two clusters in the same row, as shown by 2507 and 2522 is 1.69334 mm.

The substrate comprises 3 fiducial marks to facilitate alignment of the microfluidic device with other components of a system. A first fiducial mark is located near the origin, where the fiducial mark is closer to the origin than any one cluster. The first fiducial mark is located 5.840 mm from the origin in one dimension (2516) and 6.687 mm from the origin in another dimension (2513). The first fiducial mark is located 1.69334 mm from a cluster in one dimension (2515) and 1.69344 mm from the same cluster in another dimension (2514). Two other fiducial marks are each located 0.500 mm from an edge of the substrate (2510 and 2520) and 16.000 mm (2511 and 2521) from the origin.

A cross section of the substrate is shown in FIG. 25E, where the total length of a grouping as indicated by 2523, is 0.430 mm.

Another view of the substrate is shown is shown in FIG. 25F, showing the arrangement of the 108 clusters and the position of a label. The label is located 1.5 mm (2603) from an edge of the substrate. The label is located at a distance between 4.0 mm (2602) to 9.0 mm (2601), as measured from the origin.

Example 4: Nanoreactor

An nanoreactor was manufactured according to the methods and compositions of the invention as shown in FIGS. 26B and 26C. A cross-section of the nanoreactor is shown in FIG. 26A. The nanoreactor comprises 108 wells. FIG. 26D is a handle view of a nanoreactor. FIG. 26E is another view of the nanoreactor shown in FIG. 26B, wherein the position of a label is visualized.

As shown in FIG. 26B, the 108 wells are arranged in rows to form a square pattern, where the individual wells are raised on the nanoreactor base. As shown by 2711, the distance between the centers of two wells in a row of wells is 1.69334 mm. The cross-section of the inside of a well, as shown by 2721, is 1.15 mm. The cross-section of a well, including the rim of the well, as shown by 2720, is 1.450 mm. The height of a well in a nanoreactor, as shown by 2702, is 0.450 mm. The total height of a nanoreactor, as shown by 2701, is 0.725 mm.

The wells in FIG. 26B are arranged in a way that facilitates delivery from a microfluidic device having 108 wells, as exemplified by FIG. 26, into the 108 reaction wells of the nanoreactor.

The width of the nanoreactor along one dimension, as indicated by 2703, is 24.000 mm. The width of the nanoreactor along another dimension, as indicated by 2704, is 24.000 mm.

The nanoreactor, as shown in FIG. 26B, comprises 108 wells. The wells are arranged in rows forming a square shape. The furthest distance from the center of a well to the origin in one dimension, as indicated by 2706, is 20.467 mm. The furthest distance from the center of a well to the origin in another dimension, as indicated by 2705, is 19.620 mm. The closest distance from the center of a well to the origin in one dimension, as shown by 2710, is 3.533 mm. The closest distance from the center of a well to the origin in another dimension, as shown by 2709, is 4.380 mm. The distance between the centers of two wells in the same row, as shown by 2711 and 2712 is 1.69334 mm. The distance from the center of a well to the edge of a nanoreactor in one dimension, as shown by 2707, is 3.387 mm. The distance from the center of a well to the edge of a nanoreactor in another dimension, as shown by 2708, is 2.540 mm.

The nanoreactor comprises 3 fiducial marks on the device face to facilitate alignment of the nanoreactor with other components of a system, for example, a microfluidic device as described in Example 3. A first fiducial mark is located near the origin, where the fiducial mark is closer to the origin than any one well. The first fiducial mark is located 1.840 mm from the origin in one dimension (2717) and 2.687 mm from the origin in another dimension (2716). The first fiducial mark is located 1.6933 mm from a well in one dimension (2719) and 1.6934 mm from the same well in another dimension (2718). Two other fiducial marks are each located 0.500 mm from an edge of the nanoreactor (2714 and 2715) and 12.000 mm (2713) from the origin.

The nanoreactor comprises 4 fiducial marks on the handle face as shown in FIG. 26D. The distance from the center or a fiducial mark and a nearest corner of the nanoreactor in one dimension is 1.000 mm (2722 and 2723). The length of a fiducial mark in one dimension is 1.000 mm (2724 and 2725). The width of a fiducial mark, as shown by 2726, is 0.050 mm.

Another view of the nanoreactor is shown is shown in FIG. 26E, showing the arrangement of the 108 wells and the position of a label. The label is located 1.5 mm (2728) from an edge of the nanoreactor. The label is located 1.0 mm (2727) from a corner of the nanoreactor. The label is 9.0 mm (2726), in length.

Example 5: Manufacturing of an Oligonucleotide Synthesis Device

Figure 27:
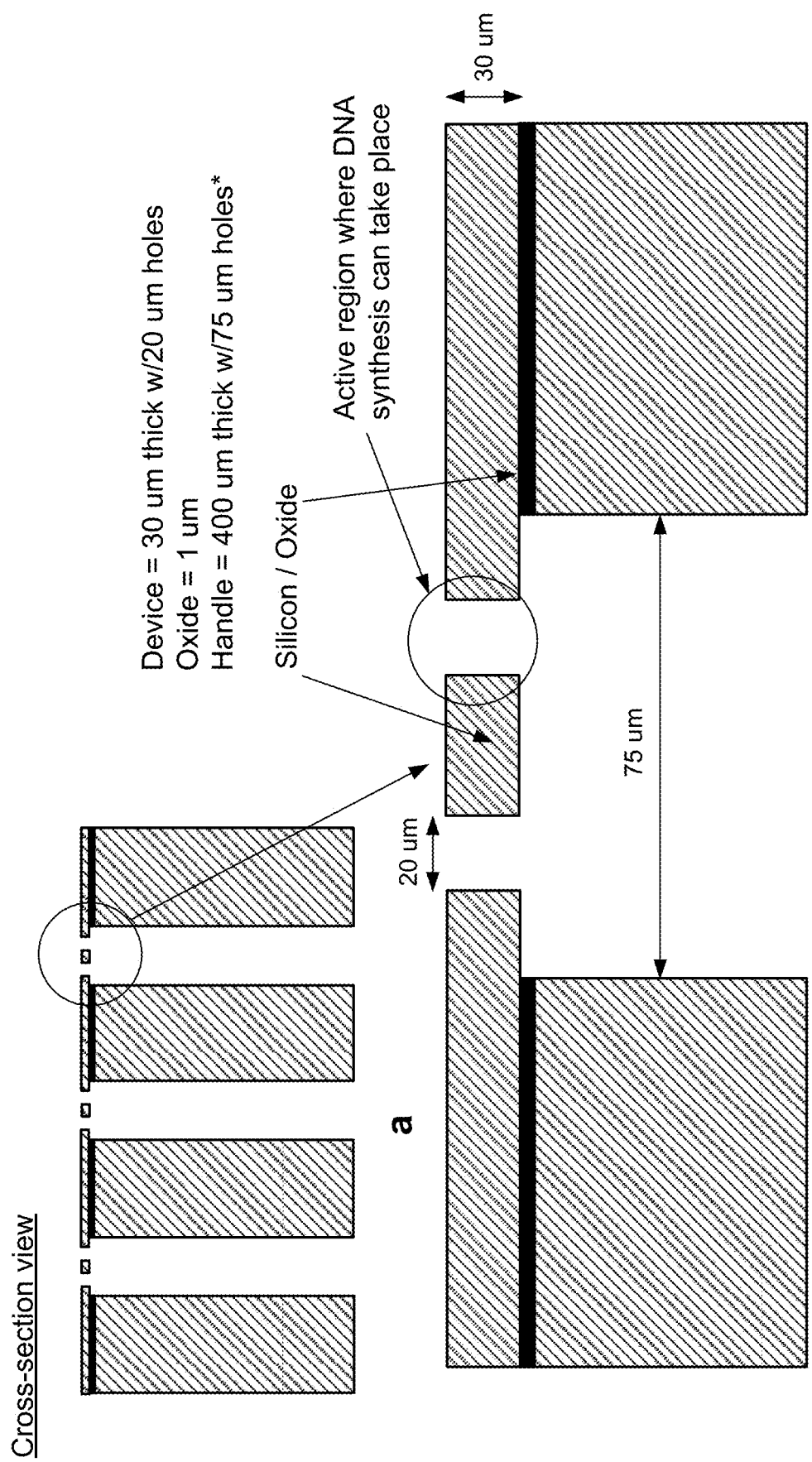
FIG. 27 illustrates in detail the design features of an exemplary oligonucleotide synthesis device that is differentially functionalized.
Figure 28:
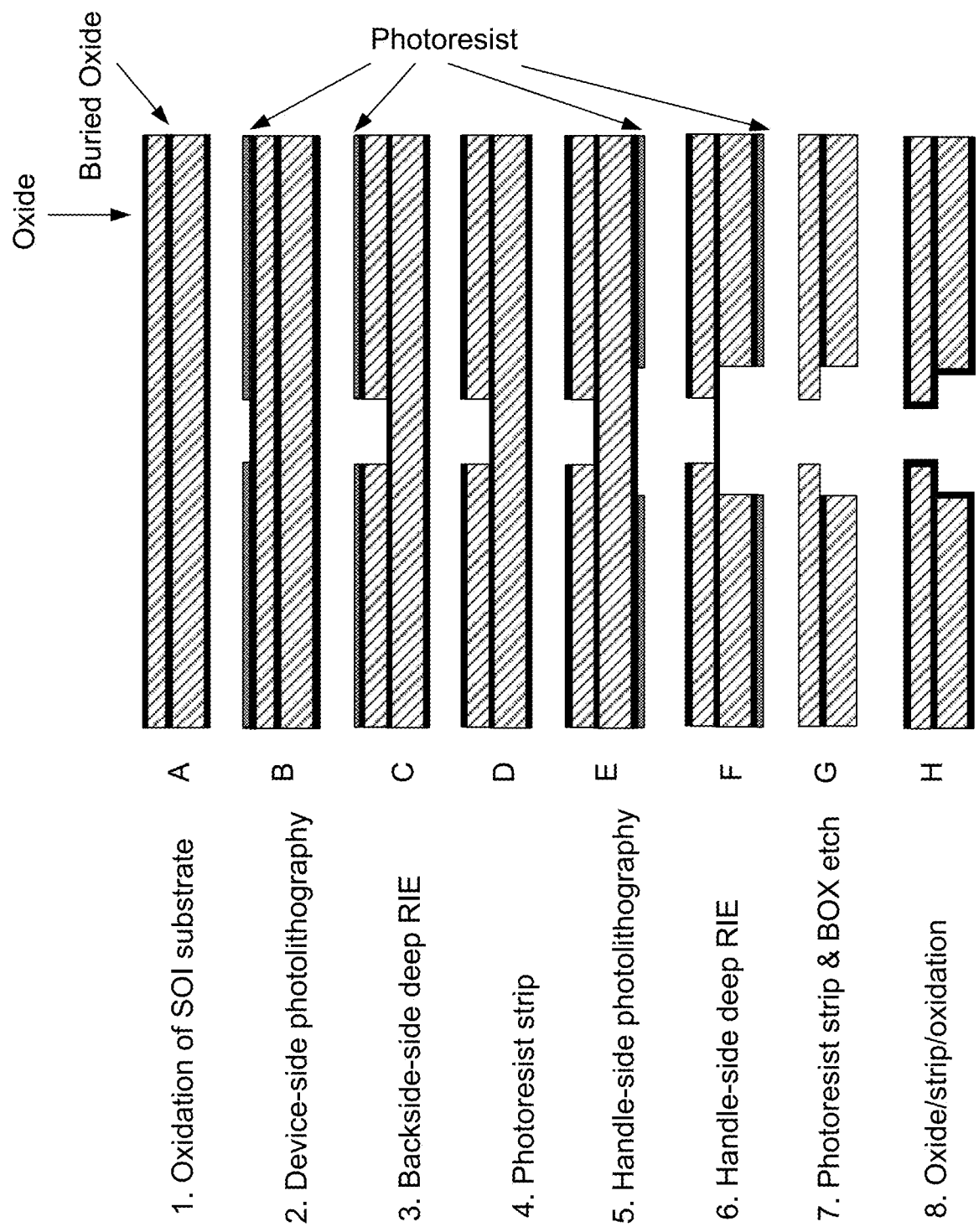
FIG. 28 illustrates a workflow for the front-end manufacturing process for the exemplary device in FIG. 15.

A silicon on insulator (SOI) wafer with an about 30 μm thick device layer and an about 400 μm thick handle layer sandwiching an electrical insulator layer of silicon dioxide was etched to create the exemplary substrate described in Example 3 comprising a plurality of features having three-dimensional microfluidic connections, using a front-end processing method as illustrated in FIG. 28. FIG. 27 illustrates in detail the design features of the device. The SOI wafer was oxidized to cover it with thermal oxide on both surfaces (FIG. 28 part A). Photolithography was applied to the device side to create a mask of photoresist (red) as shown in FIG. 28 part B. A deep reactive-ion etching (DRIE) step was used to etch vertical side-walls to a depth of about 30 μm up until the SOI oxide layer (FIG. 28 part C) at locations devoid of the photoresist. The photoresist was stripped using standard resist stripping process known in the art.

The photolithography, DRIE, and stripping of photoresist was repeated on the handle side (FIG. 28 part E to part G) to generate the desired pattern according to the device described in Example 3. The buried oxide (BOX) was removed using a wet etch process (FIG. 28 part G). Contaminating fluoropolymers that may have been deposited on the side walls of the microfluidic features were removed by thermal oxidation. The thermal oxidation was stripped using a wet etching process.

Figure 29:
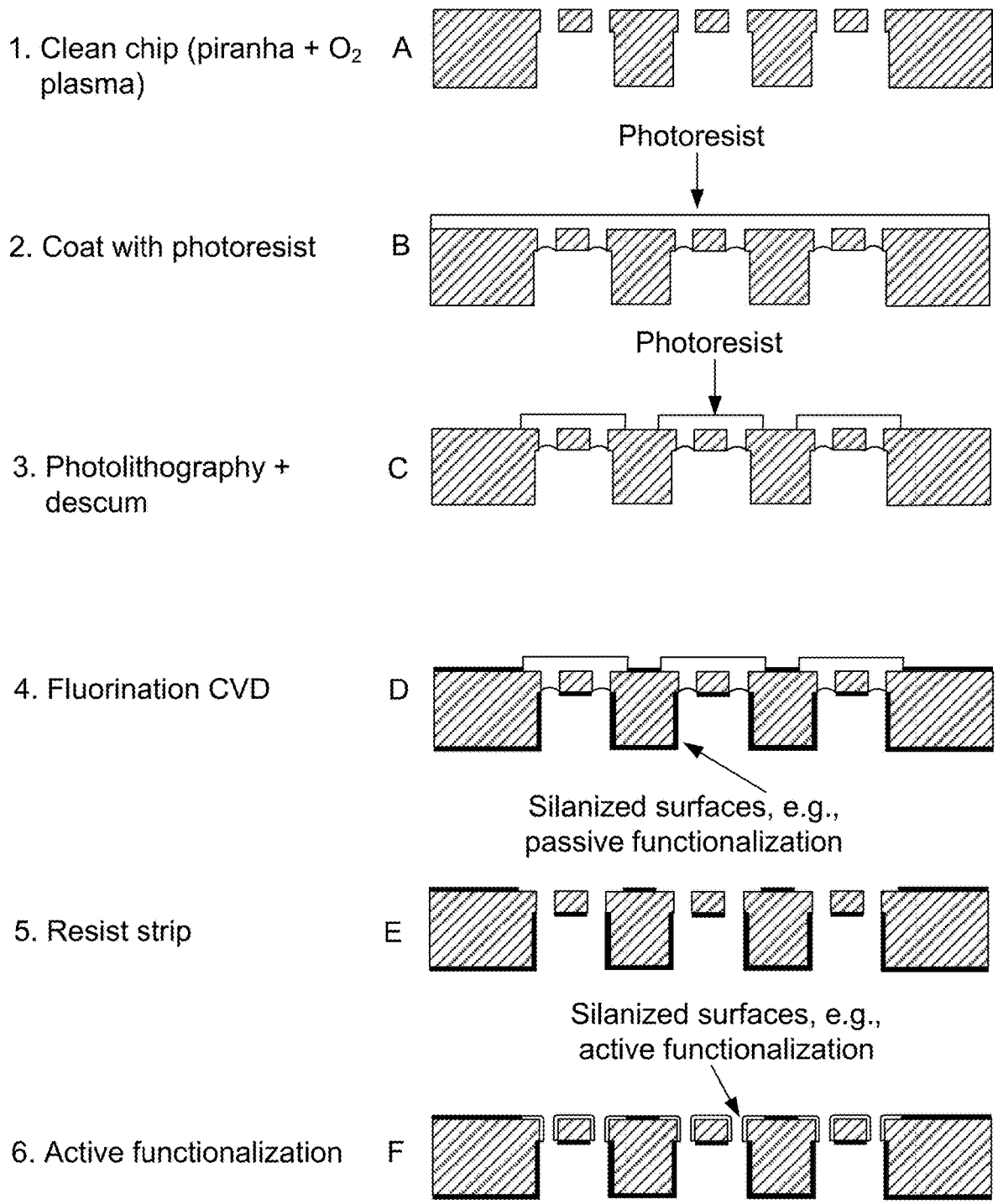
FIG. 29 illustrates an exemplary baseline process flow for the back-end manufacturing of the exemplary oligonucleotide synthesis device of FIG. 15 for differential functionalization.

The etched SOI wafers were subjected to processing steps as described in FIG. 29 parts A-F.

First, the wafer was cleaned by a wet cleaning step using piranha solution followed by a dry $O_2$ plasma exposure. The device layer (on top in FIG. 29 part B) of the chip was coated with photoresist in a process governed by wicking into the device layer channels that are about 20 μm wide. The photoresist was patterned using photolithography to expose the areas that are desired to be passive (no future oligonucleotide synthesis). This process works by exposing the resist to light through a binary mask that has the pattern of interest. After exposure, the resist in the exposed regions was removed in developer solution. (FIG. 29 part C).

The surfaces without photoresist were exposed to a fluorosilane gas by chemical vapor deposition (CVD). This results in the deposition of a fluorocarbon on the surfaces without photoresist. In alternative applications, a hydrocarbon silane is used for this step. The silanized surfaces are unresponsive to additional layers of silane creating a monolayer on the surface. The photoresist was then dissolved in organic solvent, leaving fluorination on the surface and exposing silicon/silicon dioxide that was underneath the photoresist. A final step of active functionalization was performed to prepare the surface for oligonucleotide growth (FIG. 29 part F).

Figure 30:
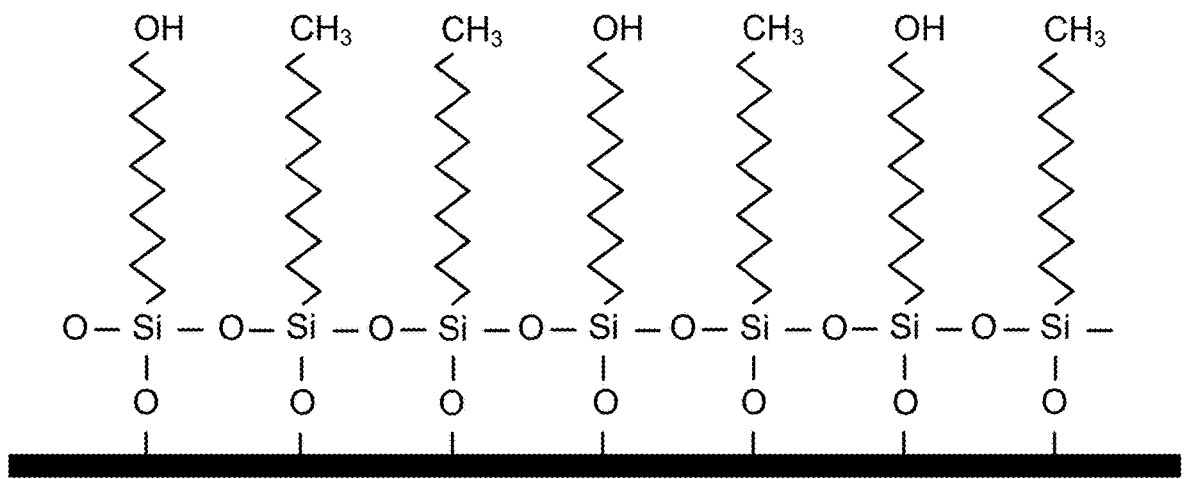
FIG. 30 illustrates a functionalized surface with a controlled density of active groups for nucleic acid synthesis.

A controlled surface density of hydroxyl groups (FIG. 30) was achieved on the surface by a wet process using a 1% solution of N-(3-TRIETHOXYSILYLPROPYL-4HY-DROXYBUTYRAMIDE in ethanol and acetic acid for 4 hours, followed by putting the chips on a hot plate at 150 C for 14 hours. In alternative applications, a CVD process is performed by delivering silane to the surface in gaseous state and applying a controlled deposition pressure of about 200 mTor and a controlled temperature of about 150 C. The CVD process allows for in-situ plasma cleaning and is well suited for producing highly ordered self-assembled monolayers (SAMs).

Figure 31:
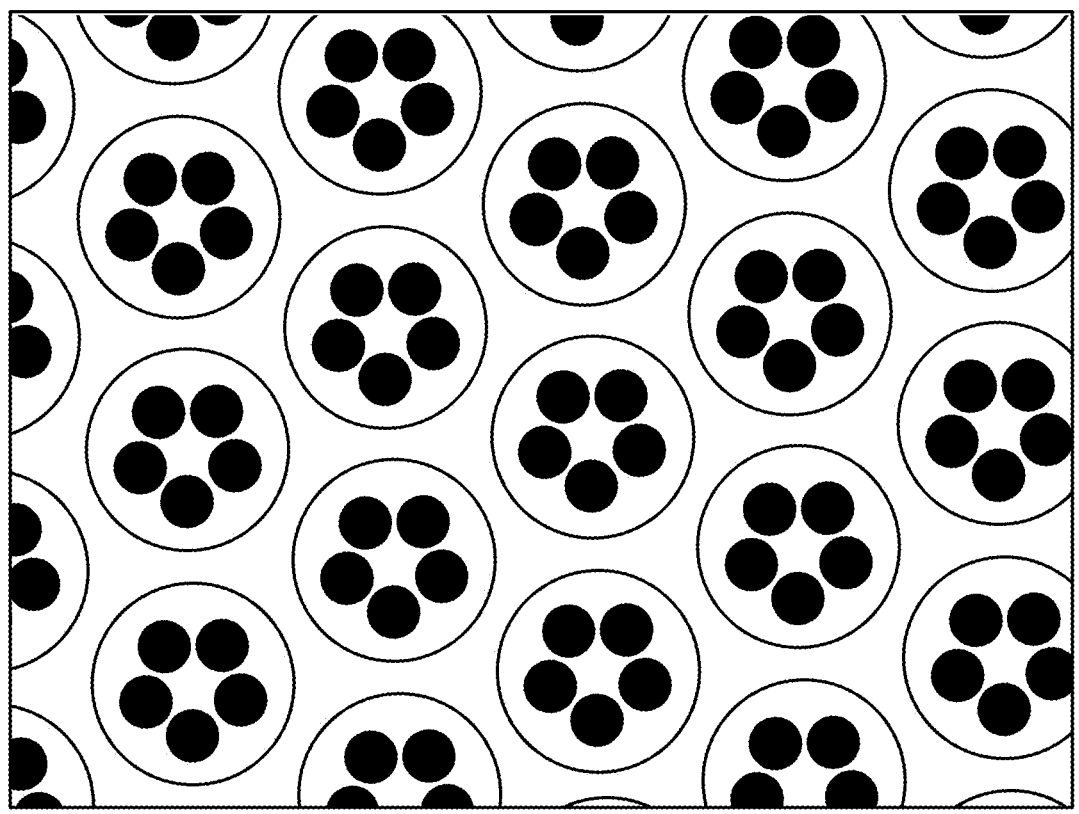
FIG. 31 shows an image of a device manufactured according to the methods described herein.
Figure 31:
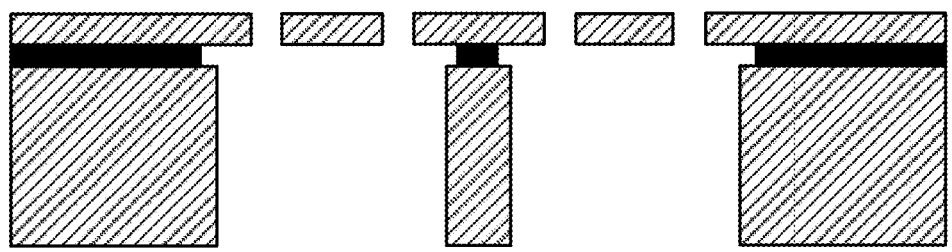

FIGS. 31A-31B shows an image of a device manufactured according to the methods above.

Example 6. Manufacturing of a Nanoreactor Device

Figure 32:
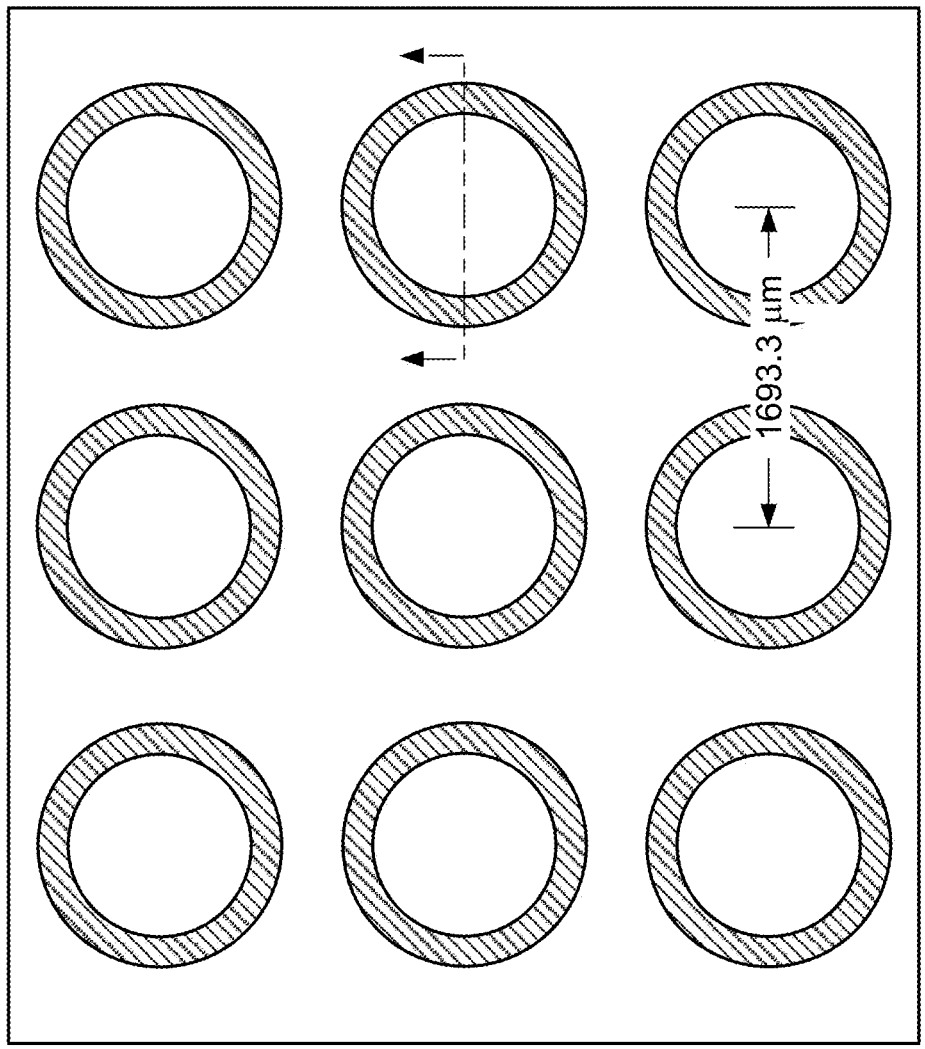
FIG. 32 illustrates the design details of an exemplary nanoreactor device.

A nanoreactor chip with nanowells as described in FIG. 32 was manufactured. A suitable sized silicon wafer was oxidized to cover it with thermal oxide on both surfaces (FIG. 33 part A).

Figure 33:
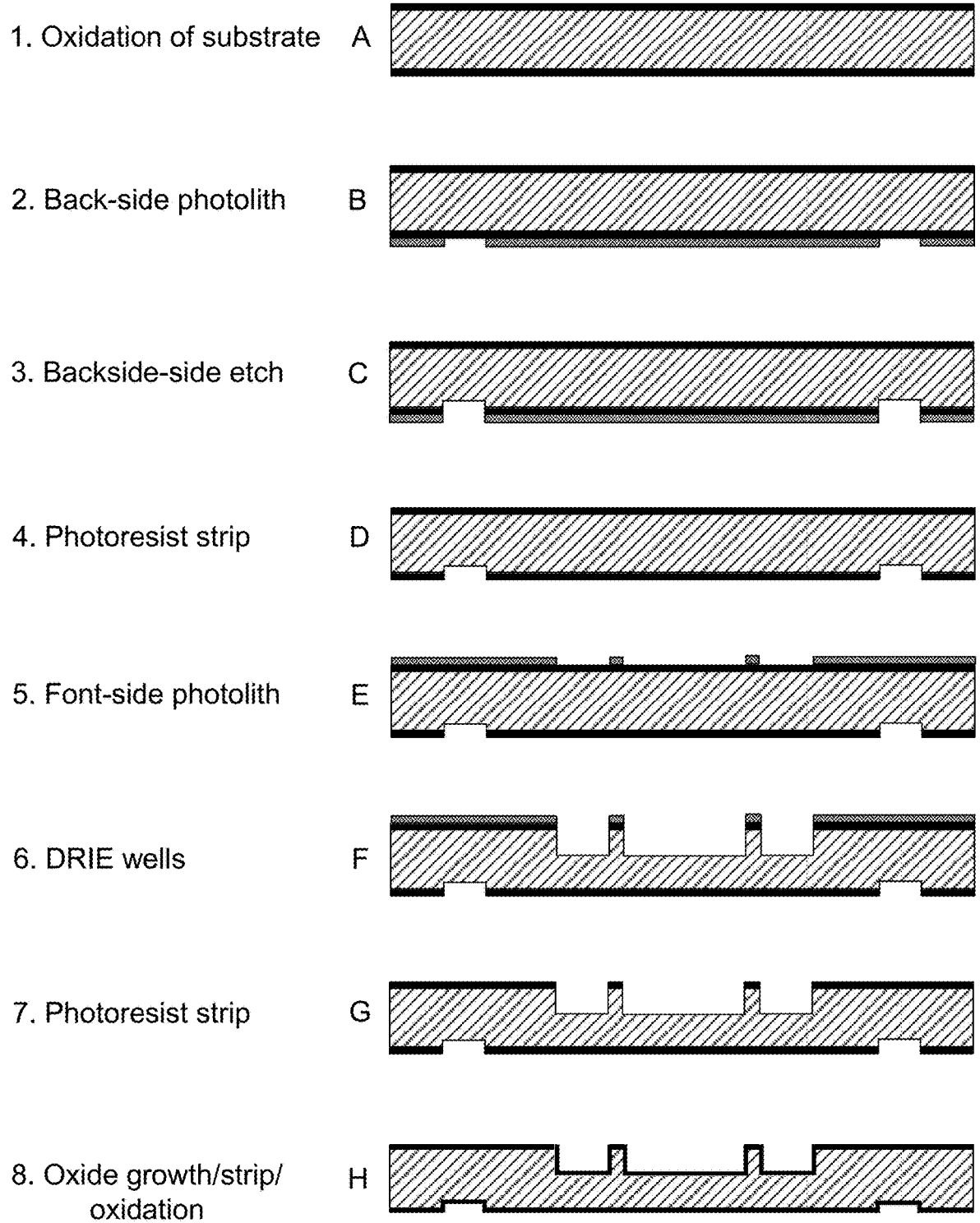
FIG. 33 illustrates an exemplary baseline process flow for the front-end manufacturing of the exemplary device described in FIG. 20.

Photolithography was applied to the back side to create a mask of photoresist (red) as shown in FIG. 33 part B. The back side was etched at locations devoid of the photoresist, beyond the thermal oxide layer, creating shallow wells (FIG. 33 part C). The photoresist was stripped using standard resist stripping process known in the art (FIG. 33 part D).

The photolithography step was repeated on the front side according to the pattern in FIG. 33 part E. A deep reactive-ion etching (DRIE) step was used to etch vertical side-walls to a depth of about 450 μm using a timed etch. In other cases, a SOI wafer is used and the handle layer is etched down to the BOX, wherein the BOX can serve as an etch stop. (FIG. 33 part F). The photoresist on the front side was stripped (FIG. 33 part G), generating the desired pattern according to the device described in FIG. 32. Contaminating fluoropolymers that may have been deposited on the side walls of the microfluidic features were removed by thermal oxidation and the thermal oxidation was stripped using a wet etching process (FIG. 33 part H).

Figure 34:
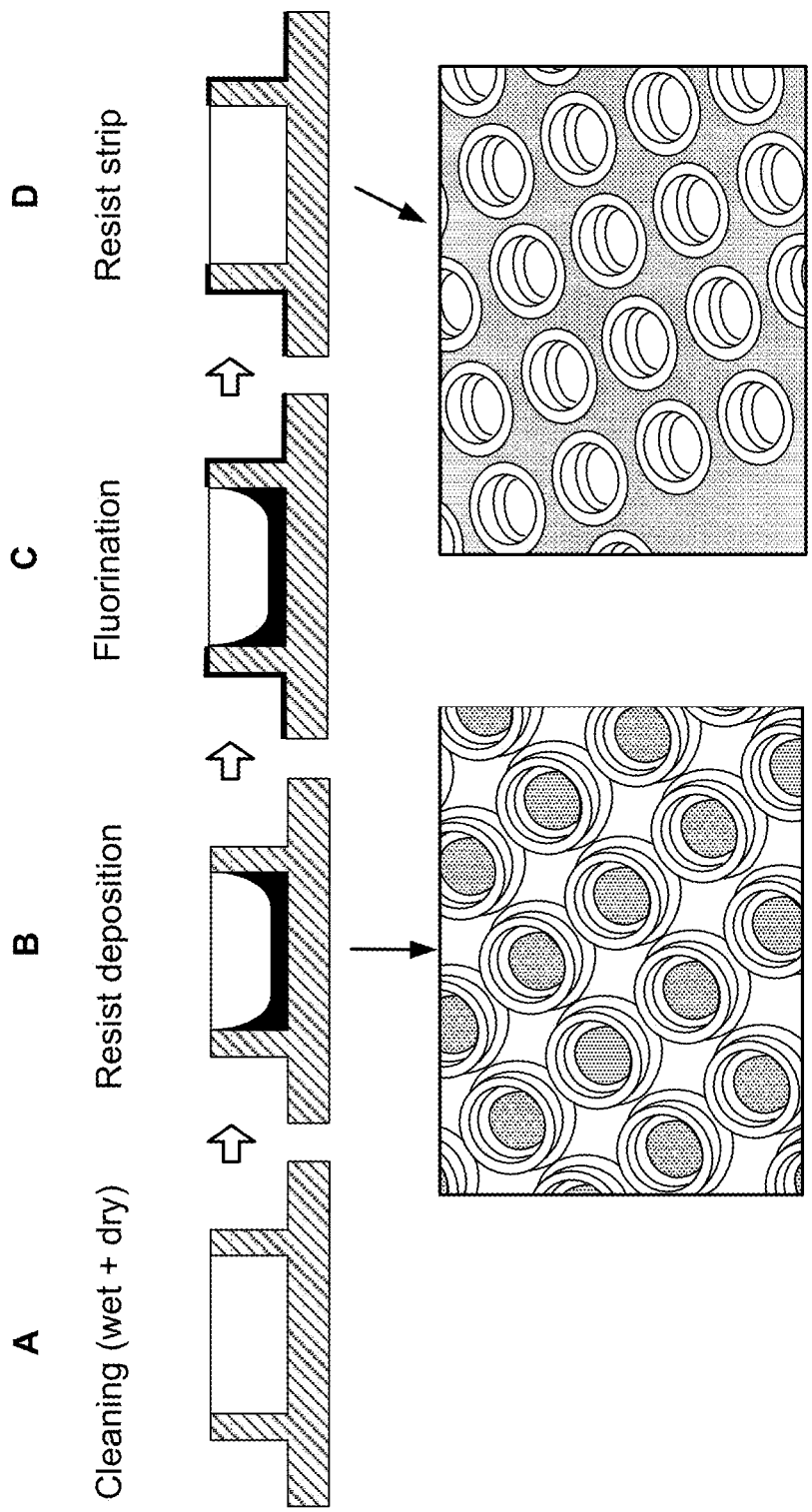
FIG. 34 illustrates an exemplary baseline process flow for the back-end manufacturing of the exemplary nanoreactor device of FIG. 20 for functionalization.

Next, the wafer was cleaned by a wet cleaning step using piranha solution followed by a dry $O_2$ plasma exposure (FIG. 34 part A). Resist was then deposited into individual wells using a microdrop deposition system (top, in FIG. 34 part B). The surfaces without resist were exposed to a fluorosilane gas by chemical vapor deposition (CVD; FIG. 34 part C). This results in the deposition of a fluorocarbon on the surfaces without the resist. In alternative applications, a hydrocarbon silane or other types of silanes are used for this step. The silanized surfaces are unresponsive to additional layers of silane creating a monolayer on the surface. The resist was then dissolved in organic solvent, leaving fluorination on the surface and exposing the silicon surface that was underneath the resist.

Figure 35:
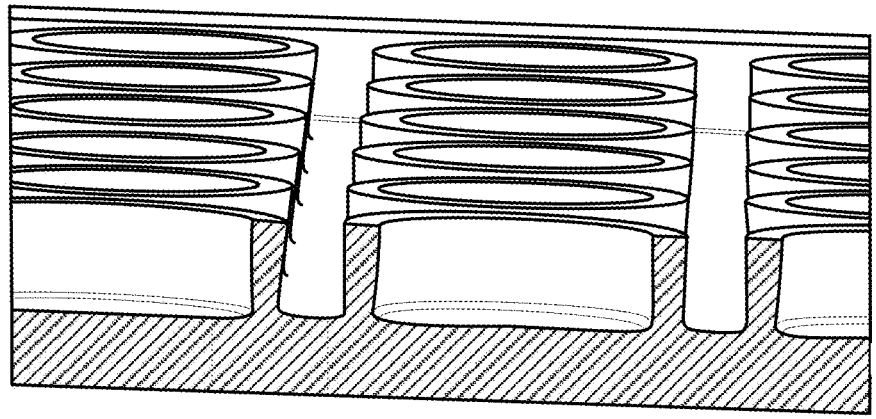
FIG. 35 illustrates the nanowells in a nanoreactor device manufactured as described herein.
Figure 35:
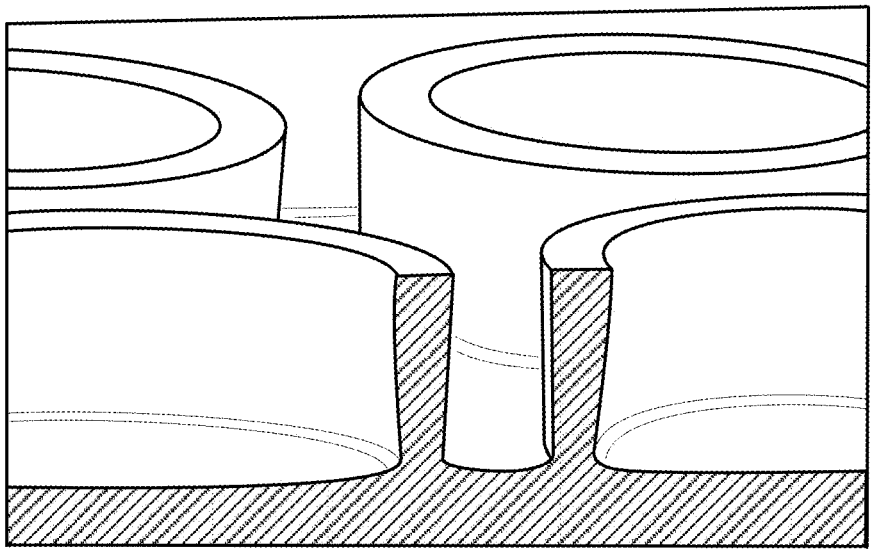

FIG. 35 parts A-B illustrate the nanowells in a nanoreactor device manufactured as described.

Example 7—Synthesis of a 50-Mer Sequence on a 2D Oligonucleotide Synthesis Device A two dimensional oligonucleotide synthesis device was assembled into a flowcell, which was connected to an flowcell (Applied Biosystems (ABI394 DNA Synthesizer"). The two-dimensional oligonucleotide synthesis device was uniformly functionalized with N-(3-TRIETHOXYSILYL-PROPYL)-4-HYDROXYBUTYRAMIDE (Gelest, shop.gelest.com/Product.aspx?catnum=SIT8189.5&Index=0&TotalCount=1) was used to synthesize an exemplary oligonucleotide of 50 bp ("50-mer oligonucleotide") using oligonucleotide synthesis methods described herein.

The sequence of the 50-mer was as described in SEQ ID NO.: 1.

5'AGACAATCAACCATTTGGGGTGGACAGCCTT-GACCTCTAGACTTCGGCA T##TTTTTTTTTT3' (SEQ ID NO.: 1), where # denotes Thymidine-succinyl hexamide CED phosphoramidite (CLP-2244 from ChemGenes), which is a cleavable linker enabling the release of oligos from the surface during deprotection.

The synthesis was done using standard DNA synthesis chemistry (coupling, capping, oxidation, and deblocking) according to the protocol in Table 3 and an ABI synthesizer.

TABLE 3

Table 3

| General DNA Synthesis Process Name | Process Step | Time (sec) |
|---|---|---|
| WASH (Acetonitrile Wash Flow) | Acetonitrile System Flush | 4 |
| | Acetonitrile to Flowcell | 23 |
| | N2 System Flush | 4 |
| | Acetonitrile System Flush | 4 |
| DNA BASE ADDITION (Phosphoramidite + Activator Flow) | Activator Manifold Flush | 2 |
| | Activator to Flowcell | 6 |
| | Activator + Phosphoramidite to Flowcell | 6 |
| | Activator to Flowcell | 0.5 |
| | Activator + Phosphoramidite to Flowcell | 5 |
| | Activator to Flowcell | 0.5 |
| | Activator + Phosphoramidite to Flowcell | 5 |
| | Activator to Flowcell | 0.5 |
| | Activator + Phosphoramidite to Flowcell | 5 |
| | Incubate for 25 sec | 25 |
| WASH (Acetonitrile Wash Flow) | Acetonitrile System Flush | 4 |
| | Acetonitrile to Flowcell | 15 |
| | N2 System Flush | 4 |
| | Acetonitrile System Flush | 4 |
| DNA BASE ADDITION (Phosphoramidite + Activator Flow) | Activator Manifold Flush | 2 |
| | Activator to Flowcell | 5 |
| | Activator + Phosphoramidite to Flowcell | 18 |
| | Incubate for 25 sec | 25 |
| WASH (Acetonitrile Wash Flow) | Acetonitrile System Flush | 4 |
| | Acetonitrile to Flowcell | 15 |
| | N2 System Flush | 4 |
| | Acetonitrile System Flush | 4 |
| CAPPING (CapA + B, 1:1, Flow) | CapA + B to Flowcell | 15 |
| WASH (Acetonitrile Wash Flow) | Acetonitrile System Flush | 4 |
| | Acetonitrile to Flowcell | 15 |
| | Acetonitrile System Flush | 4 |
| OXIDATION (Oxidizer Flow) | Oxidizer to Flowcell | 18 |
| WASH (Acetonitrile Wash Flow) | Acetonitrile System Flush | 4 |
| | N2 System Flush | 4 |
| | Acetonitrile System Flush | 4 |
| | Acetonitrile to Flowcell | 15 |
| | Acetonitrile System Flush | 4 |
| | Acetonitrile to Flowcell | 15 |
| | N2 System Flush | 4 |
| | Acetonitrile System Flush | 4 |
| | Acetonitrile to Flowcell | 23 |
| | N2 System Flush | 4 |
| | Acetonitrile System Flush | 4 |
| DEBLOCKING (Deblock Flow) | Deblock to Flowcell | 36 |
| WASH (Acetonitrile Wash Flow) | Acetonitrile System Flush | 4 |
| | N2 System Flush | 4 |
| | Acetonitrile System Flush | 4 |
| | Acetonitrile to Flowcell | 18 |
| | N2 System Flush | 4.13 |
| | Acetonitrile System Flush | 4.13 |
| | Acetonitrile to Flowcell | 15 |

The phosphoramidite/activator combination was delivered similar to the delivery of bulk reagents through the flowcell. No drying steps were performed as the environment stays "wet" with reagent the entire time.

The flow restrictor was removed from the ABI 394 synthesizer to enable faster flow. Without flow restrictor, flow rates for amidites (0.1M in ACN), Activator, (0.25M Benzoylthiotetrazole ("BTT"; 30-3070-xx from GlenResearch) in ACN), and Ox (0.02M I2 in 20% pyridine, 10% water, and 70% THF) were roughly ~100 uL/sec, for acetonitrile ("ACN") and capping reagents (1:1 mix of CapA and CapB, wherein CapA is acetic anhydride in THF/Pyridine and CapB is 16% 1-methylimidizole in THF), roughly ~200 uL/sec, and for Deblock (3% dichloroacetic acid in toluene), roughly ~300 uL/sec (compared to ~50 uL/sec for all reagents with flow restrictor).

The time to completely push out Oxidizer was observed, the timing for chemical flow times was adjusted accordingly and an extra ACN wash was introduced between different chemicals.

Figure 45:
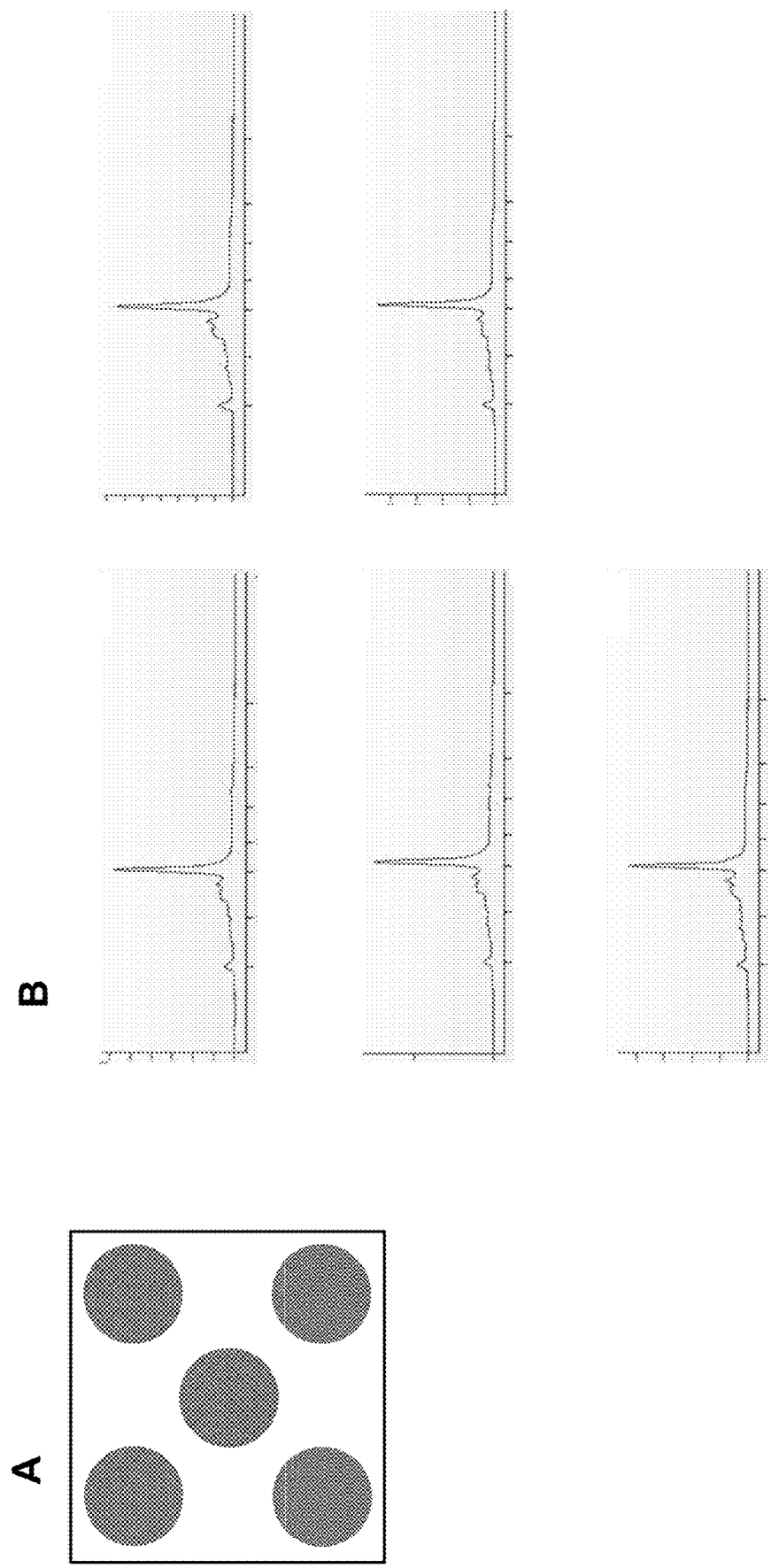
FIG. 45 parts A-B indicate a spot sampling configuration from an oligonucleotide synthesis device (A) and corresponding BioAnalyzer data (B) for each of the five spots in FIG. 45 part A.

After oligonucleotide synthesis, the chip was deprotected in gaseous ammonia overnight at 75 psi. Five drops of water were applied to the surface to recover oligos (FIG. 45 part A). The recovered oligos were then analyzed on a BioAnalyzer small RNA chip (FIG. 45 part B).

Figure 46:
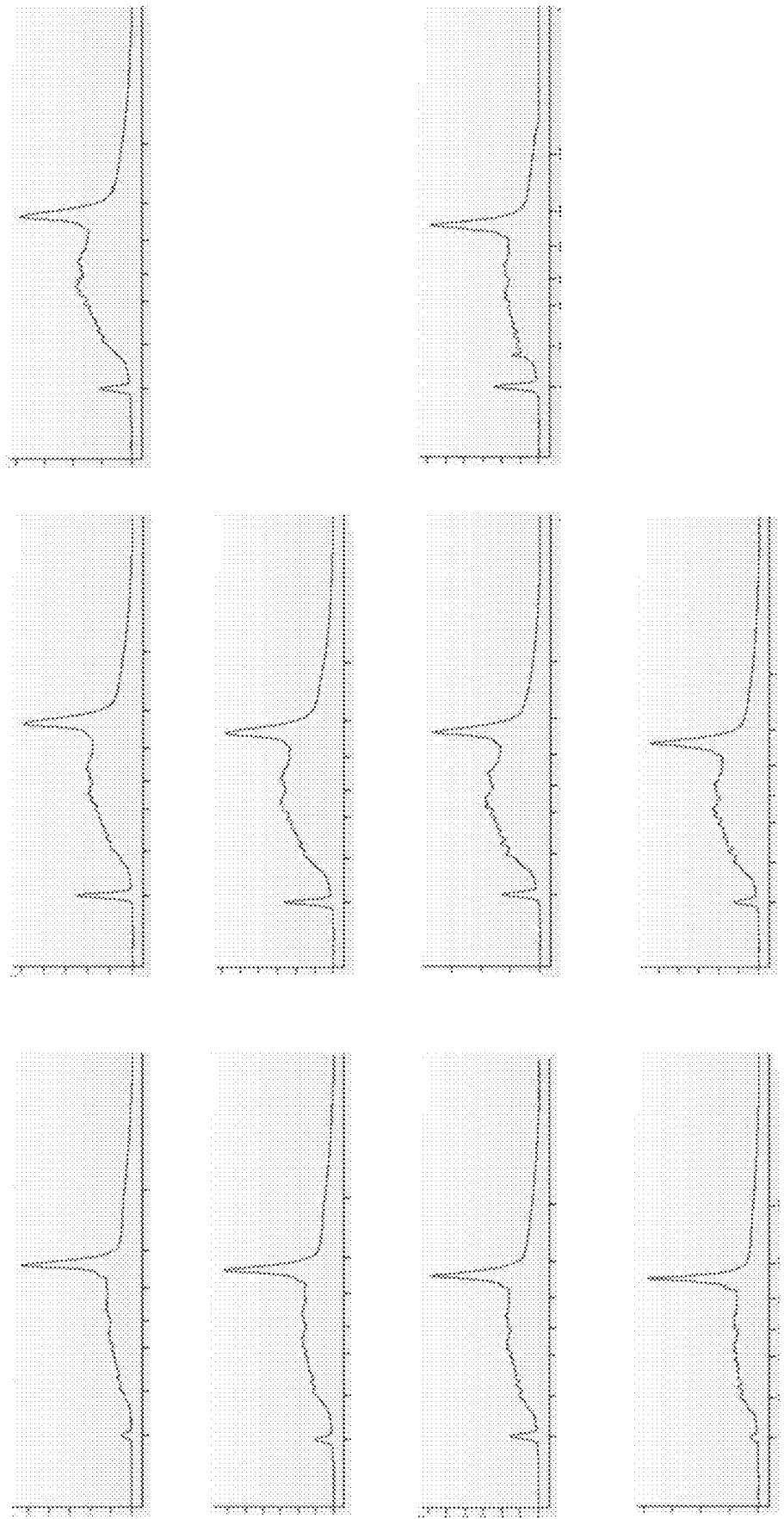
FIG. 46 indicates BioAnalyzer data of surface extracted 100-mer oligonucleotides synthesized on a silicon oligonucleotide synthesis device.

Example 8: Synthesis of a 100-Mer Sequence on a 2D Oligonucleotide Synthesis Device The same process as described in Example 7 for the synthesis of the 50-mer sequence was used for the synthesis of a 100-mer oligonucleotide ("100-mer oligonucleotide"; 5' CGGGATCCTTATCGTCATCGTCGTACAGATCCCGA-CCCATTTGCTGTCCACCAGTCATGCTAGCCATACC-ATGATGATGATGATGATGAGAACCCCGCAT##TTTT-TTTTTT3', where # denotes Thymidine-succinyl hexamide CED phosphoramidite (CLP-2244 from ChemGenes); SEQ ID NO.: 2) on two different silicon chips, the first one uniformly functionalized with N-(3-TRIETHOXYSILYL-PROPYL)-4-HYDROXYBUTYRAMIDE and the second one functionalized with 5/95 mix of 11-acetoxyundecyltriethoxysilane and n-decyltriethoxysilane, and the oligos extracted from the surface were analyzed on a BioAnalyzer instrument (FIG. 46).

Figure 47:
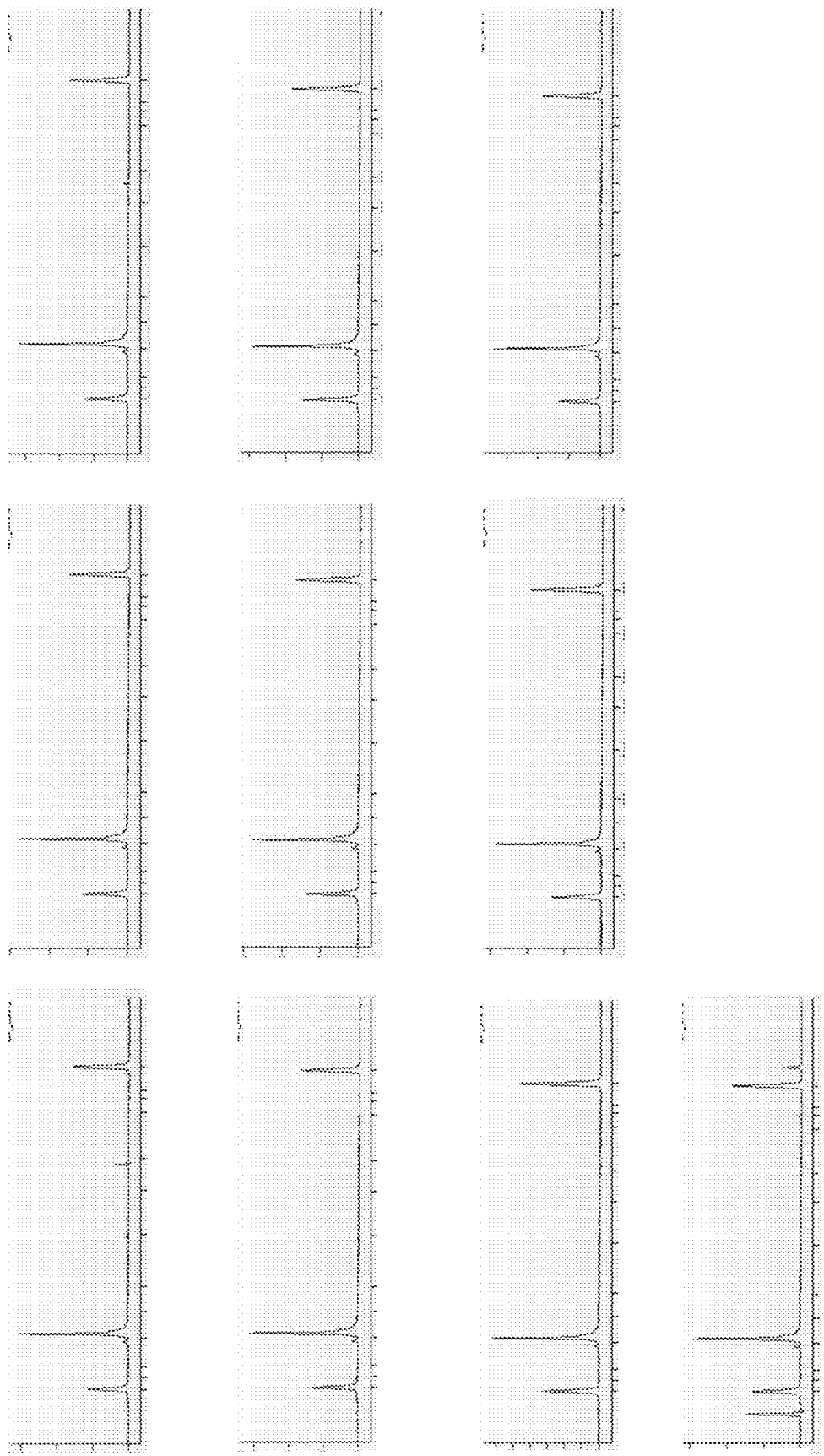
FIG. 47 indicates BioAnalyzer data of surface extracted 100-mer oligonucleotides synthesized on a silicon oligonucleotide synthesis device after PCR amplification.

All ten samples from the two chips were further PCR amplified using a forward (5'ATGCGGGGTTCTCATCATC3'; SEQ ID NO.: 3) and a reverse (5'CGGGATCCTTATCGTCATCG3; SEQ ID NO.: 4) primer in a 50 uL PCR mix (25 uL NEB Q5 mastermix, 2.5 uL 10 uM Forward primer, 2.5 uL 10 uM Reverse primer, 1 uL oligo extracted from the surface, and water up to 50 uL) using the following thermalcycling program:

98 C, 30 sec
98 C, 10 sec; 63 C, 10 sec; 72 C, 10 sec; repeat 12 cycles
72 C, 2 min The PCR products were also run on a BioAnalyzer (FIG. 47), demonstrating sharp peaks at the 100-mer position.

Next, the PCR amplified samples were cloned, and Sanger sequenced. Table 4 summarizes the results from the Sanger sequencing for samples taken from spots 1-5 from chip 1 and for samples taken from spots 6-10 from chip 2.

TABLE 4

| Spot | Error rate | Cycle efficiency |
|---|---|---|
| 1 | 1/763 bp | 99.87% |
| 2 | 1/824 bp | 99.88% |
| 3 | 1/780 bp | 99.87% |

TABLE 4-continued

| Spot | Error rate | Cycle efficiency |
|---|---|---|
| 4 | 1/429 bp | 99.77% |
| 5 | 1/1525 bp | 99.93% |
| 6 | 1/1615 bp | 99.94% |
| 7 | 1/531 bp | 99.81% |
| 8 | 1/1769 bp | 99.94% |
| 9 | 1/854 bp | 99.88% |
| 10 | 1/1451 bp | 99.93% |

Thus, the high quality and uniformity of the synthesized oligonucleotides were repeated on two chips with different surface chemistries. Overall, 89%, corresponding to 233 out of 262 of the 100-mers that were sequenced were perfect sequences with no errors.

Figure 48:
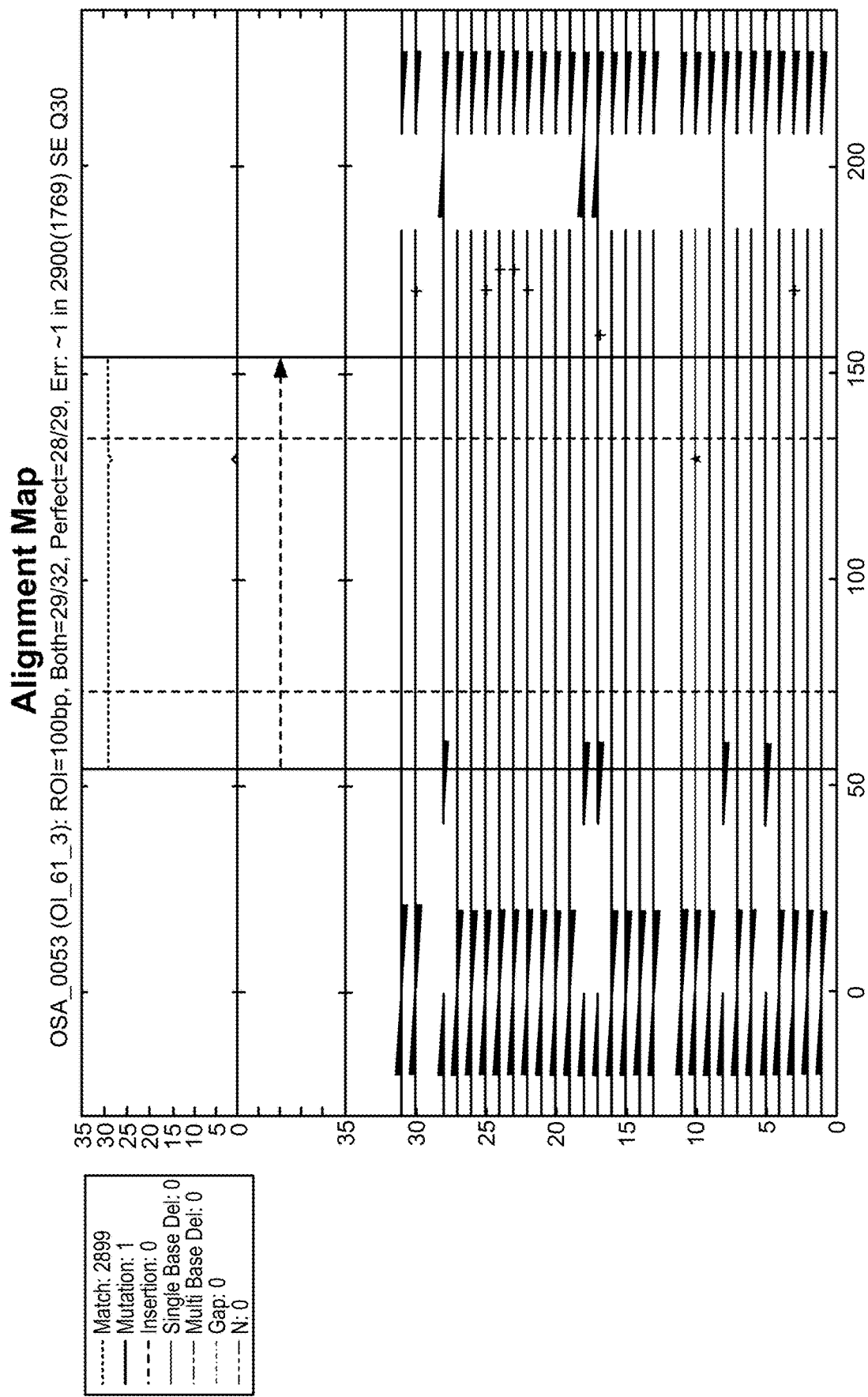
FIG. 48 represents a sequence alignment for the samples taken from spot 8, where "x" denotes a single base deletion, "star" denotes single base mutation, and "+" denotes low quality spots in Sanger sequencing.
Figure 49:
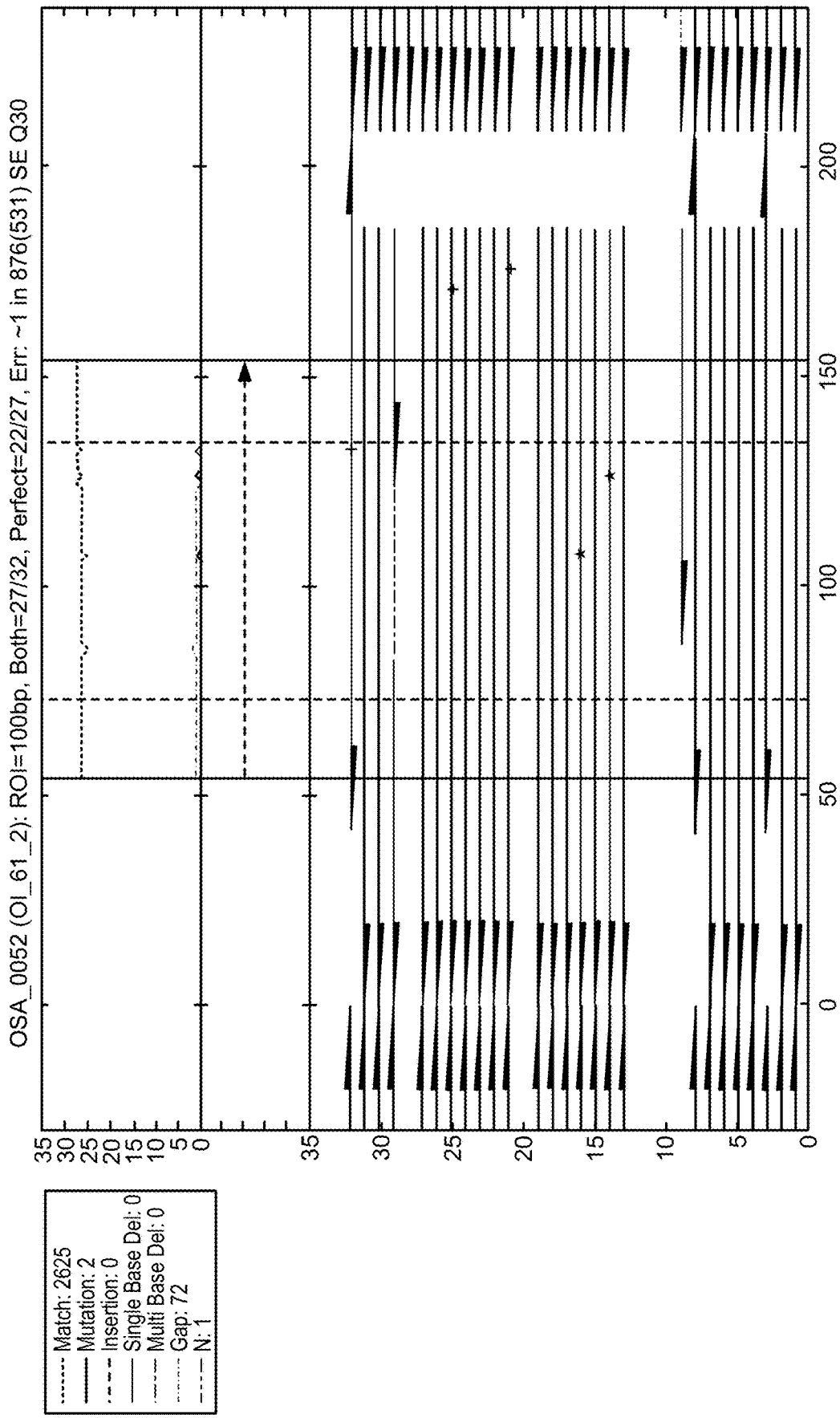
FIG. 49 represents a sequence alignment for the samples taken from spot 7, where "x" denotes a single base deletion, "star" denotes single base mutation, and "+" denotes low quality spots in Sanger sequencing.

FIGS. 48 and 49 show alignment maps for samples taken from spots 8 and 7, respectively, where "x" denotes a single base deletion, "star" denotes single base mutation, and "+" denotes low quality spots in Sanger sequencing. The aligned sequences in FIG. 48 together represent an error rate of about 97%, where 28 out of 29 reads correspond to perfect sequences. The aligned sequences in FIG. 49 together represent an error rate of about 81%, where 22 out of 27 reads correspond to perfect sequences.

Finally, Table 5 summarizes key error characteristics for the sequences obtained from the oligonucleotides samples from spots 1-10.

TABLE 5

| | Sample ID/Spot no. | | | | |
|---|---|---|---|---|---|
| | OSA_0046/1 | OSA_0047/2 | OSA_0048/3 | OSA_0049/4 | OSA_0050/5 |
| Total Sequences | 32 | 32 | 32 | 32 | 32 |
| Sequencing Quality | 25 of 28 | 27 of 27 | 26 of 30 | 21 of 23 | 25 of 26 |
| Oligo Quality | 23 of 25 | 25 of 27 | 22 of 26 | 18 of 21 | 24 of 25 |
| ROI Match Count | 2500 | 2698 | 2561 | 2122 | 2499 |
| ROI Mutation | 2 | 2 | 1 | 3 | 1 |
| ROI Multi Base Deletion | 0 | 0 | 0 | 0 | 0 |
| ROI Small Insertion | 1 | 0 | 0 | 0 | 0 |
| ROI Single Base Deletion | 0 | 0 | 0 | 0 | 0 |
| Large Deletion Count | 0 | 0 | 1 | 0 | 0 |
| Mutation: G > A | 2 | 2 | 1 | 2 | 1 |
| Mutation: T > C | 0 | 0 | 0 | 1 | 0 |
| ROI Error Count | 3 | 2 | 2 | 3 | 1 |
| ROI Error Rate | Err: ~1 in 834 | Err: ~1 in 1350 | Err: ~1 in 1282 | Err: ~1 in 708 | Err: ~1 in 2500 |
| ROI Minus Primer Error Rate | MP Err: ~1 in 763 | MP Err: ~1 in 824 | MP Err: ~1 in 780 | MP Err: ~1 in 429 | MP Err: ~1 in 1525 |

| | Sample ID/Spot no. | | | | |
|---|---|---|---|---|---|
| | OSA_0051/6 | OSA_0052/7 | OSA_0053/8 | OSA_0054/9 | OSA_0055/10 |
| Total Sequences | 32 | 32 | 32 | 32 | 32 |
| Sequencing Quality | 29 of 30 | 27 of 31 | 29 of 31 | 28 of 29 | 25 of 28 |
| Oligo Quality | 25 of 29 | 22 of 27 | 28 of 29 | 26 of 28 | 20 of 25 |
| ROI Match Count | 2666 | 2625 | 2899 | 2798 | 2348 |
| ROI Mutation | 0 | 2 | 1 | 2 | 1 |
| ROI Multi Base Deletion | 0 | 0 | 0 | 0 | 0 |
| ROI Small Insertion | 0 | 0 | 0 | 0 | 0 |

TABLE 5-continued

| | | | | | |
|---|---|---|---|---|---|
| ROI Single Base Deletion | 0 | 0 | 0 | 0 | 0 |
| Large Deletion Count | 1 | 1 | 0 | 0 | 0 |
| Mutation: G > A | 0 | 2 | 1 | 2 | 1 |
| Mutation: T > C | 0 | 0 | 0 | 0 | 0 |
| ROI Error Count | 1 | 3 | 1 | 2 | 1 |
| ROI Error Rate | Err: ~1 in 2667 | Err: ~1 in 876 | Err: ~1 in 2900 | Err: ~1 in 1400 | Err: ~1 in 2349 |
| ROI Minus Primer Error Rate | MP Err: ~1 in 1615 | MP Err: ~1 in 531 | MP Err: ~1 in 1769 | MP Err: ~1 in 854 | MP Err: ~1 in 1451 |

Figure 50:
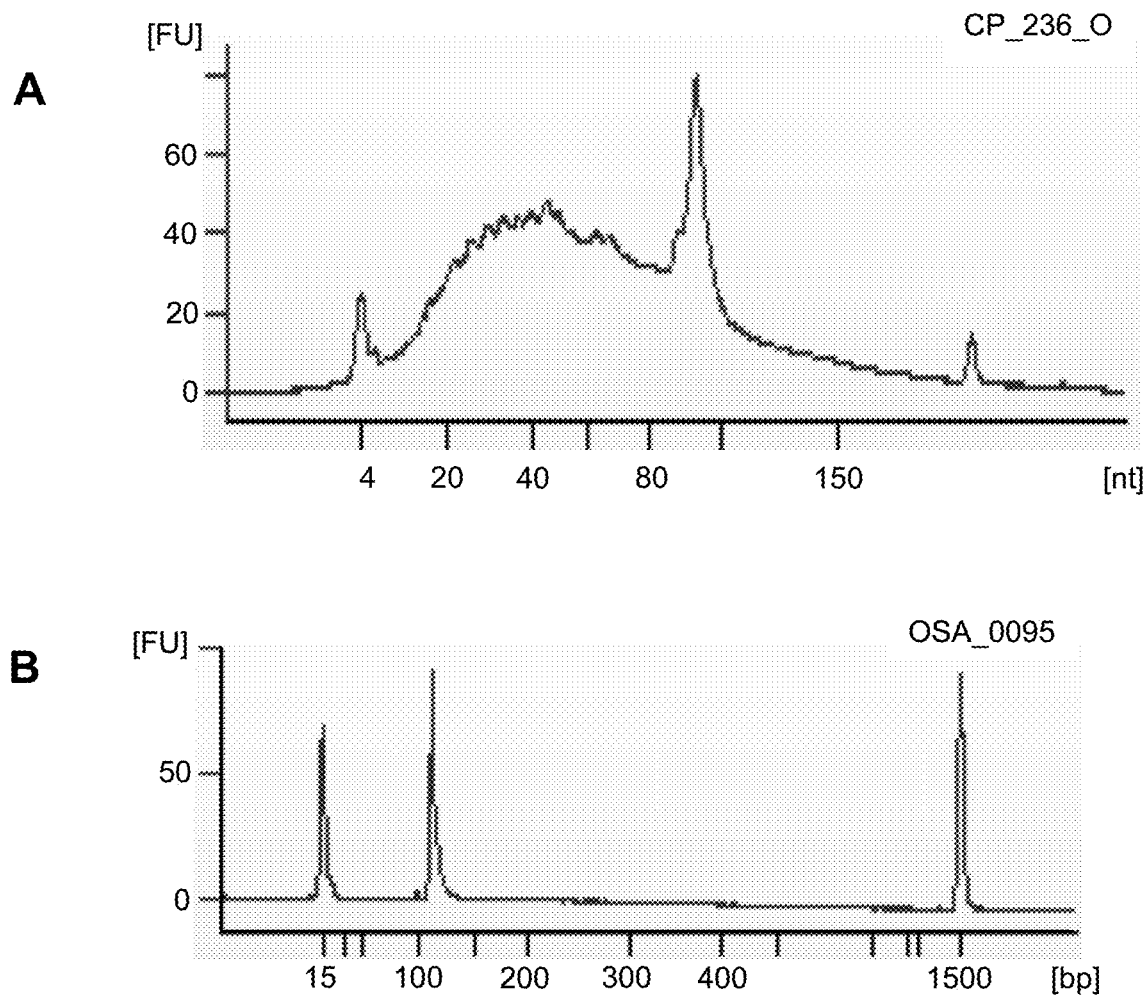
FIG. 50 parts A-B provide BioAnalzyer results for a 100-mer oligonucleotide synthesized on a three dimensional oligonucleotide device after extraction (part A) and after PCR amplification (part B).

Example 9: Synthesis of a 100-Mer Sequence on a 3D Oligonucleotide Synthesis Device A three dimensional oligonucleotide synthesis device as described in Example 3 that was differentially functionalized with a 5/95 mix of 11-acetoxyundecyltriethoxysilane and n-decyltriethoxysilane on active areas for synthesis was assembled into a flowcell to synthesize the 100-mer oligonucleotide of Example 8 using oligonucleotide synthesis methods described herein. The synthesis was done using standard DNA synthesis chemistry (coupling, capping, oxidation, and deblocking) as described in Example 7, according to the protocol in Table 3. The chip was deprotected in gaseous ammonia, at 75 psi, overnight and the oligos were eluted in 500 uL water. After evaporation, all oligos were re-suspended in 20 uL water for downstream analysis. The re-suspended sample was analyzed on a BioAnalzyer instrument (FIG. 50 part A).

The re-suspended sample was also PCR amplified using forward (5'ATGCGGGGTTCTCATCATC3; SEQ ID NO.: 5) and reverse (5'CGGGATCCTTATCGTCATCG3; SEQ ID NO.: 6) primers in a 50 uL PCR mix including 25 uL NEB Q5 mastermix, 2.5 uL 10 uM forward primer, 2.5 uL 10 uM reverse primer, 1 uL oligo extracted from the surface, and water up to 50 uL, according to the following thermalcycling program:
  1 cycle: 98 C, 30 sec
  12 cycles: 98 C, 10 sec; 63 C, 10 sec; 72 C, 10 sec
  1 cycle: 72 C, 2 min The PCR product was also run on the BioAnalyzer (FIG. 50 part B) showing a sharp peak at the 100-mer position.

Figure 51:
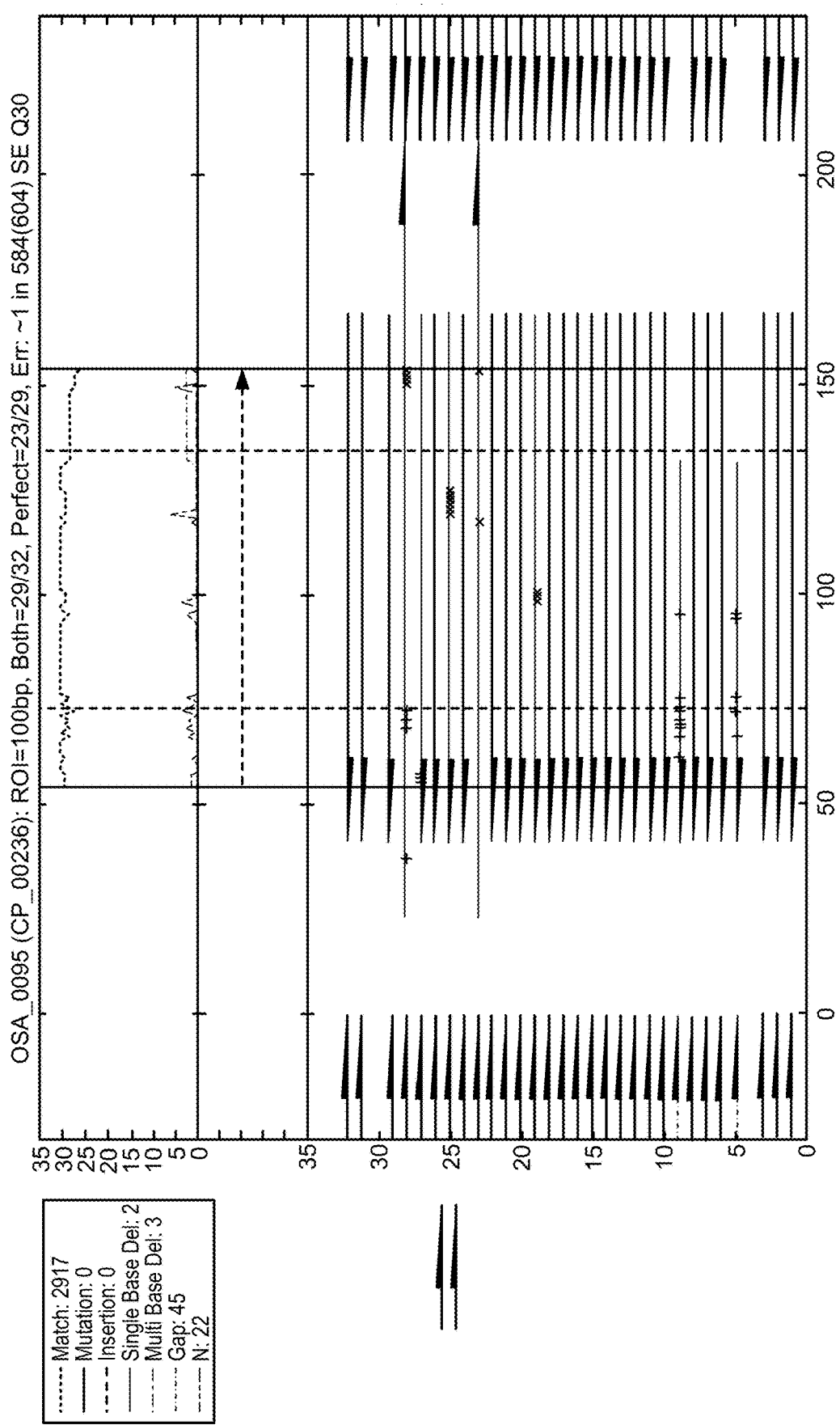
FIG. 51 represents a sequence alignment map for a PCR amplified sample of a 100-mer oligonucleotide that was synthesized on a 3D oligonucleotide device.

The sequencing result of the PCR products showed that 23 out of 29 sequences were perfect and error rate was ~1 in 600 bp as illustrated by the alignment maps in FIG. 51, where "x" denotes a single base deletion, "star" denotes single base mutation, and "+" denotes low quality spots in Sanger sequencing.

Example 10: Parallel Oligonucleotide Synthesis on a Three Dimensional Microfluidic Oligonucleotide Synthesis Device The synthesis protocol of EXAMPLE 7 is modified using a house set-up to perform parallel oligonucleotide synthesis on the three dimensional microfluidic device of EXAMPLE 9.

Table 6 illustrates a side by side comparison of the two protocols.

TABLE 6

| General DNA Synthesis Process Name | EXAMPLE 7 Protocol | | Twist In-House Synthesizer Protocol | |
|---|---|---|---|---|
| | EXAMPLE 7 Process Step | Time (sec) | Twist Process Step | Time (sec) |
| WASH (Acetonitrile Wash Flow) | Acetonitrile System Flush | 4 | NA | |
| | Acetonitrile to Flowcell | 23 | | |
| | N2 System Flush | 4 | | |
| | Acetonitrile System Flush | 4 | | |
| DNA BASE ADDITION (Phosphoramidite + Activator Flow) | Activator Manifold Flush | 2 | Print heads print 1:1 of Activator + Phosphoramidite directly on chip active sites | 120 |
| | Activator to Flowcell | 6 | | |
| | Activator + Phosphoramidite to Flowcell | 6 | | |
| | Activator to Flowcell | 0.5 | | |
| | Activator + Phosphoramidite to Flowcell | 5 | | |
| | Activator to Flowcell | 0.5 | | |
| | Activator + Phosphoramidite to Flowcell | 5 | | |
| | Activator to Flowcell | 0.5 | | |
| | Activator + Phosphoramidite to Flowcell | 5 | | |
| | Incubate for 25 sec | 25 | | |
| WASH (Acetonitrile Wash Flow) | Acetonitrile System Flush | 4 | | |
| | Acetonitrile to Flowcell | 15 | | |
| | N2 System Flush | 4 | | |
| | Acetonitrile System Flush | 4 | | |

TABLE 6-continued

| General DNA Synthesis Process Name | EXAMPLE 7 Protocol | | Twist In-House Synthesizer Protocol | |
|---|---|---|---|---|
| | EXAMPLE 7 Process Step | Time (sec) | Twist Process Step | Time (sec) |
| DNA BASE ADDITION (Phosphoramidite + Activator Flow) | Activator Manifold Flush | 2 | | |
| | Activator to Flowcell | 5 | | |
| | Activator + Phosphoramidite to Flowcell | 18 | | |
| | Incubate for 25 sec | 25 | | |
| WASH (Acetonitrile Wash Flow) | Acetonitrile System Flush | 4 | Acetonitrile System Flush | 4 |
| | Acetonitrile to Flowcell | 15 | Acetonitrile to Flowcell | 15 |
| | N2 System Flush | 4 | N2 System Flush | 4 |
| | Acetonitrile System Flush | 4 | Acetonitrile System Flush | 4 |
| CAPPING (CapA + B, 1:1, Flow) | CapA + B to Flowcell | 15 | CapA + B to Flowcell | 15 |
| WASH (Acetonitrile Wash Flow) | Acetonitrile System Flush | 4 | Acetonitrile System Flush | 4 |
| | Acetonitrile to Flowcell | 15 | Acetonitrile to Flowcell | 15 |
| | Acetonitrile System Flush | 4 | Acetonitrile System Flush | 4 |
| OXIDATION (Oxidizer Flow) | Oxidizer to Flowcell | 18 | Oxidizer to Flowcell | 18 |
| WASH (Acetonitrile Wash Flow) | Acetonitrile System Flush | 4 | Acetonitrile System Flush | 4 |
| | N2 System Flush | 4 | N2 System Flush | 4 |
| | Acetonitrile System Flush | 4 | Acetonitrile System Flush | 4 |
| | Acetonitrile to Flowcell | 15 | Acetonitrile to Flowcell | 15 |
| | Acetonitrile System Flush | 4 | Acetonitrile System Flush | 4 |
| | Acetonitrile to Flowcell | 15 | Acetonitrile to Flowcell | 15 |
| | N2 System Flush | 4 | N2 System Flush | 4 |
| | Acetonitrile System Flush | 4 | Acetonitrile System Flush | 4 |
| | Acetonitrile to Flowcell | 23 | Acetonitrile to Flowcell | 23 |
| | N2 System Flush | 4 | N2 System Flush | 4 |
| | Acetonitrile System Flush | 4 | Acetonitrile System Flush | 4 |
| DEBLOCKING (Deblock Flow) | Deblock to Flowcell | 36 | Deblock to Flowcell | 36 |
| WASH (Acetonitrile Wash Flow) | Acetonitrile System Flush | 4 | Acetonitrile System Flush | 4 |
| | N2 System Flush | 4 | N2 System Flush | 4 |
| | Acetonitrile System Flush | 4 | Acetonitrile System Flush | 4 |
| | Acetonitrile to Flowcell | 18 | Acetonitrile to Flowcell | 18 |
| | N2 System Flush | 4 | N2 System Flush | 4 |
| | Acetonitrile System Flush | 4 | Acetonitrile System Flush | 4 |
| | Acetonitrile to Flowcell | 15 | Acetonitrile to Flowcell | 15 |
| FLOWCELL DRY (Specific to Twist synthesizer) | NA | | N2 System Flush | 4 |
| | | | N2 to Flowcell | 19.5 |
| | | | N2 System Flush | 4 |
| | | | Vacuum Dry Pull on Flowcell | 10 |
| | | | N2 System Flush | 4 |
| | | | N2 to Flowcell | 19.5 |

Acetonitrile (ACN) is passed through an in-line degasser (Model No. 403-0202-1; Random Technologies), passing the liquid along side a very hydrophobic membrane, which was previously shown to function at flow rates ranging from 50-400 uL/sec and to eliminate gas bubbles that form on a flow cell, without being bound by theory, likely by dissolving them in the undersaturated solvent.

Reagents are exchanged in the flowcell with different reagents as follows:

1) Start reagent flow to the flowcell.
2) Prime by setting the valves to "push" the previous reagent out of the delivery line with the new reagent. This valve state is kept on for 3.75 sec.
3) 2D Valve State: Set the valves to replace the previous reagent resident on the surface of the flowcell with the new reagent. This occurs whilst step 2 has been active for 3.75 sec. Step 2 and 3 are simultaneously active for 0.25 sec, after which the priming valve state turns off
4) 3D Valve State: The valves switch to allow for reagents to flow through the three-dimensional microfluidic features of the silicon in the flowcell, which starts after 0.75 sec of the 2D Valve State in step 3 has flowed.
5) The flow of reagent: 2D valve state and 3D valve states remain open for a designated time to allow for adequate dosage of reagent to the silicon surface in the chip.

Accordingly, during a 5 second cycle of reagent exchange, the fluid delivery is performed by priming during the initial period spanning 0-4 seconds, by turning on the 2D Valve State during the period spanning the 3.75-5 seconds and by turning on the 3D Valve State during the period spanning 4.5-5 seconds.

The phosphoramidite/activator combination is delivered using an ink jet printing step. The delivery can be a 1:1, drop-on-drop deposition onto the silicon surface. The droplet size may be about 10 pL. In some embodiments, the droplet size is at least or at least about 0.1, 1, 2, 3, 4, 5, 10, 15, 20, 25, 50, 75, 100, 150, 200, 250, 300, 400, 500 picoliters, or more. In some embodiments, the droplet size is at most or at most about 500, 400, 300, 250, 200, 150, 100, 75, 50, 25, 20, 15, 10, 5, 4, 3, 2, 1, 0.1 picoliters, or less. The droplet size may be between 0.1-50, 1-150, or 5-75 picoliters. The droplet size may fall within a range that is bound by any of these values, e.g. 2-50 picoliters. The droplets may be deposited with an initial velocity of 1-100 m/sec. In some cases, the droplets may be deposited with an initial velocity of at least or at least about 1, 2, 3, 4, 5, 6, 7, 8, 9, 10, 15, 20, 25, 40, 35, 40, 45, 50, 75, 100 m/sec, or higher. In some cases, the droplets may be deposited with an initial velocity of at most or at most about 100, 75, 50, 45, 40, 35, 30, 25, 20, 15, 10, 9, 8, 7, 6, 5, 4, 3, 2, 1, m/sec or lower. 1, 2, 3, 4, 5, 6, 7, 8, 9, 10, 15, 20, 25, 40, 35, 40, 45, 50, 75, 100, or higher. The droplets may be deposited with an initial velocity that falls between about 1-50 m/sec., 5-15 m/sec, 5-30 m/sec, or 1-30 m/sec. Those having skill in the art will understand that the droplets may be deposited with an initial velocity that falls under a range bound by any of these values.

A drying step prepares the silicon surface for the printing steps after the bulk reagent sequences. To achieve dry conditions which facilitate printed reagents to react, the flowcell is flushed with $N_2$ gas at about 5 PSI for about 19.5 seconds, a small vacuum is pulled on the flowcell chamber for 10 seconds, and the flowcell is flushed again with N2 gas for another 19.5 seconds. All reagents are flown at about 200-400 uL/sec Flow rates can be controlled in the in-house system using varying pressures. Flow rate is one of the limiting aspects of commercially available synthesizers. In the in-house machine set-up, flow rates can either be matched to their values in Example 7 or to increased or decreased flowrates, as appropriate, to improve the synthesis process. Generally, flowing faster presents advantages as it allows to displace bubbles much more effectively and allows for more exchange of fresh reagents to the surface during a given time interval when compared with the slower flow rates.

Figure 53:
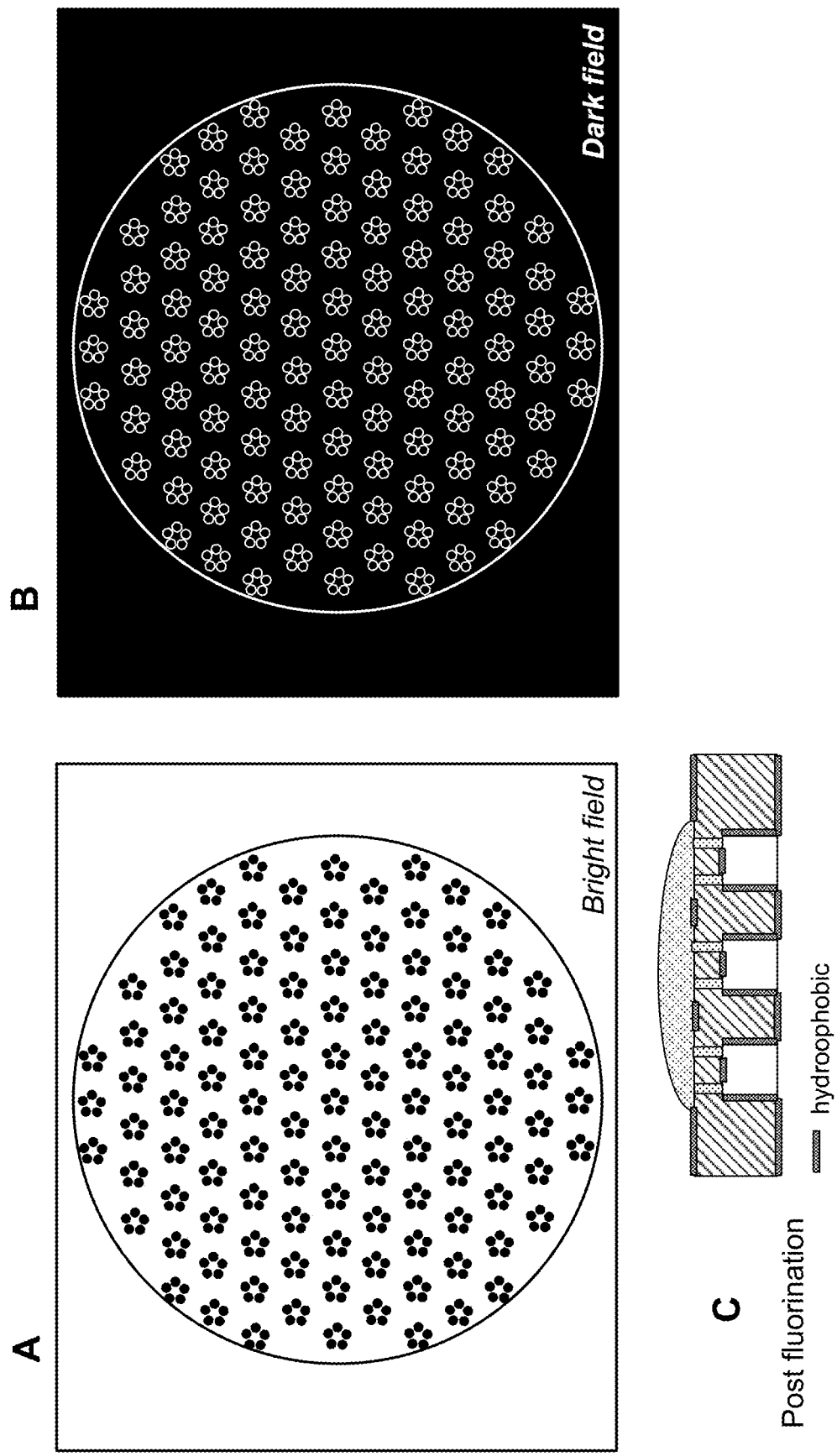
FIG. 53 parts A-C illustrate a surface functionalization pattern in an exemplary differential functionalization configuration after functionalization.

Example 11: Blotting Based Oligonucleotide Transfer from an Oligonucleotide Synthesis Device to a Nanoreactor Device 50-mer oligonucleotides were synthesized on a 3-D oligonucleotide synthesis device as described in Example 9. No active functionalization was applied. FIG. 53 parts A-B illustrates the oligonucleotide synthesis channel distribution in a cluster on the device side of the oligonucleotide synthesis device and FIG. 53 part C illustrates the surface functionalization. The oligonucleotides were released from the surface by treatment in a gaseous ammonia chamber at 75 psi for 14 hours.

Figure 54:
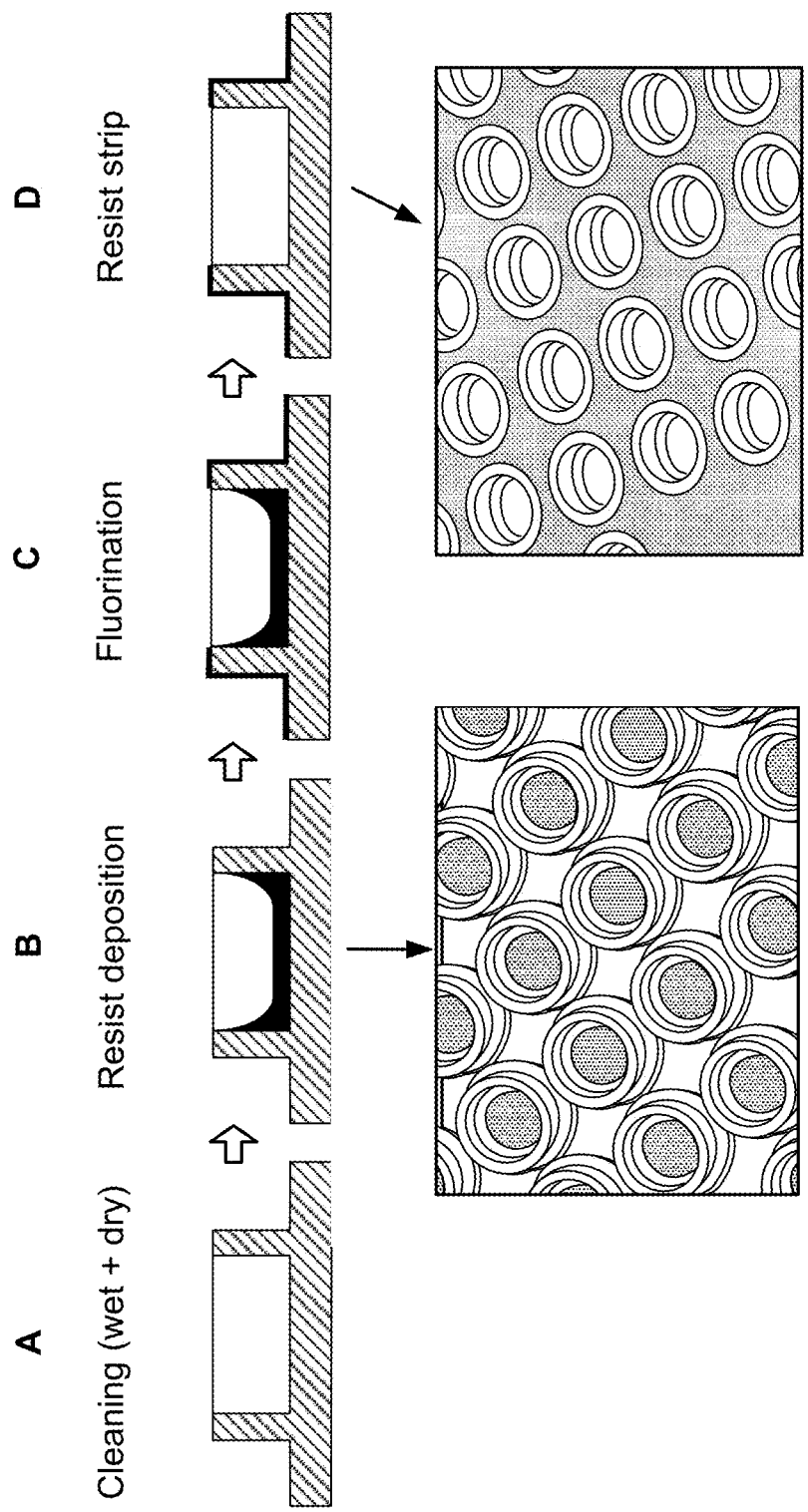
FIG. 54 depicts an exemplary workflow for functionalization of an nanoreactor device. Cleaning is followed by resist deposition, functionalization, and finally a resist strip.
Figure 55:
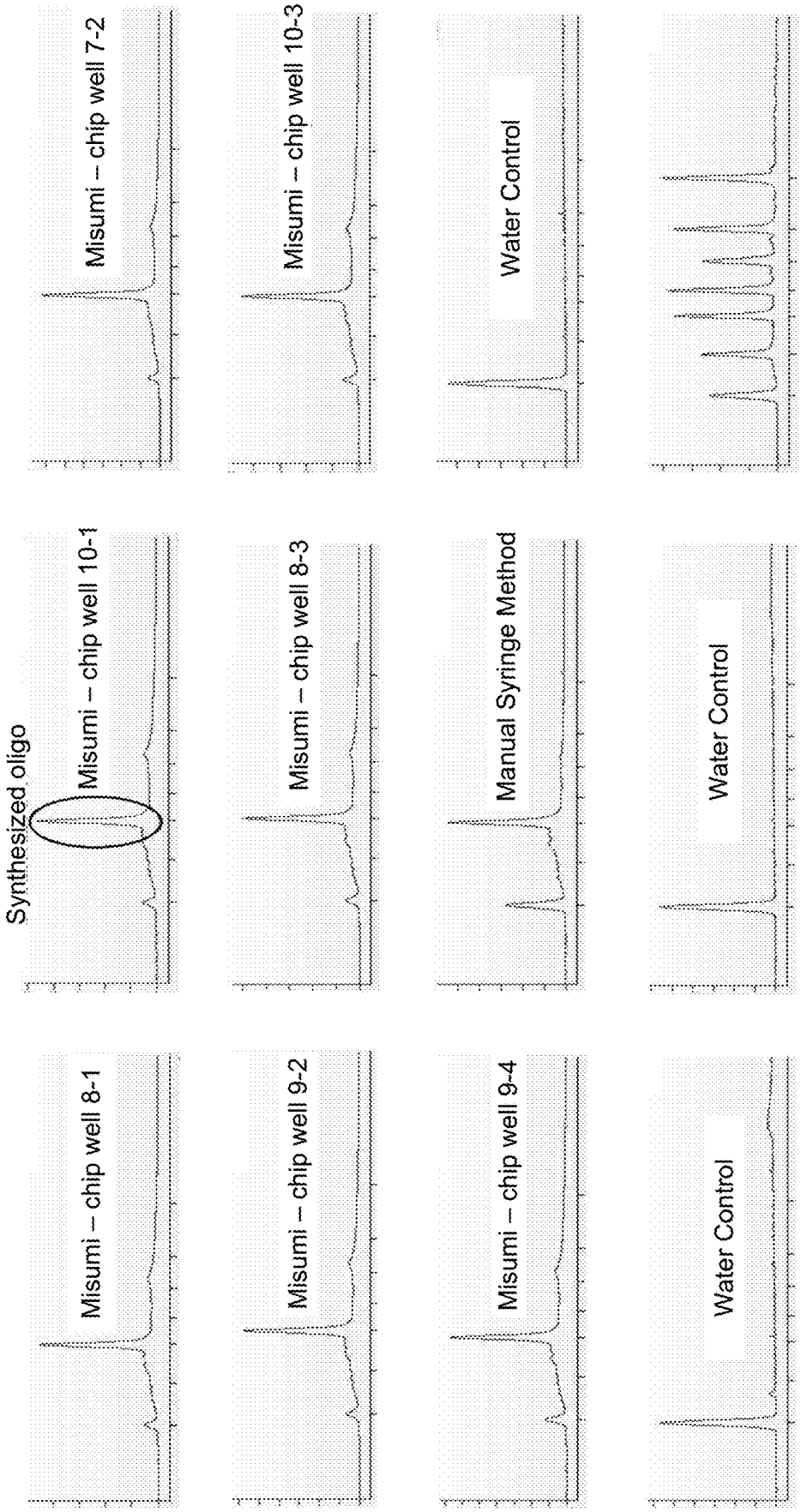
FIG. 55 depicts BioAnalyzer results for a number of oligonucleotides transferred into individual nanoreactor wells from an oligonucleotide synthesis device following a blotting method.

Wells of a nanoreactor device that was manufactured according to Example 4 with hydrophilic inner walls and hydrophobic top lips (FIG. 54) were first filled with a PCA suitable buffer as a negative control (5×Q5 buffer; New England Biolabs). 200-300 nL aliquots were hand-pipetted to feed into a BioAnalyzer to show the absence of any contaminating nucleic acids in the individual nanoreactors (FIG. 55).

Figure 57:
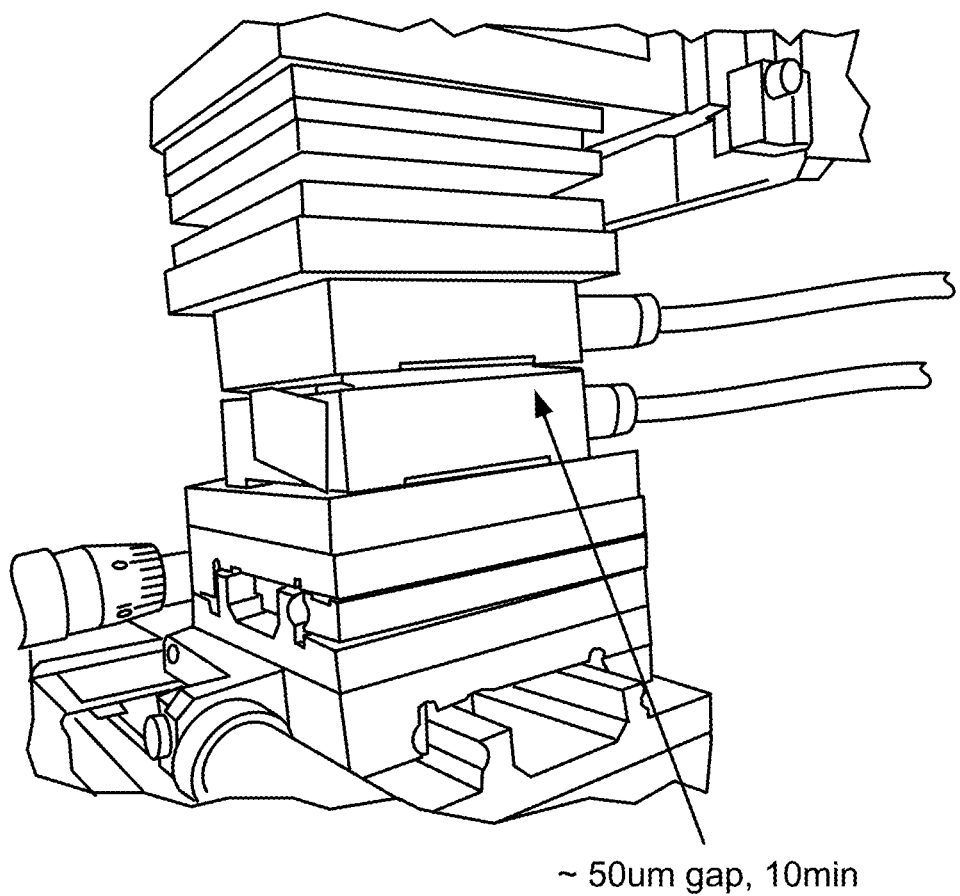
FIG. 57 illustrates an oligonucleotide synthesis device and a nanoreactor device mounted in a configuration having a 50 µm gap. In an exemplary embodiment, the devices are maintained in this configuration for 10 minutes.
Figure 58:
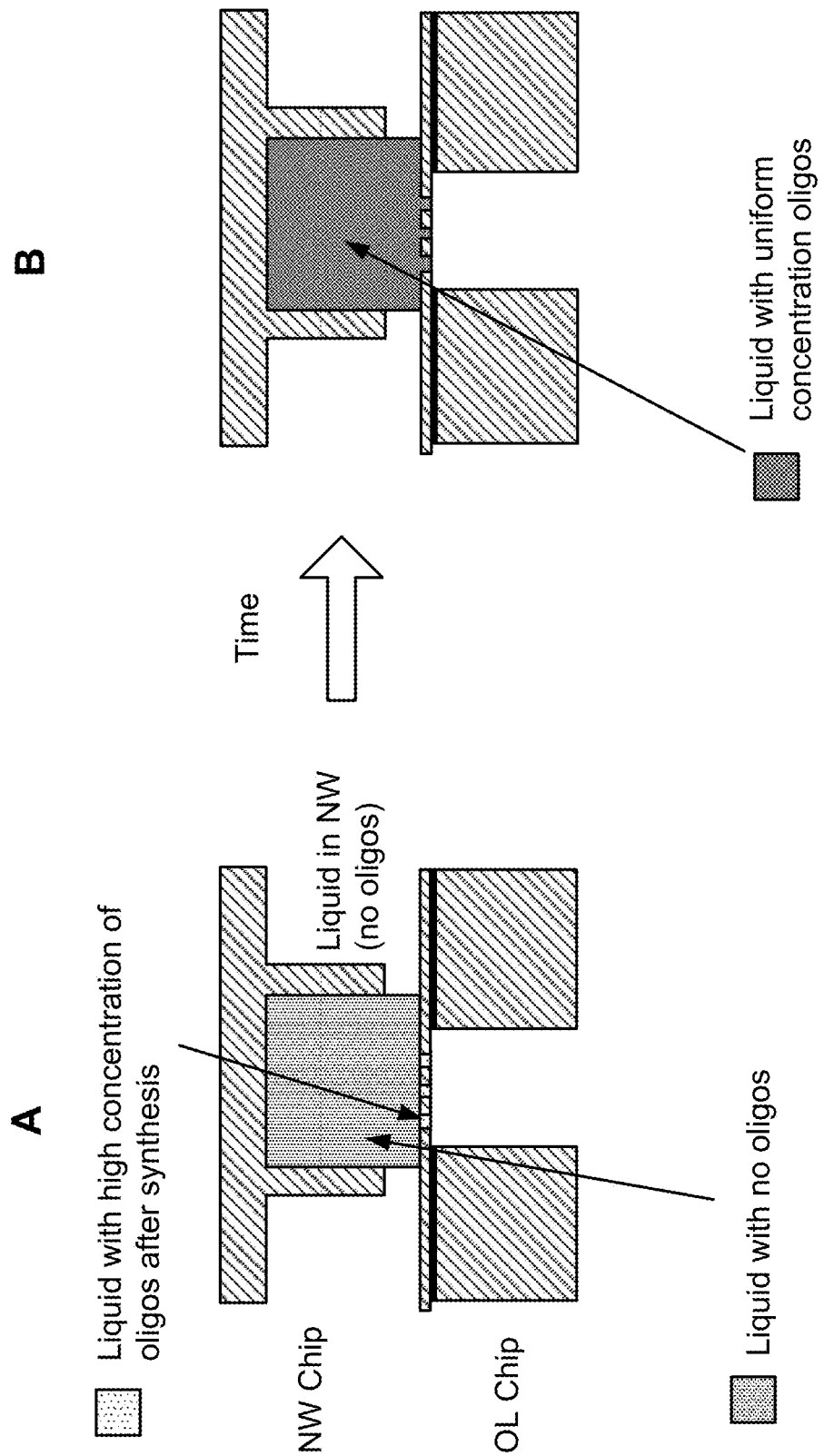
FIG. 58 parts A-B show the redistribution of oligos over time, without being bound by theory, by diffusion, from an oligonucleotide synthesis device to a nanoreactor device.

The nanoreactors were next filled with about 650 nL of PCA buffer forming a meniscus that slightly bulged out (FIG. 53). The nanoreactor device was mated with the oligonucleotide device to submerge the oligonucleotide synthesis channels ("revolver") with the PCA buffer at a rate of about 5 mm/sec. In other cases, the mantling velocity for mating the two devices may be varied as described herein, to achieve, among other things, more or less efficient liquid transfer between the devices giving rise to controlled aliquoting of desired volumes of liquid or to control evaporation. The oligonucleotide device and the nanoreactor were kept mated with a gap of about 50 μm between the two devices, for about 10 minutes, allowing the oligonucleotides to diffuse into the solution (FIG. 57). In some cases, the assembly or the oligonucleotide synthesis device alone can be vibrated or oscillated to facilitate faster diffusion. Diffusion times longer than 10 min, such as at least or at least about 11, 12, 13, 14, 15, 20, 25 min, or longer may also be used to facilitate higher yield. The nanoreactor device was released from the oligonucleotide device at a rate of about 5 mm/sec, capturing the released oligonucleotides in the individual nanoreactors. In other cases, the dismantling velocity for mating the two devices may be varied as described herein, to achieve, among other things, more or less efficient liquid transfer between the devices giving rise to controlled aliquoting of desired volumes of liquid. A tiny amount of liquid was observed to be left over on the oligonucleotide device.

Samples of about 300 nL were pipetted out from several individual nanoreactors in the nanoreactor device and diluted into a volume of 1 uL, establishing a 4.3× dilution. The diluted samples were individually run in a BioAnalyzer establishing the release of the oligonucleotides into the nanoreactors (FIG. 55).

Additional samples were taken as a positive control using a manual syringe. Tygon tubing was used to create a face seal with the oligonucleotide synthesis device. The syringe, filled with 500 ul of water, was used to flush down liquid through one entire cluster as well as parts of neighboring clusters from the handle side. The flushed liquid was collected in a 1.5 ml Eppendorf tube on the device side. The sample was dried down in vacuum and then re-suspended in 10 uL water. The sample was then similarly analyzed in a BioAnalyzer. When accounting for the dilution rates, a comparable concentration of oligonucleotides were released using the positive control method and the nanoreactor blot method.

Example 12: Injection Based Oligonucleotide Transfer from an Oligonucleotide Synthesis Device to a Nanoreactor 50-mer oligonucleotides are synthesized on a 3-D oligonucleotide synthesis device as described in Example 9. The oligonucleotides are released from the surface by treatment in an ammonia chamber at about 75 psi for about 14 hours. Alternatively, pressures from 20-120 psi can be used for 1-48 hours or longer for the release of the oligonucleotides. The temperature is room temperature. In some cases, the deprotection rate may be increased by increasing the temperature, for example to at least or at least about 25 C, 30 C, 35 C, 40 C, 45 C, 50 C, 55 C, 60 C, 65 C or higher. Gaseous methylamine may also be used for deprotection at room temperature or at an elevated temperature of at least or at least about 25 C, 30 C, 35 C, 40 C, 45 C, 50 C, 55 C, 60 C, 65 C or higher. The deprotection in methylamine typically proceeds faster than in gaseous ammonia.

Figure 56:
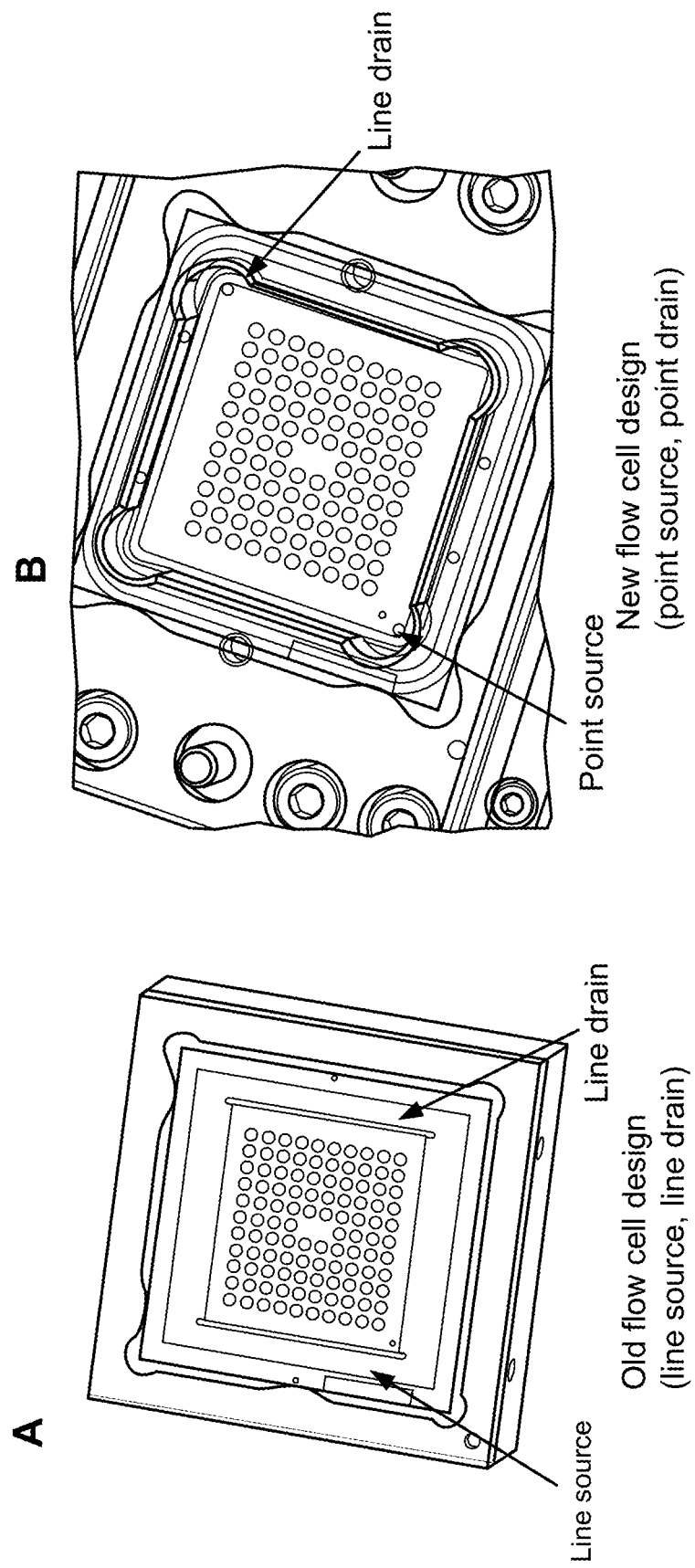
FIG. 56 parts A-B depict alternate flow cell designs.

The oligonucleotide synthesis device is assembled into a Hele Shaw flow cell with a single inlet and a single outlet. Flow is generated using a syringe that is connected to the flow cell via tygon tubing and is manually controlled (FIG. 57). FIG. 56 illustrates a schematic of the fluidics in the flow cell. The fluidic circuit is used to flow fluid from the handle side into the first channels (or vias) and the fluid is further drawn into the second channels, e.g. those forming a revolver pattern comprising oligonucleotide synthesis sites. The fluid is delivered from a single point inlet and collected from a single point outlet (FIG. 56 part B. In other cases, a line source and a line sink can be used to pass fluids (FIG. 56 part A). Without being bound by theory, point source/sink combinations are expected to form a uniform air front, which can be more efficient to push all of the liquid out from the Hele-Shaw flow cell. Upon clearing of liquid from the flow cell, liquid is contained only in the vias on the handle side and the second channels or oligonucleotide synthesis channels, e.g. in a revolver pattern on the device side. This volume is estimated to be 300 nL per cluster of vias (or first channels). Such containment of fluid can facilitate the formation of uniform sessile droplets on the device layer surface of the oligonucleotide synthesis device.

For this step, a suitable release buffer, such as a PCA compatible buffer, is selected to dissolve the released oligonucleotides into solution. Upon filling the vias and the second channels, the liquid is flushed out from the Heleshaw flow cell on the handle surface of the oligonucleotide synthesis chip using about 500-1000 Pa, leaving liquid only in the stagnant zone (handle and revolver) of the device, which is estimated to be 300 nL per assembly cluster (FIG. 56 part C). The single point outlet is blocked and pressurized air is flown on the handle layer surface at about 3000-5000 Pa to eject droplets onto the device layer surface (FIG. 56 part D). Sufficient release buffer is pushed through the flow cell to form sessile drops emerging from the second channels (or oligonucleotide synthesis channels) onto the device side surface of the oligonucleotide synthesis device. The sessile drop size can be about 300-400 nL, but can be varied to a suitable size according to the particular dimensions of the oligonucleotide synthesis clusters and/or the nanoreactors as well as according to the desired concentration of the oligonucleotides. For example, sessile drop sizes of about 500 nL can be formed. The sessile drop formation is optionally monitored with a microscope to make sure that the drop formation is complete across the oligonucleotide synthesis device. In some cases, the liquid forming the sessile drops may be prepared from a mixture of components so that a desired contact angle is achieved on the device layer. Accordingly, the solution may be supplemented with a component, such as a detergent, e.g. polysorbate 20 (Polyoxyethylene (20) sorbitan monolaurate, aka Tween-20).

Alternatively, a suitable amount of release buffer is deposited into the individual wells/first channels from the handle side and pushed through the oligonucleotide synthesis channel, for example by applying pressure from the handle side by forming a Hele-shaw flow cell on the handle side. A nanoreactor device is mantled against the device side of the oligonucleotide synthesis device at a suitable rate, e.g. about 1-10 mm/s and distance, e.g. about 50 µm. The mantling can be performed quickly after drop formation to avoid evaporation. Evaporation is also minimal once the two devices (nanoreactor and oligo synthesis reactor) are mantled.

Example 13: Gene Assembly in Nanoreactors Using PCA from Reaction Mixtures Transferred from the Device Side of an Oligonucleotide Synthesis A PCA reaction mixture was prepared as described in Table 7 using the SEQ ID NOs.: 7-66 from Table 8, to assemble the 3075 bp LacZ gene (SEQ ID NO.: 67; Table 8).

TABLE 7

| PCA | 1 (×100 ul) | final conc. |
|---|---|---|
| H2O | 62.00 | |
| 5 × Q5 buffer | 20.00 | 1× |
| 10 mM dNTP | 1.00 | 100 uM |
| BSA 20 mg/ml | 5.00 | 1 mg/ml |
| Oligo mix 50 nM each | 10.00 | 5 nM |
| Q5 pol 2 U/ul | 2.00 | 2 u/50 ul |

TABLE 8

| Sequence Name | Sequence |
|---|---|
| Oligo_1, SEQ ID NO.: 7 | 5'ATGACCATGATTACGGATTCACTGGCCGTCGTTTTACAACGTCGTGACTGGGAAAACCCTGG3' |
| Oligo_2, SEQ ID NO.: 8 | 5'GCCAGCTGGCGAAAGGGGGATGTGCTGCAAGGCGATTAAGTTGGGTAACGCCAGGGTTTTCCCAGTCACGAC3' |
| Oligo_3, SEQ ID NO.: 9 | 5'CCCCCTTTCGCCAGCTGGCGTAATAGCGAAGAGGCCCGCACCGATCGCCCTTCCCAACAGTTGCGCAGCC3' |
| Oligo_4, SEQ ID NO.: 10 | 5'CGGCACCGCTTCTGGTGCCGGAAACCAGGCAAAGCGCCATTCGCCATTCAGGCTGCGCAACTGTTGGGA3' |
| Oligo_5, SEQ ID NO.: 11 | 5'CACCAGAAGCGGTGCCGGAAAGCTGGCTGGAGTGCGATCTTCCTGAGGCCGATACTGTCGTCGTCCCCTC3' |
| Oligo_6, SEQ ID NO.: 12 | 5'GATAGGTCACGTTGGTGTAGATGGGCGCATCGTAACCGTGCATCTGCCAGTTTGAGGGGACGACGACAGTATCGG3' |
| Oligo_7, SEQ ID NO.: 13 | 5'CCCATCTACACCAACGTGACCTATCCCATTACGGTCAATCCGCCGTTTGTTCCCACGGAGAATCCGACGGGTTG3' |
| Oligo_8, SEQ ID NO.: 14 | 5'GTCTGGCCTTCCTGTAGCCAGCTTTCATCAACATTAAATGTGAGCGAGTAACAACCCGTCGGATTCTCCGTG3' |

TABLE 8-continued

| Sequence Name | Sequence |
|---|---|
| Oligo_9, SEQ ID NO.: 15 | 5'GCTGGCTACAGGAAGGCCAGACGCGAATTATTTTTGATGGCGTTAACTCGGCGTTTCATCTGTGGTGCAACGG3' |
| Oligo_10, SEQ ID NO.: 16 | 5'CAGGTCAAATTCAGACGGCAAACGACTGTCCTGGCCGTAACCGACCCAGCGCCCGTTGCACCACAGATGAAACG3' |
| Oligo_11, SEQ ID NO.: 17 | 5'CGTTTGCCGTCTGAATTTGACCTGAGCGCATTTTTACGCGCCGGAGAAAACCGCCTCGCGGTGATGGTGCTG3' |
| Oligo_12, SEQ ID NO.: 18 | 5'GCCGCTCATCCGCCACATATCCTGATCTTCCAGATAACTGCCGTCACTCCAGCGCAGCACCATCACCGCGAG3' |
| Oligo_13, SEQ ID NO.: 19 | 5'AGGATATGTGGCGGATGAGCGGCATTTTCCGTGACGTCTCGTTGCTGCATAAACCGACTACACAAATCAGCGATTTC3' |
| Oligo_14, SEQ ID NO.: 20 | 5'CTCCAGTACAGCGCGGCTGAAATCATCATTAAAGCGAGTGGCAACATGGAAATCGCTGATTTGTGTAGTCGGTTTATG3' |
| Oligo_15, SEQ ID NO.: 21 | 5'ATTTCAGCCGCGCTGTACTGGAGGCTGAAGTTCAGATGTGCGGCGAGTTGCGTGACTACCTACGGGTAACAGTTT3' |
| Oligo_16, SEQ ID NO.: 22 | 5'AAAGGCGCGGTGCCGCTGGCGACCTGCGTTTCACCCTGCCATAAAGAAACTGTTACCCGTAGGTAGTCACG3' |
| Oligo_17, SEQ ID NO.: 23 | 5'GCGGCACCGCGCCTTTCGGCGGTGAAATTATCGATGAGCGTGGTGGTTATGCCGATCGCGTCACACTACG3' |
| Oligo_18, SEQ ID NO.: 24 | 5'GATAGAGATTCGGGATTTCGGCGCTCCACAGTTTCGGGTTTTCGACGTTCAGACGTAGTGTGACGCGATCGGCA3' |
| Oligo_19, SEQ ID NO.: 25 | 5'GAGCGCCGAAATCCCGAATCTCTATCGTGCGGTGGTTGAACTGCACACCGCCGACGGCACGCTGATTGAAGCAG3' |
| Oligo_20, SEQ ID NO.: 26 | 5'CAGCAGCAGACCATTTTCAATCCGCACCTCGCGGAAACCGACATCGCAGGCTTCTGCTTCAATCAGCGTGCCG3' |
| Oligo_21, SEQ ID NO.: 27 | 5'CGGATTGAAAATGGTCTGCTGCTGCTGAACGGCAAGCCGTTGCTGATTCGAGGCGTTAACCGTCACGAGCATCA3' |
| Oligo_22, SEQ ID NO.: 28 | 5'GCAGGATATCCTGCACCATCGTCTGCTCATCCATGACCTGACCATGCAGAGGATGATGCTCGTGACGGTTAACGC3' |
| Oligo_23, SEQ ID NO.: 29 | 5'CAGACGATGGTGCAGGATATCCTGCTGATGAAGCAGAACAACTTTAACGCCGTGCGCTGTTCGCATTATCCGAAC3' |
| Oligo_24, SEQ ID NO.: 30 | 5'TCCACCACATACAGGCCGTAGCGGTCGCACAGCGTGTACCACAGCGGATGGTTCGGATAATGCGAACAGCGCAC3' |
| Oligo_25, SEQ ID NO.: 31 | 5'GCTACGGCCTGTATGTGGTGGATGAAGCCAATATTGAAACCCACGGCATGGTGCCAATGAATCGTCTGACCGATG3' |
| Oligo_26, SEQ ID NO.: 32 | 5'GCACCATTCGCGTTACGCGTTCGCTCATCGCCGGTAGCCAGCGCGGATCATCGGTCAGACGATTCATTGGCAC3' |
| Oligo_27, SEQ ID NO.: 33 | 5'CGCGTAACGCGAATGGTGCAGCGCGATCGTAATCACCCGAGTGTGATCATCTGGTCGCTGGGGAATGAATCAG3' |
| Oligo_28, SEQ ID NO.: 34 | 5'GGATCGACAGATTTGATCCAGCGATACAGCGCGTCGTGATTAGCGCCGTGGCCTGATTCATTCCCCAGCGACCAGATG3' |
| Oligo_29, SEQ ID NO.: 35 | 5'GTATCGCTGGATCAAATCTGTCGATCCTTCCCGCCCGGTGCAGTATGAAGGCGGCGGAGCCGACACCACGGC3' |
| Oligo_30, SEQ ID NO.: 36 | 5'CGGGAAGGGCTGGTCTTCATCCACGCGCGCGTACATCGGGCAAATAATATCGGTGGCCGTGGTGTCGGCTC3' |
| Oligo_31, SEQ ID NO.: 37 | 5'TGGATGAAGACCAGCCCTTCCCGGCTGTGCCGAAATGGTCCATCAAAAAATGGCTTTCGCTACCTGGAGAGAC3' |
| Oligo_32, SEQ ID NO.: 38 | 5'CCAAGACTGTTACCCATCGCGTGGGCGTATTCGCAAAGGATCAGCGGGCGCGTCTCTCCAGGTAGCGAAAGCC3' |
| Oligo_33, SEQ ID NO.: 39 | 5'CGCGATGGGTAACAGTCTTGGCGGTTTCGCTAAATACTGGCAGGCGTTTCGTCAGTATCCCCGTTTACAGGGC3' |
| Oligo_34, SEQ ID NO.: 40 | 5'GCCGTTTTCATCATATTTAATCAGCGACTGATCCACCCAGTCCCAGACGAAGCCGCCCTGTAAACGGGGATACTGACG3' |

TABLE 8-continued

| Sequence Name | Sequence |
|---|---|
| Oligo_35, SEQ ID NO.: 41 | 5'CAGTCGCTGATTAAATATGATGAAAACGGCAACCCGTGGTCGGCTTACGGCGGTGATTTTGGCGATACGCCGAACG3' |
| Oligo_36, SEQ ID NO.: 42 | 5'GCGGCGTGCGGTCGGCAAAGACCAGACCGTTCATACAGAACTGGCGATCGTTCGGCGTATCGCCAAA3' |
| Oligo_37, SEQ ID NO.: 43 | 5'CGACCGCACGCCGCATCCAGCGCTGACGGAAGCAAAACACCAGCAGCAGTTTTTCCAGTTCCGTTTATCCG3' |
| Oligo_38, SEQ ID NO.: 44 | 5'CTCGTTATCGCTATGACGGAACAGGTATTCGCTGGTCACTTCGATGGTTTGCCCGGATAAACGGAACTGGAAAAACTGC3' |
| Oligo_39, SEQ ID NO.: 45 | 5'AATACCTGTTCCGTCATAGCGATAACGAGCTCCTGCACTGGATGGTGGCGCTGGATGGTAAGCCGCTGGCAAGCG3' |
| Oligo_40, SEQ ID NO.: 46 | 5'GTTCAGGCAGTTCAATCAACTGTTTACCTTGTGGAGCGACATCCAGAGGCACTTCACCGCTTGCCAGCGGCTTACC3' |
| Oligo_41, SEQ ID NO.: 47 | 5'CAAGGTAAACAGTTGATTGAACTGCCTGAACTACCGCAGCCGGAGAGCGCCGGGCAACTCTGGCTCACAGTACGCGTA3' |
| Oligo_42, SEQ ID NO.: 48 | 5'GCGCTGATGTGCCCGGCTTCTGACCATGCGGTCGCGTTCGGTTGCACTACGCGTACTGTGAGCCAGAGTTG3' |
| Oligo_43, SEQ ID NO.: 49 | 5'CCGGGCACATCAGCGCCTGGCAGCAGTGGCGTCTGGCGGAAAACCTCAGTGTGACGCTCCCCGCCGC3' |
| Oligo_44, SEQ ID NO.: 50 | 5'CCAGCTCGATGCAAAAATCCATTTCGCTGGTGGTCAGATGCGGGATGGCGTGGGACGCGGCGGGGAGCGTC3' |
| Oligo_45, SEQ ID NO.: 51 | 5'CGAAATGGATTTTTGCATCGAGCTGGGTAATAAGCGTTGGCAATTTAACCGCCAGTCAGGCTTTCTTTCACAGATGTG3' |
| Oligo_46, SEQ ID NO.: 52 | 5'TGAACTGATCGCGCAGCGGCGTCAGCAGTTGTTTTTATCGCCAATCCACATCTGTGAAAGAAAGCCTGACTGG3' |
| Oligo_47, SEQ ID NO.: 53 | 5'GCCGCTGCGCGATCAGTTCACCCGTGCACCGCTGGATAACGACATTGGCGTAAGTGAAGCGACCCGCATTGAC3' |
| Oligo_48, SEQ ID NO.: 54 | 5'GGCCTGGTAATGGCCCGCCGCCTTCCAGCGTTCGACCCAGGCGTTAGGGTCAATGCGGGTCGCTTCACTTA3' |
| Oligo_49, SEQ ID NO.: 55 | 5'CGGGCCATTACCAGGCCGAAGCAGCGTTGTTGCAGTGCACGGCAGATACACTTGCTGATGCGGTGCTGAT3' |
| Oligo_50, SEQ ID NO.: 56 | 5'TCCGGCTGATAAATAAGGTTTTCCCCTGATGCTGCCACGCGTGAGCGGTCGTAATCAGCACCGCATCAGCAAGTG3' |
| Oligo_51, SEQ ID NO.: 57 | 5'GGGGAAAACCTTATTTATCAGCCGGAAAACCTACCGGATTGATGGTAGTGGTCAAATGGCGATTACCGTTGATGTTGA3' |
| Oligo_52, SEQ ID NO.: 58 | 5'GGCAGTTCAGGCCAATCCGCGCCGGATGCGGTGTATCGCTCGCCACTTCAACATCAACGGTAATCGCCATTTGAC3' |
| Oligo_53, SEQ ID NO.: 59 | 5'GCGGATTGGCCTGAACTGCCAGCTGGCGCAGGTAGCAGAGCGGGTAAACTGGCTCGGATTAGGGCCGCAAG3' |
| Oligo_54, SEQ ID NO.: 60 | 5'GGCAGATCCCAGCGGTCAAAACAGGCGGCAGTAAGGCGGTCGGGATAGTTTTCTTGCGGCCCTAATCCGAGC3' |
| Oligo_55, SEQ ID NO.: 61 | 5'GTTTTGACCGCTGGGATCTGCCATTGTCAGACATGTATACCCCGTACGTCTTCCCGAGCGAAAACGGTCTGC3' |
| Oligo_56, SEQ ID NO.: 62 | 5'GTCGCCGCGCCACTGGTGTGGGCCATAATTCAATTCGCGCGTCCCGCAGCGCAGACCGTTTTCGCTCGG3' |
| Oligo_57, SEQ ID NO.: 63 | 5'ACCAGTGGCGCGGCGACTTCCAGTTCAACATCAGCCGCTACAGTCAACAGCAACTGATGGAAACCAGCCATC3' |
| Oligo_58, SEQ ID NO.: 64 | 5'GAAACCGTCGATATTCAGCCATGTGCCTTCTTCCGCGTGCAGCAGATGGCGATGGCTGGTTTCCATCAGTTGCTG3' |
| Oligo_59, SEQ ID NO.: 65 | 5'CATGGCTGAATATCGACGGTTTCCATATGGGGATTGGTGGCGACGACTCCTGGAGCCCGTCAGTATCGGCG3' |
| Oligo_60, SEQ ID NO.: 66 | 5'TTATTTTTGACACCAGACCAACTGGTAATGGTAGCGACCGGCGCTCAGCTGGAATTCCGCCGATACTGACGGGC3' |

TABLE 8-continued

| Sequence Name | Sequence |
| --- | --- |
| LacZ gene - SEQ ID NO: 67 | 5'ATGACCATGATTACGGATTCACTGGCCGTCGTTTTACAA<br>CGTCGTGACTGGGAAAACCCTGGCGTTACCCAACTTAATC<br>GCCTTGCAGCACATCCCCCTTTCGCCAGCTGGCGTAATAG<br>CGAAGAGGCCCGCACCGATCGCCCTTCCCAACAGTTGCG<br>CAGCCTGAATGGCGAATGGCGCTTTGCCTGGTTTCCGGCA<br>CCAGAAGCGGTGCCGGAAAGCTGGCTGGAGTGCGATCTT<br>CCTGAGGCCGATACTGTCGTCGTCCCCTCAAACTGGCAGA<br>TGCACGGTTACGATGCGCCCATCTACACCAACGTGACCTA<br>TCCCATTACGGTCAATCCGCCGTTTGTTCCCACGGAGAAT<br>CCGACGGGTTGTTACTCGCTCACATTTAATGTTGATGAAA<br>GCTGGCTACAGGAAGGCCAGACGCGAATTATTTTTGATG<br>GCGTTAACTCGGCGTTTCATCTGTGGTGCAACGGGCGCTG<br>GGTCGGTTACGGCCAGGACAGTCGTTTGCCGTCTGAATTT<br>GACCTGAGCGCATTTTTACGCGCCGGAGAAAACCGCCTC<br>GCGGTGATGGTGCTGCGCTGGAGTGACGGCAGTTATCTG<br>GAAGATCAGGATATGTGGCGGATGAGCGGCATTTTCCGT<br>GACGTCTCGTTGCTGCATAAACCGACTACACAAATCAGC<br>GATTTCCATGTTGCCACTCGCTTTAATGATGATTTCAGCC<br>GCGCTGTACTGGAGGCTGAAGTTCAGATGTGCGGCGAGT<br>TGCGTGACTACCTACGGGTAACAGTTTCTTTATGGCAGGG<br>TGAAACGCAGGTCGCCAGCGGCACCGCGCCTTTCGGCGG<br>TGAAATTATCGATGAGCGTGGTGGTTATGCCGATCGCGTC<br>ACACTACGTCTGAACGTCGAAAACCCGAAACTGTGGAGC<br>GCCGAAATCCCGAATCTCTATCGTGCGGTGGTTGAACTGC<br>ACACCGCCGACGGCACGCTGATTGAAGCAGAAGCCTGCG<br>ATGTCGGTTTCCGCGAGGTGCGGATTGAAAATGGTCTGCT<br>GCTGCTGAACGGCAAGCCGTTGCTGATTCGAGGCGTTAA<br>CCGTCACGAGCATCATCCTCTGCATGGTCAGGTCATGGAT<br>GAGCAGACGATGGTGCAGGATATCCTGCTGATGAAGCAG<br>AACAACTTTAACGCCGTGCGCTGTTCGCATTATCCGAACC<br>ATCCGCTGTGGTACACGCTGTGCGACCGCTACGGCCTGTA<br>TGTGGTGGATGAAGCCAATATTGAAACCCACGGCATGGT<br>GCCAATGAATCGTCTGACCGATGATCCGCGCTGGCTACCG<br>GCGATGAGCGAACGCGTAACGCGAATGGTGCAGCGCGAT<br>CGTAATCACCCGAGTGTGATCATCTGGTCGCTGGGGAATG<br>AATCAGGCCACGGCGCTAATCACGACGCGCTGTATCGCT<br>GGATCAAATCTGTCGATCCTTCCCGCCCGGTGCAGTATGA<br>AGGCGGCGGAGCCGACACCACGGCCACCGATATTATTTG<br>CCCGATGTACGCGCGCGTGGATGAAGACCAGCCCTTCCC<br>GGCTGTGCCGAAATGGTCCATCAAAAAATGGCTTTCGCTA<br>CCTGGAGAGACGCGCCCGCTGATCCTTTGCGAATACGCCC<br>ACGCGATGGGTAACAGTCTTGGCGGTTTCGCTAAATACTG<br>GCAGGCGTTTCGTCAGTATCCCCGTTTACAGGGCGGCTTC<br>GTCTGGGACTGGGTGGATCAGTCGCTGATTAAATATGATG<br>AAAACGGCAACCCGTGGTCGGCTTACGGCGGTGATTTTG<br>GCGATACGCCGAACGATCGCCAGTTCTGTATGAACGGTCT<br>GGTCTTTGCCGACCGCACGCCGCATCCAGCGCTGACGGA<br>AGCAAAACACCAGCAGCAGTTTTTCCAGTTCCGTTTATCC<br>GGGCAAACCATCGAAGTGACCAGCGAATACCTGTTCCGT<br>CATAGCGATAACGAGCTCCTGCACTGGATGGTGGCGCTG<br>GATGGTAAGCCGCTGGCAAGCGGTGAAGTGCCTCTGGAT<br>GTCGCTCCACAAGGTAAACAGTTGATTGAACTGCCTGAA<br>CTACCGCAGCCGGAGAGCGCCGGGCAACTCTGGCTCACA<br>GTACGCGTAGTGCAACCGAACGCGACCGCATGGTCAGAA<br>GCCGGGCACATCAGCGCCTGGCAGCAGTGGCGTCTGGCG<br>GAAAACCTCAGTGTGACGCTCCCCGCCGCGTCCCACGCC<br>ATCCCGCATCTGACCACCAGCGAAATGGATTTTTGCATCG<br>AGCTGGGTAATAAGCGTTGGCAATTTAACCGCCAGTCAG<br>GCTTTCTTTCACAGATGTGGATTGGCGATAAAAAACAACT<br>GCTGACGCCGCTGCGCGATCAGTTCACCCGTGCACCGCTG<br>GATAACGACATTGGCGTAAGTGAAGCGACCCGCATTGAC<br>CCTAACGCCTGGGTCGAACGCTGGAAGGCGCGGGCCAT<br>TACCAGGCCGAAGCAGCGTTGTTGCAGTGCACGGCAGAT<br>ACACTTGCTGATGCGGTGCTGATTACGACCGCTCACGCGT<br>GGCAGCATCAGGGGAAAACCTTATTTATCAGCCGGAAAA<br>CCTACCGGATTGATGGTAGTGGTCAAATGGCGATTACCGT<br>TGATGTTGAAGTGGCGAGCGATACACCGCATCCGGCGCG<br>GATTGGCCTGAACTGCCAGCTGGCGCAGGTAGCAGAGCG<br>GGTAAACTGGCTCGGATTAGGGCCGCAAGAAAACTATCC<br>CGACCGCCTTACTGCCGCCTGTTTTGACCGCTGGGATCTG<br>CCATTGTCAGACATGTATACCCCGTACGTCTTCCCGAGCG<br>AAAACGGTCTGCGCTGCGGGACGCGCGAATTGAATTATG<br>GCCCACACCAGTGGCGCGGCGACTTCCAGTTCAACATCA<br>GCCGCTACAGTCAACAGCAACTGATGGAAACCAGCCATC<br>GCCATCTGCTGCACGCGGAAGAAGGCACATGGCTGAATA<br>TCGACGGTTTCCATATGGGGATTGGTGGCGACGACTCCTG |

TABLE 8-continued

| Sequence Name | Sequence |
|---|---|
| | GAGCCCGTCAGTATCGGCGGAATTCCAGCTGAGCGCCGG<br>TCGCTACCATTACCAGTTGGTCTGGTGTCAAAAATAA3' |

Figure 59:
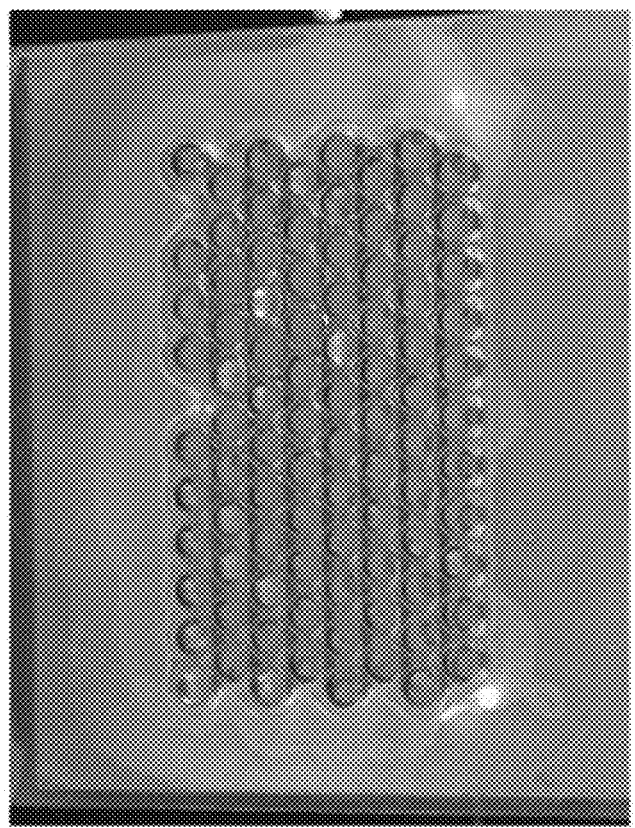
FIG. 59 shows views of a nanoreactor well array used for gene assembly before and after a PCA reaction.
Figure 59:
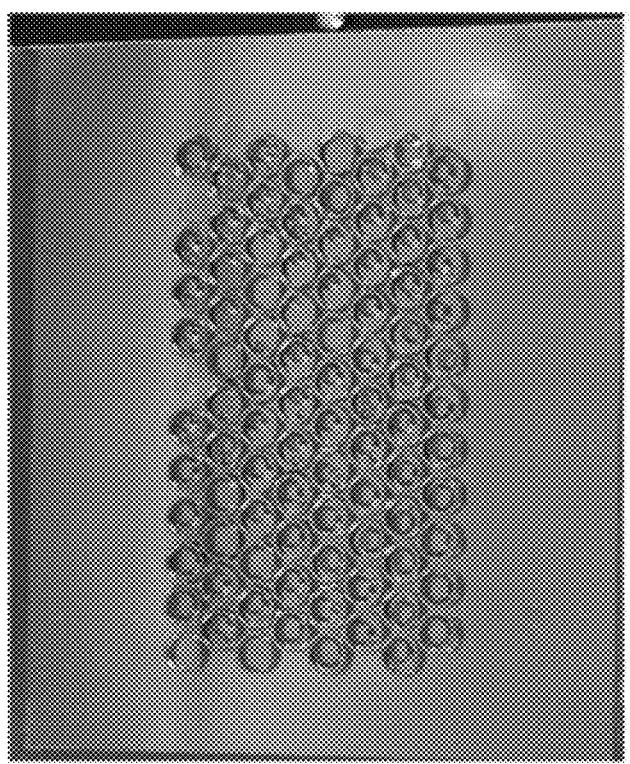

Drops of about 400 nL were dispensed using a Mantis dispenser (Formulatrix, MA) on top of the revolvers (oligonucleotide synthesis channels) on the device side of an oligonucleotide synthesis device. A nanoreactor chip was manually mated with the oligonucleotide device to pick up the droplets having the PCA reaction mixture. The droplets were picked up into the individual nanoreactors in the nanoreactor chip by releasing the nanoreactor from the oligonucleotide synthesis device immediately after pick-up (FIG. 59).

The nanoreactors were sealed with a Heat Sealing Film/Tape cover (Eppendorf, eshop.eppendorfna.com/products/Eppendorf Heat Sealing PCR Film and Foil) and placed in a suitably configured thermocycler that was constructed using a thermocycler kit (OpenPCR).

Figure 60:
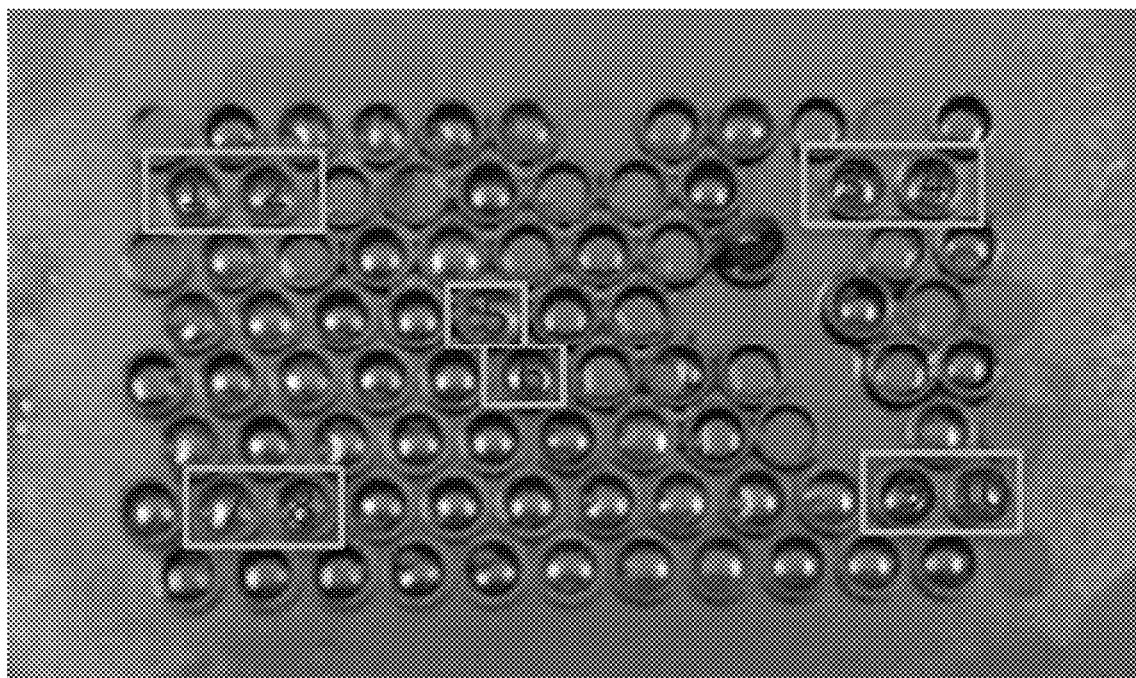
FIG. 60 parts A-C depict the results of the assembly of a gene in various wells of a nanoreactor device.
Figure 60:
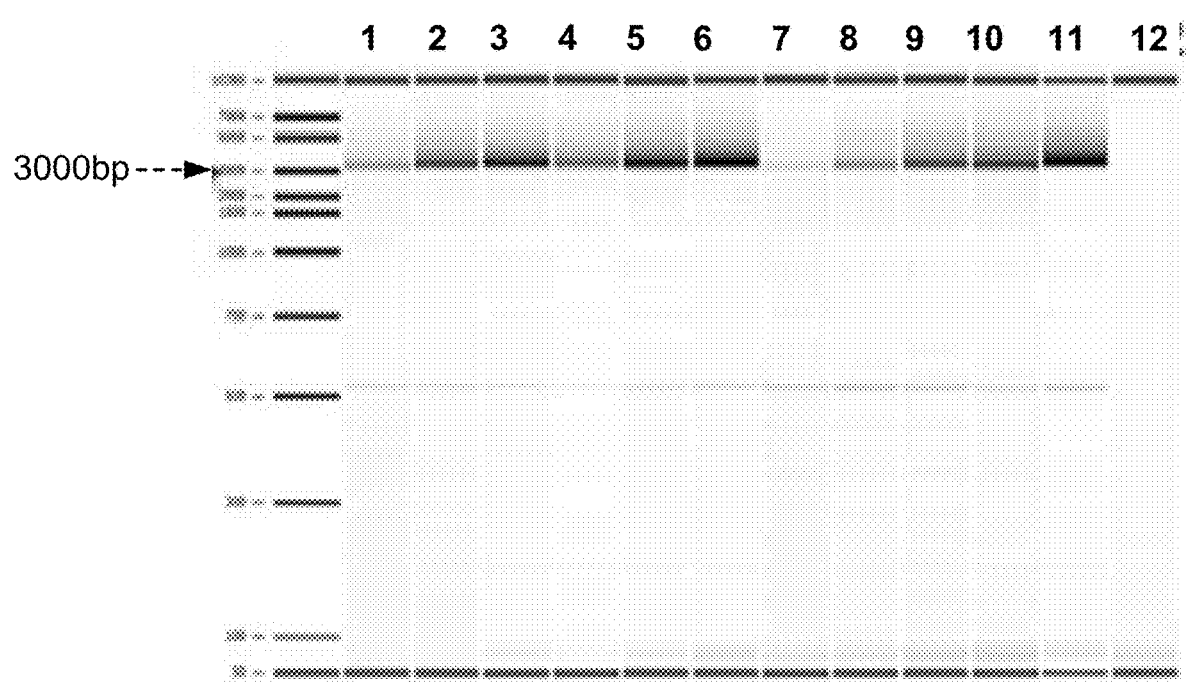
Figure 60:
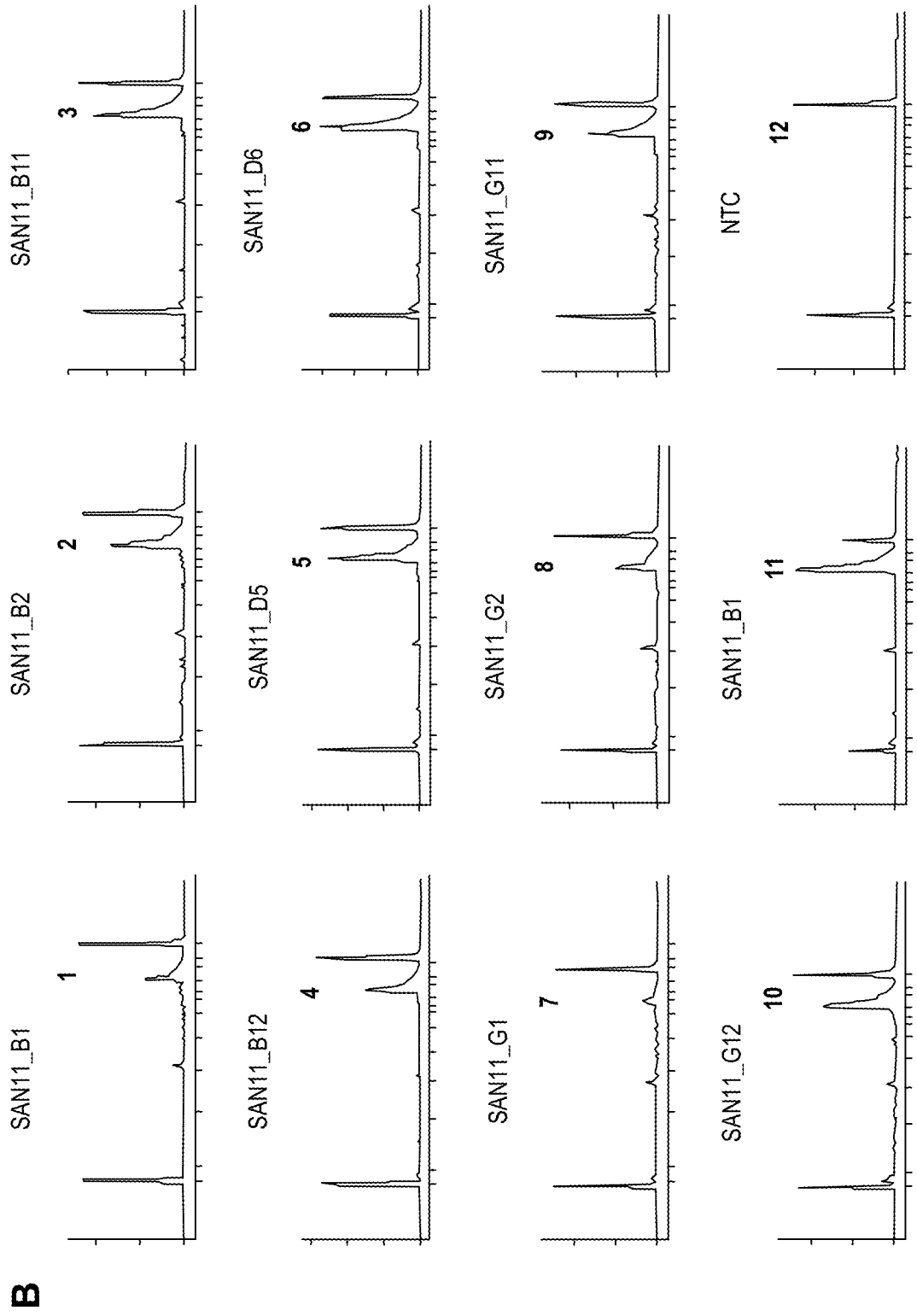

The following temperature protocol was used on the thermocycler:

1 cycle: 98 C, 45 seconds
40 cycles: 98 C, 15 seconds; 63 C, 45 seconds; 72 C, 60 seconds;
1 cycle: 72 C, 5 minutes
1 cycle: 4 C, hold An aliquot of 0.50 ul was collected from individual wells 1-10 as shown in FIG. 60 and the aliquots were amplified in plastic tubes, in a PCR reaction mixture (Table 9) and according to the following thermocycler program, using a forward (F-primer; 5'ATGACCATGATTACGGAT-TCACTGGCC3; SEQ ID NO: 68) and a reverse (R-primer; 5'TTATTTTTGACACCAGACCAACTGGTAATGG3; SEQ ID NO: 69) primer:

Thermocycler:
1 cycle: 98 C, 30 seconds
30 cycles: 98 C, 7 seconds; 63 C, 30 seconds; 72 C, 90 seconds
1 cycle: 72 C, 5 minutes
1 cycle: 4 C, hold

TABLE 9

| PCR | 1 (x25 ul) | final conc. |
|---|---|---|
| H2O | 17.50 | |
| 5x Q5 buffer | 5.00 | 1x |
| 10 mM dNTP | 0.50 | 200 uM |
| F-primer 20 uM | 0.63 | 0.5 uM |
| R-primer 20 uM | 0.63 | 0.5 uM |
| BSA 20 mg/ml | 0.00 | |
| Q5 pol 2 U/ul | 0.25 | 1u/50 ul |
| template (PCA assembly) | 0.50 | 1 ul/50 ul rxn |

The resulting amplification products were run on a Bio-Analyzer instrument (FIG. 60 part B, panels 1-10) as well as on a gel (FIG. 60 part C), showing a product that is slightly larger than 3000 bp. An 11th PCR reaction was run using a PCA reaction performed in a plastic tube as a positive control (FIG. 60 part B, panel 11 and FIG. 60 part C). A 12th PCR reaction was run without the PCA template as a negative control showing no product (FIG. 60 part B, panel 12 and FIG. 60 part C).

Example 14: Error correction of assembled nucleic acids

TABLE 10

| Nucleic Acid | Sequence |
|---|---|
| Assembled Gene, SEQ ID NO.: 70 | 5'ATGACCATGATTACGGATTCACTGGCCGTCGTTTTACAACGTCGT<br>GACTGGGAAAACCCTGGCGTTACCCAACTTAATCGCCTTGCAGCAC<br>ATCCCCCTTTCGCCAGCTGGCGTAATAGCGAAGAGGCCCGCACCG<br>ATCGCCCTTCCCAACAGTTGCGCAGCCTGAATGGCGAATGGCGCTT<br>TGCCTGGTTTCCGGCACCAGAAGCGGTGCCGGAAAGCTGGCTGGA<br>GTGCGATCTTCCTGAGGCCGATACTGTCGTCGTCCCCTCAAACTGG<br>CAGATGCACGGTTACGATGCGCCCATCTACACCAACGTGACCTATC<br>CCATTACGGTCAATCCGCCGTTTGTTCCCACGGAGAATCCGACGGG<br>TTGTTACTCGCTCACATTTAATGTTGATGAAAGCTGGCTACAGGAA<br>GGCCAGACGCGAATTATTTTTGATGGCGTTAACTCGGCGTTTCATC<br>TGTGGTGCAACGGGCGCTGGGTCGGTTACGGCCAGGACAGTCGTTT<br>GCCGTCTGAATTTGACCTGAGCGCATTTTTACGCGCCGGAGAAAAC<br>CGCCTCGCGGTGATGGTGCTGCGCTGGAGTGACGGCAGTTATCTGG<br>AAGATCAGGATATGTGGCGGATGAGCGGCATTTTCCGTGACGTCTC<br>GTTGCTGCATAAACCGACTACACAAATCAGCGATTTCCATGTTGCC<br>ACTCGCTTTAATGATGATTTCAGCCGCGCTGTACTGGAGGCTGAAG<br>TTCAGATGTGCGGCGAGTTGCGTGACTACCTACGGGTAACAGTTTC<br>TTTATGGCAGGGTGAAACGCAGGTCGCCAGCGGCACCGCGCCTTTC<br>GGCGGTGAAATTATCGATGAGCGTGGTGGTTATGCCGATCGCGTCA<br>CACTACGTCTGAACGTCGAAAACCCGAAACTGTGGAGCGCCGAAA<br>TCCCGAATCTCTATC3' |
| Assembly Oligonucleotide 1, SEQ ID NO.: 71 | 5'ATGACCATGATTACGGATTCACTGGCCGTCGTTTTACAACGTCGT<br>GACTGGGAAAACCCTGGCGTTACCCAACTTAATCGCCTTGCAGCAC<br>ATCCCCCTTTCGCCAGCTGGCGTAATAGCGAAGAGGCCCGCACCG<br>ATCGCCCTTCCCAACAGTTGCGCAGCC 3' |

TABLE 10-continued

| Nucleic Acid | Sequence |
|---|---|
| Assembly Oligonucleotide 2, SEQ ID NO.: 72 | 5'GATAGGTCACGTTGGTGTAGATGGGCGCATCGTAACCGTGCATCT GCCAGTTTGAGGGGACGACGACAGTATCGGCCTCAGGAAGATCGC ACTCCAGCCAGCTTTCCGGCACCGCTTCTGGTGCCGGAAACCAGGC AAAGCGCCATTCGCCATTCAGGCTGCGCAACTGTTGGGA3' |
| Assembly Oligonucleotide 3, SEQ ID NO.: 73 | 5'CCCATCTACACCAACGTGACCTATCCCATTACGGTCAATCCGCCG TTTGTTCCCACGGAGAATCCGACGGGTTGTTACTCGCTCACATTTA ATGTTGATGAAAGCTGGCTACAGGAAGGCCAGACGCGAATTATTT TTGATGGCGTTAACTCGGCGTTTCATCTGTGGTGCAACGG3' |
| Assembly Oligonucleotide 4, SEQ ID NO.: 74 | 5' GCCGCTCATCCGCCACATATCCTGATCTTCCAGATAACTGCCGTCA CTCCAGCGCAGCACCATCACCGCGAGGCGGTTTTCTCCGGCGCGTA AAAATGCGCTCAGGTCAAATTCAGACGGCAAACGACTGTCCTGGC CGTAACCGACCCAGCGCCCGTTGCACCACAGATGAAACG 3' |
| Assembly Oligonucleotide 5, SEQ ID NO.: 75 | 5'AGGATATGTGGCGGATGAGCGGCATTTTCCGTGACGTCTCGTTGC TGCATAAACCGACTACACAAATCAGCGATTTCCATGTTGCCACTCG CTTTAATGATGATTTCAGCCGCGCTGTACTGGAGGCTGAAGTTCAG ATGTGCGGCGAGTTGCGTGACTACCTACGGGTAACAGTTT 3' |
| Assembly Oligonucleotide 6, SEQ ID NO.: 76 | 5'GATAGAGATTCGGGATTTCGGCGCTCCACAGTTTCGGGTTTTCGA CGTTCAGACGTAGTGTGACGCGATCGGCATAACCACCACGCTCATC GATAATTTCACCGCCGAAAGGCGCGGTGCCGCTGGCGACCTGCGTT TCACCCTGCCATAAAGAAACTGTTACCCGTAGGTAGTCACG 3' |

An gene of about 1 kb (SEQ ID NO.: 70; Table 10) was assembled using 6 purchased oligonucleotides (5 nM each during PCA) (Ultramer; SEQ ID NO.: 71-76; Table 10) and assembled in a PCA reaction using a 1×NEB Q5 buffer with 0.02 U/uL Q5 hot-start high-fidelity polymerase and 100 uM dNTP as follows:

1 cycle: 98 C, 30 sec
15 cycles: 98 C, 7 sec; 62 C 30 sec; 72 C, 30 sec
1 cycle: 72 C, 5 min Ultramer oligonucleotides are expected to have error rates of at least 1 in 500 nucleotides, more likely at least 1 in 200 nucleotides or more.

Figure 52:
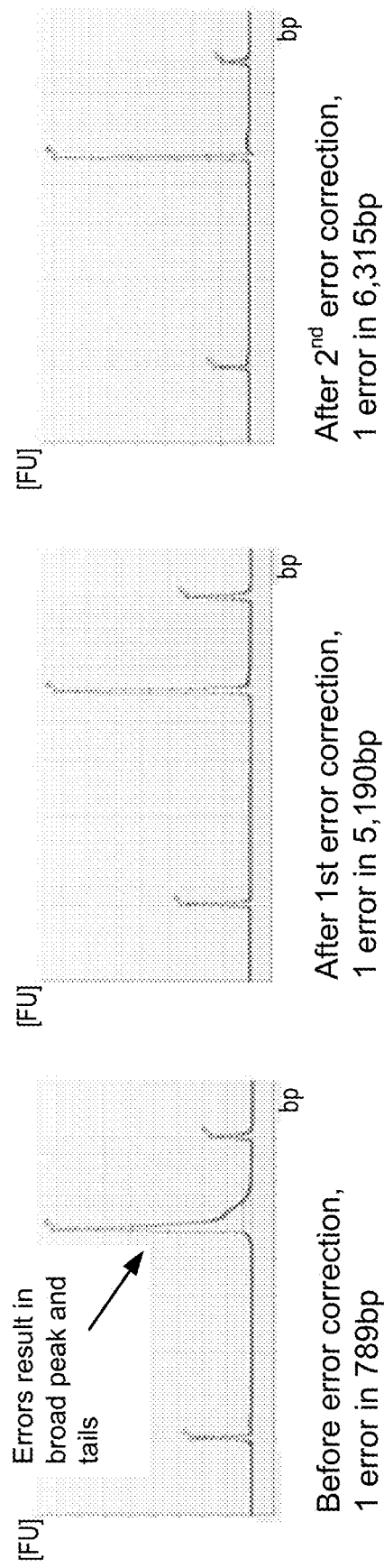
FIG. 52 represents correction results through the application of two rounds of error correction using CorrectASE.

The assembled gene was amplified in a PCR reaction using a forward primer (5' ATGACCATGATTACGGAT-TCACTGGCC3' SEQ ID NO.: 77) and a reverse primer (5'GATAGAGATTCGGGATTTCGGCGCTCC
3' SEQ ID NO.: 78), using 1×NEB Q5 buffer with 0.02 U/uL Q5 hot-start high-fidelity polymerase, 200 uM dNTP, and 0.5 uM primers as follows:

1 cycle: 98 C, 30 sec
30 cycles: 98 C, 7 sec; 65 C 30 sec; 72 C, 45 sec
1 cycle: 72 C, 5 min The amplified assembled gene was analyzed in a Bio-Analyzer (FIG. 52 part A) and cloned. Mini-preps from ~24 colonies were Sanger sequenced. The BioAnalyzer analysis provided a broad peak and a tail for the uncorrected gene, indicated a high error rate. The sequencing indicated an error rate of 1/789 (data not shown). Two rounds of error correction were followed using CorrectASE (Life Technologies, www.lifetechnologies.com/order/catalog/product/A14972) according to the manufacturer's instructions. The resulting gene samples were similarly analyzed in the BioAnalyzer after round one (FIG. 60 part B) and round two (FIG. 60 part C) and cloned. 24 colonies were picked for sequencing. The sequencing results indicated an error rate of 1/5190 bp and 1/6315 bp after the first and second rounds of error correction, respectively.

Example 15: Generation of a Large Quantity of Primer-Free Single-Stranded Oligonucleotides Reagents.

All enzymes and buffers except phi29 DNA polymerase were purchased from NEB unless stated otherwise. Phi29 DNA polymerase was purchased from Enzymatics.

Generation of Oligonucleotides.

A padlock oligonucleotide (OS_1518) having a reverse complement sequence to a desired oligonucleotide was synthesized by IDT (Table 1). Additional padlock oligonucleotides OS_1515, OS_1516, OS_1517, OS_1519 were also synthesized to work with adaptor/auxiliary oligonucleotide combinations that work with different restriction enzyme sets. The padlock oligonucleotide was phosphorylated by mixing 5 padlock (200 nM) with 5 μL T4 PNK buffer, 0.5 μL ATP (100 mM), 2 μL T4 PNK (10 U/μL), 1 μL BSA (100 μg/μL), 2 μL DTT (100 mM), and 32.5 μL water, and incubating the mixture for 60 min at 37° C., followed by incubation for 20 min at 65° C. An adaptor oligonucleotide having a complement sequence to the padlock oligonucleotide was synthesized by IDT (Table 11). An auxiliary oligonucleotide having a complementary sequence to the adaptor oligonucleotide was synthesized by IDT and biotinylated.

TABLE 11

| Oligonucleotide sequences. | | |
|---|---|---|
| Padlock, | SEQ ID NO.: 79 | 5'<u>ATCTTTGAGTCTTCTGCTTGGTCAGACGAGTGCATGTGCGTGACA</u> AATTGGCGCGAGGAGCTCGTGTCATTCACAACTGCTCTTAGGCTAC TCAGGCATGGTGAGATGCTACGGTGG<u>TTGATGGATACCTAGAT</u>3' |
| Adaptor, | SEQ ID NO.: 80 | 5'CAGAAGACTCAAAGATATCTAGGTATCCATCAAC3' |

TABLE 11-continued

Oligonucleotide sequences.

Auxiliary, SEQ /5Biosg/GTTGATGGATACCTAGATATCTTTGAGTCTTCTG3'
ID NO.: 81

Underline = complementarity to adaptor oligonucleotide
Squiggly underline = restriction site
/5Biosg/ = biotinylation site Hybridization and Ligation.

48 µL of the padlock phosphorylation reaction mixture was combined with 1.5 µL adaptor oligonucleotide (2 µM) and 0.5 µL T4 ligase. The reaction was incubated for 60 min at 37° C., followed by 20 min at 65° C. A 5 µL sample of the reaction was mixed with 5 µL 2× loading buffer and analyzed on a 15% TBE-urea gel (180 V, 75 min).

An optional exonuclease treatment was performed as follows. A 10 µL ligation product was treated with 0.15 µL ExoI and ExoIII (NEB or Enzymatics) at 37° C. for 60 min, followed by 95° C. for 20 min. Following incubation, 0.3 µL adaptor oligonucleotide (2 µM) was added to each 10 µL solution, heated to 95° C. for 5 min, and slowly cooled. A 5 µL sample of the reaction was mixed with 5 µL 2× loading buffer and analyzed on a 15% TBE-urea gel (180 V, 75 min).

Rolling Circle Amplification.

A 10 µL 2×RCA master mix was prepared by combining 0.6 µL phi29 DNA polymerase (low concentration, Enzymatics), 0.5 µL 10 mM dNTP, 1 µL T4 PNK buffer, 0.2 µL 100×BSA, 0.5 µL 100 mM DTT, and 7.2 µL water on ice. In some instances, PCR additives, such as betaine, for example 5M betaine, may be used to reduce amplification bias. The 10 µL of RCA mastermix was combined with 10 µL ligation product (with or without exonuclease treatment) and incubated at 40° C. for 90 min or 4 hr. The reaction was then incubated at 70° C. for 10 min to de-activate the phi29 DNA polymerase. A 0.1 µL sample of the reaction was mixed with 4.9 µL water and 5 µL 2× loading buffer, and the mixture analyzed on a 15% TBE-urea gel (180 V, 75 min).

Restriction Endonuclease Digestion.

A 2 µL sample of the RCA product was mixed with 2 µL 10× CutSmart, 2 µL biotinylated auxiliary oligonucleotide (20 µM), and 12 µL water. The mixture was heated to 98° C. and slowly cooled to room temperature. 1 µL each of BciVI and MlyI were added to the mixture, followed by an incubation for 1 hr at 37° C., then 20 min at 80° C. A 1 µL sample of the reaction was mixed with 4 µL water and 5 µL 2× loading buffer, and the mixture analyzed on a 15% TBE-urea gel (180 V, 75 min).

An optional purification step was performed as follows. 1 µL of the restriction endonuclease digestion sample is retained as a pre-purification sample. NanoLink beads (Solulink) are resuspended by vortexing vigorously. A 5 µL aliquot of beads were added to a 1.5 mL tube. Nucleic Acid Binding and Wash Buffer or NABWB (50 mM Tris-HCl, 150 mM NaCl, 0.05% Tween 20, pH 8.0) was added to the tube to a final volume of 250 µL, and the tube was mixed to resuspend. The tube was placed on a magnetic stand for 2 min, followed by removal of the supernatant. The tube was removed from the magnet and the beads resuspended with 180 µL NABWB. 180 µL of the resuspended beads were added to 20 µL of the restriction endonuclease digestion reaction, and the mixture vortexed. The mixture was incubated for 60 min at 40° C. on a platform shaker, so that the beads do not settle. The tube was then placed on a magnet for 2 min and the supernatant comprising purified product was transferred to a new tube. A 10 µL sample of the purified product was mixed with 5 µL 2× loading buffer and analyzed on a 15% TBE-urea gel (180 V, 75 min). The concentration of the purified RCA product was measured using Qubit ssDNA kit.

Alternative Purification.

In some workflows, the digested oligonucleotides can be purified using (high-performance liquid chromatography) HPLC.

Figure 63:
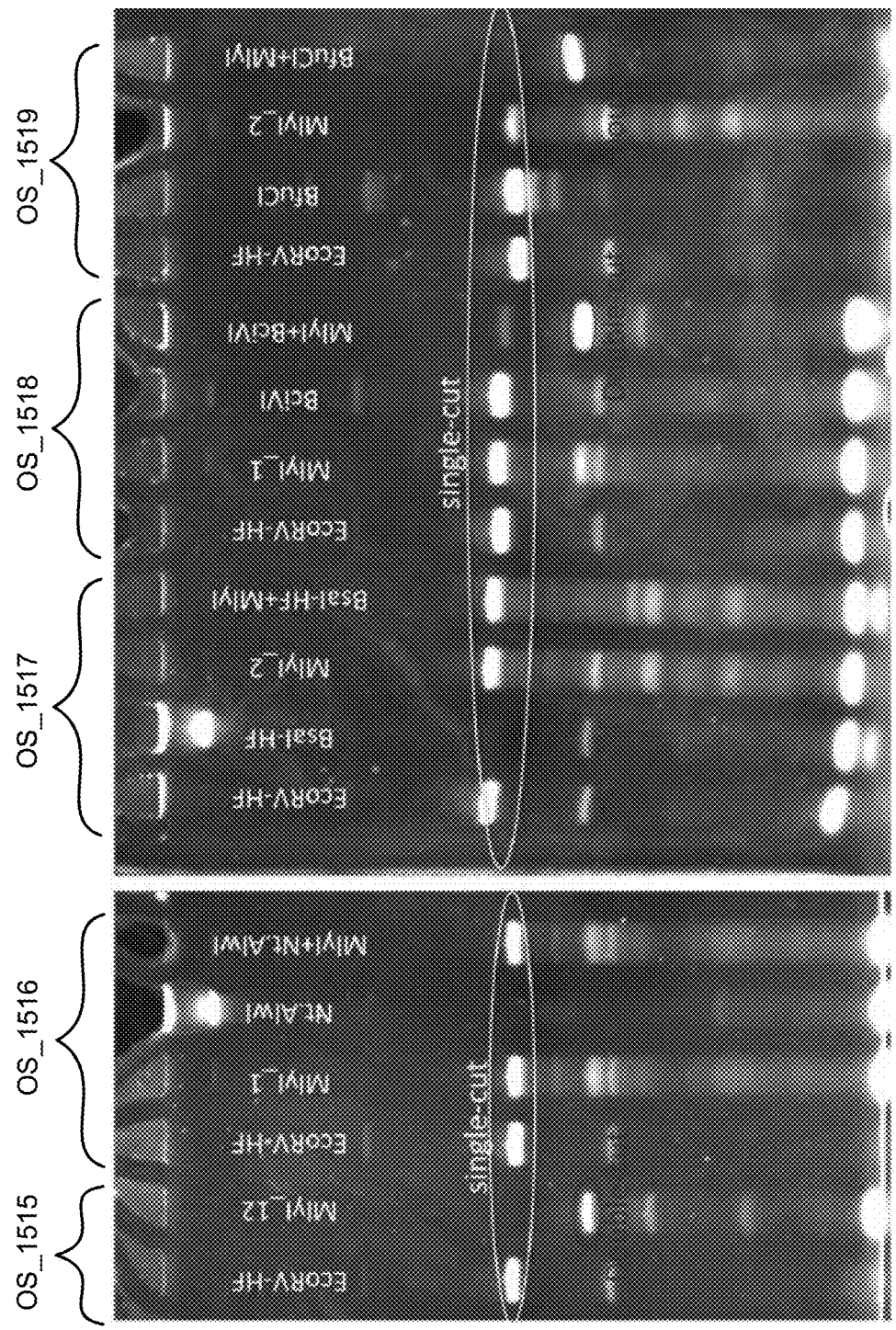
FIG. 63 depicts electrophoresis of amplified single stranded nucleic acids using rolling circle amplification, wherein the amplification product is cut with various combinations of cleaving agents.

FIG. 63 depicts the separation of restriction enzyme cleaved amplification products, where each single stranded amplification product has been hybridized with an auxiliary oligonucleotide complementary to the amplification product at adaptor copy sites, prior to cleavage. Data relating to the amplification of single stranded nucleic acids using padlock probes OS_1515, OS_1516, OS_1517, OS_1518, OS_1519, with different sets of restriction enzymes are also shown.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

The invention claimed is:

1. A method for synthesizing oligonucleotides, comprising:
synthesizing a plurality of oligonucleotides at a rate of extending each of the oligonucleotides by at least 10 nucleotides per hour, wherein each of the oligonucleotides has a preselected sequence, and wherein the synthesizing comprises extending each oligonucleotide by a single base in an extension reaction.

2. The method of claim 1, wherein the rate of extending each of the oligonucleotides is at least 20 nucleotides per hour.

3. The method of claim 1, wherein the rate of extending each of the oligonucleotides is at least 25 nucleotides per hour.

4. The method of claim 1, wherein the plurality oligonucleotides are synthesized in parallel.

5. The method of claim 1, wherein at least 20,000 oligonucleotides are synthesized.

6. The method of claim 1, wherein at least 500,000 oligonucleotides are synthesized.

7. The method of claim 1, wherein each of the oligonucleotides is at least 25 nucleotides in length.

8. The method of claim 1, wherein the plurality of oligonucleotides are synthesized on a solid substrate.

9. The method of claim 8, wherein the solid substrate comprises silicon, silicon dioxide or silicon nitride.

10. The method of claim 1, wherein each of the oligonucleotides has a different preselected sequence.

11. The method of claim 1, wherein each of the oligonucleotides comprises 100 to 200 nucleotides in length and is synthesized in less than 5 hours.

12. The method of claim 1, wherein the rate of extending each of the oligonucleotides is at least 12 nucleotides per hour.

13. The method of claim 1, wherein the rate of extending each of the oligonucleotides is at least 15 nucleotides per hour.

14. The method of claim 1, wherein each of the oligonucleotides comprises 100 to 200 nucleotides in length.

15. The method of claim 1, wherein each of the oligonucleotides comprises 80 to 200 nucleotides in length.

16. The method of claim 1, wherein each of the oligonucleotides is at least 100 nucleotides in length.

17. The method of claim 1, wherein each of the oligonucleotides are the same length.

18. The method of claim 1, wherein the plurality of oligonucleotides comprise DNA.

19. The method of claim 1, wherein the plurality of oligonucleotides comprise RNA.

20. The method of claim 1, wherein each of the oligonucleotides comprises 100 to 300 nucleotides in length.

21. The method of claim 1, wherein each of the oligonucleotides comprises 10 to 500 nucleotides in length.

* * * * *